US008895308B1

(12) United States Patent
Zhang et al.

(10) Patent No.: US 8,895,308 B1
(45) **Date of Patent: *Nov. 25, 2014**

(54) ENGINEERING AND OPTIMIZATION OF IMPROVED SYSTEMS, METHODS AND ENZYME COMPOSITIONS FOR SEQUENCE MANIPULATION

(71) Applicants: The Broad Institute, Inc., Cambridge, MA (US); Massachusetts Institute of Technology, Cambridge, MA (US)

(72) Inventors: Feng Zhang, Cambridge, MA (US); Fei Ran, Boston, MA (US)

(73) Assignees: The Broad Institute Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,498

(22) Filed: Jun. 2, 2014

Related U.S. Application Data

(63) Continuation of application No. 14/104,977, filed on Dec. 12, 2013.

(60) Provisional application No. 61/736,527, filed on Dec. 12, 2012, provisional application No. 61/748,427, filed on Jan. 2, 2013, provisional application No. 61/758,468, filed on Jan. 30, 2013, provisional application No. 61/769,046, filed on Feb. 25, 2013, provisional application No. 61/791,409, filed on Mar. 15, 2013, provisional application No. 61/802,174, filed on Mar. 15, 2013, provisional application No. 61/806,375, filed on Mar. 28, 2013, provisional application No. 61/814,263, filed on Apr. 20, 2013, provisional application No. 61/819,803, filed on May 6, 2013, provisional application No. 61/828,130, filed on May 28, 2013, provisional application No. 61/835,931, filed on Jun. 17, 2013, provisional application No. 61/836,101, filed on Jun. 17, 2013.

(51) Int. Cl.

| | |
|---|---|
| ***C12N 15/00*** | (2006.01) |
| ***C12N 5/00*** | (2006.01) |
| ***C12N 5/071*** | (2010.01) |
| ***C12N 15/86*** | (2006.01) |

(52) U.S. Cl.
CPC .................................... *C12N 15/86* (2013.01)
USPC ........................... 435/455; 435/325; 435/366

(58) Field of Classification Search
CPC ............. C12N 15/85; C12N 9/96; C12N 9/22
USPC .............. 435/6.1, 6.13, 195, 196, 199, 320.1, 435/220; 424/94.61; 536/23.1, 23.2, 23.7, 536/24.1
See application file for complete search history.

(56) References Cited

U.S. PATENT DOCUMENTS

| | | | |
|---|---|---|---|
| 2003/0186238 | A1 | 10/2003 | Allawi et al. |
| 2010/0055798 | A1 | 3/2010 | Battersby |
| 2010/0076057 | A1 | 3/2010 | Sontheimer et al. |
| 2011/0189776 | A1 | 8/2011 | Terns et al. |
| 2011/0223638 | A1 | 9/2011 | Wiedenheft et al. |
| 2013/0130248 | A1 | 5/2013 | Haurwitz et al. |
| 2014/0068797 | A1 | 3/2014 | Doudna et al. |

FOREIGN PATENT DOCUMENTS

| | | | |
|---|---|---|---|
| WO | WO/2008/108989 | | 9/2008 |
| WO | WO/2010/054108 | | 5/2010 |
| WO | WO/2012/164565 | | 12/2012 |
| WO | WO/2013/098244 | | 7/2013 |
| WO | 2013/141680 | A1 | 9/2013 |
| WO | 2013/0142578 | A1 | 9/2013 |
| WO | WO/2013176772 | | 11/2013 |
| WO | WO 2014/065596 | | 5/2014 |
| WO | WO 2014/089290 | | 6/2014 |
| WO | WO 2014/093479 | | 6/2014 |
| WO | WO 2014/099744 | | 6/2014 |
| WO | WO 2014/099750 | | 6/2014 |

OTHER PUBLICATIONS

Wu X et al. Genome-wide binding of the CRISPR endonuclease Cas9 in mammalian cells. 2014. Nature Biotechnology. doi:10.1038/nbt.2889 p. 1-9.*
Le Cong, et al., Supplementary Material: Multiplex Genome Engineering Using CRISPR-Cas Systems, Science Express (Jan. 3, 2013).
U.S. Appl. No. 61/735,876, filed Dec. 11, 2012, Blake A. Wiedenheft.
U.S. Appl. No. 61/799,531, filed Mar. 15, 2013, Blake A. Wiedenheft.
Al-Attar et al., Clustered Regularly Interspaced Short Palindromic Repeats (CRISPRs): The Hallmark of an Ingenious Antiviral Defense Mechanism in Prokaryotes, *Biol Chem.*(2011) vol. 392, Issue 4, pp. 277-289.
Carroll, A CRISPR Approach to Gene Targeting, Molecular Therapy (2012) vol. 20, No. 9, p. 1658-1660.
Gasiunas, et al., Cas9-crRNA Ribonucleoprotein Complex Mediates Specific DNA cleavage for Adaptive Immunity in Bacteria, PNAS USA (2012) vol. 109, No. 39, p. E2579-E2586.
Hale et al., Essential Features and Rational Design of CRISPR RNAs That Function With the Cas RAMP Module Complex to Cleave RNAs, *Molecular Cell*,(2012) vol. 45, Issue 3, 292-302.
Jinek et al, A Programmable Dual-RNA-Guided DNA Endonuclease in Adaptive Bacterial Immunity, Science (2012) vol. 337, p. 816-821.
Makarova et al., Evolution and Classification of the CRISPR-CAS Systems, Nature Reviews Microbiology (2011) vol. 9, No. 6, p. 467-477.

(Continued)

*Primary Examiner* — Manjunath Rao
*Assistant Examiner* — Paul Holland
(74) *Attorney, Agent, or Firm* — Vedder Price P.C.; Thomas J. Kowalski; Deborah L. Lu

(57) ABSTRACT

The invention provides for engineering and optimization of systems, methods, and compositions for manipulation of sequences and/or activities of target sequences. Provided are compositions and methods related to components of a CRISPR complex particularly comprising a Cas ortholog enzyme.

30 Claims, 119 Drawing Sheets

(56) References Cited

OTHER PUBLICATIONS

Erik Sontheimer, Project 7: Establishing RNA-Directed DNA Targeting in Eukaryotic Cells; Project dates: Nov. 16, 2011 to Dec. 31, 2012 (Feb. 4, 2012).

Wiedenheft, et al., RNA-Guided Genetic Silencing Systems in Bacteria and Archaea, Nature (2012) vol. 482, p. 331-338.

U.S. Appl. No. 61/613,373, filed Mar. 20, 2012.

U.S. Appl. No. 61/625,420, filed Apr. 17, 2012.

Kirill A. Datsenko, et al., Molecular Memory of Prior Infections Activates the CRISPR/Cas Adaptive Bacterial Immunity System, Nature Communications, Jul. 10, 2012, DOI:10.1038/ncomms1937.

Ksenia Pougach, et al., Transcription, Processing and Function of CRISPR Cassettes in *Escherichia coli*, Mol. Microbiol, Sep. 2010, 77(6), p. 1367-1379.

U.S. Appl. No. 61/738,355, filed Dec. 17, 2012, George M. Church.

U.S. Appl. No. 61/779,169, filed Mar. 13, 2013, Prashant Mali.

Le Cong, et al., Multiplex Genome Engineering Using CRISPR-Cas Systems, Science (Feb. 2013) vol. 339, p. 819-823.

Le Cong, et al., Supplementary Material: Multiplex Genome Engineering Using CRISPR-Cas Systems, Science Express (Jul. 5, 2012).

Seung Woo Cho, et al., Targeted Genome Engineering in Human Cells With the Cas9 RNA-Guided Endonuclease, Nature Biotechnology (Mar. 2013) vol. 31, No. 3, p. 230-232.

Seung Woo Cho, et al., Supplementary Information: Targeted Genome Engineering in Human Cells With the Cas9 RNA-Guided Endonuclease, Nature Biotechnology (Mar. 2013) vol. 31, No. 3, p. 1-10.

U.S. Appl. No. 61/734,256, filed Dec. 6, 2012, Fuqiang Chen.

U.S. Appl. No. 61/758,624, filed Jan. 30, 2013, Fuqiang Chen.

U.S. Appl. No. 61/761,046, filed Feb. 5, 2013, Scott Knight.

U.S. Appl. No. 61/794,422, filed Mar. 15, 2013, Scott Knight.

* cited by examiner

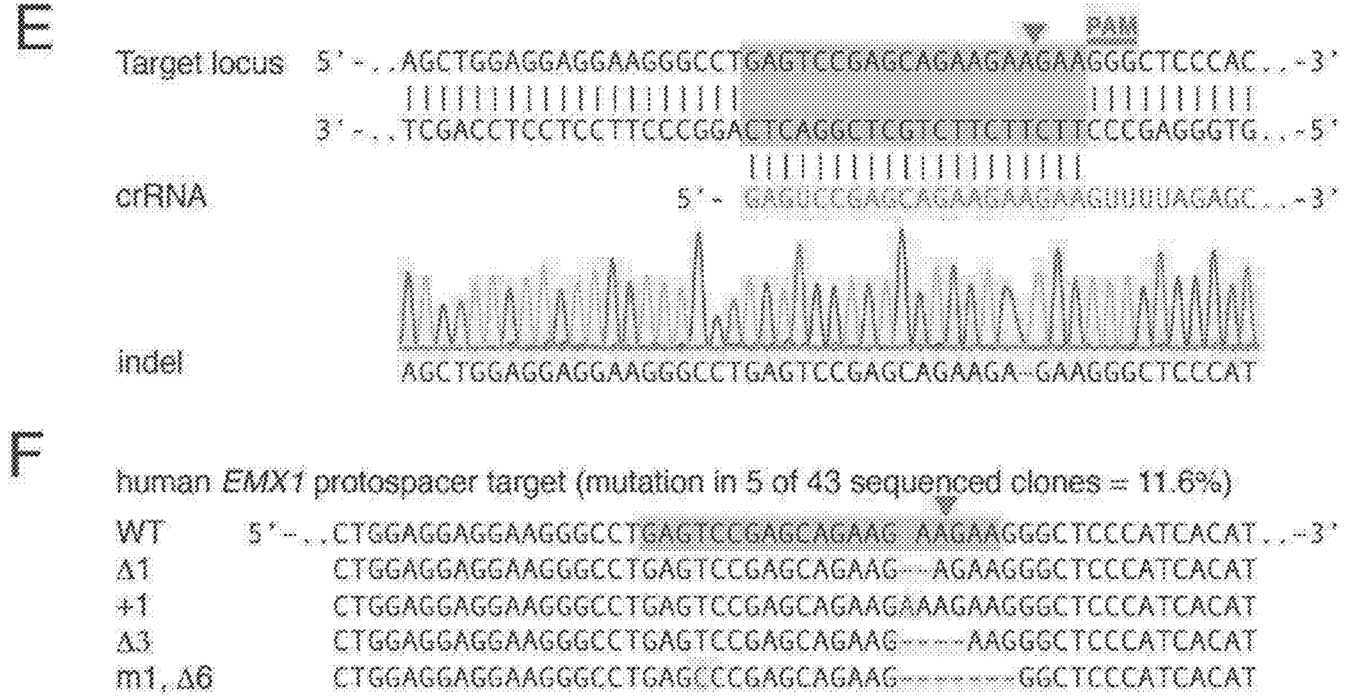
FIG. 2E-F

* depending on size of the entire construct, can contain one or more Pol3-chimeric guide RNA (gRNA) cassette

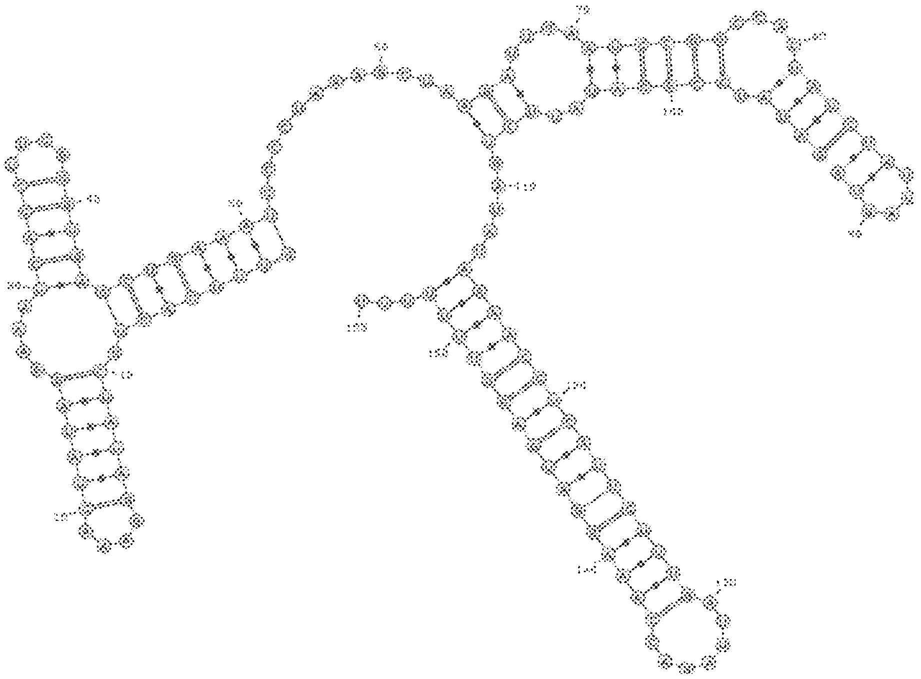
Chimeric guide RNA for Cas9 homolog 2
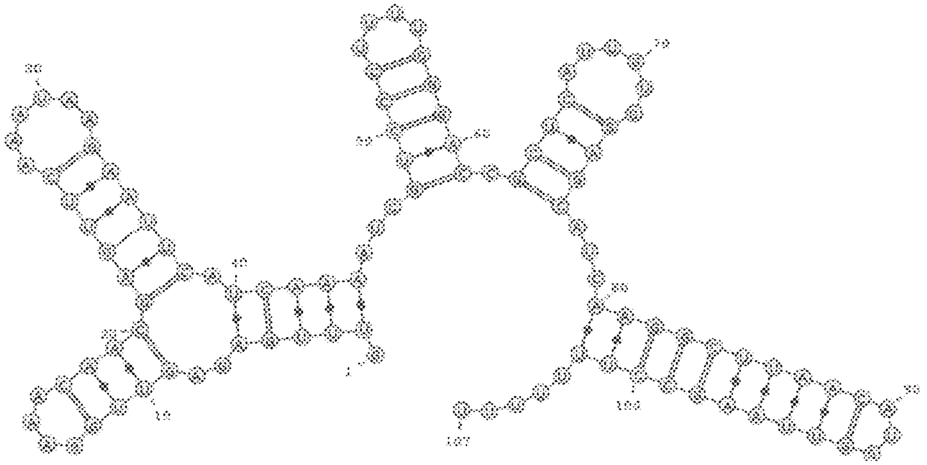
Chimeric guide RNA for Cas9 homolog 4
FIG. 8A

Chimeric guide RNA for Cas9 homolog 5
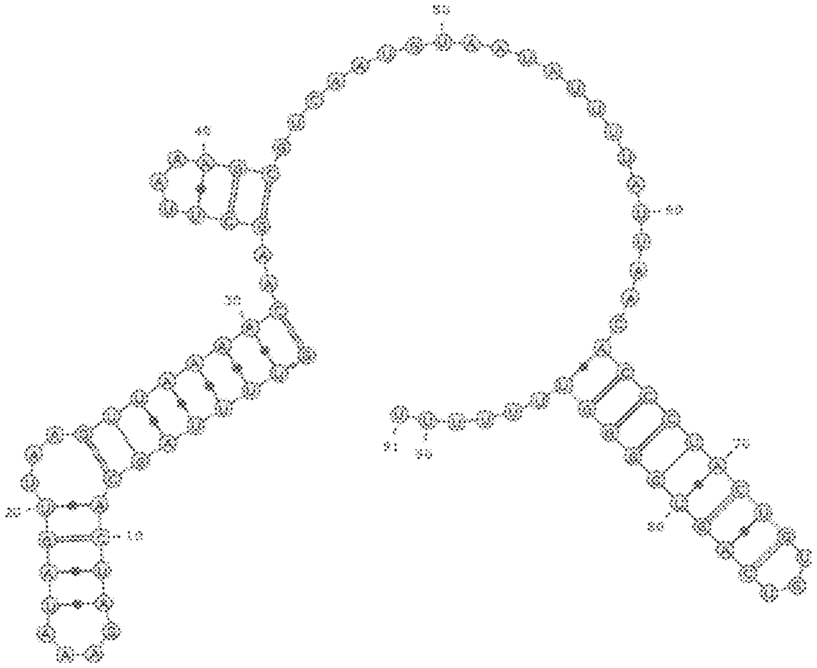
Chimeric guide RNA for Cas9 homolog 6
FIG. 8B

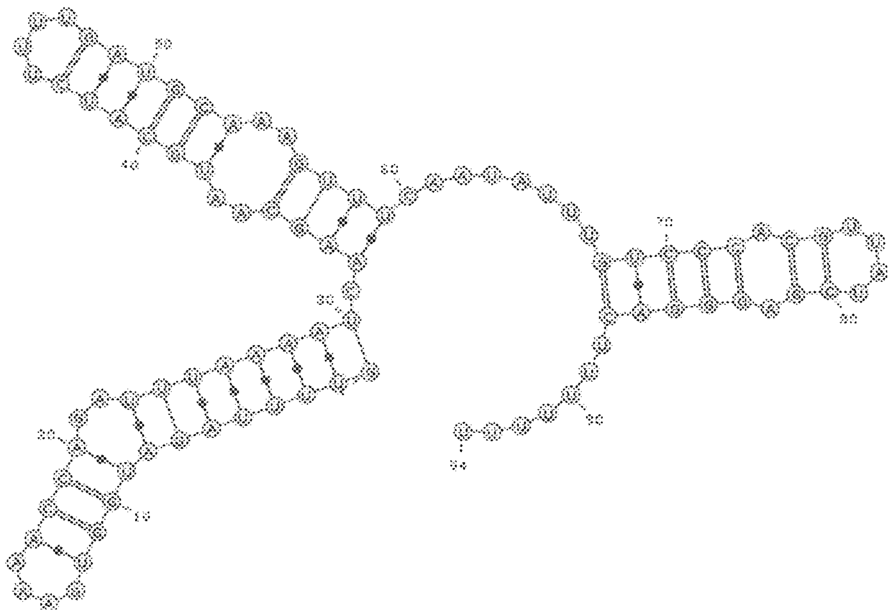
Chimeric guide RNA for Cas9 homolog 7
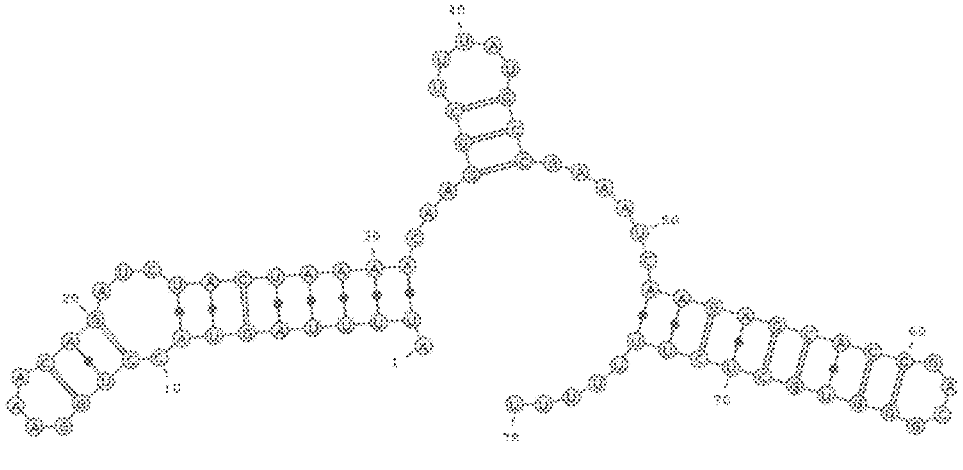
Chimeric guide RNA for Cas9 homolog 8
FIG. 8C

Chimeric guide RNA for Cas9 homolog 9
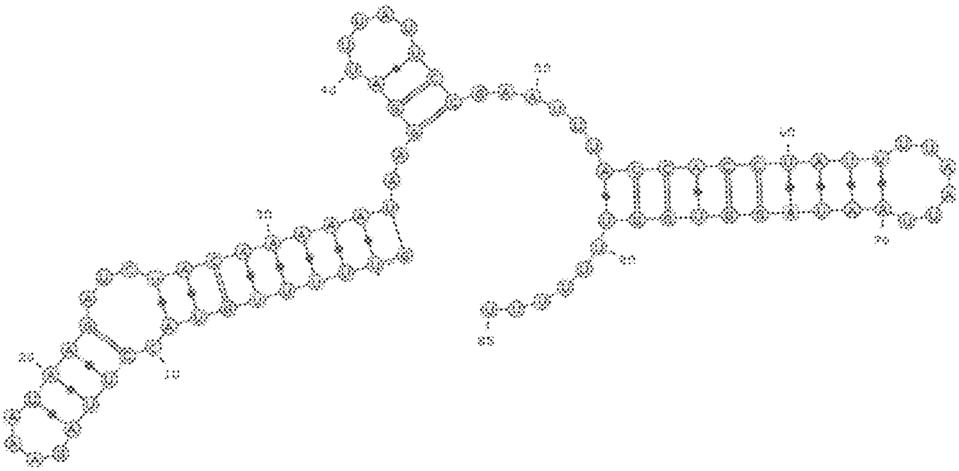
Chimeric guide RNA for Cas9 homolog 10
FIG. 8D

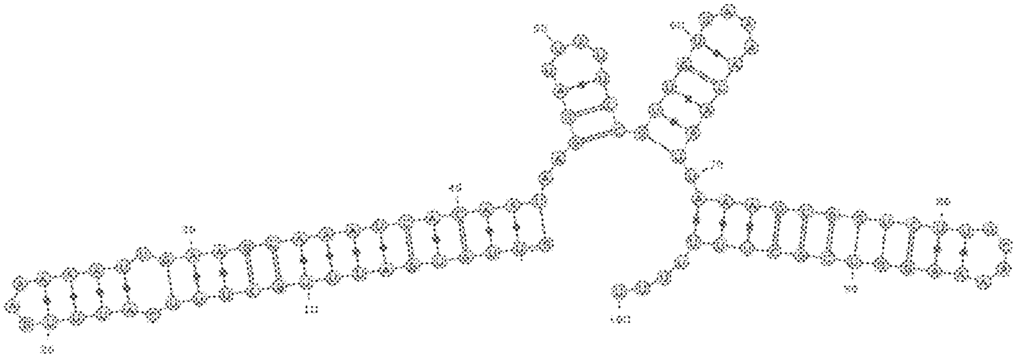
Chimeric guide RNA for Cas9 homolog 12
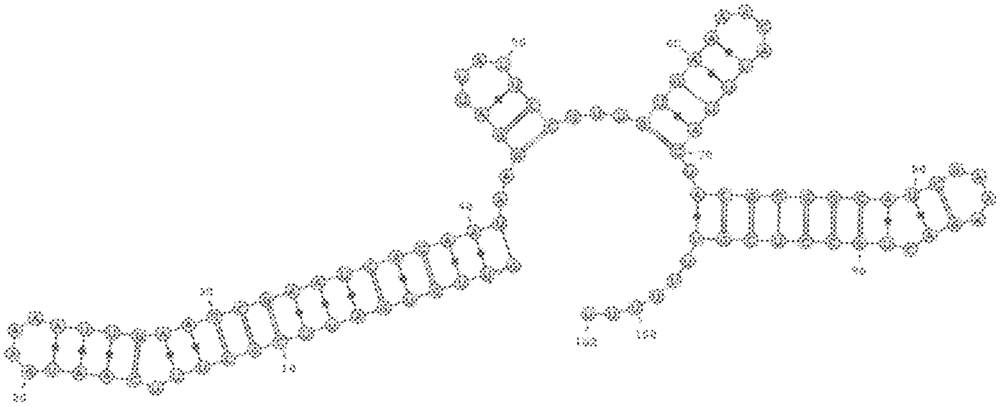
Chimeric guide RNA for Cas9 homolog 13
FIG. 8E Chimeric guide RNA for Cas9 homolog 14

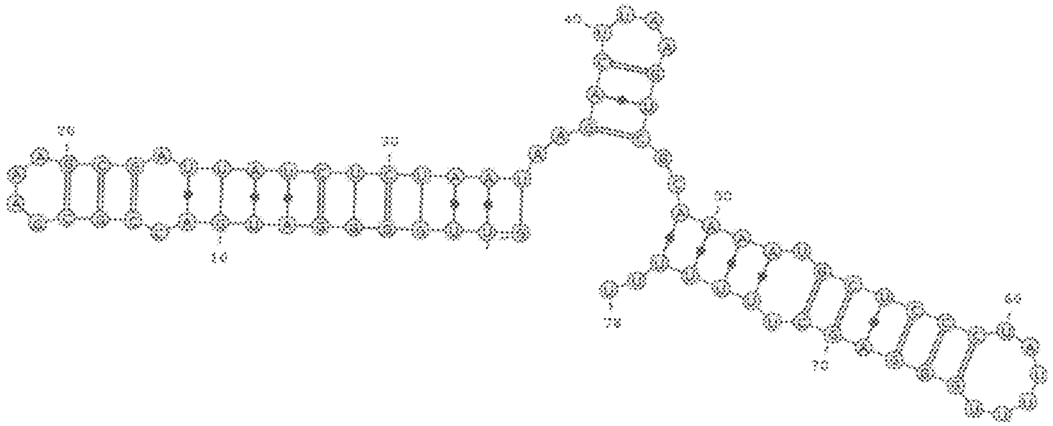
Chimeric guide RNA for Cas9 homolog 15
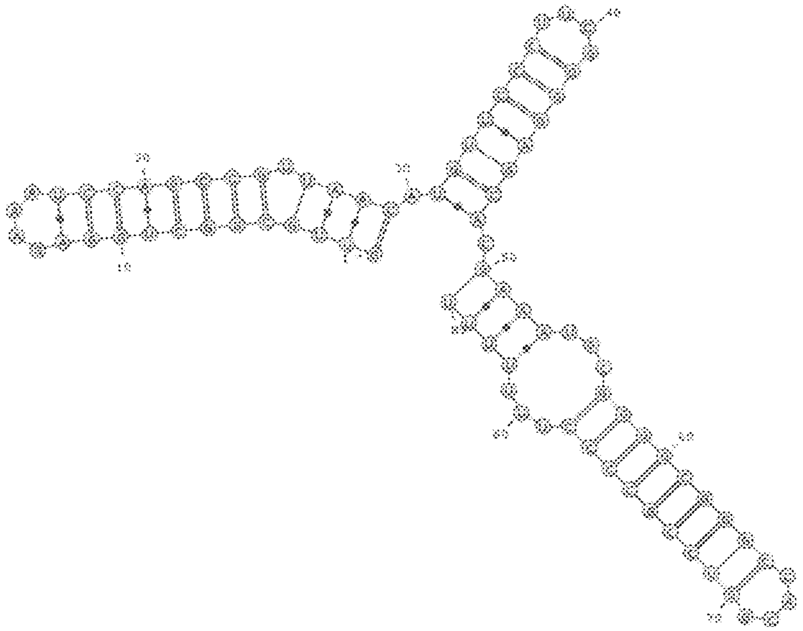
Chimeric guide RNA for Cas9 homolog 16
FIG. 8G Chimeric guide RNA for Cas9 homolog 17

Chimeric guide RNA for Cas9 homolog 19

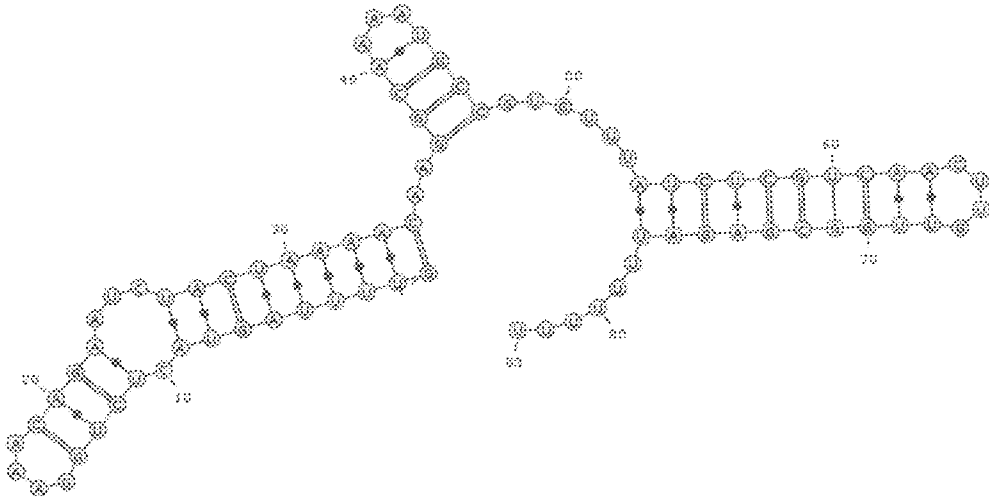
Chimeric guide RNA for Cas9 homolog 21
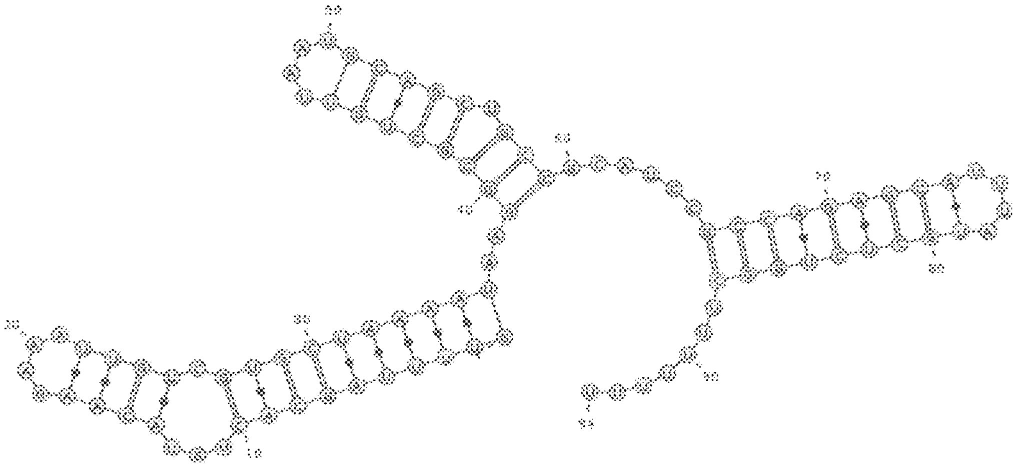
Chimeric guide RNA for Cas9 homolog 23
FIG. 8J

FIG. 9A human codon optimized Cas9 sequences

#2

ACCGGTGCCACCATGTACCCATACGATGTTCCAGATTACGCTTCGCCGAAGAAAAAGCGCAAGGTCGAAGCGTCCATGACTCAG
AGCGAGCGACGATTTTCTTGCAGCATTGGCATTGACATGGGGGCTAAGTACACTGGGGTGTTCTACGCACTGTTCGACCGGGAG
GAACTGCCCACAAACCTGAACAGCAAGGCCATGACCCTGGTCATGCCTGAGACAGGGCCAAGATACGTGCAGGCACAGAGAACT
GCCGTCAGACACAGGCTGCGCGGACAGAAGAGATATACCCTGGCTAGGAAACTGGCATTTCTGGTGGTCGACGATATGATCAAG
AAACAGGAAAAGAGGCTGACTGATGAGGAATGGAAACGAGGACGGGAGGCCCTGTCCGGCCTGCTGAAGCGGAGAGGGTACTCT
CGGCCCAACGCTGACGGCGAAGATCTGACCCCTCTGGAGAATGTGAGAGCAGACGTGTTCGCCGCTCATCCTGCCTTCAGCACA
TATTTTTCCGAAGTGCGCTCTCTGGCTGAGCAGTGGGAGGAGTTCACCGCAAACATCAGCAATGTCGAGAAGTTTCTGGGCGAC
CCAAACATCCCCGCCGATAAAGAGTTCATTGAATTTGCCGTGGCTGAAGGGCTGATTGACAAGACCGAGAAGAAAGCCTACCAG
TCAGCTCTGAGCACCCTGAGGGCAAACGCCAATGTGCTGACAGGACTGCGGCAGATGGGCCACAAGCCTAGATCAGAATATTTT
AAAGCAATCGAGGCCGACCTGAAGAAAGATAGCCGCCTGGCCAAGATTAACGAAGCATTCGGAGGAGCAGAGCGCCTGGCTCGA
CTGCTGGGAAACCTGTCCAATCTGCAGCTGCGGGCAGAAAGATGGTACTTCAATGCCCCCGACATCATGAAGGATAGGGGCTGG
GAGCCTGATCGCTTCAAGAAAACACTGGTGCGGGCTTTTAAGTTCTTTCACCCAGCAAAGGACCAGAACAAACAGCATCTGGAA
CTGATCAAACAGATTGAGAACAGCGAAGATATCATTGAGACTCTGTGCACCCTGGACCCAAACAGAACCATCCCCCCTTACGAG
GATCAGAACAATAGGCGCCCACCCCTGGACCAGACTCTGCTGCTGAGTCCCGAAAAGCTGACCCGGCAGTATGGCGAGATCTGG
AAAACATGGAGCGCCAGACTGACCTCCGCTGAACCCACACTGGCACCTGCAGCCGAGATTCTGGAAAGATCTACCGACAGGAAG
AGTCGCGTGGCAGTCAACGGACACGAGCCACTGCCTACACTGGCTTACCAGCTGAGTTATGCACTGCAGAGAGCCTTCGACAGG
TCAAAAGCCCTGGATCCATATGCTCTGAGGGCACTGGCTGCAGGCTCAAAAAGCAATAAGCTGACATCCGCCCGCACTGCTCTG
GAGAACTGCATCGGAGGCCAGAATGTGAAAACCTTCCTGGACTGTGCCCGACGGTACTATCGGGAAGCAGACGATGCCAAAGTC
GGGCTGTGGTTCGACAACGCCGATGGACTGCTGGAGAGATCTGACCTGCATCCTCCAATGAAGAAAAAGATCCTGCCCCTGCTG
GTGGCCAATATTCTGCAGACAGATGAAACCACAGGCCAGAAGTTTCTGGACGAGATCTGGCGAAAACAGATTAAGGGGCGGGAA
ACTGTGGCTAGCCGATGTGCACGGATCGAGACAGTGCGGAAATCCTTCGGGGGAGGCTTTAACATTGCCTACAATACCGCTCAG
TATAGGGAGGTGAACAAGCTGCCCCGCAATGCCCAGGATAAAGAACTGCTGACAATCAGAGATAGGGTGGCTGAGACTGCAGAC
TTCATTGCCGCTAACCTGGGGCTGTCTGACGAGCAGAAAAGAAAGTTCGCCAATCCTTTTAGTCTGGCTCAGTTCTACACCCTG
ATCGAGACAGAAGTGTCCGGATTTTCTGCAACTACCCTGGCCGTCCACCTGGAGAACGCCTGGAGGATGACAATCAAGGATGCT
GTGATTAATGGGGAAACTGTCAGAGCAGCACAGTGCAGCAGGCTGCCTGCAGAGACAGCTCGCCCATTCGATGGACTGGTGAGA
AGGCTGGTCGACAGACAGGCTTGGGAGATCGCAAAGAGGGTGTCAACTGACATTCAGAGCAAAGTCGATTTCTCCAACGGCATC
GTGGACGTCAGCATTTTTGTGGAGGAAAATAAGTTCGAGTTTTCCGCATCTGTGGCCGATCTGAAAAAGAACAAACGGGTCAAA
GACAAGATGCTGTCCGAGGCCGAAAAGCTGGAAACCAGATGGCTGATCAAAAATGAGCGGATCAAGAAGGCCAGCCGGGGAACT
TGTCCCTACACCGGCGATAGGCTGGCTGAGGGGGGAGAAATCGACCACATTCTGCCCCGAAGCCTGATCAAGGATGCCCGGGGA
ATTGTGTTTAACGCTGAGCCTAATCTGATCTATGCAAGCTCCCGCGGCAACCAGCTGAAAAAGAATCAGCGATACAGTCTGTCA
GATCTGAAGGCCAACTATCGGAATGAGATCTTCAAAACTAGCAACATCGCTGCAATTACCGCCGAGATTGAGGACGTGGTCACT
AAGCTGCAGCAGACCCATAGACTGAAATTCTTTGATCTGCTGAATGAGCACGAACAGGACTGCGTGCGGCACGCCCTGTTCCTG
GACGATGGCAGCGAAGCTCGCGACGCAGTGCTGGAGCTGCTGGCAACACAGCGCCGAACTCGCGTCAACGGGACACAGATCTGG
ATGATTAAGAACCTGGCCAACAAGATCCGAGAGGAACTGCAGAATTGGTGTAAGACAACTAACAATAGACTGCACTTTCAGGCC
GCTGCAACTAACGTGTCCGATGCAAAGAATCTGAGGCTGAAACTGGCCCAGAACCAGCCCGACTTCGAGAAGCCAGATATCCAG
CCCATTGCCAGCCATTCCATCGACGCCCTGTGCTCTTTCGCTGTGGGGAGTGCTGACGCAGAACGCGATCAGAATGGATTTGAC
TACCTGGATGGCAAGACCGTGCTGGGACTGTATCCACAGAGCTGTGAGGTCATTCACCTGCAGGCCAAGCCCCAGGAGGAAAAA
AGTCATTTCGATTCAGTGGCTATCTTTAAGGAAGGCATCTACGCAGAGCAGTTCCTGCCTATCTTTACCCTGAACGAAAAGATC
TGGATTGGATATGAGACACTGAATGCCAAAGGCGAAAGATGCGGGGCTATTGAGGTGAGTGGCAAACAGCCAAAGGAGCTGCTG
GAAATGCTGGCCCCCTTCTTTAACAAGCCTGTGGGCGACCTGTCAGCCCACGCTACTTACCGGATCCTGAAAAAGCCTGCATAT
GAGTTTCTGGCAAAGGCAGCTCTGCAGCCACTGAGCGCAGAGGAAAAAAGACTGGCAGCCCTGCTGGATGCTCTGCGCTACTGT
ACCAGTCGAAAGTCACTGATGAGCCTGTTCATGGCTGCAAACGGGAAATCCCTGAAAAAGCGGGAGGACGTGCTGAAACCCAAG
CTGTTCCAGCTGAAGGTCGAGCTGAAAGGCGAAAAGAGCTTCAAGCTGAACGGGAGCCTGACCCTGCCTGTGAAGCAGGACTGG
CTGAGAATCTGCGATAGCCCAGAACTGGCAGACGCCTTTGGCAAACCCTGTTCCGCCGATGAGCTGACATCTAAGCTGGCTCGC
ATTTGGAAACGACCTGTGATGCGGGATCTGGCTCATGCACCAGTCCGGAGAGAGTTCAGCCTGCCCGCAATCGACAACCCAAGT
GGAGGGTTCAGGATTAGGCGCACCAACCTGTTTGGCAATGAGCTGTACCAGGTGCACGCCATCAACGCTAAAAAGTATCGCGGC
TTCGCCTCCGCTGGGTCTAATGTCGACTGGTCCAAGGGGATCCTGTTTAACGAGCTGCAGCATGAAAATCTGACCGAGTGCGGA
GGCAGGTTCATTACAAGCGCCGATGTGACTCCTATGTCCGAATGGCGCAAGGTGGTCGCAGAGGACAACCTGTCTATCTGGATT
GCTCCAGGGACAGAAGGACGACGGTACGTGAGGGTCGAGACAACATTCATCCAGGCCAGTCACTGGTTTGAACAGTCAGTGGAG
AATTGGGCCATTACTAGTCCTCTGTCACTGCCAGCTTCCTTCAAGGTGGACAAACCAGCTGAGTTTCAGAAGGCAGTCGGAACC
GAGCTGTCAGAACTGCTGGGCCAGCCCAGGAGCGAAATCTTCATTGAGAACGTGGGCAATGCCAAGCATATCCGCTTTTGGTAC
ATTGTGGTGAGCAGCAACAAAAAGATGAACGAGTCTTACAACAATGTGTCTAAGAGTTAAGAATTC

#4

ACCGGTGCCACCATGTACCCATACGATGTTCCAGATTACGCTTCGCCGAAGAAAAAGCGCAAGGTCGAAGCGTCCATGAAAAAA
GAAATCAAAGACTACTTCCTGGGGCTGGATGTGGGGACTGGGAGCGTGGGGTGGGCTGTGACCGATACTGACTACAAACTGCTG
AAGGCTAACCGAAAAGACCTGTGGGGCATGAGATGCTTCGAGACAGCCGAAACTGCTGAGGTGCGGAGACTGCACAGGGGAGCC
AGGCGCCGAATCGAGCGGAGAAAGAAACGCATTAAGCTGCTGCAGGAGCTGTTCTCTCAGGAAATCGCCAAAACCGATGAGGGC
TTCTTTCAGAGAATGAAGGAAAGCCCCTTTTACGCTGAGGACAAAACAATCCTGCAGGAAAACACTCTGTTCAATGACAAGGAT
TTTGCTGATAAGACTTACCACAAAGCATATCCTACCATTAATCATCTGATCAAGGCTTGGATTGAGAACAAGGTGAAACCAGAC
CCCCGACTGCTGTACCTGGCATGTCACAACATCATTAAGAAAAGGGGACATTTCCTGTTTGAAGGCGACTTCGATTCAGAGAAT
CAGTTTGATACCAGCATCCAGGCACTGTTCGAGTATCTGCGCGAGGACATGGAGGTGGACATCGATGCCGACAGCCAGAAGGTC

FIG. 9B

AAAGAGATTCTGAAGGATAGCTCCCTGAAGAACTCTGAAAAACAGAGTCGGCTGAATAAGATCCTGGGGCTGAAGCCTTCCGAC
AAACAGAAGAAAGCCATCACAAACCTGATTTCTGGAAACAAGATCAATTTCGCCGATCTGTACGACAATCCAGATCTGAAGGAC
GCTGAGAAAAAACTCAATCAGCTTCTCCAAGGACGATTTTGATGCACTGAGTGACGATCTGGCCTCAATTCTGGGCGACAGCTTT
GAACTGCTGCTGAAGGCCAAAGCTGTCTATAACTGCTCTGTGCTGAGTAAGGTCATCGGGGACGAGCAGTACCTGAGCTTCGCC
AAGGTGAAAATCTACGAAAAGCACAAAACCGATCTGACAAAGCTGAAAAACGTGATCAAGAAACATTTCCCCAAGGACTACAAG
AAGGTCTTTGGATACAACAAGAACGAGAAAAACAACAACAATTACTCCGGCTATGTGGGAGTCTGTAAGACCAAGAGTAAGAAA
CTGATCATTAACAACTCAGTCAACCAGGAAGATTTCTACAAGTTTCTGAAAACTATCCTGTCAGCCAAGAGCGAGATCAAGGAA
GTGAATGACATCCTGACCGAGATTGAAACTGGCACCTTTCTGCCAAAGCAGATCTCTAAAAGTAACGCAGAGATTCCCTATCAG
CTGAGGAAAATGGAGCTGGAAAAGATCCTGTCCAATGCCGAAAAGCACTTCTCTTTTCTGAAGCAGAAAGACGAAAAAGGACTG
TCACATAGCGAGAAGATCATTATGCTGCTGACCTTCAAGATCCCTTACTATATTGGCCCAATCAACGATAATCACAAGAAATTC
TTTCCCGACAGATGCTGGGTGGTCAAGAAAGAGAAATCCCCTTCTGGCAAGACCACACCATGGAACTTCTTTGATCATATCGAC
AAGGAAAAAACAGCAGAGGCCTTCATTACTTCTAGGACCAATTTTTGCACTTACCTGGTGGGAGAGAGCGTCCTGCCTAAGTCT
AGTCTGCTGTACTCCGAATATACCGTGCTGAACGAGATCAACAATCTGCAGATCATTATCGATGGCAAGAATATTTGTGACATC
AAGCTGAAACAGAAGATCTACGAGGACCTGTTCAAGAAGTACAAGAAAATTACCCAGAAGCAGATCAGCACCTTCATCAAGCAC
GAAGGCATCTGCAACAAAACCGATGAAGTGATCATCCTGGGGATTGACAAGGAATGTACATCAAGCCTGAAAAGCTACATCGAG
CTGAAAAACATTTTCGGCAAGCAGGTGGATGAGATCTCCACTAAGAATATGCTGGAGGAAATTATCAGATGGGCTACCATCTAC
GACGAGGGGGAAGGAAAGACCATCCTGAAAACAAAGATCAAGGCAGAATACGGAAAGTATTGCTCCGACGAGCAGATTAAGAAA
ATCCTGAACCTGAAGTTCTCCGGCTGGGGGCGACTGTCTCGGAAATTTCTGGAGACAGTGACTAGTGAAATGCCCGGCTTCTCA
GAACCTGTCAATATTATCACCGCCATGAGGGAGACACAGAACAATCTGATGGAGCTGCTGTCCTCTGAGTTCACCTTCACCGAG
AACATTAAGAAAATCAATTCTGGATTCGAAGATGCCGAGAAGCAGTTTAGTTACGACGGCCTGGTGAAACCACTGTTTCTGAGT
CCCTCAGTCAAGAAAATGCTGTGGCAGACCCTGAAGCTGGTGAAAGAGATTAGCCATATCACACAGGCCCCCCCTAAGAAAATT
TTCATCGAAATGGCAAAGGGGGCCGAGCTGGAACCTGCTCGGACTAAGACCAGACTGAAAATCCTGCAGGATCTGTATAACAAT
TGTAAGAACGATGCTGACGCCTTCAGCTCAGAGATCAAAGACCTGAGCGGAAAGATTGAGAACGAAGATAATCTGAGGCTGCGC
TCCGACAAGCTGTACCTGTACTATACTCAGCTGGGGAAATGCATGTATTGTGGAAAGCCAATTGAGATCGGCCACGTGTTCGAT
ACCTCAAACTACGATATTGACCATATCTATCCCCAGAGCAAGATCAAAGACGATAGCATTTCCAATCGGGTGCTGGTCTGCAGC
TCCTGTAACAAGAACAAGGAGGACAAGTACCCACTGAAATCAGAGATCCAGAGCAAGCAGCGCGGCTTCTGGAACTTTCTGCAG
CGAAACAATTTCATTTCTCTGGAGAAGCTGAATAGACTGACAAGGGCCACTCCAATCAGTGACGATGAGACAGCCAAGTTTATT
GCTAGGCAGCTGGTGGAAACTCGCCAGGCTACCAAGGTGGCCGCTAAAGTCCTGGAAAAGATGTTCCCCGAGACAAAAATCGTG
TACAGCAAGGCCGAGACTGTCTCCATGTTCCGGAACAAGTTTGATATCGTGAAGTGCAGAGAAATTAACGATTTTCACCATGCT
CACGACGCATACCTGAATATCGTGGTCGGCAACGTGTATAATACCAAGTTCACAAACAATCCTTGGAACTTTATCAAGGAGAAA
AGAGATAATCCAAAGATTGCTGACACCTACAACTACTATAAGGTGTTCGATTATGACGTCAAAAGGAACAATATCACAGCATGG
GAGAAGGGGAAAACTATTATCACCGTGAAAGACATGCTGAAGAGAAACACACCAATCTACACTAGGCAGGCAGCCTGTAAGAAA
GGGGAGCTGTTCAATCAGACCATTATGAAGAAAGGACTGGGCCAGCACCCCCTGAAGAAAGAAGGACCTTTTTCCAATATCTCT
AAATACGGCGGGTATAACAAGGTGAGCGCTGCATACTATACACTGATTGAGTATGAGGAAAAGGGCAACAAAATCCGCTCCCTG
GAAACTATTCCCCTGTACCTGGTGAAAGATATCCAGAAGGATCAGGACGTCCTGAAGTCTTATCTGACAGACCTGCTGGGGAAG
AAAGAGTTCAAGATCCTGGTGCCCAAGATCAAGATCAACAGCCTGCTGAAGATCAATGGGTTTCCTTGCCATATTACAGGAAAA
ACTAACGATAGTTTCCTGCTGCGCCCTGCCGTGCAGTTTTGCTGTTCAAACAATGAGGTCCTGTACTTCAAGAAAATTATCCGG
TTTTCCGAAATCCGCTCTCAGCGAGAGAAGATCGGGAAAACAATTAGCCCATACGAGGACCTGAGCTTCCGGTCATATATCAAG
GAGAACCTGTGGAAGAAAACTAAGAACGATGAAATCGGAGAGAAGGAATTTTACGACCTGCTGCAGAAGAAAAACCTGGAGATC
TATGATATGCTGCTGACTAAGCACAAAGACACCATCTACAAGAAACGCCCTAATTCTGCCACCATTGATATCCTGGTGAAGGGG
AAAGAGAAGTTCAAAAGCCTGATTATCGAAAACCAGTTTGAAGTGATCCTGGAGATCCTGAAGCTGTTTTCTGCAACACGGAAT
GTCAGTGACCTGCAGCATATCGGAGGCAGCAAGTACTCCGGCGTGGCCAAAATCGGGAACAAGATCTCTAGTCTGGATAACTGT
ATCCTGATCTATCAGTCCATCACCGGCATCTTCGAGAAACGGATCGACCTGCTGAAGGTGTAAGAATTC

#5
ACCGGTGCCACCATGTACCCATACGATGTTCCAGATTACGCTTCGCCGAAGAAAAAGCGCAAGGTCGAAGCGTCCATGACCAAG
GAGTATTACCTGGGGCTGGATGTGGGGACCAATTCCGTGGGATGGGCAGTGACCGATTCTCAGTACAACCTGTGCAAGTTTAAG
AAAAAGGATATGTGGGGCATCCGGCTGTTCGAAAGCGCCAACACAGCAAAGGACCGGAGACTGCAGAGAGGGAATAGGCGCCGA
CTGGAGCGGAAAAAGCAGAGAATTGATCTGCTGCAGGAAATCTTCTCCCCAGAGATCTGCAAGATTGACCCCACTTTCTTTATC
CGACTGAACGAATCCCGGCTGCACCTGGAGGACAAGTCTAACGATTTCAAATACCCACTGTTTATTGAGAAGGACTATTCTGAT
ATCGAGTACTATAAAGAGTTCCCCACCATTTTTCACCTGAGGAAGCATCTGATCGAGAGTGAGGAAAAACAGGATATCCGGCTG
ATCTACCTGGCCCTGCACAACATCATTAAGACCCGAGGACATTTTCTGATTGACGGCGATCTGCAGAGCGCCAAGCAGCTGAGG
CCCATCCTGGATACATTCCTGCTGTCCCTGCAGGAGGAACAGAACCTGTCAGTGAGCCTGTCCGAAAATCAGAAGGACGAGTAT
GAGGAAATTCTGAAAAACCGCAGCATCGCCAAGTCCGAAAAAGTGAAAAAGCTGAAGAATCTGTTTGAGATCTCAGACGAGCTG
GAAAAAGAGGAGAAGAAGGCCCAGAGCGCCGTGATCGAGAACTTCTGCAAGTTTATCGTGGGAAATAAGGGCGATGTCTGTAAA
TTCCTGCGGGTGTCTAAGGAGGAACTGGAGATTGACTCTTTCAGTTTTTCAGAGGGCAAGTACGAGGACGACATCGTGAAAAAC
CTGGAGGAAAAAGTGCCTGAAAAGGTCTACCTGTTTGAGCAGATGAAGGCAATGTATGATTGGAATATTCTGGTCGACATCCTG
GAAACCGAGGAATACATCAGCTTCGCCAAAGTGAAGCAGTATGAGAAACACAAGACTAACCTGCGGCTGCTGAGAGACATCATT
CTGAAATACTGCACCAAGGATGAGTATAATCGGATGTTTAACGACGAGAAGGAAGCTGGCAGCTACACCGCATATGTGGGGAAA
CTGAAAAAGAACAACAAGAAGTACTGGATCGAGAAAAAGAGAAATCCCGAGGAGTTCTACAAATCCCTGGGCAAGCTGCTGGAT
AAAATTGAGCCTCTGAAGGAGGACCTGGAAGTGCTGACTATGATGATCGAGGAGTGTAAGAACCACACCCTGCTGCCAATTCAG
AAAAATAAGGACAACGGCGTGATCCCCCACCAGGTGCATGAGGTCGAACTGAAAAAGATCCTGGAAAATGCCAAAAAGTACTAT
TCCTTCCTGACCGAGACAGACAAGGATGGGTACTCAGTGGTCCAGAAAATCGAGAGCATTTTCAGGTTTCGCATCCCCTACTAT

FIG. 9C

GTGGGGCCTCTGAGTACCCGGCACCAGGAAAAGGGATCAAACGTGTGGATGGTCAGAAAACCTGGCAGGGAGGATCGCATCTAC
CCATGGAATATGGAGGAAATCATTGACTTTGAGAAGAGCAACGAAAATTTCATTACACGGATGACTAACAAATGTACATATCTG
ATCGGGGAAGATGTCCTGCCCAAGCATTCTCTGCTGTACAGTAAATATATGGTGCTGAATGAGCTGAACAATGTGAAGGTCAGA
GGAAAAAAGCTGCCTACATCTCTGAAACAGAAGGTGTTCGAGGACCTGTTTGAAAACAAATCCAAAGTGACTGGAAAGAATCTG
CTGGAGTACCTGCAGATCCAGGACAAAGATATCCAGATTGACGATCTGTCTGGCTTCGACAAGGACTTCAAGACCAGCCTGAAG
AGCTATCTGGACTTCAAAAAGCAGATTTTTGGGGAGGAAATCGAGAAGGAAAGCATTCAGAACATGATCGAAGATATCATTAAG
TGGATCACCATCTACGGCAATGACAAGGAGATGCTGAAACGAGTGATTCGGGCTAATTATAGCAACCAGCTGACAGAGGAACAG
ATGAAAAAGATCACTGGATTTCAGTACAGTGGCTGGGGGAACTTCTCAAAGATGTTTCTGAAAGGGATCAGCGGATCCGACGTG
AGCACCGGCGAAACATTCGACATCATTACCGCAATGTGGGAGACAGACAACAATCTGATGCAGATCCTGTCAAAAAAGTTCACC
TTTATGGACAACGTCGAGGACTTCAACAGCGGCAAGGTCGGGAAAATCGACAAGATTACTTACGATAGCACCGTGAAGGAAATG
TTCCTGTCCCCTGAGAACAAAAGGGCCGTCTGGCAGACCATTCAGGTGGCTGAGGAGATCAAGAAAGTGATGGGCTGCGAGCCA
AAAAAGATCTTTATTGAAATGGCACGGGGCGGGGAGAAGGTGAAAAAGAGGACAAAATCTCGCAAGGCCCAGCTGCTGGAGCTG
TACGCCGCTTGCGAGGAAGATTGTAGAGAACTGATCAAGGAGATTGAGGACCGGGACGAGAGGGACTTCAATAGCATGAAGCTG
TTTCTGTACTATACCCAGTTCGGGAAATGTATGTATTCCGGCGACGACATCGATATTAACGAGCTGATTCGCGGCAATTCTAAG
TGGGACCGAGATCACATCTACCCCCAGAGCAAAATTAAGGACGATTCCATCGATAACCTGGTGCTGGTCAATAAGACATATAAT
GCCAAAAAGTCCAATGAGCTGCTGTCTGAGGACATCCAGAAAAAGATGCATTCATTCTGGCTGAGCCTGCTGAACAAAAAGCTG
ATCACTAAAAGCAAGTACGACCGCCTGACTCGAAAGGGCGACTTTACCGATGAGGAACTGAGTGGGTTCATCGCTAGACAGCTG
GTGGAAACAAGGCAGTCAACTAAGGCAATCGCCGATATCTTCAAGCAGATCTACAGCTCCGAGGTGGTCTATGTGAAGAGCAGC
CTGGTGAGCGACTTCAGGAAAAAGCCACTGAACTACCTGAAGTCTCGGAGAGTCAATGATTACCACCATGCAAAAGACGCCTAT
CTGAACATTGTGGTCGGGAACGTGTACAACAAAAAGTTTACCAGTAATCCCATCCAGTGGATGAAAAAGAATCGCGATACAAAC
TATAGCCTGAACAAGGTGTTCGAACACGACGTGGTCATTAACGGAGAAGTGATCTGGGAAAAGTGCACATACCATGAGGACACT
AATACCTATGATGGAGGCACTCTGGACCGAATCCGGAAGATTGTGGAACGCGATAACATTCTGTACACCGAGTACGCTTATTGT
GAGAAGGGCGAACTGTTTAATGCAACCATCCAGAACAAAAATGGAAACTCCACAGTCTCTCTGAAAAAGGGCCTGGACGTGAAA
AAGTACGGGGGATACTTCAGCGCCAACACAAGTTACTTCTCACTGATCGAGTTTGAGGACAAGAAGGGGGATAGAGCAAGGCAC
ATCATTGGAGTGCCTATCTATATTGCAAACATGCTGGAGCATTCTCCAAGTGCCTTCCTGGAGTACTGCGAACAGAAGGGGTAT
CAGAATGTGCGGATTCTGGTCGAGAAAATCAAAAAGAACAGCCTGCTGATCATTAATGGATACCCTCTGCGCATTCGAGGCGAG
AACGAAGTGGATACTTCCTTTAAGAGGGCCATCCAGCTGAAGCTGGACCAGAAAAACTATGAGCTGGTCCGCAATATCGAGAAG
TTCCTGGAAAAATACGTGGAGAAAAAGGGAAACTATCCAATTGACGAGAATAGAGATCACATCACACATGAAAAGATGAACCAG
CTGTACGAGGTGCTGCTGTCCAAAATGAAAAAGTTCAACAAGAAGGGCATGGCCGACCCCTCTGATAGGATCGAAAAGAGTAAG
CCTAAATTCATCAAGCTGGAGGACCTGATCGATAAGATTAATGTGATCAACAAAATGCTGAACCTGCTGCGCTGTGACAATGAT
ACTAAGGCCGACCTGTCTCTGATTGAGCTGCCCAAAAACGCTGGGAGTTTCGTGGTCAAAAAGAATACCATCGGAAAGTCAAAA
ATCATCCTGGTGAATCAGAGCGTGACTGGACTGTACGAGAATAGACGGGAACTGTAAGAATTC

#6

ACCGGTGCCACCATGTACCCATACGATGTTCCAGATTACGCTTCGCCGAAGAAAAAGCGCAAGGTCGAAGCGTCCATGGGGAGG
AAACCTTACATTCTGTCTCTGGATATTGGAACTGGGTCCGTCGGCTACGCTTGCATGGATAAAGGATTCAACGTGCTGAAGTAC
CACGACAAAGATGCCCTGGGAGTGTATCTGTTCGACGGCGCTCTGACTGCACAGGAGCGGAGACAGTTTAGGACCTCCAGGCGC
CGAAAGAACCGGAGAATCAAACGCCTGGGCCTGCTGCAGGAACTGCTGGCACCCCTGGTGCAGAACCCTAATTTCTACCAGTTT
CAGCGGCAGTTCGCCTGGAAGAACGACAATATGGATTTTAAGAACAAGAGCCTGTCTGAGGTGCTGAGCTTCCTGGGATATGAA
TCCAAGAAATACCCTACCATCTACCACCTGCAGGAGGCTCTGCTGCTGAAAGACGAGAAGTTTGATCCAGAACTGATCTACATG
GCACTGTATCATCTGGTGAAATACAGAGGCCACTTTCTGTTCGATCATCTGAAGATCGAGAACCTGACTAACAATGACAATATG
CACGATTTCGTGGAGCTGATTGAAACCTATGAGAACCTGAACAATATCAAGCTGAATCTGGACTACGAGAAAACCAAAGTGATC
TATGAGATTCTGAAAGACAACGAAATGACTAAGAATGATAGAGCCAAAAGGGTCAAGAACATGGAGAAGAAACTGGAACAGTTC
TCTATCATGCTGCTGGGGCTGAAGTTCAATGAGGGAAAACTGTTTAACCACGCCGATAATGCTGAGGAACTGAAGGGGGCTAAC
CAGAGCCATACATTTGCAGACAACTACGAGGAAAATCTGACTCCCTTCCTGACCGTGGAACAGTCAGAGTTTATTGAAAGGGCC
AACAAAATCTATCTGAGCCTGACTCTGCAGGATATCCTGAAGGGCAAGAAATCAATGGCTATGAGCAAAGTGGCCGCTTACGAC
AAGTTCAGAAATGAGCTGAAACAGGTGAAGGACATTGTCTATAAGGCTGATTCTACCAGGACACAGTTCAAGAAAATCTTTGTG
AGCTCCAAGAAAAGTCTGAAGCAGTACGACGCAACTCCCAACGATCAGACCTTCTCTAGTCTGTGCCTGTTTGACCAGTACCTG
ATTCGCCCAAAGAAACAGTATAGCCTGCTGATCAAGGAGCTGAAGAAAATCATTCCCCAGGACTCCGAACTGTACTTTGAGGCA
GAAAATGATACCCTGCTGAAGGTGCTGAACACCACAGACAATGCTAGCATCCCTATGCAGATTAACCTGTACGAGGCAGAAACC
ATCCTGCGAAATCAGCAGAAATATCACGCCGAGATCACAGATGAGATGATTGAAAAGGTGCTGTCTCTGATCCAGTTCCGCATT
CCATACTATGTGGGGCCCCTGGTCAACGACCATACAGCCAGTAAGTTTGGATGGATGGAGCGCAAAAGTAACGAATCAATCAAG
CCTTGGAATTTCGACGAGGTGGTCGATCGAAGTAAATCAGCCACTCAGTTTATTAGGCGCATGACCAACAAGTGTTCCTACCTG
ATCAATGAGGATGTGCTGCCAAAAAACTCTCTGCTGTATCAGGAGATGGAAGTCCTGAACGAACTGAATGCCACACAGATCAGG
CTGCAGACTGACCCAAAAAACCGCAAGTACCGAATGATGCCCCAGATTAAGCTGTTCGCTGTGGAGCACATCTTTAAGAAATAT
AAAACCGTCAGCCATTCCAAGTTCCTGGAAATTATGCTGAACAGCAATCACAGGGAGAACTTTATGAATCATGGAGAAAAGCTG
AGTATCTTCGGCACACAGGACGATAAGAAATTTGCATCAAAGCTGTCAAGCTACCAGGACATGACTAAAATCTTCGGGGATATT
GAGGGAAAGCGCGCCCAGATTGAGGAAATCATTCAGTGGATCACCATTTTTGAGGACAAGAAAATCCTGGTGCAGAAGCTGAAA
GAGTGCTATCCTGAACTGACATCCAAGCAGATCAACCAGCTGAAGAAACTGAATTACTCTGGCTGGGGGAGGCTGAGTGAGAAG
CTGCTGACTCACGCCTATCAGGGCCATAGCATCATTGAACTGCTGCGCCACTCCGATGAGAATTTCATGGAAATTCTGACCAAC
GACGTGTACGGGTTCCAGAATTTTATCAAAGAGGAAAACCAGGTCCAGAGCAATAAGATCCAGCATCAGGATATTGCCAACCTG
ACTACCTCTCCCGCTCTGAAGAAAGGCATCTGGAGTACAATTAAGCTGGTGCGGGAGCTGACTTCCATTTTCGGGGAGCCTGAA
AAGATCATTATGGAGTTTGCTACCGAGGACCAGCAGAAAGGCAAGAAACAGAAATCAAGAAAGCAGCTGTGGGACGATAACATC

FIG. 9D

AAGAAAAATAAGCTGAAAAGCGTGGACGAGTACAAATATATCATTGATGTCGCCAATAAGCTGAACAATGAGCAGCTGCAGCAG
GAAAAACTGTGGCTGTACCTGAGCCAGAACGGCAAGTGTATGTATAGCGGGCAGTCCATCGACCTGGATGCCCTGCTGTCCCCC
AATGCTACCAAGCACTACGAGGTGGATCATATTTTCCCTCGGAGCTTCATCAAGGACGATAGCATTGACAACAAGGTGCTGGTC
ATCAAGAAAATGAATCAGACAAAGGGCGATCAGGTGCCCCTGCAGTTCATTCAGCAGCCTTACGAGAGAATCGCATATTGGAAG
AGCCTGAACAAAGCCGGGCTGATCTCTGATAGTAAACTGCACAAGCTGATGAAACCAGAGTTCACAGCTATGGACAAGGAAGGC
TTCATCCAGCGGCAGCTGGTGGAGACTAGACAGATCAGCGTGCATGTCCGGGATTTTCTGAAAGAGGAATACCCTAATACCAAA
GTGATCCCAATGAAGGCCAAAATGGTGAGCGAGTTCCGGAAGAAATTTGACATCCCAAAGATTAGACAGATGAACGACGCACAC
CATGCCATCGATGCTTACCTGAATGGCGTGGTCTATCACGGGGCACAGCTGGCCTACCCCAACGTGGACCTGTTTGATTTCAAT
TTTAAGTGGGAGAAAGTCCGAGAAAAGTGGAAAGCCCTGGGAGAGTTCAACACAAAGCAGAAATCTCGGGAACTGTTCTTTTTC
AAGAAACTGGAGAAGATGGAAGTGTCCCAGGGCGAGCGGCTGATCTCTAAGATCAAGCTGGACATGAACCACTTCAAGATCAAC
TACTCCAGAAAGCTGGCCAACATCCCTCAGCAGTTTTATAATCAGACCGCAGTGTCTCCAAAGACAGCCGAGCTGAAATACGAA
TCTAACAAGAGTAATGAGGTGGTCTATAAGGGACTGACACCATACCAGACTTATGTGGTCGCCATCAAGAGCGTGAACAAGAAA
GGCAAGGAGAAAATGGAATACCAGATGATCGACCACTACGTGTTCGATTTTTATAAATTCCAGAACGGCAATGAGAAGGAACTG
GCTCTGTACCTGGCACAGAGGGAGAACAAGGACGAAGTGCTGGATGCTCAGATTGTCTATAGTCTGAATAAGGGGGATCTGCTG
TACATCAACAATCATCCCTGCTATTTCGTGTCACGCAAAGAGGTCATCAACGCAAAGCAGTTTGAGCTGACCGTGGAACAGCAG
CTGTCTCTGTACAACGTGATGAACAACAAGGAGACAAATGTCGAAAAGCTGCTGATCGAGTATGACTTCATTGCCGAGAAAGTG
ATCAACGAATACCACCATTATCTGAATAGCAAGCTGAAAGAAAAGCGAGTCCGGACCTTTTTCTCAGAGAGCAACCAGACACAC
GAGGACTTCATCAAGGCCCTGGACGAGCTGTTTAAGGTGGTCACCGCATCCGCCACAAGGTCTGATAAAATCGGGAGTCGCAAG
AACAGCATGACTCATCGAGCCTTCCTGGGAAAAGGCAAGGACGTGAAGATTGCTTACACCTCCATCTCTGGACTGAAAACAACT
AAACCTAAGAGTCTGTTTAAGCTGGCCGAGTCAAGAAACGAACTGTAAGAATTC

#7

ACCGGTGCCACCATGTACCCATACGATGTTCCAGATTACGCTTCGCCGAAGAAAAAGCGCAAGGTCGAAGCGTCCATGACAAAA
ATCAAAGACGACTACATCGTGGGACTGGACATCGGCACAGACTCCTGCGGGTGGGTGGCTATGAACAGCAATAATGACATTCTG
AAACTGCAGGGCAAGACCGCAATCGGGTCACGCCTGTTCGAGGGAGGGAAGAGCGCAGCTGAACGGAGACTGTTTCGCACCACA
CACAGGCGCATCAAACGACGGAGATGGCGACTGAAGCTGCTGGAGGAGTTCTTCGACCCCTACATGGCAGAGGTGGATCCTTAT
TTCTTTGCCCGGCTGAAGGAATCTGGCCTGAGTCCACTGGACAAAAGAAAGACCGTGAGCTCCATTGTGTTCCCCACATCCGCC
GAGGATAAGAAGTTCTACGACGATTACCCTACAATCTACCATCTGAGGTATAAACTGATGACTGAGGACGAAAAGTTCGATCTG
CGCGAAGTGTACCTGGCTATCCACCATATCATTAAGTACCGAGGAAACTTCCTGTATAATACCAGTGTGAAAGACTTCAAGGCA
TCAAAGATCGATGTCAAATCTAGTATCGAGAAGCTGAACGAGCTGTATGAAAATCTGGGCCTGGACCTGAACGTGGAGTTCAAC
ATTAGCAATACTGCCGAGATCGAAAAGGTGCTGAAAGACAAGCAGATCTTCAAGCGGGATAAAGTCAAGAAAATTGCCGAGCTG
TTTGCTATCAAAACCGACAACAAGGAACAGAGCAAGAGAATCAAAGATATTTCCAAACAGGTGGCCAATGCTGTCCTGGGGTAC
AAGACCAGGTTCGACACAATCGCTCTGAAAGAGATTTCCAAGGACGAACTGTCTGATTGGAACTTCAAACTGTCAGACATCGAT
GCAGACAGCAAGTTTGAGGCCCTGATGGGAAACCTGGATGAGAATGAACAGGCCATCCTGCTGACTATTAAGGAGCTGTTTAAC
GAAGTGACCCTGAATGGAATTGTCGAGGACGGCAACACCCTGAGCGAATCCATGATCAACAAGTACAATGATCACCGGGACGAT
CTGAAGCTGCTGAAAGAAGTGATCGAAAATCATATTGACAGAAAGAAAGCCAAGGAGCTGGCACTGGCCTACGATCTGTATGTC
AACAATAGGCACGGACAGCTGCTGCAGGCTAAGAAAAAGCTGGGCAAAATCAAGCCCCGCTCTAAGGAGGACTTCTACAAAGTG
GTCAACAAGAATCTGGACGATTCACGGGCAAGCAAGGAGATCAAAAAGAAAATTGAACTGGACAGCTTTATGCCTAAGCAGAGA
ACCAACGCCAATGGCGTGATCCCATACCAGCTGCAGCAGCTGGAGCTGGATAAGATCATCGAAAACCAGTCTAAGTACTATCCA
TTCCTGAAGGAGATTAATCCCGTGTCAAGCCACCTGAAAGAGGCCCCCTATAAGCTGGACGAACTGATCCGATTTCGGGTGCCT
TACTATGTCGGCCCCCTGATTTCTCCTAACGAGAGTACCAAGGATATCCAGACAAAGAAAAACCAGAATTTCGCCTGGATGATT
CGCAAAGAGGAAGGGCGAATCACACCTTGGAACTTTGACCAGAAGGTGGATCGAATTGAGAGCGCCAATAAGTTCATCAAACGG
ATGACTACCAAGGACACTTACCTGTTTGGGGAGGATGTGCTGCCAGCTAACAGCCTGCTGTATCAGAAGTTCACCGTCCTGAAC
GAACTGAACAACATCCGGATTAATGGAAAAAGAATCTCCGTGGACCTGAAGCAGGAGATCTACGAAAACCTGTTTAAGAAACAC
ACAACTGTGACCGTCAAGAAACTGGAGAATTATCTGAAGGAAAACCATAATCTGGTGAAAGTCGAGATCAAGGGGCTGGCCGAT
GAAAAGAAATTCAACAGCGGACTGACCACATACAATAGATTCAAGAACCTGAACATCTTTGACAACCAGATTGACGATCTGAAG
TACAGGAACGATTTCGAGAAGATCATCGAATGGTCTACAATTTTTGAGGACAAGAGTATCTACAAAGAAAAGCTGAGGAGCATC
GATTGGCTGAACGAGAAGCAGATTAACGCTCTGTCTAATATCAGACTGCAGGGGTGGGGAAGGCTGAGTAAGAAACTGCTGGCA
CAGCTGCACGACCATAATGGCCAGACCATCATTGAGCAGCTGTGGGATTCCCAGAACAATTTCATGCAGATTGTGACACAGGCC
GACTTTAAAGATGCTATCGCAAAGGCCAACCAGAATCTGCTGGTGGCTACCTCAGTCGAGGACATTCTGAACAATGCATACACA
AGCCCCGCAAACAAGAAAGCCATCAGACAGGTCATCAAGGTGGTCGACGATATCGTGAAGGCAGCCTCCGGAAAGGTCCCAAAA
CAGATCGCCATTGAGTTCACTAGGGATGCTGACGAAAATCCCAAGAGAAGTCAGACCAGGGGCTCAAAGCTGCAGAAAGTGTAC
AAGGACCTGAGCACTGAGCTGGCCTCCAAGACCATTGCTGAGGAACTGAACGAAGCAATCAAAGACAAGAAACTGGTGCAGGAT
AAGTACTATCTGTACTTTATGCAGCTGGGGCGGGACGCCTATACAGGAGAGCCTATCAATATCGATGAAATCCAGAAGTACGAT
ATCGACCACATTCTGCCACAGTCTTTCATCAAGGACGATGCCCTGGACAACAGGGTGCTGGTGAGCCGGGCTGTGAACAATGGC
AAATCTGATAATGTGCCTGTCAAGCTGTTTGGCAACGAGATGGCTGCAAATCTGGGGATGACTATCAGGAAAATGTGGGAGGAA
TGGAAGAACATCGGCCTGATTAGCAAAACAAAGTACAACAATCTGCTGACTGATCCCGACCACATTAACAAGTATAAGAGTGCC
GGGTTCATCAGGCGCCAGCTGGTGGAGACATCACAGATCATCAAGCTGGTGAGCACTATCCTGCAGAGTCGCTACCCTAACACT
GAAATCATTACCGTGAAGGCTAAGTACAATCATTATCTGCGGGAGAAATTTGACCTGTATAAGAGCAGAGAAGTCAACGACTAC
CACCATGCTATTGATGCATATCTGTCCGCCATCTGCGGAAATCTGCTGTACCAGAACTATCCAAATCTGCGGCCCTTCTTTGTG
TACGGCCAGTATAAGAAATTCTCCTCTGATCCTGACAAAGAGAAGGCCATTTTTAACAAAACCCGCAAGTTCTCCTTTATCTCT
CAGCTGCTGAAAAACAAGAGTGAGAACAGCAAGGAAATCGCTAAGAAACTGAAACGGGCATACCAGTTCAAGTATATGCTGGTG
TCTCGAGAGACTGAAACCCGGGACCAGGAGATGTTCAAAATGACCGTGTACCCCCGGTTCAGCCACGATACAGTCAAGGCTCCT

FIG. 9E

AGGAACCTGATTCCAAAGAAAATGGGCATGTCCCCTGACATCTACGGAGGCTATACAAACAATTCTGACGCATACATGGTCATC
GTCCGCATTGATAAGAAAAAGGGAACTGAGTATAAGATCCTGGGCATTCCAACCCGGGAACTGGTGAATCTGAAAAAGGCCGAG
AAGGAGGACCATTACAAAAGCTATCTGAAGGAGATCCTGACACCAAGGATTCTGTACAACAAAAATGGGAAGCGCGATAAAAAG
ATCACTTCCTTCGAAATTGTGAAATCTAAGATCCCCTATAAGCAGGTCATCCAGGATGGGGACAAAAAGTTTATGCTGGGAAGT
TCAACATACGTGTATAACGCAAAGCAGCTGACACTGAGCACTGAGTCCATGAAAGCCATCACTAACAATTTCGATAAGGACAGC
GATGAGAACGACGCTCTGATTAAGGCATACGATGAAATCCTGGACAAAGTGGATAAGTATCTGCCACTGTTCGACATCAACAAG
TTCCGGGAGAAGCTGCACAGTGGGCGAGAAAAGTTCATCAAGCTGAGCCTGGAGGACAAAAAGGATACCATCCTGAAAGTGCTG
GAAGGACTGCATGATAACGCTGTCATGACAAAGATCCCTACTATTGGCCTGTCCACACCACTGGGGTTCATGCAGTTTCCCAAC
GGCGTGATTCTGAGCGAGAATGCCAAACTGATCTACCAGTCCCCCACCGGGCTGTTCAAAAAGTCAGTGAAGATCAGCGACCTG
TAAGAATTC

#8
ACCGGTGCCACCATGTACCCATACGATGTTCCAGATTACGCTTCGCCGAAGAAAAAGCGCAAGGTCGAAGCGTCCATGGGCTAC
ACTGTGGGACTGGATATTGGGGTGGCTTCCGTCGGGGTGGCTGTGCTGGATGAGAATGACAACATCGTGGAGGCTGTGTCAAAC
ATCTTTGATGAAGCCGACACAAGCAACAATAAGGTGCGGAGAACTCTGAGGGAGGGCAGGCGCACAAAGCGGCGGCAGAAAACC
CGCATTGAGGACTTCAAGCAGCTGTGGGAGACTTCAGGCTACATCATTCCTCACAAGCTGCATCTGAATATCATTGAGCTGCGC
AACAAAGGGCTGACCGAACTGCTGAGCCTGGATGAGCTGTATTGCGTGCTGCTGTCCATGCTGAAGCACCGGGGGATCTCCTAC
CTGGAGGACGCCGACGATGGCGAGAAGGGGAATGCCTATAAGAAAGGACTGGCTTTTAACGAAAAACAGCTGAAGGAGAAAATG
CCATGTGAGATCCAGCTGGAACGCATGAAGAAATACGGGAAGTACCATGGAGAGTTCATCATCGAAATTAATGATGAGAAGGAA
TACCAGAGCAACGTGTTCACCACAAAGGCTTATAAGAAGGAGCTGGAAAAGATCTTCGAGACACAGCGGTGCAACGGCAACAAG
ATCAACACAAAGTTCATTAAGAAATACATGGAGATCTACGAACGAAAGCGGGAATACTATATCGGACCAGGCAATGAGAAAAGC
AGAACAGACTACGGCATCTATACTACCAGGACTGATGAGGAAGGGAATTTCATCGACGAGAAGAACATTTTTGGCAAACTGATC
GGGAAGTGTAGTGTGTACCCCGAGGAATATAGAGCAAGCTCCGCCTCATACACCGCCCAGGAGTTCAATCTGCTGAACGATCTG
AACAATCTGAAAATCAACAATGAGAAGCTGACAGAATTTCAGAAGAAAGAGATTGTCGAAATCATTAAGGACGCTTCTAGTGTG
AACATGAGGAAAATCATTAAGAAAGTCATCGATGAGGACATTGAACAGTACAGCGGAGCACGAATCGATAAGAAAGGCAAGGAA
ATCTACCACACCTTCGAGATCTATCGGAAGCTGAAGAAAGAGCTGAAAACAATCAATGTGGATATCGACTCTTTTACTAGAGAG
GAACTGGATAAGACCATGGACATCCTGACCCTGAACACAGAGAGGGAAAGTATTGTGAAGGCCTTCGACGAACAGAAATTTGTC
TACGAGGAAAATCTGATCAAGAAACTGATTGAGTTTCGGAAGAACAATCAGAGACTGTTCAGCGGCTGGCATAGTTTTTCATAC
AAGGCTATGCTGCAGCTGATCCCAGTGATGTACAAGGAGCCCAAAGAACAGATGCAGCTGCTGACCGAAATGAACGTGTTCAAA
AGTAAGAAAGAGAAGTACGTCAACTACAAGTACATCCCAGAGAACGAAGTGGTCAAGGAGATCTATAACCCCGTGGTCGTGAAG
AGCATTAGAACAACTGTGAAAATTCTGAATGCACTGATCAAGAAATACGGGTATCCTGAATCCGTCGTGATCGAGATGCCAAGG
GATAAGAACTCTGACGATGAGAAGGAAAAGATCGACATGAACCAGAAGAAAAACCAGGAGGAATACGAGAAAATCCTGAACAAG
ATCTACGATGAGAAGGGAATCGAAATTACCAACAAGGACTACAAGAAACAGAAGAAACTGGTGCTGAAGCTGAAACTGTGGAAC
GAGCAGGAAGGACTGTGCCTGTATTCCGGCAAGAAAATCGCTATTGAGGATCTGCTGAATCACCCCGAGTTCTTTGAAATTGAC
CATATCATTCCTAAGAGCATCTCCCTGGACGATTCTCGCAGTAACAAGGTCCTGGTGTACAAAACAGAAAATTCTATCAAGGAG
AACGATACCCCCTACCACTATCTGACACGGATTAACGGAAAGTGGGGCTTTGACGAATATAAAGCTAATGTGCTGGAGCTGAGA
AGGCGCGGCAAGATCGACGATAAGAAAGTGAACAATCTGCTGTGCATGGAGGATATCACTAAGATTGACGTCGTGAAAGGGTTC
ATTAACCGCAATCTGAACGACACCAGATACGCATCCAGGGTGGTGCTGAACGAAATGCAGTCCTTCTTTGAGTCTCGAAAGTAC
TGTAATACTAAGGTCAAAGTGATCCGAGGCTCTCTGACCTATCAGATGCGGCAGGATCTGCACCTGAAGAAAAACAGAGAGGAA
TCATACAGCCACCATGCTGTGGACGCAATGCTGATCGCATTCTCCCAGAAGGGGTACGAGGCCTATAGGAAGATCCAGAAAGAT
TGCTACGACTTTGAGACAGGCGAAATTCTGGACAAGGAAAAATGGAATAAGTACATTGACGATGACGAGTTTGATGACATCCTG
TATAAAGAGAGGATGAACGAAATCCGCAAGAAAATCATTGAGGCCGAGGAAAAGGTGAAGTACAACTACAAGATCGATAAGAAG
TGCAATCGCGGGCTGTGTAACCAGACTATCTACGGGACCCGAGAAAAGGACGGAAAAATCCACAAGATTTCAAGCTACAACATC
TATGATGACAAGGAGTGTAATTCCCTGAAGAAAATGATTAACAGTGGGAAAGGATCAGATCTGCTGATGTACAACAATGATCCT
AAGACATATCGCGACATGCTGAAAATCCTGGAAACTTACTCCTCTGAGAAGAATCCATTCGTGGCATATAACAAAGAGACAGGA
GACTACTTTCGGAAATATTCTAAGAATCACAACGGACCCAAGGTCGAGAAGGTGAAATACTATAGCGGCCAGATCAACTCCTGC
ATCGATATTTCTCACAAGTACGGCCATGCCAAAAATAGTAAGAAAGTCGTGCTGGTGTCACTGAACCCTTATAGAACCGACGTC
TACTATGATAATGACACAGGCAAGTACTATCTGGTCGGGGTGAAGTACAATCATATCAAATGTGTCGGAAACAAGTACGTGATT
GATAGCGAGACATATAACGAACTGCTGAGGAAGGAGGGCGTGCTGAACAGCGATGAGAACCTGGAGGACCTGAACAGCAAAAAC
ATCACTTACAAGTTCAGTCTGTACAAGAACGACATCATCCAGTACGAGAAGGGCGGGGAATACTATACAGAGCGCTTTCTGAGC
CGAATCAAAGAACAGAAGAACCTGATTGAGACTAAACCCATCAATAAGCCTAACTTCCAGCGGAAGAATAAGAAAGGCGAGTGG
GAAAATACCAGAAACCAGATCGCCCTGGCTAAGACTAAATACGTGGGGAAGCTGGTCACCGATGTGCTGGGAAACTGTTACATC
GTGAACATGGAGAAGTTCTCCCTGGTCGTGGACAAATAAGAATTC

#9
ACCGGTGCCACCATGTACCCATACGATGTTCCAGATTACGCTTCGCCGAAGAAAAAGCGCAAGGTCGAAGCGTCCATGACTAAC
GGCAAGATTCTGGGGCTGGACATTGGCATCGCAAGCGTGGGGGTGGGGATTATTGAGGCAAAAACTGGAAAGGTGGTGCATGCC
AATTCCCGGCTGTTCTCTGCCGCTAACGCTGAGAACAATGCAGAACGGAGAGGGTTTAGGGGATCTAGGCGCCTGAATCGACGG
AAGAAACACCGCGTGAAGCGAGTCCGGGATCTGTTCGAGAAATACGGAATCGTCACCGACTTTCGCAACCTGAATCTGAACCCT
TATGAGCTGCGAGTGAAGGGCCTGACCGAACAGCTGAAAAACGAGGAACTGTTCGCAGCCCTGAGAACAATCTCTAAGAGAAGG
GGGATTAGTTACCTGGACGATGCCGAGGACGATAGTACCGGATCAACAGACTATGCTAAGAGCATCGATGAGAATCGCCGACTG
CTGAAAAACAAGACACCAGGCCAGATTCAGCTGGAGAGGCTGGAAAAGTACGGCCAGCTGCGCGGGAATTTCACCGTCTATGAC
GAGAACGGGGAAGCCCATCGCCTGATCAATGTGTTTAGTACATCAGATTACGAGAAAGAAGCACGGAAGATCCTGGAGACACAG

FIG. 9F

GCCGACTACAACAAGAAAATCACAGCTGAGTTCATTGACGATTATGTGGAAATCCTGACCCAGAAACGAAAGTACTATCACGGC
CCCGGGAACGAAAAGAGCCGGACTGACTACGGACGGTTCCGGACCGATGGGACCACACTGGAGAATATTTTCGGAATCCTGATT
GGCAAGTGCAACTTTTACCCTGATGAATATCGAGCAAGCAAGGCCAGCTACACCGCACAGGAGTATAATTTCCTGAACGACCTG
AACAATCTGAAGGTGAGCACCGAAACAGGGAAGCTGTCAACAGAGCAGAAAGAAAGCCTGGTGGAGTTTGCCAAGAATACTGCT
ACCCTGGGACCCGCTAAACTGCTGAAGGAGATCGCAAAAATTCTGGACTGTAAGGTGGATGAGATCAAAGGATACAGAGAGGAC
GATAAAGGCAAGCCAGATCTGCATACCTTCGAGCCCTATAGGAAACTGAAGTTTAATCTGGAAAGCATCAACATTGACGATCTG
TCCCGCGAAGTGATCGACAAGCTGGCTGATATTCTGACTCTGAACACCGAGAGAGAAGGAATCGAGGACGCAATTAAGAGGAAT
CTGCCAAACCAGTTCACAGAGGAACAGATCAGCGAGATCATCAAGGTGCGGAAGAGCCAGTCCACTGCTTTCAATAAGGGCTGG
CACTCTTTTAGTGCAAAACTGATGAACGAGCTGATCCCCGAACTGTACGCCACCTCCGACGAGCAGATGACAATTCTGACTCGG
CTGGAAAAAATTCAAGGTCAATAAGAAAAGCTCCAAAAACACAAAGACTATCGACGAGAAGGAAGTCACTGATGAGATCTACAAT
CCTGTGGTCGCCAAGAGCGTGAGACAGACCATCAAAATCATTAACGCTGCAGTCAAGAAATATGGCGACTTCGATAAGATCGTG
ATTGAAATGCCACGGGATAAAAATGCTGACGATGAGAAGAAGTTCATCGACAAGAGAAATAAGGAGAACAAGAAGGAAAAGGAC
GATGCCCTGAAAAGGGCCGCTTACCTGTATAATTCTAGTGACAAGCTGCCCGATGAGGTGTTCCACGGCAACAAGCAGCTGGAA
ACCAAAATCCGACTGTGGTATCAGCAGGGGGAGCGGTGCCTGTATAGTGGAAAGCCCATCTCAATTCAGGAGCTGGTGCATAAC
TCTAACAATTTCGAAATCGATCACATTCTGCCTCTGTCACTGAGCTTTGACGATAGTCTGGCCAATAAGGTGCTGGTCTACGCT
TGGACAAACCAGGAGAAAGGCCAGAAAACCCCTTATCAGGTCATCGACTCCATGGATGCAGCCTGGTCTTTCAGGGAGATGAAG
GACTACGTGCTGAAACAGAAGGGACTGGGCAAGAAAAAGCGCGACTATCTGCTGACTACCGAGAACATCGATAAGATTGAAGTG
AAGAAGAAGTTCATCGAGAGGAATCTGGTGGATACTCGCTACGCATCTCGAGTGGTCCTGAACTCTCTGCAGAGTGCCCTGAGA
GAGCTGGGGAAAGACACTAAGGTGTCTGTGGTCAGGGGACAGTTCACCAGTCAGCTGCGGAGAAAATGGAAGATCGATAAGAGC
CGCGAGACATACCACCATCACGCAGTGGACGCCCTGATCATTGCTGCATCAAGCCAGCTGAAACTGTGGGAGAAGCAGGACAAT
CCCATGTTTGTGGATTATGGCAAGAACCAGGTGGTCGACAAACAGACTGGGGAGATCCTGTCCGTGTCTGACGATGAGTACAAG
GAACTGGTGTTCCAGCCCCCTTATCAGGGCTTTGTGAATACCATCTCCTCTAAAGGGTTCGAGGACGAAATTCTGTTTAGCTAC
CAGGTGGATTCCAAATATAACCGGAAGGTCAGTGACGCAACCATCTACTCAACAAGAAAAGCCAAGATTGGCAAGGATAAGAAA
GAGGAAACCTACGTGCTGGGAAAAATCAAGGACATCTACTCCCAGAATGGCTTCGATACCTTCATCAAGAAGTACAACAAAGAT
AAGACTCAGTTCCTGATGTATCAGAAGGACTCTCTGACATGGGAGAACGTGATCGAAGTCATTCTGAGGGACTACCCAACAACT
AAGAAAAGCGAGGACGGCAAAAATGATGTGAAGTGCAACCCCTTTGAGGAATACAGGCGCGAGAATGGGCTGATCTGTAAGTAT
TCCAAGAAAGGGAAAGGAACTCCCATCAAGAGCCTGAAGTACTATGACAAGAAACTGGGGAACTGCATCGATATTACCCCAGAG
GAATCACGCAATAAGGTCATCCTGCAGAGCATTAACCCTTGGCGAGCCGACGTGTACTTCAATCCAGAGACACTGAAGTACGAA
CTGATGGGCCTGAAATATTCAGATCTGAGCTTTGAAAAGGGCACTGGGAACTACCATATCAGCCAGGAGAAATATGACGCTATC
AAAGAGAAGGAAGGAATTGGCAAGAAATCCGAGTTCAAGTTTACACTGTACCGCAACGACCTGATCCTGATCAAGGATATCGCC
AGTGGCGAGCAGGAAATCTACAGATTCCTGTCAAGAACTATGCCCAATGTGAACCACTACGTCGAGCTGAAGCCTTACGACAAG
GAAAAGTTCGATAACGTGCAGGAGCTGGTCGAAGCACTGGGAGAGGCAGATAAAGTGGGACGATGTATCAAAGGACTGAATAAG
CCAAACATCAGCATCTACAAGGTGAGAACCGACGTCCTGGGAAACAAATATTTCGTGAAGAAAAAGGGCGACAAACCCAAGCTG
GATTTTAAGAACAACAAGAAGTAAGAATTC

#10
ACCGGTGCCACCATGTACCCATACGATGTTCCAGATTACGCTTCGCCGAAGAAAAAGCGCAAGGTCGAAGCGTCCATGGCCGAC
CGAATCTCTCTGGGGCTGGACATTGGGGTGGCAAGCGTGGGGTTCTCAGTGCTGGACATTGATAAGGGAAAAGTCATTGAGCTG
GGCGCCAGGCTGTTCTCTGCTACTGTGGCCGCTGGCAACCAGGATCGAAGAGACATGCGAGGAGCCAGGCGCCTGCTGAACCGG
AACAAGCAGCGACGGCAGGATACCGGAAAGCTGTTCAAGAAATTTGGCCTGATCGACGATTTTGATAAGGGCAGCTTCTACGAC
AACTTTAATCAGAACCTGAATCCTTATGAGCTGAGAGTGAAAGGCCTGACAGAACAGCTGACTAAGGAGGAACTGGCCGAGTCT
CTGTACCAGATCGTGAAACATAGGGGGATTAGTTATGCACTGAAGGACGCCGATGTGGACGAAGGCGGGACAGACTACTCAGTC
AGCCTGAAAATCAACAGCCAGGAGCTGGCAGAAAAGACTCCAGCCCAGATTCAGCTGCAGAGACTGAATGATTATGGAAAGGTG
AGGGGCCAGGTGGTCATCGGCGACGATCCAGACAACCAGAAGGTGCTGCTGAATGTGTTCCCCACATCAGCTTACGAGAAAGAA
GCAAAGCAGATCATTGCCACTCAGCAGCAGTTCTATCCTGAGAGCCTGACCGACAAGTTCACCGAGGAATACTGCCAGATCCTG
ACTCGCAAGCGAGATTATTTTGTGGGGCCAGGAAACGAGAAAAGCCGGACCGACTACGGGATCTACAAGACTGATGGAAGAACC
CTGGACAATCTGTTCGAGGAACTGATCGGCCACGATAAGATCTACCCCGAGGAACTGCGGGCATCTGCAGCCAGTTATACCGCC
CAGCTGTTTAACGTGCTGAATGACCTGAACAATCTGAGAATCCTGAACTACGAGGATGGGAAACTGACAAAGGAGGACAAGGAA
AAGATCATCGCTGAAATTAAGAACAACACCACAACTATCAACATGCTGAATGTGATTAAGAAAGTCGCCGGGTGTTCCAAGGAC
GATATCAAAGGATTCCGAGTGAATGAGAAGGATAAACCCGAAATCAGCTCCATGCCTGTGTACCGCAAAATTCATAAGGACCTG
CTGAAGGCCGGCGTGGATATCTCAGACTGGCCCGTCGAGTTCATCGACGAACTGAGCTTTATTCTGACACTGAACACTGAGAAT
GGGGAAATTCGCAAACAGCTGAACAATCGACTGGCCCCTAAGTTCGATTTTCTGAACGCTGACCTGATCCAGCTGATCATTGAT
AATAAGGACTCCTTTGAGATTAAGACTAACAACAAGTGGCACAGATTCAGCGTGAAAACCATGAACAAACTGATCCCAGAGATG
ATGGAAAGACCCGTGGAGCAGATGACCCTGCTGAATGAAATGGGACTGGTCAAGAAAGATAAGAAACGCTTTGAGAACAATAAG
TACCTGCCTTACAAGGAAATCGCAAAGGACATTTTCAACCCAGTGGCCTCCAAATCTGTCCGCGAGGCCCTGAAGATCGTGAAT
GCTGTCCTGAAGAAATACGGCCACATTGATTATCTGGTGGTCGAAATGCCTCGGGATAAAAACCTGAAGGAGGAACAGGACAAT
ATCAAGGAGTTCCAGAACAAAAATAAGAAAGCTAAGGACGCTGCATTCGAAGCATTTGTGAAATCAGTCGGGAGCGAGCAGAGA
GTGAAGGAAGCCCTGTCTAAAAACCGGAAGCTGCAGATGAAGATGAGACTGTGGTATCAGCAGCAGGAGATCGATCCATATAAT
GGAAAGACAATCGATGCCACTGACCTGATTAACAATCCTGATAAGTTCGAGATTGACCATATCATTCCACAGAGTATCTCATTT
TACGACAGTATTAACAATAAGACCCTGTGCTTCGCCTCAATGAACCAGGTGAAAGGACAGAAAACCCCCTACGAGTTTATGCTG
GAAGGCCACGGGCAGTCCTATGACAAGTTCAAAGCTACAGTGATGGCAAACAAGAATTTTGGCAAGGCTAAAAGGGCAAACTAC
CTGTTCGAGGAAAATGTGAGCGATATCGAGACTCGGAAGAGATTCCTGTCCCGCAACCTGGTGGACACCCGATATTCTAGTCGG
GTGGTGCTGAACAGCCTGCAGGATTTCTTTCGGGAGAAATCTGCCGACACCAAGGTGACAGTCATTCGCGGCAAGTTTACCTCC

FIG. 9G

AACATGCGAAAACATTGGCACATCGATAAGACTAGGGAGACATTCCACCATCACGCCATTGACGCTTCTATCATTGCCGCTACA
CCATTTCTGCGCATGTGGAAGAAAGGAGGCACTATCTTCCCCGTGAAGGTCGGAGAAGAAAGTATCGATATTGAGACAGGCGAA
ATTCTGGACGATAAGAATTTTGACAAAGCAATGTACGAGGAACCCTATAGTGGCTTCGTGTCAGAGATCATGAACGCCGACGAT
CGGATCAAGTTCAGCCACCAGGTGGATAAGAAAATGAATAGGAAGGTGAGCGACGCCACCATCTACAGTACTCGCACCGGGAAA
CTGGCTAAGGATAAGAAAGACGCTGAGTACATCGTGGCAAAGGTCAAAGATATCTACAGCGTGGACGGATTCAAGAAGTTCAAG
AAAGTCTACGATAAGGACAAAACCAAGTTTCTGCTGTACAAATATGATCCTAGGACATTCTCAAAGCTGGAGCGCATCATTAGC
GATTGCCCAGACAAAGTGGAAAAGGTCCAGACAAACGGCAAAGTGAAGGCTGTCGATATCAGTCCATTCGAGATGTACAGAAGG
GACCATGGGATGATCAAGAAATACTCAAAGAAAGGAAACGGCCCCGCCATCAAGCAGCTGAAGTACCTGGATAAGAAACTGGGC
AGCCACATCGACATTACCCCCGCAAACGCCAATGGAAAACACGTGATCCTGCAGAGTCTGAAGCCTTGGAGAACCGACGTCTAT
CTGAACCACGAGACAGGCGAGTACGAAATCATGGGGATTAAGTATAGCGATCTGAAGTTCAACAAGAATGAGGGGTACGGAATC
AAGAAAGACAAGTATCTGGAAATTAAGAAAGTGGAGGAAGTCTCCGAGAAGTCTGAGTTCATGTTTAGCCTGTACAGGAAGGAT
CGCGTGAAAGTCCAGGACATGAAAACCGGCGAGTCCGTGGAACTGCTGTTCTGGAGCAGGAACTTTTCCAATAAGAAATACGCT
GAGCTGAAGCCCATCTCCCAGGCAGAAAACGACAAGAAACTGCCTGTGTATGGCAAAGGGAGACTGATCAAGAGGCTGATTCCC
AAAAACTGTAAGATCTGGAAAGTGAATACCACAATTCTGGGCGATCCCTACTATCTGGAGAAAGAAAGCGACTCCCCTAAGGAT
ATCCTGGACTAAGAATTC

#12
ACCGGTGCCACCATGTACCCATACGATGTTCCAGATTACGCTTCGCCGAAGAAAAAGCGCAAGGTCGAAGCGTCCATGAAGAAA
ACACTGGGACTGGACCTGGGGACTAACAGCATTGGGTGGGCCGTCATCAACTCAAACATCGACTCAGAAGGAAAAGAAAAGCTG
GTGGGGATCAGCTCCTGCGGAAGCCGGATCATTCCTATGGACGCTACCACACTGGGAGATTTCGGAAAGGGCAACACTAAAAGT
CCAGTGGCAGAGCGAACCCGACTGCGGGGCATTCGGAGACTGCTGGAAAGGTCACTGCTGAGGCGCGAGCGACTGCACCGAGTG
CTGTCAGTCATGGGGTTCCTGCCAGAGCATTACGCTAGCCAGCTGGACCGCTATGGAAAGTTTCTGCCAGAAACCGAGCCCAAG
CTGGCATGGTACAAAGACGATAGCGGCAGGTATCAGTTCCTGTTTCAGAAGTCCTTCCACGAGATGCTGGAGGACTTTCGACAG
CATCAGCCAGAACTGGTGGCAGGAGAGAAGAAAATCCCTTACGATTGGACAATCTACTATCTGCGGAAGAAAGCACTGTCTCAG
GAGATCACTAAGGAGGAACTGGCCTGGATTCTGCTGAATTTCAACCAGAAACGCGGCTACTATCAGCTGCGAGGGGAGGAAGAG
CAGGAAGAGAACAATAAGAGCGTGGAGTATCACGCCCTGAAAGTGGTGAGCGTCGAGGACTCTGGAGAAAGAAAGGGCAAAGAT
ATCTGGTACAATGTGACTCTGGAGAACGGATGGGTCTATCGACGGGCTAGCAACATTCCCCTGGACTGGACCGGCAAGGTGAAA
GAGTTCGTGGTCACTACCGAGCTGGACGATGCCGGGAACCCAAAGAAAGATAAGGAAGGAAATGTGAAAAGATCCTTTAGGGCA
CCAAAGGAGGACGATTGGGGGCTGCTGAAAACTAGGACCCAGGCTCAGATCGACGAATCCGGCAAGACCGTGGGAACTTACATC
TACGAGTCTCTGCTGTGTATGCCCAACCAGAAGATCCGGGGAAAACTGGTGAGGACCATTGAACGCAAGTACTATAAAGACGAG
CTGAGACAGATCCTGGTGAAGCAGAGCGAGTTCCACGCCGCTCTGCAGGATCATAATCTGCTGCTGTCCTGTATCGAAGAGCTG
TACCCTAACAATGAGGCCCACAGAAGGCTGCTGAGCGCCAGCAGCTTCATCTACTTCCTGATCGAGGACATTCTGTTTTATCAG
CGCCCACTGAAGTCCCAGAAAGGGCTGATCGATAACTGCCCCTACGAGTCTCACATCTACAAGGATAAGAAAGATGGAAGTCTG
CACCATGTGCCTCTGAAGTGTGTCAGCAAATCCCATCCACTGTTCCAGGAATTTCGCCTGTGGCAGTTCCTGTCTAACCTGCGA
ATCTACCAGAGAGAGAGGATGATGGACGGCAGTCTGAAACTGGACGTGGATGTCACCCGGGAGTTCCTGCCCTCAGAAGAGGAC
TACGTGAAGCTGTTTGATTGGCTGAATGAGAGAAAGGAAATCTCTCAGAAATTCCTGCTGGCTTATAAACCTTTTGGGCTGAAG
AAAAACGAACAGGCAAATTACAGATGGAACTATGTGGAGGACAAGAGCTACCCCTGCAACGAGACACGGGCAGAAATCAAGAGC
AGACTGTCCAAAGCCGGAGTGCCTGAAGAGTTTCTGACTGAAGAGAAGGAAGAGGCCCTGTGGCACATCCTGTATTCTATTAGT
GATAAGAAAGAGCTGACTAAGGCTCTGGGCACCTTCGCAGCCAAAAACTGTCTGAATGAGTCTTTCGTGGAAGTCTTTGCCAAG
ATCCCCCCTTTTGAGTCAAACTACGCTGCATATAGCCTGAAGGCTATTAGGAAACTGCTGGCACTGATGCGCATGGGGAAGTAC
TGGAATGAACAGGCCATCGACAGGCAGACTCGCGATCGAATCGAGAAAATTCTGACCGGAGAGTATGACGAAACAATCCGGAGC
AGAGTGAGGGAGAAGGCAATGCTGCTGACCGATATTAGCAGCTTCCGGGGCCTGCCTCTGTGGCTGGCCTGTTACATCGTGTAT
GACCGCCACTCAGAGAGCAAGGAACTGGTCAAATGGGAGACACCAGCCGACATCGATCATTTCCTGTCCAAGTTTAAACAGAAC
AGCCTGCGGAACCCCATCGTGGAACAGGTCATTACAGAGTCCCTGCGCACTGTGCGAGACATTTGGAAGCAGGAGGGAAAAATC
GATGAGATTCACGTGGAACTGGGCCGGGAGATGAAGAACCCTGCAAAAGAGCGCGCCCGAATTACAGCTCAGGTGCAGGAAAAT
GAGAACACTAATCTGAGAATCAAGGCTCTGCTGGCAGAGTTCATGAACCCCGAATTTGAGATTGAAAATGTGCATCCATACTCA
CCCGGCCAGCAGGAAATCCTGCGGATCTACGAGGACGGCGTGCTGAGCGGGATCGCTGAGAAGGATCTGCCTGACGATATCACA
GCAATTCTGAAGAAATTCCGAGAAAACGACGTGAAGAAACGGCCAACAACTAGCGAAGTCCTGCGGTACAAACTGTGGCTGGAG
CAGCGGTACAGATCCCCATATACCGGAAGAGTGATCCCCCTGGGCAAGCTGTTCACACCTGCTTACGAGATCGAACACGTGATT
CCCCAGAGCCGGTATTTTGACGATTCCATCTCTAACAAAGTGATCTGCGAAAGTGCCGTCAATAAGCTGAAAGATAACTGTCTG
GGCTATGAGTTCATCAAGAAACATTCCGGGGAGATGGTGGAACTGGGGAATGGAGAGACAGTGCCCGTGTTCAGCGTGGAAGAG
TACGAACGGTTCGTCAAGGAGTCTTACTTCGGCAACAGTAAGAAAATGAAGAAACTGCTGCTGGAGGACATCCCAGATAGCTTC
ATTGAGAGACAGCTGAATGACAGTCGATACATCTCACGGGTGGTCACATCTCTGCTGAGTAACCTGGTGTGCGAAGAGGGAGAG
CAGGATGGCCTGTCCAAGAATGTGATCGTCTGTACCGGCGGGATTACAGACAGGCTGAAGAAAGATTGGGGAGTGCAGGAAGTC
TGGAACCGCATCATTCTGCCTCGGTTCCTGAGACTGAATGAGATCACCGGACGGACAGACTTTACAAGTACTTCAGTGAACGGC
CACCTGCTGCCTGCCCTGCCACTGTACCTGCAGAAGGGCTTTAATAAGAAAAGAATTGACCATAGGCACCATGCCATGGATGCT
ATCGTGATTGCCTGCGCTAACCGGAATATCGTCAACTACCTGAACAATTCCTCTGCTAGAAAGAACAGCGAAATTAGCCGATAT
GACCTGCAGCGGCTGCTGTGTGAGAAGGTGAAAACCGATGCCAACGGCAATTACAAGTGGATCCTGAGGAAACCATGGGAGACA
TTCACCCAGGATGTGTATGCCGCTCTGACAAACATCGTGGTCAGCTTTAAGCAGAATCTGCGCGTGATTAATCGAACCACAAAC
TACTATCAGCACTACAACGAGGCAGGGGAAAAGCGCATGATCCCTCAGACCAAAGGCGACAGATGGGCCATTAGAAAGCCAATG
CATAAAGATACTGTGTATGGCGAAGTCAATCTGAGAAAGGAGAAAACCCTGCCACTGAGGGACGTGGTCAAGAACCCCAGTATC
GTGGTCGATAAATCACTGAAGAACAAGCTGTACGAGCTGCTGAAGAGCCAGTATGACCTGAAGGCAATCGCCAAATACTTCGAG
ACACACCAGGACGTGTGGGCAGATGTCAACCTGAAGAAAATTAAGGTGTACTACTTCACTAAGGAGACAAACGAAAGATTCTTT

FIG. 9H

GCCACTAGGAAGAGCCTGGACCCATCCTTTGATCAGAAGAAAATCGAAGAGGAAGTGACTGATACCGGCGTCCAGAAGATTCTG
CTGCACCATCTGCAGCAGAACAATAACGACCCTGATATGGCCTTTTCCCCAGACGGCATCGATAGGATGAACCAGAATATGACC
ATTCTGAATGACGGGAAGTGGCACCAGCCCATCTACAAAGTGCGCACATATGAAAAGGCAGATAAATTCGCCGTCGGCGAGTCT
GGGAACAAGGCCAAGAAATTTGTGGAAGCAGCCAAAGGCACCAATCTGTTCTTTGCCGTGTACGAGAGTGTCCAGGAGGACGAA
GCTATCGGGAAGCAGGTCTGCAAACGGACATTCGCCACTATCCCCCTGAACGAAGTGATCAAGAGAAAGAAACAGGGCCTGCCC
GCTGCACCTGAGGACCTGAACGGGAATCTGCCCAAGTTTGTGCTGAGCCCTAACGATCTGGTCTACCTGCCCACCGAGGAAGAG
AGGAATAGTTCACGCATCATTCAGCCTCTGGACAGGGAGCGCATCTATAAGATGGTGAGCTCCTCTGGGAGTCAGTGCTTCTTT
ATCAAAGTGTTCGTCGCCAATTCAATTTGGGATAAGAACGAATACAGCAGCCTGAACAAGATGGAGAGGGCTATTACAAACGAA
ATGATCAAGGAGATTTGTGTGCCTATCAAAATTGACCGCCTGGGCAATGTCAGCCTGATCCAGATTTAAGAATTC

#13
ACCGGTGCCACCATGTACCCATACGATGTTCCAGATTACGCTTCGCCGAAGAAAAAGCGCAAGGTCGAAGCGTCCATGACAAAG
ACTATTCTGGGACTGGATCTGGGGACTAACAGCATTGGATGGGCACTGATTAACCAGGACTTCGATAACAAAAAGGGGGAGATC
CTGGGCATGGGCAGCCGGATCATTCCTATGACACAGGATATTAAGGACGAGTTCGGAAAAGGCAACTCTATCAGTCAGACAGCT
GAGCGAACTCGACTGCGGGGAGTCCGGAGACTGATCCACAGAACTCTGCTGAGGCGCGAGCGGCTGCATAGAGTGCTGAATATC
ATTGGCTTCCTGCCAGAACACTATGCCAACCAGATTGACTTTGAGAAGAGGTTCGGCAAGTTCAAGCCTGAATCTGAGCCAAAA
ATCAGTTTCGATGGAAATGACGTGTTCCTGTTTGAGAAGAGCTACCAGGAAATGCTGGTCGACTTTAAAATCCACCAGCCACAG
CTGGTGAGCAACGGCAAGAAAATTCCCCATGACTGGACAATCTACTATCTGAGAAAGAAAGCTCTGTCTAAGAAAATTGAGAAG
GAGGAACTGGCATGGATCCTGCTGAACTTCAATCAGAAACGGGGATACTATCAGCTGAGAGGCGAGGAAGAGGAAGAGACACCA
AATAAGCTGGTGGAGTTTCATAGCCTGAAAATTGTGGAGGTCAACGCCGATGAACCCCAGAAAGGAAAGCCTGAGATCTGGTAC
TCACTGGTGCTGGAAAACGGCTGGGTCTATCGACGGGCTAGCAAGACTCCCCTGTTCGATTGGAAAGACAAGATTAGGGAGTTT
ATCGTGACCACAGAAATCAACAATGATGGAACTGTCAAAACCGACAAGGAGGGCACCGAAAAGAGGAGCTTCCGCGCACCAAAA
CCCGAGGACTGGACTCTGCAGAAGAAAAAGACCGAGTTCGAGCTGTCAAAGAGCGGGAATGAAGTGGGAGCCTTCATCTACGAA
AGTATCCTGCAGAAACCCAACCAGAAGATTAGAGGCAAACTGATTTCAACCATCGAGAGGAAATTTTATAAGGAAGAGCTGAAA
ACCATCCTGAAAACACAGCTGTTCTTTCACAAAGAACTGAAGGATGAGAAACTGTACAATGCCTGCATCGAAGAGCTGTATAAG
AACAATGAAGCTCACCGGAGCCTGCTGTCCAACAAGGGGTTCGAGCATCTGTTTATTAACGACATCCTGTTCTACCAGCGACCT
CTGCGGTCTAAAAAGAGTCAGATCTCAAACTGCCCACTGGAGAAGCGCACATATAAAAAGGAGGGGATTGAAATCACTGAGGGC
ATCAAAGTGATCTCCAAATCTAATCCAATCTACCAGGAGTTCCGGCTGTGGCAGTGGATTAGCAACCTGTCCCTGTATTGTATC
GAACCCACCGAGACAATGTGACTTCAACCTTTCTGAACAGCATTGAAGATTACGAGAATCTGTTCGAATTTCTGAACAATCGC
AAGGAAATCGAGCAGAAGCACCTGCTGAAATATCTGCTGGAGAACCAGGGGTTTAAAGGAAAGCTGCTGACAAACGAACTGGAG
AAGTTCCGCTGGAATTTTGTCGCTGACAAAAAGTACCCCTGTAATGAGACAGGCAGCCTGCTGCATACTCGGCTGAGCAAAGTG
AAGAACATTTCCCCTGATTTCCTGACCAAGGAAATCGAGCACCAGCTGTGGCATATCATCTACAGCGTGACCGACAAGATTGAA
TATGAGCAGGCCCTGAAAACCTTTGCTCGGAAAAACAATCTGGATGTGGACTCCTTCTTTGAGCACTTCAAAAAGATCCCCCCT
TTTGAGTCTACCTACGGAGCATATAGTGAAAAGGCCATCAAGAAGCTGCTGCCACTGATCAGACTGGGCAAATACTGGAACTGG
GAGGCCATTGATAGTATCTCAAAGGACAGGATTAGTAAAATCCTGTCAGGGGAATACGATGAGAACATTAAGAACAGAGTGAGG
GAGAAAGCAGTCCACCTGACCTCCGAAAACAATTTCCAGGGACTGCAGGAGTGGCTGGCCAAGTACATCGTCTATGATCGCCAT
TCTGAGGGCAATGACCTGGGGAAGTGGACTAGCGTGTCCGACCTGGAGACATACCTGAAGGAGTTCAAGCAGCATAGCCTGCGG
AACCCTATTGTGGAGCAGGTCATCACAGAAACTCTGAGAGTGGTCAAGGATATTTGGATCAAGCACGGGAAAGGAACCGAAAAT
TTCTTTGACGAAATCCATGTGGAGCTGGGCCGGGAAATGAAGAACAATTCCGAGGATCGCAAACGACTGACCAACACAATTACT
GAAAACGAGAATACAAACCTGAGAATCAAGGCCCTGCTGATGGAAATGATGAATGATAACGACGTGGAGAACGTCAGGCCTTAC
TCTCCAAGTCAGCAGGAGATTCTGAAGATCTATGAGGACGGAGCTCTGAATAGCAACATCGAGCTGGACGATGAAATTGTGAAG
ATCTCCAAAAAGGCAGAGCCCACCAAATCTGAACTGCAGCGCTACAAGCTGTGGCTGGAGCAGAAATACCGATCCCCTTATACT
GGCCAGGTCATCCCACTGAACAAGCTGTTCACCTCTGAATATGAGATCGAACACGTGGTCCCTCAGAGTCGCTTCTTTGACGAT
AGCTTCAGCAACAAAGTGATCTGCGAGTCAGCCGTCAACAAGCGGAAGGATAACCAGCTGGGGCTGCAGTTCATCAAGAACCAT
AGCGGAGAAAAAGTGGAGCTGGGCTTCGGGAAGGTGGTCCAGGTCTTTACAGAAGAGCAGTACCTGGATTTTGTGAAGGAGCAC
TATAGCAAAAATCGCTCCAAGCATAACAAACTGCTGCTGGAAGAGATTCCCGAGAAGATGATCGAAAGGCAGCTGAATGACACT
CGCTACATCAGTAAGTTCGTGAGCTCCATTCTGTCCAACATCGTCAGATCTGAGAAGGACGATGACGGCCTGAATAGCAAAAAC
ATTCTGCCTGGAAATGGCAAGATCACTACCGAACTGAAAAGGGACTGGGGGCTGAATGATGTGTGGAACGACCTGATTCTGCCA
AGATTCGAGAGGATGAATACCATCACAAACAGCGATCTGTTTACAACTTACAACGACAAGTATCAGAAACACCTGCCCACCGTG
CCTTTCGAGTACTCCAAGGGCTTTCAGAAAAAGCGCATTGATCACCGACACCATGCTATGGACGCACTGGTCATCGCATGTGCC
ACACGGGATCATCTGAATCTGATGAACAATCAGTCTGCCAAGAGTGAACTGAAACGATACGACCTGCAGAACAAGCTGCGGAAA
AAGGAGCCTTACTTCAACCAGAAGGAGAACAAACAGAAGGAAGCCTTCAAGGATTTTATCAAACCATGGGGCACTTTCACCGAG
GACAGCAAGAATGCTCTGGAAAAAATCATTATCTCCTTTAAGCAGAACCTGAGAGTGATCAACAAGGCAACAAACTCATACGAG
AGCTATAAGGATGAGGACGGGAATCTGAGGATCGGCAAGGATGGGAAACCAGAGAAGGGCCTGATCAAGCAGAAGGGGCTGAAC
TGGGCAATCAGAAAGCCCCTGCACAAAGACACCGTGTCAGGCCAGATTAACCTGAGCAGGATCAAGCTGCCCAATGGGAAAATC
CTGACAGCCACTCGCAAGAATCTGGATACCAGTTTCGACCTGAAAACAATTGAGAACTCAATCACCGACACAGGCATTCAGAAA
ATCCTGAAGAATTACCTGCTGTCCAAGGAATCTCCAGAGCTGGCCTTCTCTCCCGAGGGCCTGGAAGAGATGAACAATGAGATC
GAAAAGTACAACAATGGGAAATTTCACCATCCTATTAACAAGGCTAGGATCTATGAACTGGGGAGCAAATTCAATGTCGGACAG
ACAGGCAACAGAAGGGATAAGTTTGTGGAGGCCGCTAAAGGAACTAATCTGTTCTTTGCTATCTACCAGGACGAGAATAAGAAC
CGCTCTTATGAAACTATTCCCCTGAACGAAGTGATCGAGCACCAGAAGTGGCGAGCAAGTCTGCCTAAGGAAGAGCAGGAGAAA
ATTCCACTGGTGCCCGTCAACAAGCTGAAGGGGACCTTCATCTTTTCCCTGTCTCCCAACGATCTGGTGTACGTCCCTTCCAAT
GACGAGCTGGAACGAAGTGCTTCAATTGACTTCTCTAAGCTGAAAAAGGAACAGATCAACCGGCTGTATAAAATGGTGTCTAGT
TCAGGATCCCAGTGCTTCTTTGTGAAGAGTGAGGTCGCAACCTCAGTGGTCAACAAAATGGAATACAGCAGCCTGAACAAGATG

FIG. 9I

GAGAAGTCTATCGATAACCTGATGGTGAAGGAGATTTGTATCAAACTGAAGATTGACAGGCTGGGCAACATCAGCAAGGCCTAA
GAATTC

#14
ACCGGTGCCACCATGTACCCATACGATGTTCCAGATTACGCTTCGCCGAAGAAAAAGCGCAAGGTCGAAGCGTCCATGACCAAA
ATCCTGGGGCTGGACCTGGGGACTAATAGCATCGGGTGGGCAATCCGCGACACAGAAAATGAGGGCATCAATCAGATCCTGGAC
AAGGGCGCCCGCATTTTCAGCGAGGGAGTGAAGTCCGAGAATGGCAAAGAAATCAGTAGGGCAGCTGAACGAACCGCTTACCGG
AGCGCAAGAAAGATCAAATATCGGAGAAAACTGCGGAAGTACGAGACACTGAAGGTGCTGTCAATTAACGGAATGTGCCCCCTG
AGCGTGGAGGAAGTCGAACAGTGGAAGAAATCTGGCTTCAAGGAATATCCCCTGAATCCTGAGTTTCTGGATTGGCTGCGGACC
AACGAGGACAAGAACATCAATCCTTACCTGTTCAGAGATAAAGCTAGCAAGCAGAAAGTGACACTGTTTGAACTGGGAAGAGCT
CTGTATCACATCGCACAGAGGCGCGGCTTCCTGAGTAACAGGCTGGACCAGTCAGCCGAGGGCGTCTTTGAGGAACATAATCCT
CAGATCCAGAACCTGATTGAGGACCTGGACAGCTCCAACACAATTCTGAATGAGCTGAAGGAATACTATATCAATCTGGGGATC
ATTGACGAGACTGAAAAGTCCGGCTTCAAGAAAGACCTGGATGAGGGGGAAAAGAAACTGAAGTCACTGTACAACAGCCTGGTG
GCCATCACAAAGAAAAACGCTAACGATATCGAAACTTGCAAGCAGGAGCTGATCGCTAGACTGAATAAGAAAGAGGACCTGGGC
AAGGTCAAAGGGAAGATCAAAGATATTTCTCAGGCAATGCTGGACAGGAACTTTAAGACTCTGGGACAGTATTTCTTTTCACTG
TACAACAAGGAGCGAATCCGGAACCAGTATACCAGCCGCGAGGAACACTACCTGGAGGAGTTCATCATTATCTGTCAGACCCAG
GGGATCGAGGGAATTAACACAAATGAGAAGCTGCCTGAGAAGAAGTTCACCGGCCTGGCAAAAGATCTGTATCGAGCCATTTTC
TTTCAGCGGCCACTGAAATCCCAGAAGGGCCTGATCGGGAAGTGCTCTTTCGAGAAGAACAAGTCTCGCTGTGCCGTGAGTCAC
CCAGACTATGAGGAATTTCGAATGTGGAGCTACCTGAACACAATCAAAATTGGCACTCAGTCCGAGAAAACCCTGCGCTTCCTG
ACACTGGAGGAAAAGCTGAAACTGGTGCCCAAGTTCTACCGAAAGAGTGATTTCAACTTCGAGGTGCTGGCTAAGGAGCTGGTC
GAAAAAGGAGCATCATTCGGCTACTACAAGTCTAGTAAGAAAAATGAGTTCTTTTACTGGTTCAACTATAAGCCCACCGATTCA
GTGAGCGCCTGCGTGGTGAGCGCTTCTCTGGAGAACGCAATCGGCAAGGACTGGAAGATCAAGACTTTCGAATATCAGACTAGA
AACACCGAGAAGAATGAAGTGACCAAATCCGTCGATTACAAGGACCTGTGGCACCTGCTGTCCGTGGCAACATCTGATACTTAC
CTGTATGACTTTGCCATCGAAAAGCTGAAACTGGAGCCTAAAAACGCAAAGGCCTTCAGCAAGACAAAACTGAAGAAAGACTTT
GCCAGTCTGTCACTGGCAGCCATCGCTAAAATTCTGCCATATCTGAAGCAGGGCCTGCTGTACTCCCACGCCGTGTTCATGGCT
AACATCGAGAATATTGTCGACGCCGATATCTGGAAGGATGAGGAACAGCAGAAGTTCATCCAGTCCAAGATTGTGGAGCTGGTC
GACAATTATATCGTGGAAAAGTCTAAACTGGAGCTGATCAATGGGCTGCTGAAGATCTACAACACCGAGGATAAGGAAGGACGG
AAAGTGTACTATTCAAAGGAGGCTGAAAGCCTGTTCGAGGCAGACCTGAGAAAGAAACTGGTCCCCTTCTACAAGGCTAACATC
ATCATCGAGGAACACGAGCAGGAAATCATTTTCCAGGATCTGTTTCCTATCCTGATGGACCAGCTGAAGAAACAGGAGTTCATC
AAAATTGGCAGACTGGATAAGCAGATTGAAGCCTTCCTGGAGGGGGAAAATGAGGAAGGACAGATCTTTTGTAACCACACAGAT
AAGCTGAAGAAACTGTACCATCCAAGCGACATCGAGGTGTTTAAGAAAAAGACTATCAAAGATGAGTGGGGGAATGAAAAGGTG
GTCCTGGGATCCCCACTGACCACATCTATCAAGAACCCCATGGCAATGAGAGCCCTGCACCAGCTGAGGAAGGTGCTGAATACA
CTGATTGCCAACGACCAGATCGACGAGGATACTCGGATCCATATTGAGATGGCCAGAGAACTGAACGATGCTAATAAGCGAAAA
GGCATCCAGGACTTCCAGAACGAGAACAAGAAGTTTCGGGAGGAAGCCATCAAGGAGATCAAGAAGCTGTACCTGGAGGAATGC
CACAAAGACGTGAACCCCACCGAGGACGATATCCTGAGGTATCAGCTGTGGCTGGAACAGGGAAAGTGCGAGATCTACGAGGAA
GGCAACAATATCAGCATTTGTGATATCATTGGCAGCAATCCCTCCTATGACATCGAGCATACCATTCCTCGGAGCATCTCCCAG
GATAACAGCCAGATGAACAAGACACTGTGTAGCCTGAAGTTCAACAGATCCATCAAAAAGCAGAAGATGCCAGTGGAGCTGTCC
AACTACAATGACATTCTGCCCAGGATCGCACACTGGAAAAAGGAGGCCGAGGAACTGACTAGGCAGATCGAAACCATTTCTCGC
AGCATCAAGAGCGCTGCAACCAAGGTGGCCAAGGATAAGAACATCAGAAAGAGGCATTACCTGACACTGAAGCGAGACTATATT
CTGGGGAAATACGAGCGGTTCACTTGGGAGGAACCTAAAGTGGGCTTTAAAAACTCCCAGATCCCAGACACTGGGATCATTACC
AAGTACGCTCAGGCATATCTGAAATCTTACTTCAAAAGGGTGGAGAGTGTCAAGGGAGGAGCAGTGGCTGAGTTCCGGAAACTG
TGGGGCATCCAGGAATCTTTTATCGATGAGAACTGGTGGAAGCACTATAAGGACAAAGATAGAGACAAACATACCCACCATACA
ATCGACGCAATCACTATTGCCTGTATGCCCAAGGATAAATACGACCTGCTGGCACACGCCTGGAGGCTGGAGGATGAACAGGAC
AAAAAGGCCGCTAAGGTGCTGATCGAGCAGGCCAAACCATGGAAAACCTTCAAGGAGGATATCGAAAAGATTGAGACTGAAATC
CTGGTGAGCCATTTTACCCCCGACAACGTCAAAAAGCAGTCAAAGAGCATCATCAAGAATCGCGGCAAAAAGGTGTACGTCCTG
AAGAACGAGCTGCCTGTGAACTTCAAGAACAAGATCGAAGGGAAGGATTATTTCAAGCTGAAATTTGACAGCAAGATTCTGTAC
AAAATCCCCAAAAAGAAAGAGAAGCAGACCGATACATTCTATGAGGAACTGCCTAAAAACTACCTGAATGGAGTGGAAGGCAAG
GACTACTTCAAAATCAATACTACCGGCAAGACCTTCTACAAAATCCCAATTTTTAACCAGGGCGACACAATCCGGGGGAGCCTG
CACCAGGAGACAACTTACGGAGCCATTAAGCTGCCAGATATCGACATTGAAACAAAGAAACCCCTGCATACTGATAAGGGAGGC
TTCATTCTGAAGAAAGACATCAAAGGCAATGAGATTGTGTTCTTTGTGGTCCGCAAGGAAATCTCTAAAATTAGTGAGAACGAT
GTGCAGAATATCGTCGACAACGTGGTCCGGAAGAAAATTGAGAATGCTATCGCAAACTCCCTGATCACTTTTAAGATCGTGAAG
AAAAAGAAAGTGGCCGTCATCAAAGAGGGGGTCACCATTTGGATGAGGGAGCCCAACATTGAAAAGGGGATCGAGGGAATCCCT
ATTAAGAAAGTGCGCATCATTACCAATTCTGTCAAAAACCCTATCGAGATTAAGGTGCACAGTCCACTGTCCAAGTCTCGCCAC
AAGCATAAACAGAAGGTCTACGGCCAGAACGATGAGAATTATGCCATGGCTCTGTACGAACTGGACGGGAAGCGGGAGTTCGAA
CTGATCAACAATTTTAATCTGGCCAAGCTGCTGAAACAGAGTCAGTCATACTATCCACTGCATAAAGAGAAGGAAATCAAGGGA
AAGAAAATTCTGGTGCCCATCGAGAAGAGAAACAACAAGGATGTCATCCTGAAGAGGGGCCAGCAGGTGGTGTTCTACGACAAA
ACCGTGGAGAACCCCAAGGATATCTCTGAAATCATTGACTTTCGCGAGCGAATCTACATCATTGAAGGGCTGACCATCCAGAGA
CAGAAAGATAAGAAAACATCCAAAGTGAATGAGTACGGAATCATTCAGCTGCGCCACTTCAAGGAAGCTCGAAAAAGTGAGGAA
ATCTCAAAGGATAACTTCAAACCTGACGGCGAGTTCAAGATCAACGAGAATAAGCCAACTAGGAAAATGAACCATAATCAGTTC
ACCGCCTTTGTGGAGGGGATCGACTTCAAGGTCCTGCCTAGCGGAAAGTTTCAGAAAATTTAAGAATTC

#15
ACCGGTGCCACCATGTACCCATACGATGTTCCAGATTACGCTTCGCCGAAGAAAAAGCGCAAGGTCGAAGCGTCCATGAGCAAG

FIG. 9J

AAAGTCAGTAGACGCTATGAAGAACAGGCACAGGAGATTTGTCAGAGGCTGGGGAGTAGACCTTATTCCATCGGGCTGGACCTG
GGAGTGGGATCTATCGGAGTGGCAGTCGCCGCTTACGACCCAATTAAGAAACAGCCCTCCGATCTGGTGTTCGTCAGCTCCAGG
ATTTTTATCCCTTCTACCGGCGCAGCCGAGCGGAGACAGAAGAGAGGACAGAGGAACAGCCTGCGCCACCGAGCAAATCGCCTG
AAATTCCTGTGGAAGCTGCTGGCTGAACGAAACCTGATGCTGTCATATAGCGAGCAGGACGTGCCAGATCCTGCACGGCTGAGA
TTTGAGGACGCTGTGGTCCGAGCAAACCCATACGAGCTGCGGCTGAAGGGCCTGAATGAACAGCTGACCCTGAGCGAGCTGGGG
TATGCACTGTACCACATCGCCAATCATAGGGGATCTAGTTCAGTGCGCACATTCCTGGATGAGGAAAAGAGCTCCGACGATAAG
AAACTGGAGGAACAGCAGGCTATGACAGAACAGCTGGCAAAAGAGAAGGGAATTTCCACTTTCATCGAAGTGCTGACAGCCTTT
AACACTAATGGCCTGATCGGGTACAGGAACTCCGAGTCTGTGAAGAGTAAGGGCGTGCCAGTCCCCACTCGCGACATCATTTCA
AATGAGATTGATGTGCTGCTGCAGACCCAGAAGCAGTTCTATCAGGAAATCCTGTCAGACGAGTACTGCGATCGGATTGTCAGC
GCAATCCTGTTTGAAAACGAGAAGATCGTGCCAGAAGCCGGCTGCTGTCCCTATTTCCCTGACGAGAAGAAACTGCCCAGATGT
CACTTTCTGAATGAGGAAAGGCGCCTGTGGGAAGCCATTAACAATGCTAGGATCAAGATGCCCATGCAGGAGGGCGCTGCAAAA
CGCTACCAGAGTGCTTCATTCAGCGACGAGCAGAGACACATTCTGTTTCATATCGCAAGGAGCGGGACTGATATCACCCCTAAA
CTGGTGCAGAAGGAGTTCCCAGCCCTGAAAACCTCCATCATTGTGCTGCAGGGAAAAGAGAAGGCTATTCAGAAGATCGCAGGC
TTCCGATTTCGACGGCTGGAGGAAAAATCTTTTTGGAAGAGACTGAGTGAGGAACAGAAGGACGATTTCTTTAGCGCCTGGACA
AACACTCCTGACGATAAAAGACTGTCCAAGTACCTGATGAAACACCTGCTGCTGACAGAAAATGAGGTGGTCGACGCCCTGAAA
ACCGTGAGCCTGATTGGAGATTATGGCCCAATCGGCAAGACCGCAACACAGCTGCTGATGAAACATCTGGAGGATGGCCTGACT
TACACCGAAGCCCTGGAGCGGGGAATGGAAACCGGCGAGTTCCAGGAACTGTCAGTGTGGGAGCAGCAGAGCCTGCTGCCCTAC
TATGGGCAGATCCTGACAGGATCTACTCAGGCCCTGATGGGGAAGTATTGGCACTCTGCTTTTAAAGAAAAGAGAGACAGTGAG
GGATTCTTTAAGCCTAACACAAATAGCGATGAGGAAAAATACGGCAGGATTGCCAACCCAGTGGTCCATCAGACTCTGAACGAA
CTGCGCAAGCTGATGAATGAGCTGATTACCATCCTGGGAGCTAAACCTCAGGAGATCACAGTGGAACTGGCACGAGAGCTGAAG
GTCGGAGCTGAGAAAAGAGAGGACATCATTAAGCAGCAGACCAAACAGGAAAAGGAGGCTGTGCTGGCATATAGCAAGTACTGC
GAGCCCAACAATCTGGACAAAAGGTATATTGAAAGGTTCCGCCTGCTGGAGGATCAGGCCTTTGTGTGCCCTTACTGTCTGGAG
CACATTAGCGTCGCAGATATCGCAGCTGGAAGGGCAGACGTGGATCATATCTTCCCACGCGACGATACAGCTGACAACTCCTAC
GGGAATAAGGTGGTCGCACACCGACAGTGTAACGATATCAAGGGAAAGCGGACCCCCTATGCAGCCTTCAGTAATACATCAGCC
TGGGGCCCCATCATGCATTACCTGGACGAAACCCCTGGGATGTGGCGCAAAAGAAGGAAGTTTGAGACAAACGAGGAAGAGTAT
GCTAAGTACCTGCAGTCAAAAGGCTTCGTGAGCAGGTTTGAAAGCGATAACTCCTATATCGCAAAAGCTGCAAAGGAGTACCTG
CGCTGCCTGTTCAATCCAAACAATGTGACTGCCGTCGGGTCCCTGAAGGGAATGGAGACATCTATCCTGCGGAAGGCCTGGAAT
CTGCAGGGAATTGACGATCTGCTGGGCAGCCGGCACTGGAGTAAGGACGCCGATACCAGCCCCACAATGCGCAAAAACCGGGAC
GACAATCGGCACCATGGCCTGGACGCCATCGTGGCTCTGTATTGTTCCAGATCTCTGGTCCAGATGATTAACACCATGTCCGAG
CAGGGCAAGCGAGCAGTGGAAATCGAGGCTATGATTCCTATCCCAGGGTACGCATCCGAACCAAATCTGTCTTTCGAAGCCCAG
CGGGAGCTGTTTAGAAAGAAAATCCTGGAGTTCATGGACCTGCACGCCTTTGTGAGTATGAAAACCGACAACGATGCAAATGGC
GCCCTGCTGAAAGATACTGTGTATTCAATTCTGGGAGCAGACACCCAGGGAGAGGATCTGGTGTTCGTGGTCAAGAAAAAGATT
AAGGACATCGGCGTGAAAATCGGGGATTATGAAGAGGTCGCATCTGCCATTCGAGGCCGGATCACCGACAAACAGCCAAAGTGG
TATCCCATGGAAATGAAAGATAAGATCGAGCAGCTGCAGTCTAAGAACGAAGCCGCTCTGCAGAAATACAAGGAGAGTCTGGTG
CAGGCAGCCGCTGTCCTGGAAGAGAGTAATAGGAAGCTGATTGAGTCAGGCAAAAAGCCCATCCAGCTGAGTGAAAAAACAATT
TCAAAAAAGGCCCTGGAGCTGGTGGGCGGGTACTATTACCTGATTAGCAACAACAAGCGCACAAAGACTTTCGTGGTCAAGGAA
CCTTCAAACGAGGTGAAAGGGTTCGCATTTGACACTGGAAGCAATCTGTGCCTGGACTTTTATCACGATGCCCAGGGAAAGCTG
TGTGGCGAGATCATTAGAAAAATCCAGGCTATGAACCCTTCCTATAAGCCAGCATACATGAAACAGGGGTATTCTCTGTACGTG
AGACTGTACCAGGGCGACGTGTGCGAGCTGAGGGCAAGCGATCTGACTGAAGCAGAGTCCAACCTGGCCAAGACCACACATGTC
CGCCTGCCCAATGCTAAACCTGGGCGAACCTTCGTGATCATTATCACCTTTACAGAGATGGGGTCTGGATATCAGATCTACTTC
AGCAACCTGGCCAAGTCCAAAAAGGGACAGGACACTAGTTTTACCCTGACTACCATCAAGAATTATGATGTGCGGAAAGTCCAG
CTGTCTAGTGCCGGGCTGGTGAGATACGTCAGCCCTCTGCTGGTGGACAAAATCGAGAAGGATGAAGTCGCTCTGTGTGGAGAG
TAAGAATTC

#16
ACCGGTGCCACCATGTACCCATACGATGTTCCAGATTACGCTTCGCCGAAGAAAAAGCGCAAGGTCGAAGCGTCCATGGCAAGA
CCTGCATTTCGGGCACCTCGGAGAGAACACGTCAACGGCTGGACCCCTGACCCACATCGGATTAGCAAACCCTTTTTCATCCTG
GTGAGCTGGCACCTGCTGTCCCGGGTGGTCATTGACAGCTCCTCTGGATGCTTCCCAGGCACCAGCCGGGACCACACCGACAAG
TTTGCCGAGTGGGAATGTGCTGTGCAGCCCTACAGGCTGAGTTTCGACCTGGGGACCAACTCAATCGGATGGGGCCTGCTGAAT
CTGGATCGCCAGGGAAAACCAAGGGAGATCCGAGCACTGGGGTCCCGCATCTTCAGCGACGGACGGGATCCCCAGGACAAGGCT
TCTCTGGCTGTGGCACGGAGACTGGCCAGACAGATGAGGCGCCGACGGGACAGATATCTCAACTAGAAGGACCAGGCTGATGGGA
GCTCTGGTGCGCTTCGGCCTGATGCCAGCAGACCCTGCAGCTAGGAAGCGCCTGGAAGTGGCCGTCGATCCATACCTGGCACGA
GAGCGGGCCACAAGAGAAAGGCTGGAGCCCTTCGAAATCGGGAGGGCCCTGTTTCACCTGAACCAGCGCCGAGGATATAAACCC
GTGCGCACCGCCACAAAGCCTGATGAGGAAGCCGGCAAGGTGAAAGAGGCTGTCGAAAGGCTGGAGGCAGCAATCGCTGCAGCC
GGAGCACCTACTCTGGGAGCTTGGTTCGCATGGCGAAAAAACACGAGGAGAAACTCTGCGAGCACGACTGGCTGGGAAGGGAAAA
GAGGCTGCATACCCATTCTATCCCGCACGGAGAATGCTGGAGGCCGAATTTGACACTCTGTGGGCAGAGCAGGCCAGGCACCAT
CCAGATCTGCTGACCGCCGAAGCTCGCGAGATCCTGCGGCACAGAATTTTTCATCAGCGGCCCCTGAAGCCACCTCCAGTGGGA
AGATGCACTCTGTACCCTGACGATGGGAGAGCTCCTAGGGCACTGCCAAGCGCTCAGAGGCTGCGCCTGTTCCAGGAGCTGGCC
AGCCTGAGAGTGATCCACCTGGACCTGTCCGAACGCCCTCTGACCCCAGCTGAGCGAGATCGGATTGTGGCATTTGTCCAGGGC
AGACCCCCTAAAGCCGGAAGGAAGCCTGGCAAAGTGCAGAAGAGCGTCCCATTCGAAAAGCTGAGGGGGCTGCTGGAGCTGCCA
CCAGGCACTGGGTTTTCTCTGGAGAGTGACAAACGGCCTGAACTGCTGGGCGACGAGACAGGCGCCAGAATCGCACCAGCATTC
GGACCTGGATGGACAGCTCTGCCTCTGGAGGAACAGGACGCCCTGGTGGAACTGCTGCTGACAGAGGCAGAACCAGAGAGGGCA
ATTGCAGCTCTGACTGCACGATGGGCTCTGGACGAGGCAACTGCAGCAAAGCTGGCTGGAGCAACCCTGCCAGATTTTCACGGA

FIG. 9K

CGATATGGCAGGCGCGCAGTGGCTGAACTGCTGCCTGTCCTGGAACGCGAGACACGAGGCGACCCAGATGGGAGAGTGAGGCCC
ATCCGGCTGGACGAGGCAGTGAAACTGCTGAGAGGCGGGAAGGATCACTCAGACTTCAGCCGGGAAGGAGCTCTGCTGGACGCA
CTGCCCTACTATGGAGCCGTGCTGGAGAGACATGTCGCTTTTGGGACAGGAAACCCCGCAGATCCTGAGGAAAAGCGGGTGGGA
AGAGTCGCCAATCCCACTGTGCACATCGCTCTGAACCAGCTGCGGCATCTGGTGAATGCAATTCTGGCCAGGCACGGCCGCCCT
GAGGAAATCGTGATTGAGCTGGCACGGGACCTGAAAAGGTCTGCCGAAGATCGACGGAGAGAGGACAAGCGGCAGGCCGATAAC
CAGAAAAGAAATGAGGAACGCAAGCGACTGATCCTGAGTCTGGGAGAGCGCCCAACCCCACGAAACCTGCTGAAGCTGCGGCTG
TGGGAGGAACAGGGCCCAGTGGAAAATAGGCGCTGCCCCTACTCTGGGGAGACAATTAGTATGAGAATGCTGCTGAGCGAGCAG
GTGGACATCGATCACATTCTGCCATTCAGCGTGTCCCTGGACGATTCCGCTGCAAACAAGGTGGTCTGTCTGCGGGAGGCCAAC
AGAATCAAGCGGAATAGATCTCCCTGGGAGGCCTTCGGCCATGACAGTGAGAGATGGGCAGGGATTCTGGCACGAGCAGAAGCT
CTGCCCAAGAACAAAAGGTGGCGCTTTGCTCCTGACGCACTGGAGAAACTGGAAGGAGAGGGAGGCCTGCGAGCACGACACCTG
AATGATACAAGGCATCTGAGTCGCCTGGCCGTGGAGTATCTGCGGTGCGTCTGTCCTAAGGTGCGGGTGAGCCCAGGCCGACTG
ACTGCACTGCTGCGACGGAGATGGGGCATCGACGCCATTCTGGCAGAAGCAGATGGACCTCCACCAGAAGTGCCCGCAGAGACA
CTGGACCCTTCCCCAGCTGAGAAGAACCGAGCAGACCACCGGCACCATGCCCTGGATGCTGTGGTCATCGGCTGTATTGATCGC
TCAATGGTGCAGCGAGTCCAGCTGGCCGCTGCAAGCGCAGAAAGAGAGGCCGCTGCAAGGGAGGACAATATCAGGCGCGTGCTG
GAGGGATTCAAAGAGGAACCTTGGGATGGCTTTAGAGCTGAACTGGAGCGACGGGCACGGACCATCGTGGTGAGCCACAGACCA
GAACATGGGATTGGGGGAGCCCTGCATAAGGAGACAGCTTACGGGCCTGTGGACCCTCCAGAGGAAGGATTCAACCTGGTGGTC
AGGAAACCAATCGACGGCCTGTCAAAGGATGAGATTAATAGCGTGCGGGACCCCCGGCTGAGAAGGGCACTGATCGATCGCCTG
GCCATTCGCCGACGGGATGCTAACGACCCTGCTACCGCACTGGCCAAAGCAGCTGAGGATCTGGCAGCACAGCCAGCCTCCCGC
GGCATCAGAAGGGTGCGGGTCCTGAAGAAAGAATCTAACCCCATTAGGGTGGAGCACGGCGGGAATCCAAGTGGACCCCGCTCA
GGAGGCCCTTTTCATAAGCTGCTGCTGGCAGGAGAGGTGCACCATGTGGACGTCGCACTGCGAGCAGATGGCCGCCGATGGGTG
GGACACTGGGTCACACTGTTCGAGGCACATGGGGGACGGGGAGCAGACGGAGCTGCAGCCCCACCTAGACTGGGCGATGGGGAA
AGATTTCTGATGAGGCTGCACAAGGGAGACTGCCTGAAACTGGAGCATAAGGGCAGAGTGAGGGTCATGCAGGTGGTCAAACTG
GAACCTAGTTCAAATAGCGTGGTCGTGGTCGAGCCACACCAGGTGAAAACCGACAGATCCAAACATGTCAAGATCTCTTGTGAT
CAGCTGCGCGCTCGAGGAGCACGGAGAGTGACCGTCGATCCACTGGGACGGGTGAGAGTCCACGCCCCAGGAGCTAGGGTGGGA
ATCGGAGGGGACGCCGGACGAACCGCTATGGAACCCGCAGAGGATATTAGCTAAGAATTC

#17

ACCGGTGCCACCATGTACCCATACGATGTTCCAGATTACGCTTCGCCGAAGAAAAAGCGCAAGGTCGAAGCGTCCATGGGAGAG
AATATGATTGACGAGAGTCTGACCTTCGGCATTGACCTGGGGATTGGGAGTTGTGGGTGGGCAGTGCTGAGGCGGCCAAGCGCC
TTCGGACGGAAGGGCGTGATCGAGGGAATGGGCTCCTGGTGCTTTGACGTCCCCGAGACATCTAAAGAACGGACTCCTACCAAC
CAGATCCGGAGATCCAATAGACTGCTGAGGCGCGTGATCCGACGGAGAAGGAACCGGATGGCCGCTATTCGCCGACTGCTGCAC
GCAGCAGGCCTGCTGCCATCAACCGACAGCGATGCCCTGAAGCGGCCCGGACATGATCCTTGGGAACTGAGGGCACGAGGCCTG
GACAAGCCACTGAAACCCGTGGAGTTCGCTGTGGTCCTGGGCCACATCGCAAAGCGGAGAGGGTTTAAATCCGCTGCAAAGAGA
AAAGCCACAAACATTAGCTCCGACGATAAGAAAATGCTGACAGCCCTGGAGGCTACTCGAGAACGGCTGGGGAGATACAGGACC
GTGGGAGAAATGTTCGCCAGGGACCCTGATTTTGCTTCTAGGCGCCGAAATCGCGAGGGCAAGTATGATAGGACCACAGCTCGC
GACGATCTGGAGCACGAAGTGCACGCCCTGTTCGCAGCTCAGCGGAGACTGGGACAGGGATTTGCCAGTCCAGAACTGGAGGAG
GCCTTCACCGCTTCAGCATTTCATCAGAGGCCCATGCAGGACAGCGAGCGCCTGGTGGGATTCTGCCCTTTTGAGCGAACCGAA
AAGCGGGCAGCCAAACTGACACCCTCTTTCGAGCGCTTTCGACTGCTGGCCCGGCTGCTGAACCTGAGAATCACTACCCCAGAC
GGAGAGCGGCCCCTGACAGTGGATGAAATTGCTCTGGTCACCCGGGACCTGGGCAAGACCGCAAAACTGAGTATCAAGCGGGTG
AGAACTCTGATTGGACTGGAGGACAATCAGAGGTTCACAACTATCCGCCCCGAGGACGAAGATCGAGACATTGTGGCTCGGACA
GGCGGGGCAATGACAGGGACTGCCACCCTGAGGAAGGCACTGGGAGAGGCCCTGTGGACTGATATGCAGGAGCGCCCTGAACAG
CTGGACGCTATCGTGCAGGTCCTGAGCTTCTTTGAGGCCAACGAAACAATCACTGAGAAGCTGAGGGAAATTGGCCTGACTCTG
GCCGTGCTGGACGTCCTGCTGACCGCACTGGATGCCGGAGTGTTCGCCAAGTTTAAAGGCGCTGCACACATCAGCACCAAAGCC
GCTAGGAATCTGCTGCCACATCTGGAGCAGGGCAGGCGCTACGATGAGGCCTGCACAATGGCAGGGTATGACCACGCAGCCTCC
CGCCTGTCTCACCATGGCCAGATCGTGGCAAAGACACAGTTCAACGCCCTGGTCACTGAGATCGGCGAATCCATTGCCAATCCA
ATCGCTCGGAAGGCACTGATCGAGGGGCTGAAACAGATTTGGGCCATGAGAAACCACTGGGGGCTGCCCGGAAGTATCCATGTG
GAGCTGGCCCGGGATGTCGGCAACTCAATTGAAAAGCGACGGGAGATTGAAAAGCACATCGAGAAAAATACTGCCCTGAGGGCT
CGCGAGAGAAGGGAGGTGCATGATCTGCTGGACCTGGAAGATGTCAATGGCGACACCCTGCTGCGATACCGGCTGTGGAAGGAG
CAGGGAGGCAAATGCCTGTATACAGGGAAGGCCATCCACATTCGGCAGATCGCTGCAACTGACAACTCCGTGCAGGTCGATCAT
ATTCTGCCTTGGAGCCGGTTCGGCGACGATAGTTTTAACAACAAGACCCTGTGTCTGGCCTCTGCTAATCAGCAGAAGAAAAGG
TCAACACCATACGAGTGGCTGAGCGGCCAGACTGGGGATGCATGGAACGCCTTCGTGCAGCGCATCGAGACAAATAAGGAACTG
AGAGGGTTTAAGAAAAGGAACTATCTGCTGAAGAATGCTAAAGAGGCAGAGGAAAAATTCAGAAGCAGGAACCTGAATGACACC
AGATACGCCGCTAGGCTGTTCGCAGAGGCCGTGAAGCTGCTGTATGCCTTTGGGGAGAGACAGGAAAAAGGGGGAAACCGCCGA
GTGTTTACTCGGCCTGGAGCACTGACCGCAGCACTGAGACAGGCTTGGGGAGTGGAGAGCCTGAAGAAACAGGATGGGAAGCGC
ATCAATGACGATCGACACCATGCCCTGGATGCTCTGACCGTGGCTGCAGTCGACGAGGCCGAAATTCAGAGGCTGACAAAATCA
TTCCACGAGTGGGAACAGCAGGGCCTGGGGCGGCCTCTGCGGAGAGTGGAGCCACCTTGGGAGAGCTTCCGGGCAGACGTCGAG
GCTACCTACCCTGAAGTGTTTGTCGCACGGCCAGAGAGGCGCCGAGCAAGAGGAGAAGGCCATGCCGCTACCATCCGGCAGGTG
AAGGAGAGAGAGAATGCACACCAATTGTGTTTGAGAGAAAGGCTGTCTCTAGTCTGAAAGAGGCAGACCTGGAACGAATCAAAGAT
GGCGAGCGCAACGAAGCAATTGTGGAGGCCATCAGGAGCTGGATTGCCACTGGACGCCCAGCTGATGCACCACCACGCTCCCCC
CGAGGCGACATCATTACCAAGATCAGGCTGGCCACCACCATCAAGGCAGCCGTGCCTGTCCGCGGAGGGACCGCAGGAAGGGGA
GAAATGGTGCGCGCAGATGTGTTCAGCAAGCCAAACCGGAGAGGGAAAGACGAGTGGTATCTGGTGCCCGTGTATCCACACCAG
ATCATGAACAGGAAGGCTTGGCCCAAACCTCCAATGCGCTCAATTGTGGCCAATAAGGATGAGGACGAATGGACCGAAGTGGGA
CCTGAACACCAGTTCCGGTTTAGCCTGTACCCTAGATCCAATATCGAGATCATTAGGCCATCTGGAGAAGTGATCGAAGGATAT

FIG. 9L

TTCGTCGGCCTGCATCGCAACACTGGCGCTCTGACCATCAGTGCACACAATGATCCCAAGAGTATCCATTCAGGCATTGGGACC
AAGACACTGCTGGCCATTTCCAAATACCAGGTGGACAGATTCGGCAGAAAGTCTCCAGTGCGCAAAGAGGTCCGAACTTGGCAC
GGGGAAGCCTGTATCTCTCCCACCCCCCCTGGATAAGAATTC

#19
ACCGGTGCCACCATGTACCCATACGATGTTCCAGATTACGCTTCGCCGAAGAAAAAGCGCAAGGTCGAAGCGTCCATGAGAGAG
AACGGGAGTGACGAAAGGCGGAGGAATATGGACGAAAAAATGGATTACAGGATTGGGCTGGACATCGGCATCGCATCAGTGGGG
TGGGCCGTCCTGCAGAACAATTCAGACGATGAGCCTGTGAGGATTGTCGACCTGGGAGTGCGCATTTTCGATACCGCAGAGATC
CCAAAGACAGGCGAAAGCCTGGCAGGACCCCGGAGAGCAGCTCGAACCACAAGGCGCCGACTGCGGAGAAGGAAACACCGCCTG
GACCGAATCAAGTGGCTGTTCGAGAACCAGGGGCTGATCAATATTGACGATTTTCTGAAGAGATACAACATGGCCGGACTGCCA
GATGTGTACCAGCTGCGGTATGAGGCTCTGGACAGAAAACTGACCGATGAGGAACTGGCCCAGGTGCTGCTGCACATCGCTAAG
CATCGGGGCTTCAGAAGCACCAGGAAAGCCGAGACAGCAGCCAAGGAAAACGGGGCAGTGCTGAAGGCCACAGACGAGAATCAG
AAACGAATGCAGGAAAAGGGATACAGGACAGTGGGCGAGATGATCTACCTGGACGAGGCCTTCCGGACTGGCTGCTCTTGGAGT
GAGAAAGGGTACATCCTGACCCCCCGCAACAAGGCTGAAAATTATCAGCACACAATGCTGCGGGCAATGCTGGTGGAGGAAGTC
AAGGAGATTTTCAGCTCCCAGCGCCGACTGGGCAACGAAAAAGCCACTGAGGAACTGGAGGAAAAGTACCTGGAGATCATGACC
TCCCAGCGCTCTTTTGACCTGGGGCCTGGAATGCAGCCAGATGGGAAGCCCTCCCCTTATGCAATGGAGGGCTTCTCTGACAGA
GTGGGGAAATGTACTTTTCTGGGGGATCAGGGAGAGCTGAGGGGCGCTAAGGGGACCTACACAGCCGAATATTTCGTGGCTCTG
CAGAAAATCAACCACACAAAGCTGGTCAATCAGGACGGCGAGACAAGGAATTTCACTGAGGAAGAGCGGAGAGCCCTGACTCTG
CTGCTGTTTACCCAGAAAGAGGTGAAGTACGCTGCAGTCCGCAAGAAACTGGGCCTGCCTGAGGACATCCTGTTCTACAACCTG
AACTACAAGAAGGCCGCTACTAAAGAAGAGCAGCAGAAGGAGAACCAGAATACCGAAAAAGCCAAGTTTATCGGGATGCCATAC
TATCACGATTACAAGAAATGCCTGGAAGAGAGAGTGAAGTATCTGACCGAGAACGAAGTCAGGGACCTGTTTGATGAGATCGGA
ATGATTCTGACTTGTTACAAAAATGACGATTCCCGCACCGAACGACTGGCCAAGCTGGGACTGGTGCCCATCGAGATGGAAGGC
CTGCTGGCTTATACTCCTACCAAATTCCAGCATCTGTCTATGAAGGCAATGCGGAACATCATTCCCTTTCTGGAGAAAGGGATG
ACCTACGACAAGGCTTGCGAAGAGGCAGGATATGACTTCAAAGCCGATAGCAAGGGGACTAAACAGAAGCTGCTGACCGGAGAG
AACGTGAATCAGACAATCAACGAAATTACTAATCCTGTGGTCAAACGCTCAGTGAGCCAGACAGTGAAGGTCATTAACGCCATC
ATTCGGACTTACGGCAGTCCACAGGCTATCAATATTGAGCTGGCAAGAGAAATGTCAAAGACCTTTGAAGAGAGGCGCAAAATC
AAGGGGGACATGGAGAAACGGCAGAAGAACAATGAAGATGTGAAGAAACAGATTCAGGAGCTGGGAAAACTGTCTCCTACAGGC
CAGGACATCCTGAAGTACAGACTGTGGCAGGAGCAGCAGGGGATTTGTATGTATAGTGGAAAAACCATCCCACTGGAAGAGCTG
TTCAAGCCCGGCTACGACATCGATCACATTCTGCCCTATTCAATTACATTCGACGATAGCTTTAGGAACAAAGTGCTGGTCACA
TCCCAGGAGAACAGACAGAAGGGCAATAGGACTCCTTACGAGTATATGGGGAACGACGAACAGCGCTGGAATGAGTTTGAAACC
AGGGTGAAAACTACCATCCGCGATTACAAGAAACAGCAGAAGCTGCTGAAGAAACATTTCTCTGAAGAGGAAAGGAGTGAGTTT
AAAGAACGGAACCTGACAGACACTAAGTACATCACAACCGTGATCTACAACATGATCAGACAGAATCTGGAGATGGCCCCCCTG
AACCGCCCTGAAAAGAAAAAGCAGGTGCGGGCTGTCAATGGCGCAATTACCGCCTACCTGCGAAAACGGTGGGGGCTGCCACAG
AAGAATCGGGAGACAGACACACACCATGCTATGGATGCAGTGGTCATCGCCTGCTGTACCGACGGCATGATCCAGAAAATTAGT
AGATACACAAAGGTGAGAGAGAGGTGCTATTCAAAGGGAACAGAGTTCGTCGATGCAGAGACTGGCGAAATCTTTAGACCCGAG
GACTACAGCAGGGCCGAGTGGGATGAAATTTTCGGCGTGCACATCCCAAAGCCCTGGGAGACATTTCGCGCCGAACTGGACGTC
CGAATGGGGGACGATCCAAAGGGATTCCTGGACACTCATAGCGATGTGGCTCTGGAGCTGGATTATCCCGAGTACATCTACGAA
AACCTGCGGCCTATCTTCGTGAGCAGAATGCCAAATCACAAGGTCACCGGAGCAGCCCATGCTGACACAATTCGGTCCCCAAGA
CACTTTAAAGATGAGGGCATCGTGCTGACTAAGACCGCACTGACCGACCTGAAACTGGACAAGGATGGGGAGATCGACGGATAC
TATAACCCCCAGTCCGATCTGCTGCTGTACGAAGCACTGAAAAAGCAGCTGCTGCTGTATGGCAATGATGCCAAAAAGGCCTTC
GCTCAGGACTTTCATAAACCCAAGGCCGATGGAACTGAGGGCCCTGTGGTCAGGAAGGTGAAGATCCAGAAAAAGCAGACCATG
GGAGTGTTCGTCGACTCTGGCAACGGGATTGCCGAGAATGGCGGGATGGTGCGCATCGATGTGTTCCGAGTCAACGGCAAGTAC
TATTTTGTGCCCGTCTACACCGCTGACGTGGTCAAAAAGGTGCTGCCTAATAGGGCCAGTACAGCTCACAAGCCATACGGCGAG
TGGAAAGTGATGGAGGACAAGGATTTCCTGTTTAGTCTGTATTCACGCGACCTGATCCATATCAAGTCTAAAAAGGATATCCCT
ATTAAGATGGTGAACGGAGGCATGGAGGGGATCAAGGAAACCTACGCATACTATATTGGAGCCGACATCAGCGCTGCAAATATC
CAGGGCATTGCCCACGATTCCAGGTATAAATTCCGCGGACTGGGCATTCAGTCTCTGGACGTGCTGGAGAAGTGTCAGATCGAT
GTGCTGGGACATGTCAGCGTGGTCCGATCCGAAAAGCGGATGGGCTTTAGCTAAGAATTC

#21
ACCGGTGCCACCATGTACCCATACGATGTTCCAGATTACGCTTCGCCGAAGAAAAAGCGCAAGGTCGAAGCGTCCATGAAAAGG
AACTACATTCTGGGGCTGGACATCGGGATTACAAGCGTGGGGTATGGGATTATTGACTATGAAACAAGGGACGTGATCGACGCA
GGCGTCAGACTGTTCAAGGAGGCCAACGTGGAAAACAATGAGGGACGGAGAAGCAAGAGGGGAGCCAGGCGCCTGAAACGACGG
AGAAGGCACAGAATCCAGAGGGTGAAGAAACTGCTGTTCGATTACAACCTGCTGACCGACCATTCTGAGCTGAGTGGAATTAAT
CCTTATGAAGCCAGGGTGAAAGGCCTGAGTCAGAAGCTGTCAGAGGAAGAGTTTTCCGCAGCTCTGCTGCACCTGGCTAAGCGC
CGAGGAGTGCATAACGTCAATGAGGTGGAAGAGGACACCGGCAACGAGCTGTCTACAAAGGAACAGATCTCACGCAATAGCAAA
GCTCTGGAAGAGAAGTATGTCGCAGAGCTGCAGCTGGAACGGCTGAAGAAAGATGGCGAGGTGAGAGGGTCAATTAATAGGTTC
AAGACAAGCGACTACGTCAAAGAAGCCAAGCAGCTGCTGAAAGTGCAGAAGGCTTACCACCAGCTGGATCAGAGCTTCATCGAT
ACTTATATCGACCTGCTGGAGACTCGGAGAACCTACTATGAGGGACCAGGAGAAGGGAGCCCCTTCGGATGGAAAGACATCAAG
GAATGGTACGAGATGCTGATGGGACATTGCACCTATTTTCCAGAAGAGCTGAGAAGCGTCAAGTACGCTTATAACGCAGATCTG
TACAACGCCCTGAATGACCTGAACAACCTGGTCATCACCAGGGATGAAAACGAGAAACTGGAATACTATGAGAAGTTCCAGATC
ATCGAAAACGTGTTTAAGCAGAAGAAAAAGCCTACACTGAAACAGATTGCTAAGGAGATCCTGGTCAACGAAGAGGACATCAAG
GGCTACCGGGTGACAAGCACTGGAAAACCAGAGTTCACCAATCTGAAAGTGTATCACGATATTAAGGACATCACAGCACGGAAA
GAAATCATTGAGAACGCCGAACTGCTGGATCAGATTGCTAAGATCCTGACTATCTACCAGAGCTCCGAGGACATCCAGGAAGAG

FIG. 9M

CTGACTAACCTGAACAGCGAGCTGACCCAGGAAGAGATCGAACAGATTAGTAATCTGAAGGGGTACACCGGAACACACAACCTG
TCCCTGAAAGCTATCAATCTGATTCTGGATGAGCTGTGGCATACAAACGACAATCAGATTGCAATCTTTAACCGGCTGAAGCTG
GTCCCAAAAAAGGTGGACCTGAGTCAGCAGAAAGAGATCCCAACCACACTGGTGGACGATTTCATTCTGTCACCCGTGGTCAAG
CGGAGCTTCATCCAGAGCATCAAAGTGATCAACGCCATCATCAAGAAGTACGGCCTGCCCAATGATATCATTATCGAGCTGGCT
AGGGAGAAGAACAGCAAGGACGCACAGAAGATGATCAATGAGATGCAGAAACGAAACCGGCAGACCAATGAACGCATTGAAGAG
ATTATCCGAACTACCGGGAAAGAGAACGCAAAGTACCTGATTGAAAAAATCAAGCTGCACGATATGCAGGAGGGAAAGTGTCTG
TATTCTCTGGAGGCCATCCCCCTGGAGGACCTGCTGAACAATCCATTCAACTACGAGGTCGATCATATTATCCCCAGAAGCGTG
TCCTTCGACAATTCCTTTAACAACAAGGTGCTGGTCAAGCAGGAAGAGAACTCTAAAAAGGGCAATAGGACTCCTTTCCAGTAC
CTGTCTAGTTCAGATTCCAAGATCTCTTACGAAACCTTTAAAAAGCACATTCTGAATCTGGCCAAAGGAAAGGGCCGCATCAGC
AAGACCAAAAAGGAGTACCTGCTGGAAGAGCGGGACATCAACAGATTCTCCGTCCAGAAGGATTTTATTAACCGGAATCTGGTG
GACACAAGATACGCTACTCGCGGCCTGATGAATCTGCTGCGATCCTATTTCCGGGTGAACAATCTGGATGTGAAAGTCAAGTCC
ATCAACGGCGGGTTCACATCTTTTCTGAGGCGCAAATGGAAGTTTAAAAAGGAGCGCAACAAAGGGTACAAGCACCATGCCGAA
GATGCTCTGATTATCGCAAATGCCGACTTCATCTTTAAGGAGTGGAAAAAGCTGGACAAAGCCAAGAAAGTGATGGAGAACCAG
ATGTTCGAAGAGAAGCAGGCCGAATCTATGCCCGAAATCGAGACAGAACAGGAGTACAAGGAGATTTTCATCACTCCTCACCAG
ATCAAGCATATCAAGGATTTCAAGGACTACAAGTACTCTCACCGGGTGGATAAAAAGCCCAACAGAGAGCTGATCAATGACACC
CTGTATAGTACAAGAAAAGACGATAAGGGGAATACCCTGATTGTGAACAATCTGAACGGACTGTACGACAAAGATAATGACAAG
CTGAAAAAGCTGATCAACAAAAGTCCCGAGAAGCTGCTGATGTACCACCATGATCCTCAGACATATCAGAAACTGAAGCTGATT
ATGGAGCAGTACGGCGACGAGAAGAACCCACTGTATAAGTACTATGAAGAGACTGGGAACTACCTGACCAAGTATAGCAAAAAG
GATAATGGCCCCGTGATCAAGAAGATCAAGTACTATGGGAACAAGCTGAATGCCCATCTGGACATCACAGACGATTACCCTAAC
AGTCGCAACAAGGTGGTCAAGCTGTCACTGAAGCCATACAGATTCGATGTCTATCTGGACAACGGCGTGTATAAATTTGTGACT
GTCAAGAATCTGGATGTCATCAAAAAGGAGAACTACTATGAAGTGAATAGCAAGTGCTACGAAGAGGCTAAAAAGCTGAAAAAG
ATTAGCAACCAGGCAGAGTTCATCGCCTCCTTTTACAACAACGACCTGATTAAGATCAATGGCGAACTGTATAGGGTCATCGGG
GTGAACAATGATCTGCTGAACCGCATTGAAGTGAATATGATTGACATCACTTACCGAGAGTATCTGGAAAACATGAATGATAAG
CGCCCCCCTCGAATTATCAAAACAATTGCCTCTAAGACTCAGAGTATCAAAAAGTACTCAACCGACATTCTGGGAAACCTGTAT
GAGGTGAAGAGCAAAAAGCACCCTCAGATTATCAAAAAGGGCTAAGAATTC

#22
ACCGGTGCCACCATGTACCCATACGATGTTCCAGATTACGCTTCGCCGAAGAAAAAGCGCAAGGTCGAAGCGTCCATGAAAAGG
AACTACATTCTGGGGCTGGACATCGGGATTACAAGCGTGGGGTATGGGATTATTGACTATGAAACAAGGGACGTGATCGACGCA
GGCGTCAGACTGTTCAAGGAGGCCAACGTGGAAAACAATGAGGGACGGAGAAGCAAGAGGGGAGCCAGGCGCCTGAAACGACGG
AGAAGGCACAGAATCCAGAGGGTGAAGAAACTGCTGTTCGATTACAACCTGCTGACCGACCATTCTGAGCTGAGTGGAATTAAT
CCTTATGAAGCCAGGGTGAAAGGCCTGAGTCAGAAGCTGTCAGAGGAAGAGTTTTCCGCAGCTCTGCTGCACCTGGCTAAGCGC
CGAGGAGTGCATAACGTCAATGAGGTGGAAGAGGACACCGGCAACGAGCTGTCTACAAAGGAACAGATCTCACGCAATAGCAAA
GCTCTGGAAGAGAAGTATGTCGCAGAGCTGCAGCTGGAACGGCTGAAGAAAGATGGCGAGGTGAGAGGGTCAATTAATAGGTTC
AAGACAAGCGACTACGTCAAAGAAGCCAAGCAGCTGCTGAAAGTGCAGAAGGCTTACCACCAGCTGGATCAGAGCTTCATCGAT
ACTTATATCGACCTGCTGGAGACTCGGAGAACCTACTATGAGGGACCAGGAGAAGGGAGCCCCTTCGGATGGAAAGACATCAAG
GAATGGTACGAGATGCTGATGGGACATTGCACCTATTTTCCAGAAGAGCTGAGAAGCGTCAAGTACGCTTATAACGCAGATCTG
TACAACGCCCTGAATGACCTGAACAACCTGGTCATCACCAGGGATGAAAACGAGAAACTGGAATACTATGAGAAGTTCCAGATC
ATCGAAAACGTGTTTAAGCAGAAGAAAAAGCCTACACTGAAACAGATTGCTAAGGAGATCCTGGTCAACGAAGAGGACATCAAG
GGCTACCGGGTGACAAGCACTGGAAAACCAGAGTTCACCAATCTGAAAGTGTATCACGATATTAAGGACATCACAGCACGGAAA
GAAATCATTGAGAACGCCGAACTGCTGGATCAGATTGCTAAGATCCTGACTATCTACCAGAGCTCCGAGGACATCCAGGAAGAG
CTGACTAACCTGAACAGCGAGCTGACCCAGGAAGAGATCGAACAGATTAGTAATCTGAAGGGGTACACCGGAACACACAACCTG
TCCCTGAAAGCTATCAATCTGATTCTGGATGAGCTGTGGCATACAAACGACAATCAGATTGCAATCTTTAACCGGCTGAAGCTG
GTCCCAAAAAAGGTGGACCTGAGTCAGCAGAAAGAGATCCCAACCACACTGGTGGACGATTTCATTCTGTCACCCGTGGTCAAG
CGGAGCTTCATCCAGAGCATCAAAGTGATCAACGCCATCATCAAGAAGTACGGCCTGCCCAATGATATCATTATCGAGCTGGCT
AGGGAGAAGAACAGCAAGGACGCACAGAAGATGATCAATGAGATGCAGAAACGAAACCGGCAGACCAATGAACGCATTGAAGAG
ATTATCCGAACTACCGGGAAAGAGAACGCAAAGTACCTGATTGAAAAAATCAAGCTGCACGATATGCAGGAGGGAAAGTGTCTG
TATTCTCTGGAGGCCATCCCCCTGGAGGACCTGCTGAACAATCCATTCAACTACGAGGTCGATCATATTATCCCCAGAAGCGTG
TCCTTCGACAATTCCTTTAACAACAAGGTGCTGGTCAAGCAGGAAGAGAACTCTAAAAAGGGCAATAGGACTCCTTTCCAGTAC
CTGTCTAGTTCAGATTCCAAGATCTCTTACGAAACCTTTAAAAAGCACATTCTGAATCTGGCCAAAGGAAAGGGCCGCATCAGC
AAGACCAAAAAGGAGTACCTGCTGGAAGAGCGGGACATCAACAGATTCTCCGTCCAGAAGGATTTTATTAACCGGAATCTGGTG
GACACAAGATACGCTACTCGCGGCCTGATGAATCTGCTGCGATCCTATTTCCGGGTGAACAATCTGGATGTGAAAGTCAAGTCC
ATCAACGGCGGGTTCACATCTTTTCTGAGGCGCAAATGGAAGTTTAAAAAGGAGCGCAACAAAGGGTACAAGCACCATGCCGAA
GATGCTCTGATTATCGCAAATGCCGACTTCATCTTTAAGGAGTGGAAAAAGCTGGACAAAGCCAAGAAAGTGATGGAGAACCAG
ATGTTCGAAGAGAAGCAGGCCGAATCTATGCCCGAAATCGAGACAGAACAGGAGTACAAGGAGATTTTCATCACTCCTCACCAG
ATCAAGCATATCAAGGATTTCAAGGACTACAAGTACTCTCACCGGGTGGATAAAAAGCCCAACAGAGAGCTGATCAATGACACC
CTGTATAGTACAAGAAAAGACGATAAGGGGAATACCCTGATTGTGAACAATCTGAACGGACTGTACGACAAAGATAATGACAAG
CTGAAAAAGCTGATCAACAAAAGTCCCGAGAAGCTGCTGATGTACCACCATGATCCTCAGACATATCAGAAACTGAAGCTGATT
ATGGAGCAGTACGGCGACGAGAAGAACCCACTGTATAAGTACTATGAAGAGACTGGGAACTACCTGACCAAGTATAGCAAAAAG
GATAATGGCCCCGTGATCAAGAAGATCAAGTACTATGGGAACAAGCTGAATGCCCATCTGGACATCACAGACGATTACCCTAAC
AGTCGCAACAAGGTGGTCAAGCTGTCACTGAAGCCATACAGATTCGATGTCTATCTGGACAACGGCGTGTATAAATTTGTGACT
GTCAAGAATCTGGATGTCATCAAAAAGGAGAACTACTATGAAGTGAATAGCAAGTGCTACGAAGAGGCTAAAAAGCTGAAAAAG
ATTAGCAACCAGGCAGAGTTCATCGCCTCCTTTTACAACAACGACCTGATTAAGATCAATGGCGAACTGTATAGGGTCATCGGG

FIG. 9N

GTGAACAATGATCTGCTGAACCGCATTGAAGTGAATATGATTGACATCACTTACCGAGAGTATCTGGAAAACATGAATGATAAG
CGCCCCCCTCGAATTATCAAAACAATTGCCTCTAAGACTCAGAGTATCAAAAAGTACTCAACCGACATTCTGGGAAACCTGTAT
GAGGTGAAGAGCAAAAAGCACCCTCAGATTATCAAAAAGGGCTAAGAATTC

#23
ACCGGTGCCACCATGTACCCATACGATGTTCCAGATTACGCTTCGCCGAAGAAAAAGCGCAAGGTCGAAGCGTCCATGAACAAT
AGCATCAAATCTAAACCTGAAGTGACCATCGGGCTGGACCTGGGAGTGGGAAGCGTGGGGTGGGCAATCGTGGATAACGAAACA
AACATCATTCACCATCTGGGCTCCAGGCTGTTTTCTCAGGCCAAGACTGCTGAGGATCGGAGATCTTTCCGCGGGGTGAGGCGC
CTGATCCGACGGAGAAAATACAAGCTGAAACGATTCGTCAATCTGATTTGGAAGTACAACAGCTATTTCGGCTTCAAGAACAAA
GAGGACATCCTGAACAATTATCAGGAGCAGCAGAAGCTGCACAATACCGTGCTGAACCTGAAATCAGAGGCACTGAATGCCAAG
ATCGATCCTAAAGCACTGAGCTGGATTCTGCACGACTACCTGAAGAACAGAGGCCATTTTTATGAGGACAATAGGGATTTCAAC
GTGTACCCAACAAAGGAGCTGGCCAAGTACTTCGATAAGTACGGGTACTACAAGGGAATCATTGACAGCAAGGAGGACAATGAT
AACAAACTGGAGGAAGAGCTGACAAAGTACAAATTCTCCAATAAGCACTGGCTGGAAGAGGTGAAGAAAGTCCTGTCTAACCAG
ACTGGCCTGCCAGAAAAGTTTAAAGAAGAGTATGAGTCACTGTTCAGCTACGTGAGAAATTATTCAGAGGGCCCAGGGAGCATC
AACTCTGTCAGTCCCTACGGGATCTACCATCTGGACGAAAAAGAGGGAAAGGTGGTCCAGAAGTACAACAACATCTGGGATAAG
ACAATCGGAAAGTGCAACATCTTCCCTGACGAGTATAGAGCTCCCAAGAACAGTCCTATCGCAATGATTTTCAATGAAATCAAC
GAGCTGTCCACAATCAGGTCATACAGCATCTACCTGACTGGCTGGTTCATTAATCAGGAGTTCAAGAAAGCCTACCTGAACAAG
CTGCTGGATCTGCTGATCAAAACCAACGGAGAGAAGCCAATTGACGCAAGGCAGTTCAAGAAACTGCGCGAAGAGACAATCGCC
GAAAGCATTGGCAAAGAGACACTGAAGGATGTGGAGAATGAAGAGAAACTGGAAAAGGAGGACCACAAGTGGAAACTGAAGGGA
CTGAAGCTGAATACCAACGGCAAAATCCAGTACAACGATCTGAGCTCCCTGGCTAAGTTTGTGCACAAACTGAAGCAGCATCTG
AAACTGGATTTCCTGCTGGAGGACCAGTATGCAACACTGGACAAGATCAATTTCCTGCAGTCCCTGTTTGTGTACCTGGGCAAG
CACCTGAGATATTCCAATAGGGTCGATTCTGCCAACCTGAAGGAATTTTCCGACTCTAACAAACTGTTCGAGCGCATCCTGCAG
AAACAGAAGGATGGGCTGTTCAAGCTGTTTGAACAGACTGACAAAGACGATGAGAAGATCCTGGCCCAGACACATAGTCTGTCA
ACTAAGGCCATGCTGCTGGCTATTACCCGGATGACAAATCTGGACAACGATGAGGACAACCAGAAAAACAATGACAAGGGCTGG
AATTTTGAGGCCATCAAAAACTTCGATCAGAAGTTTATCGACATCACCAAGAAAAACAACAACCTGAGCCTGAAACAGAATAAG
CGCTACCTGGACGATCGATTCATCAACGATGCTATTCTGTCCCCTGGGGTGAAGCGAATCCTGCGGGAGGCAACCAAGGTCTTT
AATGCCATTCTGAAACAGTTCTCTGAAGAGTACGACGTGACAAAGGTGGTCATCGAACTGGCTCGCGAGCTGAGCGAAGAGAAG
GAACTGGAGAACACAAAGAACTACAAGAAACTGATCAAGAAAAACGGCGACAAGATTAGTGAGGGCCTGAAAGCACTGGGGATC
TCAGAAGATGAGATCAAAGACATTCTGAAGAGTCCCACTAAATCATACAAGTTTCTGCTGTGGCTGCAGCAGGACCACATCGAT
CCTTATAGCCTGAAGGAGATCGCCTTCGACGATATTTTTACCAAAACAGAAAAGTTCGAGATCGACCATATCATTCCCTACAGC
ATTTCCTTCGACGATTCTAGTTCAAACAAGCTGCTGGTGCTGGCTGAAAGTAATCAGGCAAAGTCAAACCAGACTCCTTATGAG
TTCATCAGCTCCGGAAACGCAGGCATTAAGTGGGAAGATTACGAGGCCTATTGCCGCAAGTTCAAGGATGGGGACTCTAGTCTG
CTGGACAGCACCCAGCGGTCCAAGAAATTCGCCAAAATGATGAAAACCGATACCTCAAGCAAGTACGACATCGGATTTCTGGCT
CGAAATCTGAACGATACTCGGTACGCAACCATTGTGTTCCGGGACGCCCTGGAGGACTATGCTAATAACCACCTGGTCGAGGAC
AAACCCATGTTTAAGGTGGTCTGTATCAATGGGTCCGTGACCTCTTTCCTGCGGAAGAACTTTGACGATTCCTCTTACGCCAAG
AAAGATAGAGACAAGAATATCCACCATGCTGTGGATGCAAGTATCATCTCAATTTTCAGCAACGAGACAAAGACTCTGTTCAAC
CAGCTGACTCAGTTTGCTGACTATAAACTGTTCAAGAACACCGATGGCAGCTGGAAGAAAATCGACCCTAAGACAGGGGTGGTC
ACTGAAGTGACCGACGAGAATTGGAAGCAGATTAGGGTGCGCAACCAGGTGAGCGAAATCGCCAAAGTCATTGAGAAGTACATC
CAGGATAGCAACATCGAAAGAAAGGCTAGGTATTCCCGCAAAATCGAGAATAAGACTAACATTTCCCTGTTTAATGACACCGTG
TACTCTGCCAAGAAAGTCGGCTATGAGGATCAGATCAAAAGAAAGAACCTGAAAACCCTGGACATTCACGAATCTGCTAAAGAG
AATAAGAACAGTAAAGTGAAGCGGCAGTTTGTCTACAGAAAGCTGGTGAATGTCAGCCTGCTGAATAACGATAAGCTGGCAGAC
CTGTTCGCCGAAAAAGAGGATATCCTGATGTATAGGGCCAATCCATGGGTCATCAACCTGGCTGAGCAGATTTTCAATGAATAC
ACTGAGAACAAGAAAATCAAGTCCCAGAACGTGTTTGAAAAATATATGCTGGACCTGACCAAAGAGTTCCCCGAGAAGTTCAGC
GAGTTTCTGGTGAAGTCCATGCTGAGAAACAAGACCGCCATCATCTACGACGATAAGAAAAACATTGTCCATCGAATCAAACGG
CTGAAGATGCTGAGTTCAGAACTGAAAGAGAATAAGCTGTCTAACGTGATCATTAGGTCTAAGAATCAGAGTGGGACCAAACTG
TCATACCAGGATACAATCAACAGCCTGGCCCTGATGATTATGCGCAGCATCGACCCTACTGCTAAGAAACAGTATATTCGAGTG
CCACTGAATACCCTGAACCTGCACCTGGGAGATCATGACTTTGATCTGCACAATATGGATGCTTACCTGAAGAAACCAAAATTC
GTGAAGTATCTGAAAGCAAACGAAATCGGCGACGAGTACAAGCCCTGGAGGGTCCTGACATCTGGCACTCTGCTGATCCATAAG
AAGGATAAGAAACTGATGTACATCAGCTCCTTCCAGAATCTGAACGACGTGATCGAAATTAAGAATCTGATCGAAACCGAGTAT
AAAGAGAACGACGATTCTGATAGTAAGAAAAAGAAAAAGGCAAACCGCTTTCTGATGACCCTGAGCACAATCCTGAATGACTAC
ATTCTGCTGGACGCCAAGGATAACTTCGACATCCTGGGGCTGTCTAAAAATCGGATCGATGAGATTCTGAACAGTAAGCTGGGA
CTGGACAAGATTGTGAAATAAGAATTC

#24
ACCGGTGCCACCATGTACCCATACGATGTTCCAGATTACGCTTCGCCGAAGAAAAAGCGCAAGGTCGAAGCGTCCATGAGGATT
CTGGGGTTTGACATTGGCATTAACAGCATCGGGTGGGCTTTTGTGGAGAACGACGAACTGAAGGACTGCGGAGTGCGGATCTTC
ACAAAGGCCGAGAACCCAAAAAATAAGGAAAGCCTGGCACTGCCCCGGAGAAATGCACGCAGCTCCAGGCGCCGACTGAAACGG
AGAAAGGCCCGGCTGATCGCTATTAAGAGAATCCTGGCCAAAGAGCTGAAGCTGAACTACAAGGACTATGTCGCAGCTGATGGA
GAGCTGCCAAAGGCCTACGAAGGATCCCTGGCATCTGTGTACGAGCTGCGGTATAAGGCCCTGACACAGAACCTGGAAACTAAA
GATCTGGCCAGAGTGATCCTGCACATTGCTAAGCATAGGGGGTACATGAACAAGAACGAGAAGAAATCAAACGACGCTAAGAAA
GGAAAGATCCTGAGCGCTCTGAAAAACAATGCACTGAAGCTGGAGAACTACCAGAGCGTGGGCGAATACTTCTACAAGGAGTTC
TTTCAGAAATACAAGAAAAACACAAAGAACTTCATCAAGATCCGCAACACTAAGGATAATTACAACAATTGCGTGCTGTCTAGT
GACCTGGAAAAAGAGCTGAAGCTGATCCTGGAAAAACAGAAGGAGTTCGGCTACAACTACTCTGAAGATTTCATCAACGAGATT

FIG. 9O

CTGAAGGTCGCCTTCTTTCAGCGGCCCCTGAAGGACTTCAGTCACCTGGTGGGGGCCTGCACTTTCTTTGAGGAAGAGAAAAGG
GCCTGTAAGAACAGCTACTCTGCCTGGGAGTTTGTGGCTCTGACCAAGATCATTAACGAGATCAAGAGCCTGGAGAAGATCAGC
GGCGAAATTGTGCCAACCCAGACAATCAACGAGGTCCTGAATCTGATCCTGGACAAGGGGTCTATCACCTACAAGAAATTCAGA
AGTTGTATCAATCTGCATGAGAGTATCAGCTTCAAGAGCCTGAAGTATGATAAAGAAAACGCCGAGAATGCTAAACTGATCGAC
TTCCGCAAGCTGGTGGAGTTTAAGAAAGCCCTGGGAGTCCACAGCCTGTCCCGGCAGGAACTGGATCAGATCTCCACTCATATC
ACCCTGATTAAGGACAACGTGAAGCTGAAAACCGTCCTGGAGAAATACAACCTGAGTAATGAACAGATCAACAATCTGCTGGAA
ATTGAGTTCAACGATTATATCAACCTGAGCTTCAAGGCCCTGGGAATGATTCTGCCACTGATGCGCGAGGGCAAACGATACGAC
GAGGCCTGCGAGATCGCCAATCTGAAACCTAAGACCGTGGACGAGAAGAAAGATTTCCTGCCAGCATTTTGTGATTCCATTTTC
GCCCACGAGCTGTCTAACCCCGTGGTCAATAGGGCTATCAGCGAATACCGCAAGGTGCTGAACGCACTGCTGAAGAAATATGGA
AAGGTCCACAAAATTCATCTGGAGCTGGCTCGCGACGTGGGCCTGTCCAAGAAAGCACGAGAGAAGATCGAAAAAGAGCAGAAG
GAAAACCAGGCCGTGAATGCATGGGCCCTGAAGGAATGCGAGAATATTGGCCTGAAGGCCAGCGCAAAGAACATCCTGAAACTG
AAGCTGTGGAAAGAACAGAAGGAGATCTGTATCTACTCCGGAAATAAGATCTCTATTGAGCACCTGAAAGATGAAAAGGCCCTG
GAGGTGGACCATATCTACCCCTATTCTAGGAGTTTCGACGATTCTTTTATCAACAAAGTGCTGGTGTTCACCAAGGAAAATCAG
GAGAAACTGAACAAGACACCTTTCGAGGCCTTTGGCAAGAATATTGAAAAATGGAGCAAGATCCAGACCCTGGCTCAGAACCTG
CCATACAAGAAAAAGAATAAGATTCTGGACGAGAACTTCAAAGATAAGCAGCAGGAGGACTTTATCTCTCGAAATCTGAACGAC
ACCCGGTATATCGCTACACTGATTGCAAAATACACAAAGGAGTATCTGAACTTCCTGCTGCTGAGCGAAAATGAGAACGCCAAT
CTGAAGAGTGGCGAAAAAGGGTCAAAGATCCACGTGCAGACTATTAGCGGGATGCTGACCTCCGTCCTGAGGCACACATGGGGG
TTTGACAAAAAGGATCGCAACAATCATCTGCACCATGCACTGGATGCCATCATTGTGGCCTACAGTACAAATTCAATCATTAAG
GCTTTCAGCGATTTCCGGAAAAACCAGGAGCTGCTGAAGGCCAGATTCTACGCTAAAGAACTGACTTCCGATAACTATAAACAT
CAGGTCAAGTTCTTTGAGCCTTTCAAGAGTTTTAGAGAAAAAATCCTGTCAAAGATCGACGAGATTTTCGTGTCCAAACCACCT
CGAAAGCGAGCTAGGCGCGCACTGCACAAGGATACCTTTCATTCTGAGAACAAGATCATTGACAAGTGCAGCTACAACTCCAAG
GAAGGCCTGCAGATTGCCCTGAGCTGTGGAAGAGTGAGGAAAATCGGCACTAAGTATGTCGAGAATGATACCATCGTGAGGGTC
GACATTTTCAAAAAGCAGAACAAGTTTTACGCTATCCCAATCTACGCAATGGATTTTGCCCTGGGGATCCTGCCCAATAAGATC
GTGATTACTGGAAAAGATAAGAACAATAACCCCAAACAGTGGCAGACCATTGACGAATCATACGAGTTCTGCTTTAGCCTGTAT
AAGAATGACCTGATCCTGCTGCAGAAAAAGAACATGCAGGAACCTGAGTTCGCCTACTATAACGATTTTTCAATCAGCACATCA
AGCATTTGTGTGGAGAAACACGACAACAAGTTCGAAAATCTGACTAGCAACCAGAAGCTGCTGTTTTCCAATGCAAAAGAGGGC
TCTGTGAAGGTCGAAAGTCTGGGGATCCAGAACCTGAAAGTGTTCGAGAAGTACATCATTACCCCCCTGGGAGATAAAATTAAG
GCTGACTTTCAGCCTCGAGAAAACATCAGCCTGAAAACCAGTAAAAAGTATGGCCTGAGGTAAGAATTC hSpCas9

```
5'  CTGGAAGAGTCCTTCCTGGTGGAAGAGGATAAGAAGCACGAGCGGCACCCCATCTTCGGC
                                                                    360
                              hSpCas9
    L   E   E   S   F   L   V   E   E   D   K   K   H   E   R   H   P   I   F   G
    101 102 103 104 105 106 107 108 109 110 111 112 113 114 115 116 117 118 119 120

5'  AACATCGTGGACGAGGTGGCCTACCACGAGAAGTACCCCACCATCTACCACCTGAGAAAG
                                                                    420
                              hSpCas9
    N   I   V   D   E   V   A   Y   H   E   K   Y   P   T   I   Y   H   L   R   K
    121 122 123 124 125 126 127 128 129 130 131 132 133 134 135 136 137 138 139 140

5'  AAACTGGTGGACAGCACCGACAAGGCCGACCTGCGGCTGATCTATCTGGCCCTGGCCCAC
                                                                    480
                              hSpCas9
    K   L   V   D   S   T   D   K   A   D   L   R   L   I   Y   L   A   L   A   H
    141 142 143 144 145 146 147 148 149 150 151 152 153 154 155 156 157 158 159 160

5'  ATGATCAAGTTCCGGGGCCACTTCCTGATCGAGGGCGACCTGAACCCCGACAACAGCGAC
                                                                    540
                              hSpCas9
    M   I   K   F   R   G   H   F   L   I   E   G   D   L   N   P   D   N   S   D
    161 162 163 164 165 166 167 168 169 170 171 172 173 174 175 176 177 178 179 180

5'  GTGGACAAGCTGTTCATCCAGCTGGTGCAGACCTACAACCAGCTGTTCGAGGAAAACCCC
                                                                    600
                              hSpCas9
    V   D   K   L   F   I   Q   L   V   Q   T   Y   N   Q   L   F   E   E   N   P
    181 182 183 184 185 186 187 188 189 190 191 192 193 194 195 196 197 198 199 200

5'  ATCAACGCCAGCGGCGTGGACGCCAAGGCCATCCTGTCTGCCAGACTGAGCAAGAGCAGA
                                                                    660
                              hSpCas9
    I   N   A   S   G   V   D   A   K   A   I   L   S   A   R   L   S   K   S   R
    201 202 203 204 205 206 207 208 209 210 211 212 213 214 215 216 217 218 219 220
```

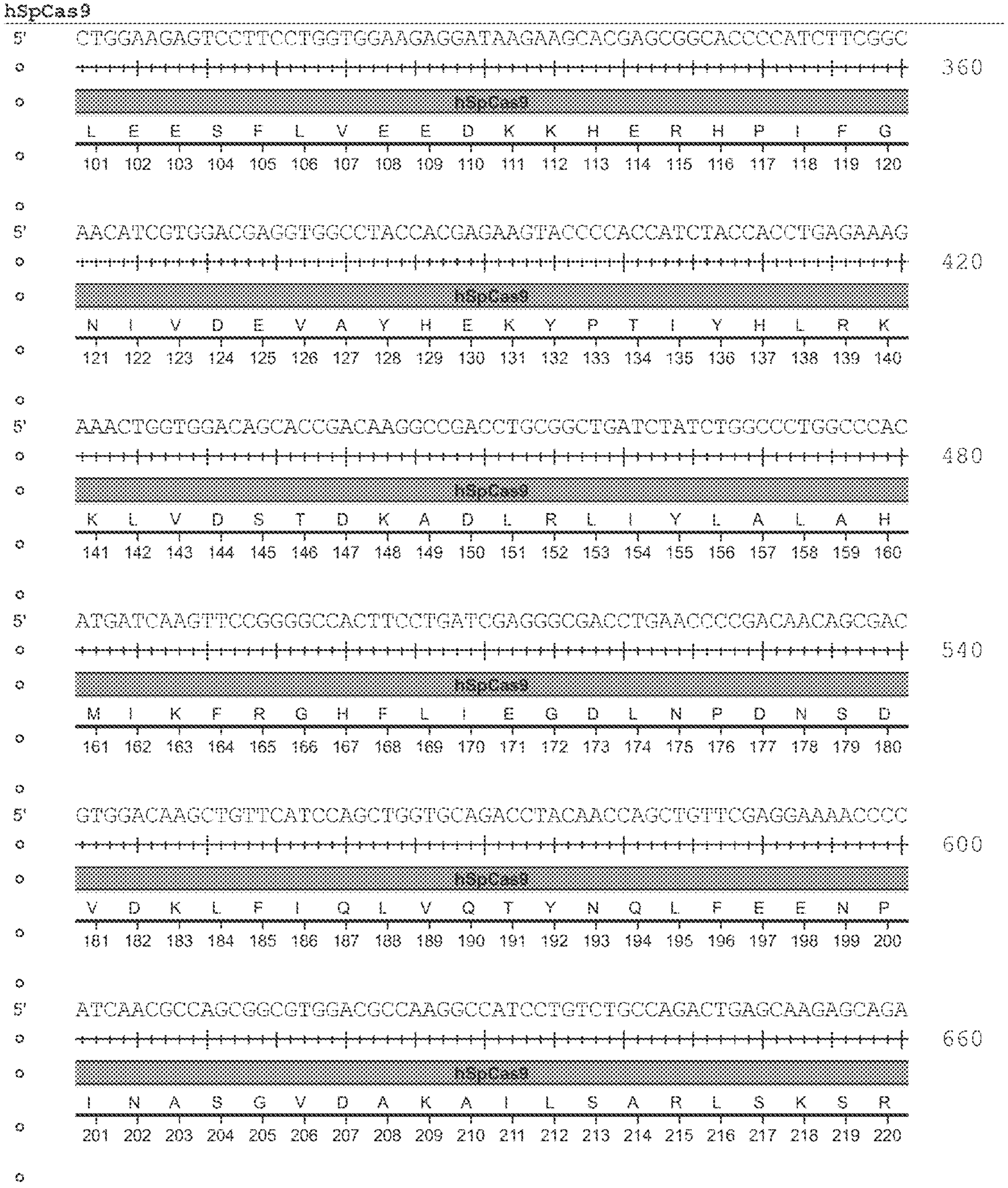

FIG. 10B hSpCas9

5' CGGCTGGAAAATCTGATCGCCCAGCTGCCCGGCGAGAAGAAGAATGGCCTGTTCGGCAAC 720 hSpCas9

R L E N L I A Q L P G E K K N G L F G N 221 222 223 224 225 226 227 228 229 230 231 232 233 234 235 236 237 238 239 240

5' CTGATTGCCCTGAGCCTGGGCCTGACCCCCAACTTCAAGAGCAACTTCGACCTGGCCGAG 780 hSpCas9

L I A L S L G L T P N F K S N F D L A E 241 242 243 244 245 246 247 248 249 250 251 252 253 254 255 256 257 258 259 260

5' GATGCCAAACTGCAGCTGAGCAAGGACACCTACGACGACGACCTGGACAACCTGCTGGCC 840 hSpCas9

D A K L Q L S K D T Y D D D L D N L L A 261 262 263 264 265 266 267 268 269 270 271 272 273 274 275 276 277 278 279 280

5' CAGATCGGCGACCAGTACGCCGACCTGTTTCTGGCCGCCAAGAACCTGTCCGACGCCATC 900 hSpCas9

Q I G D Q Y A D L F L A A K N L S D A I 281 282 283 284 285 286 287 288 289 290 291 292 293 294 295 296 297 298 299 300

5' CTGCTGAGCGACATCCTGAGAGTGAACACCGAGATCACCAAGGCCCCCCTGAGCGCCTCT 960 hSpCas9

L L S D I L R V N T E I T K A P L S A S 301 302 303 304 305 306 307 308 309 310 311 312 313 314 315 316 317 318 319 320

5' ATGATCAAGAGATACGACGAGCACCACCAGGACCTGACCCTGCTGAAAGCTCTCGTGCGG 1020 hSpCas9

M I K R Y D E H H Q D L T L L K A L V R 321 322 323 324 325 326 327 328 329 330 331 332 333 334 335 336 337 338 339 340

FIG. 10C hSpCas9

5' CAGCAGCTGCCTGAGAAGTACAAAGAGATTTTCTTCGACCAGAGCAAGAACGGCTACGCC 1080 hSpCas9

Q Q L P E K Y K E I F F D Q S K N G Y A 341 342 343 344 345 346 347 348 349 350 351 352 353 354 355 356 357 358 359 360

5' GGCTACATTGACGGCGGAGCCAGCCAGGAAGAGTTCTACAAGTTCATCAAGCCCATCCTG 1140 hSpCas9

G Y I D G G A S Q E E F Y K F I K P I L 361 362 363 364 365 366 367 368 369 370 371 372 373 374 375 376 377 378 379 380

5' GAAAAGATGGACGGCACCGAGGAACTGCTCGTGAAGCTGAACAGAGAGGACCTGCTGCGG 1200 hSpCas9

E K M D G T E E L L V K L N R E D L L R 381 382 383 384 385 386 387 388 389 390 391 392 393 394 395 396 397 398 399 400

5' AAGCAGCGGACCTTCGACAACGGCAGCATCCCCCACCAGATCCACCTGGGAGAGCTGCAC 1260 hSpCas9

K Q R T F D N G S I P H Q I H L G E L H 401 402 403 404 405 406 407 408 409 410 411 412 413 414 415 416 417 418 419 420

5' GCCATTCTGCGGCGGCAGGAAGATTTTTACCCATTCCTGAAGGACAACCGGGAAAAGATC 1320 hSpCas9

A I L R R Q E D F Y P F L K D N R E K I 421 422 423 424 425 426 427 428 429 430 431 432 433 434 435 436 437 438 439 440

5' GAGAAGATCCTGACCTTCCGCATCCCCTACTACGTGGGCCCTCTGGCCAGGGGAAACAGC 1380 hSpCas9

E K I L T F R I P Y Y V G P L A R G N S 441 442 443 444 445 446 447 448 449 450 451 452 453 454 455 456 457 458 459 460

FIG. 10D hSpCas9

5' AGATTCGCCTGGATGACCAGAAAGAGCGAGGAAACCATCACCCCCTGGAACTTCGAGGAA 1440 hSpCas9

R F A W M T R K S E E T I T P W N F E E 461 462 463 464 465 466 467 468 469 470 471 472 473 474 475 476 477 478 479 480

5' GTGGTGGACAAGGGCGCTTCCGCCCAGAGCTTCATCGAGCGGATGACCAACTTCGATAAG 1500 hSpCas9

V V D K G A S A Q S F I E R M T N F D K 481 482 483 484 485 486 487 488 489 490 491 492 493 494 495 496 497 498 499 500

5' AACCTGCCCAACGAGAAGGTGCTGCCCAAGCACAGCCTGCTGTACGAGTACTTCACCGTG 1560 hSpCas9

N L P N E K V L P K H S L L Y E Y F T V 501 502 503 504 505 506 507 508 509 510 511 512 513 514 515 516 517 518 519 520

5' TATAACGAGCTGACCAAAGTGAAATACGTGACCGAGGGAATGAGAAAGCCCGCCTTCCTG 1620 hSpCas9

Y N E L T K V K Y V T E G M R K P A F L 521 522 523 524 525 526 527 528 529 530 531 532 533 534 535 536 537 538 539 540

5' AGCGGCGAGCAGAAAAAGGCCATCGTGGACCTGCTGTTCAAGACCAACCGGAAAGTGACC 1680 hSpCas9

S G E Q K K A I V D L L F K T N R K V T 541 542 543 544 545 546 547 548 549 550 551 552 553 554 555 556 557 558 559 560

5' GTGAAGCAGCTGAAAGAGGACTACTTCAAGAAAATCGAGTGCTTCGACTCCGTGGAAATC 1740 hSpCas9

V K Q L K E D Y F K K I E C F D S V E I 561 562 563 564 565 566 567 568 569 570 571 572 573 574 575 576 577 578 579 580

FIG. 10E hSpCas9

5' TCCGGCGTGGAAGATCGGTTCAACGCCTCCCTGGGCACATACCACGATCTGCTGAAAATT 1800 hSpCas9

S G V E D R F N A S L G T Y H D L L K I 581 582 583 584 585 586 587 588 589 590 591 592 593 594 595 596 597 598 599 600

5' ATCAAGGACAAGGACTTCCTGGACAATGAGGAAAACGAGGACATTCTGGAAGATATCGTG 1860 hSpCas9

I K D K D F L D N E E N E D I L E D I V 601 602 603 604 605 606 607 608 609 610 611 612 613 614 615 616 617 618 619 620

5' CTGACCCTGACACTGTTTGAGGACAGAGAGATGATCGAGGAACGGCTGAAAACCTATGCC 1920 hSpCas9

L T L T L F E D R E M I E E R L K T Y A 621 622 623 624 625 626 627 628 629 630 631 632 633 634 635 636 637 638 639 640

5' CACCTGTTCGACGACAAAGTGATGAAGCAGCTGAAGCGGCGGAGATACACCGGCTGGGGC 1980 hSpCas9

H L F D D K V M K Q L K R R R Y T G W G 641 642 643 644 645 646 647 648 649 650 651 652 653 654 655 656 657 658 659 660

5' AGGCTGAGCCGGAAGCTGATCAACGGCATCCGGGACAAGCAGTCCGGCAAGACAATCCTG 2040 hSpCas9

R L S R K L I N G I R D K Q S G K T I L 661 662 663 664 665 666 667 668 669 670 671 672 673 674 675 676 677 678 679 680

5' GATTTCCTGAAGTCCGACGGCTTCGCCAACAGAAACTTCATGCAGCTGATCCACGACGAC 2100 hSpCas9

D F L K S D G F A N R N F M Q L I H D D 681 682 683 684 685 686 687 688 689 690 691 692 693 694 695 696 697 698 699 700

FIG. 10F hSpCas9

```
5'  AGCCTGACCTTTAAAGAGGACATCCAGAAAGCCCAGGTGTCCGGCCAGGGCGATAGCCTG   2160
        S  L  T  F  K  E  D  I  Q  K  A  Q  V  S  G  Q  G  D  S  L
        701 702 703 704 705 706 707 708 709 710 711 712 713 714 715 716 717 718 719 720

5'  CACGAGCACATTGCCAATCTGGCCGGCAGCCCCGCCATTAAGAAGGGCATCCTGCAGACA   2220
        H  E  H  I  A  N  L  A  G  S  P  A  I  K  K  G  I  L  Q  T
        721 722 723 724 725 726 727 728 729 730 731 732 733 734 735 736 737 738 739 740

5'  GTGAAGGTGGTGGACGAGCTCGTGAAAGTGATGGGCCGGCACAAGCCCGAGAACATCGTG   2280
        V  K  V  V  D  E  L  V  K  V  M  G  R  H  K  P  E  N  I  V
        741 742 743 744 745 746 747 748 749 750 751 752 753 754 755 756 757 758 759 760

5'  ATCGCCATGGCCAGAGAGAACCAGACCACCCAGAAGGGACAGAAGAACAGCCGCGAGAGA   2340
        I  A  M  A  R  E  N  Q  T  T  Q  K  G  Q  K  N  S  R  E  R
        761 762 763 764 765 766 767 768 769 770 771 772 773 774 775 776 777 778 779 780

5'  ATGAAGCGGATCGAAGAGGGCATCAAAGAGCTGGGCAGCCAGATCCTGAAAGAACACCCC   2400
        M  K  R  I  E  E  G  I  K  E  L  G  S  Q  I  L  K  E  H  P
        781 782 783 784 785 786 787 788 789 790 791 792 793 794 795 796 797 798 799 800
```

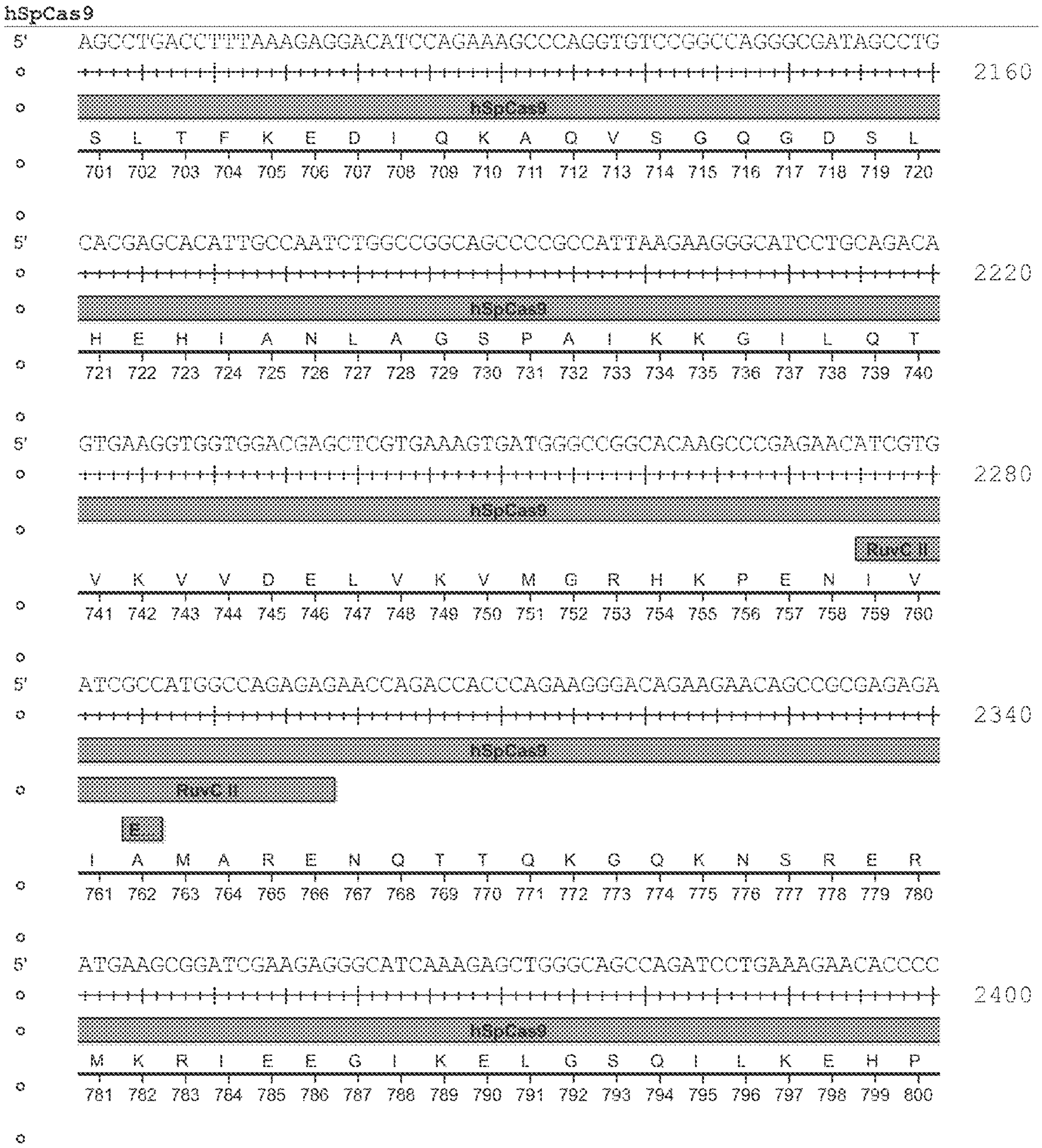

FIG. 10G hSpCas9

```
5'  GTGGAAAACACCCAGCTGCAGAACGAGAAGCTGTACCTGTACTACCTGCAGAATGGGCGG
                                                                        2460
                              hSpCas9
     V   E   N   T   Q   L   Q   N   E   K   L   Y   L   Y   Y   L   Q   N   G   R
    801 802 803 804 805 806 807 808 809 810 811 812 813 814 815 816 817 818 819 820

5'  GATATGTACGTGGACCAGGAACTGGACATCAACCGGCTGTCCGACTACGATGTGGACGCC
                                                                        2520
                              hSpCas9
                                                              HNH
                                                                    H
     D   M   Y   V   D   Q   E   L   D   I   N   R   L   S   D   Y   D   V   D   A
    821 822 823 824 825 826 827 828 829 830 831 832 833 834 835 836 837 838 839 840

5'  ATCGTGCCTCAGAGCTTTCTGAAGGACGACTCCATCGACGCCAAGGTGCTGACCAGAAGC
                                                                        2580
                              hSpCas9
                              HNH
                                              N
     I   V   P   Q   S   F   L   K   D   D   S   I   D   A   K   V   L   T   R   S
    841 842 843 844 845 846 847 848 849 850 851 852 853 854 855 856 857 858 859 860

5'  GACAAGGCCCGGGGCAAGAGCGACAACGTGCCCTCCGAAGAGGTCGTGAAGAAGATGAAG
                                                                        2640
                              hSpCas9
         HNH
          N
     D   K   A   R   G   K   S   D   N   V   P   S   E   E   V   V   K   K   M   K
    861 862 863 864 865 866 867 868 869 870 871 872 873 874 875 876 877 878 879 880

5'  AACTACTGGCGGCAGCTGCTGAACGCCAAGCTGATTACCCAGAGAAAGTTCGACAATCTG
                                                                        2700
                              hSpCas9
     N   Y   W   R   Q   L   L   N   A   K   L   I   T   Q   R   K   F   D   N   L
    881 882 883 884 885 886 887 888 889 890 891 892 893 894 895 896 897 898 899 900
```

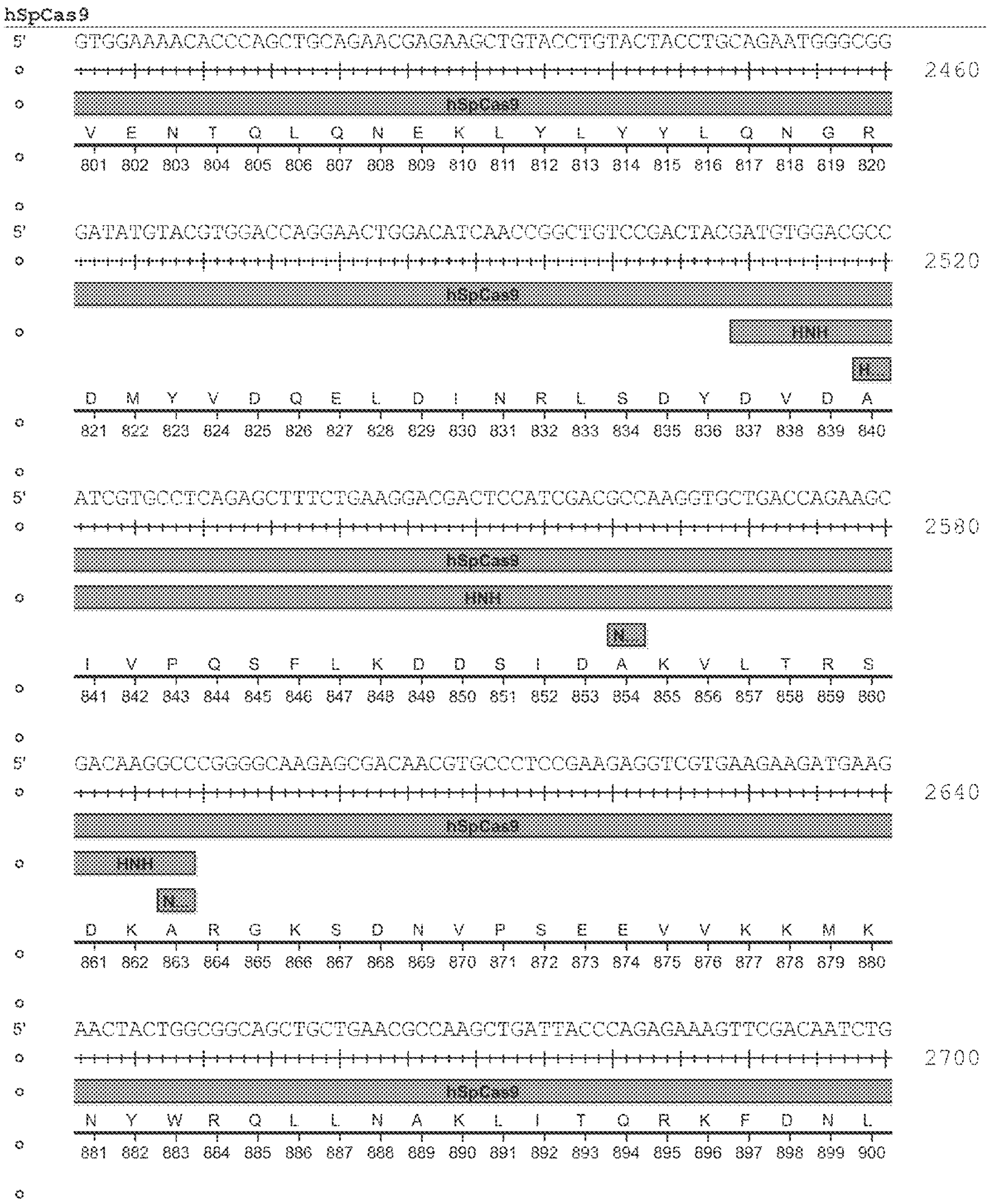

FIG. 10H hSpCas9

5' ACCAAGGCCGAGAGAGGCGGCCTGAGCGAACTGGATAAGGCCGGCTTCATCAAGAGACAG 2760 hSpCas9

T K A E R G G L S E L D K A G F I K R Q 901 902 903 904 905 906 907 908 909 910 911 912 913 914 915 916 917 918 919 920

5' CTGGTGGAAACCCGGCAGATCACAAAGCACGTGGCACAGATCCTGGACTCCCGGATGAAC 2820 hSpCas9

L V E T R Q I T K H V A Q I L D S R M N 921 922 923 924 925 926 927 928 929 930 931 932 933 934 935 936 937 938 939 940

5' ACTAAGTACGACGAGAATGACAAGCTGATCCGGGAAGTGAAAGTGATCACCCTGAAGTCC 2880 hSpCas9

T K Y D E N D K L I R E V K V I T L K S 941 942 943 944 945 946 947 948 949 950 951 952 953 954 955 956 957 958 959 960

5' AAGCTGGTGTCCGATTTCCGGAAGGATTTCCAGTTTTACAAAGTGCGCGAGATCAACAAC 2940 hSpCas9

K L V S D F R K D F Q F Y K V R E I N N 961 962 963 964 965 966 967 968 969 970 971 972 973 974 975 976 977 978 979 980

5' TACCACCACGCCCACGCCGCCTACCTGAACGCCGTCGTGGGAACCGCCCTGATCAAAAAG 3000 hSpCas9

RuvC III

D...

Y H H A H A A Y L N A V V G T A L I K K 981 982 983 984 985 986 987 988 989 990 991 992 993 994 995 996 997 998 999 1000

FIG. 10I hSpCas9

5' TACCCTAAGCTGGAAAGCGAGTTCGTGTACGGCGACTACAAGGTGTACGACGTGCGGAAG 3060 hSpCas9

Y P K L E S E F V Y G D Y K V Y D V R K 1001 1002 1003 1004 1005 1006 1007 1008 1009 1010 1011 1012 1013 1014 1015 1016 1017 1018 1019 1020

5' ATGATCGCCAAGAGCGAGCAGGAAATCGGCAAGGCTACCGCCAAGTACTTCTTCTACAGC 3120 hSpCas9

M I A K S E Q E I G K A T A K Y F F Y S 1021 1022 1023 1024 1025 1026 1027 1028 1029 1030 1031 1032 1033 1034 1035 1036 1037 1038 1039 1040

5' AACATCATGAACTTTTTCAAGACCGAGATTACCCTGGCCAACGGCGAGATCCGGAAGCGG 3180 hSpCas9

N I M N F F K T E I T L A N G E I R K R 1041 1042 1043 1044 1045 1046 1047 1048 1049 1050 1051 1052 1053 1054 1055 1056 1057 1058 1059 1060

5' CCTCTGATCGAGACAAACGGCGAAACCGGGGAGATCGTGTGGGATAAGGGCCGGGATTTT 3240 hSpCas9

P L I E T N G E T G E I V W D K G R D F 1061 1062 1063 1064 1065 1066 1067 1068 1069 1070 1071 1072 1073 1074 1075 1076 1077 1078 1079 1080

5' GCCACCGTGCGGAAAGTGCTGAGCATGCCCCAAGTGAATATCGTGAAAAAGACCGAGGTG 3300 hSpCas9

A T V R K V L S M P Q V N I V K K T E V 1081 1082 1083 1084 1085 1086 1087 1088 1089 1090 1091 1092 1093 1094 1095 1096 1097 1098 1099 1100

5' CAGACAGGCGGCTTCAGCAAAGAGTCTATCCTGCCCAAGAGGAACAGCGATAAGCTGATC 3360 hSpCas9

Q T G G F S K E S I L P K R N S D K L I 1101 1102 1103 1104 1105 1106 1107 1108 1109 1110 1111 1112 1113 1114 1115 1116 1117 1118 1119 1120

FIG. 10J hSpCas9

5' GCCAGAAAGAAGGACTGGGACCCTAAGAAGTACGGCGGCTTCGACAGCCCCACCGTGGCC 3420 hSpCas9

A R K K D W D P K K Y G G F D S P T V A 1121 1122 1123 1124 1125 1126 1127 1128 1129 1130 1131 1132 1133 1134 1135 1136 1137 1138 1139 1140

5' TATTCTGTGCTGGTGGTGGCCAAAGTGGAAAAGGGCAAGTCCAAGAAACTGAAGAGTGTG 3480 hSpCas9

Y S V L V V A K V E K G K S K K L K S V 1141 1142 1143 1144 1145 1146 1147 1148 1149 1150 1151 1152 1153 1154 1155 1156 1157 1158 1159 1160

5' AAAGAGCTGCTGGGGATCACCATCATGGAAAGAAGCAGCTTCGAGAAGAATCCCATCGAC 3540 hSpCas9

K E L L G I T I M E R S S F E K N P I D 1161 1162 1163 1164 1165 1166 1167 1168 1169 1170 1171 1172 1173 1174 1175 1176 1177 1178 1179 1180

5' TTTCTGGAAGCCAAGGGCTACAAAGAAGTGAAAAAGGACCTGATCATCAAGCTGCCTAAG 3600 hSpCas9

F L E A K G Y K E V K K D L I I K L P K 1181 1182 1183 1184 1185 1186 1187 1188 1189 1190 1191 1192 1193 1194 1195 1196 1197 1198 1199 1200

5' TACTCCCTGTTCGAGCTGGAAAACGGCCGGAAGAGAATGCTGGCCTCTGCCGGCGAACTG 3660 hSpCas9

Y S L F E L E N G R K R M L A S A G E L 1201 1202 1203 1204 1205 1206 1207 1208 1209 1210 1211 1212 1213 1214 1215 1216 1217 1218 1219 1220

5' CAGAAGGGAAACGAACTGGCCCTGCCCTCCAAATATGTGAACTTCCTGTACCTGGCCAGC 3720 hSpCas9

Q K G N E L A L P S K Y V N F L Y L A S 1221 1222 1223 1224 1225 1226 1227 1228 1229 1230 1231 1232 1233 1234 1235 1236 1237 1238 1239 1240

FIG. 10K hSpCas9

5' CACTATGAGAAGCTGAAGGGCTCCCCCGAGGATAATGAGCAGAAACAGCTGTTTGTGGAA 3780 hSpCas9

H Y E K L K G S P E D N E Q K Q L F V E 1241 1242 1243 1244 1245 1246 1247 1248 1249 1250 1251 1252 1253 1254 1255 1256 1257 1258 1259 1260

5' CAGCACAAGCACTACCTGGACGAGATCATCGAGCAGATCAGCGAGTTCTCCAAGAGAGTG 3840 hSpCas9

Q H K H Y L D E I I E Q I S E F S K R V 1261 1262 1263 1264 1265 1266 1267 1268 1269 1270 1271 1272 1273 1274 1275 1276 1277 1278 1279 1280

5' ATCCTGGCCGACGCTAATCTGGACAAAGTGCTGTCCGCCTACAACAAGCACCGGGATAAG 3900 hSpCas9

I L A D A N L D K V L S A Y N K H R D K 1281 1282 1283 1284 1285 1286 1287 1288 1289 1290 1291 1292 1293 1294 1295 1296 1297 1298 1299 1300

5' CCCATCAGAGAGCAGGCCGAGAATATCATCCACCTGTTTACCCTGACCAATCTGGGAGCC 3960 hSpCas9

P I R E Q A E N I I H L F T L T N L G A 1301 1302 1303 1304 1305 1306 1307 1308 1309 1310 1311 1312 1313 1314 1315 1316 1317 1318 1319 1320

5' CCTGCCGCCTTCAAGTACTTTGACACCACCATCGACCGGAAGAGGTACACCAGCACCAAA 4020 hSpCas9

P A A F K Y F D T T I D R K R Y T S T K 1321 1322 1323 1324 1325 1326 1327 1328 1329 1330 1331 1332 1333 1334 1335 1336 1337 1338 1339 1340

5' GAGGTGCTGGACGCCACCCTGATCCACCAGAGCATCACCGGCCTGTACGAGACACGGATC 4080 hSpCas9

| Species: Corynebacter_diphtheriae | |
|---|---|
| Sequencing Barcode | AGCAATTC |
| ID | 1 |
| **Chimeric Guide RNA** | **NNNNNNNNNNNNNNNNNNNNACUGGGGUUCAGGAAACUGAACCUCAGUAAGCAUUGGCUCGUUUCCAAUG<br>UUGAUUGCUCCGCCGGUGCUCCUUAUUUUUAAGGGCGCCGGCUUUUUU** |
| Cas9 Protein Sequence (wildtype, without NLS added) | MKYHVGIDVGTFSVGLAAIEVDDAGMPIKTLSLVSHIHDSGLDPDEIKSAVTRLASSGIARRTRRLYRRKRRRLQQLDK<br>FIQRQGWPVIELEDYSDPLYPWKVRAELAASYIADEKERGEKLSVALRHIARHRGWRNPYAKVSSLYLPDGPSDAFKA<br>IREEIKRASGQPVPETATVGQMVTLCELGTLKLRGEGGVLSARLQQSDYAREIQEICRMQEIGQELYRKIIDVVFAAESP<br>KGSASSRVGKDPLQPGKNRALKASDAFQRYRIAALIGNLRVRVDGEKRILSVEEKNLVFDHLVNLTPKKEPEWVTIAEI<br>LGIDRGQLIGTATMTDDGERAGARPPTHDTNRSIVNSRIAPLVDWWKTASALEQHAMVKALSNAEVDDFDSPEGAKV<br>QAFFADLDDDVHAKLDSLHLPVGRAAYSEDTLVRLTRRMLSDGVDLYTARLQEFGIEPSWTPPTPRIGEPVGNPAVDR<br>VLKTVSRWLESATKTWGAPERVIIEHVREGFVTEKRAREMDGDMRRRAARNAKLFQEMQEKLNVQGKPSRADLWR<br>YQSVQRQNCQCAYCGSPITFSNSEMDHIVPRAGQGSTNTRENLVAVCHRCNQSKGNTPFAIWAKNTSIEGVSVKEAVE<br>RTRHWVTDTGMRSTDFKKFTKAVVERFQRATMDEEIDARSMESVAWMANELRSRVAQHFASHGTTVRVYRGSLTA<br>EARRASGISGKLKFFDGVGKSRLDRRHHAIDAAVIAFTSDYVAETLAVRSNLKQSQAHRQEAPQWREFTGKDAEHRA<br>AWRVWCQKMEKLSALLTEDLRDDRVVVMSNVRLRLGNGSAHKETIGKLSKVKLSSQLSVSDIDKASSEALWCALTR<br>EPGFDPKEGLPANPERHIRVNGTHVYAGDNIGLFPVSAGSIALRGGYAELGSSFHHARVYKITSGKKPAFAMLRVYTID<br>LLPYRNQDLFSVELKPQTMSMRQAEKKLRDALATGNAEYLGWLVVDDELVVDTSKIATDQVKAVEAELGTIRRWRV<br>DGFFSPSKLRLRPLQMSKEGIKKESAPELSKIIDRPGWLPAVNKLFSDGNVTVVRRDSLGRVRLESTAHLPVTWKVQ |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGAAGTACCATGTCGGAATCGATGTCGGAACCTTTTCTGTGGGGCTGGCTGCTATTGAAGTGGATGACGCTGG<br>AATGCCTATTAAGACCCTGAGTCTGGTGTCACACATTCATGACTCAGGACTGGATCCTGACGAGATCAAGAGCGC<br>TGTGACCAGGCTGGCAAGCTCCGGAATCGCCCGGAGAACAAGGCGCCTGTACCGACGGAAGAGAAGGCGCCTGC<br>AGCAGCTGGATAAGTTCATCCAGAGGCAGGGCTGGCCAGTGATCGAGCTGGAAGATTACAGCGACCCCCTGTAT<br>CCTTGGAAGGTGCGCGCCGAACTGGCCGCTTCTTATATTGCTGACGAGAAGGAACGGGGGGAGAAACTGAGTGT<br>GGCTCTGAGACACATCGCAAGGCATCGCGGATGGAGGAACCCTTACGCCAAGGTGTCTAGTCTGTATCTGCCAGA<br>TGGCCCCTCAGACGCCTTCAAGGCTATTAGGGAGGAAATCAAACGCGCTAGCGGCCAGCCTGTGCCAGAGACTG<br>CAACCGTCGGGCAGATGGTGACCCTGTGCGAACTGGGCACACTGAAGCTGCGAGGAGAGGGAGGAGTGCTGAGT<br>GCACGGCTGCAGCAGTCAGATTACGCCCGCGAGATCCAGGAAATTTGTCGAATGCAGGAGATCGGCCAGGAACT<br>GTATCGCAAGATCATTGACGTGGTGTTCGCAGCCGAGTCCCCAAAGGGCTCTGCCTCAAGCCGGGTGGGGAAAG<br>ATCCTCTGCAGCCAGGAAAGAACAGAGCACTGAAAGCCAGCGACGCTTTTCAGCGATACCGGATTGCTGCACTG |

FIG. 13B

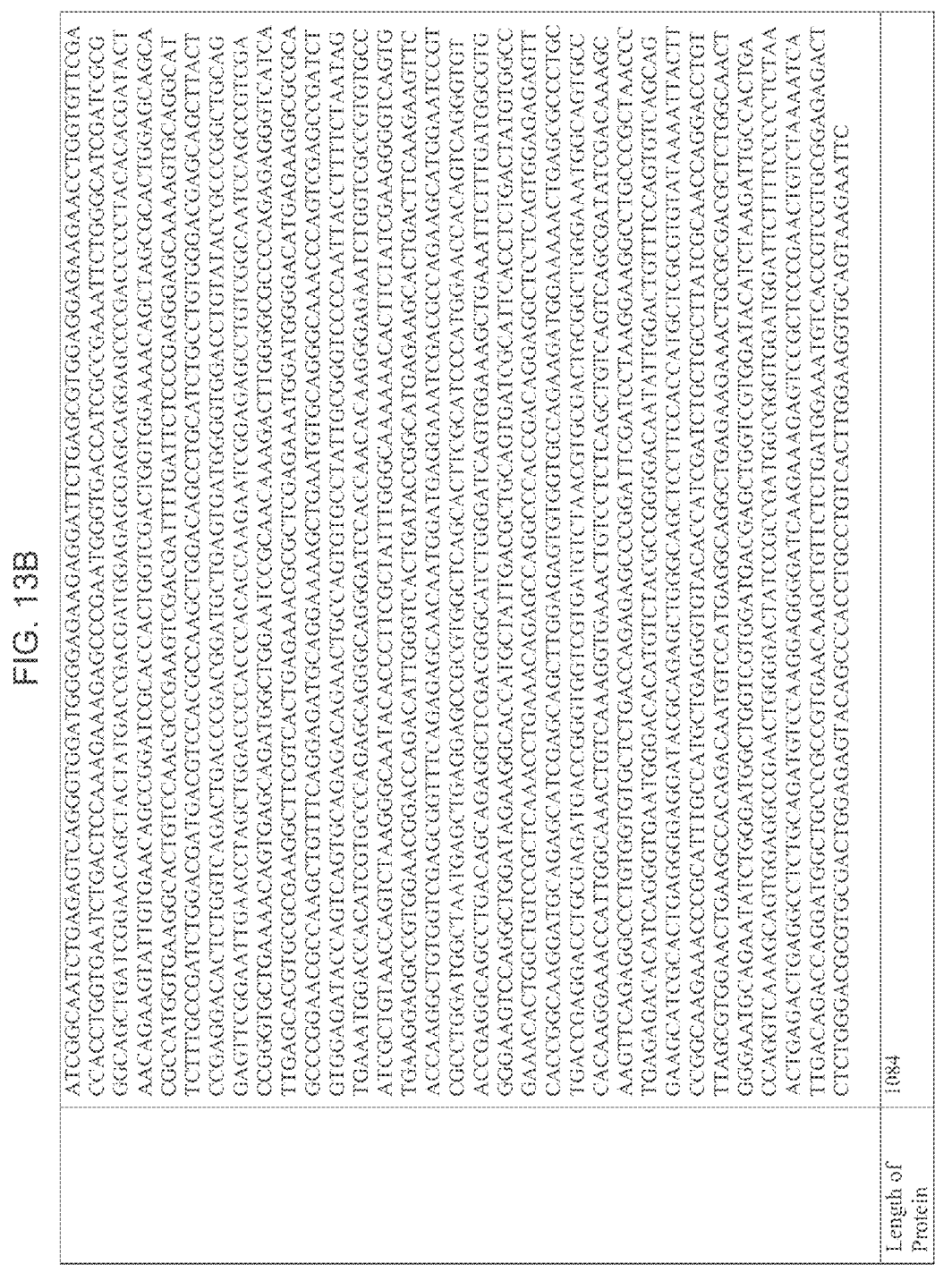

| | |
|---|---|
| | ATCGGCAATCTGAGAGTCAGGGTGGATGGGGAGAAGAGGATTCTGAGCGTGGAGGAGAAGAACCTGGTGTTCGA<br>CCACCTGGTGAATCTGACTCCAAAGAAAGAGCCCGAATGGGTGACCATCGCCGAAATTCTGGGCATCGATCGCG<br>GGCAGCTGATCGGAACAGCTACTATGACCGACGATGGAGAGCGAGCAGGAGCCCGACCCCCTACACACGATACT<br>AACAGAAGTATTGTGAACAGCCGGATCGCACCACTGGTCGACTGGTGGAAAACAGCTAGCGCACTGGAGCAGCA<br>CGCCATGGTGAAGGCACTGTCCAACGCCGAAGTCGACGATTTTGATTCTCCCGAGGGAGCAAAAGTGCAGGCAT<br>TCTTTGCCGATCTGGACGATGACGTCCACGCCAAGCTGGACAGCCTGCATCTGCCTGTGGGACGAGCAGCTTACT<br>CCGAGGACACTCTGGTCAGACTGACCCGACGGATGCTGAGTGATGGGGTGGACCTGTATACCGCCCGGCTGCAG<br>GAGTTCGGAATTGAACCTAGCTGGACCCCACCCACACCAAGAATCGGAGAGCCTGTCGGCAATCCAGCCGTCGA<br>CCGGGTGCTGAAAACAGTGAGCAGATGGCTGGAATCCGCAACAAAGACTTGGGGCGCCCCAGAGAGGGTCATCA<br>TTGAGCACGTGCGCGAAGGCTTCGTCACTGAGAAACGCGCTCGAGAAATGGATGGGGACATGAGAAGGCGCGCA<br>GCCCGGAACGCCAAGCTGTTTCAGGAGATGCAGGAAAAGCTGAATGTGCAGGGCAAACCCAGTCGAGCCGATCT<br>GTGGAGATACCAGTCAGTGCAGAGACAGAACTGCCAGTGTGCCTATTGCGGGTCCCCAATTACCTTTTCTAATAG<br>TGAAATGGACCACATCGTGCCCAGAGCAGGGCAGGGATCCACCAACACAAGGGAGAATCTGGTCGCCGTGTGCC<br>ATCGCTGTAACCAGTCTAAGGGCAATACACCCTTCGCTATTTGGGCAAAAAACACTTCTATCGAAGGGGTCAGTG<br>TGAAGGAGGCCGTGGAACGGACCAGACATTGGGTCACTGATACCGGCATGAGAAGCACTGACTTCAAGAAGTTC<br>ACCAAGGCTGTGGTCGAGCGGTTTCAGAGAGCAACAATGGATGAGGAAATCGACGCCAGAAGCATGGAATCCGT<br>CGCCTGGATGGCTAATGAGCTGAGGAGCCGCGTGGCTCAGCACTTCGCATCCCATGGAACCACAGTCAGGGTGT<br>ACCGAGGCAGCCTGACAGCAGAGGCTCGACGGGCATCTGGGATCAGTGGAAAGCTGAAATTCTTTGATGGCGTG<br>GGGAAGTCCAGGCTGGATAGAAGGCACCATGCTATTGACGCTGCAGTGATCGCATTCACCTCTGACTATGTGGCC<br>GAAACACTGGCTGTCCGCTCAAACCTGAAACAGAGCCAGGCCCACCGACAGGAGGCTCCTCAGTGGAGAGAGTT<br>CACCGGCAAGGATGCAGAGCATCGAGCAGCTTGGAGAGTGTGGTGCCAGAAGATGGAAAAACTGAGCGCCCTGC<br>TGACCGAGGACCTGCGAGATGACCGGGTGGTCGTGATGTCTAACGTGCGACTGCGGCTGGGAAATGGCAGTGCC<br>CACAAGGAAACCATTGGCAAACTGTCAAAGGTGAAACTGTCCTCTCAGCTGTCAGTCAGCGATATCGACAAAGC<br>AAGTTCAGAGGCCCTGTGGTGTGCTCTGACCAGAGAGCCCGGATTCGATCCTAAGGAAGGCCTGCCCGCTAACCC<br>TGAGAGACACATCAGGGTGAATGGGACACATGTCTACGCCGGGGACAATATTGGACTGTTTCCAGTGTCAGCAG<br>GAAGCATCGCACTGAGGGGAGGATACGCAGAGCTGGGCAGCTCCTTCCACCATGCTCGCGTGTATAAAATTACTT<br>CCGGCAAGAAACCCGCATTTGCCATGCTGAGGGTGTACACCATCGATCTGCTGCCTTATCGCAACCAGGACCTGT<br>TTAGCGTGGAACTGAAGCCACAGACAATGTCCATGAGGCAGGCTGAGAAGAAACTGCGCGACGCTCTGGCAACT<br>GGGAATGCAGAATATCTGGGATGGCTGGTCGTGGATGACGAGCTGGTCGTGGATACATCTAAGATTGCCACTGA<br>CCAGGTCAAAGCAGTGGAGGCCGAACTGGGGACTATCCGCCGATGGCGGGTGGATGGATTCTTTTCCCCCTCTAA<br>ACTGAGACTGAGGCCTCTGCAGATGTCCAAGGAGGGGATCAAGAAAGAGTCCGCTCCCGAACTGTCTAAAATCA<br>TTGACAGACCAGGATGGCTGCCCGCCGTGAACAAGCTGTTCTCTGATGGAAATGTCACCGTCGTGCGGAGAGACT<br>CTCTGGGACGCGTGCGACTGGAGAGTACAGCCCACCTGCCTGTCACTTGGAAGGTGCAGTAAGAATTC |
| Length of Protein | 1084 |

FIG. 13C

| | |
|---|---|
| (without NLS and HA tag) | |
| **PAM** | NGG |
| Spacer Length | 28 |
| **Species: Sutterella_wadsworthensis** | |
| Sequencing Barcode | AACTTGAC |
| ID | 2 |
| **Chimeric Guide RNA** | **NNNNNNNNNNNNNNNNNNNNGUUUCAGUGCUAUAGGAAACUAUAGGAAAUCACCUUCGGGUGAGCUGAAAUCCCCUAAAGCUAAGAUUGAAUCCGGCCACUAUCUAUUAGUAGAUAUCCGGAUAUUCUGAUAUAAAACCUCAUUCUUUGAUUAGACCAAAGGAUGAGGUUUUUUU** |
| Cas9 Protein Sequence (wildtype, without NLS added) | MTQSERRFSCSIGIDMGAKYTGVFYALFDREELPTNLNSKAMTLVMPETGPRYVQAQRTAVRHRLRGQKRYTLARKLAFLVVDDMIKKQEKRLTDEEWKRGREALSGLLKRRGYSRPNADGEDLTPLENVRADVFAAHPAFSTYFSEVRSLAEQWEEFTANISNVEKFLGDPNIPADKEFIEFAVAEGLIDKTEKKAYQSALSTLRANANVLTGLRQMGHKPRSEYFKAIEADLKKDSRLAKINEAFGGAERLARLLGNLSNLQLRAERWYFNAPDIMKDRGWEPDRFKKTLVRAFKFFHPAKDQNKQHLELIKQIENSEDIIETLCTLDPNRTIPPYEDQNNRRPPLDQTLLLSPEKLTRQYGEIWKTWSARLTSAEPTLAPAAEILERSTDRKSRVAVNGHEPLPTLAYQLSYALQRAFDRSKALDPYALRALAAGSKSNKLTSARTALENCIGGQNVKTFLDCARRYYREADDAKVGLWFDNADGLLERSDLHPPMKKKILPLLVANILQTDETTGQKFLDEIWRKQIKGRETVASRCARIETVRKSFGGGFNIAYNTAQYREVNKLPRNAQDKELLTIRDRVAETADFIAANLGLSDEQKRKFANPFSLAQFYTLIETEVSGFSATTLAVHLENAWRMTIKDAVINGETVRAAQCSRLPAETARPFDGLVRRLVDRQAWEIAKRVSTDIQSKVDFSNGIVDVSIFVEENKFEFSASVADLKKNKRVKDKMLSEAEKLETRWLIKNERIKKASRGTCPYTGDRLAEGGEIDHILPRSLIKDARGIVFNAEPNLIYASSRGNQLKKNQRYSLSDLKANYRNEIFKTSNIAAITAEIEDVVTKLQQTHRLKFFDLLNEHEQDCVRHALFLDDGSEARDAVLELLATQRRTRVNGTQIWMIKNLANKIREELQNWCKTTNNRLHFQAAATNVSDAKNLRLKLAQNQPDFEKPDIQPIASHSIDALCSFAVGSADAERDQNGFDYLDGKTVLGLYPQSCEVIHLQAKPQEEKSHFDSVAIFKEGIYAEQFLPIFTLNEKIWIGYETLNAKGERCGAIEVSGKQPKELLEMLAPFFNKPVGDLSAHATYRILKKPAYEFLAKAALQPLSAEEKRLAALLDALRYCTSRKSLMSLFMAANGKSLKKREDVLKPKLFQLKVELKGEKSFKLNGSLTLPVKQDWLRICDSPELADAFGKPCSADELTSKLARIWKRPVMRDLAHAPVRREFSLPAIDNPSGGFRIRRTNLFGNELYQVHAINAKKYRGFASAGSNVDWSKGILFNELQHENLTECGGRFITSADVTPMSEWRKVVAEDNLSIWIAPGTEGRRYVRVETTFIQASHWFEQSVENWAITSPLSLPASFKVDKPAEFQKAVGTELSELLGQPRSEIFIENVGNAKHIRFWYIVVSSNKKMNESYNNVSKS |

FIG. 13D

| | |
|---|---|
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGACTCAGAGCGAGCGACGATTTTCTTGCAGCATTGGCATTGACATGGGGGCTAAGTACACTGGGGTGTTCTA<br>CGCACTGTTCGACCGGGAGGAACTGCCCACAAACCTGAACAGCAAGGCCATGACCCTGGTCATGCCTGAGACAG<br>GGCCAAGATACGTGCAGGCACAGAGAACTGCCGTCAGACACAGGCTGCGCGGACAGAAGAGATATACCCTGGCT<br>AGGAAACTGGCATTTCTGGTGGTCGACGATATGATCAAGAAACAGGAAAAGAGGCTGACTGATGAGGAATGGAA<br>ACGAGGACGGGAGGCCCTGTCCGGCCTGCTGAAGCGGAGAGGGTACTCTCGGCCCAACGCTGACGGCGAAGATC<br>TGACCCCTCTGGAGAATGTGAGAGCAGACGTGTTCGCCGCTCATCCTGCCTTCAGCACATATTTTTCCGAAGTGC<br>GCTCTCTGGCTGAGCAGTGGGAGGAGTTCACCGCAAACATCAGCAATGTCGAGAAGTTTCTGGGCGACCCAAAC<br>ATCCCCGCCGATAAAGAGTTCATTGAATTTGCCGTGGCTGAAGGGCTGATTGACAAGACCGAGAAGAAAGCCTA<br>CCAGTCAGCTCTGAGCACCCTGAGGGCAAACGCCAATGTGCTGACAGGACTGCGGCAGATGGGCCACAAGCCTA<br>GATCAGAATATTTTAAAGCAATCGAGGCCGACCTGAAGAAAGATAGCCGCCTGGCCAAGATTAACGAAGCATTC<br>GGAGGAGCAGAGCGCCTGGCTCGACTGCTGGGAAACCTGTCCAATCTGCAGCTGCGGGCAGAAAGATGGTACTT<br>CAATGCCCCCGACATCATGAAGGATAGGGGCTGGGAGCCTGATCGCTTCAAGAAAACACTGGTGCGGGCTTTTA<br>AGTTCTTTCACCCAGCAAAGGACCAGAACAAACAGCATCTGGAACTGATCAAACAGATTGAGAACAGCGAAGAT<br>ATCATTGAGACTCTGTGCACCCTGGACCCAAACAGAACCATCCCCCCTTACGAGGATCAGAACAATAGGCGCCCA<br>CCCCTGGACCAGACTCTGCTGCTGAGTCCCGAAAAGCTGACCCGGCAGTATGGCGAGATCTGGAAAACATGGAG<br>CGCCAGACTGACCTCCGCTGAACCCACACTGGCACCTGCAGCCGAGATTCTGGAAAGATCTACCGACAGGAAGA<br>GTCGCGTGGCAGTCAACGGACACGAGCCACTGCCTACACTGGCTTACCAGCTGAGTTATGCACTGCAGAGAGCCT<br>TCGACAGGTCAAAAGCCCTGGATCCATATGCTCTGAGGGCACTGGCTGCAGGCTCAAAAAGCAATAAGCTGACA<br>TCCGCCCGCACTGCTCTGGAGAACTGCATCGGAGGCCAGAATGTGAAAACCTTCCTGGACTGTGCCCGACGGTAC<br>TATCGGGAAGCAGACGATGCCAAAGTCGGGCTGTGGTTCGACAACGCCGATGGACTGCTGGAGAGATCTGACCT<br>GCATCCTCCAATGAAGAAAAAGATCCTGCCCCTGCTGGTGGCCAATATTCTGCAGACAGATGAAACCACAGGCC<br>AGAAGTTTCTGGACGAGATCTGGCGAAAACAGATTAAGGGGCGGGAAACTGTGGCTAGCCGATGTGCACGGATC<br>GAGACAGTGCGGAAATCCTTCGGGGGAGGCTTTAACATTGCCTACAATACCGCTCAGTATAGGGAGGTGAACAA<br>GCTGCCCCGCAATGCCCAGGATAAAGAACTGCTGACAATCAGAGATAGGGTGGCTGAGACTGCAGACTTCATTG<br>CCGCTAACCTGGGGCTGTCTGACGAGCAGAAAAGAAAGTTCGCCAATCCTTTTAGTCTGGCTCAGTTCTACACCC<br>TGATCGAGACAGAAGTGTCCGGATTTTCTGCAACTACCCTGGCCGTCCACCTGGAGAACGCCTGGAGGATGACAA<br>TCAAGGATGCTGTGATTAATGGGGAAACTGTCAGAGCAGCACAGTGCAGCAGGCTGCCTGCAGAGACAGCTCGC<br>CCATTCGATGGACTGGTGAGAAGGCTGGTCGACAGACAGGCTTGGGAGATCGCAAAGAGGGTGTCAACTGACAT<br>TCAGAGCAAAGTCGATTTCTCCAACGGCATCGTGGACGTCAGCATTTTTGTGGAGGAAAATAAGTTCGAGTTTTC<br>CGCATCTGTGGCCGATCTGAAAAAGAACAAACGGGTCAAAGACAAGATGCTGTCCGAGGCCGAAAAGCTGGAA<br>ACCAGATGGCTGATCAAAAATGAGCGGATCAAGAAGGCCAGCCGGGGAACTTGTCCCTACACCGGCGATAGGCT<br>GGCTGAGGGGGGAGAAATCGACCACATTCTGCCCCGAAGCCTGATCAAGGATGCCCGGGGAATTGTGTTTAACG<br>CTGAGCCTAATCTGATCTATGCAAGCTCCCGCGGCAACCAGCTGAAAAAGAATCAGCGATACAGTCTGTCAGATC<br>TGAAGGCCAACTATCGGAATGAGATCTTCAAAACTAGCAACATCGCTGCAATTACCGCCGAGATTGAGGACGTG |

FIG. 13E

| | |
|---|---|
| | GTCACTAAGCTGCAGCAGACCCATAGACTGAAATTCTTTGATCTGCTGAATGAGCACGAACAGGACTGCGTGCGG<br>CACGCCCTGTTCCTGGACGATGGCAGCGAAGCTCGCGACGCAGTGCTGGAGCTGCTGGCAACACAGCGCCGAAC<br>TCGCGTCAACGGGACACAGATCTGGATGATTAAGAACCTGGCCAACAAGATCCGAGAGGAACTGCAGAATTGGT<br>GTAAGACAACTAACAATAGACTGCACTTTCAGGCCGCTGCAACTAACGTGTCCGATGCAAAGAATCTGAGGCTG<br>AAACTGGCCCAGAACCAGCCCGACTTCGAGAAGCCAGATATCCAGCCCATTGCCAGCCATTCCATCGACGCCCTG<br>TGCTCTTTCGCTGTGGGGAGTGCTGACGCAGAACGCGATCAGAATGGATTTGACTACCTGGATGGCAAGACCGTG<br>CTGGGACTGTATCCACAGAGCTGTGAGGTCATTCACCTGCAGGCCAAGCCCCAGGAGGAAAAAAGTCATTTCGA<br>TTCAGTGGCTATCTTTAAGGAAGGCATCTACGCAGAGCAGTTCCTGCCTATCTTTACCCTGAACGAAAAGATCTG<br>GATTGGATATGAGACACTGAATGCCAAAGGCGAAAGATGCGGGGCTATTGAGGTGAGTGGCAAACAGCCAAAG<br>GAGCTGCTGGAAATGCTGGCCCCCTTCTTTAACAAGCCTGTGGGCGACCTGTCAGCCCACGCTACTTACCGGATC<br>CTGAAAAAGCCTGCATATGAGTTTCTGGCAAAGGCAGCTCTGCAGCCACTGAGCGCAGAGGAAAAAAGACTGGC<br>AGCCCTGCTGGATGCTCTGCGCTACTGTACCAGTCGAAAGTCACTGATGAGCCTGTTCATGGCTGCAAACGGGAA<br>ATCCCTGAAAAAGCGGGAGGACGTGCTGAAACCCAAGCTGTTCCAGCTGAAGGTCGAGCTGAAAGGCGAAAAG<br>AGCTTCAAGCTGAACGGGAGCCTGACCCTGCCTGTGAAGCAGGACTGGCTGAGAATCTGCGATAGCCCAGAACT<br>GGCAGACGCCTTTGGCAAACCCTGTTCCGCCGATGAGCTGACATCTAAGCTGGCTCGCATTTGGAAACGACCTGT<br>GATGCGGGATCTGGCTCATGCACCAGTCCGGAGAGAGTTCAGCCTGCCCGCAATCGACAACCCAAGTGGAGGGT<br>TCAGGATTAGGCGCACCAACCTGTTTGGCAATGAGCTGTACCAGGTGCACGCCATCAACGCTAAAAAGTATCGCG<br>GCTTCGCCTCCGCTGGGTCTAATGTCGACTGGTCCAAGGGGATCCTGTTTAACGAGCTGCAGCATGAAAATCTGA<br>CCGAGTGCGGAGGCAGGTTCATTACAAGCGCCGATGTGACTCCTATGTCCGAATGGCGCAAGGTGGTCGCAGAG<br>GACAACCTGTCTATCTGGATTGCTCCAGGGACAGAAGGACGACGGTACGTGAGGGTCGAGACAACATTCATCCA<br>GGCCAGTCACTGGTTTGAACAGTCAGTGGAGAATTGGGCCATTACTAGTCCTCTGTCACTGCCAGCTTCCTTCAA<br>GGTGGACAAACCAGCTGAGTTTCAGAAGGCAGTCGGAACCGAGCTGTCAGAACTGCTGGGCCAGCCCAGGAGCG<br>AAATCTTCATTGAGAACGTGGGCAATGCCAAGCATATCCGCTTTTGGTACATTGTGGTGAGCAGCAACAAAAAGA<br>TGAACGAGTCTTACAACAATGTGTCTAAGAGTTAAGAATTC |
| Length of Protein (without NLS and HA tag) | 1422 |
| **PAM** | **NGG** |
| Spacer Length | 35-39 |
| **Species: Legionella_pneumophila_Paris** | |

FIG. 13F

| | |
|---|---|
| Sequencing Barcode | TGTCGGAT |
| ID | 3 |
| **Chimeric Guide RNA** | **NNNNNNNNNNNNNNNNNNNNGUUUCAGUGGUGAAAACCCUGAAAUCAACAAAAUUAAAGAUUGAAUCGUU<br>UUUCUAUGCUCGUCUUAAUAGCGAGCAUAUAACGAUUUUUUU** |
| Cas9 Protein Sequence (wildtype, without NLS added) | MESSQILSPIGIDLGGKFTGVCLSHLEAFAELPNHANTKYSVILIDHNNFQLSQAQRRATRHRVRNKKRNQFVKRVALQ<br>LFQHILSRDLNAKEETALCHYLNNRGYTYVDTDLDEYIKDETTINLLKELLPSESEHNFIDWFLQKMQSSEFRKILVSKV<br>EEKKDDKELKNAVKNIKNFITGFEKNSVEGHRHRKVYFENIKSDITKDNQLDSIKKKIPSVCLSNLLGHLSNLQWKNLH<br>RYLAKNPKQFDEQTFGNEFLRMLKNFRHLKGSQESLAVRNLIQQLEQSQDYISILEKTPPEITIPPYEARTNTGMEKDQS<br>LLLNPEKLNNLYPNWRNLIPGIIDAHPFLEKDLEHTKLRDRKRIISPSKQDEKRDSYILQRYLDLNKKIDKFKIKKQLSFL<br>GQGKQLPANLIETQKEMETHFNSSLVSVLIQIASAYNKEREDAAQGIWFDNAFSLCELSNINPPRKQKILPLLVGAILSE<br>DFINNKDKWAKFKIFWNTHKIGRTSLKSKCKEIEEARKNSGNAFKIDYEEALNHPEHSNNKALIKIIQTIPDIIQAIQSHL<br>GHNDSQALIYHNPFSLSQLYTILETKRDGFHKNCVAVTCENYWRSQKTEIDPEISYASRLPADSVRPFDGVLARMMQR<br>LAYEIAMAKWEQIKHIPDNSSLLIPIYLEQNRFEFEESFKKIKGSSSDKTLEQAIEKQNIQWEEKFQRIINASMNICPYKG<br>ASIGGQGEIDHIYPRSLSKKHFGVIFNSEVNLIYCSSQGNREKKEEHYLLEHLSPLYLKHQFGTDNVSDIKNFISQNVANI<br>KKYISFHLLTPEQQKAARHALFLDYDDEAFKTITKFLMSQQKARVNGTQKFLGKQIMEFLSTLADSKQLQLEFSIKQIT<br>AEEVHDHRELLSKQEPKLVKSRQQSFPSHAIDATLTMSIGLKEFPQFSQELDNSWFINHLMPDEVHLNPVRSKEKYNKP<br>NISSTPLFKDSLYAERFIPVWVKGETFAIGFSEKDLFEIKPSNKEKLFTLLKTYSTKNPGESLQELQAKSKAKWLYFPINK<br>TLALEFLHHYFHKEIVTPDDTTVCHFINSLRYYTKKESITVKILKEPMPVLSVKFESSKKNVLGSFKHTIALPATKDWER<br>LFNHPNFLALKANPAPNPKEFNEFIRKYFLSDNNPNSDIPNNGHNIKPQKHKAVRKVFSLPVIPGNAGTMMRIRRKDNK<br>GQPLYQLQTIDDTPSMGIQINEDRLVKQEVLMDAYKTRNLSTIDGINNSEGQAYATFDNWLTLPVSTFKPEIIKLEMKP<br>HSKTRRYIRITQSLADFIKTIDEALMIKPSDSIDDPLNMPNEIVCKNKLFGNELKPRDGKMKIVSTGKIVTYEFESDSTPQ<br>WIQTLYVTQLKKQP |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGGAGTCCTCTCAGATCCTGTCACCTATCGGCATCGACCTGGGCGGAAAGTTTACTGGAGTCTGCCTGTCACA<br>CCTGGAAGCATTTGCTGAGCTGCCTAACCACGCAAATACAAAGTACTCAGTGATCCTGATTGATCATAACAATTT<br>CCAGCTGAGCCAGGCACAGCGGAGAGCCACTAGACACAGGGTGCGCAACAAGAAAAGAAATCAGTTCGTGAAG<br>AGGGTCGCCCTGCAGCTGTTTCAGCACATCCTGTCCCGGGACCTGAACGCCAAGGAGGAAACCGCTCTGTGCCAT<br>TACCTGAACAATAGAGGCTACACCTATGTGGACACAGATCTGGACGAGTATATCAAAGATGAAACCACAATTAA<br>CCTGCTGAAGGAGCTGCTGCCAAGCGAGTCCGAACATAATTTCATTGACTGGTTTCTGCAGAAGATGCAGAGCTC<br>CGAGTTCCGGAAGATCCTGGTGAGCAAAGTCGAGGAAAAGAAAGACGATAAAGAACTGAAGAACGCCGTGAAG<br>AACATCAAGAACTTCATCACCGGATTCGAGAAAAATAGCGTGGAAGGCCACCGACATCGGAAGGTCTACTTTGA<br>GAACATCAAGTCCGATATTACAAAAGACAATCAGCTGGATTCTATCAAGAAAAAGATTCCTAGCGTGTGTCTGTC |

FIG. 13G

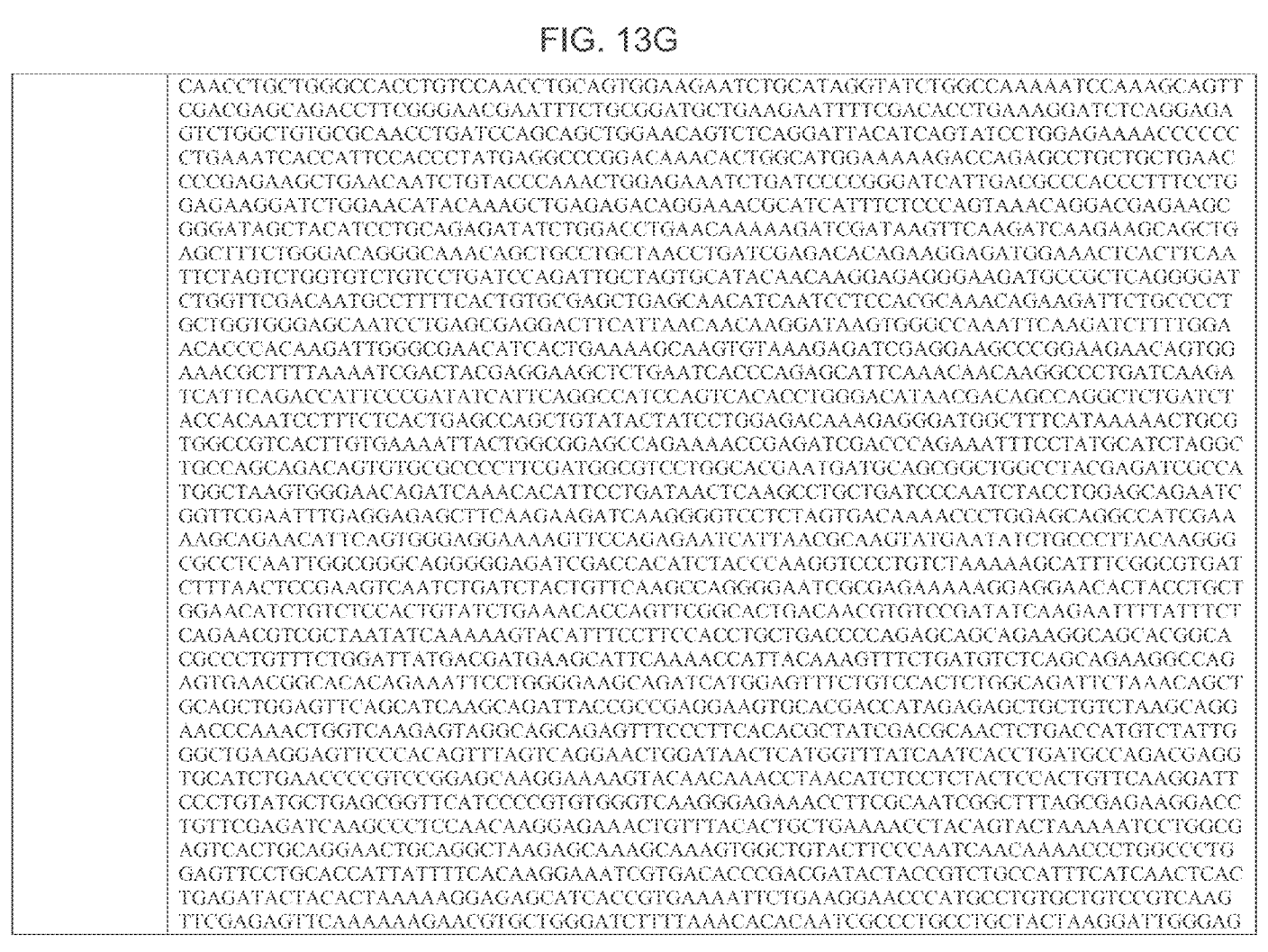

CAACCTGCTGGGCCACCTGTCCAACCTGCAGTGGAAGAATCTGCATAGGTATCTGGCCAAAAATCCAAAGCAGTT
CGACGAGCAGACCTTCGGGAACGAATTTCTGCGGATGCTGAAGAATTTTCGACACCTGAAAGGATCTCAGGAGA
GTCTGGCTGTGCGCAACCTGATCCAGCAGCTGGAACAGTCTCAGGATTACATCAGTATCCTGGAGAAAACCCCCC
CTGAAATCACCATTCCACCCTATGAGGCCCGGACAAACACTGGCATGGAAAAAGACCAGAGCCTGCTGCTGAAC
CCCGAGAAGCTGAACAATCTGTACCCAAACTGGAGAAATCTGATCCCCGGGATCATTGACGCCCACCCTTTCCTG
GAGAAGGATCTGGAACATACAAAGCTGAGAGACAGGAAACGCATCATTTCTCCCAGTAAACAGGACGAGAAGC
GGGATAGCTACATCCTGCAGAGATATCTGGACCTGAACAAAAAGATCGATAAGTTCAAGATCAAGAAGCAGCTG
AGCTTTCTGGGACAGGGCAAACAGCTGCCTGCTAACCTGATCGAGACACAGAAGGAGATGGAAACTCACTTCAA
TTCTAGTCTGGTGTCTGTCCTGATCCAGATTGCTAGTGCATACAACAAGGAGAGGGAAGATGCCGCTCAGGGGAT
CTGGTTCGACAATGCCTTTTCACTGTGCGAGCTGAGCAACATCAATCCTCCACGCAAACAGAAGATTCTGCCCCT
GCTGGTGGGAGCAATCCTGAGCGAGGACTTCATTAACAACAAGGATAAGTGGGCCAAATTCAAGATCTTTTGGA
ACACCCACAAGATTGGGCGAACATCACTGAAAAGCAAGTGTAAAGAGATCGAGGAAGCCCGGAAGAACAGTGG
AAACGCTTTTAAAATCGACTACGAGGAAGCTCTGAATCACCCAGAGCATTCAAACAACAAGGCCCTGATCAAGA
TCATTCAGACCATTCCCGATATCATTCAGGCCATCCAGTCACACCTGGGACATAACGACAGCCAGGCTCTGATCT
ACCACAATCCTTTCTCACTGAGCCAGCTGTATACTATCCTGGAGACAAAGAGGGATGGCTTTCATAAAAACTGCG
TGGCCGTCACTTGTGAAAATTACTGGCGGAGCCAGAAAACCGAGATCGACCCAGAAATTTCCTATGCATCTAGGC
TGCCAGCAGACAGTGTGCGCCCCTTCGATGGCGTCCTGGCACGAATGATGCAGCGGCTGGCCTACGAGATCGCCA
TGGCTAAGTGGGAACAGATCAAACACATTCCTGATAACTCAAGCCTGCTGATCCCAATCTACCTGGAGCAGAATC
GGTTCGAATTTGAGGAGAGCTTCAAGAAGATCAAGGGGTCCTCTAGTGACAAAACCCTGGAGCAGGCCATCGAA
AAGCAGAACATTCAGTGGGAGGAAAAGTTCCAGAGAATCATTAACGCAAGTATGAATATCTGCCCTTACAAGGG
CGCCTCAATTGGCGGGCAGGGGGAGATCGACCACATCTACCCAAGGTCCCTGTCTAAAAAGCATTTCGGCGTGAT
CTTTAACTCCGAAGTCAATCTGATCTACTGTTCAAGCCAGGGGAATCGCGAGAAAAAGGAGGAACACTACCTGCT
GGAACATCTGTCTCCACTGTATCTGAAACACCAGTTCGGCACTGACAACGTGTCCGATATCAAGAATTTTATTTCT
CAGAACGTCGCTAATATCAAAAAGTACATTTCCTTCCACCTGCTGACCCCAGAGCAGCAGAAGGCAGCACGGCA
CGCCCTGTTTCTGGATTATGACGATGAAGCATTCAAAACCATTACAAAGTTTCTGATGTCTCAGCAGAAGGCCAG
AGTGAACGGCACACAGAAATTCCTGGGGAAGCAGATCATGGAGTTTCTGTCCACTCTGGCAGATTCTAAACAGCT
GCAGCTGGAGTTCAGCATCAAGCAGATTACCGCCGAGGAAGTGCACGACCATAGAGAGCTGCTGTCTAAGCAGG
AACCCAAACTGGTCAAGAGTAGGCAGCAGAGTTTCCCTTCACACGCTATCGACGCAACTCTGACCATGTCTATTG
GGCTGAAGGAGTTCCCACAGTTTAGTCAGGAACTGGATAACTCATGGTTTATCAATCACCTGATGCCAGACGAGG
TGCATCTGAACCCCGTCCGGAGCAAGGAAAAGTACAACAAACCTAACATCTCCTCTACTCCACTGTTCAAGGATT
CCCTGTATGCTGAGCGGTTCATCCCCGTGTGGGTCAAGGGAGAAACCTTCGCAATCGGCTTTAGCGAGAAGGACC
TGTTCGAGATCAAGCCCTCCAACAAGGAGAAACTGTTTACACTGCTGAAAACCTACAGTACTAAAAATCCTGGCG
AGTCACTGCAGGAACTGCAGGCTAAGAGCAAAGCAAAGTGGCTGTACTTCCCAATCAACAAAACCCTGGCCCTG
GAGTTCCTGCACCATTATTTTCACAAGGAAATCGTGACACCCGACGATACTACCGTCTGCCATTTCATCAACTCAC
TGAGATACTACACTAAAAAGGAGAGCATCACCGTGAAAATTCTGAAGGAACCCATGCCTGTGCTGTCCGTCAAG
TTCGAGAGTTCAAAAAAGAACGTGCTGGGATCTTTTAAACACACAATCGCCCTGCCTGCTACTAAGGATTGGGAG

FIG. 13H

| | |
|---|---|
| | AGGCTGTTCAACCATCCAAATTTTCTGGCACTGAAGGCCAACCCAGCTCCCAATCCTAAAGAGTTCAATGAGTTC<br>ATCCGCAAGTACTTCCTGAGCGACAACAATCCCAACTCCGATATCCCTAACAATGGCCACAATATCAAGCCCCAG<br>AAACATAAGGCCGTGCGAAAGGTCTTTAGCCTGCCAGTGATCCCCGGGAACGCTGGAACCATGATGCGCATTAG<br>GCGCAAAGACAATAAGGGACAGCCACTGTATCAGCTGCAGACAATCGACGATACTCCCAGCATGGGCATCCAGA<br>TTAACGAGGATCGCCTGGTGAAACAGGAAGTCCTGATGGACGCCTACAAGACACGAAATCTGAGCACTATCGAT<br>GGGATTAACAATTCCGAGGGACAGGCATATGCCACATTCGACAACTGGCTGACCCTGCCCGTGAGCACCTTCAAG<br>CCTGAGATCATCAAGCTGGAAATGAAGCCTCACTCTAAAACCCGACGGTACATCAGAATTACACAGAGTCTGGC<br>CGACTTCATCAAAACTATTGATGAGGCTCTGATGATCAAGCCCAGTGACTCAATTGACGATCCTCTGAACATGCC<br>AAATGAGATCGTGTGTAAAAACAAGCTGTTCGGGAATGAACTGAAGCCTAGGGATGGAAAAATGAAGATCGTGA<br>GCACTGGCAAGATTGTCACCTACGAGTTTGAAAGCGACTCCACCCCCCAGTGGATCCAGACCCTGTATGTGACAC<br>AGCTGAAAAAGCAGCCTTAAGAATTC |
| Length of Protein (without NLS and HA tag) | 1372 |
| **PAM** | **NGG** |
| Spacer Length | 34-36 |
| **Species: Treponema_denticola** | |
| Sequencing Barcode | TCGCCTTG |
| ID | 4 |
| **Chimeric Guide RNA** | **NNNNNNNNNNNNNNNNNNNNGUUUGAGAGUUGGAAACAACGAGUUCAAAUAAGAAUUCAUCAAAAUCGUC<br>CCUUUUGGGACCGCUCAUUGUGGAGCAUCAAGGCUUAACAUGGUUAAGCCUUUUUUU** |
| Cas9 Protein Sequence (wildtype, without NLS added) | MKKEIKDYFLGLDVGTGSVGWAVTDTDYKLLKANRKDLWGMRCFETAETAEVRRLHRGARRRIERRKKRIKLLQEL<br>FSQEIAKTDEGFFQRMKESPFYAEDKTILQENTLFNDKDFADKTYHKAYPTINHLIKAWIENKVKPDPRLLYLACHNIIK<br>KRGHFLFEGDFDSENQFDTSIQALFEYLREDMEVDIDADSQKVKEILKDSSLKNSEKQSRLNKILGLKPSDKQKKAITN<br>LISGNKINFADLYDNPDLKDAEKNSISFSKDDFDALSDDLASILGDSFELLLKAKAVYNCSVLSKVIGDEQYLSFAKVKI<br>YEKHKTDLTKLKNVIKKHFPKDYKKVFGYNKNEKNNNNYSGYVGVCKTKSKKLIINNSVNQEDFYKFLKTILSAKSEI<br>KEVNDILTEIETGTFLPKQISKSNAEIPYQLRKMELEKILSNAEKHFSFLKQKDEKGLSHSEKIIMLLTFKIPYYIGPINDN |

FIG. 13I

| | |
|---|---|
| | HKKFFPDRCWVVKKEKSPSGKTTPWNFFDHIDKEKTAEAFITSRTNFCTYLVGESVLPKSSLLYSEYTVLNEINNLQIII<br>DGKNICDIKLKQKIYEDLFKKYKKITQKQISTFIKHEGICNKTDEVIILGIDKECTSSLKSYIELKNIFGKQVDEISTKNML<br>EEIIRWATIYDEGEGKTILKTKIKAEYGKYCSDEQIKKILNLKFSGWGRLSRKFLETVTSEMPGFSEPVNIITAMRETQNN<br>LMELLSSEFTFTENIKKINSGFEDAEKQFSYDGLVKPLFLSPSVKKMLWQTLKLVKEISHITQAPPKKIFIEMAKGAELEP<br>ARTKTRLKILQDLYNNCKNDADAFSSEIKDLSGKIENEDNLRLRSDKLYLYYTQLGKCMYCGKPIEIGHVFDTSNYDID<br>HIYPQSKIKDDSISNRVLVCSSCNKNKEDKYPLKSEIQSKQRGFWNFLQRNNFISLEKLNRLTRATPISDDETAKFIARQL<br>VETRQATKVAAKVLEKMFPETKIVYSKAETVSMFRNKFDIVKCREINDFHHAHDAYLNIVVGNVYNTKFTNNPWNFI<br>KEKRDNPKIADTYNYYKVFDYDVKRNNITAWEKGKTIITVKDMLKRNTPIYTRQAACKKGELFNQTIMKKGLGQHPL<br>KKEGPFSNISKYGGYNKVSAAYYTLIEYEEKGNKIRSLETIPLYLVKDIQKDQDVLKSYLTDLLGKKEFKILVPKIKINSL<br>LKINGFPCHITGKTNDSFLLRPAVQFCCSNNEVLYFKKIIRFSEIRSQREKIGKTISPYEDLSFRSYIKENLWKKTKNDEIG<br>EKEFYDLLQKKNLEIYDMLLTKHKDTIYKKRPNSATIDILVKGKEKFKSLIIENQFEVILEILKLFSATRNVSDLQHIGGS<br>KYSGVAKIGNKISSLDNCILIYQSITGIFEKRIDLLKV |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGAAAAAAGAAATCAAAGACTACTTCCTGGGGCTGGATGTGGGGACTGGGAGCGTGGGGTGGGCTGTGACCG<br>ATACTGACTACAAACTGCTGAAGGCTAACCGAAAAGACCTGTGGGGCATGAGATGCTTCGAGACAGCCGAAACT<br>GCTGAGGTGCGGAGACTGCACAGGGGAGCCAGGCGCCGAATCGAGCGGAGAAAGAAACGCATTAAGCTGCTGC<br>AGGAGCTGTTCTCTCAGGAAATCGCCAAAACCGATGAGGGCTTCTTTCAGAGAATGAAGGAAAGCCCCTTTTACG<br>CTGAGGACAAAACAATCCTGCAGGAAAACACTCTGTTCAATGACAAGGATTTTGCTGATAAGACTTACCACAAA<br>GCATATCCTACCATTAATCATCTGATCAAGGCTTGGATTGAGAACAAGGTGAAACCAGACCCCCGACTGCTGTAC<br>CTGGCATGTCACAACATCATTAAGAAAAGGGGACATTTCCTGTTTGAAGGCGACTTCGATTCAGAGAATCAGTTT<br>GATACCAGCATCCAGGCACTGTTCGAGTATCTGCGCGAGGACATGGAGGTGGACATCGATGCCGACAGCCAGAA<br>GGTCAAAGAGATTCTGAAGGATAGCTCCCTGAAGAACTCTGAAAAACAGAGTCGGCTGAATAAGATCCTGGGGC<br>TGAAGCCTTCCGACAAACAGAAGAAAGCCATCACAAACCTGATTTCTGGAAACAAGATCAATTTCGCCGATCTGT<br>ACGACAATCCAGATCTGAAGGACGCTGAGAAAAACTCAATCAGCTTCTCCAAGGACGATTTTGATGCACTGAGT<br>GACGATCTGGCCTCAATTCTGGGCGACAGCTTTGAACTGCTGCTGAAGGCCAAAGCTGTCTATAACTGCTCTGTG<br>CTGAGTAAGGTCATCGGGGACGAGCAGTACCTGAGCTTCGCCAAGGTGAAAATCTACGAAAAGCACAAAACCGA<br>TCTGACAAAGCTGAAAAACGTGATCAAGAAACATTTCCCCAAGGACTACAAGAAGGTCTTTGGATACAACAAGA<br>ACGAGAAAAACAACAACAATTACTCCGGCTATGTGGGAGTCTGTAAGACCAAGAGTAAGAAACTGATCATTAAC<br>AACTCAGTCAACCAGGAAGATTTCTACAAGTTTCTGAAAACTATCCTGTCAGCCAAGAGCGAGATCAAGGAAGT<br>GAATGACATCCTGACCGAGATTGAAACTGGCACCTTTCTGCCAAAGCAGATCTCTAAAAGTAACGCAGAGATTCC<br>CTATCAGCTGAGGAAAATGGAGCTGGAAAAGATCCTGTCCAATGCCGAAAAGCACTTCTCTTTTCTGAAGCAGAA<br>AGACGAAAAAGGACTGTCACATAGCGAGAAGATCATTATGCTGCTGACCTTCAAGATCCCTTACTATATTGGCCC<br>AATCAACGATAATCACAAGAAATTCTTTCCCGACAGATGCTGGGTGGTCAAGAAAGAGAAATCCCCTTCTGGCA<br>AGACCACACCATGGAACTTCTTTGATCATATCGACAAGGAAAAAACAGCAGAGGCCTTCATTACTTCTAGGACCA<br>ATTTTTGCACTTACCTGGTGGGAGAGAGCGTCCTGCCTAAGTCTAGTCTGCTGTACTCCGAATATACCGTGCTGAA |

FIG. 13J

CGAGATCAACAATCTGCAGATCATTATCGATGGCAAGAATATTTGTGACATCAAGCTGAAACAGAAGATCTACG
AGGACCTGTTCAAGAAGTACAAGAAAATTACCCAGAAGCAGATCAGCACCTTCATCAAGCACGAAGGCATCTGC
AACAAAACCGATGAAGTGATCATCCTGGGGATTGACAAGGAATGTACATCAAGCCTGAAAAGCTACATCGAGCT
GAAAAACATTTTCGGCAAGCAGGTGGATGAGATCTCCACTAAGAATATGCTGGAGGAAATTATCAGATGGGCTA
CCATCTACGACGAGGGGGAAGGAAAGACCATCCTGAAAACAAAGATCAAGGCAGAATACGGAAAGTATTGCTC
CGACGAGCAGATTAAGAAAATCCTGAACCTGAAGTTCTCCGGCTGGGGGCGACTGTCTCGGAAATTTCTGGAGA
CAGTGACTAGTGAAATGCCCGGCTTCTCAGAACCTGTCAATATTATCACCGCCATGAGGGAGACACAGAACAATC
TGATGGAGCTGCTGTCCTCTGAGTTCACCTTCACCGAGAACATTAAGAAAATCAATTCTGGATTCGAAGATGCCG
AGAAGCAGTTTAGTTACGACGGCCTGGTGAAACCACTGTTTCTGAGTCCCTCAGTCAAGAAAATGCTGTGGCAGA
CCCTGAAGCTGGTGAAAGAGATTAGCCATATCACACAGGCCCCCCCTAAGAAAATTTTCATCGAAATGGCAAAG
GGGGCCGAGCTGGAACCTGCTCGGACTAAGACCAGACTGAAAATCCTGCAGGATCTGTATAACAATTGTAAGAA
CGATGCTGACGCCTTCAGCTCAGAGATCAAAGACCTGAGCGGAAAGATTGAGAACGAAGATAATCTGAGGCTGC
GCTCCGACAAGCTGTACCTGTACTATACTCAGCTGGGGAAATGCATGTATTGTGGAAAGCCAATTGAGATCGGCC
ACGTGTTCGATACCTCAAACTACGATATTGACCATATCTATCCCCAGAGCAAGATCAAAGACGATAGCATTTCCA
ATCGGGTGCTGGTCTGCAGCTCCTGTAACAAGAACAAGGAGGACAAGTACCCACTGAAATCAGAGATCCAGAGC
AAGCAGCGCGGCTTCTGGAACTTTCTGCAGCGAAACAATTTCATTTCTCTGGAGAAGCTGAATAGACTGACAAGG
GCCACTCCAATCAGTGACGATGAGACAGCCAAGTTTATTGCTAGGCAGCTGGTGGAAACTCGCCAGGCTACCAA
GGTGGCCGCTAAAGTCCTGGAAAAGATGTTCCCCGAGACAAAAATCGTGTACAGCAAGGCCGAGACTGTCTCCA
TGTTCCGGAACAAGTTTGATATCGTGAAGTGCAGAGAAATTAACGATTTTCACCATGCTCACGACGCATACCTGA
ATATCGTGGTCGGCAACGTGTATAATACCAAGTTCACAAACAATCCTTGGAACTTTATCAAGGAGAAAAGAGAT
AATCCAAAGATTGCTGACACCTACAACTACTATAAGGTGTTCGATTATGACGTCAAAAGGAACAATATCACAGCA
TGGGAGAAGGGGAAAACTATTATCACCGTGAAAGACATGCTGAAGAGAAACACACCAATCTACACTAGGCAGGC
AGCCTGTAAGAAAGGGGAGCTGTTCAATCAGACCATTATGAAGAAAGGACTGGGCCAGCACCCCCTGAAGAAAG
AAGGACCTTTTTCCAATATCTCTAAATACGGCGGGTATAACAAGGTGAGCGCTGCATACTATACACTGATTGAGT
ATGAGGAAAAGGGCAACAAAATCCGCTCCCTGGAAACTATTCCCCTGTACCTGGTGAAAGATATCCAGAAGGAT
CAGGACGTCCTGAAGTCTTATCTGACAGACCTGCTGGGGAAGAAAGAGTTCAAGATCCTGGTGCCCAAGATCAA
GATCAACAGCCTGCTGAAGATCAATGGGTTTCCTTGCCATATTACAGGAAAAACTAACGATAGTTTCCTGCTGCG
CCCTGCCGTGCAGTTTTGCTGTTCAAACAATGAGGTCCTGTACTTCAAGAAAATTATCCGGTTTTCCGAAATCCGC
TCTCAGCGAGAGAAGATCGGGAAAACAATTAGCCCATACGAGGACCTGAGCTTCCGGTCATATATCAAGGAGAA
CCTGTGGAAGAAAACTAAGAACGATGAAATCGGAGAGAAGGAATTTTACGACCTGCTGCAGAAGAAAAACCTG
GAGATCTATGATATGCTGCTGACTAAGCACAAAGACACCATCTACAAGAAACGCCCTAATTCTGCCACCATTGAT
ATCCTGGTGAAGGGGAAAGAGAAGTTCAAAAGCCTGATTATCGAAAACCAGTTTGAAGTGATCCTGGAGATCCT
GAAGCTGTTTTCTGCAACACGGAATGTCAGTGACCTGCAGCATATCGGAGGCAGCAAGTACTCCGGCGTGGCCA
AAATCGGGAACAAGATCTCTAGTCTGGATAACTGTATCCTGATCTATCAGTCCATCACCGGCATCTTCGAGAAAC
GGATCGACCTGCTGAAGGTGTAAGAATTC

FIG. 13K

| | |
|---|---|
| Length of Protein (without NLS and HA tag) | 1395 |
| **PAM** | **NYAAAT** |
| Spacer Length | 30 |
| **Species: Filifactor_alocis** | |
| Sequencing Barcode | AAGACACT |
| ID | 5 |
| **Chimeric Guide RNA** | **NNNNNNNNNNNNNNNNNNNNGUUUGAGAGUAGGAAACUACACGGUUCAAAUAAAGAAUUUUUCUAAUCGCCCAAUGGGCCCAUAUUGAUAUGGAUGAAACUCGCUUAGCGAGUUUUUUU** |
| Cas9 Protein Sequence (wildtype, without NLS added) | MTKEYYLGLDVGTNSVGWAVTDSQYNLCKFKKKDMWGIRLFESANTAKDRRLQRGNRRRLERKKQRIDLLQEIFSPEICKIDPTFFIRLNESRLHLEDKSNDFKYPLFIEKDYSDIEYYKEFPTIFHLRKHLIESEEKQDIRLIYLALHNIIKTRGHFLIDGDLQSAKQLRPILDTFLLSLQEEQNLSVSLSENQKDEYEEILKNRSIAKSEKVKKLKNLFEISDELEKEEKKAQSAVIENFCKFIVGNKGDVCKFLRVSKEELEIDSFSFSEGKYEDDIVKNLEEKVPEKVYLFEQMKAMYDWNILVDILETEEYISFAKVKQYEKHKTNLRLLRDIILKYCTKDEYNRMFNDEKEAGSYTAYVGKLKKNNKKYWIEKKRNPEEFYKSLGKLLDKIEPLKEDLEVLTMMIEECKNHTLLPIQKNKDNGVIPHQVHEVELKKILENAKKYYSFLTETDKDGYSVVQKIESIFRFRIPYYVGPLSTRHQEKGSNVWMVRKPGREDRIYPWNMEEIIDFEKSNENFITRMTNKCTYLIGEDVLPKHSLLYSKYMVLNELNNVKVRGKKLPTSLKQKVFEDLFENKSKVTGKNLLEYLQIQDKDIQIDDLSGFDKDFKTSLKSYLDFKKQIFGEEIEKESIQNMIEDIIKWITIYGNDKEMLKRVIRANYSNQLTEEQMKKITGFQYSGWGNFSKMFLKGISGSDVSTGETFDIITAMWETDNNLMQILSKKFTFMDNVEDFNSGKVGKIDKITYDSTVKEMFLSPENKRAVWQTIQVAEEIKKVMGCEPKKIFIEMARGGEKVKKRTKSRKAQLLELYAACEEDCRELIKEIEDRDERDFNSMKLFLYYTQFGKCMYSGDDIDINELIRGNSKWDRDHIYPQSKIKDDSIDNLVLVNKTYNAKKSNELLSEDIQKKMHSFWLSLLNKKLITKSKYDRLTRKGDFTDEELSGFIARQLVETRQSTKAIADIFKQIYSSEVVYVKSSLVSDFRKKPLNYLKSRRVNDYHHAKDAYLNIVVGNVYNKKFTSNPIQWMKKNRDTNYSLNKVFEHDVVINGEVIWEKCTYHEDTNTYDGGTLDRIRKIVERDNILYTEYAYCEKGELFNATIQNKNGNSTVSLKKGLDVKKYGGYFSANTSYFSLIEFEDKKGDRARHIIGVPIYIANMLEHSPSAFLEYCEQKGYQNVRILVEKIKKNSLLIINGYPLRIRGENEVDTSFKRAIQLKLDQKNYELVRNIEKFLEKYVEKKGNYPIDENRDHITHEKMNQLYEVLLSKMKKFNKKGMADPSDRIEKSKPKFIKLEDLIDKINVINKMLNLLRCDNDTKADLSLIELPKNAGSFVVKKNTIGKSKIILVNQSVTGLYENRREL |

FIG. 13L

| | |
|---|---|
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGACCAAGGAGTATTACCTGGGGCTGGATGTGGGGACCAATTCCGTGGGATGGGCAGTGACCGATTCTCAGT<br>ACAACCTGTGCAAGTTTAAGAAAAAGGATATGTGGGGCATCCGGCTGTTCGAAAGCGCCAACACAGCAAAGGAC<br>CGGAGACTGCAGAGAGGGAATAGGCGCCGACTGGAGCGGAAAAAGCAGAGAATTGATCTGCTGCAGGAAATCT<br>TCTCCCCAGAGATCTGCAAGATTGACCCCACTTTCTTTATCCGACTGAACGAATCCCGGCTGCACCTGGAGGACA<br>AGTCTAACGATTTCAAATACCCACTGTTTATTGAGAAGGACTATTCTGATATCGAGTACTATAAAGAGTTCCCCA<br>CCATTTTTCACCTGAGGAAGCATCTGATCGAGAGTGAGGAAAAACAGGATATCCGGCTGATCTACCTGGCCCTGC<br>ACAACATCATTAAGACCCGAGGACATTTTCTGATTGACGGCGATCTGCAGAGCGCCAAGCAGCTGAGGCCCATCC<br>TGGATACATTCCTGCTGTCCCTGCAGGAGGAACAGAACCTGTCAGTGAGCCTGTCCGAAAATCAGAAGGACGAG<br>TATGAGGAAATTCTGAAAAACCGCAGCATCGCCAAGTCCGAAAAAGTGAAAAAGCTGAAGAATCTGTTTGAGAT<br>CTCAGACGAGCTGGAAAAAGAGGAGAAGAAGGCCCAGAGCGCCGTGATCGAGAACTTCTGCAAGTTTATCGTGG<br>GAAATAAGGGCGATGTCTGTAAATTCCTGCGGGTGTCTAAGGAGGAACTGGAGATTGACTCTTTCAGTTTTTCAG<br>AGGGCAAGTACGAGGACGACATCGTGAAAAACCTGGAGGAAAAAGTGCCTGAAAAGGTCTACCTGTTTGAGCAG<br>ATGAAGGCAATGTATGATTGGAATATTCTGGTCGACATCCTGGAAACCGAGGAATACATCAGCTTCGCCAAAGTG<br>AAGCAGTATGAGAAACACAAGACTAACCTGCGGCTGCTGAGAGACATCATTCTGAAATACTGCACCAAGGATGA<br>GTATAATCGGATGTTTAACGACGAGAAGGAAGCTGGCAGCTACACCGCATATGTGGGGAAACTGAAAAAGAACA<br>ACAAGAAGTACTGGATCGAGAAAAAGAGAAATCCCGAGGAGTTCTACAAATCCCTGGGCAAGCTGCTGGATAAA<br>ATTGAGCCTCTGAAGGAGGACCTGGAAGTGCTGACTATGATGATCGAGGAGTGTAAGAACCACACCCTGCTGCC<br>AATTCAGAAAAATAAGGACAACGGCGTGATCCCCCACCAGGTGCATGAGGTCGAACTGAAAAAGATCCTGGAAA<br>ATGCCAAAAAGTACTATTCCTTCCTGACCGAGACAGACAAGGATGGGTACTCAGTGGTCCAGAAAATCGAGAGC<br>ATTTTCAGGTTTCGCATCCCCTACTATGTGGGGCCTCTGAGTACCCGGCACCAGGAAAAGGGATCAAACGTGTGG<br>ATGGTCAGAAAACCTGGCAGGGAGGATCGCATCTACCCATGGAATATGGAGGAAATCATTGACTTTGAGAAGAG<br>CAACGAAAATTTCATTACACGGATGACTAACAAATGTACATATCTGATCGGGGAAGATGTCCTGCCCAAGCATTC<br>TCTGCTGTACAGTAAATATATGGTGCTGAATGAGCTGAACAATGTGAAGGTCAGAGGAAAAAAGCTGCCTACAT<br>CTCTGAAACAGAAGGTGTTCGAGGACCTGTTTGAAAACAAATCCAAAGTGACTGGAAAGAATCTGCTGGAGTAC<br>CTGCAGATCCAGGACAAAGATATCCAGATTGACGATCTGTCTGGCTTCGACAAGGACTTCAAGACCAGCCTGAA<br>GAGCTATCTGGACTTCAAAAAGCAGATTTTTGGGGAGGAAATCGAGAAGGAAAGCATTCAGAACATGATCGAAG<br>ATATCATTAAGTGGATCACCATCTACGGCAATGACAAGGAGATGCTGAAACGAGTGATTCGGGCTAATTATAGC<br>AACCAGCTGACAGAGGAACAGATGAAAAAGATCACTGGATTTCAGTACAGTGGCTGGGGGAACTTCTCAAAGAT<br>GTTTCTGAAAGGGATCAGCGGATCCGACGTGAGCACCGGCGAAACATTCGACATCATTACCGCAATGTGGGAGA<br>CAGACAACAATCTGATGCAGATCCTGTCAAAAAAGTTCACCTTTATGGACAACGTCGAGGACTTCAACAGCGGC<br>AAGGTCGGGAAAATCGACAAGATTACTTACGATAGCACCGTGAAGGAAATGTTCCTGTCCCCTGAGAACAAAAG<br>GGCCGTCTGGCAGACCATTCAGGTGGCTGAGGAGATCAAGAAAGTGATGGGCTGCGAGCCAAAAAAGATCTTTA<br>TTGAAATGGCACGGGGCGGGGAGAAGGTGAAAAAGAGGACAAAATCTCGCAAGGCCCAGCTGCTGGAGCTGTA<br>CGCCGCTTGCGAGGAAGATTGTAGAGAACTGATCAAGGAGATTGAGGACCGGGACGAGAGGGACTTCAATAGCA |

FIG. 13M

| | |
|---|---|
| | TGAAGCTGTTTCTGTACTATACCCAGTTCGGGAAATGTATGTATTCCGGCGACGACATCGATATTAACGAGCTGA<br>TTCGCGGCAATTCTAAGTGGGACCGAGATCACATCTACCCCCAGAGCAAAATTAAGGACGATTCCATCGATAACC<br>TGGTGCTGGTCAATAAGACATATAATGCCAAAAAGTCCAATGAGCTGCTGTCTGAGGACATCCAGAAAAAGATG<br>CATTCATTCTGGCTGAGCCTGCTGAACAAAAAGCTGATCACTAAAAGCAAGTACGACCGCCTGACTCGAAAGGG<br>CGACTTTACCGATGAGGAACTGAGTGGGTTCATCGCTAGACAGCTGGTGGAAACAAGGCAGTCAACTAAGGCAA<br>TCGCCGATATCTTCAAGCAGATCTACAGCTCCGAGGTGGTCTATGTGAAGAGCAGCCTGGTGAGCGACTTCAGGA<br>AAAAGCCACTGAACTACCTGAAGTCTCGGAGAGTCAATGATTACCACCATGCAAAAGACGCCTATCTGAACATT<br>GTGGTCGGGAACGTGTACAACAAAAAGTTTACCAGTAATCCCATCCAGTGGATGAAAAAGAATCGCGATACAAA<br>CTATAGCCTGAACAAGGTGTTCGAACACGACGTGGTCATTAACGGAGAAGTGATCTGGGAAAAGTGCACATACC<br>ATGAGGACACTAATACCTATGATGGAGGCACTCTGGACCGAATCCGGAAGATTGTGGAACGCGATAACATTCTG<br>TACACCGAGTACGCTTATTGTGAGAAGGGCGAACTGTTTAATGCAACCATCCAGAACAAAAATGGAAACTCCAC<br>AGTCTCTCTGAAAAAGGGCCTGGACGTGAAAAAGTACGGGGGATACTTCAGCGCCAACACAAGTTACTTCTCACT<br>GATCGAGTTTGAGGACAAGAAGGGGGATAGAGCAAGGCACATCATTGGAGTGCCTATCTATATTGCAAACATGC<br>TGGAGCATTCTCCAAGTGCCTTCCTGGAGTACTGCGAACAGAAGGGGTATCAGAATGTGCGGATTCTGGTCGAGA<br>AAATCAAAAAGAACAGCCTGCTGATCATTAATGGATACCCTCTGCGCATTCGAGGCGAGAACGAAGTGGATACT<br>TCCTTTAAGAGGGCCATCCAGCTGAAGCTGGACCAGAAAAACTATGAGCTGGTCCGCAATATCGAGAAGTTCCTG<br>GAAAAATACGTGGAGAAAAAGGGAAACTATCCAATTGACGAGAATAGAGATCACATCACACATGAAAAGATGA<br>ACCAGCTGTACGAGGTGCTGCTGTCCAAAATGAAAAAGTTCAACAAGAAGGGCATGGCCGACCCCTCTGATAGG<br>ATCGAAAAGAGTAAGCCTAAATTCATCAAGCTGGAGGACCTGATCGATAAGATTAATGTGATCAACAAAATGCT<br>GAACCTGCTGCGCTGTGACAATGATACTAAGGCCGACCTGTCTCTGATTGAGCTGCCCAAAAACGCTGGGAGTTT<br>CGTGGTCAAAAAGAATACCATCGGAAAGTCAAAAATCATCCTGGTGAATCAGAGCGTGACTGGACTGTACGAGA<br>ATAGACGGGAACTGTAAGAATTC |
| Length of Protein (without NLS and HA tag) | 1365 |
| **PAM** | **NNNAAGC** |
| Spacer Length | 30-31 |
| **Species: Staphylococcus_pseudintermedius** | |
| Sequencing | TCTCGGTC |

FIG. 13N

| | |
|---|---|
| Barcode | |
| ID | 6 |
| **Chimeric Guide RNA** | **NNNNNNNNNNNNNNNNNNNNGUUUUAGCACUAGAAAUAGUUAAGUUAAAACAAGCUUAAAGCGUCAAUGU<br>AAUAUUUUAUUAACACCCUACUGUGUCAGUGGGGUUUUUU** |
| Cas9 Protein Sequence (wildtype, without NLS added) | MGRKPYILSLDIGTGSVGYACMDKGFNVLKYHDKDALGVYLFDGALTAQERRQFRTSRRRKNRRIKRLGLLQELLAP<br>LVQNPNFYQFQRQFAWKNDNMDFKNKSLSEVLSFLGYESKKYPTIYHLQEALLLKDEKFDPELIYMALYHLVKYRGH<br>FLFDHLKIENLTNNDNMHDFVELIETYENLNNIKLNLDYEKTKVIYEILKDNEMTKNDRAKRVKNMEKKLEQFSIMLL<br>GLKFNEGKLFNHADNAEELKGANQSHTFADNYEENLTPFLTVEQSEFIERANKIYLSLTLQDILKGKKSMAMSKVAAY<br>DKFRNELKQVKDIVYKADSTRTQFKKIFVSSKKSLKQYDATPNDQTFSSLCLFDQYLIRPKKQYSLLIKELKKIIPQDSE<br>LYFEAENDTLLKVLNTTDNASIPMQINLYEAETILRNQQKYHAEITDEMIEKVLSLIQFRIPYYVGPLVNDHTASKFGW<br>MERKSNESIKPWNFDEVVDRSKSATQFIRRMTNKCSYLINEDVLPKNSLLYQEMEVLNELNATQIRLQTDPKNRKYRM<br>MPQIKLFAVEHIFKKYKTVSHSKFLEIMLNSNHRENFMNHGEKLSIFGTQDDKKFASKLSSYQDMTKIFGDIEGKRAQI<br>EEHQWITIFEDKKILVQKLKECYPELTSKQINQLKKLNYSGWGRLSEKLLTHAYQGHSIIELLRHSDENFMEILTNDVY<br>GFQNFIKEENQVQSNKIQHQDIANLTTSPALKKGIWSTIKLVRELTSIFGEPEKIIMEFATEDQQKGKKQKSRKQLWDD<br>NIKKNKLKSVDEYKYIIDVANKLNNEQLQQEKLWLYLSQNGKCMYSGQSIDLDALLSPNATKHYEVDHIFPRSFIKDD<br>SIDNKVLVIKKMNQTKGDQVPLQFIQQPYERIAYWKSLNKAGLISDSKLHKLMKPEFTAMDKEGFIQRQLVETRQISV<br>HVRDFLKEEYPNTKVIPMKAKMVSEFRKKFDIPKIRQMNDAHHAIDAYLNGVVYHGAQLAYPNVDLFDFNFKWEKV<br>REKWKALGEFNTKQKSRELFFFKKLEKMEVSQGERLISKIKLDMNHFKINYSRKLANIPQQFYNQTAVSPKTAELKYE<br>SNKSNEVVYKGLTPYQTYVVAIKSVNKKGKEKMEYQMIDHYVFDFYKFQNGNEKELALYLAQRENKDEVLDAQIVY<br>SLNKGDLLYINNHPCYFVSRKEVINAKQFELTVEQQLSLYNVMNNKETNVEKLLIEYDFIAEKVINEYHHYLNSKLKE<br>KRVRTFFSESNQTHEDFIKALDELFKVVTASATRSDKIGSRKNSMTHRAFLGKGKDVKIAYTSISGLKTTKPKSLFKLA<br>ESRNEL |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGGGGAGGAAACCTTACATTCTGTCTCTGGATATTGGAACTGGGTCCGTCGGCTACGCTTGCATGGATAAAGG<br>ATTCAACGTGCTGAAGTACCACGACAAAGATGCCCTGGGAGTGTATCTGTTCGACGGCGCTCTGACTGCACAGGA<br>GCGGAGACAGTTTAGGACCTCCAGGCGCCGAAAGAACCGGAGAATCAAACGCCTGGGCCTGCTGCAGGAACTGC<br>TGGCACCCCTGGTGCAGAACCCTAATTTCTACCAGTTTCAGCGGCAGTTCGCCTGGAAGAACGACAATATGGATT<br>TTAAGAACAAGAGCCTGTCTGAGGTGCTGAGCTTCCTGGGATATGAATCCAAGAAATACCCTACCATCTACCACC<br>TGCAGGAGGCTCTGCTGCTGAAAGACGAGAAGTTTGATCCAGAACTGATCTACATGGCACTGTATCATCTGGTGA<br>AATACAGAGGCCACTTTCTGTTCGATCATCTGAAGATCGAGAACCTGACTAACAATGACAATATGCACGATTTCG<br>TGGAGCTGATTGAAACCTATGAGAACCTGAACAATATCAAGCTGAATCTGGACTACGAGAAAACCAAAGTGATC<br>TATGAGATTCTGAAAGACAACGAAATGACTAAGAATGATAGAGCCAAAAGGGTCAAGAACATGGAGAAGAAAC<br>TGGAACAGTTCTCTATCATGCTGCTGGGGCTGAAGTTCAATGAGGGAAAACTGTTTAACCACGCCGATAATGCTG<br>AGGAACTGAAGGGGGCTAACCAGAGCCATACATTTGCAGACAACTACGAGGAAAATCTGACTCCCTTCCTGACC |

FIG. 13O

GTGGAACAGTCAGAGTTTATTGAAAGGGCCAACAAAATCTATCTGAGCCTGACTCTGCAGGATATCCTGAAGGG
CAAGAAATCAATGGCTATGAGCAAAGTGGCCGCTTACGACAAGTTCAGAAATGAGCTGAAACAGGTGAAGGACA
TTGTCTATAAGGCTGATTCTACCAGGACACAGTTCAAGAAAATCTTTGTGAGCTCCAAGAAAAGTCTGAAGCAGT
ACGACGCAACTCCCAACGATCAGACCTTCTCTAGTCTGTGCCTGTTTGACCAGTACCTGATTCGCCCAAAGAAAC
AGTATAGCCTGCTGATCAAGGAGCTGAAGAAAATCATTCCCCAGGACTCCGAACTGTACTTTGAGGCAGAAAAT
GATACCCTGCTGAAGGTGCTGAACACCACAGACAATGCTAGCATCCCTATGCAGATTAACCTGTACGAGGCAGA
AACCATCCTGCGAAATCAGCAGAAATATCACGCCGAGATCACAGATGAGATGATTGAAAAGGTGCTGTCTCTGA
TCCAGTTCCGCATTCCATACTATGTGGGGCCCCTGGTCAACGACCATACAGCCAGTAAGTTTGGATGGATGGAGC
GCAAAAGTAACGAATCAATCAAGCCTTGGAATTTCGACGAGGTGGTCGATCGAAGTAAATCAGCCACTCAGTTT
ATTAGGCGCATGACCAACAAGTGTTCCTACCTGATCAATGAGGATGTGCTGCCAAAAAACTCTCTGCTGTATCAG
GAGATGGAAGTCCTGAACGAACTGAATGCCACACAGATCAGGCTGCAGACTGACCCAAAAAACCGCAAGTACCG
AATGATGCCCCAGATTAAGCTGTTCGCTGTGGAGCACATCTTTAAGAAATATAAAACCGTCAGCCATTCCAAGTT
CCTGGAAATTATGCTGAACAGCAATCACAGGGAGAACTTTATGAATCATGGAGAAAAGCTGAGTATCTTCGGCA
CACAGGACGATAAGAAATTTGCATCAAAGCTGTCAAGCTACCAGGACATGACTAAAATCTTCGGGGATATTGAG
GGAAAGCGCGCCCAGATTGAGGAAATCATTCAGTGGATCACCATTTTTGAGGACAAGAAAATCCTGGTGCAGAA
GCTGAAAGAGTGCTATCCTGAACTGACATCCAAGCAGATCAACCAGCTGAAGAAACTGAATTACTCTGGCTGGG
GGAGGCTGAGTGAGAAGCTGCTGACTCACGCCTATCAGGGCCATAGCATCATTGAACTGCTGCGCCACTCCGATG
AGAATTTCATGGAAATTCTGACCAACGACGTGTACGGGTTCCAGAATTTTATCAAAGAGGAAAACCAGGTCCAG
AGCAATAAGATCCAGCATCAGGATATTGCCAACCTGACTACCTCTCCCGCTCTGAAGAAAGGCATCTGGAGTACA
ATTAAGCTGGTGCGGGAGCTGACTTCCATTTTCGGGGAGCCTGAAAAGATCATTATGGAGTTTGCTACCGAGGAC
CAGCAGAAAGGCAAGAAACAGAAATCAAGAAAGCAGCTGTGGGACGATAACATCAAGAAAAATAAGCTGAAAA
GCGTGGACGAGTACAAATATATCATTGATGTCGCCAATAAGCTGAACAATGAGCAGCTGCAGCAGGAAAAACTG
TGGCTGTACCTGAGCCAGAACGGCAAGTGTATGTATAGCGGGCAGTCCATCGACCTGGATGCCCTGCTGTCCCCC
AATGCTACCAAGCACTACGAGGTGGATCATATTTTCCCTCGGAGCTTCATCAAGGACGATAGCATTGACAACAAG
GTGCTGGTCATCAAGAAAATGAATCAGACAAAGGGCGATCAGGTGCCCCTGCAGTTCATTCAGCAGCCTTACGA
GAGAATCGCATATTGGAAGAGCCTGAACAAAGCCGGGCTGATCTCTGATAGTAAACTGCACAAGCTGATGAAAC
CAGAGTTCACAGCTATGGACAAGGAAGGCTTCATCCAGCGGCAGCTGGTGGAGACTAGACAGATCAGCGTGCAT
GTCCGGGATTTTCTGAAAGAGGAATACCCTAATACCAAAGTGATCCCAATGAAGGCCAAAATGGTGAGCGAGTT
CCGGAAGAAATTTGACATCCCAAAGATTAGACAGATGAACGACGCACACCATGCCATCGATGCTTACCTGAATG
GCGTGGTCTATCACGGGGCACAGCTGGCCTACCCCAACGTGGACCTGTTTGATTTCAATTTTAAGTGGGAGAAAG
TCCGAGAAAAGTGGAAAGCCCTGGGAGAGTTCAACACAAAGCAGAAATCTCGGGAACTGTTCTTTTTCAAGAAA
CTGGAGAAGATGGAAGTGTCCCAGGGCGAGCGGCTGATCTCTAAGATCAAGCTGGACATGAACCACTTCAAGAT
CAACTACTCCAGAAAGCTGGCCAACATCCCTCAGCAGTTTTATAATCAGACCGCAGTGTCTCCAAAGACAGCCGA
GCTGAAATACGAATCTAACAAGAGTAATGAGGTGGTCTATAAGGGACTGACACCATACCAGACTTATGTGGTCG
CCATCAAGAGCGTGAACAAGAAAGGCAAGGAGAAAATGGAATACCAGATGATCGACCACTACGTGTTCGATTTT
TATAAATTCCAGAACGGCAATGAGAAGGAACTGGCTCTGTACCTGGCACAGAGGGAGAACAAGGACGAAGTGCT

FIG. 13P

| | |
|---|---|
| | GGATGCTCAGATTGTCTATAGTCTGAATAAGGGGGATCTGCTGTACATCAACAATCATCCCTGCTATTTCGTGTCA<br>CGCAAAGAGGTCATCAACGCAAAGCAGTTTGAGCTGACCGTGGAACAGCAGCTGTCTCTGTACAACGTGATGAA<br>CAACAAGGAGACAAATGTCGAAAAGCTGCTGATCGAGTATGACTTCATTGCCGAGAAAGTGATCAACGAATACC<br>ACCATTATCTGAATAGCAAGCTGAAAGAAAAGCGAGTCCGGACCTTTTTCTCAGAGAGCAACCAGACACACGAG<br>GACTTCATCAAGGCCCTGGACGAGCTGTTTAAGGTGGTCACCGCATCCGCCACAAGGTCTGATAAAATCGGGAGT<br>CGCAAGAACAGCATGACTCATCGAGCCTTCCTGGGAAAAGGCAAGGACGTGAAGATTGCTTACACCTCCATCTCT<br>GGACTGAAAACAACTAAACCTAAGAGTCTGTTTAAGCTGGCCGAGTCAAGAAACGAACTGTAAGAATTC |
| Length of Protein (without NLS and HA tag) | 1334 |
| **PAM** | **NGG** |
| Spacer Length | 29 |
| **Species: Lactobacillus_johnsonii** | |
| Sequencing Barcode | AATGTTCT |
| ID | 7 |
| **Chimeric Guide RNA** | **NNNNNNNNNNNNNNNNNNNNGUUUUAGAUGGUGAAAACCAGAUUUAAAAUCAAGCAAUGCAUCUUUUGAU<br>GCAAAGUUUCAAUAUUUGUCCCACGUUAUCGAGGGACUUUUUUU** |
| Cas9 Protein Sequence (wildtype, without NLS added) | MTKIKDDYIVGLDIGTDSCGWVAMNSNNDILKLQGKTAIGSRLFEGGKSAAERRLFRTTHRRIKRRRWRLKLLEEFFD<br>PYMAEVDPYFFARLKESGLSPLDKRKTVSSIVFPTSAEDKKFYDDYPTIYHLRYKLMTEDEKFDLREVYLAIHHIIKYR<br>GNFLYNTSVKDFKASKIDVKSSIEKLNELYENLGLDLNVEFNISNTAEIEKVLKDKQIFKRDKVKKIAELFAIKTDNKEQ<br>SKRIKDISKQVANAVLGYKTRFDTIALKEISKDELSDWNFKLSDIDADSKFEALMGNLDENEQAILLTIKELFNEVTLNG<br>IVEDGNTLSESMINKYNDHRDDLKLLKEVIENHIDRKKAKELALAYDLYVNNRHGQLLQAKKKLGKIKPRSKEDFYK<br>VVNKNLDDSRASKEIKKKIELDSFMPKQRTNANGVIPYQLQQLELDKIIENQSKYYPFLKEINPVSSHLKEAPYKLDELI<br>RFRVPYYVGPLISPNESTKDIQTKKNQNFAWMIRKEEGRITPWNFDQKVDRIESANKFIKRMTTKDTYLFGEDVLPANS<br>LLYQKFTVLNELNNIRINGKRISVDLKQEIYENLFKKHTTVTVKKLENYLKENHNLVKVEIKGLADEKKFNSGLTTYN<br>RFKNLNIFDNQIDDLKYRNDFEKIIEWSTIFEDKSIYKEKLRSIDWLNEKQINALSNIRLQGWGRLSKKLLAQLHDHNGQ<br>TIIEQLWDSQNNFMQIVTQADFKDAIAKANQNLLVATSVEDILNNAYTSPANKKAIRQVIKVVDDIVKAASGKVPKQI |

FIG. 13Q

| | |
|---|---|
| | AIEFTRDADENPKRSQTRGSKLQKVYKDLSTELASKTIAEELNEAIKDKKLVQDKYYLYFMQLGRDAYTGEPINIDEIQ<br>KYDIDHILPQSFIKDDALDNRVLVSRAVNNGKSDNVPVKLFGNEMAANLGMTIRKMWEEWKNIGLISKTKYNNLLTD<br>PDHINKYKSAGFIRRQLVETSQIIKLVSTILQSRYPNTEIITVKAKYNHYLREKFDLYKSREVNDYHHAIDAYLSAICGNL<br>LYQNYPNLRPFFVYGQYKKFSSDPDKEKAIFNKTRKFSFISQLLKNKSENSKEIAKKLKRAYQFKYMLVSRETETRDQE<br>MFKMTVYPRFSHDTVKAPRNLIPKKMGMSPDIYGGYTNNSDAYMVIVRIDKKKGTEYKILGIPTRELVNLKKAEKED<br>HYKSYLKEILTPRILYNKNGKRDKKITSFEIVKSKIPYKQVIQDGDKKFMLGSSTYVYNAKQLTLSTESMKAITNNFDK<br>DSDENDALIKAYDEILDKVDKYLPLFDINKFREKLHSGREKFIKLSLEDKKDTILKVLEGLHDNAVMTKIPTIGLSTPLG<br>FMQFPNGVILSENAKLIYQSPTGLFKKSVKISDL |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGACAAAAATCAAAGACGACTACATCGTGGGACTGGACATCGGCACAGACTCCTGCGGGTGGGTGGCTATGA<br>ACAGCAATAATGACATTCTGAAACTGCAGGGCAAGACCGCAATCGGGTCACGCCTGTTCGAGGGAGGGAAGAGC<br>GCAGCTGAACGGAGACTGTTTCGCACCACACACAGGCGCATCAAACGACGGAGATGGCGACTGAAGCTGCTGGA<br>GGAGTTCTTCGACCCCTACATGGCAGAGGTGGATCCTTATTTCTTTGCCCGGCTGAAGGAATCTGGCCTGAGTCC<br>ACTGGACAAAAGAAAGACCGTGAGCTCCATTGTGTTCCCCACATCCGCCGAGGATAAGAAGTTCTACGACGATT<br>ACCCTACAATCTACCATCTGAGGTATAAACTGATGACTGAGGACGAAAAGTTCGATCTGCGCGAAGTGTACCTGG<br>CTATCCACCATATCATTAAGTACCGAGGAAACTTCCTGTATAATACCAGTGTGAAAGACTTCAAGGCATCAAAGA<br>TCGATGTCAAATCTAGTATCGAGAAGCTGAACGAGCTGTATGAAAATCTGGGCCTGGACCTGAACGTGGAGTTCA<br>ACATTAGCAATACTGCCGAGATCGAAAAGGTGCTGAAAGACAAGCAGATCTTCAAGCGGGATAAAGTCAAGAAA<br>ATTGCCGAGCTGTTTGCTATCAAAACCGACAACAAGGAACAGAGCAAGAGAATCAAAGATATTTCCAAACAGGT<br>GGCCAATGCTGTCCTGGGGTACAAGACCAGGTTCGACACAATCGCTCTGAAAGAGATTTCCAAGGACGAACTGT<br>CTGATTGGAACTTCAAACTGTCAGACATCGATGCAGACAGCAAGTTTGAGGCCCTGATGGGAAACCTGGATGAG<br>AATGAACAGGCCATCCTGCTGACTATTAAGGAGCTGTTTAACGAAGTGACCCTGAATGGAATTGTCGAGGACGG<br>CAACACCCTGAGCGAATCCATGATCAACAAGTACAATGATCACCGGGACGATCTGAAGCTGCTGAAAGAAGTGA<br>TCGAAAATCATATTGACAGAAAGAAAGCCAAGGAGCTGGCACTGGCCTACGATCTGTATGTCAACAATAGGCAC<br>GGACAGCTGCTGCAGGCTAAGAAAAAGCTGGGCAAAATCAAGCCCCGCTCTAAGGAGGACTTCTACAAAGTGGT<br>CAACAAGAATCTGGACGATTCACGGGCAAGCAAGGAGATCAAAAAGAAAATTGAACTGGACAGCTTTATGCCTA<br>AGCAGAGAACCAACGCCAATGGCGTGATCCCATACCAGCTGCAGCAGCTGGAGCTGGATAAGATCATCGAAAAC<br>CAGTCTAAGTACTATCCATTCCTGAAGGAGATTAATCCCGTGTCAAGCCACCTGAAAGAGGCCCCCTATAAGCTG<br>GACGAACTGATCCGATTTCGGGTGCCTTACTATGTCGGCCCCCTGATTTCTCCTAACGAGAGTACCAAGGATATC<br>CAGACAAAGAAAAACCAGAATTTCGCCTGGATGATTCGCAAAGAGGAAGGGCGAATCACACCTTGGAACTTTGA<br>CCAGAAGGTGGATCGAATTGAGAGCGCCAATAAGTTCATCAAACGGATGACTACCAAGGACACTTACCTGTTTG<br>GGGAGGATGTGCTGCCAGCTAACAGCCTGCTGTATCAGAAGTTCACCGTCCTGAACGAACTGAACAACATCCGG<br>ATTAATGGAAAAAGAATCTCCGTGGACCTGAAGCAGGAGATCTACGAAAACCTGTTTAAGAAACACACAACTGT<br>GACCGTCAAGAAACTGGAGAATTATCTGAAGGAAAACCATAATCTGGTGAAAGTCGAGATCAAGGGGCTGGCCG<br>ATGAAAAGAAATTCAACAGCGGACTGACCACATACAATAGATTCAAGAACCTGAACATCTTTGACAACCAGATT |

FIG. 13R

| | |
|---|---|
| | GACGATCTGAAGTACAGGAACGATTTCGAGAAGATCATCGAATGGTCTACAATTTTTGAGGACAAGAGTATCTAC<br>AAAGAAAAGCTGAGGAGCATCGATTGGCTGAACGAGAAGCAGATTAACGCTCTGTCTAATATCAGACTGCAGGG<br>GTGGGGAAGGCTGAGTAAGAAACTGCTGGCACAGCTGCACGACCATAATGGCCAGACCATCATTGAGCAGCTGT<br>GGGATTCCCAGAACAATTTCATGCAGATTGTGACACAGGCCGACTTTAAAGATGCTATCGCAAAGGCCAACCAG<br>AATCTGCTGGTGGCTACCTCAGTCGAGGACATTCTGAACAATGCATACACAAGCCCCGCAAACAAGAAAGCCAT<br>CAGACAGGTCATCAAGGTGGTCGACGATATCGTGAAGGCAGCCTCCGGAAAGGTCCCAAAACAGATCGCCATTG<br>AGTTCACTAGGGATGCTGACGAAAATCCCAAGAGAAGTCAGACCAGGGGCTCAAAGCTGCAGAAAGTGTACAAG<br>GACCTGAGCACTGAGCTGGCCTCCAAGACCATTGCTGAGGAACTGAACGAAGCAATCAAAGACAAGAAACTGGT<br>GCAGGATAAGTACTATCTGTACTTTATGCAGCTGGGGCGGGACGCCTATACAGGAGAGCCTATCAATATCGATGA<br>AATCCAGAAGTACGATATCGACCACATTCTGCCACAGTCTTTCATCAAGGACGATGCCCTGGACAACAGGGTGCT<br>GGTGAGCCGGGCTGTGAACAATGGCAAATCTGATAATGTGCCTGTCAAGCTGTTTGGCAACGAGATGGCTGCAA<br>ATCTGGGGATGACTATCAGGAAAATGTGGGAGGAATGGAAGAACATCGGCCTGATTAGCAAAACAAAGTACAAC<br>AATCTGCTGACTGATCCCGACCACATTAACAAGTATAAGAGTGCCGGGTTCATCAGGCGCCAGCTGGTGGAGAC<br>ATCACAGATCATCAAGCTGGTGAGCACTATCCTGCAGAGTCGCTACCCTAACACTGAAATCATTACCGTGAAGGC<br>TAAGTACAATCATTATCTGCGGGAGAAATTTGACCTGTATAAGAGCAGAGAAGTCAACGACTACCACCATGCTAT<br>TGATGCATATCTGTCCGCCATCTGCGGAAATCTGCTGTACCAGAACTATCCAAATCTGCGGCCCTTCTTTGTGTAC<br>GGCCAGTATAAGAAATTCTCCTCTGATCCTGACAAAGAGAAGGCCATTTTTAACAAAACCCGCAAGTTCTCCTTT<br>ATCTCTCAGCTGCTGAAAAACAAGAGTGAGAACAGCAAGGAAATCGCTAAGAAACTGAAACGGGCATACCAGTT<br>CAAGTATATGCTGGTGTCTCGAGAGACTGAAACCCGGGACCAGGAGATGTTCAAAATGACCGTGTACCCCCGGTT<br>CAGCCACGATACAGTCAAGGCTCCTAGGAACCTGATTCCAAAGAAAATGGGCATGTCCCCTGACATCTACGGAG<br>GCTATACAAACAATTCTGACGCATACATGGTCATCGTCCGCATTGATAAGAAAAAGGGAACTGAGTATAAGATC<br>CTGGGCATTCCAACCCGGGAACTGGTGAATCTGAAAAAGGCCGAGAAGGAGGACCATTACAAAAGCTATCTGAA<br>GGAGATCCTGACACCAAGGATTCTGTACAACAAAAATGGGAAGCGCGATAAAAAGATCACTTCCTTCGAAATTG<br>TGAAATCTAAGATCCCCTATAAGCAGGTCATCCAGGATGGGGACAAAAAGTTTATGCTGGGAAGTTCAACATAC<br>GTGTATAACGCAAAGCAGCTGACACTGAGCACTGAGTCCATGAAAGCCATCACTAACAATTTCGATAAGGACAG<br>CGATGAGAACGACGCTCTGATTAAGGCATACGATGAAATCCTGGACAAAGTGGATAAGTATCTGCCACTGTTCG<br>ACATCAACAAGTTCCGGGAGAAGCTGCACAGTGGGCGAGAAAAGTTCATCAAGCTGAGCCTGGAGGACAAAAA<br>GGATACCATCCTGAAAGTGCTGGAAGGACTGCATGATAACGCTGTCATGACAAAGATCCCTACTATTGGCCTGTC<br>CACACCACTGGGGTTCATGCAGTTTCCCAACGGCGTGATTCTGAGCGAGAATGCCAAACTGATCTACCAGTCCCC<br>CACCGGGCTGTTCAAAAAGTCAGTGAAGATCAGCGACCTGTAAGAATTC |
| Length of Protein (without NLS and HA tag) | 1375 |
| **PAM** | **NTAAA** |

FIG. 13S

| | |
|---|---|
| Spacer Length | 30 |
| **Species: Neisseria_cinerea** | |
| Sequencing Barcode | ATTGTCTG |
| ID | 18 |
| **Chimeric Guide RNA** | **NNNNNNNNNNNNNNNNNNNNGUUGUAGCUCCCAUUCUCGAAAGAGAACCGUUGCUACAAUAAGGCCGUCU<br>GAAAAGAUGUGCCGCAACGCUCUGCCCCUUAAAGCUUCUGCUUUAAGGGGCAUCGUUUAUUUCGGUUAA<br>AAAUGCCGUCUGAAACCGGUUUUUAGGUUUCAGACGGCA** |
| Cas9 Protein Sequence (wildtype, without NLS added) | MAAFKPNPMNYILGLDIGIASVGWAIVEIDEEENPIRLIDLGVRVFERAEVPKTGDSLAAARRLARSVRRLTRRRAHRL<br>LRARRLLKREGVLQAADFDENGLIKSLPNTPWQLRAAALDRKLTPLEWSAVLLHLIKHRGYLSQRKNEGETADKELG<br>ALLKGVADNTHALQTGDFRTPAELALNKFEKESGHIRNQRGDYSHTFNRKDLQAELNLLFEKQKEFGNPHVSDGLKE<br>GIETLLMTQRPALSGDAVQKMLGHCTFEPTEPKAAKNTYTAERFVWLTKLNNLRILEQGSERPLTDTERATLMDEPYR<br>KSKLTYAQARKLLDLDDTAFFKGLRYGKDNAEASTLMEMKAYHAISRALEKEGLKDKKSPLNLSPELQDEIGTAFSLF<br>KTDEDITGRLKDRVQPEILEALLKHISFDKFVQISLKALRRIVPLMEQGNRYDEACTEIYGDHYGKKNTEEKIYLPPIPA<br>DEIRNPVVLRALSQARKVINGVVRRYGSPARIHIETAREVGKSFKDRKEIEKRQEENRKDREKSAAKFREYFPNFVGEP<br>KSKDILKLRLYEQQHGKCLYSGKEINLGRLNEKGYVEIDHALPFSRTWDDSFNNKVLALGSENQNKGNQTPYEYFNG<br>KDNSREWQEFKARVETSRFPRSKKQRILLQKFDEDGFKERNLNDTRYINRFLCQFVADHMLLTGKGKRRVFASNGQIT<br>NLLRGFWGLRKVRAENDRHHALDAVVVACSTIAMQQKITRFVRYKEMNAFDGKTIDKETGEVLHQKAHFPQPWEFF<br>AQEVMIRVFGKPDGKPEFEEADTPEKLRTLLAEKLSSRPEAVHKYVTPLFISRAPNRKMSGQGHMETVKSAKRLDEGI<br>SVLRVPLTQLKLKDLEKMVNREREPKLYEALKARLEAHKDDPAKAFAEPFYKYDKAGNRTQQVKAVRVEQVQKTG<br>VWVHNHNGIADNATIVRVDVFEKGGKYYLVPIYSWQVAKGILPDRAVVQGKDEEDWTVMDDSFEFKFVLYANDLIK<br>LTAKKNEFLGYFVSLNRATGAIDIRTHDTDSTKGKNGIFQSVGVKTALSFQKYQIDELGKEIRPCRLKKRPPVR |
| Mammalian Codon Optimized Sequences (AgeI-HA-NLS-Cas9-NLS-taa- | ACCGGTGCCACCATGTACCCATACGATGTTCCAGATTACGCTTCGCCGAAGAAAAAGCGCAAGGTCGAAGCGTC<br>CATGGCTGCCTTCAAACCTAATCCTATGAACTACATCCTGGGCCTGGACATTGGAATCGCTTCTGTCGGGTGGGCT<br>ATCGTGGAAATCGACGAGGAAGAGAACCCTATCAGACTGATTGATCTGGGAGTCAGAGTGTTTGAAAGGGCAGA<br>GGTGCCAAAGACCGGCGACTCCCTGGCCGCTGCACGGAGACTGGCTCGGTCTGTCAGGCGCCTGACACGACGGA<br>GAGCACACAGGCTGCTGCGAGCTAGGCGCCTGCTGAAGAGAGAGGGCGTGCTGCAGGCCGCTGACTTCGATGAA<br>AACGGCCTGATCAAGAGCCTGCCCAATACTCCTTGGCAGCTGAGAGCAGCCGCTCTGGACAGGAAGCTGACCCC<br>ACTGGAGTGGTCTGCCGTGCTGCTGCACCTGATCAAGCATCGCGGCTACCTGAGTCAGCGAAAAAATGAAGGGG |

FIG. 13T

| | |
|---|---|
| EcoRI) | AGACAGCAGATAAGGAGCTGGGAGCACTGCTGAAAGGAGTGGCCGACAACACTCATGCTCTGCAGACCGGCGAT<br>TTTAGGACACCCGCTGAGCTGGCACTGAATAAGTTCGAAAAAGAGAGTGGACACATTCGAAACCAGCGGGGCGA<br>CTATTCACATACCTTCAACCGCAAGGATCTGCAGGCCGAGCTGAATCTGCTGTTTGAAAAGCAGAAAGAGTTCGG<br>GAATCCCCACGTGTCCGACGGGCTGAAAGAAGGAATCGAGACACTGCTGATGACTCAGAGGCCTGCACTGTCTG<br>GCGATGCCGTGCAGAAGATGCTGGGGCATTGCACCTTTGAACCAACAGAGCCCAAGGCAGCCAAAAACACCTAC<br>ACAGCCGAGAGGTTCGTGTGGCTGACAAAGCTGAACAATCTGCGCATCCTGGAACAGGGCAGTGAGCGGCCCCT<br>GACTGACACCGAAAGAGCCACACTGATGGATGAGCCTTACAGGAAGTCTAAACTGACTTATGCCCAGGCTCGCA<br>AGCTGCTGGACCTGGACGATACTGCCTTCTTTAAGGGCCTGAGGTACGGGAAAGATAATGCAGAAGCCAGCACC<br>CTGATGGAGATGAAGGCCTATCACGCTATCTCCCGCGCCCTGGAAAAAGAGGGCCTGAAGGACAAGAAATCTCC<br>CCTGAACCTGAGTCCTGAACTGCAGGATGAGATTGGGACCGCTTTTAGCCTGTTCAAGACTGACGAGGATATCAC<br>CGGACGCCTGAAAGACCGAGTGCAGCCCGAAATTCTGGAGGCACTGCTGAAGCACATCAGTTTTGATAAATTCGT<br>GCAGATTTCACTGAAGGCCCTGCGACGGATCGTCCCTCTGATGGAGCAGGGCAATCGGTACGACGAGGCCTGCA<br>CCGAGATCTACGGAGATCATTATGGCAAGAAAAACACAGAAGAGAAAATCTATCTGCCCCCTATTCCTGCCGAC<br>GAGATCCGGAATCCAGTGGTCCTGAGAGCTCTGTCACAGGCAAGAAAAGTGATCAACGGAGTGGTCAGAAGGTA<br>CGGCAGCCCTGCTAGGATCCACATTGAAACCGCACGCGAAGTGGGAAAGTCCTTTAAAGACCGCAAGGAAATCG<br>AGAAGCGACAGGAAGAGAATAGAAAAGATAGGGAAAAGTCTGCTGCAAAATTCAGGGAGTACTTTCCAAACTTC<br>GTGGGCGAACCCAAGAGTAAAGACATCCTGAAGCTGCGCCTGTACGAGCAGCAGCACGGGAAGTGTCTGTATAG<br>CGGAAAAGAAATTAACCTGGGCCGGCTGAATGAAAAGGGCTATGTGGAGATCGATCATGCACTGCCCTTTTCCA<br>GAACATGGGACGATTCTTTCAACAATAAGGTCCTGGCTCTGGGGAGCGAGAACCAGAACAAGGGAAATCAGACT<br>CCTTACGAATATTTCAACGGGAAGGACAATAGCCGAGAATGGCAGGAGTTTAAAGCCCGCGTGGAGACAAGCCG<br>GTTCCCACGAAGCAAGAAACAGCGGATTCTGCTGCAGAAGTTTGACGAAGATGGATTCAAAGAGAGAAACCTGA<br>ATGACACCCGGTACATCAACAGATTTCTGTGCCAGTTCGTGGCTGATCACATGCTGCTGACCGGAAAGGGCAAAC<br>GCCGAGTCTTTGCAAGCAACGGCCAGATCACAAATCTGCTGAGGGGCTTCTGGGGGCTGCGGAAGGTGAGAGCC<br>GAGAATGACCGCCACCATGCACTGGATGCCGTGGTCGTGGCTTGTTCCACTATTGCAATGCAGCAGAAGATCACC<br>AGGTTTGTGCGCTATAAAGAGATGAACGCCTTCGACGGAAAGACAATTGATAAAGAAACTGGCGAGGTGCTGCA<br>CCAGAAGGCACATTTTCCTCAGCCATGGGAGTTCTTCGCCCAGGAAGTGATGATCCGGGTCTTTGGGAAGCCTGA<br>CGGAAAACCAGAGTTCGAAGAGGCCGATACCCCAGAAAAGCTGCGGACACTGCTGGCTGAAAAACTGAGCTCCA<br>GACCCGAGGCAGTGCACAAGTACGTCACCCCCCTGTTCATTAGCAGGGCCCCTAATCGCAAAATGTCCGGGCAG<br>GGACATATGGAGACTGTGAAATCAGCTAAGCGGCTGGACGAAGGCATCAGCGTGCTGAGAGTCCCACTGACCCA<br>GCTGAAGCTGAAAGATCTGGAGAAGATGGTGAACCGGGAAAGAGAGCCCAAGCTGTATGAAGCTCTGAAAGCA<br>AGACTGGAGGCCCACAAGGACGATCCAGCTAAAGCATTTGCCGAGCCCTTCTACAAATATGACAAGGCCGGCAA<br>TCGGACACAGCAGGTGAAGGCTGTCAGAGTGGAGCAGGTCCAGAAAACTGGGGTCTGGGTGCACAACCATAATG<br>GAATTGCCGACAACGCTACAATCGTCCGGGTGGATGTGTTCGAGAAAGGCGGGAAGTACTATCTGGTGCCTATCT<br>ACTCCTGGCAGGTCGCCAAGGGAATCCTGCCAGATAGAGCTGTCGTGCAGGGCAAAGACGAAGAGGATTGGACT<br>GTGATGGACGATTCTTTCGAGTTTAAGTTCGTCCTGTACGCAAACGACCTGATCAAGCTGACAGCCAAGAAAAAT<br>GAATTTCTGGGGTATTTCGTGTCACTGAACAGGGCAACTGGAGCCATCGATATTCGCACACATGACACTGATAGC |

FIG. 13U

| | |
|---|---|
| | ACCAAGGGAAAAAACGGCATCTTTCAGTCTGTGGGCGTCAAGACCGCCCTGAGTTTCCAGAAATATCAGATTGAC<br>GAACTGGGGAAGGAGATCCGACCCTGTCGGCTGAAGAAACGACCACCCGTGCGGTAAGAATTC |
| Length of Protein (without NLS and HA tag) | 1082 |
| **PAM** | **NNNNGTAA** |
| Spacer Length | 30 |
| **Species: Parvibaculum_lavamentivorans** | |
| Sequencing Barcode | CGCCTTCC |
| ID | 20 |
| **Chimeric Guide RNA** | **NNNNNNNNNNNNNNNNNNNNGCUGCGGAUUGCGGGAAAUCGCUUUUCGCAAGCAAAUUGACCCCUUGUGC<br>GGGCUCGGCAUCCCAAGGUCAGCUGCCGGUUAUUAUCGAAAAGGCCCACCGCAAGCAGCGCGUGGGCCU<br>UUUUUU** |
| Cas9 Protein Sequence (wildtype, without NLS added) | MERIFGFDIGTTSIGFSVIDYSSTQSAGNIQRLGVRIFPEARDPDGTPLNQQRRQKRMMRRQLRRRRIRRKALNETLHEA<br>GFLPAYGSADWPVVMADEPYELRRRGLEEGLSAYEFGRAIYHLAQHRHFKGRELEESDTPDPDVDDEKEAANERAAT<br>LKALKNEQTTLGAWLARRPPSDRKRGIHAHRNVVAEEFERLWEVQSKFHPALKSEEMRARISDTIFAQRPVFWRKNT<br>LGECRFMPGEPLCPKGSWLSQQRRMLEKLNNLAIAGGNARPLDAEERDAILSKLQQQASMSWPGVRSALKALYKQR<br>GEPGAEKSLKFNLELGGESKLLGNALEAKLADMFGPDWPAHPRKQEIRHAVHERLWAADYGETPDKKRVIILSEKDR<br>KAHREAAANSFVADFGITGEQAAQLQALKLPTGWEPYSIPALNLFLAELEKGERFGALVNGPDWEGWRRTNFPHRNQ<br>PTGEILDKLPSPASKEERERISQLRNPTVVRTQNELRKVVNNLIGLYGKPDRIRIEVGRDVGKSKREREEIQSGIRRNEKQ<br>RKKATEDLIKNGIANPSRDDVEKWILWKEGQERCPYTGDQIGFNALFREGRYEVEHIWPRSRSFDNSPRNKTLCRKDV<br>NIEKGNRMPFEAFGHDEDRWSAIQIRLQGMVSAKGGTGMSPGKVKRFLAKTMPEDFAARQLNDTRYAAKQILAQLK<br>RLWPDMGPEAPVKVEAVTGQVTAQLRKLWTLNNILADDGEKTRADHRHHAIDALTVACTHPGMTNKLSRYWQLRD<br>DPRAEKPALTPPWDTIRADAEKAVSEIVVSHRVRKKVSGPLHKETTYGDTGTDIKTKSGTYRQFVTRKKIESLSKGELD<br>EIRDPRIKEIVAAHVAGRGGDPKKAFPPYPCVSPGGPEIRKVRLTSKQQLNLMAQTGNGYADLGSNHHIAIYRLPDGKA<br>DFEIVSLFDASRRLAQRNPIVQRTRADGASFVMSLAAGEAIMIPEGSKKGIWIVQGVWASGQVVLERDTDADHSTTTR<br>PMPNPILKDDAKKVSIDPIGRVRPSND |

FIG. 13V

| | |
|---|---|
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGGAGAGGATTTTCGGCTTTGACATCGGCACAACAAGTATCGGATTCAGCGTGATTGATTACAGTAGCACCCA<br>GTCCGCAGGCAACATCCAGAGGCTGGGCGTGCGCATTTTCCCTGAGGCAAGGGACCCAGATGGACCCCCCTGA<br>ACCAGCAGCGGAGACAGAAACGCATGATGAGGCGCCAGCTGCGACGGAGAAGGATTCGCCGAAAGGCACTGAA<br>TGAGACACTGCACGAAGCCGGCTTTCTGCCAGCTTACGGGTCTGCAGATTGGCCCGTGGTCATGGCCGACGAGCC<br>TTATGAACTGCGGAGAAGGGGACTGGAGGAAGGCCTGAGTGCTTACGAGTTCGGACGGGCAATCTATCATCTGG<br>CCCAGCACCGGCATTTTAAAGGCAGAGAACTGGAGGAATCCGATACACCCGACCCTGATGTGGACGATGAGAAG<br>GAAGCCGCTAACGAGAGAGCAGCCACTCTGAAGGCCCTGAAAAATGAACAGACCACACTGGGAGCATGGCTGG<br>CCCGCCGACCCCCTTCTGACCGCAAGCGAGGAATCCACGCCCATAGGAACGTGGTCGCTGAGGAGTTCGAGCGC<br>CTGTGGGAAGTGCAGTCCAAGTTTCACCCCGCTCTGAAATCTGAGGAAATGCGGGCAAGAATCAGTGATACAATT<br>TTCGCCCAGAGGCCTGTGTTTTGGCGCAAGAACACTCTGGGAGAGTGCAGATTCATGCCTGGCGAACCACTGTGT<br>CCCAAGGGGTCCTGGCTGTCTCAGCAGCGGAGAATGCTGGAGAAACTGAACAATCTGGCTATCGCAGGCGGGAA<br>TGCTAGGCCACTGGATGCAGAGGAACGCGACGCCATTCTGAGTAAGCTGCAGCAGCAGGCCAGCATGTCCTGGC<br>CAGGCGTGCGGTCAGCTCTGAAGGCACTGTACAAACAGAGAGGCGAGCCCGGGGCTGAAAAGAGCCTGAAATTC<br>AACCTGGAGCTGGGAGGCGAATCCAAGCTGCTGGGAAATGCCCTGGAGGCTAAACTGGCAGATATGTTTGGCCC<br>TGACTGGCCAGCTCACCCCCGAAAGCAGGAGATCCGGCACGCAGTGCATGAACGGCTGTGGGCTGCAGATTACG<br>GCGAGACACCCGACAAGAAAAGAGTCATCATTCTGTCCGAGAAGGATCGAAAAGCTCATCGGGAAGCCGCTGCA<br>AACTCTTTCGTGGCAGACTTTGGAATTACTGGCGAGCAGGCAGCTCAGCTGCAGGCCCTGAAGCTGCCAACCGGC<br>TGGGAACCTTATAGCATCCCAGCACTGAACCTGTTCCTGGCCGAGCTGGAAAAGGGGGAGAGGTTTGGAGCCCT<br>GGTGAATGGACCTGATTGGGAAGGCTGGAGGCGCACAAACTTCCCCCACCGCAATCAGCCTACTGGGGAGATCC<br>TGGACAAGCTGCCAAGTCCCGCCTCAAAAGAGGAAAGGGAACGCATTAGCCAGCTGCGCAACCCAACCGTGGTC<br>CGAACACAGAATGAGCTGAGAAAGGTGGTCAACAATCTGATCGGGCTGTATGGAAAACCCGATCGAATCCGGAT<br>TGAAGTGGGCCGGGACGTCGGGAAGTCCAAAAGAGAAAGGGAGGAAATCCAGTCTGGCATTCGACGGAACGAG<br>AAGCAGAGAAAGAAAGCCACTGAAGATCTGATCAAAAACGGAATTGCTAATCCTAGCCGGGACGATGTGGAGA<br>AGTGGATCCTGTGGAAAGAGGGCCAGGAAAGATGCCCATACACCGGCGACCAGATTGGCTTCAATGCCCTGTTT<br>AGAGAAGGCAGATATGAGGTGGAACACATCTGGCCTCGCTCTCGAAGTTTTGATAACAGCCCAAGGAATAAGAC<br>ACTGTGTCGCAAAGACGTGAACATCGAGAAGGGAAATAGGATGCCTTTCGAGGCATTTGGCCATGACGAAGATC<br>GGTGGAGCGCCATCCAGATTAGACTGCAGGGCATGGTGTCAGCCAAAGGGGGAACTGGGATGAGCCCCGGAAA<br>GGTCAAACGCTTCCTGGCTAAGACCATGCCTGAGGATTTTGCAGCCCGGCAGCTGAACGACACAAGATACGCTGC<br>AAAGCAGATCCTGGCCCAGCTGAAAAGGCTGTGGCCAGACATGGGACCTGAGGCTCCAGTGAAGGTCGAAGCAG<br>TGACTGGACAGGTCACCGCCCAGCTGCGCAAACTGTGGACTCTGAACAATATTCTGGCTGACGATGGGGAGAAA<br>ACCAGAGCAGATCACAGGCACCATGCCATCGACGCTCTGACAGTGGCCTGCACTCATCCTGGAATGACCAACAA<br>GCTGAGCAGGTATTGGCAGCTGCGCGACGATCCACGAGCAGAGAAGCCAGCTCTGACTCCACCCTGGGATACCA<br>TCCGCGCCGACGCTGAGAAAGCCGTGTCTGAAATTGTGGTCAGTCACCGGGTGAGAAAGAAAGTCAGCGGCCCA<br>CTGCATAAGGAGACTACCTACGGCGATACAGGGACTGACATTAAGACCAAATCCGGCACATATAGACAGTTCGT |

FIG. 13W

| | |
|---|---|
| | GACCAGGAAGAAAATCGAGTCACTGAGCAAGGGGGAGCTGGATGAAATTCGCGACCCCCGAATCAAAGAAATT<br>GTGGCAGCTCACGTCGCAGGACGAGGAGGCGACCCCAAGAAGGCCTTCCCTCCATACCCCTGTGTGTCTCCCGGA<br>GGCCCTGAGATCCGGAAGGTCAGACTGACCAGTAAACAGCAGCTGAACCTGATGGCCCAGACAGGGAATGGATA<br>CGCTGACCTGGGCTCCAACCACCATATCGCAATCTACCGGCTGCCCGATGGGAAGGCCGACTTCGAGATTGTGTC<br>ACTGTTTGATGCTAGCAGAAGGCTGGCACAGAGAAATCCAATCGTGCAGAGGACACGAGCAGACGGAGCCAGCT<br>TCGTCATGTCCCTGGCAGCCGGAGAGGCCATCATGATTCCCGAAGGCTCAAAGAAAGGGATCTGGATTGTGCAG<br>GGAGTCTGGGCAAGCGGACAGGTGGTCCTGGAGAGGGACACCGATGCTGACCACTCTACAACTACCCGCCCTAT<br>GCCAAACCCCATCCTGAAGGACGATGCCAAGAAAGTGAGTATCGATCCTATTGGCCGAGTCCGGCCATCAAATG<br>ACTAAGAATTC |
| Length of Protein (without NLS and HA tag) | 1037 |
| **PAM** | **NNNCAT** |
| Spacer Length | 30 |
| **Species: Staphylococcus aureus subsp. Aureus -- double check** | |
| Sequencing Barcode | CTATGCGT |
| ID | 21 |
| **Chimeric Guide RNA** | **NNNNNNNNNNNNNNNNNNNNNGUUUUAGUACUCUGGAAACAGAAUCUACUAAAACAAGGCAAAAUGCCGUG<br>UUUAUCUCGUCAACUUGUUGGCGAGAUUUUUU** |
| Cas9 Protein Sequence (wildtype, without NLS added) | MKRNYILGLDIGITSVGYGIIDYETRDVIDAGVRLFKEANVENNEGRRSKRGARRLKRRRRHRIQRVKKLLFDYNLLTD<br>HSELSGINPYEARVKGLSQKLSEEEFSAALLHLAKRRGVHNVNEVEEDTGNELSTKEQISRNSKALEEKYVAELQLERL<br>KKDGEVRGSINRFKTSDYVKEAKQLLKVQKAYHQLDQSFIDTYIDLLETRRTYYEGPGEGSPFGWKDIKEWYEMLMG<br>HCTYFPEELRSVKYAYNADLYNALNDLNNLVITRDENEKLEYYEKFQIIENVFKQKKKPTLKQIAKEILVNEEDIKGYR<br>VTSTGKPEFTNLKVYHDIKDITARKEIIENAELLDQIAKILTIYQSSEDIQEELTNLNSELTQEEIEQISNLKGYTGTHNLSL<br>KAINLILDELWHTNDNQIAIFNRLKLVPKKVDLSQQKEIPTTLVDDFILSPVVKRSFIQSIKVINAIIKKYGLPNDIIIELAR<br>EKNSKDAQKMINEMQKRNRQTNERIEEIIRTTGKENAKYLIEKIKLHDMQEGKCLYSLEAIPLEDLLNNPFNYEVDHIIP<br>RSVSFDNSFNNKVLVKQEENSKKGNRTPFQYLSSSDSKISYETFKKHILNLAKGKGRISKTKKEYLLEERDINRFSVQK |

FIG. 13X

| | |
|---|---|
| | DFINRNLVDTRYATRGLMNLLRSYFRVNNLDVKVKSINGGFTSFLRRKWKFKKERNKGYKHHAEDALIIANADFIFKE<br>WKKLDKAKKVMENQMFEEKQAESMPEIETEQEYKEIFITPHQIKHIKDFKDYKYSHRVDKKPNRELINDTLYSTRKDD<br>KGNTLIVNNLNGLYDKDNDKLKKLINKSPEKLLMYHHDPQTYQKLKLIMEQYGDEKNPLYKYYEETGNYLTKYSKK<br>DNGPVIKKIKYYGNKLNAHLDITDDYPNSRNKVVKLSLKPYRFDVYLDNGVYKFVTVKNLDVIKKENYYEVNSKCYE<br>EAKKLKKISNQAEFIASFYNNDLIKINGELYRVIGVNNDLLNRIEVNMIDITYREYLENMNDKRPPRIIKTIASKTQSIKK<br>YSTDILGNLYEVKSKKHPQIIKKG |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGAAAAGGAACTACATTCTGGGGCTGGACATCGGGATTACAAGCGTGGGGTATGGGATTATTGACTATGAAA<br>CAAGGGACGTGATCGACGCAGGCGTCAGACTGTTCAAGGAGGCCAACGTGGAAAACAATGAGGGACGGAGAAG<br>CAAGAGGGGAGCCAGGCGCCTGAAACGACGGAGAAGGCACAGAATCCAGAGGGTGAAGAAACTGCTGTTCGAT<br>TACAACCTGCTGACCGACCATTCTGAGCTGAGTGGAATTAATCCTTATGAAGCCAGGGTGAAAGGCCTGAGTCAG<br>AAGCTGTCAGAGGAAGAGTTTTCCGCAGCTCTGCTGCACCTGGCTAAGCGCCGAGGAGTGCATAACGTCAATGA<br>GGTGGAAGAGGACACCGGCAACGAGCTGTCTACAAAGGAACAGATCTCACGCAATAGCAAAGCTCTGGAAGAG<br>AAGTATGTCGCAGAGCTGCAGCTGGAACGGCTGAAGAAAGATGGCGAGGTGAGAGGGTCAATTAATAGGTTCAA<br>GACAAGCGACTACGTCAAAGAAGCCAAGCAGCTGCTGAAAGTGCAGAAGGCTTACCACCAGCTGGATCAGAGCT<br>TCATCGATACTTATATCGACCTGCTGGAGACTCGGAGAACCTACTATGAGGGACCAGGAGAAGGGAGCCCCTTC<br>GGATGGAAAGACATCAAGGAATGGTACGAGATGCTGATGGGACATTGCACCTATTTTCCAGAAGAGCTGAGAAG<br>CGTCAAGTACGCTTATAACGCAGATCTGTACAACGCCCTGAATGACCTGAACAACCTGGTCATCACCAGGGATGA<br>AAACGAGAAACTGGAATACTATGAGAAGTTCCAGATCATCGAAAACGTGTTTAAGCAGAAGAAAAAGCCTACAC<br>TGAAACAGATTGCTAAGGAGATCCTGGTCAACGAAGAGGACATCAAGGGCTACCGGGTGACAAGCACTGGAAA<br>ACCAGAGTTCACCAATCTGAAAGTGTATCACGATATTAAGGACATCACAGCACGGAAAGAAATCATTGAGAACG<br>CCGAACTGCTGGATCAGATTGCTAAGATCCTGACTATCTACCAGAGCTCCGAGGACATCCAGGAAGAGCTGACTA<br>ACCTGAACAGCGAGCTGACCCAGGAAGAGATCGAACAGATTAGTAATCTGAAGGGGTACACCGGAACACACAA<br>CCTGTCCCTGAAAGCTATCAATCTGATTCTGGATGAGCTGTGGCATACAAACGACAATCAGATTGCAATCTTTAA<br>CCGGCTGAAGCTGGTCCCAAAAAAGGTGGACCTGAGTCAGCAGAAAGAGATCCCAACCACACTGGTGGACGATT<br>TCATTCTGTCACCCGTGGTCAAGCGGAGCTTCATCCAGAGCATCAAAGTGATCAACGCCATCATCAAGAAGTACG<br>GCCTGCCCAATGATATCATTATCGAGCTGGCTAGGGAGAAGAACAGCAAGGACGCACAGAAGATGATCAATGAG<br>ATGCAGAAACGAAACCGGCAGACCAATGAACGCATTGAAGAGATTATCCGAACTACCGGGAAAGAGAACGCAA<br>AGTACCTGATTGAAAAAATCAAGCTGCACGATATGCAGGAGGGAAAGTGTCTGTATTCTCTGGAGGCCATCCCCC<br>TGGAGGACCTGCTGAACAATCCATTCAACTACGAGGTCGATCATATTATCCCCAGAAGCGTGTCCTTCGACAATT<br>CCTTTAACAACAAGGTGCTGGTCAAGCAGGAAGAGAACTCTAAAAAGGGCAATAGGACTCCTTTCCAGTACCTG<br>TCTAGTTCAGATTCCAAGATCTCTTACGAAACCTTTAAAAAGCACATTCTGAATCTGGCCAAAGGAAAGGGCCGC<br>ATCAGCAAGACCAAAAAGGAGTACCTGCTGGAAGAGCGGGACATCAACAGATTCTCCGTCCAGAAGGATTTTAT<br>TAACCGGAATCTGGTGGACACAAGATACGCTACTCGCGGCCTGATGAATCTGCTGCGATCCTATTTCCGGGTGAA<br>CAATCTGGATGTGAAAGTCAAGTCCATCAACGGCGGGTTCACATCTTTTCTGAGGCGCAAATGGAAGTTTAAAAA |

FIG. 13Y

| | |
|---|---|
| | GGAGCGCAACAAAGGGTACAAGCACCATGCCGAAGATGCTCTGATTATCGCAAATGCCGACTTCATCTTTAAGG<br>AGTGGAAAAAGCTGGACAAAGCCAAGAAAGTGATGGAGAACCAGATGTTCGAAGAGAAGCAGGCCGAATCTAT<br>GCCCGAAATCGAGACAGAACAGGAGTACAAGGAGATTTTCATCACTCCTCACCAGATCAAGCATATCAAGGATT<br>TCAAGGACTACAAGTACTCTCACCGGGTGGATAAAAAGCCCAACAGAGAGCTGATCAATGACACCCTGTATAGT<br>ACAAGAAAAGACGATAAGGGGAATACCCTGATTGTGAACAATCTGAACGGACTGTACGACAAAGATAATGACA<br>AGCTGAAAAAGCTGATCAACAAAAGTCCCGAGAAGCTGCTGATGTACCACCATGATCCTCAGACATATCAGAAA<br>CTGAAGCTGATTATGGAGCAGTACGGCGACGAGAAGAACCCACTGTATAAGTACTATGAAGAGACTGGGAACTA<br>CCTGACCAAGTATAGCAAAAAGGATAATGGCCCCGTGATCAAGAAGATCAAGTACTATGGGAACAAGCTGAATG<br>CCCATCTGGACATCACAGACGATTACCCTAACAGTCGCAACAAGGTGGTCAAGCTGTCACTGAAGCCATACAGAT<br>TCGATGTCTATCTGGACAACGGCGTGTATAAATTTGTGACTGTCAAGAATCTGGATGTCATCAAAAAGGAGAACT<br>ACTATGAAGTGAATAGCAAGTGCTACGAAGAGGCTAAAAAGCTGAAAAAGATTAGCAACCAGGCAGAGTTCATC<br>GCCTCCTTTTACAACAACGACCTGATTAAGATCAATGGCGAACTGTATAGGGTCATCGGGGTGAACAATGATCTG<br>CTGAACCGCATTGAAGTGAATATGATTGACATCACTTACCGAGAGTATCTGGAAAACATGAATGATAAGCGCCCC<br>CCTCGAATTATCAAAACAATTGCCTCTAAGACTCAGAGTATCAAAAAGTACTCAACCGACATTCTGGGAAACCTG<br>TATGAGGTGAAGAGCAAAAAGCACCCTCAGATTATCAAAAAGGGCTAAGAATTC |
| Length of Protein (without NLS and HA tag) | 1053 |
| **PAM** | **NNGRRT** |
| Spacer Length | 30 |
| **Species: *Mycoplasma gallisepticum* str. F** | |
| Sequencing Barcode | CGCTATGT |
| ID | 23 |
| **Chimeric Guide RNA** | **NNNNNNNNNNNNNNNNNNNNGUUUUAGCACUGUACAAGAAAUUGUCGUGCUAAAAUAAGGCGCUGUUAAU<br>GCAGCUGCCGCAUCCGCCAGAGCAUUUAUGCUCUGGCUUUUUUU** |
| Cas9 Protein Sequence | MNNSIKSKPEVTIGLDLGVGSVGWAIVDNETNIIHHLGSRLFSQAKTAEDRRSFRGVRRLIRRRKYKLKRFVNLIWKYN<br>SYFGFKNKEDILNNYQEQQKLHNTVLNLKSEALNAKIDPKALSWILHDYLKNRGHFYEDNRDFNVYPTKELAKYFDK |

FIG. 13Z

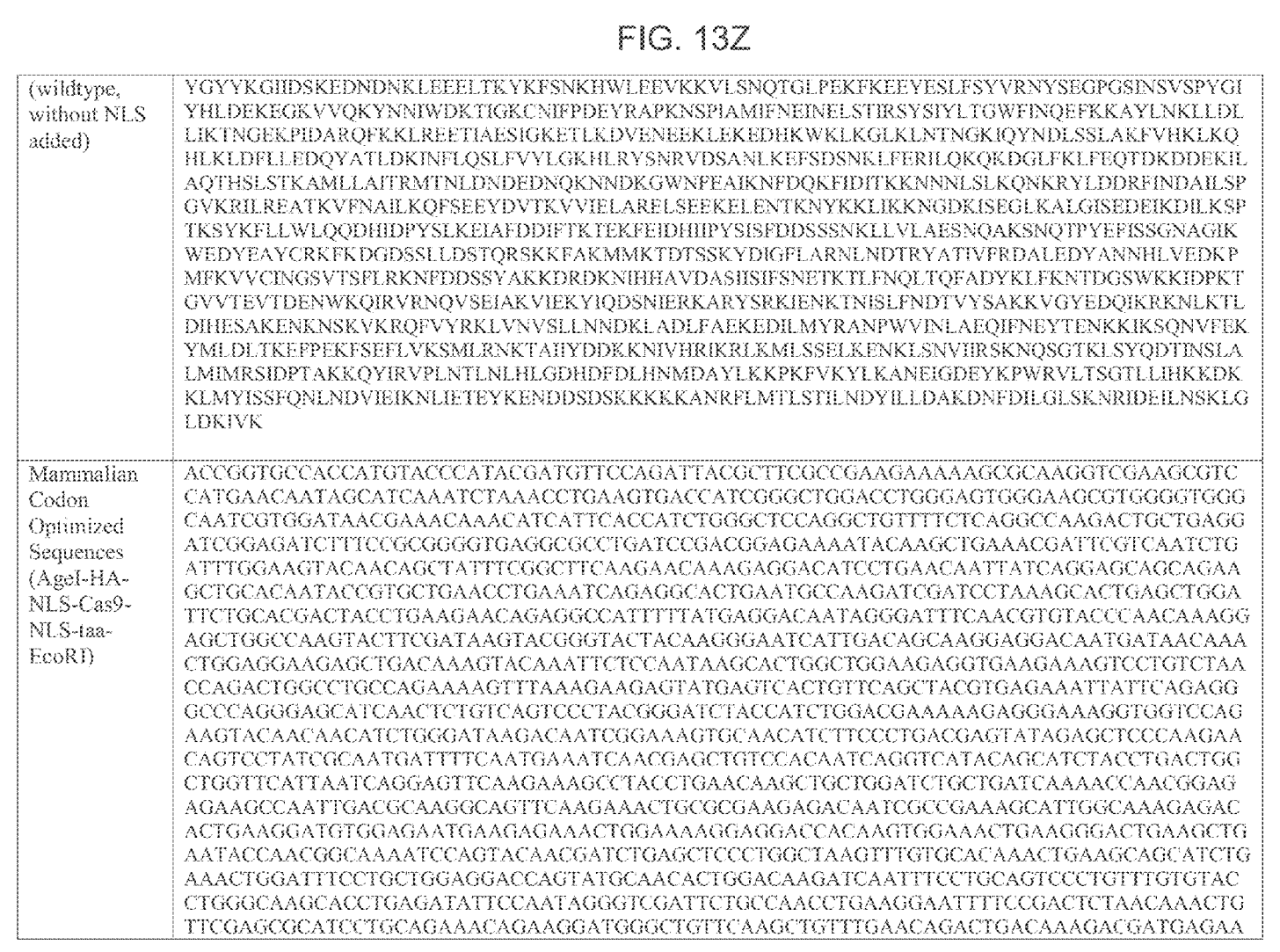

| | |
|---|---|
| (wildtype, without NLS added) | YGYYKGIIDSKEDNDNKLEEELTKYKFSNKHWLEEVKKVLSNQTGLPEKFKEEYESLFSYVRNYSEGPGSINSVSPYGI<br>YHLDEKEGKVVQKYNNIWDKTIGKCNIFPDEYRAPKNSPIAMIFNEINELSTIRSYSIYLTGWFINQEFKKAYLNKLLDL<br>LIKTNGEKPIDARQFKKLREETIAESIGKETLKDVENEEKLEKEDHKWKLKGLKLNTNGKIQYNDLSSLAKFVHKLKQ<br>HLKLDFLLEDQYATLDKINFLQSLFVYLGKHLRYSNRVDSANLKEFSDSNKLFERILQKQKDGLFKLFEQTDKDDEKIL<br>AQTHSLSTKAMLLAITRMTNLDNDEDNQKNNDKGWNFEAIKNFDQKFIDITKKNNNLSLKQNKRYLDDRFINDAILSP<br>GVKRILREATKVFNAILKQFSEEYDVTKVVIELARELSEEKELENTKNYKKLIKKNGDKISEGLKALGISEDEIKDILKSP<br>TKSYKFLLWLQQDHIDPYSLKEIAFDDIFTKTEKFEIDHIIPYSISFDDSSSNKLLVLAESNQAKSNQTPYEFISSGNAGIK<br>WEDYEAYCRKFKDGDSSLLDSTQRSKKFAKMMKTDTSSKYDIGFLARNLNDTRYATIVFRDALEDYANNHLVEDKP<br>MFKVVCINGSVTSFLRKNFDDSSYAKKDRDKNIHHAVDASIISIFSNETKTLFNQLTQFADYKLFKNTDGSWKKIDPKT<br>GVVTEVTDENWKQIRVRNQVSEIAKVIEKYIQDSNIERKARYSRKIENKTNISLFNDTVYSAKKVGYEDQIKRKNLKTL<br>DIHESAKENKNSKVKRQFVYRKLVNVSLLNNDKLADLFAEKEDILMYRANPWVINLAEQIFNEYTENKKIKSQNVFEK<br>YMLDLTKEFPEKFSEFLVKSMLRNKTAIIYDDKKNIVHRIKRLKMLSSELKENKLSNVIIRSKNQSGTKLSYQDTINSLA<br>LMIMRSIDPTAKKQYIRVPLNTLNLHLGDHDFDLHNMDAYLKKPKFVKYLKANEIGDEYKPWRVLTSGTLLIHKKDK<br>KLMYISSFQNLNDVIEIKNLIETEYKENDDSDSKKKKKANRFLMTLSTILNDYILLDAKDNFDILGLSKNRIDEILNSKLG<br>LDKIVK |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CATGAACAATAGCATCAAATCTAAACCTGAAGTGACCATCGGGCTGGACCTGGGAGTGGGAAGCGTGGGGTGGG<br>CAATCGTGGATAACGAAACAAACATCATTCACCATCTGGGCTCCAGGCTGTTTTCTCAGGCCAAGACTGCTGAGG<br>ATCGGAGATCTTTCCGCGGGGTGAGGCGCCTGATCCGACGGAGAAAATACAAGCTGAAACGATTCGTCAATCTG<br>ATTTGGAAGTACAACAGCTATTTCGGCTTCAAGAACAAAGAGGACATCCTGAACAATTATCAGGAGCAGCAGAA<br>GCTGCACAATACCGTGCTGAACCTGAAATCAGAGGCACTGAATGCCAAGATCGATCCTAAAGCACTGAGCTGGA<br>TTCTGCACGACTACCTGAAGAACAGAGGCCATTTTTATGAGGACAATAGGGATTTCAACGTGTACCCAACAAAGG<br>AGCTGGCCAAGTACTTCGATAAGTACGGGTACTACAAGGGAATCATTGACAGCAAGGAGGACAATGATAACAAA<br>CTGGAGGAAGAGCTGACAAAGTACAAATTCTCCAATAAGCACTGGCTGGAAGAGGTGAAGAAAGTCCTGTCTAA<br>CCAGACTGGCCTGCCAGAAAAGTTTAAAGAAGAGTATGAGTCACTGTTCAGCTACGTGAGAAATTATTCAGAGG<br>GCCCAGGGAGCATCAACTCTGTCAGTCCCTACGGGATCTACCATCTGGACGAAAAAGAGGGAAAGGTGGTCCAG<br>AAGTACAACAACATCTGGGATAAGACAATCGGAAAGTGCAACATCTTCCCTGACGAGTATAGAGCTCCCAAGAA<br>CAGTCCTATCGCAATGATTTTCAATGAAATCAACGAGCTGTCCACAATCAGGTCATACAGCATCTACCTGACTGG<br>CTGGTTCATTAATCAGGAGTTCAAGAAAGCCTACCTGAACAAGCTGCTGGATCTGCTGATCAAAACCAACGGAG<br>AGAAGCCAATTGACGCAAGGCAGTTCAAGAAACTGCGCGAAGAGACAATCGCCGAAAGCATTGGCAAAGAGAC<br>ACTGAAGGATGTGGAGAATGAAGAGAAACTGGAAAAGGAGGACCACAAGTGGAAACTGAAGGGACTGAAGCTG<br>AATACCAACGGCAAAATCCAGTACAACGATCTGAGCTCCCTGGCTAAGTTTGTGCACAAACTGAAGCAGCATCTG<br>AAACTGGATTTCCTGCTGGAGGACCAGTATGCAACACTGGACAAGATCAATTTCCTGCAGTCCCTGTTTGTGTAC<br>CTGGGCAAGCACCTGAGATATTCCAATAGGGTCGATTCTGCCAACCTGAAGGAATTTTCCGACTCTAACAAACTG<br>TTCGAGCGCATCCTGCAGAAACAGAAGGATGGGCTGTTCAAGCTGTTTGAACAGACTGACAAAGACGATGAGAA |

FIG. 13AA

| | |
|---|---|
| | GATCCTGGCCCAGACACATAGTCTGTCAACTAAGGCCATGCTGCTGGCTATTACCCGGATGACAAATCTGGACAA<br>CGATGAGGACAACCAGAAAAACAATGACAAGGGCTGGAATTTTGAGGCCATCAAAAACTTCGATCAGAAGTTTA<br>TCGACATCACCAAGAAAAACAACAACCTGAGCCTGAAACAGAATAAGCGCTACCTGGACGATCGATTCATCAAC<br>GATGCTATTCTGTCCCCTGGGGTGAAGCGAATCCTGCGGGAGGCAACCAAGGTCTTTAATGCCATTCTGAAACAG<br>TTCTCTGAAGAGTACGACGTGACAAAGGTGGTCATCGAACTGGCTCGCGAGCTGAGCGAAGAGAAGGAACTGGA<br>GAACACAAAGAACTACAAGAAACTGATCAAGAAAAACGGCGACAAGATTAGTGAGGGCCTGAAAGCACTGGGG<br>ATCTCAGAAGATGAGATCAAAGACATTCTGAAGAGTCCCACTAAATCATACAAGTTTCTGCTGTGGCTGCAGCAG<br>GACCACATCGATCCTTATAGCCTGAAGGAGATCGCCTTCGACGATATTTTTACCAAAACAGAAAAGTTCGAGATC<br>GACCATATCATTCCCTACAGCATTTCCTTCGACGATTCTAGTTCAAACAAGCTGCTGGTGCTGGCTGAAAGTAATC<br>AGGCAAAGTCAAACCAGACTCCTTATGAGTTCATCAGCTCCGGAAACGCAGGCATTAAGTGGGAAGATTACGAG<br>GCCTATTGCCGCAAGTTCAAGGATGGGGACTCTAGTCTGCTGGACAGCACCCAGCGGTCCAAGAAATTCGCCAA<br>AATGATGAAAACCGATACCTCAAGCAAGTACGACATCGGATTTCTGGCTCGAAATCTGAACGATACTCGGTACGC<br>AACCATTGTGTTCCGGGACGCCCTGGAGGACTATGCTAATAACCACCTGGTCGAGGACAAACCCATGTTTAAGGT<br>GGTCTGTATCAATGGGTCCGTGACCTCTTTCCTGCGGAAGAACTTTGACGATTCCTCTTACGCCAAGAAAGATAG<br>AGACAAGAATATCCACCATGCTGTGGATGCAAGTATCATCTCAATTTTCAGCAACGAGACAAAGACTCTGTTCAA<br>CCAGCTGACTCAGTTTGCTGACTATAAACTGTTCAAGAACACCGATGGCAGCTGGAAGAAAATCGACCCTAAGA<br>CAGGGGTGGTCACTGAAGTGACCGACGAGAATTGGAAGCAGATTAGGGTGCGCAACCAGGTGAGCGAAATCGCC<br>AAAGTCATTGAGAAGTACATCCAGGATAGCAACATCGAAAGAAAGGCTAGGTATTCCCGCAAAATCGAGAATAA<br>GACTAACATTTCCCTGTTTAATGACACCGTGTACTCTGCCAAGAAAGTCGGCTATGAGGATCAGATCAAAAGAAA<br>GAACCTGAAAACCCTGGACATTCACGAATCTGCTAAAGAGAATAAGAACAGTAAAGTGAAGCGGCAGTTTGTCT<br>ACAGAAAGCTGGTGAATGTCAGCCTGCTGAATAACGATAAGCTGGCAGACCTGTTCGCCGAAAAAGAGGATATC<br>CTGATGTATAGGGCCAATCCATGGGTCATCAACCTGGCTGAGCAGATTTTCAATGAATACACTGAGAACAAGAA<br>AATCAAGTCCCAGAACGTGTTTGAAAAATATATGCTGGACCTGACCAAAGAGTTCCCCGAGAAGTTCAGCGAGTT<br>TCTGGTGAAGTCCATGCTGAGAAACAAGACCGCCATCATCTACGACGATAAGAAAAACATTGTCCATCGAATCA<br>AACGGCTGAAGATGCTGAGTTCAGAACTGAAAGAGAATAAGCTGTCTAACGTGATCATTAGGTCTAAGAATCAG<br>AGTGGGACCAAACTGTCATACCAGGATACAATCAACAGCCTGGCCCTGATGATTATGCGCAGCATCGACCCTACT<br>GCTAAGAAACAGTATATTCGAGTGCCACTGAATACCCTGAACCTGCACCTGGGAGATCATGACTTTGATCTGCAC<br>AATATGGATGCTTACCTGAAGAAACCAAAATTCGTGAAGTATCTGAAAGCAAACGAAATCGGCGACGAGTACAA<br>GCCCTGGAGGGTCCTGACATCTGGCACTCTGCTGATCCATAAGAAGGATAAGAAACTGATGTACATCAGCTCCTT<br>CCAGAATCTGAACGACGTGATCGAAATTAAGAATCTGATCGAAACCGAGTATAAAGAGAACGACGATTCTGATA<br>GTAAGAAAAAGAAAAAGGCAAACCGCTTTCTGATGACCCTGAGCACAATCCTGAATGACTACATTCTGCTGGAC<br>GCCAAGGATAACTTCGACATCCTGGGGCTGTCTAAAAATCGGATCGATGAGATTCTGAACAGTAAGCTGGGACT<br>GGACAAGATTGTGAAATAAGAATTC |
| Length of Protein | 1269 |

FIG. 13BB

| | |
|---|---|
| (without NLS and HA tag) | |
| **PAM** | NNGAT |
| Spacer Length | 30 |
| **Species: Campylobacter lari CF89-12** | |
| Sequencing Barcode | CTGTGGCG |
| ID | 24 |
| **Chimeric Guide RNA** | **NNNNNNNNNNNNNNNNNNNNGUUUUAGUCUCUGAAAAGAGACUAAAAUAAGUGGUUUUGGUCAUCCACG CAGGGUUACAAUCCCUUUAAAACCAUUAAAAUUCAAAUAAACUAGGUUGUAUCAACUUAGUUUUUU** |
| Cas9 Protein Sequence (wildtype, without NLS added) | MRILGFDIGINSIGWAFVENDELKDCGVRIFTKAENPKNKESLALPRRNARSSRRRLKRRKARLIAIKRILAKELKLNYK DYVAADGELPKAYEGSLASVYELRYKALTQNLETKDLARVILHIAKHRGYMNKNEKKSNDAKKGKILSALKNNALK LENYQSVGEYFYKEFFQKYKKNTKNFIKIRNTKDNYNNCVLSSDLEKELKLILEKQKEFGYNYSEDFINEILKVAFFQR PLKDFSHLVGACTFFEEEKRACKNSYSAWEFVALTKIINEIKSLEKISGEIVPTQTINEVLNLILDKGSITYKKFRSCINLH ESISFKSLKYDKENAENAKLIDFRKLVEFKKALGVHSLSRQELDQISTHITLIKDNVKLKTVLEKYNLSNEQINNLLEIEF NDYINLSFKALGMILPLMREGKRYDEACEIANLKPKTVDEKKDFLPAFCDSIFAHELSNPVVNRAISEYRKVLNALLKK YGKVHKIHLELARDVGLSKKAREKIEKEQKENQAVNAWALKECENIGLKASAKNILKLKLWKEQKEICIYSGNKISIE HLKDEKALEVDHIYPYSRSFDDSFINKVLVFTKENQEKLNKTPFEAFGKNIEKWSKIQTLAQNLPYKKKNKILDENFKD KQQEDFISRNLNDTRYIATLIAKYTKEYLNFLLLSENENANLKSGEKGSKIHVQTISGMLTSVLRHTWGFDKKDRNNH LHHALDAIIVAYSTNSIIKAFSDFRKNQELLKARFYAKELTSDNYKHQVKFFEPFKSFREKILSKIDEIFVSKPPRKRARR ALHKDTFHSENKIIDKCSYNSKEGLQIALSCGRVRKIGTKYVENDTIVRVDIFKKQNKFYAIPIYAMDFALGILPNKIVIT GKDKNNNPKQWQTIDESYEFCFSLYKNDLILLQKKNMQEPEFAYYNDFSISTSSICVEKHDNKFENLTSNQKLLFSNAK EGSVKVESLGIQNLKVFEKYIITPLGDKIKADFQPRENISLKTSKKYGLR |
| Mammalian Codon Optimized Sequences (AgeI-HA- | ACCGGTGCCACCATGTACCCATACGATGTTCCAGATTACGCTTCGCCGAAGAAAAAGCGCAAGGTCGAAGCGTC CATGAGGATTCTGGGGTTTGACATTGGCATTAACAGCATCGGGTGGGCTTTTGTGGAGAACGACGAACTGAAGG ACTGCGGAGTGCGGATCTTCACAAAGGCCGAGAACCCAAAAAATAAGGAAAGCCTGGCACTGCCCCGGAGAAAT GCACGCAGCTCCAGGCGCCGACTGAAACGGAGAAAGGCCCGGCTGATCGCTATTAAGAGAATCCTGGCCAAAGA GCTGAAGCTGAACTACAAGGACTATGTCGCAGCTGATGGAGAGCTGCCAAAGGCCTACGAAGGATCCCTGGCAT CTGTGTACGAGCTGCGGTATAAGGCCCTGACACAGAACCTGGAAACTAAAGATCTGGCCAGAGTGATCCTGCAC |

FIG. 13CC

| | |
|---|---|
| NLS-Cas9-NLS-taa-EcoRI) | ATTGCTAAGCATAGGGGGTACATGAACAAGAACGAGAAGAAATCAAACGACGCTAAGAAAGGAAAGATCCTGA<br>GCGCTCTGAAAAACAATGCACTGAAGCTGGAGAACTACCAGAGCGTGGGCGAATACTTCTACAAGGAGTTCTTT<br>CAGAAATACAAGAAAAACACAAAGAACTTCATCAAGATCCGCAACACTAAGGATAATTACAACAATTGCGTGCT<br>GTCTAGTGACCTGGAAAAAGAGCTGAAGCTGATCCTGGAAAAACAGAAGGAGTTCGGCTACAACTACTCTGAAG<br>ATTTCATCAACGAGATTCTGAAGGTCGCCTTCTTTCAGCGGCCCCTGAAGGACTTCAGTCACCTGGTGGGGGCCT<br>GCACTTTCTTTGAGGAAGAGAAAAGGGCCTGTAAGAACAGCTACTCTGCCTGGGAGTTTGTGGCTCTGACCAAGA<br>TCATTAACGAGATCAAGAGCCTGGAGAAGATCAGCGGCGAAATTGTGCCAACCCAGACAATCAACGAGGTCCTG<br>AATCTGATCCTGGACAAGGGGTCTATCACCTACAAGAAATTCAGAAGTTGTATCAATCTGCATGAGAGTATCAGC<br>TTCAAGAGCCTGAAGTATGATAAAGAAAACGCCGAGAATGCTAAACTGATCGACTTCCGCAAGCTGGTGGAGTT<br>TAAGAAAGCCCTGGGAGTCCACAGCCTGTCCCGGCAGGAACTGGATCAGATCTCCACTCATATCACCCTGATTAA<br>GGACAACGTGAAGCTGAAAACCGTCCTGGAGAAATACAACCTGAGTAATGAACAGATCAACAATCTGCTGGAAA<br>TTGAGTTCAACGATTATATCAACCTGAGCTTCAAGGCCCTGGGAATGATTCTGCCACTGATGCGCGAGGGCAAAC<br>GATACGACGAGGCCTGCGAGATCGCCAATCTGAAACCTAAGACCGTGGACGAGAAGAAAGATTTCCTGCCAGCA<br>TTTTGTGATTCCATTTTCGCCCACGAGCTGTCTAACCCCGTGGTCAATAGGGCTATCAGCGAATACCGCAAGGTGC<br>TGAACGCACTGCTGAAGAAATATGGAAAGGTCCACAAAATTCATCTGGAGCTGGCTCGCGACGTGGGCCTGTCC<br>AAGAAAGCACGAGAGAAGATCGAAAAAGAGCAGAAGGAAAACCAGGCCGTGAATGCATGGGCCCTGAAGGAAT<br>GCGAGAATATTGGCCTGAAGGCCAGCGCAAAGAACATCCTGAAACTGAAGCTGTGGAAAGAACAGAAGGAGAT<br>CTGTATCTACTCCGGAAATAAGATCTCTATTGAGCACCTGAAAGATGAAAAGGCCCTGGAGGTGGACCATATCTA<br>CCCCTATTCTAGGAGTTTCGACGATTCTTTTATCAACAAAGTGCTGGTGTTCACCAAGGAAAATCAGGAGAAACT<br>GAACAAGACACCTTTCGAGGCCTTTGGCAAGAATATTGAAAAATGGAGCAAGATCCAGACCCTGGCTCAGAACC<br>TGCCATACAAGAAAAAGAATAAGATTCTGGACGAGAACTTCAAAGATAAGCAGCAGGAGGACTTTATCTCTCGA<br>AATCTGAACGACACCCGGTATATCGCTACACTGATTGCAAAATACACAAAGGAGTATCTGAACTTCCTGCTGCTG<br>AGCGAAAATGAGAACGCCAATCTGAAGAGTGGCGAAAAAGGGTCAAAGATCCACGTGCAGACTATTAGCGGGA<br>TGCTGACCTCCGTCCTGAGGCACACATGGGGGTTTGACAAAAAGGATCGCAACAATCATCTGCACCATGCACTGG<br>ATGCCATCATTGTGGCCTACAGTACAAATTCAATCATTAAGGCTTTCAGCGATTTCCGGAAAAACCAGGAGCTGC<br>TGAAGGCCAGATTCTACGCTAAAGAACTGACTTCCGATAACTATAAACATCAGGTCAAGTTCTTTGAGCCTTTCA<br>AGAGTTTTAGAGAAAAAATCCTGTCAAAGATCGACGAGATTTTCGTGTCCAAACCACCTCGAAAGCGAGCTAGG<br>CGCGCACTGCACAAGGATACCTTTCATTCTGAGAACAAGATCATTGACAAGTGCAGCTACAACTCCAAGGAAGG<br>CCTGCAGATTGCCCTGAGCTGTGGAAGAGTGAGGAAAATCGGCACTAAGTATGTCGAGAATGATACCATCGTGA<br>GGGTCGACATTTTCAAAAAGCAGAACAAGTTTTACGCTATCCCAATCTACGCAATGGATTTTGCCCTGGGGATCC<br>TGCCCAATAAGATCGTGATTACTGGAAAAGATAAGAACAATAACCCCAAACAGTGGCAGACCATTGACGAATCA<br>TACGAGTTCTGCTTTAGCCTGTATAAGAATGACCTGATCCTGCTGCAGAAAAAGAACATGCAGGAACCTGAGTTC<br>GCCTACTATAACGATTTTTCAATCAGCACATCAAGCATTTGTGTGGAGAAACACGACAACAAGTTCGAAAATCTG<br>ACTAGCAACCAGAAGCTGCTGTTTTCCAATGCAAAAGAGGGCTCTGTGAAGGTCGAAAGTCTGGGGATCCAGAA<br>CCTGAAAGTGTTCGAGAAGTACATCATTACCCCCCTGGGAGATAAAATTAAGGCTGACTTTCAGCCTCGAGAAAA<br>CATCAGCCTGAAAACCAGTAAAAAGTATGGCCTGAGGTAAGAATTC |

FIG. 13DD

| | |
|---|---|
| Length of Protein (without NLS and HA tag) | 1003 |
| **PAM** | **NNGGGYA** |
| Spacer Length | 29 |
| **Species: Streptococcus pyogenes SF370** | |
| Sequencing Barcode | CCAGTTAG |
| ID | 25 |
| **Chimeric Guide RNA** | **NNNNNNNNNNNNNNNNNNNNGUUUUAGAGCUAGAAAUAGCAAGUUAAAAUAAGGCUAGUCCGUUAUCAAC<br>UUGAAAAAGUGGCACCGAGUCGGUGCUUUUUU** |
| Cas9 Protein Sequence (wildtype, without NLS added) | MDKKYSIGLDIGTNSVGWAVITDEYKVPSKKFKVLGNTDRHSIKKNLIGALLFDSGETAEATRLKRTARRRYTRRKNR<br>ICYLQEIFSNEMAKVDDSFFHRLEESFLVEEDKKHERHPIFGNIVDEVAYHEKYPTIYHLRKKLVDSTDKADLRLIYLAL<br>AHMIKFRGHFLIEGDLNPDNSDVDKLFIQLVQTYNQLFEENPINASGVDAKAILSARLSKSRRLENLIAQLPGEKKNGLF<br>GNLIALSLGLTPNFKSNFDLAEDAKLQLSKDTYDDDLDNLLAQIGDQYADLFLAAKNLSDAILLSDILRVNTEITKAPLS<br>ASMIKRYDEHHQDLTLLKALVRQQLPEKYKEIFFDQSKNGYAGYIDGGASQEEFYKFIKPILEKMDGTEELLVKLNRE<br>DLLRKQRTFDNGSIPHQIHLGELHAILRRQEDFYPFLKDNREKIEKILTFRIPYYVGPLARGNSRFAWMTRKSEETITPW<br>NFEEVVDKGASAQSFIERMTNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENEDILEDIVLTLTLFEDREMIEE<br>RLKTYAHLFDDKVMKQLKRRRYTGWGRLSRKLINGIRDKQSGKTILDFLKSDGFANRNFMQLIHDDSLTFKEDIQKA<br>QVSGQGDSLHEHIANLAGSPAIKKGILQTVKVVDELVKVMGRHKPENIVIEMARENQTTQKGQKNSRERMKRIEEGIK<br>ELGSQILKEHPVENTQLQNEKLYLYYLQNGRDMYVDQELDINRLSDYDVDHIVPQSFLKDDSIDNKVLTRSDKNRGKS<br>DNVPSEEVVKKMKNYWRQLLNAKLITQRKFDNLTKAERGGLSELDKAGFIKRQLVETRQITKHVAQILDSRMNTKYD<br>ENDKLIREVKVITLKSKLVSDFRKDFQFYKVREINNYHHAHDAYLNAVVGTALIKKYPKLESEFVYGDYKVYDVRKM<br>IAKSEQEIGKATAKYFFYSNIMNFFKTEITLANGEIRKRPLIETNGETGEIVWDKGRDFATVRKVLSMPQVNIVKKTEVQ<br>TGGFSKESILPKRNSDKLIARKKDWDPKKYGGFDSPTVAYSVLVVAKVEKGKSKKLKSVKELLGITIMERSSFEKNPID<br>FLEAKGYKEVKKDLIIKLPKYSLFELENGRKRMLASAGELQKGNELALPSKYVNFLYLASHYEKLKGSPEDNEQKQLF<br>VEQHKHYLDEIIEQISEFSKRVILADANLDKVLSAYNKHRDKPIREQAENIIHLFTLTNLGAPAAFKYFDTTIDRKRYTST |

FIG. 13EE

| | |
|---|---|
| | KEVLDATLIHQSITGLYETRIDLSQLGGD |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC<br>CGACAAGAAGTACAGCATCGGCCTGGACATCGGCACCAACTCTGTGGGCTGGGCCGTGATCACCGACGAGTACA<br>AGGTGCCCAGCAAGAAATTCAAGGTGCTGGGCAACACCGACCGGCACAGCATCAAGAAGAACCTGATCGGAGCC<br>CTGCTGTTCGACAGCGGCGAAACAGCCGAGGCCACCCGGCTGAAGAGAACCGCCAGAAGAAGATACACCAGAC<br>GGAAGAACCGGATCTGCTATCTGCAAGAGATCTTCAGCAACGAGATGGCCAAGGTGGACGACAGCTTCTTCCAC<br>AGACTGGAAGAGTCCTTCCTGGTGGAAGAGGATAAGAAGCACGAGCGGCACCCCATCTTCGGCAACATCGTGGA<br>CGAGGTGGCCTACCACGAGAAGTACCCCACCATCTACCACCTGAGAAAGAAACTGGTGGACAGCACCGACAAGG<br>CCGACCTGCGGCTGATCTATCTGGCCCTGGCCCACATGATCAAGTTCCGGGGCCACTTCCTGATCGAGGGCGACC<br>TGAACCCCGACAACAGCGACGTGGACAAGCTGTTCATCCAGCTGGTGCAGACCTACAACCAGCTGTTCGAGGAA<br>AACCCCATCAACGCCAGCGGCGTGGACGCCAAGGCCATCCTGTCTGCCAGACTGAGCAAGAGCAGACGGCTGGA<br>AAATCTGATCGCCCAGCTGCCCGGCGAGAAGAAGAATGGCCTGTTCGGCAACCTGATTGCCCTGAGCCTGGGCCT<br>GACCCCCAACTTCAAGAGCAACTTCGACCTGGCCGAGGATGCCAAACTGCAGCTGAGCAAGGACACCTACGACG<br>ACGACCTGGACAACCTGCTGGCCCAGATCGGCGACCAGTACGCCGACCTGTTTCTGGCCGCCAAGAACCTGTCCG<br>ACGCCATCCTGCTGAGCGACATCCTGAGAGTGAACACCGAGATCACCAAGGCCCCCCTGAGCGCCTCTATGATCA<br>AGAGATACGACGAGCACCACCAGGACCTGACCCTGCTGAAAGCTCTCGTGCGGCAGCAGCTGCCTGAGAAGTAC<br>AAAGAGATTTTCTTCGACCAGAGCAAGAACGGCTACGCCGGCTACATTGACGGCGGAGCCAGCCAGGAAGAGTT<br>CTACAAGTTCATCAAGCCCATCCTGGAAAAGATGGACGGCACCGAGGAACTGCTCGTGAAGCTGAACAGAGAGG<br>ACCTGCTGCGGAAGCAGCGGACCTTCGACAACGGCAGCATCCCCCACCAGATCCACCTGGGAGAGCTGCACGCC<br>ATTCTGCGGCGGCAGGAAGATTTTTACCCATTCCTGAAGGACAACCGGGAAAAGATCGAGAAGATCCTGACCTTC<br>CGCATCCCCTACTACGTGGGCCCTCTGGCCAGGGGAAACAGCAGATTCGCCTGGATGACCAGAAAGAGCGAGGA<br>AACCATCACCCCCTGGAACTTCGAGGAAGTGGTGGACAAGGGCGCTTCCGCCCAGAGCTTCATCGAGCGGATGA<br>CCAACTTCGATAAGAACCTGCCCAACGAGAAGGTGCTGCCCAAGCACAGCCTGCTGTACGAGTACTTCACCGTGT<br>ATAACGAGCTGACCAAAGTGAAATACGTGACCGAGGGAATGAGAAAGCCCGCCTTCCTGAGCGGCGAGCAGAA<br>AAAGGCCATCGTGGACCTGCTGTTCAAGACCAACCGGAAAGTGACCGTGAAGCAGCTGAAAGAGGACTACTTCA<br>AGAAAATCGAGTGCTTCGACTCCGTGGAAATCTCCGGCGTGGAAGATCGGTTCAACGCCTCCCTGGGCACATACC<br>ACGATCTGCTGAAAATTATCAAGGACAAGGACTTCCTGGACAATGAGGAAAACGAGGACATTCTGGAAGATATC<br>GTGCTGACCCTGACACTGTTTGAGGACAGAGAGATGATCGAGGAACGGCTGAAAACCTATGCCCACCTGTTCGA<br>CGACAAAGTGATGAAGCAGCTGAAGCGGCGGAGATACACCGGCTGGGGCAGGCTGAGCCGGAAGCTGATCAAC<br>GGCATCCGGGACAAGCAGTCCGGCAAGACAATCCTGGATTTCCTGAAGTCCGACGGCTTCGCCAACAGAAACTT<br>CATGCAGCTGATCCACGACGACAGCCTGACCTTTAAAGAGGACATCCAGAAAGCCCAGGTGTCCGGCCAGGGCG<br>ATAGCCTGCACGAGCACATTGCCAATCTGGCCGGCAGCCCCGCCATTAAGAAGGGCATCCTGCAGACAGTGAAG<br>GTGGTGGACGAGCTCGTGAAAGTGATGGGCCGGCACAAGCCCGAGAACATCGTGATCGAAATGGCCAGAGAGA<br>ACCAGACCACCCAGAAGGGACAGAAGAACAGCCGCGAGAGAATGAAGCGGATCGAAGAGGGCATCAAAGAGCT<br>GGGCAGCCAGATCCTGAAAGAACACCCCGTGGAAAACACCCAGCTGCAGAACGAGAAGCTGTACCTGTACTACC |

FIG. 13FF

| | |
|---|---|
| | TGCAGAATGGGCGGGATATGTACGTGGACCAGGAACTGGACATCAACCGGCTGTCCGACTACGATGTGGACCAT<br>ATCGTGCCTCAGAGCTTTCTGAAGGACGACTCCATCGACAACAAGGTGCTGACCAGAAGCGACAAGAACCGGGG<br>CAAGAGCGACAACGTGCCCTCCGAAGAGGTCGTGAAGAAGATGAAGAACTACTGGCGGCAGCTGCTGAACGCCA<br>AGCTGATTACCCAGAGAAAGTTCGACAATCTGACCAAGGCCGAGAGAGGCGGCCTGAGCGAACTGGATAAGGCC<br>GGCTTCATCAAGAGACAGCTGGTGGAAACCCGGCAGATCACAAAGCACGTGGCACAGATCCTGGACTCCCGGAT<br>GAACACTAAGTACGACGAGAATGACAAGCTGATCCGGGAAGTGAAAGTGATCACCCTGAAGTCCAAGCTGGTGT<br>CCGATTTCCGGAAGGATTTCCAGTTTTACAAAGTGCGCGAGATCAACAACTACCACCACGCCCACGACGCCTACC<br>TGAACGCCGTCGTGGGAACCGCCCTGATCAAAAAGTACCCTAAGCTGGAAAGCGAGTTCGTGTACGGCGACTAC<br>AAGGTGTACGACGTGCGGAAGATGATCGCCAAGAGCGAGCAGGAAATCGGCAAGGCTACCGCCAAGTACTTCTT<br>CTACAGCAACATCATGAACTTTTTCAAGACCGAGATTACCCTGGCCAACGGCGAGATCCGGAAGCGGCCTCTGAT<br>CGAGACAAACGGCGAAACCGGGGAGATCGTGTGGGATAAGGGCCGGGATTTTGCCACCGTGCGGAAAGTGCTGA<br>GCATGCCCCAAGTGAATATCGTGAAAAAGACCGAGGTGCAGACAGGCGGCTTCAGCAAAGAGTCTATCCTGCCC<br>AAGAGGAACAGCGATAAGCTGATCGCCAGAAAGAAGGACTGGGACCCTAAGAAGTACGGCGGCTTCGACAGCC<br>CCACCGTGGCCTATTCTGTGCTGGTGGTGGCCAAAGTGGAAAAGGGCAAGTCCAAGAAACTGAAGAGTGTGAAA<br>GAGCTGCTGGGGATCACCATCATGGAAAGAAGCAGCTTCGAGAAGAATCCCATCGACTTTCTGGAAGCCAAGGG<br>CTACAAAGAAGTGAAAAAGGACCTGATCATCAAGCTGCCTAAGTACTCCCTGTTCGAGCTGGAAAACGGCCGGA<br>AGAGAATGCTGGCCTCTGCCGGCGAACTGCAGAAGGGAAACGAACTGGCCCTGCCCTCCAAATATGTGAACTTC<br>CTGTACCTGGCCAGCCACTATGAGAAGCTGAAGGGCTCCCCCGAGGATAATGAGCAGAAACAGCTGTTTGTGGA<br>ACAGCACAAGCACTACCTGGACGAGATCATCGAGCAGATCAGCGAGTTCTCCAAGAGAGTGATCCTGGCCGACG<br>CTAATCTGGACAAAGTGCTGTCCGCCTACAACAAGCACCGGGATAAGCCCATCAGAGAGCAGGCCGAGAATATC<br>ATCCACCTGTTTACCCTGACCAATCTGGGAGCCCCTGCCGCCTTCAAGTACTTTGACACCACCATCGACCGGAAG<br>AGGTACACCAGCACCAAAGAGGTGCTGGACGCCACCCTGATCCACCAGAGCATCACCGGCCTGTACGAGACACG<br>GATCGACCTGTCTCAGCTGGGAGGCGACAGCCCCAAGAAGAAGAGAAAGGTGGAGGCCAGCTAAGAATTC |
| Length of Protein (without NLS and HA tag) | 1368 |
| **PAM** | NGG |
| Spacer Length | 30 |
| **Species: Streptococcus thermophilus LMD9 (CRISPR I)** | |

FIG. 13GG

| | |
|---|---|
| Sequencing Barcode | TCGGAATG |
| ID | 26 |
| **Chimeric Guide RNA** | **NNNNNNNNNNNNNNNNNNNNGUUUUUGUACUCUCAAGAUUUAGAAACUUGCAGAAGCUACAAAGAUAAGG CUUCAUGCCGAAAUCAACACCCUGUCAUUUUAUGGCAGGGUGUUUU** |
| Cas9 Protein Sequence (wildtype, without NLS added) | MSDLVLGLDIGIGSVGVGILNKVTGEIIHKNSRIFPAAQAENNLVRRTNRQGRRLARRKKHRRVRLNRLFEESGLITDFT KISINLNPYQLRVKGLTDELSNEELFIALKNMVKHRGISYLDDASDDGNSSVGDYAQIVKENSKQLETKTPGQIQLERY QTYGQLRGDFTVEKDGKKHRLINVFPTSAYRSEALRILQTQQEFNPQITDEFINRYLEILTGKRKYYHGPGNEKSRTDY GRYRTSGETLDNIFGILIGKCTFYPDEFRAAKASYTAQEFNLLNDLNNLTVPTETKKLSKEQKNQIINYVKNEKAMGPA KLFKYIAKLLSCDVADIKGYRIDKSGKAEIHTFEAYRKMKTLETLDIEQMDRETLDKLAYVLTLNTEREGIQEALEHEF ADGSFSQKQVDELVQFRKANSSIFGKGWHNFSVKLMMELIPELYETSEEQMTILTRLGKQKTTSSSNKTKYIDEKLLTE EIYNPVVAKSVRQAIKIVNAAIKEYGDFDNIVIEMARETNEDDEKKAIQKIQKANKDEKDAAMLKAANQYNGKAELP HSVFHGHKQLATKIRLWHQQGERCLYTGKTISIHDLINNSNQFEVDHILPLSITFDDSLANKVLVYATANQEKGQRTPY QALDSMDDAWSFRELKAFVRESKTLSNKKKEYLLTEEDISKFDVRKKFIERNLVDTRYASRVVLNALQEHFRAHKIDT KVSVVRGQFTSQLRRHWGIEKTRDTYHHHAVDALIIAASSQLNLWKKQKNTLVSYSEDQLLDIETGELISDDEYKESV FKAPYQHFVDTLKSKEFEDSILFSYQVDSKFNRKISDATIYATRQAKVGKDKADETYVLGKIKDIYTQDGYDAFMKIY KKDKSKFLMYRHDPQTFEKVIEPILENYPNKQINEKGKEVPCNPFLKYKEEHGYIRKYSKKGNGPEIKSLKYYDSKLGN HIDITPKDSNNKVVLQSVSPWRADVYFNKTTGKYEILGLKYADLQFEKGTGTYKISQEKYNDIKKKEGVDSDSEFKFT LYKNDLLLVKDTETKEQQLFRFLSRTMPKQKHYVELKPYDKQKFEGGEALIKVLGNVANSGQCKKGLGKSNISIYKV RTDVLGNQHIIKNEGDKPKLM |
| Mammalian Codon Optimized Sequences (AgeI-HA-NLS-Cas9-NLS-taa-EcoRI) | ACCGGTGCCACCATGTACCCATACGATGTTCCAGATTACGCTTCGCCGAAGAAAAAGCGCAAGGTCGAAGCGTC CTCCGACCTGGTACTTGGACTGGATATTGGTATCGGTTCGGTGGGAGTCGGAATCCTCAACAAGGTCACGGGGGA GATCATTCACAAGAACTCGCGGATCTTCCCCGCAGCTCAGGCTGAGAACAACTTGGTGCGGAGAACGAATAGGC AGGGCAGGCGACTGGCGAGGAGGAAGAAACACAGGAGAGTCCGATTGAACCGGCTGTTCGAGGAGTCCGGTTT GATCACCGACTTTACGAAAATCTCGATTAACCTTAATCCCTATCAGCTTCGGGTGAAAGGCCTGACAGACGAACT TTCGAATGAGGAACTTTTCATCGCGCTGAAAAACATGGTCAAGCACAGAGGGATTTCCTACCTCGATGACGCCTC GGATGACGGAAATTCCTCAGTAGGAGATTATGCACAGATCGTGAAAGAGAACTCAAAGCAACTGGAAACAAAG ACACCGGGGCAGATCCAACTTGAAAGATACCAGACATACGGACAGCTCAGAGGAGATTTTACGGTGGAGAAGGA CGGTAAAAAGCACAGACTCATTAACGTATTTCCCACGTCGGCGTACAGATCCGAAGCGCTCCGCATCCTTCAGAC TCAACAGGAGTTCAACCCGCAAATTACTGATGAGTTCATCAACCGCTATTTGGAAATCTTGACCGGAAAGCGCAA GTATTATCATGGGCCGGGTAATGAGAAATCCAGAACAGATTACGGCCGATACAGAACTTCGGGGGAAACCTTGG ATAACATCTTTGGTATTTTGATTGGAAAGTGCACCTTTTACCCGGACGAGTTTCGAGCGGCCAAGGCGTCATACA CAGCACAAGAGTTTAATCTCTTGAATGATTTGAACAACTTGACGGTCCCCACGGAGACAAAGAAGCTCTCCAAAG AGCAAAAGAACCAAATCATCAACTACGTCAAGAACGAGAAGGCTATGGGGCCAGCGAAGCTGTTCAAGTATATC |

FIG. 13HH

| | |
|---|---|
| | GCTAAACTTCTCAGCTGTGATGTGGCGGACATCAAAGGGTACCGAATCGACAAGTCGGGAAAAGCGGAAATTCA<br>CACGTTTGAAGCATATCGAAAGATGAAAACGTTGGAAACACTGGACATTGAGCAGATGGACCGGGAAACGCTCG<br>ACAAACTGGCATACGTGCTCACGTTGAATACTGAACGAGAGGGAATCCAAGAGGCCCTTGAACATGAGTTCGCC<br>GATGGATCGTTCAGCCAGAAGCAGGTCGACGAACTTGTGCAATTCCGCAAGGCGAATAGCTCCATCTTCGGGAA<br>GGGATGGCACAACTTTTCGGTCAAACTCATGATGGAGTTGATCCCAGAACTTTATGAGACTTCGGAGGAGCAAAT<br>GACGATCTTGACGCGCTTGGGGAAACAGAAAACGACAAGCTCATCGAACAAAACTAAGTACATTGATGAGAAAT<br>TGCTGACGGAAGAAATCTATAATCCGGTAGTAGCGAAATCGGTAAGACAAGCGATCAAAATCGTGAACGCGGCG<br>ATCAAGGAATATGGTGACTTTGATAACATCGTAATTGAAATGGCTAGAGAGACGAACGAAGATGACGAGAAAAA<br>GGCAATCCAGAAGATCCAGAAGGCCAACAAGGATGAAAAAGATGCAGCGATGCTTAAAGCGGCCAACCAATAC<br>AATGGAAAGGCGGAGCTGCCCCATTCAGTGTTTCACGGTCATAAACAGTTGGCGACCAAGATCCGACTCTGGCAT<br>CAGCAGGGTGAGCGGTGTCTCTACACCGGAAAGACTATCTCCATCCATGACTTGATTAACAATTCGAACCAGTTT<br>GAAGTGGATCATATTCTGCCCCTGTCAATCACCTTTGACGACTCGCTTGCGAACAAGGTGCTCGTGTACGCAACG<br>GCAAATCAGGAGAAAGGCCAGCGGACTCCGTATCAGGCGCTCGACTCAATGGACGATGCGTGGTCATTCCGGGA<br>GCTGAAGGCGTTCGTACGCGAGAGCAAGACACTGAGCAACAAAAAGAAAGAGTATCTGCTGACAGAGGAGGAC<br>ATCTCGAAATTCGATGTCAGGAAGAAGTTCATCGAGCGGAATCTTGTCGACACTCGCTACGCTTCCAGAGTAGTA<br>CTGAACGCGCTCCAGGAACACTTTAGAGCGCACAAAATTGACACGAAGGTGTCAGTGGTGAGAGGGCAGTTCAC<br>ATCCCAACTCCGCCGACATTGGGGCATCGAAAAGACGCGGACACATATCACCATCATGCGGTGGACGCGCTGA<br>TTATTGCCGCTTCGTCCCAGTTGAATCTCTGGAAAAAGCAGAAGAACACGCTGGTGTCGTATTCGGAGGATCAGC<br>TTTTGGACATCGAAACCGGGGAGCTGATTTCCGACGATGAATACAAAGAATCGGTGTTTAAGGCACCATATCAGC<br>ATTTCGTGGACACGCTGAAGAGCAAAGAGTTTGAGGACAGCATCCTCTTTTCGTACCAAGTGGACTCGAAGTTTA<br>ATCGCAAGATTTCAGACGCCACAATCTACGCGACGAGGCAGGCGAAGGTGGGCAAAGATAAAGCAGATGAAAC<br>CTACGTCCTTGGTAAAATCAAGGACATCTACACTCAGGACGGGTACGATGCGTTCATGAAAATCTACAAGAAGG<br>ATAAGTCGAAGTTTCTCATGTACCGCCACGATCCACAGACTTTCGAAAAAGTCATTGAGCCTATTTTGGAGAACT<br>ACCCTAACAAGCAAATCAACGAGAAAGGGAAAGAAGTCCCGTGCAACCCCTTTCTGAAGTACAAGGAAGAGCAC<br>GGTTATATCCGCAAATACTCGAAGAAAGGAAATGGGCCTGAGATTAAGTCGCTTAAGTATTACGACTCAAAGTTG<br>GGTAACCACATCGACATTACCCCGAAAGACTCCAACAACAAAGTCGTGTTGCAGTCCGTCTCGCCCTGGCGAGCA<br>GATGTGTATTTTAATAAGACGACCGGCAAATATGAGATCCTTGGACTCAAATACGCAGACCTTCAATTCGAAAAG<br>GGGACGGGCACTTATAAGATTTCACAAGAGAAGTACAACGACATCAAGAAAAAGGAAGGGGTCGATTCAGATTC<br>GGAGTTCAAATTCACCCTCTACAAAAACGACCTCCTGCTTGTGAAGGACACAGAAACGAAGGAGCAGCAGCTCT<br>TTCGGTTCCTCTCACGCACGATGCCCAAACAAAAACATTACGTCGAACTTAAACCTTACGATAAGCAAAAGTTTG<br>AAGGGGGAGAGGCACTGATCAAAGTATTGGGTAACGTAGCCAATAGCGGACAGTGTAAGAAAGGGCTGGGAAA<br>GTCCAATATCTCGATCTATAAAGTACGAACAGATGTATTGGGAAACCAGCATATCATCAAAAATGAGGGGGATA<br>AACCCAAACTCGATTTCAGCCCCAAGAAGAAGAGAAAGGTGGAGGCCAGCTAAGAATTC |
| Length of Protein | 1120 |

FIG. 13II

| | |
|---|---|
| (without NLS and HA tag) | |
| **PAM** | NNAGAA |
| Spacer Length | 30 |

PAM testing: NNGRR

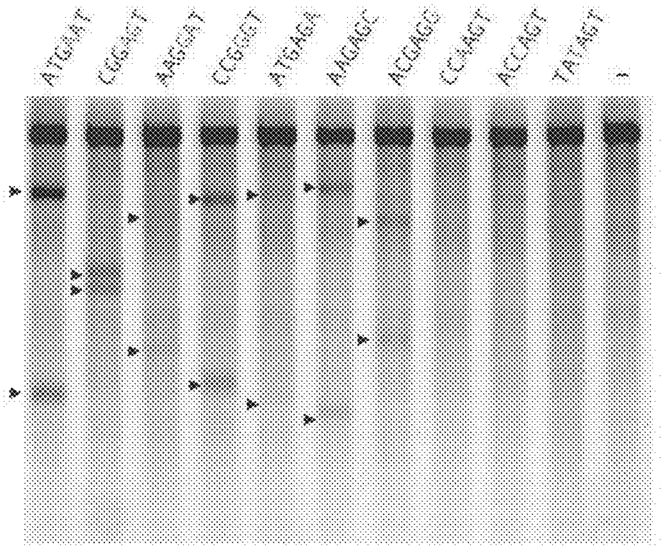

Spacer sequences for PAMs tested:

| Spacer | PAM |
|---|---|
| GCCCGGGTGGAACTGGTAGCC | ATGAAT |
| GTTGAAGATGAAGCCCAGAG | CGGAGT |
| GCTTCCGACGAGGTGGCCATC | AAGGAT |
| GCACCATCTCTCCGTGGTACC | CCGGGT |
| GGTGGAACTGGTAGCCATGA | ATGAGA |
| GCCATGAATGAGACCGACCCA | AAGAGC |
| GCATCCTCGTGGGCACTTCCG | ACGAGG |
| GCAGAGCGGAGTGCTGTTCTC | CCAAGT |
| GGTCGGTCTCATTCATGGCT | ACCAGT |
| GCAATAAAAGGTGCTATTGC | TATAGT |

Figure 19A:
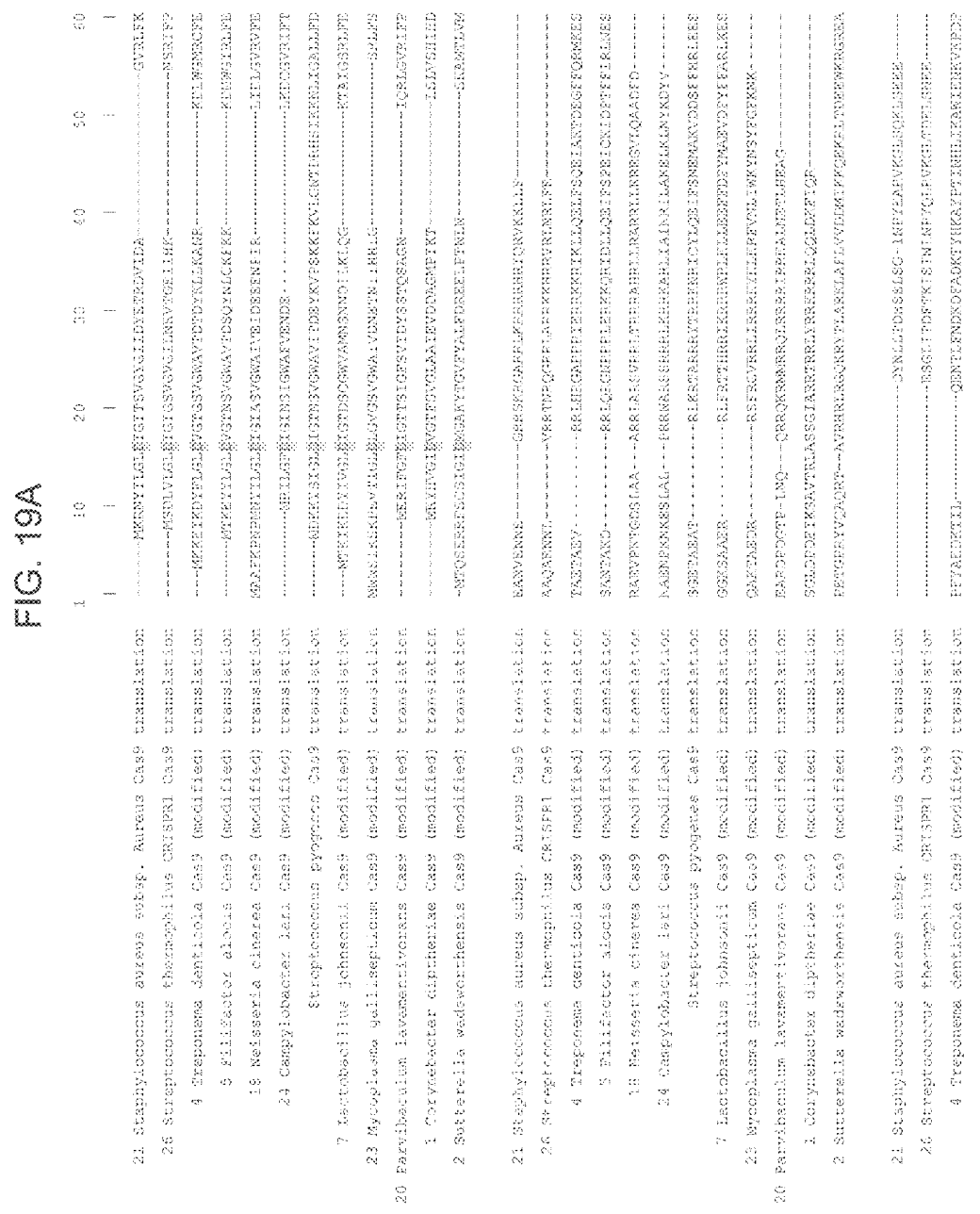

```
                                                              1        10        20        30        40        50        60
                                                              |        |         |         |         |         |         |
21 Staphylococcus aureus subsp. Aureus Cas9 translation       ------MKRNYILGLDIGITSVGYGIIDYETRDVIDA-----------------GVRLFK
26 Streptococcus thermophilus CRISPR1 Cas9 translation       -------MSDLVLGLDIGIGSVGVGILNKVTGEIIHK-----------------NSRIFP
4 Treponema denticola Cas9 (modified) translation            ---MKKEIKDYFLGLDVGTGSVGWAVTDTDYKLLKANR------------KDLWGMRCFE
5 Filifactor alocis Cas9 (modified) translation              ------MTKEYYLGLDVGTNSVGWAVTDSQYNLCKFKK------------KDNWGIRLFE
18 Neisseria cinerea Cas9 (modified) translation             MAAFKPNPMNYILGLDIGIASVGWAIVEIDEEENPIR-------------LIDLGVRVFE
24 Campylobacter lari Cas9 (modified) translation            ---------MRILGFDIGINSIGWAFVENDE-------------------LKDCGVRIFT
Streptococcus pyogenes Cas9 translation                      ------MDKKYSIGLDIGTNSVGWAVITDEYKVPSKKFKVLGNTDRHSIKKNLIGALLFD
7 Lactobacillus johnsonii Cas9 (modified) translation        ---MTKIKDDYIVGLDIGTDSCGWVAMNSNNDILKLQG------------KTAIGSRLFE
23 Mycoplasma gallisepticum Cas9 (modified) translation      MNNSIKSKPEVTIGLDLGVGSVGWAIVDNETNIIHHLG-----------------SRLFS
20 Parvibaculum lavamentivorans Cas9 (modified) translation  --------MERIFGFDIGTTSIGFSVIDYSSTQSAGN-------------IQRLGVRIFP
1 Corynebacter diptheriae Cas9 (modified) translation        --------MKYHVGIDVGTFSVGLAAIEVDDAGMPIKT-------------LSLVSHIHD
2 Sutterella wadsworthensis Cas9 (modified) translation      -MTQSERRFSCSIGIDMGAKYTGVFYALFDREELPTNLN-------------SKAMTLVM

21 Staphylococcus aureus subsp. Aureus Cas9 translation       EANVENNE---------GRRSKRGARRLKRRRRHRIQRVKKLLF----------------
26 Streptococcus thermophilus CRISPR1 Cas9 translation       AAQAENNL---------VRRTNRQGRRLARRKKHRRVRLNRLFE----------------
4 Treponema denticola Cas9 (modified) translation            TAETAEV-----------RRLHRGARRRIERRKKRIKLLQELFSQEIAKTDEGFFQRMKES
5 Filifactor alocis Cas9 (modified) translation              SANTAKD-----------RRLQRGNRRRLERRKQRIDLLQEIFSPEICKIDPTFFIRLNES
18 Neisseria cinerea Cas9 (modified) translation             RAEVPKTGDSLAA---ARRLARSVRRLTRRRAHRLLRARRLLKREGVLQAADFD------
24 Campylobacter lari Cas9 (modified) translation            KAENPKNKESLAL---PRRNARSSRRRLKRRKARLIAIKRILAKELKLNYKDYV------
Streptococcus pyogenes Cas9 translation                      SGETAEAT----------RLKRTARRRYTRRKNRICYLQEIFSNEMAKVDDSFFHRLEES
7 Lactobacillus johnsonii Cas9 (modified) translation        GGKSAAER----------RLFRTTHRRIKRRRWRLKLLEEFFDPYMAEVDPYFFARLKES
23 Mycoplasma gallisepticum Cas9 (modified) translation      QAKTAEDR----------RSFRGVRRLIRRRKYRLKRFVNLIWKYNSYFGFKNK------
20 Parvibaculum lavamentivorans Cas9 (modified) translation  EARDPDGTP-LNQ---QRRQKRMMRRQLRRRRIRRKALNETLHEAG--------------
1 Corynebacter diptheriae Cas9 (modified) translation        SGLDPDEIKSAVTRLASSGIARRTRRLYRRKRRRLQQLDKFIQR----------------
2 Sutterella wadsworthensis Cas9 (modified) translation      PETGPRYVQAQRT--AVRHRLRGQKRYTLARKLAFLVVDDMIKKQEKRLTDEEWKRGREA

21 Staphylococcus aureus subsp. Aureus Cas9 translation       ----------------------DYNLLTDHSELSG-INPYEAPVKGLSQKLSEEE-----
26 Streptococcus thermophilus CRISPR1 Cas9 translation       ----------------------ESGLIPDFTKISINLNPYQLPVKGLTDELSNEE-----
4 Treponema denticola Cas9 (modified) translation            PFYAEDKTIL-----------QENTLENDKDFADKTYHKAYPTINHLIKAWIENKVKPDP
```

FIG. 19B

```
5 Filifactor alocis Cas9 (modified) translation                   RLHLEDKSND-----------FKYPLFIEKLYSDISYYKEFPTIFHLRKHLIESSEKQDI
18 Neisseria cinerea Cas9 (modified) translation                  ----------------------ENG-----LIKSLPNTPWQLRAAALDRKLTPLE-----
24 Campylobacter lari Cas9 (modified) translation                 ----------------------AADGELPKAYEGSLASVYELRYKALTQNLETKD-----
Streptococcus pyogenes Cas9 translation                           FLVEEDKK------------HFERHPIFGNIVDEVAYHEKYPTIYHLRKKLVDSTDKADL
7 Lactobacillus johnsonii Cas9 (modified) translation             GLSPLDKEK------------TVSSIVFPTSAEDKKFYDDYPTIYHLRYKLMTEDEKFDL
23 Mycoplasma gallisepticum Cas9 (modified) translation           ----------------------EDILNNYQEQQKLHNTVLNLKSEALNAKIDPKA-----
20 Parvibaculum lavamentivorans Cas9 (modified) translation       ---------------------FLPAYGSADNFVVMADEPYELRRRGLEEGLSAYE-----
1 Corynebacter diptheriae Cas9 (modified) translation             ---------------------QGWFVIELLEDYSDFLYPWKVRAELAASYIADELEPGL-
2 Sutterella wadsworthensis Cas9 (modified) translation           LSGLLKRRGYSRPNADGEDLTFLENVRADVFAAHPAFSTYFSEVRSLAEQWEEFTANISN

21 Staphylococcus aureus subsp. Aureus Cas9 translation           --FSAALLHLAKRRGVHNVN-----------------------EVEEDTGNELSTKEQIS
26 Streptococcus thermophilus CRISPR1 Cas9 translation           --LFIALKNMVKHRGISYLD-----------------------DASDDGNSSVGDYAQIV
4 Treponema denticola Cas9 (modified) translation                RLLYLACHNIIKKRGHFLFEGDFDSEN----QFDTSIQAL-FEYLREDMEVDIDADSQK-
5 Filifactor alocis Cas9 (modified) translation                  RLIYLALHNIIKTRGHFLIDGDLQSAK----QLRPILDTF-LLSLQEEQNLSVSLSENQK
18 Neisseria cinerea Cas9 (modified) translation                 --WSAVLLHLIKHRGYLSQR----------------------KNEGETADKELGALLKGV
24 Campylobacter lari Cas9 (modified) translation                --LARVILHIAKHRGYMN------------------------KNEKKSNDAKKGKILSAL
Streptococcus pyogenes Cas9 translation                          RLIYLALAHMIKFRGHFLIEGDLNPDNSDVDKLFIQLVQT-YNQLFEENPINASGVDAKA
7 Lactobacillus johnsonii Cas9 (modified) translation            PEVYLAIHHIIKYRGNFLYNTSVKDFKASKIDVKSSIEKLNELYENLGLDLNVEFNISNT
23 Mycoplasma gallisepticum Cas9 (modified) translation          ---LSWILHDYLENRGHFYEDN--------------------RDFNVYPTKELAKYFDKY
20 Parvibaculum lavamentivorans Cas9 (modified) translation      ---FGRAIYHLAQHRHFKGRE---------------------LEESDTPDPDVDDEKEAA
1 Corynebacter diptheriae Cas9 (modified) translation            -KLSVALRHIARHRGWRNPYAKVSS-----------------LYLPDGPSDAFKAIREEI
2 Sutterella wadsworthensis Cas9 (modified) translation          VEKFLGDPNIPADKEEIEEFAVAEG------------------LIDKTEKKAYQSALSTL

21 Staphylococcus aureus subsp. Aureus Cas9 translation           R-NSKALEEKYVA-----------------------------------------------
26 Streptococcus thermophilus CRISPR1 Cas9 translation           KENSKQLETKTPG-----------------------------------------------
4 Treponema denticola Cas9 (modified) translation                --VKEILKDSSLKNSEKQSRLNKILGLK--ESDKQKKAITNLIS-------GNKINFADL
5 Filifactor alocis Cas9 (modified) translation                  DEYEEILKNRSIAKSEKVKKLKNLFEEISDELEKEEEKAQSAVIENFCKFIVGNHGDVCHF
18 Neisseria cinerea Cas9 (modified) translation                 ADNTHALQTGD-------------------------------------------------
24 Campylobacter lari Cas9 (modified) translation                KNNALKLENYQSVC----------------------------------------------
Streptococcus pyogenes Cas9 translation                          ILSARLSKSRRLENLIAQLPGEKKNGLFGNLIALSLGLTPNFKSN---------------
7 Lactobacillus johnsonii Cas9 (modified) translation            AEIEKVLKDKQIFKRDKVKKIAELFAIKTDNKEQSKRIKDISKQVANAVLGYKTHFDTIA
23 Mycoplasma gallisepticum Cas9 (modified) translation          GYYRGIIDSKEDND----------------------------------------------
```

FIG. 19C

```
20 Parvibaculum lavamentivorans Cas9 (modified) translation   NERAATLKALKNEQ----------------------------------------------
 1 Corynebacter diptheriae Cas9 (modified) translation        KRASGQPVPETATVG---------------------------------------------
 2 Sutterella wadsworthensis Cas9 (modified) translation      RANANVLTGLRQMG----------------------------------------------

21 Staphylococcus aureus subsp. Aureus Cas9 translation       ------------------------------------------------------------
26 Streptococcus thermophilus CRISPR1 Cas9 translation        ------------------------------------------------------------
 4 Treponema denticola Cas9 (modified) translation            YDNPDLKDAEKNSISFSKDDFD-ALSDDLASILGDSTELLLKAKAVYNCSVLSKVIGD--
 5 Filifactor alocis Cas9 (modified) translation              LP-VSKEELEIDSFSFSEGKYEDDIVKNLEEKVPEKVYLFEQMLAMYDWNILVDILET--
18 Neisseria cinerea Cas9 (modified) translation              ------------------------------------------------------------
24 Campylobacter lari Cas9 (modified) translation             ------------------------------------------------------------
   Streptococcus pyogenes Cas9 translation                    -----FDLAEDAKLQLSKDTYDDDLDNLLAQIGDQYADLFLAAKNLSDAILLSDILRVNT
 7 Lactobacillus johnsonii Cas9 (modified) translation        LKEISKDELSDWNFKLSDIDADSKFEALMGNLDENEQAILLTIKELFNEVTLNGIVED--
23 Mycoplasma gallisepticum Cas9 (modified) translation       ------------------------------------------------------------
20 Parvibaculum lavamentivorans Cas9 (modified) translation   ------------------------------------------------------------
 1 Corynebacter diptheriae Cas9 (modified) translation        ------------------------------------------------------------
 2 Sutterella wadsworthensis Cas9 (modified) translation      ------------------------------------------------------------

21 Staphylococcus aureus subsp. Aureus Cas9 translation       -----ELQLERLKKDGEVRG----------------------------------------
26 Streptococcus thermophilus CRISPR1 Cas9 translation        -----QIQLERYQTYGQLRGDFTVEK----------------------------------
 4 Treponema denticola Cas9 (modified) translation            ---EQYLSFAKVKIYEKHKTDLTKLENVIKKHFPK-DYKKVFGYNKNEKNNNNYSGYVGV
 5 Filifactor alocis Cas9 (modified) translation              ---EEYISFAKVKQYEKHKTNLPLLPDIILKYCTKDEYNRMFN---DEKEAGSYTAYVGK
18 Neisseria cinerea Cas9 (modified) translation              ------FRTPAELALNKFEKLSCHIR----------------------------------
24 Campylobacter lari Cas9 (modified) translation             ----EYFYKEFFQKYKKNTKNFIKIR----------------------------------
   Streptococcus pyogenes Cas9 translation                    EITKAPLSASMIKRYDEHHQDLTLLKALVRQQLPEKYKEIFFD-----------------
 7 Lactobacillus johnsonii Cas9 (modified) translation        ---GNTLSESMINKYNDHRDDLKLLKEVIENHIDRKKAKELALAYDLYVNN-----RHGQ
23 Mycoplasma gallisepticum Cas9 (modified) translation       ----NKLEEELTKYKFSNKHWLEEVKKVLSNQTG--------------------------
20 Parvibaculum lavamentivorans Cas9 (modified) translation   ----TTLGAWLARRPPSDRKR---------------------------------------
 1 Corynebacter diptheriae Cas9 (modified) translation        -----QMVTLCELGTLKLRGE---------------------------------------
 2 Sutterella wadsworthensis Cas9 (modified) translation      ----HKPRSEYFKAIEADLKKDSRLAKINEAFGGAERLAPLLG-----------------

21 Staphylococcus aureus subsp. Aureus Cas9 translation       -----------------------------------------------------------S
26 Streptococcus thermophilus CRISPR1 Cas9 translation        -----------------------------------------------------DCKKHRL
```

FIG. 19D

```
 4 Treponema denticola Cas9 (modified) translation        CKTKSFKLIINNSVNQEDFYKFLKTILSAKSEIKSVNDILT----EIEFGTFLPKQISKS
 5 Filifactor alocis Cas9 (modified) translation          LKENNKKYWIEKKRNPEEFYKSLGKLLDKIEPLKEDLEVLTMMIEECKNHTLLPIQKNKD
18 Neisseria cinerea Cas9 (modified) translation          ------------------------------------------------------NQPGDY
24 Campylobacter lari Cas9 (modified) translation         ------------------------------------------------------NTKDNY
   Streptococcus pyogenes Cas9 translation                QSKKGYAGYIDGGASQEEFYKFIKPILEKMDGTEELLVKLN-------REDLLRKQRTFD
 7 Lactobacillus johnsonii Cas9 (modified) translation    LLQAKKKLGKIKPESKEDFYKVVNKNLDDSRASKEIKKKIELDS-------FMPKQRTNA
23 Mycoplasma gallisepticum Cas9 (modified) translation   ---------------------------------------------------LPEKFKEEY
20 Parvibaculum lavamentivorans Cas9 (modified) translation ------------------------------------------------------------
 1 Corynebacter diptheriae Cas9 (modified) translation    ------------------------------------------------------------
 2 Sutterella wadsworthensis Cas9 (modified) translation  -------------------------------------------NLSNLQLRAERWYFNAF

21 Staphylococcus aureus subsp. Aureus Cas9 translation   INRFKTSDYVKEAKQLLKVQKAYH-QLDQS---------FIDTYIDLLETRRTYYEGPGE
26 Streptococcus thermophilus CRISPR1 Cas9 translation    INVFPTSAYRSEALRILQTQQEFNPQITDE---------FINRYLEILTGKRKYYHGPGN
 4 Treponema denticola Cas9 (modified) translation        NAEIPYQLRKMELEKILSNAEKHFSFLKQKD---ENGLSHSEKIIMLLTFKIPYYIGPIN
 5 Filifactor alocis Cas9 (modified) translation          NCVIPHQVHEVELKKILENAKKYYSFLTETD---NDGYSVVQKIESIFRFRIPYYVGPLS
18 Neisseria cinerea Cas9 (modified) translation          SHTFNRKDLQAELNLLFEKQKEFGNPHVSD---------GLKEGIETLLMTQRPAL----
24 Campylobacter lari Cas9 (modified) translation         NNCVLSSDLEKELKLILEKQKEFGYNYSED---------FINEILKVAFFQR--------
   Streptococcus pyogenes Cas9 translation                NGSIPHQIHLGELHAILRRQEDFYPFLKDN----------REKIEKILTFRIPYYVGPLA
 7 Lactobacillus johnsonii Cas9 (modified) translation    NGVIPYQLQQLELDKIIENQSKYYPFLKEINEVSSHLKEAPYKLDELIRFRVPYYVGPLI
23 Mycoplasma gallisepticum Cas9 (modified) translation   ESLFSYVRNYSECPCSINSVSPYCIYHLDEK-----EGKVVQKYNNIWDKTIGKCNIFPD
20 Parvibaculum lavamentivorans Cas9 (modified) translation GIHAHRNVVAEEFERLWEVQSKFHPALKSEE--------MRARISDTIFAQRPVFWR---
 1 Corynebacter diptheriae Cas9 (modified) translation    GGVLSARLQQSDYARKIQEICRMQEIGQELY----------RKTTDVVFAAES-------
 2 Sutterella wadsworthensis Cas9 (modified) translation  DIMKDRGWEPDRFKKTLVRAFKFTHFAKDQNKQHLELIKQIENSEDIIETLCTLDPNRTI

21 Staphylococcus aureus subsp. Aureus Cas9 translation   ---GSPFG-------------------------------WKDIKEWYEMLMGHCTYFPEE
26 Streptococcus thermophilus CRISPR1 Cas9 translation    EKSRTDYGR--------------------------YKTSGETLDNIFGILIGKCTFYPDE
 4 Treponema denticola Cas9 (modified) translation        DNHKKFFPDRGW---VVRKEKSPSGKTTPWNFFDHIDKEKTAEAIITSRTNFCTYLVGE
 5 Filifactor alocis Cas9 (modified) translation          TRHQEKGSN-VW----MVRKP-GREDRIYPWNMEEIIDFEKSNENFITRMTNKCTYLIGE
18 Neisseria cinerea Cas9 (modified) translation          ------------------------------------------SGDAVQKMLGHCTFEPTE
24 Campylobacter lari Cas9 (modified) translation         ------------------------------------------PLKDFSHLVGACTFFEEE
   Streptococcus pyogenes Cas9 translation                RGNSRFAWMTR------------KSEETITPWNFEEVVDKGASAQSFIERMTNFDKNLPNE
 7 Lactobacillus johnsonii Cas9 (modified) translation    SPNESTKDIQTKKNQNFAWMIRKEEGRITPWNFIQKVDREIESANKFIKRMTTKDTYLFGE
```

FIG. 19E

```
23 Mycoplasma gallisepticum Cas9 (modified) translation    EYRAPFNSP---------------------------IAMIFNEINELSTIRSYSIYLTGW
20 Parvibaculum lavamentivorans Cas9 (modified) translation -----------------------------------------------KNTLGECRFMPGE
 1 Corynebacter diptheriae Cas9 (modified) translation      ------------------------------------------PKGSASSRVGKDPLQPGK
 2 Sutterella wadsworthensis Cas9 (modified) translation    PPYEDQNNRRPP-------LDQTLLLSPEKLTRQYGEIWKTWSARLTSAEPTLAPAAEILER

21 Staphylococcus aureus subsp. Aureus Cas9 translation     LRSVKYAYNADLYNALNDLNNLVITRDENEKLEYYEKFQIIENVFKQKKK---PTLKQIA
26 Streptococcus thermophilus CRISPR1 Cas9 translation      FRAAKASYTAQEFNLLNDLNNLTVP-TETKKLSKEQKNQIINYVKNEKAMGPAKLFKYIA
 4 Treponema denticola Cas9 (modified) translation          SVLPKSSLLYSEYTVLNEINNLQIIIDGKNICDIKLKQKIYEDLFKKYKK---ITQKQIS
 5 Filifactor alocis Cas9 (modified) translation            DVLPKHSLLYSKYMVLNELN--NVKVRGKKLP-TSLKQKVFEDLFENKSK---VTGKNLL
18 Neisseria cinerea Cas9 (modified) translation            PKAAKNTYTAERFVWLTKLN--NLRILEQGSERPLTDTERATLMDEPYRKSKLTYAQARK
24 Campylobacter lari Cas9 (modified) translation           KRACKNSYSAWEFVALTKIIN-EIKSLEKISGEIVPTQTINEVLNLILDKGSITYKKFRS
   Streptococcus pyogenes Cas9 translation                  KVLPKHSLLYEYFTVYNELTKVKYVTEGMRKPAFLSGEQKKAIVDLLFKTNRKVTVKQLK
 7 Lactobacillus johnsonii Cas9 (modified) translation      DVLPANSLLYQKFTVLNELNN---IRINGKRISVDLKQEIYENLFKKHTT----VTVKKL
23 Mycoplasma gallisepticum Cas9 (modified) translation     FTNQEFKKAYLNKLLDLLIKTNGEKPIDARQFKKLREETIAESIGKETLKDVENEEKLEK
20 Parvibaculum lavamentivorans Cas9 (modified) translation PLCPKGSWLSQQRRMLEKLNNLAIAGGNARPLDAEERDAILSKLQQQASMSWPGVRSALK
 1 Corynebacter diptheriae Cas9 (modified) translation      NRALKASDAFQRYRIAALIGNLRVRVDGEKRILSVEEKNLVFDHLVNLTPKKEPEWVTIA
 2 Sutterella wadsworthensis Cas9 (modified) translation    STDRKSRVAVNGHEPLPTLAYQLSYALQRAFDRSKALDPYALRALAAGSKSNKLTSARTA

21 Staphylococcus aureus subsp. Aureus Cas9 translation     KEILVNEEDIKG---YRVT--STGKPEFTNLKVYHDIKD--ITA--RKEIIENAELLDQI
26 Streptococcus thermophilus CRISPR1 Cas9 translation      KLLSCDVADIKG---YRID--KSGKAEIHTFEAYRKMKT--LET--LDIEQMDRETLDKL
 4 Treponema denticola Cas9 (modified) translation          TFIKHEGICNKT---DEVIILGIDKECTSSLKSYIELKN-IFGK--QVDEISTKNMLEEI
 5 Filifactor alocis Cas9 (modified) translation            EYLQIQDKDIQI---DDLS--GFDKDFKTSLKSYLDFKKQIFGE--EIEKESIQNMIEDI
18 Neisseria cinerea Cas9 (modified) translation            LLDLDDTAFFKG---LRYGKDNAEASTLMEMKAYHAISR-ALEK--EGLKDKKSPLNLSP
24 Campylobacter lari Cas9 (modified) translation           CINLKESISEKS---LKYDKENAENAKLIDIRKLVEEKK-ALG-----------VHSLSR
   Streptococcus pyogenes Cas9 translation                  EDYFKKIECFDS---VEIS--GVEDRFNASLGTYHDLLKIIKDKD-FLDNEENEDILEDI
 7 Lactobacillus johnsonii Cas9 (modified) translation      ENYLKENHNLVK---VEIKGLADEKKFNSGLTTYNRFKNLNIFDN-QIDDLKYRNDFEKI
23 Mycoplasma gallisepticum Cas9 (modified) translation     EDHKWKLKGLKLNTNGKIQYNDLSSLAKFVHKLKQHLKLDFLLED-QYATLDKINFLQSL
20 Parvibaculum lavamentivorans Cas9 (modified) translation ALYKQRGEPGAEKS-LKFNLELGGESKLLGNALSAKLADMFGPDWPAHPRKQEIRHAVHE
 1 Corynebacter diptheriae Cas9 (modified) translation      EILGIDRGQLIG------TATMTDDGERAGARPPTHDTNRSIVNSRIAPLVDWWKTASAL
 2 Sutterella wadsworthensis Cas9 (modified) translation    LENCIGGQNVKT--ELDCARRYYREADDAKVGLWFDNADGLLERSDLHPPMKKKIILPLLV

21 Staphylococcus aureus subsp. Aureus Cas9 translation     AKILTIYQ--SSEDIQEELTN--LNSELTQEEIEQISNLKGYT-----------------
```

FIG. 19F

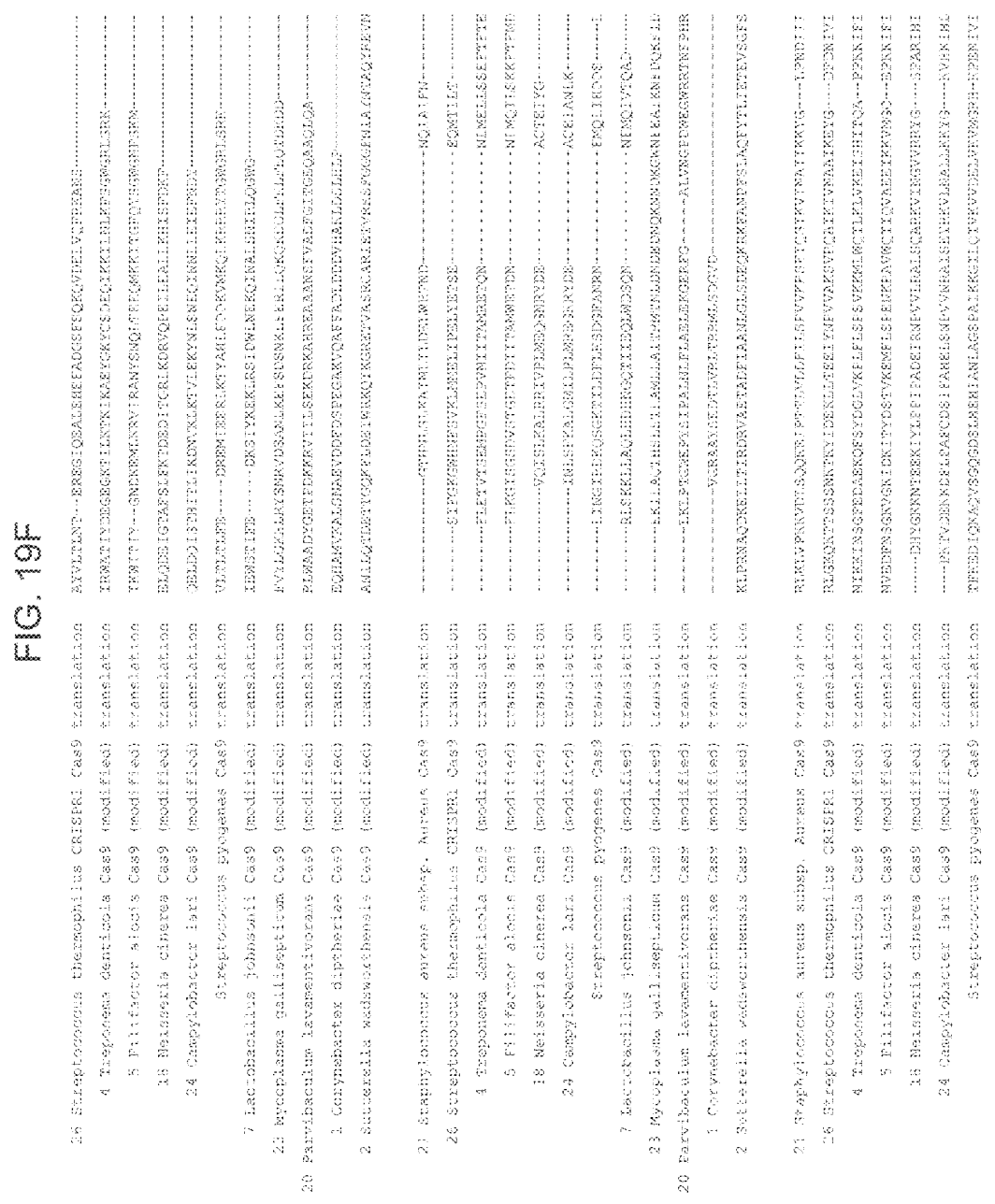

```
26 Streptococcus thermophilus CRISPR1 Cas9 translation   AYVLTLNT--EREGIQEALEHEFADGSFSQKQVDELVQFRKANS----------------
4 Treponema denticola Cas9 (modified) translation        IRWATIYDEGEGKTILKTKIKAEYGKYCSDEQIKKILNLKFSGWGRLSRK----------
5 Filifactor alocis Cas9 (modified) translation          TKWITTY--GNDKEMLKRVIRANYSNQLTEEQMKKITGFQYSGWGNFSKM----------
18 Neisseria cinerea Cas9 (modified) translation         ELQDEIGTAFSLFKTDEDITGRLKDRVQPEILEALLKHISFDKF----------------
24 Campylobacter lari Cas9 (modified) translation        QELDQISTHITLIKDNVKLKTVLEKYNLSNEQINNILEIEFNDY----------------
Streptococcus pyogenes Cas9 translation                  VLTLTLFE----DREMIEERLKTYAHLFDDKVMKQLKRRRYTGWGRLSRK----------
7 Lactobacillus johnsonii Cas9 (modified) translation    IEWSTIFE-----DKSIYKEKLRSIDWLNEKQINALSNIRLQGWG---------------
23 Mycoplasma gallisepticum Cas9 (modified) translation  FVYLGKHLRYSNRVDSANLKEFSDSNKLFERILQKQKDGLFKLFEQTDKDD---------
20 Parvibaculum lavamentivorans Cas9 (modified) translation RLWAADYGETFDKKRVIILSEKDRKAHREAAANSFVADFGITGEQAAQLQA---------
1 Corynebacter diptheriae Cas9 (modified) translation    EQHAMVKALSNAEVDDFDSPEGAKVQAFFADLDDDVHAKLDSLHLP--------------
2 Sutterella wadsworthensis Cas9 (modified) translation  ANILQTDETTGQKFLDEIWKKQIKGRETVASRCARIEYVRKSFGGGFNIAQNTAQYREVN

21 Staphylococcus aureus subsp. Aureus Cas9 translation  ------------GTHNLSLKAINLILDELWHTND------------NQIAIFN-------
26 Streptococcus thermophilus CRISPR1 Cas9 translation   -------SIFGKGNHNFSVKLMNELIPELYETSE------------EQMTILT-------
4 Treponema denticola Cas9 (modified) translation        -------FLETVTSEMPGFSEPVNIITAMRETQN------------NLMELLSSEFTFTE
5 Filifactor alocis Cas9 (modified) translation          -------FLKGISGSDVSTGETFDIITAMWETDN------------NIMQILSKKFTFMD
18 Neisseria cinerea Cas9 (modified) translation         -----------VQISLKALRRIVPLMEQGNRYDE------------ACTEIYG-------
24 Campylobacter lari Cas9 (modified) translation        -----------INLSFKALGMILPLMREGKRYDE------------ACEIANLK------
Streptococcus pyogenes Cas9 translation                  -------LINGIRDKQSGKTILDFLKSDGFANRN------------EMQLIHDDS----L
7 Lactobacillus johnsonii Cas9 (modified) translation    -------RLSKKLLAQLHDEHGQTIIEQLWDSQN------------NEMQIVTQAD----
23 Mycoplasma gallisepticum Cas9 (modified) translation  -------EKILAQTHSLSTIAMLLAITRWTNLDNDEDNQKNNDKGWNIEAIKNFDQKFLD
20 Parvibaculum lavamentivorans Cas9 (modified) translation -------LKLPTGWEPYSIPALNLFLAELEKGERFG-----ALVNGFDWEGWRRTNFPHR
1 Corynebacter diptheriae Cas9 (modified) translation    -----------VGRAAYSEDTLVRLTRRMLSDGVD-------------------------
2 Sutterella wadsworthensis Cas9 (modified) translation  KLPRNAQDKELLTIRDRVAETADFIAANLGLSDEQKRKFANPFSLAQFYTLIETEVSGFS

21 Staphylococcus aureus subsp. Aureus Cas9 translation  RLKLVPKKVDLSQQKEIPTTLVDDFILSPVVKRSFIQSIKVINAIIKKYG---LPNDIII
26 Streptococcus thermophilus CRISPR1 Cas9 translation   RLGKQKTTSSSNKTKYIDEKLLTEEIYNPVVAKSVRQAIKIVNAAIKEYG---DFDNIVI
4 Treponema denticola Cas9 (modified) translation        NIKKINSGFEDAEKQFSYDGLVKPLFLSPSVKKMLWQTLKLVKEIGHITQA--PPKKIFI
5 Filifactor alocis Cas9 (modified) translation          NVEDFNSGKVGKIDKITYDSTVKEMFLSPENKPAVWQTIQVAEEIKKVMGC--EPKKIFI
18 Neisseria cinerea Cas9 (modified) translation         ----DHYGKKNTEEKIYLPPIPADEIRNPVVLRALSQARKVINGVVRRYG---SPARIHI
24 Campylobacter lari Cas9 (modified) translation        ---PKTVDENKDFLPAFCDSIFAHELSNPVVNRAISEYRKVLNALLKKYG---KVHKIHL
Streptococcus pyogenes Cas9 translation                  TFKEDIQKAQVSGQGDSLHEHIANLAGSPAIKKGILQTVKVVDELVKVMGRH-KPENIVI
```

FIG. 19G

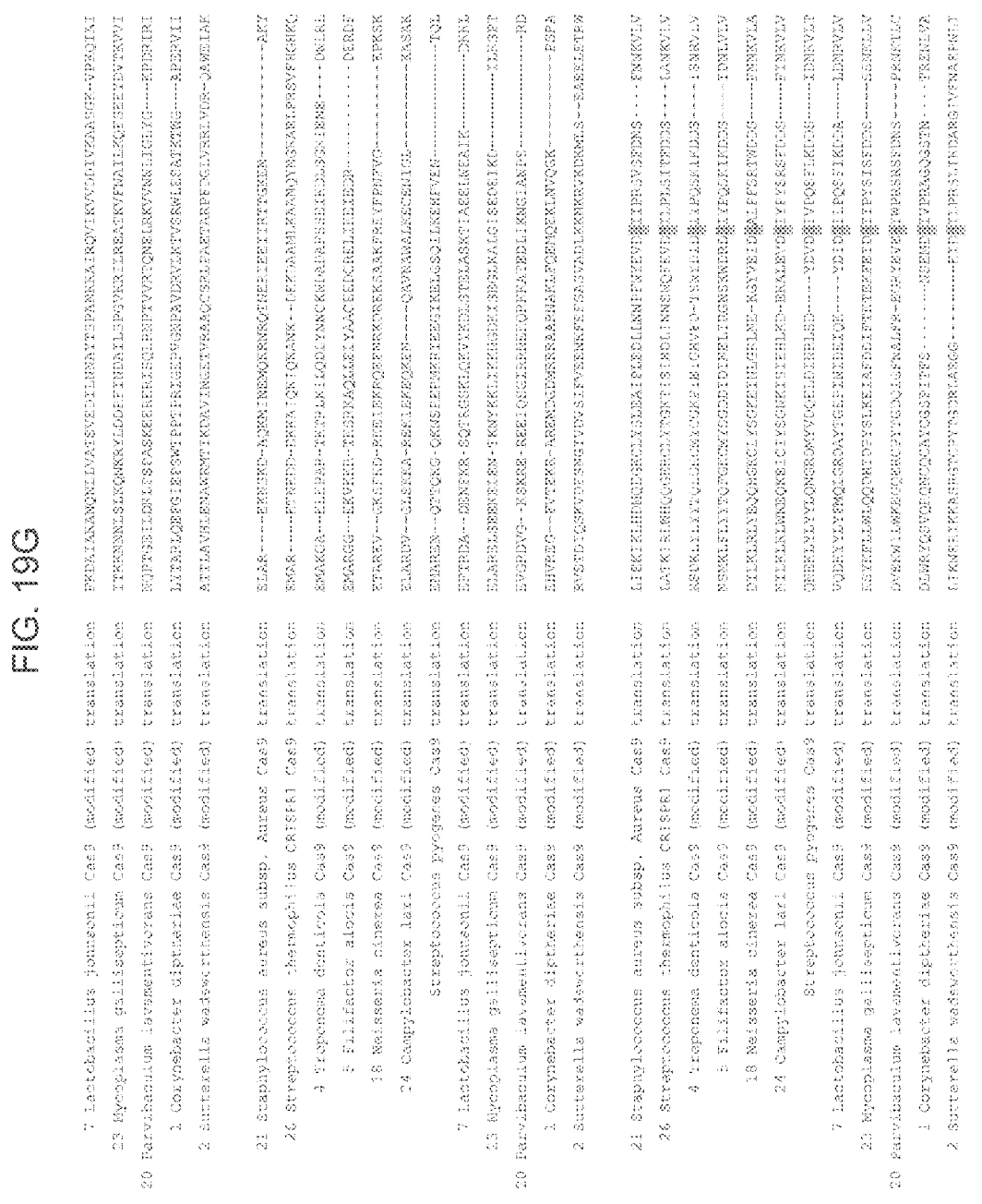

```
7 Lactobacillus johnsonii Cas9 (modified) translation          FKDAIAKANQNILVATSVEDILNNAYTSPANKKAIRQVIKVVDDIVKAASGK-VPKQIAI
23 Mycoplasma gallisepticum Cas9 (modified) translation        ITKKNNNLSLKQNKRYLDDFFINDAILSPGVKRILREATKVFNAILKQFSEEYDVTKVVI
20 Parvibaculum lavamentivorans Cas9 (modified) translation    NQPTGEILDKLFSPASKEERERISQLRNPTVVRTQNELRKVVNNLIGLYG----KPDRIRI
1 Corynebacter diptheriae Cas9 (modified) translation          LYTARLQEFGIEPSWTPPTPRIGEPVGNPAVDRVLKTVSRWLESATKTWG----APERVII
2 Sutterella wadsworthensis Cas9 (modified) translation        ATTLAVHLENAWRMTIKDAVINGETVRAAQCSRLPAETARPFDGLVRRLVDR-QAWEIAK

21 Staphylococcus aureus subsp. Aureus Cas9 translation        ELAR----EKNSKD-AQKMINEMQKRNRQTNERIEEIIRTTGKEN------------AKY
26 Streptococcus thermophilus CRISPR1 Cas9 translation        EMAR-----ETNEDD-EKKAIQKIQKANK--DEKDAAMLKAANQYNGKAELPHSVFHGHKQ
4 Treponema denticola Cas9 (modified) translation              EMAKGA--ELEPAR-TKTPLKILQDLYNNCKNDADAFSSEIKDLSGNIENE----DNLRL
5 Filifactor alocis Cas9 (modified) translation                EMARGG--EKVKKR-TKSRKAQLLEIYAACEEDCRELIKEIEDR------------DERDF
18 Neisseria cinerea Cas9 (modified) translation               ETAREV--GKSFKD-RKEIEKRQEENRKDREKSAAKFREYFPNFVG----------EPKSK
24 Campylobacter lari Cas9 (modified) translation              ELARDV--GLSKKA-REKIEKEQKEN----QAVNAWALKECENIGL----------KASAK
Streptococcus pyogenes Cas9 translation                        EMAREN--QTTQKG-QKNSRERMKRIEEGIKELGSQILKEHPVEN-----------------TQL
7 Lactobacillus johnsonii Cas9 (modified) translation          EFTRDA--DENFKR-SQTRGSKLQKVYKDLSTELASKTIAEELNEAIK-----------DKKL
23 Mycoplasma gallisepticum Cas9 (modified) translation        ELAREL.SEEKEIEN-TKNYKKLIKKNGDKISEGLKALGISEDEIKD-------------ILKSPT
20 Parvibaculum lavamentivorans Cas9 (modified) translation    EVGRDVG--KSKRE-REEIQSGIRRNEFQRKKATEDLIKNGIANPS-----------------RD
1 Corynebacter diptheriae Cas9 (modified) translation          EHVREG--FVTEKR-AREMDGDMRRRAARNAKLFQEMQEKLNVQGK-----------PSPA
2 Sutterella wadsworthensis Cas9 (modified) translation        RVSTDIQSKVDESNGIVDVSIFVEENKFEFSAGVADLKKNKRVKDKMLS--EAEKLETRW

21 Staphylococcus aureus subsp. Aureus Cas9 translation        LIEKIKLHDMQEGKCLYSLEAIPLEDLLNNPFNYEVDHIIPRSVSFDNS----FNNKVLV
26 Streptococcus thermophilus CRISPR1 Cas9 translation        LATKIRLWHQQGERCLYTGKTISIHDLINNSNQFEVDHILPLSITFDDS----LANKVLV
4 Treponema denticola Cas9 (modified) translation              RSDKLYLYYTQLGKCMYCGKPIEIGHVFD-TSNYDIDHIYPQSKIKDDS----ISNRVLV
5 Filifactor alocis Cas9 (modified) translation                NSMKLFLYYTQFGKCMYSGDDIDINELIRGNSKWDRDHIYPQSKIKDDS----IDNLVLV
18 Neisseria cinerea Cas9 (modified) translation               DILKLRLYEQQHGKCLYSGKEINLGRLNE-KGYVEIDHALPFSRTWDDS-----FNNKVLA
24 Campylobacter lari Cas9 (modified) translation              NILKLNLWKEQKEICIYSGNKISIEHLKD-EKALEVDHIYPYSRSFDDS------FINKVLV
Streptococcus pyogenes Cas9 translation                        QNEKLYLYYLQNGRDMYVDQELDINRLSD-----YDVDHIVPQSFLKDDS-----IDNKVLT
7 Lactobacillus johnsonii Cas9 (modified) translation          VQDKYYLYFMQLGRDAYTGEPINIDEIQK-----YDIDHILPQSFIKDDA-----LDNRVLV
23 Mycoplasma gallisepticum Cas9 (modified) translation        KSYKFLLWLQQDHIDPYSLKEIAFDDIFTKTEKFEIDHIIPYSISFDDS-----SSNKLLV
20 Parvibaculum lavamentivorans Cas9 (modified) translation    DVEKWILWKEGQERCPYTGDQIGFNALFR-EGRYEVEHIWPRSRSFDNS----PRNKTLC
1 Corynebacter diptheriae Cas9 (modified) translation          DLWRYQSVQEQNCQCAYCGSPITFS---------NSEMDHIVPRAGQGSTN----TRENLVA
2 Sutterella wadsworthensis Cas9 (modified) translation        LIKNERIKKASRGTCPYTGDRLAEGG----------EIDHILPRSLIKDARGIVFNAEPNLI
```

FIG. 19H

```
21 Staphylococcus aureus subsp. Aureus Cas9 translation       KQEENSKKGNRTPFQYLSSSDSKISYETFKKHILNLA-KGKGRISKTKKEYLLEERDINR
26 Streptococcus thermophilus CRISPR1 Cas9 translation       YATANQEKGQRTPYQALDSMDDAWSFRELKAFVR-----ESKTLSNKKKEYLLTEEDISK
4 Treponema denticola Cas9 (modified) translation            CSSCNKNKEDKYPLKSEIQSKQRGFWNFLQ---------RNNFISLEKLNRLTRATPISD
5 Filifactor alocis Cas9 (modified) translation             NKTYNAKKSNE-LLSEDIQKKVHSFWLSLL---------NKKLTTKSKYDRLTRKGDFTD
18 Neisseria cinerea Cas9 (modified) translation            LGSENQNKGNQTPYEYFNGKDNSREWQEFKAR------VETSRFPRSKKQRILLQK--FD
24 Campylobacter lari Cas9 (modified) translation           FTKENQEKLNKTPFEAFG--KNIEKWSKIQTL------AQN--LPYKKKNKILDEN--FK
Streptococcus pyogenes Cas9 translation                     RSDKNRGKSDNVPSEEVVKKMKNYWRQLLN----------AKLITQRKFDNLTKAERGGL
7 Lactobacillus johnsonii Cas9 (modified) translation        SRAVNNGKSDNVPVKLFGNEMAANLGMTIRKMWEEW--KNIGLISKTKYNNLLTDPDHIN
23 Mycoplasma gallisepticum Cas9 (modified) translation     LAESNQAKSNQTPYEFISSGNAGIKWEDYFAYCRKFKDGDSSLLDSTQRSKKPAKMMKTD
20 Parvibaculum lavamentivorans Cas9 (modified) translation RKDVNIEKGNRMPFEAFGHDEDRWSAIQIR---------LQGMVSAKGGTGMSPGKVKRF
1 Corynebacter diptheriae Cas9 (modified) translation        VCHRCNQSKGNTPFAIWAKNTSIEGVSVKEAVERTRHRVTIDTGMRSTDPKKFTKAVVERF
2 Sutterella wadsworthensis Cas9 (modified) translation      YASSRGNQLKKNQRYSLSDLKANYRNEIFKTSNIAAITAEIEDVVTKLQQTHRLKFFDLL

21 Staphylococcus aureus subsp. Aureus Cas9 translation       FSVQKD--FINRNLVDTRYATRGLMNLLRSYFRVNNLD----------------------
26 Streptococcus thermophilus CRISPR1 Cas9 translation       FDVRKK--FIERNLVDTRYASRVVLNALQEHFRAHKID----------------------
4 Treponema denticola Cas9 (modified) translation            DETAK---FIARQLVETRQATKVAAKVLEKMFPETKIV----------------------
5 Filifactor alocis Cas9 (modified) translation             EELSG---FIARQLVETRQSTKAIADIFKQIY-SSEVV----------------------
18 Neisseria cinerea Cas9 (modified) translation            E---DG--FKERNLNDTRYINRFLCQFVADHMLLTGKG----------------------
24 Campylobacter lari Cas9 (modified) translation           DKQQED--FISRNLNDTRYIATLIAKYTKEYLNFLLLSENENANL---------------
Streptococcus pyogenes Cas9 translation                     SELDKAG-FIKRQLVETRQITKHVAQILDSRMNTKYDENDK-------------------
7 Lactobacillus johnsonii Cas9 (modified) translation        KYKSAG--FIERQLVETSQIIKLVSTILQSRYPNTEII----------------------
23 Mycoplasma gallisepticum Cas9 (modified) translation     TSSKYDIGFLARNLNDTRYATIVFRDALEDYANNHLVEDKP-------------------
20 Parvibaculum lavamentivorans Cas9 (modified) translation LAKTMPEDFAARQLNDTRYAAKQILAQLKRLWPDMGPEAP--------------------
1 Corynebacter diptheriae Cas9 (modified) translation        QRATMDEEIDARSMESVAWMANELRSRVAQHFASHGTT----------------------
2 Sutterella wadsworthensis Cas9 (modified) translation      NEHEQDCVPHALFLDDGSEARDAVLELLATQRRTRVNGTQIWMIKNLANKIREELQNWCK

21 Staphylococcus aureus subsp. Aureus Cas9 translation       ---------VKVKSINGGFTSFLRR---KWKFKK------ERNKGYKHHAFDAIIIANAD
26 Streptococcus thermophilus CRISPR1 Cas9 translation       ---------TKVSVVRGQFTSQLRR---HWGIEK------TRDT-YHHHAVDALIIAASS
4 Treponema denticola Cas9 (modified) translation            ---------YSKAETVSMFRNK-------FDIVK------CREINDFHHAHDAYLNIVVG
5 Filifactor alocis Cas9 (modified) translation             ---------YVKSSLVSDFRKKP------LNYLK------SRRVNDYHHAKDAYLNIVVG
18 Neisseria cinerea Cas9 (modified) translation            --------KRRVFASHGQITNLLRG---FWGLRK------VRAENDRHHALDAVVVACST
24 Campylobacter lari Cas9 (modified) translation           -KSGEKGSKIHVQTISGMLTSVLRH---TWGFDK------KDRNNHLHHALDAIIVAYST
```

FIG. 19I

```
Streptococcus pyogenes Cas9 translation                      -------LIREVKVITLKSKLVSDFRK---DFQFYK------VREINNYHHAHDAYLNAVVG
7 Lactobacillus johnsonii Cas9 (modified) translation        ----------------TVKAKYNHYLRE---KFDLYK------SREVNDYHHAIDAYLSAICG
23 Mycoplasma gallisepticum Cas9 (modified) translation      ----------MFKVVCINGSVTSFLRKNFDDSSYAK------KDRDKNIHHAVDASIISIFS
20 Parvibaculum lavamentivorans Cas9 (modified) translation  -----------VKVEAVTGQVTAQLRKLWTLNNILADDG--EKTRADHRHHAIDALTVACTH
1 Corynebacter diptheriae Cas9 (modified) translation        -------------VRVYRGSLTAEARRASGISGKLKFFDGVGKSRLDRRHHAIDAAVIAFTS
2 Sutterella wadsworthensis Cas9 (modified) translation      TTNNRLHFQAAATNVSDAKNLRLKLAQNQFDFEK------FDIQFIASHSIDALCSFAVG

21 Staphylococcus aureus subsp. Aureus Cas9 translation      FIFKEWKKLDKAKKVM--------------------ENQMFEEKQAESMPEIET-EQEYKE
26 Streptococcus thermophilus CRISPR1 Cas9 translation      QLNLWKKQKNTLVSYS--------------------EDQLLDIETGELISDDEYKESVFKA
4 Treponema denticola Cas9 (modified) translation           NVYNTKFTNNPWNFIK--------------------EKRDNPKIADTYNYYKVFDYDVKRN
5 Filifactor alocis Cas9 (modified) translation             NVYNKKFTSNPIQWMK--------------------KNRD-----TNYSLNKVFEHDVVIN
18 Neisseria cinerea Cas9 (modified) translation            IAMQQKIT-RFVRYKE--------------------MNAFDGKTIDKETGEVLHQKAHFPQ
24 Campylobacter lari Cas9 (modified) translation           NSIIKAFS-DFKKNQE--------------------LLKAR---------------------
Streptococcus pyogenes Cas9 translation                      TALIKKYPKLESEFVYGDYK-----VYDVRKMIAKSEQEIGKATAKYFFYSNIMNFFKTE
7 Lactobacillus johnsonii Cas9 (modified) translation        NLLYQNYPNLRPFFVYG-------------------QYKKFSSDPDKEKAIFNKTRKFSFI
23 Mycoplasma gallisepticum Cas9 (modified) translation      NETKTLFNQLTQFADYKLFK-----NTDGSWKKIDPKTGVVTEVTDENWKQIRVRNQVSE
20 Parvibaculum lavamentivorans Cas9 (modified) translation  PGMTNKLSRYWQLRDD---------------------------------------------
1 Corynebacter diptheriae Cas9 (modified) translation        DYVAETLAVRSNLKQSQ-------------------AHRQEAPQWREFTGKDAEHRAAWRV
2 Sutterella wadsworthensis Cas9 (modified) translation      SADAERDQNGFDYLDGKTVLGLYPQSCEVIHLQAKPQEEKSHFDSVAIFKEGIYAEQFLP

21 Staphylococcus aureus subsp. Aureus Cas9 translation      IFITPHQIKHIKDFKD-YKYSHRVDKKPNRELINDTLYSTR-----KDDKGNTLIVNNLN
26 Streptococcus thermophilus CRISPR1 Cas9 translation      PYQHFVDTLKSKEFEDSILFSYQVDSKFNRKISDATIYATRQAKVGKDKADETYVLGKIK
4 Treponema denticola Cas9 (modified) translation           NIIAWEK---------------GKTIITVKDMLKRNTPIYTRQAACKKGELFNQTIMKKGL
5 Filifactor alocis Cas9 (modified) translation             GEVIWEKCTYHEDTNT---YDGGTLDRIRKIVERDNILYTEYAYCEKGELFNATIQNKNG
18 Neisseria cinerea Cas9 (modified) translation            PWEFFAQEVMIRVFGK--PDGKPEFEEADTPEKLRTLLAEKLSSRPEAVHKYVTPLFISR
24 Campylobacter lari Cas9 (modified) translation           ----FYAKELTSDNY--------------------KHQVKFFEPFKSFREKILSKIDEIFVSK
Streptococcus pyogenes Cas9 translation                      ITLANGEIRKRPLIETNGETGEIVWDKGRDFATVRKVLSMPQVNIVKKTEVQTGGFSKES
7 Lactobacillus johnsonii Cas9 (modified) translation        SQLLNNKSENSKEIAK-----------KLKRAYQFKYMLVSRETETRDQEMFKMTVYPRFS
23 Mycoplasma gallisepticum Cas9 (modified) translation      IANVIEKYIQDSNIERKARYSRKIENKTNISLFNDTVYSAKKVGYEDQIKRKNLKTLDIH
20 Parvibaculum lavamentivorans Cas9 (modified) translation  ----------------------------------PRAEKPALTPPWDTIRADAEKAVSEIVVSH
1 Corynebacter diptheriae Cas9 (modified) translation        WCQKMEKLSALLTEDLR-----------DDRVVVMSNVRLRLGNGSAHKETIGKLSKVKLSS
2 Sutterella wadsworthensis Cas9 (modified) translation      IFTLNEKIWIGYETLNAKGERCGAIEVSGKQPKELLEMLAPFFNKPVGDLSAHATYRILK
```

FIG. 19J

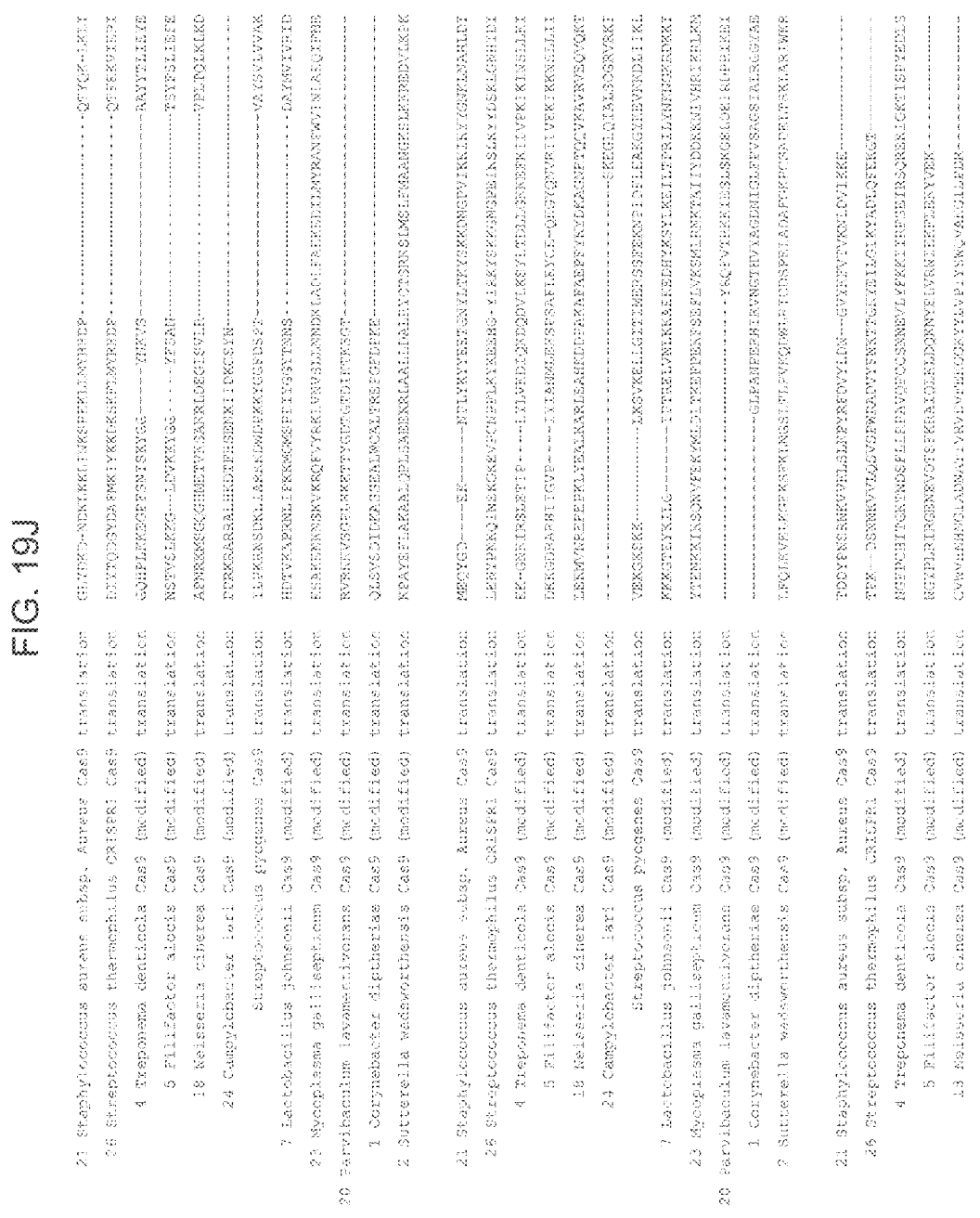

```
21 Staphylococcus aureus subsp. Aureus Cas9 translation      GLYDKD-NDKLKKLINKSPEKLLMYHHDP---------------------QTYQK-LKLI
26 Streptococcus thermophilus CRISPR1 Cas9 translation       DIYTQDGYDAFMKIYKKDKSKFLMYRHDP---------------------QTFEKVIEPI
4 Treponema denticola Cas9 (modified) translation            GQHPLKKEGPFSNISKYGG-----YHKVS---------------------RAYYTLLIYE
5 Filifactor alocis Cas9 (modified) translation              NSTVSLKEG---LDVKKYGG-----YFSAN---------------------TSYFSLIEFE
18 Neisseria cinerea Cas9 (modified) translation             APNRKMSGQGHMETVKSAKRLDEGISVLR---------------------VPLTQLKLKD
24 Campylobacter lari Cas9 (modified) translation            PFRKRARRALHKDTFHSENKIIDKCSYN--------------------------------
Streptococcus pyogenes Cas9 translation                      ILPKKNSDKLIARKKDWDPKKYGGFDSPT---------------------VAYSVLVVAK
7 Lactobacillus johnsonii Cas9 (modified) translation        HDTVKAPRNLIPKKMGMSPIIYGGYTNNS---------------------DAYMVIVRID
23 Mycoplasma gallisepticum Cas9 (modified) translation      ESAKENKNSKVKRQFVYRKLVNVSLLNNDKLADLFAEKEDILMYRANFWVINLAEQIPNE
20 Parvibaculum lavamentivorans Cas9 (modified) translation  RVRKKVSGPLHKETTYGDTGTDIFTKSGT-------------------------------
1 Corynebacter diptheriae Cas9 (modified) translation        QLSVSDIDKASSEALWCALTREPGFDPKE-------------------------------
2 Sutterella wadsworthensis Cas9 (modified) translation      KPAYEFLAKAALQPLSAEEKRLAALLDALRYCTSRRSLMSLFMAANGKSLKKREDVLKPK

21 Staphylococcus aureus subsp. Aureus Cas9 translation      MEQYGD----EK------NPLYKYYEETGNYLTKYSKKDNGPVIKKIKYYGNKLNAHLDI
26 Streptococcus thermophilus CRISPR1 Cas9 translation       LENYPNKQINEKGKEVPCNPFLKYKEERG-YIRKYSKKGNGPEIKSLKYYDSKLGNHIDI
4 Treponema denticola Cas9 (modified) translation            EK-GNKIRSLETIP----LYLVKDIQKDQDVLKSYLTDLLGKKEFKIIVPKIKINSLLKI
5 Filifactor alocis Cas9 (modified) translation              DKKGDRAPHIIGVP----IYIANMLEHSPSAFLEYCE-QKGYQNVRIIVEKIKKNSLLII
18 Neisseria cinerea Cas9 (modified) translation             LEKMVNREFEPKLYEALKARLEAHKDDPAKAFAEPFYKYDKAGNRTQQVKAVRVEQVQKT
24 Campylobacter lari Cas9 (modified) translation            -------------------------------------------SKEGLQIALSCGRVRKI
Streptococcus pyogenes Cas9 translation                      VEKGKSKK----------LKSVKELLGITIMERSSFEKNPIDFLEAKGYKEVKKDLIIKL
7 Lactobacillus johnsonii Cas9 (modified) translation        KKKGTEYKILG-------IPTRELVNLKKAEKEDHYKSYLKEILTPRILYNKNGKRDKKI
23 Mycoplasma gallisepticum Cas9 (modified) translation      YTENKKIKSQNVPEKYMLDLTKEFPEKFSEFLVKSMLRNKTAIIYDDKKNIVHRIKRLKM
20 Parvibaculum lavamentivorans Cas9 (modified) translation  -----------------------------YKQFVTRKKIESLSKGELDEIRDPRIKEI
1 Corynebacter diptheriae Cas9 (modified) translation        -------------------GLPANPERHIRVNGTHVYAGDNIGLPPVSAGSIALRGGYAE
2 Sutterella wadsworthensis Cas9 (modified) translation      LFQLKVELKGFKSFKLNGSLFLPVKQDWLRICDSPELADAFCKPCSADELTSKLARIWKR

21 Staphylococcus aureus subsp. Aureus Cas9 translation      TDDYPNSRNKVVKLSLKPYRFDVYLDN---GVYKFVTVKNLDVIKKE-------------
26 Streptococcus thermophilus CRISPR1 Cas9 translation       TPK--DSNNKVVLQSVSPWRADVYFNKTTGKYEILGLKYADLQFEKGT------------
4 Treponema denticola Cas9 (modified) translation            NGFPCHITGKYNDSPLLRPAVQFCCSNNEVLYFKKIIRFSEIRSQREKIGKTISPYEDLS
5 Filifactor alocis Cas9 (modified) translation              NGYPLRIRGENEVDTSFKRAIQLKLDQKNYELVRNIEKPLEKYVEK--------------
18 Neisseria cinerea Cas9 (modified) translation             CVWVHNHNGIADNATIVRVDVFEKGGKYYLVPIYSWQVAKGILPDR--------------
```

FIG. 19K

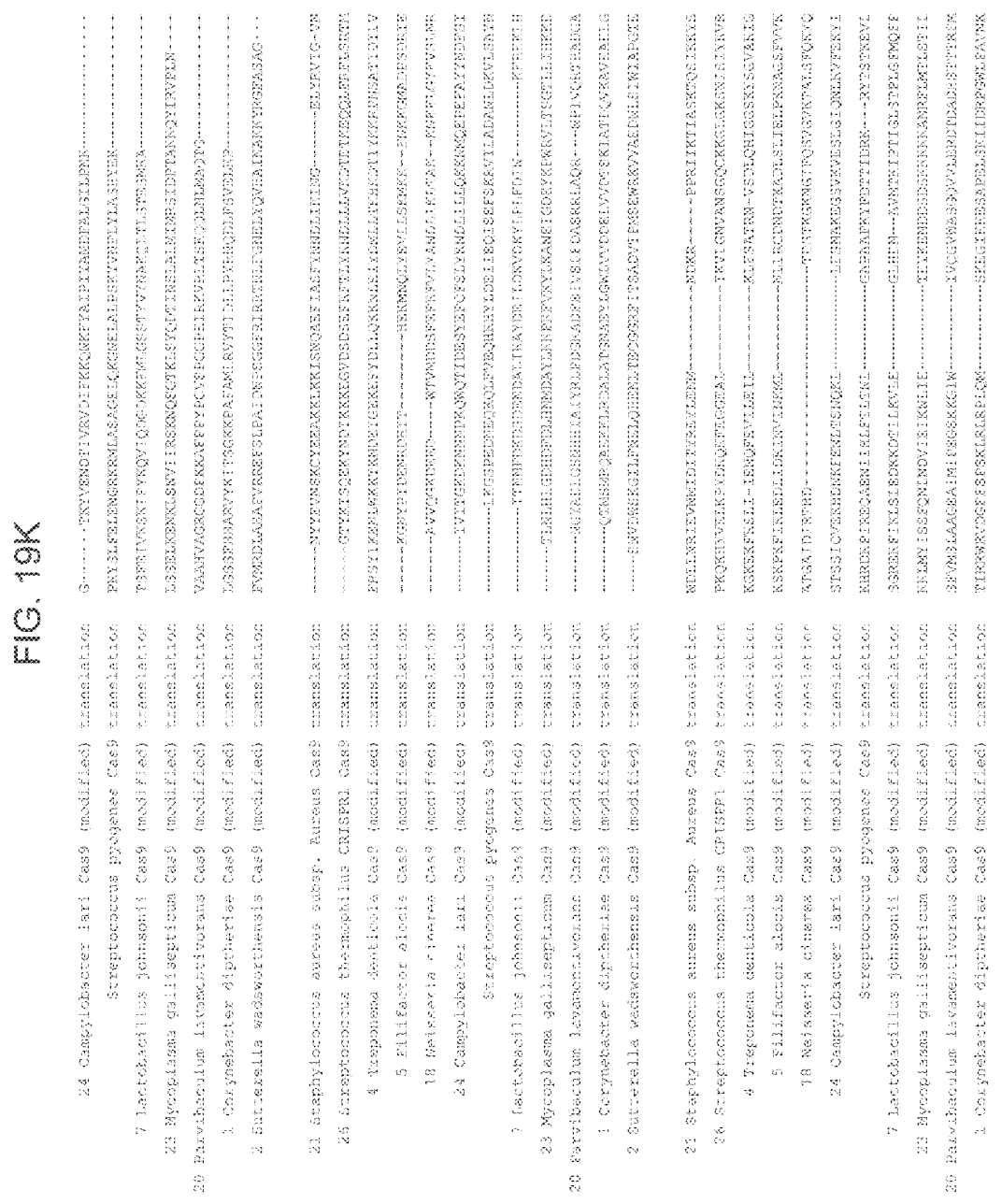

```
24 Campylobacter lari Cas9 (modified) translation          G------TKYVENDTIVRVDIFKKQNKFYAIPIYAMDFALGILPNK--------------
Streptococcus pyogenes Cas9 translation                    PKYSLFELENGRKRMLASAGELQKGNELALPSKYVNFLYLASHYEK--------------
7 Lactobacillus johnsonii Cas9 (modified) translation      TSFEIVKSNIFYKQVIQDGDKKFMLGSSTYVYNAKQLTLSTEGMKA--------------
23 Mycoplasma gallisepticum Cas9 (modified) translation    LSSELKENKLSNVIIRSKNQSGTKLSYQDTINSLALMIMRSIDPTANKQYIRVPLN----
20 Parvibaculum lavamentivorans Cas9 (modified) translation VAAHVAGRCGDFKKAFPPYPCVSPCGPEIRKVRLTSKQQLNLMAQTG-------------
1 Corynebacter diptheriae Cas9 (modified) translation      LGSSFHHARVYKITSGKKPAFAMLRVYTIDLLPYRNQDLFSVELKP--------------
2 Sutterella wadsworthensis Cas9 (modified) translation    FVMRDLAHAFVRREFSLPAIDNPSGGFRIRRTHLFGNELYQVHAINAKKYRGFASAG---

21 Staphylococcus aureus subsp. Aureus Cas9 translation    -----NYYEVNSKCYEEAKKLKKISNQAEFIASFYNNDLIKING------ELYRVIG-VN
26 Streptococcus thermophilus CRISPR1 Cas9 translation    -----GTYKISQEKYNDIKKKEGVDSDSEFKFTLYKNDLLLVKDTETKEQQLFRFLSRTM
4 Treponema denticola Cas9 (modified) translation         EPSYIKENLWKKTKNDEIGEKEFYDLLQKKNLEIYDMLLTKHKDTIYKKRENSATIDILV
5 Filifactor alocis Cas9 (modified) translation          -----KGNYPIDENRDHIT--------HEKMNQLYEVLLSKMKK--ENKKGMADFSDRIE
18 Neisseria cinerea Cas9 (modified) translation         ------AVVQGKDEED----WTVMDDSFEFKFVLYANDLIKLTAK--KNEELGYFVSLNR
24 Campylobacter lari Cas9 (modified) translation        ------IVITGKDKNNNPKQWQTIDESYEFCFSLYKNDLILLQKKNMQEPEFAYYNDFSI
Streptococcus pyogenes Cas9 translation                  ---------LKGSPEDNEQKQLFVEQHKHYLDEIIEQISEFSKRVILADANLDKVLSAYN
7 Lactobacillus johnsonii Cas9 (modified) translation    ---------TTNNFDKDSDENDALIKAYDEILDKVDKYLPLFDIN--------KFREKLH
23 Mycoplasma gallisepticum Cas9 (modified) translation  -----TLNLHLGDHDFDLHNMDAYLKKPKFVKYLKANEIGDEYKPWRVLTSGTLLIHKKD
20 Parvibaculum lavamentivorans Cas9 (modified) translation ------NGKADLGSNHHIAIYRLPDGKADFEIVSLFDASRRLAQR---NPIVQRTHADGA
1 Corynebacter diptheriae Cas9 (modified) translation    -------QTMSMRQAEKKLRDALATGNAEYLGWLVVDDELVVDTSKIATDQVKAVEAELG
2 Sutterella wadsworthensis Cas9 (modified) translation  ----SNVDKSKGILFNELQHENLTEGGGRFITSADVTPMSEWRKVVAEDNLSIWIAPGTE

21 Staphylococcus aureus subsp. Aureus Cas9 translation    NDLLNRIEVNMIDITYREYLENM---------NDKR-----PPRIIKTIASKTQSIKKYS
26 Streptococcus thermophilus CRISPR1 Cas9 translation    PKQKHYVELKPYDRQKFEGGEAL---------TKVIGNVANSGQCKKGLGKSNISIYKVR
4 Treponema denticola Cas9 (modified) translation         KGKEKFKSLI-IENQFEVILEIL---------KLFSATRN-VSDLQHIGGSKYSGVAKIG
5 Filifactor alocis Cas9 (modified) translation          KSKPKFIKLEDLIDKINVINKML---------NLIRCDNDTKADLSLIELPKNAGSFVVK
18 Neisseria cinerea Cas9 (modified) translation         ATGAIDIRTHD-----------------------TDSTKGKNGIFQSVGVKTALSFQKYQ
24 Campylobacter lari Cas9 (modified) translation        STSSICVEKHDNKFENLTSNQKL----------LISNAKEGSVKVESLGIQNLKVFEKYI
Streptococcus pyogenes Cas9 translation                  KHRDKPIREQAENIIHLFTLTNL---------GAPAAFKYFDTTIDRK---RYTSTKEVL
7 Lactobacillus johnsonii Cas9 (modified) translation    SGREKFIKLSLEDKKDTILKVLE---------GLHDN---AVNTKIPTIGLSTPLGFMQFF
23 Mycoplasma gallisepticum Cas9 (modified) translation  KNLMYISSFQNINDVIEIKNLIE---------TEYKENDDSDSKKKKANRFLMTLSTII
20 Parvibaculum lavamentivorans Cas9 (modified) translation SEVMSLAAGEAIMIPEGSKKGIW---------IVQGVEASGQVVLERDTDADHSTTTRFM
1 Corynebacter diptheriae Cas9 (modified) translation    TIKKWRVDGFFSPSKLRLRPLQM---------SKEGIKKESAPELSKIIDRPGWLPAVNK
```

FIG. 19L

```
2 Sutterella wadsworthensis Cas9 (modified) translation   GRPYVRVETTFIQASHWFEQSVENWAITSPLSLPASFKVDKPAEFQKAVGTELSELLGQP

21 Staphylococcus aureus subsp. Aureus Cas9 translation   TDILGNLYEVKSKKHPQIIKKG-----------------
26 Streptococcus thermophilus CRISPR1 Cas9 translation    TDVLGNQHIIKNEGDKPKLDF------------------
4 Treponema denticola Cas9 (modified) translation         NKISSLONCILIYQSITGIFEKRIDLLNV----------
5 Filifactor alocis Cas9 (modified) translation           KNTIGKSKIILVNQSVTGLYENRREL-------------
13 Neisseria cinerea Cas9 (modified) translation          IDELGKEIRP----------CRLKKRPPVR---------
24 Campylobacter lari Cas9 (modified) translation         ITPLGDKIKADFQPRENISLKTSKKYGLR----------
Streptococcus pyogenes Cas9 translation                   DATLIHQSITGLYETRIDLSQLGGD--------------
7 Lactobacillus johnsonii Cas9 (modified) translation     NGVILSENAKLIYQSPTGLFKKSVKISDL----------
23 Mycoplasma gallisepticum Cas9 (modified) translation   NDYILLDAKDNFDILGLSKNRIDEILNSKLGLDKIVK--
20 Parvibaculum lavamentivorans Cas9 (modified) translation  FNPILKDDAKKVSIDPIGRVRPSND--------------
1 Corynebacter diptheriae Cas9 (modified) translation     LFSDGNVTVVRRDSLGRVRLESTAHLPVTWKVQ------
2 Sutterella wadsworthensis Cas9 (modified) translation   RSSEIFIENVGNAKHIRFWYIVVSSNKKMNESYNNVSKS
```

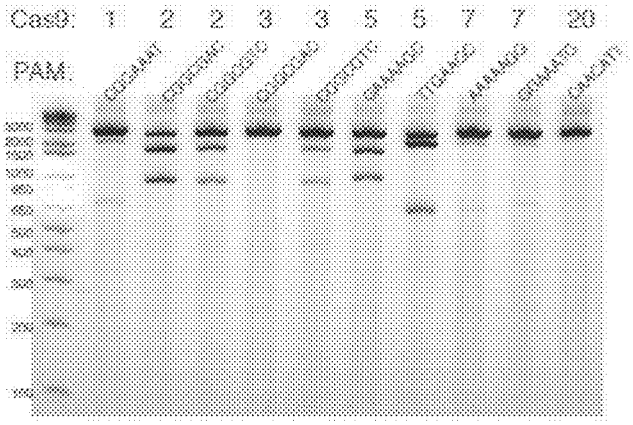

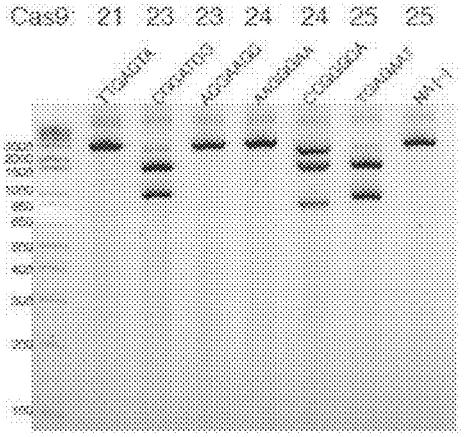

| Cas9 # | Species | Putative PAM | pUC19 target |
|---|---|---|---|
| 1 | Corynebacter_diphtheriae | | AAAAGGGAATAAGGGCGACA |
| 2 | Sutterella_wadsworthensis | NGGNNNN | CATTCTGAGAATAGTGTATG |
| 2 | Sutterella_wadsworthensis | | GCGACCGAGTTGCTCTTGCC |
| 3 | Legionella_pneumophila_Paris | NGGNNNN | CATTCTGAGAATAGTGTATG |
| 3 | Legionella_pneumophila_Paris | | GCGACCGAGTTGCTCTTGCC |
| 5 | Filifactor_alocis | NNNAAGC | TTGAGTACTCACCAGTCACA |
| 5 | Filifactor_alocis | | CTCTTCCTTTTTCAATATTA |
| 7 | Lactobacillus_johnsonii | NNAAAAN | TAAATGCTTCAATAATATTG |
| 7 | Lactobacillus_johnsonii | | AAAGGGAATAAGGGCGACAC |
| 20 | Parvibaculum_lavamentivorans | NNNCATN | AAAGGAAGAGTATGAGTATT |
| 21 | Staphylococcus aureus subsp. Aureus | | CTATTCTCAGAATGACTTGG |
| 23 | Mycoplasma gallisepticum str. F | NNGAAgg | AGTCACAGAAAAGCATCTTA |
| 23 | Mycoplasma gallisepticum str. F | | GTTTCTGGGTGAGCAAAAAC |
| 24 | Campylobacter lari CF89-12 | NNGGGNA | GAAGGCAAAATGCCGCAAAA |
| 24 | Campylobacter lari CF89-12 | | GGTATTATCCCGTATTGACG |
| 25 | SpCas9 | | [illegible] |
| 25 | SpCas9 | | |

FIG. 21

ENGINEERING AND OPTIMIZATION OF IMPROVED SYSTEMS, METHODS AND ENZYME COMPOSITIONS FOR SEQUENCE MANIPULATION

RELATED APPLICATIONS AND INCORPORATION BY REFERENCE

This application is a continuation of U.S. application Ser. No. 14/104,977 filed Dec. 12, 2013 and which claims priority to U.S. provisional patent application 61/836,101 entitled ENGINEERING AND OPTIMIZATION OF IMPROVED SYSTEMS, METHODS AND ENZYME COMPOSITIONS FOR SEQUENCE MANIPULATION filed on Jun. 17, 2013. This application also claims priority to U.S. provisional patent applications 61/758,468; 61/769,046; 61/802,174; 61/806,375; 61/814,263; 61/819,803 and 61/828,130 each entitled ENGINEERING AND OPTIMIZATION OF SYSTEMS, METHODS AND COMPOSITIONS FOR SEQUENCE MANIPULATION, filed on Jan. 30, 2013; Feb. 25, 2013; Mar. 15, 2013; Mar. 28, 2013; Apr. 20, 2013; May 6, 2013 and May 28, 2013, respectively. This application also claims priority to U.S. provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively. Priority is also claimed to U.S. provisional patent applications 61/791,409 and 61/835,931 filed on Mar. 15, 2013 and Jun. 17, 2013 respectively.

Reference is also made to U.S. provisional patent applications 61/836,127, 61/835,936, 61/836,080, 61/836,123, and 61/835,973 each filed Jun. 17, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under the NIH Pioneer Award (1DP1MH100706) awarded by the National Institutes of Health. The government has certain rights in the invention.

FIELD OF THE INVENTION

The present invention generally relates to the engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

SEQUENCE LISTING

The instant application contains a Sequence Listing which has been submitted electronically in ASCII format and is hereby incorporated by reference in its entirety. Said ASCII copy, created on Feb. 24, 2014, is named 44790.00.2042_SL.txt and is 476,273 bytes in size.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

Accordingly, there exists a pressing need for alternative and robust systems and techniques for sequence targeting with a wide array of applications. Aspects of this invention address this need and provide related advantages. An exemplary CRISPR complex comprises a CRISPR enzyme complexed with a guide sequence hybridized to a target sequence within the target polynucleotide, wherein the CRISPR enzyme is a Cas ortholog, e.g. a Cas9 ortholog, of a genus which includes but is not limited to Corynebacter, Sutterella, *Legionella, Treponemna, Filifactor, Eubacterium, Streptococcus, Lactobacillus, Mycoplasma, Bacteroides, Flaviivola, Flavobacterium, Sphaerochaeta, Azospirillumn, Gluconacetobacter, Neisseria, Roseburia, Parvibaculum, Staphylococcus, Nitratifractor, Mycoplasma* and *Campylobacter*. The guide sequence is linked to a tracr mate sequence, which in turn hybridizes to a tracr sequence.

In one aspect, the invention provides methods for using one or more elements of a CRISPR system. The CRISPR complex of the invention provides an effective means for modifying a target polynucleotide. The CRISPR complex of the invention has a wide variety of utilities including modifying (e.g., deleting, inserting, translocating, inactivating, activating, repressing, altering methylation, transferring specific moieties) a target polynucleotide in a multiplicity of cell types. As such the CRISPR complex of the invention has a broad spectrum of applications in, e.g., gene or genome editing, gene regulation, gene therapy, drug discovery, drug screening, disease diagnosis, and prognosis. In preferred aspects of the invention, the CRISPR complex comprises a Cas enzyme, preferably a Cas9 ortholog, of a genus which includes but is not limited to *Corynebacter, Sutterella, Legionella. Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter.*

Aspects of the invention relate to CRISPR enzymes having optimized function. With regard to the CRISPR enzyme being a Cas enzyme, preferred embodiments of the invention relate to Cas9 orthologs having improved target specificity in a CRISPR-Cas9 system. This may be accomplished by approaches that include but are not limited to designing and preparing guide RNAs having optimal activity, selecting Cas9 enzymes of a specific length, truncating the Cas9 enzyme making it smaller in length than the corresponding wild-type Cas9 enzyme by truncating the nucleic acid molecules coding therefor and generating chimeric Cas9 enzymes wherein different parts of the enzyme are swapped or exchanged between different orthologs to arrive at chimeric enzymes having tailored specificity. Aspects of the invention also relate to methods of improving the target specificity of a Cas9 ortholog enzyme or of designing a CRISPR-Cas9 system comprising designing or preparing guide RNAs having optimal activity and/or selecting or preparing a Cas9 ortholog enzyme having a smaller size or length than the corresponding wild-type Cas9 whereby packaging a nucleic acid coding therefor into a delivery vector is advanced as there is less coding sequence therefor in the delivery vector than for the corresponding wild-type Cas9 and/or generating chimeric Cas9 enzymes.

Also provided are uses of the present sequences, vectors, enzymes or systems, in medicine. Also provided are the same for use in gene or genome editing. Also provided is use of the same in the manufacture of a medicament for gene or genome editing, for instance treatment by gene or genome editing. Also provided are the present sequences, vectors, enzymes or systems for use in therapy.

In an additional aspect of the invention, a CRISPR enzyme, e.g. a Cas9 enzyme may comprise one or more mutations and may be used as a generic DNA binding protein with or without fusion to or being operably linked to a functional domain. The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains. Preferred examples of suitable mutations are the catalytic residue(s) in the N-term RuvC I domain of Cas9 or the catalytic residue(s) in the internal HNH domain. In some embodiments, the Cas9 is (or is derived from) the *Streptococcus pyogenes* Cas9 (SpCas9). In such embodiments, preferred mutations are at any or all of positions 10, 762, 840, 854, 863 and/or 986 of SpCas9 or corresponding positions in other Cas9 orthologs with reference to the position numbering of SpCas9 (which may be ascertained for instance by standard sequence comparison tools, e.g. ClustalW or MegAlign by Lasergene 10 suite). In particular, any or all of the following mutations are preferred in SpCas9: D10A, E762A, H840A, N854A, N863A and/or D986A; as well as conservative substitution for any of the replacement amino acids is also envisaged. The same mutations (or conservative substitutions of these mutations) at corresponding positions with reference to the position numbering of SpCas9 in other Cas9 orthologs are also preferred. Particularly preferred are D10 and H840 in SpCas9. However, in other Cas9s, residues corresponding to SpCas9 D10 and H840 are also preferred. These are advantageous as when singly mutated they provide nickase activity and when both mutations are present the Cas9 is converted into a catalytically null mutant which is useful for generic DNA binding. Further mutations have been identified and characterized. Other aspects of the invention relate to the mutated Cas 9 enzyme being fused to or operably linked to domains which include but are not limited to a transcriptional activator, transcriptional repressor, a recombinase, a transposase, a histone remodeler, a DNA methyltransferase, a cryptochrome, a light inducible/controllable domain or a chemically inducible/controllable domain.

A further aspect of the invention provides for chimeric Cas9 proteins and methods of generating chimeric Cas9 proteins. Chimeric Cas9 proteins are proteins that comprise fragments that originate from different Cas9 orthologs. For instance, the N-terminal of a first Cas9 ortholog may be fused with the C-terminal of a second Cas9 ortholog to generate a resultant Cas9 chimeric protein. These chimeric Cas9 proteins may have a higher specificity or a higher efficiency than the original specificity or efficiency of either of the individual Cas9 enzymes from which the chimeric protein was generated. These chimeric proteins may also comprise one or more mutations or may be linked to one or more functional domains. Therefore, aspects of the invention relate to a chimeric Cas enzyme wherein the enzyme comprises one or more fragments from a first Cas ortholog and one or more fragments from a second Cas ortholog. In a embodiment of the invention the one or more fragments of the first or second Cas ortholog are from the C- or N-terminal of the first or second Cas ortholog. In a further embodiment the first or second Cas ortholog is selected from a genus belonging to the group consisting of *Corynebacter, Sutterella, Legionella, Treponenuz, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter.*

In a further embodiment, the invention provides for methods to generate mutant components of the CRISPR complex comprising a Cas enzyme, e.g. Cas9 ortholog. The mutant components may include but are not limited to mutant tracrRNA and tracr mate sequences or mutant chimeric guide sequences that allow for enhancing performance of these RNAs in cells. Use of the present composition or the enzyme in the preparation of a medicament for modification of a target sequence is also provided.

The invention in yet a further aspect provides compositions and methods related to a non-naturally occurring or engineered composition comprising:

A)-I. a CRISPR-Cas system chimeric RNA (chiRNA) polynucleotide sequence, wherein the polynucleotide sequence comprises:

(a) a guide sequence capable of hybridizing to a target sequence in a eukaryotic cell, (b) a tracr mate sequence, and (c) a tracr sequence, and II. a polynucleotide sequence encoding a CRISPR enzyme comprising at least one or more nuclear localization sequences, wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence and the polynucleotide sequence encoding a CRISPR enzyme is DNA or RNA, or (B) I. polynucleotides comprising:

(a) a guide sequence capable of hybridizing to a target sequence in a prokaryotic cell, and (b) at least one or more tracr mate sequences, II. a polynucleotide sequence encoding a CRISPR enzyme, and III. a polynucleotide sequence comprising a tracr sequence, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, and the polynucleotide sequence encoding a CRISPR enzyme is DNA or RNA, and wherein the CRISPR enzyme is a Cas9 ortholog of a genus belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter.*

The invention in yet a further aspect provides: (A) A non-naturally occurring or engineered composition comprising a vector system comprising one or more vectors comprising: I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme is a Cas9 ortholog of a genus belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter* or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, wherein the CRISPR enzyme is a Cas9 ortholog of a genus belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*, and wherein: at least one of the following criteria applies.

The criteria are as follows and it will be appreciated that any number of these may apply, preferably 1 or more, preferably 2 or more, and preferably 3 or more, 4 or more, or 5 or more, or all may apply:

the CRISPR enzyme having a specific size is selected and has a length of at least 500 amino acids, at least 800-899 amino acids, at least 900-999 amino acids, at least 1000-1099 amino acids, at least 1100-1199 amino acids, at least 1200-1299 amino acids, at least 1300-1399 amino acids, at least 1400-1499 amino acids, at least 1500-1599 amino acids, at least 1600-1699 amino acids or at least 2000 amino acids;

and/or the CRISPR enzyme is truncated in comparison to the corresponding wild type CRISPR enzyme;

and/or the CRISPR enzyme is a nuclease directing cleavage of both strands at the location of the target sequence, or the CRISPR enzyme is a nickase directing cleavage of one strand at the location of the target sequence;

and/or the guide sequence comprises at least 10, at least 15 or at least 20 nucleotides;

and/or the CRISPR enzyme is codon-optimized or codon-optimized for expression in a eukaryotic cell;

and/or the CRISPR enzyme comprises one or more mutations;

and/or the CRISPR enzyme comprises a chimeric CRISPR enzyme;

and/or the CRISPR enzyme has one or more other attributes herein discussed.

In some embodiments, the CRISPR enzyme is truncated in comparison to a wild type CRISPR enzyme or the CRISPR enzyme is comprised of at least 500 amino acids, at least 800-899 amino acids, at least 900-999 amino acids, at least 1000-1099 amino acids, at least 1100-1199 amino acids, at least 1200-1299 amino acids, at least 1300-1399 amino acids, at least 1400-1499 amino acids, at least 1500-1599 amino acids, at least 1600-1699 amino acids or at least 2000 amino acids. In preferred embodiments the CRISPR enzyme is a Cas enzyme, e.g. a Cas9 ortholog.

In some embodiments, the CRISPR enzyme is a nuclease directing cleavage of both strands at the location of the target sequence, or the CRISPR enzyme is a nickase directing cleavage of one strand at the location of the target sequence. In further embodiments, the CRISPR enzyme is a catalytically null mutant that is a generic DNA binding protein. In preferred embodiments the CRISPR enzyme is a Cas enzyme, e.g. a Cas9 ortholog.

In some embodiments, the guide sequence comprises at least fifteen nucleotides. In some embodiments, the CRISPR enzyme is codon-optimized or codon-optimized for expression in a eukaryotic cell. In some embodiments, the CRISPR enzyme comprises one or more mutations. In some embodiments, the CRISPR enzyme comprises a chimeric CRISPR enzyme. In some embodiments, the CRISPR enzyme has one or more other attributes herein discussed. In preferred embodiments the CRISPR enzyme is a Cas enzyme, e.g. a Cas9 ortholog.

In certain embodiments, the CRISPR enzyme comprises one or more mutations. The one or more mutations may be in a particular domain of the enzyme. In a preferred embodiment, the one or more mutations may be in a catalytic domain. In a further preferred embodiment the catalytic domain is a RuvC I, RuvC II, RuvC III or HNH domain. In a more preferred embodiment, the one or more mutations is in a RuvC1 or HNH domain of the CRISPR enzyme. In a further preferred embodiment the CRISPR enzyme is a Cas enzyme, e.g. a Cas9 ortholog and the mutation may be at one or positions that include but are not limited to positions that correspond to D10A, E762A, H840A, N854A, N863A or D986A with reference to the position numbering of SpCas9 and/or is a mutation as otherwise discussed herein. In some embodiments, the CRISPR enzyme has one or more mutations in a particular domain of the enzyme, wherein when transcribed, the tracr mate sequence hybridizes to the tracr sequence and the guide sequence directs sequence-specific binding of a CRISPR complex to the target sequence, and wherein the enzyme further comprises a functional domain. The functional domain may include but is not limited to transcriptional activator, transcriptional repressor, a recombinase, a transposase, a histone remodeler, a DNA methyltransferase, a cryptochrome, a light inducible/controllable domain or a chemically inducible/controllable domain.

In some embodiments, the functional domain is the transcriptional activator domain VP64. In some embodiments, the functional domain is the transcriptional repressor domain KRAB. In some embodiments, the transcriptional repressor domain is SID, or concatemers of SID (i.e. SID4X). In some embodiments, an epigenetic modifying enzyme is provided, e.g. a histone modifying protein or an epigenetic chromatin modifying protein. In some embodiments, an activator domain is provided, which may be the P65 activator domain.

A further aspect of the invention comprehends methods of modifying two or more genomic loci of interest. In a preferred embodiment of the invention two or more genomic loci are differentially modulated by utilizing one or more CRISPR enzymes, e.g. two or more Cas9 orthologs, each ortholog being operably linked to one or more functional domain. In one aspect, the invention provides for a method of modifying two or more genomic loci in a eukaryotic cell. Therefore, aspects of the invention provide for a method of modulating the expression of two or more genomic loci of interest in an organism comprising delivering a non-naturally occurring or engineered composition comprising a vector system comprising one or more vectors comprising I. a first regulatory element operably linked to a first CRISPR-Cas system chimeric RNA (chiRNA) polynucleotide sequence, wherein the first polynucleotide sequence comprises (i) a first guide sequence capable of hybridizing to a first target sequence at a first genomic locus in a cell of the organism, (ii) a first tracr mate sequence, and (iii) a first tracr sequence, and II. a second regulatory element operably linked to a second CRISPR-Cas system chimeric RNA (chiRNA) polynucleotide sequence, wherein the second polynucleotide sequence comprises (i) a second guide sequence capable of hybridizing to a second target sequence at a second genomic locus in the cell of the organism, (ii) a second tracr mate sequence, and (iii) a second tracr sequence, and III. a third regulatory element operably linked to an enzyme-coding sequence encoding a first CRISPR enzyme comprising at least one or more nuclear localization sequences and operably linked to a first functional domain, IV. a fourth regulatory element operably linked to an enzyme-coding sequence encoding a second CRISPR enzyme comprising at least one or more nuclear localization sequences and operably linked to a second functional domain, wherein (i), (ii) and (iii) in I and II are arranged in a 5' to 3' orientation, wherein components I, II, III and IV are located on the same or different vectors of the system, wherein when transcribed, each tracr mate sequences hybridizes to its corresponding tracr sequence and the first and second guide sequences direct sequence-specific binding of the first and second CRISPR complex to the first and second target sequence, wherein the CRISPR complex comprises the CRISPR enzyme complexed with (1) the guide sequence that is hybridized to the target sequence, and (2) the tracr mate sequence that is hybridized to the tracr sequence and wherein expression of the CRISPR enzyme provides manipulation of the target sequence, wherein the first and second CRISPR enzyme each comprise two or more mutations, wherein the first and second CRISPR enzyme is a Cas9 ortholog of a genus belonging to the group consisting of Corynebacter, Sutterella, *Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*, and wherein the first genomic locus is modulated by the activity of the first functional domain and the second genomic locus is modulated by the activity of the second functional domain. In a further embodiment the first functional domain is selected from the group consisting of a transcriptional activator, transcriptional repressor, a recombinase, a transposase, a histone remodeler, a DNA methyltransferase, a cryptochrome and a light inducible/controllable domain or a chemically inducible/controllable domain. In a further embodiment the second functional domain is selected from the group consisting of a transcriptional activator, transcriptional repressor, a recombinase, a transposase, a histone remodeler, a DNA methyltransferase, a cryptochrome and a light inducible/controllable domain or a chemically inducible/controllable domain. In preferred embodiments the first or second CRISPR enzyme is a Sutterella wadsworthensis Cas9, a Filifactor alocis Cas9, a *Lactobacillus johnsonii* Cas9, a *Campylobacter lari* Cas9, a *Corynebacter diptheriae* Cas9, a *Parvibaculum lavamentivorans* Cas9, a *Mycoplasma gallisepticum* Cas9, a *Staphylococcus aureus* subsubspecies *Aureus* Cas9, a *Legionella pneumophila* Paris Cas9, a *Treponema denticola* Cas9, a *Staphylococcus pseudintermedius* Cas9, a *Neisseria cinerea* Cas9.

In some embodiments, the CRISPR enzyme is a type I, II or III CRISPR enzyme, preferably a type II CRISPR enzyme. This type II CRISPR enzyme may be any Cas enzyme. A Cas enzyme may be identified as Cas9 as this can refer to the general class of enzymes that share homology to the biggest nuclease with multiple nuclease domains from the type II CRISPR system. Most preferably, the Cas9 enzyme is from, or is derived from, SpCas9 or *Staphylococcus aureus* subsubspecies *Aureus* SaCas9. By derived, it is meant that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptotoccus pyogenes*. However, it will be appreciated that this invention includes many more Cas9s from other species of microbes such as those belonging to the genus *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* or *Campylobacter*, such as SpCas9, SaCas9, St1Cas9, St3Cas9 and so forth, wherein St is *Streptococcus thermophilus*.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

Further aspects of the invention relate to improved cleavage specificity, optimized tracr sequence, optimized chimeric guide RNA, co-fold structure of tracrRNA and tracr mate sequence, stabilizing secondary structures of tracr RNA, tracrRNA with shortened region of base pairing, tracrRNA with fused RNA elements, simplified cloning and delivery, reduced toxicity and/or inducible systems. Another aspect of the invention relates to the stabilization of chimeric RNA, and/or guide sequence and or a portion thereof of CRISPR complexes wherein the CRISPR enzyme is a CRISPR ortholog, wherein the chimeric RNA, and/or guide sequence and or a portion thereof is stabilized by synthetic or chemically modified nucleotides (e.g. LNA/BNA: thiol-modification, 2'/3'-OH crosslink modification), is modified to be degradation/hydrolysis resistant and to which elements of structural stability have been added.

The invention further comprehends in certain embodiments a method of modifying an organism or a non-human organism by manipulation of a target sequence in a genomic locus of interest comprising delivering a non-naturally occurring or engineered composition comprising a vector system comprising one or more vectors operably encoding a composition herein discussed for expression thereof. Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided.

Various means of delivery are described herein, and further discussed in this section.

Viral delivery: The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while othertimes the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chosen, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, an adjuvant to enhance antigenicity, an immunostimulatory compound or molecule, and/or other compounds known in the art. The adjuvant herein may contain a suspension of minerals (alum, aluminum hydroxide, aluminum phosphate) on which antigen is adsorbed; or water-in-oil emulsion in which antigen solution is emulsified in oil (MF-59, Freund's incomplete adjuvant), sometimes with the inclusion of killed mycobacteria (Freund's complete adjuvant) to further enhance antigenicity (inhibits degradation of antigen and/or causes influx of macrophages). Adjuvants also include immunostimulatory molecules, such as cytokines, costimulatory molecules, and for example, immunostimulatory DNA or RNA molecules, such as CpG oligonucleotides. Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1*\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about 4×10[9] pu, about 1×10[10] pu, about 2×10[10] pu, about 4×10[10] pu, about 1×10[11] pu, about 2×10[11] pu, about 4×10[11] pu, about 1×10[12] pu, about 2×10[12] pu, or about 4×10[12] pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^{5}$ to $1\times10^{50}$ genomes AAV, from about $1\times10^{8}$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg.

The doses herein are based on an average 70 kg individual. The frequency of administration is within the ambit of the medical or veterinary practitioner (e.g., physician, veterinarian), or scientist skilled in the art.

The viral vectors can be injected into the tissue of interest. For cell-type specific genome modification, the expression of Cas9 can be driven by a cell-type specific promoter. For example, liver-specific expression might use the Albumin promoter and neuron-specific expression might use the Synapsin I promoter.

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce toxicity, the CRISPR enzyme and/or guide RNA can be modified using pseudo-U or 5-Methyl-C.

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol. Pharm. 2011 Jun. 6; 8(3):774-87. doi: 10.1021/mp100390w. Epub 2011 Apr. 1) describes biodegradable core-shell structured nanoparticles with a poly(3-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Furthermore, Michael S D Kormann et al. ("Expression of therapeutic proteins after delivery of chemically modified mRNA in mice: Nature Biotechnology, Volume:29, Pages: 154-157 (2011) Published online 9 Jan. 2011) describes the use of lipid envelopes to deliver RNA. Use of lipid envelopes is also preferred in the present invention.

mRNA delivery methods are especially promising for liver delivery currently.

CRISPR enzyme mRNA and guideRNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guideRNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guideRNA.

Additional administrations of CRISPR enzyme mRNA and/or guide RNA might be useful to achieve the most efficient levels of genome modification.

For minimization of toxicity and off-target effects, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing to analyze the extent of modification at potential off-target genomic loci. For example, for the guide sequence targeting 5'-GAGTCCGAGCAGAAGAAGAA-3' (SEQ ID NO: 1) in the EMX1 gene of the human genome, deep sequencing can be used to assess the level of modification at the following two off-target loci, 1: 5'-GAGTCCTAGCAGGAGAAGAA-3' (SEQ ID NO: 2) and 2: 5'-GAGTCTAAGCAGAAGAAGAA-3' (SEQ ID NO: 3). The concentration that gives the highest level of on-target modification while minimizing the level of off-target modification should be chosen for in vivo delivery.

Alternatively, to minimize the level of toxicity and off-target effects, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences in red (single underline) and blue (double underline) respectively (these examples are based on the PAM requirement for *Streptococcus pyogenes* Cas9).

| Overhang length (bp) | Guide RNA design (guide sequence and PAM color coded) |
|---|---|
| 14 | 5'-NNNNNNNNNNNNNNNNNNNNCCNNNNNNNNNNNNNNNNNNNNNNGGNNNNNNNNNNNNNN-3' (SEQ ID NO: 4) |
| | 3'-NNNNNNNNNNNNNNNNNNNNGGNNNNNNNNNNNNNNNNNNNNNNCCNNNNNNNNNNNNNN-5' (SEQ ID NO: 5) |

-continued

| Overhang length (bp) | Guide RNA design (guide sequence and PAM color coded) |
|---|---|
| 13 | 5'-NNNNNNNNNNNNNNNNNNNNCCNNNNNNNNNNNNNNNNNNNNNGGNNNNNNNNNNNNNNN-3' (SEQ ID NO: 6)<br>3'-NNNNNNNNNNNNNNNNNNNNGGNNNNNNNNNNNNNNNNNNNNNCCNNNNNNNNNNNNNNN-5' (SEQ ID NO: 7) |
| 12 | 5'-NNNNNNNNNNNNNNNNNNNNCCNNNNNNNNNNNNNNNNNNNNGGNNNNNNNNNNNNNNNN-3' (SEQ ID NO: 8)<br>3'-NNNNNNNNNNNNNNNNNNNNGGNNNNNNNNNNNNNNNNNNNNNCCNNNNNNNNNNNNNNN-5' (SEQ ID NO: 9) |
| 11 | 5'-NNNNNNNNNNNNNNNNNNNNCCNNNNNNNNNNNNNNNNNNNGGNNNNNNNNNNNNNNNNN-3' (SEQ ID NO: 10)<br>3'-NNNNNNNNNNNNNNNNNNNNGGNNNNNNNNNNNNNNNNNNNCCNNNNNNNNNNNNNNNNN-5' (SEQ ID NO: 11) |
| 10 | 5'-NNNNNNNNNNNNNNNNNNNNCCNNNNNNNNNNNNNNNNNNGGNNNNNNNNNNNNNNNNNN-3' (SEQ ID NO: 12)<br>3'-NNNNNNNNNNNNNNNNNNNNGGNNNNNNNNNNNNNNNNNNCCNNNNNNNNNNNNNNNNNN-5' (SEQ ID NO: 13) |
| 9 | 5'-NNNNNNNNNNNNNNNNNNNNCCNNNNNNNNNNNNNNNNNGGNNNNNNNNNNNNNNNNNNN-3' (SEQ ID NO: 14)<br>3'-NNNNNNNNNNNNNNNNNNNNGGNNNNNNNNNNNNNNNNNCCNNNNNNNNNNNNNNNNNNN-5' (SEQ ID NO: 15) |
| 8 | 5'-NNNNNNNNNNNNNNNNNNNNCCNNNNNNNNNNNNNNNNGGNNNNNNNNNNNNNNNNNNNN-3' (SEQ ID NO: 16)<br>3'-NNNNNNNNNNNNNNNNNNNNGGNNNNNNNNNNNNNNNNCCNNNNNNNNNNNNNNNNNNNN-5' (SEQ ID NO: 17) |
| 7 | 5'-NNNNNNNNNNNNNNNNNNNNCCNNNNNNNNNNNNNNNGGNNNNNNNNNNNNNNNNNNNNN-3' (SEQ ID NO: 18)<br>3'-NNNNNNNNNNNNNNNNNNNNGGNNNNNNNNNNNNNNNCCNNNNNNNNNNNNNNNNNNNNN-5' (SEQ ID NO: 19) |
| 6 | 5'-NNNNNNNNNNNNNNNNNNNNCCNNNNNNNNNNNNNNGGNNNNNNNNNNNNNNNNNNNNNN-3' (SEQ ID NO: 20)<br>3'-NNNNNNNNNNNNNNNNNNNNGGNNNNNNNNNNNNNNCCNNNNNNNNNNNNNNNNNNNNNN-5' (SEQ ID NO: 21) |
| 5 | 5'-NNNNNNNNNNNNNNNNNNNNCCNNNNNNNNNNNNNGGNNNNNNNNNNNNNNNNNNNNNNN-3' (SEQ ID NO: 22)<br>3'-NNNNNNNNNNNNNNNNNNNNGGNNNNNNNNNNNNNCCNNNNNNNNNNNNNNNNNNNNNNN-5' (SEQ ID NO: 23) |
| 4 | 5'-NNNNNNNNNNNNNNNNNNNNCCNNNNNNNNNNNNGGNNNNNNNNNNNNNNNNNNNNNNNN-3' (SEQ ID NO: 24)<br>3'-NNNNNNNNNNNNNNNNNNNNGGNNNNNNNNNNNNCCNNNNNNNNNNNNNNNNNNNNNNNN-5' (SEQ ID NO: 25) |
| 3 | 5'-NNNNNNNNNNNNNNNNNNNNCCNNNNNNNNNNNGGNNNNNNNNNNNNNNNNNNNNNNNNN-3' (SEQ ID NO: 26)<br>3'-NNNNNNNNNNNNNNNNNNNNGGNNNNNNNNNNNCCNNNNNNNNNNNNNNNNNNNNNNNNN-5' (SEQ ID NO: 27) |
| 2 | 5'-NNNNNNNNNNNNNNNNNNNNCCNNNNNNNNNNGGNNNNNNNNNNNNNNNNNNNNNNNNNN-3' (SEQ ID NO: 28)<br>3'-NNNNNNNNNNNNNNNNNNNNGGNNNNNNNNNNCCNNNNNNNNNNNNNNNNNNNNNNNNNN-5' (SEQ ID NO: 29) |
| 1 | 5'-NNNNNNNNNNNNNNNNNNNNCCNNNNNNNNNGGNNNNNNNNNNNNNNNNNNNNNNNNNNN-3' (SEQ ID NO: 30)<br>3'-NNNNNNNNNNNNNNNNNNNNGGNNNNNNNNNCCNNNNNNNNNNNNNNNNNNNNNNNNNNN-5' (SEQ ID NO: 31) |
| blunt | 5'-NNNNNNNNNNNNNNNNNNNNCCNNNNNNNNGGNNNNNNNNNNNNNNNNNNNNNNNNNNNN-3' (SEQ ID NO: 32)<br>3'-NNNNNNNNNNNNNNNNNNNNGGNNNNNNNNCCNNNNNNNNNNNNNNNNNNNNNNNNNNNN-5' (SEQ ID NO: 33) |
| 1 | 5'-NNNNNNNNNNNNNNNNNNNNCCNNNNNNNGGNNNNNNNNNNNNNNNNNNNNNNNNNNNNN-3' (SEQ ID NO: 34)<br>3'-NNNNNNNNNNNNNNNNNNNNGGNNNNNNNCCNNNNNNNNNNNNNNNNNNNNNNNNNNNNN-5' (SEQ ID NO: 35) |
| 2 | 5'-NNNNNNNNNNNNNNNNNNNNCCNNNNNNGGNNNNNNNNNNNNNNNNNNNNNNNNNNNNNN-3' (SEQ ID NO: 36)<br>3'-NNNNNNNNNNNNNNNNNNNNGGNNNNNNCCNNNNNNNNNNNNNNNNNNNNNNNNNNNNNN-5' (SEQ ID NO: 37) |
| 3 | 5'-NNNNNNNNNNNNNNNNNNNNCCNNNNNGGNNNNNNNNNNNNNNNNNNNNNNNNNNNNNNN-3' (SEQ ID NO: 38)<br>3'-NNNNNNNNNNNNNNNNNNNNGGNNNNNCCNNNNNNNNNNNNNNNNNNNNNNNNNNNNNNN-5' (SEQ ID NO: 39) |
| 4 | 5'-NNNNNNNNNNNNNNNNNNNNCCNNNNGGNNNNNNNNNNNNNNNNNNNNNNNNNNNNNNNN-3' (SEQ ID NO: 40)<br>3'-NNNNNNNNNNNNNNNNNNNNGGNNNNCCNNNNNNNNNNNNNNNNNNNNNNNNNNNNNNNN-5' (SEQ ID NO: 41) |
| 5 | 5'-NNNNNNNNNNNNNNNNNNNNCCNNNGGNNNNNNNNNNNNNNNNNNNNNNNNNNNNNNNNN-3' (SEQ ID NO: 42)<br>3'-NNNNNNNNNNNNNNNNNNNNGGNNNCCNNNNNNNNNNNNNNNNNNNNNNNNNNNNNNNNN-5' (SEQ ID NO: 43) |
| 6 | 5'-NNNNNNNNNNNNNNNNNNNNCCNNGGNNNNNNNNNNNNNNNNNNNNNNNNNNNNNNNNNN-3' (SEQ ID NO: 44)<br>3'-NNNNNNNNNNNNNNNNNNNNGGNNCCNNNNNNNNNNNNNNNNNNNNNNNNNNNNNNNNNN-5' (SEQ ID NO: 45) |
| 7 | 5'-NNNNNNNNNNNNNNNNNNNNCCNGGNNNNNNNNNNNNNNNNNNNNNNNNNNNNNNNNNNN-3' (SEQ ID NO: 46)<br>3'-NNNNNNNNNNNNNNNNNNNNGGNCCNNNNNNNNNNNNNNNNNNNNNNNNNNNNNNNNNNN-5' (SEQ ID NO: 47) |
| 8 | 5'-NNNNNNNNNNNNNNNNNNNNNCCGGNNNNNNNNNNNNNNNNNNNNNNNNNNNNNNNNNNN-3' (SEQ ID NO: 48)<br>3'-NNNNNNNNNNNNNNNNNNNNNGGCCNNNNNNNNNNNNNNNNNNNNNNNNNNNNNNNNNNN-5' (SEQ ID NO: 49) |
| 12 | 5'-NNNNNNNNNNNNNNNNNNNNNNNGGNNNNNNNNNNNNNNNNNNNNNNNNNNNNNNNNNNN-3' (SEQ ID NO: 50)<br>3'-NNNNNNNNNNNNNNNNNNNNNNNCCGGNNNNNNNNNNNNNNNNNNNNNNNNNNNNNNNNN-5' (SEQ ID NO: 51) |
| 13 | 5'-NNNNNNNNNNNNNNNNNNNNNNCGGNNNNNNNNNNNNNNNNNNNNNNNNNNNNNNNNNNN-3' (SEQ ID NO: 52)<br>3'-NNNNNNNNNNNNNNNNNNNNNNNCCNGGNNNNNNNNNNNNNNNNNNNNNNNNNNNNNNNN-5' (SEQ ID NO: 53) |
| 14 | 5'-NNNNNNNNNNNNNNNNNNNNNNCGGNNNNNNNNNNNNNNNNNNNNNNNNNNNNNNNNNNN-3' (SEQ ID NO: 52)<br>3'-NNNNNNNNNNNNNNNNNNNNNNNCCNNGGNNNNNNNNNNNNNNNNNNNNNNNNNNNNNNN-5' (SEQ ID NO: 54) |

-continued

| Overhang length (bp) | Guide RNA design (guide sequence and PAM color coded) |
|---|---|
| 15 | 5'-NNNNNNNNNNNNNNNNNNNNNNCGGNNNNNNNNNNNNNNNNNNNNNNNNNNNNNNNNNNN-3' (SEQ ID NO: 52)<br>3'-NNNNNNNNNNNNNNNNNNNNNNNCCNNNGGNNNNNNNNNNNNNNNNNNNNNNNNNNNNNN-5' (SEQ ID NO: 55) |
| 16 | 5'-NNNNNNNNNNNNNNNNNNNNNNCGGNNNNNNNNNNNNNNNNNNNNNNNNNNNNNNNNNNN-3' (SEQ ID NO: 52)<br>3'-NNNNNNNNNNNNNNNNNNNNNNNCCNNNNGGNNNNNNNNNNNNNNNNNNNNNNNNNNNNN-5' (SEQ ID NO: 56) |
| 17 | 5'-NNNNNNNNNNNNNNNNNNNNNNCGGNNNNNNNNNNNNNNNNNNNNNNNNNNNNNNNNNNN-3' (SEQ ID NO: 52)<br>3'-NNNNNNNNNNNNNNNNNNNNNNNCCNNNNNGGNNNNNNNNNNNNNNNNNNNNNNNNNNNN-5' (SEQ ID NO: 57) |

Further interrogation of the system has given Applicants evidence of the 5' overhang (see, e.g., Ran et al., Cell. 2013 Sep. 12; 154(6):1380-9 and U.S. Provisional Patent Application Ser. No. 61/871,301 filed Aug. 28, 2013). Applicants have further identified parameters that relate to efficient cleavage by the Cas9 nickase mutant when combined with two guide RNAs and these parameters include but are not limited to the length of the 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 base pairs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from −278 to +58 bp), but were unable to observe indel formation. Further work may be needed to identify the necessary design rules for sgRNA pairing to allow double nicking by Cas9H840A.

Additional delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia CF and Boado R J, Pardridge W M ("Antibody-mediated targeting of siRNA via the human insulin receptor using avidin-biotin technology." Mol. Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang Y. Schlachetzki F. Pardridge W M. ("Global non-viral gene transfer to the primate brain following intravenous administration." Mol. Ther. 2003 January; 7(1):11-8.) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjuction with antibodies to target specific tissues or cell surface proteins.

Other means of delivery or RNA are also preferred, such as via nanoparticles (Cho, S., Goldberg, M., Son, S., Xu, Q. Yang. F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010. PMID: 20059641). Indeed, exozomes have been shown to be particularly useful in delivery siRNA, a system with some parallels to the CRISPR system. For instance, El-Andaloussi S, et al. ("Exosome-mediated delivery of siRNA in vitro and in vivo." Nat. Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then siRNA is loaded into the exosomes.

One aspect of manipulation of a target sequence also refers to the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting or reducing 3D folding.

A vector may mean not only a viral or yeast system (for instance, where the nucleic acids of interest may be operably linked to and under the control of (in terms of expression, such as to ultimately provide a processed RNA) a promoter, but also direct delivery of nucleic acids into a host cell.

The invention also comprehends, in certain embodiments, a method of treating or inhibiting a condition caused by a defect in a target sequence in a genomic locus of interest in a subject or a non-human subject in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising a vector system comprising one or more vectors comprising operably encoding a composition herein discussed for expression thereof, wherein the target sequence is manipulated by the composition when expressed.

In certain embodiments of the herein methods, the methods can include inducing expression, which can be inducing expression of the CRISPR enzyme and/or inducing expression of the guide, tracr or tracr mate sequences. In certain embodiments of the herein methods, the organism or subject is a eukaryote or a non-human eukaryote. In certain embodiments of the herein methods, the organism or subject is a plant. In certain embodiments of the herein methods, the organism or subject is a mammal or a non-human mammal. In certain embodiments of the herein methods, the organism or subject is algae.

While in herein methods the vector may be a viral vector and this is advantageously an AAV, other viral vectors as herein discussed can be employed. For example, baculoviruses may be used for expression in insect cells. These insect cells may, in turn be useful for producing large quantities of further vectors, such as AAV vectors adapted for delivery of the present invention.

Also envisaged is a method of delivering the present CRISPR enzyme comprising delivering to a cell mRNA encoding the CRISPR enzyme. It will be appreciated that the CRISPR enzyme is truncated, is of a specific size as described herein, is a nuclease or nickase or generic DNA binding protein, is codon-optimized, comprises one or more mutations, and/or comprises a chimeric CRISPR enzyme, or the other options as herein discussed.

Also envisaged is a method of preparing an vector for delivery of the compositions or the present CRISPR enzymes of the invention and for use in the present methods.

AAV viral vectors are preferred. Thus, in a further aspect, there is provided a method of preparing an AAV viral vector, comprising transfecting plasmid(s) containing or consisting essentially of nucleic acid molecule(s) coding for the AAV into AAV-infected cells, and supplying AAV rep and/or cap obligatory for replication and packaging of the AAV. In this regard, it will be appreciated that the CRISPR enzyme is truncated, comprised of less than one thousand amino acids or less than four thousand amino acids, is a nuclease or nickase, is codon-optimized comprises one or more mutations, and/or comprises a chimeric CRISPR enzyme, as herein discussed. In some embodiments the AAV rep and/or cap obligatory for replication and packaging of the AAV are supplied by transfecting the cells with helper plasmid(s) or helper virus(es). In some embodiments the helper virus is a poxvirus, adenovirus, herpesvirus or baculovirus. In some embodiments the poxvirus is a vaccinia virus. In some embodiments the cells are mammalian cells. And in some embodiments the cells are insect cells and the helper virus is baculovirus.

The invention further comprehends in certain embodiments a modified CRISPR enzyme. Differences from the wild type CRISPR enzyme can comprise: the modified CRISPR enzyme is truncated in comparison to a wild type CRISPR enzyme, or the CRISPR enzyme is of a specific size, e.g. at least 500 amino acids, at least 800-899 amino acids, at least 900-999 amino acids, at least 1000-1099 amino acids, at least 1100-1199 amino acids, at least 1200-1299 amino acids, at least 1300-1399 amino acids, at least 1400-1499 amino acids, at least 1500-1599 amino acids, at least 1600-1699 amino acids or at least 2000 amino acids; and/or the CRISPR enzyme is a nuclease directing cleavage of both strands at the location of the target sequence, or the CRISPR enzyme is a nickase directing cleavage of one strand at the location of the target sequence, or the CRISPR enzyme is a catalytic null mutant that functions as a DNA binding protein; and/or the CRISPR enzyme is codon-optimized or codon-optimized for expression in a eukaryotic cell, and/or the CRISPR enzyme comprises one or more mutations, and/or the CRISPR enzyme comprises a chimeric CRISPR enzyme and/or the CRISPR enzyme has one or more other attributes herein discussed. Accordingly, in certain embodiments, the CRISPR enzyme comprises one or more mutations in catalytic residues such as spCa9 D10A, E762A, H840A, N854A, N863A or D986A or those corresponding to them in other Cas enzymes (as described herein) with reference to the position numbering of SpCas9, and/or has one or more mutations is in a RuvC I, RuvC II, RuvC III, HNH or other domain described herein of the CRISPR enzyme and/or the CRISPR enzyme has one or more mutations in a catalytic domain, wherein when transcribed, a tracr mate sequence hybridizes to a tracr sequence and a guide sequence directs sequence-specific binding of a CRISPR complex to a target sequence, and wherein the enzyme further comprises a functional domain. The functional domain may include but is not limited to transcriptional activator, transcriptional repressor, a recombinase, a transposase, a histone remodeler, a DNA methyltransferase, a cryptochrome, a light inducible/controllable domain or a chemically inducible/controllable domain. The CRISPR enzyme in certain embodiments can have the functional domain be a transcriptional activator domain, e.g., VP64. In some embodiments, a transcription repressor domains is KRAB. In some embodiments, a transcription repressor domain is SID, or concatemers of SID (i.e. SID4X). In some embodiments, an epigenetic modifying enzyme is provided.

In preferred embodiments the CRSIPR enzyme is a Cas enzyme, e.g. a Cas9 ortholog.

Aspects of the invention also comprehend identifying novel orthologs of CRISPR enzymes. Methods of identifying novel orthologs of CRISPR enzymes may involve identifying tracr sequences in genomes of interest. Identification of tracr sequences may relate to the following steps: Search for the direct repeats or tracr mate sequences in a database to identify a CRISPR region comprising a CRISPR enzyme, e.g. FIG. 18. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat of tracr mate sequence as a potential tracr sequence. Take the potential tracr sequence and analyze for transcriptional terminator sequences associated therewith.

The invention comprehends in certain embodiments use of a composition as described herein or a CRISPR enzyme in medicine. The invention further comprehends in certain embodiments a composition or CRISPR enzyme of the invention used in a method of the invention. The invention also comprehends, in certain embodiments, use of a composition or a CRISPR enzyme of the invention in, preferably ex vivo, gene or genome editing or, preferably an ex vivo, gene or genome editing method. The invention accordingly also comprehends in certain embodiments use of a composition according or a CRISPR enzyme of the invention in the manufacture of a medicament for ex vivo gene or genome editing or for use in a method as herein discussed.

In addition, the invention in certain embodiments comprehends a composition or a CRISPR enzyme of the invention, wherein the target sequence is flanked or followed, at its 3' end, by a PAM suitable for the CRISPR enzyme, typically a Cas and in particular a Cas9. This PAM sequence is specific for each Cas9 but may be readily determined by methods described herein.

For example, a suitable PAM is 5'-NRG or 5'-NNGRR for SpCas9 or SaCas9 enzymes (or derived enzymes), respectively. It will be appreciated that reference made herein to *Staphylococcus aureus* preferably includes *Staphylococcus aureus* subspecies *Aureus.*

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-F shows an exemplary CRISPR system and a possible mechanism of action (A), an example adaptation for expression in eukaryotic cells, and results of tests assessing nuclear localization and CRISPR activity (B-F). FIG. 2C discloses SEQ ID NOS 92 and 93, respectively, in order of appearance. FIG. 2E discloses SEQ ID NOS 94-96, respectively, in order of appearance. FIG. 2F discloses SEQ ID NOS 97-101, respectively, in order of appearance.

FIG. 8 A-J shows 18 chimeric RNA structures that preserved the sequence and secondary structures of the tracr mate:tracr sequence duplex while shortening the region of base-pairing and fusing the two RNA elements through an artificial loop. FIGS. 8A-J disclose SEQ ID NOS 102-118, respectively, in order of appearance.

FIG. 9 A-O shows a list of the human codon optimized Cas9 sequences to pair with the chimeric guide RNAs provided in FIGS. 8 A-J. FIGS. 9A-O disclose SEQ ID NOS 119-137. respectively, in order of appearance.

FIG. 10 A-M shows sequences where the mutation points are located within the SpCas9 gene. FIGS. 10A-M disclose the nucleotide sequence as SEQ ID NO: 138 and the amino acid sequence as SEQ ID NO: 139.

FIG. 13 A-II shows a table listing Cas9 orthologs and their corresponding PAM sequences. FIG. 13 A-II discloses SEQ ID NOS 158-199, respectively, in order of appearance.

FIG. 14 shows that the PAM for *Staphylococcus aureus* subspecies *Aureus* Cas9 is NNGRR. FIG. 14 discloses SEQ ID NOS 200-209, respectively, in order of appearance.

FIG. 16 discloses SEQ ID NOS 210 and 211, respectively, in order of appearance.

FIG. 19 A-L shows a multiple sequence alignment for 12 Cas9 orthologs. Two catalytic residues are highlighted. The first residue highlighted is the catalytic Asp residue in the RuvCI domain, and the second residue highlighted is the catalytic His residue in the HNH domain. Mutation of one or the other residue into Ala can convert Cas9 into a nickase. Mutation of both residues converts Cas9 into a catalytically null mutant—useful for generic DNA binding. FIGS. 19A-L disclose SEQ ID NOS 186, 212, 168, 171, 180, 192, 195, 177, 189, 183, 159 and 162, respectively, in order of appearance.

FIG. 21 shows in vitro cleavage of candidate targets on pUC19 plasmid by 10 Cas9 orthologs. Consensus PAMs are predicted by sequence logos (FIG. 7), based on which candidate targets on pUC19 are chosen. 7 of 9 new Cas9 orthologs tested have successfully cleaved at least one pUC9 target. SpCas9 can also cleave NGA in vitro. FIG. 21 discloses SEQ ID NOS 213-228, respectively, in order of appearance.

Figure 1:
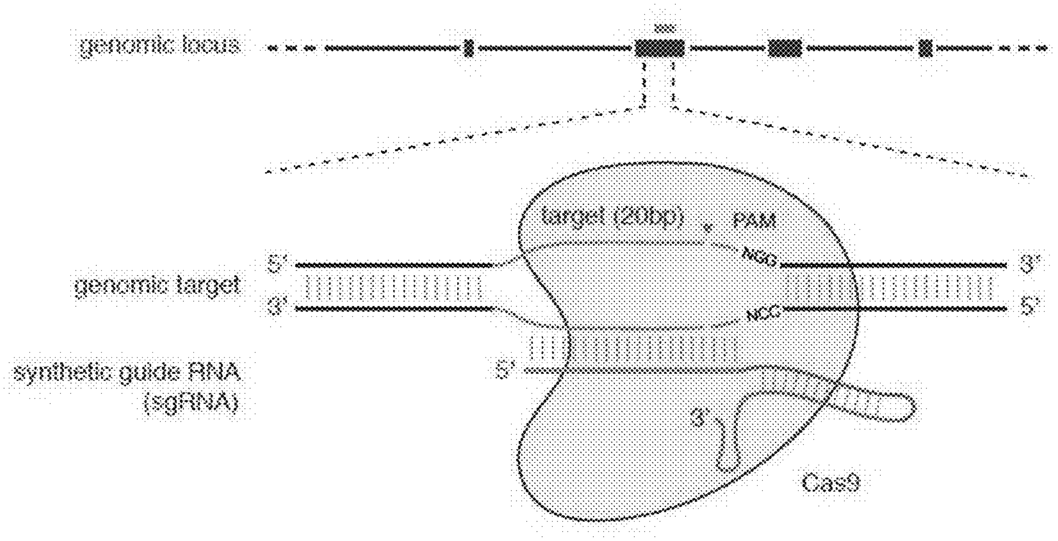
FIG. 1 shows a schematic of RNA-guided Cas9 nuclease. The Cas9 nuclease from *Streptococcus pyogenes* is targeted to genomic DNA by a synthetic guide RNA (sgRNA) consisting of a 20-nt guide sequence and a scaffold. The guide sequence base-pairs with the DNA target, directly upstream of a requisite 5'-NGG protospacer adjacent motif (PAM), and Cas9 mediates a double-stranded break (DSB) ~3 bp upstream of the PAM (indicated by triangle).

The figures herein are for illustrative purposes only and are not necessarily drawn to scale.

DETAILED DESCRIPTION OF THE INVENTION

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the CRISPR enzyme is a Cas enzyme, e.g. a Cas9 ortholog.

The invention uses nucleic acids to bind target DNA sequences. This is advantageous as nucleic acids are much easier and cheaper to produce than, for example, peptides, and the specificity can be varied according to the length of the stretch where homology is sought. Complex 3-D positioning of multiple fingers, for example is not required.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide. 5×SSC. and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA. expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. Sequence homologies may be generated by any of a number of computer programs known in the art, for example BLAST or FASTA, etc. A suitable computer program for carrying out such an alignment is the GCG Wisconsin Bestfit package (University of Wisconsin. U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

% homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software that may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASISTM (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides for vectors that are used in the engineering and optimization of CRISPR-Cas systems.

As used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Further discussion of vectors is provided herein.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element (s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects and embodiments of the invention relate to bicistronic vectors for chimeric RNA and Cas9 or a Cas9 ortholog. In some embodiments, the Cas9 is driven by the CBh promoter. In some embodiments, the chimeric RNA is driven by a U6 promoter. Preferably, the CBh and U6 are used together in the sense that the Cas9 is driven by the CBh promoter and the chimeric RNA is driven by a U6 promoter. In some embodiments, the chimeric guide RNA consists of a 20 bp guide sequence (Ns) joined to the tracr sequence (running from the first "U" of the lower strand to the end of the transcript), which is truncated at various positions as indicated. The guide and tracr sequences are preferably separated by the tracr-mate sequence. A preferred example of a tracr-mate sequence is GUUUUAGAGCUA (SEQ ID NO: 58). This is preferably followed by a loop sequence. The loop is preferably GAAA, but it is not limited to this sequence or indeed to being only 4 bp in length. Indeeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. Throughout this application, chimeric RNA may also be called single guide, or synthetic guide RNA (sgRNA).

Figure 6:
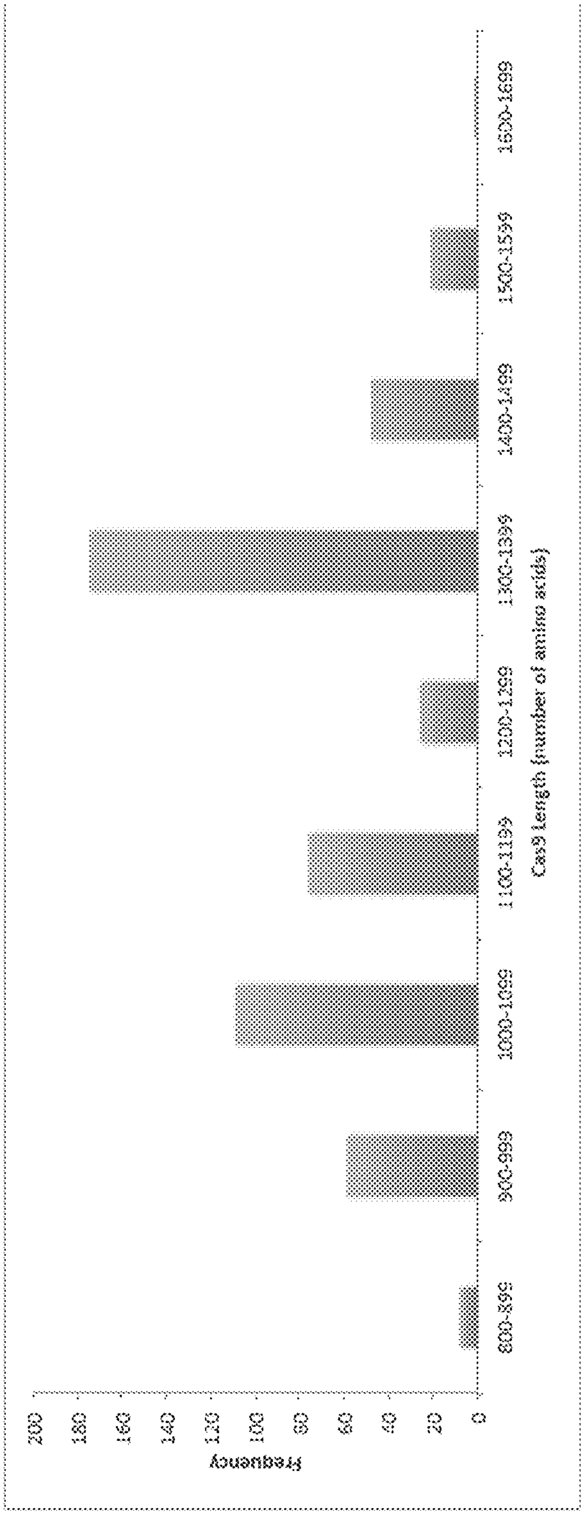
FIG. 6 shows a graph representing the length distribution of Cas9 orthologs.
Figure 11:
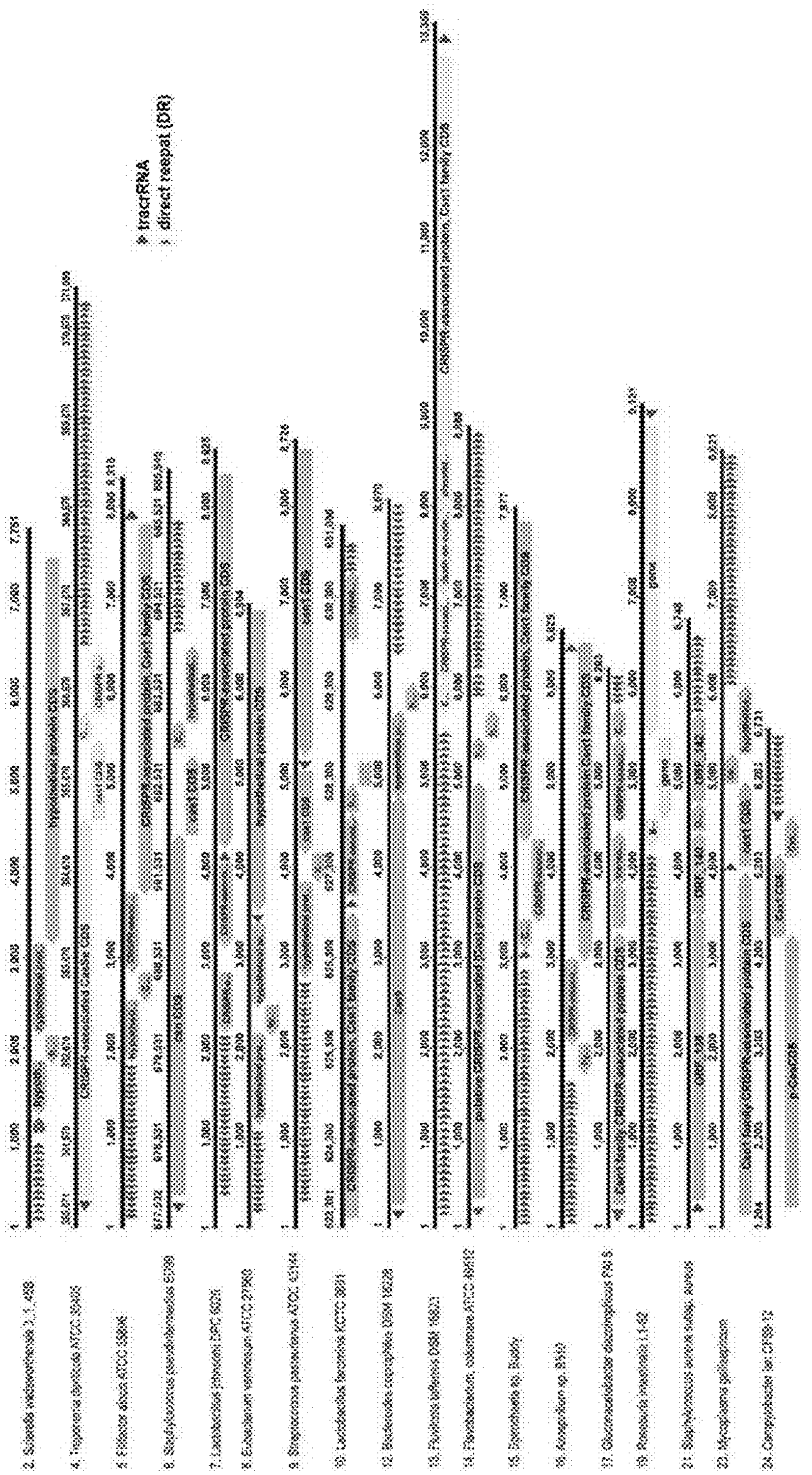
FIG. 11 shows Type II CRISPR loci in different organisms.
Figure 12:
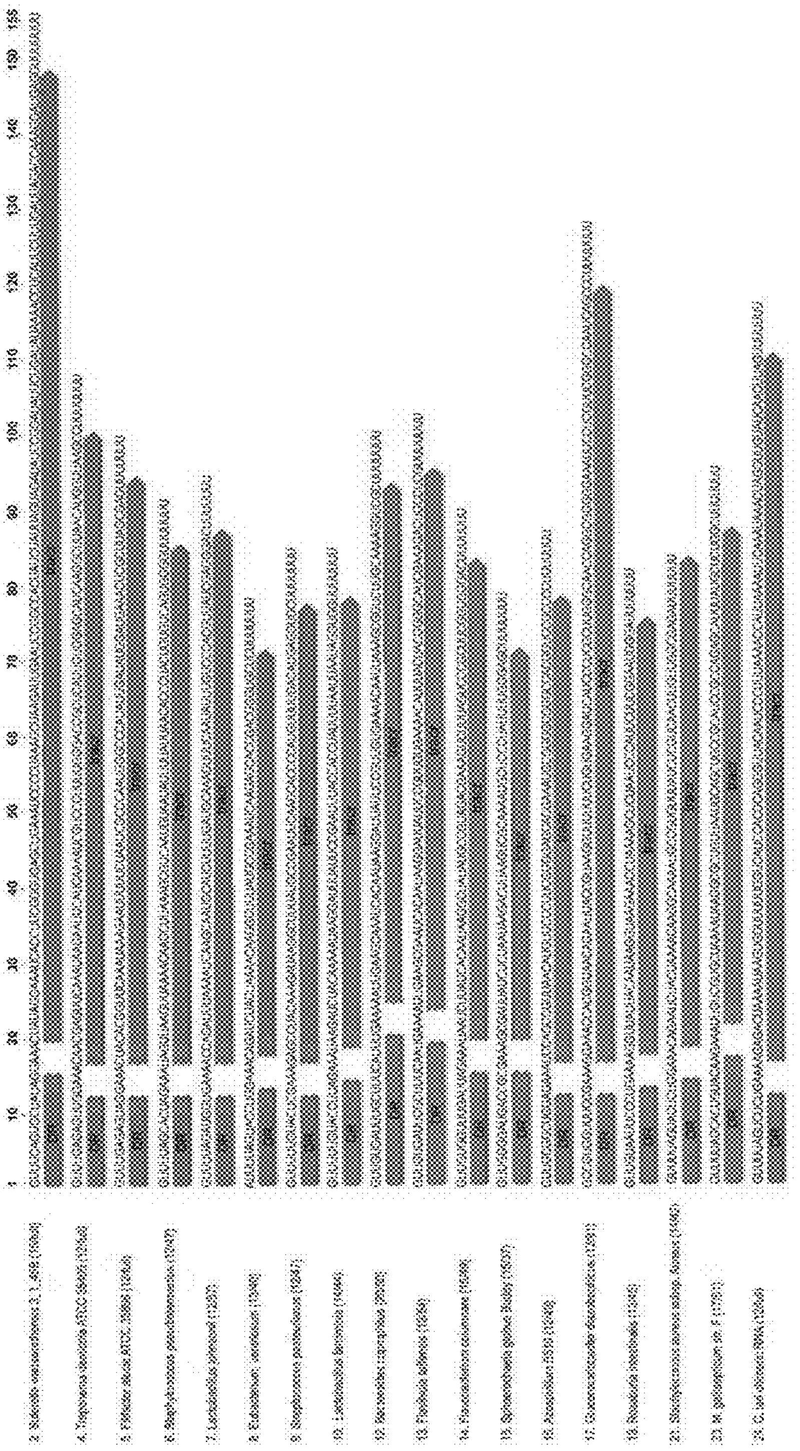
FIG. 12 shows guide RNA sequences (SEQ ID NOS 140-157, respectively, in order of appearance) corresponding to CRISPR loci in different organisms.

For instance, as described in specific detail in Example 2, chimeric guide RNAs may be designed as shown in FIG. 8. The CRISPR loci in some of these families is depicted in FIG. 11. The corresponding guide RNA sequences are shown in FIG. 12. We analyzed the genomic DNA sequence within ~2 kb of the Cas9 proteins and identified direct repeats ranging from 35 bp to 50 bp, with intervening spacers ranging from 29 bp to 35 bp. Based on the direct repeat sequence, we searched for tracrRNA candidate sequences with the following criteria: outside the crRNA array but containing high degree of homology to direct repeats (as required for direct repeat:tracrRNA base-pairing; custom computational analysis), outside the coding regions of the protein components, containing Rho-independent transcriptional termination signals ~60 bp-120 bp downstream from region of homology from with direct repeats, and co-folding with direct repeat to form a duplex, followed by two or more hairpin structures in the distal end of tracrRNA sequence. Based on these prediction criteria, we selected an initial set of 18 Cas9 proteins and their uniquely associated direct repeats and tracrRNAs distributed across all five Cas9 families. Applicants further generated a set of 18 chimeric RNA structures that preserved the sequence and secondary structures of the native direct repeat:tracrRNA duplex while shortening the region of base-pairing and fusing the two RNA elements through an artificial loop (FIGS. 6 A-J).

The term "regulatory element" is intended to include promoters, enhancers, internal ribosomal entry sites (IRES). and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*. insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory. Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264.166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra).

Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence NGG/NRG (for example, as discussed elsewhere, a suitable PAM is 5'-NRG or 5'-NNGRR for SpCas9 or SaCas9 enzymes (or derived enzymes), respectively) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archae, Mole Cell 2010, Jan. 15; 37(1): 7.

Figure 2A:
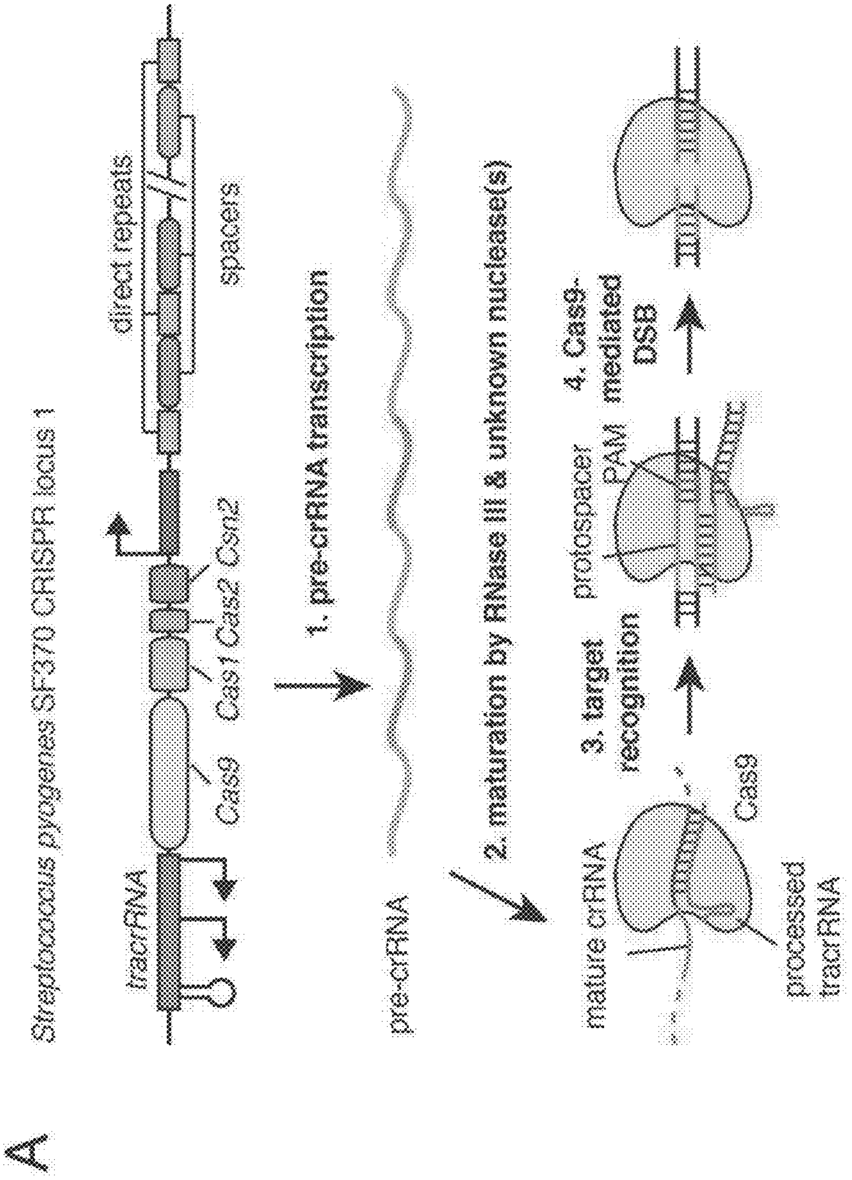
Figure 2B:
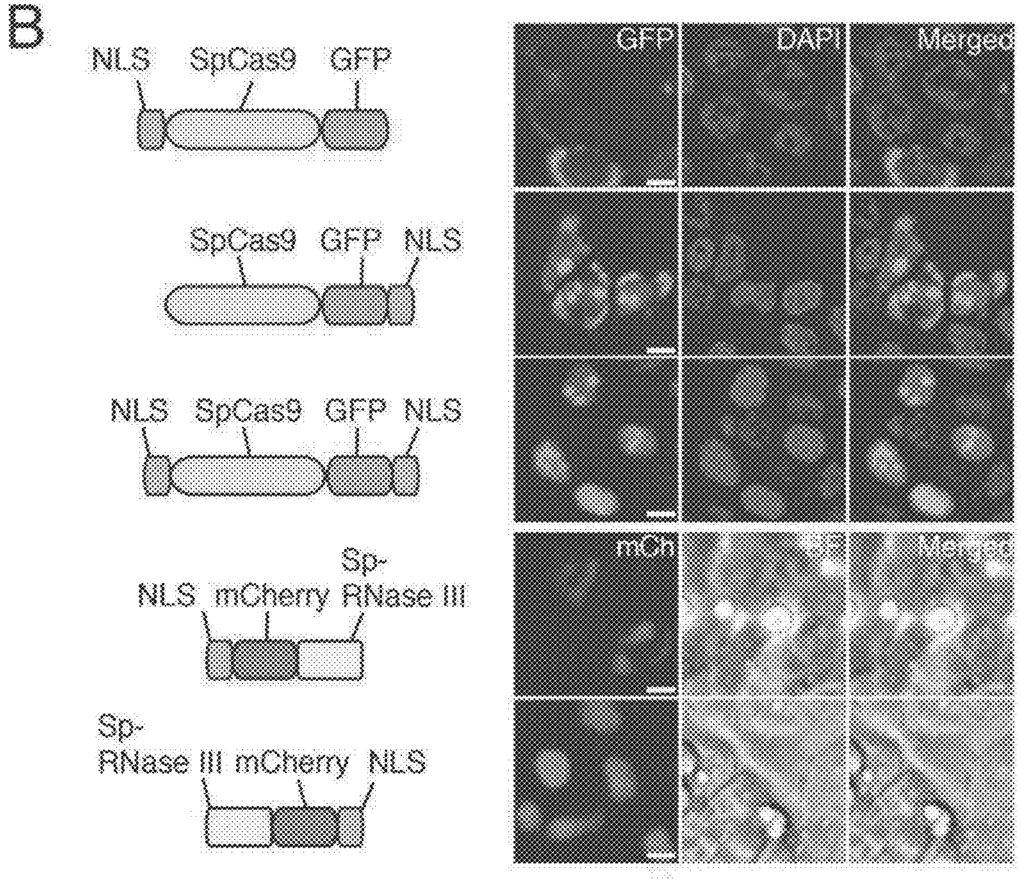
Figure 2C:
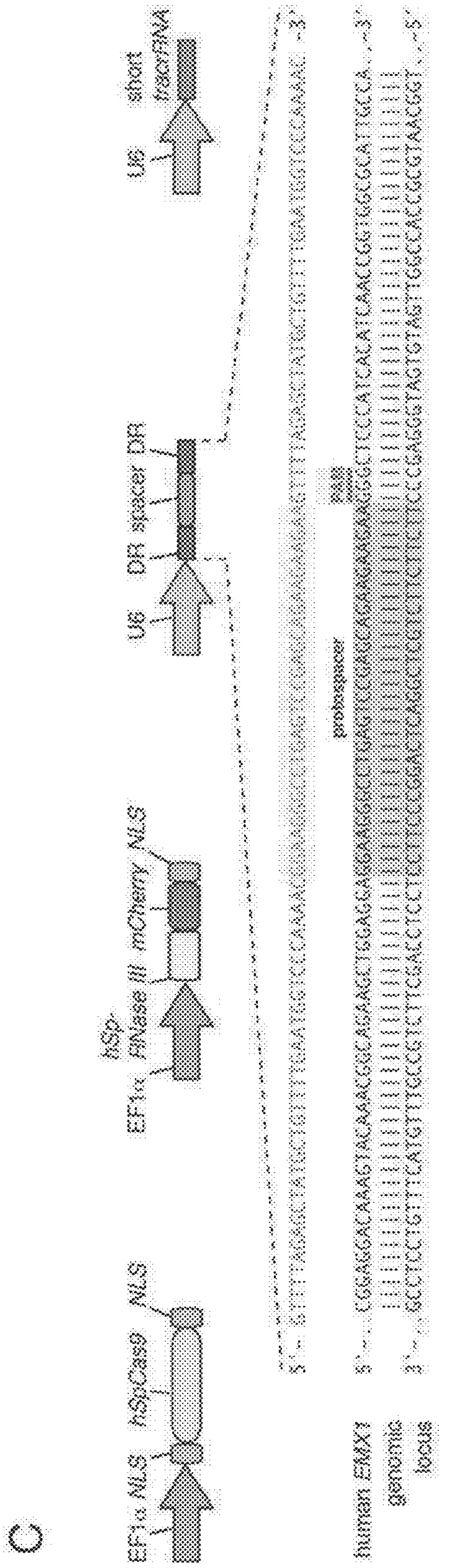
Figure 2D:
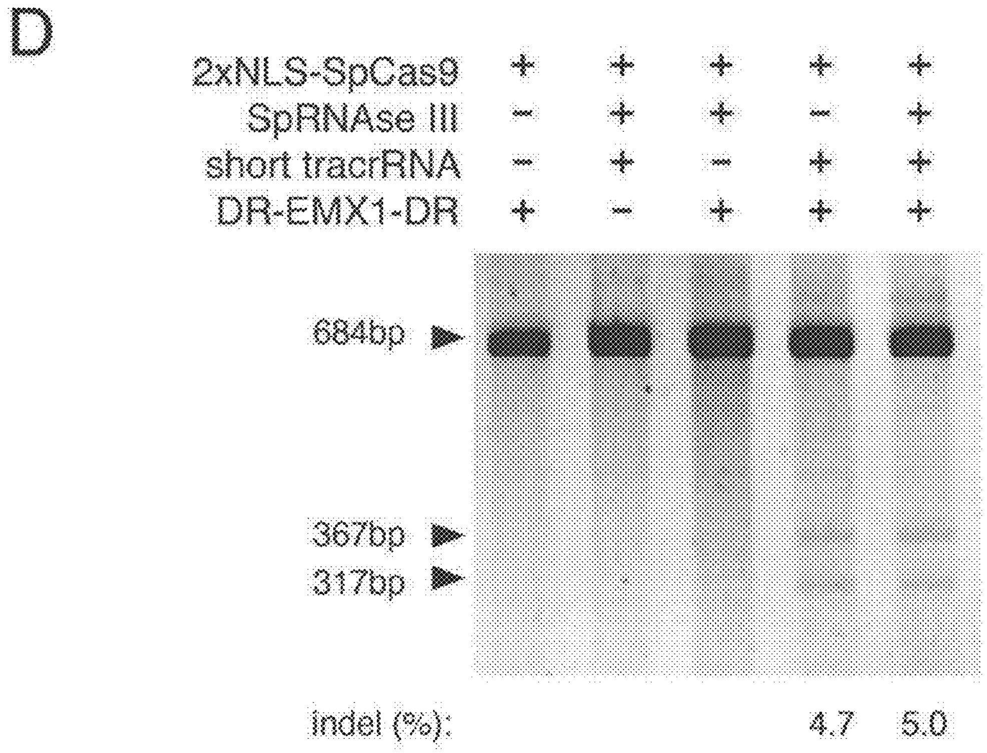

The type II CRISPR locus from *Streptooccus pyogenes* SF370 contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 16:
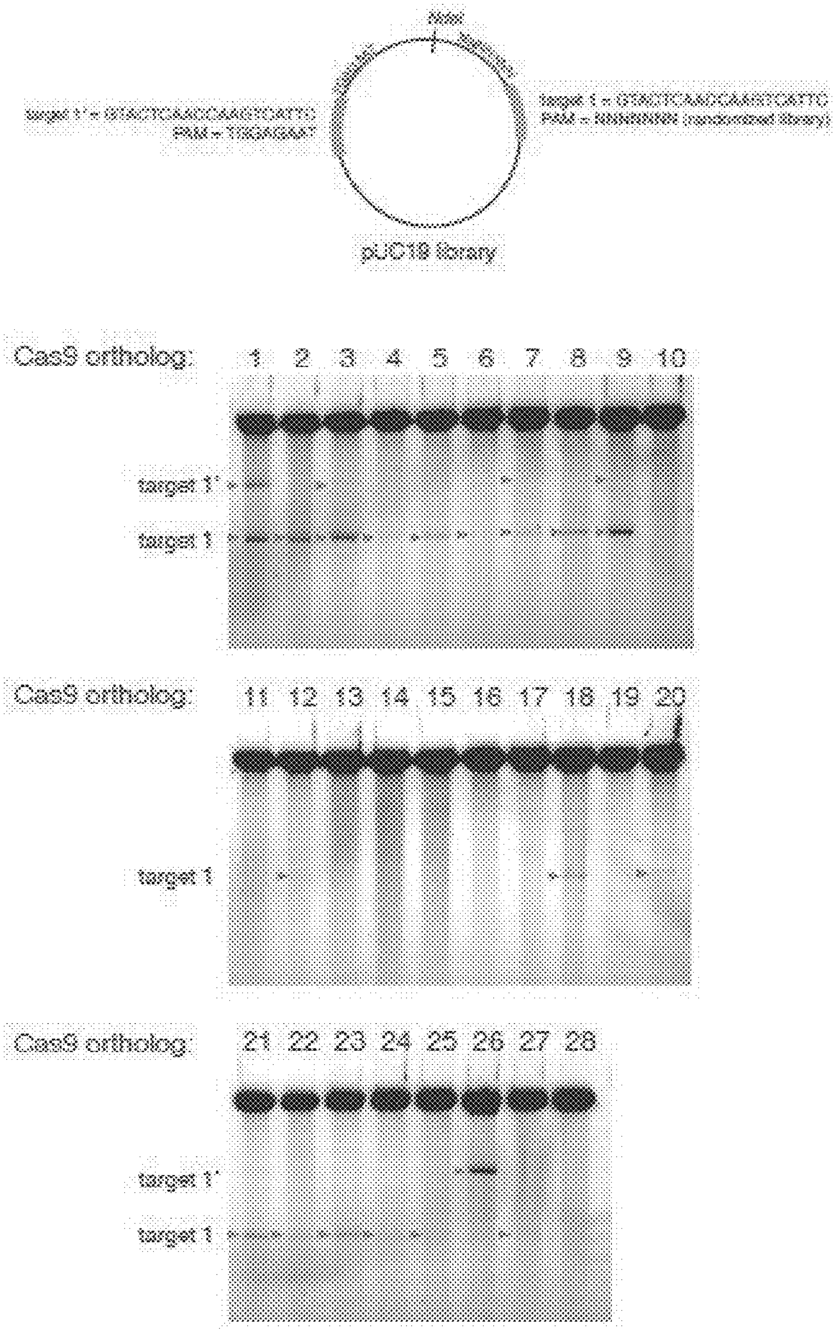
FIG. 16 shows a vector design and gel images for Cas9 orthologs and respective sgRNAs being used to cleave two candidate targets present in a pUC19-based library.

FIG. 16 shows Cas9 orthologs and respective sgRNAs are used to cleave two candidate targets present in a pUC19-based library. Target 1 is followed by a randomized PAM containing 7 degenerate bases (5'-NNNNNNN-3'), and target 1', which contains the same target sequence as target 1, is followed by a fixed PAM (5'-TGGAGAAT-3'). The sgRNA of each Cas9 ortholog contains the guide sequence against target 1 or target 1'. Gel images show successful cleavage by 20 Cas9 orthologs, indicating that these sgRNA designs are functional with their respective Cas9 enzymes.

In some embodiments, direct repeats or tracr mate sequences are either downloaded from the CRISPRs database or identified in silico by searching for repetitive motifs that are 1. found in a 2 kb window of genomic sequence flanking the type II CRISPR locus, 2. span from 20 to 50 bp, and 3. interspaced by 20 to 50 bp. In some embodiments, 2 of these criteria may be used, for instance 1 and 2, 2 and 3, or 1 and 3. In some embodiments, all 3 criteria may be used.

In some embodiments candidate tracrRNA are subsequently predicted by 1. sequence homology to direct repeats (motif search in Geneious with up to 18-bp mismatches), 2. presence of a predicted Rho-independent transcriptional terminator in direction of transcription, and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used. In some embodiments, chimeric synthetic guide RNAs (sgRNAs) designs incorporate at least 8 bp of duplex structure between the direct repeat and tracrRNA.

Several aspects of the CRISPR system can be further improved to increase the efficiency and versatility of CRISPR targeting. Optimal Cas9 activity may depend on the availability of free Mg2+ at levels higher than that present in the mammalian nucleus (see e.g. Jinek et al., 2012, Science, 337:816), and the preference for an NGG/NRG motif immediately downstream of the protospacer restricts the ability to target on average every 12-bp in the human genome.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4. Cas5, Cas6, Cas7, Cas8. Cas9 (also known as Csn1 and Csx12), Cas10, Csy1, Csy2, Csy3, Cse1, Cse2, Csc1, Csc2, Csa5, Csn2, Csm2, Csm3, Csm4, Csm5. Csm6, Cmr1, Cmr3, Cmr4, Cmr5, Cmr6, Csb1, Csb2, Csb3, Csx17, Csx14, Csx100, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand).

Other examples of mutations that render Cas9 a nickase include, without limitation. H840A, N854A, and N863A in SpCas9. As discussed herein, corresponding positions may be conserved in other Cas9s, i.e. in Cas9 orthologs from or derived from other bacterial species, with reference to the position numbering of SpCas9. (FIG. 19) shows a multiple sequence alignment of 12 Cas9 orthologs and indicates the conserved catalytic Asp residue in the RuvC I domain and the conserved catalytic His residue in the HNH domain. Mutation of one or the other residue into Ala may convert the Cas9 ortholog into a nickase. Mutation of both residues may convert the Cas9 ortholog into a catalytically null mutant—useful for generic DNA binding. As a further example, two or more catalytic domains of Cas9 (RuvC I, RuvC II, and RuvC III or the HNH domain) may be mutated to produce a mutated Cas9 ortholog substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%. or lower with respect to its non-mutated form.

An aspartate-to-alanine substitution (D10A) in the RuvC I catalytic domain of SpCas9 was engineered to convert the nuclease into a nickase (see e.g. Sapranauskas et al., 2011, Nucleic Acis Research, 39: 9275; Gasiunas et al., 2012, Proc. Natl. Acad. Sci. USA, 109:E2579), such that nicked genomic DNA undergoes the high-fidelity homology-directed repair (HDR). Applicants used SURVEYOR assay to confirm that SpCas9n does not generate indels at the EMX1 protospacer target. It was seen that co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. SpCas9 and SpCas9n indeed catalyzed integration of the HR template into the EMX1 locus. PCR amplification of the target region followed by restriction digest with HindIII revealed cleavage products corresponding to expected fragment sizes, with SpCas9 and SpCas9n mediating similar levels of HR efficiencies. Applicants further verified HR using Sanger sequencing of genomic amplicons and demonstrated the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway. FIG. 10A-M provides a scheme indicating positions of mutations in SpCas9 and Cas9 orthologs typically share the general organization of 3-4 RuvC domains and a HNH domain. The 5' most RuvC domain cleaves the non-complementary strand, and the HNH domain cleaves the complementary strand.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human mammal including non-human primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 59); the NLS from nucleoplasmin (e.g. the nucleoplasmin bipartite NLS with the sequence KRPAATKKAGQAKKKK (SEQ ID NO: 60)); the c-myc NLS having the amino acid sequence PAAKRVKLD (SEQ ID NO: 61) or RQRRNELKRSP (SEQ ID NO: 62); the hRNPA1 M9 NLS having the sequence NQSSNFGPMKG-GNFGGRSSGPYGGGGQYFAKPRNQGGY (SEQ ID NO: 63); the sequence RMRIZFKNKGKDTAELRRRRVEVS-VELRKAKKDEQILKRRNV (SEQ ID NO: 64) of the IBB domain from importin-alpha; the sequences VSRKRPRP (SEQ ID NO: 65) and PPKKARED (SEQ ID NO: 66) of the myoma T protein; the sequence PQPKKKPL (SEQ ID NO: 67) of human p53; the sequence SALIKKKKKMAP (SEQ ID NO: 68) of mouse c-abl IV; the sequences DRLRR (SEQ ID NO: 69) and PKQKKRK (SEQ ID NO: 70) of the influenza virus NS1; the sequence RKLKKKIKKL (SEQ ID NO: 71) of the Hepatitis virus delta antigen; the sequence REKKKFLKRR (SEQ ID NO: 72) of the mouse Mx1 protein; the sequence KRKGDEVDGVDEVAKKKSKK (SEQ ID NO: 73) of the human poly(ADP-ribose) polymerase; and the sequence RKCLQAGMNLEARKTKK (SEQ ID NO: 74) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

Multiplexed Nickase: Aspects of optimization and the teachings of Cas9 detailed in this application may also be used to generate Cas9 nickases. Cas9 nickases may be advantageously used in combination with pairs of guide RNAs to generate DNA double strand breaks with defined overhangs. When two pairs of guide RNAs are used, it is possible to excise an intervening DNA fragment. If an exogenous piece of DNA is cleaved by the two pairs of guide RNAs to generate compatible overhangs with the genomic DNA, then the exogenous DNA fragment may be ligated into the genomic DNA to replace the excised fragment. For example, this may be used to remove trinucleotide repeat expansion in the huntingtin (HTT) gene to treat Huntington's Disease.

Cas9 and its chimeric guide RNA, or combination of tracrRNA and crRNA. can be delivered either as DNA or RNA. Delivery of Cas9 and guide RNA both as RNA (normal or containing base or backbone modifications) molecules can be used to reduce the amount of time that Cas9 protein persist in the cell. This may reduce the level of off-target cleavage activity in the target cell. Since delivery of Cas9 as mRNA takes time to be translated into protein, it might be advantageous to deliver the guide RNA several hours following the delivery of Cas9 mRNA, to maximize the level of guide RNA available for interaction with Cas9 protein.

In situations where guide RNA amount is limiting, it may be desirable to introduce Cas9 as mRNA and guide RNA in the form of a DNA expression cassette with a promoter driving the expression of the guide RNA. This way the amount of guide RNA available will be amplified via transcription.

A variety of delivery systems can be introduced to introduce Cas9 (DNA or RNA) and guide RNA (DNA or RNA) into the host cell. These include the use of liposomes, viral vectors, electroporation, nanoparticles, nanowires (Shalek et al., Nano Letters, 2012), exosomes. Molecular trojan horses liposomes (Pardridge et al., Cold Spring Harb Protoc; 2010; doi: 10.1101/pdb.prot5407) may be used to deliver Cas9 and guide RNA across the blood brain barrier.

Discussion of guide RNAs for orthologs: In some embodiments, a guide sequence is selected to reduce the degree secondary structure within the guide RNA. In some embodiments, about or less than about 75%, 50%, 40%, 30%, 25%, 20%. 15%, 10%, 5%, 1%, or fewer of the nucleotides of the guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008. Cell 106(1): 23-24; and PA Carr and GM Church, 2009, Nature Biotechnology 27(12): 1151-62). A method of optimizing the guide RNA of a Cas9 ortholog comprises breaking up polyU tracts in the guide RNA. PolyU tracts that may be broken up may comprise a series of 4, 5, 6, 7, 8, 9 or 10 Us.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%. 40%, 50%, 60%, 70%. 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgtttttg-tactctcaagatttaGAAAtaaatcttgcagaagctacaaagataaggctt catgccgaaatcaacaccctgtcattttatggcagggtgttttcgttatttaaTTTTTT (SEQ ID NO: 75); (2) NNNNNNNNNNNNNNNNNNgtttttg-tactctcaGAAAtgcagaagctacaaagataaggcttcatgccgaaatca acaccctgtcattttatggcagggtgttttcgttatttaaTTTTTT (SEQ ID NO: 76); (3) NNNNNNNNNNNNNNgtttttgtactctcaGAAAtgcagaagctacaaagataaggcttcatgccgaaatca acaccctgtcattttatggcagggtgtTTTTTT (SEQ ID NO: 77); (4) NNNNNNNNNNNNNNNNNNNNgtttta-gagctaGAAAtagcaagttaaaataaggctagtccgttatcaacttgaaaa agtggcaccgagtcggtgcTTTTTT (SEQ ID NO: 78); (5) NNNNNNNNNNNNNNNNNNNNgtttta-gagctaGAAATAGcaagttaaaataaggctagtccgttatcaacttgaa aaagtgTTTTTTT (SEQ ID NO: 79); and (6) NNNNNNNNNNNNNNNNNNNNgtttta-gagctagAAATAGcaagttaaaataaggctagtccgttatcaTTTTT TTT (SEQ ID NO: 80). In some embodiments, sequences (1) to (3) are used in combination with Cas9 from S. thermophilus CRISPR1. In some embodiments, sequences (4) to (6) are used in combination with Cas9 from *S. pyogenes*. In some embodiments, the tracr sequence is a separate transcript from a transcript comprising the tracr mate sequence.

Discussion of tracr mates for orthologs: In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20. or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochorome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon. TIBTECH 11:167-175 (1993); Miller, Nature 357: 455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and V2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV and methods for preparing rAAV. For example, plasmid(s) containing or consisting essentially of the desired viral construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep.

The rAAV can be from an AAV as herein described, and advantageously can be an rAAV1, rAAV2, AAV5 or rAAV having hybrid or capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue, AAV8 for targeting of liver tissue.

In addition to 293 cells, other cells that can be used in the practice of the invention and the relative infectivity of certain AAV serotypes in vitro as to these cells (see Grimm, D. et al, J. Virol. 82: 5887-5911 (2008)) are as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA 1-terminator. Promoter-gRNA2-terminator . . . Promoter-gRNA (N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA 1-terminator, Promoter-gRNA2-terminator . . . Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

Two ways to package Cas9 coding nucleic acid molecules, e.g., DNA, into viral vectors to mediate genome modification in vivo are preferred:

To achieve NHEJ-mediated gene knockout:

Single virus vector:

Vector containing two or more expression cassettes:

Promoter-Cas9 coding nucleic acid molecule-terminator

Promoter-gRNA 1-terminator

Promoter-gRNA2-terminator

Promoter-gRNA(N)-terminator (up to size limit of vector)

Double virus vector:

Vector 1 containing one expression cassette for driving the expression of Cas9

Promoter-Cas9 coding nucleic acid molecule-terminator

Vector 2 containing one more expression cassettes for driving the expression of one or more guideRNAs Promoter-gRNA 1-terminator Promoter-gRNA(N)-terminator (up to size limit of vector)

To mediate homology-directed repair. In addition to the single and double virus vector approaches described above, an additional vector is used to deliver a homology-direct repair template.

Promoter used to drive Cas9 coding nucleic acid molecule expression can include: AAV1TR can serve as a promoter: this is advantageous for eliminating the need for an additional promoter element (which can take up space in the vector). The additional space freed up can be used to drive the expression of additional elements (gRNA, etc). Also, ITR activity is relatively weaker, so can be used to reduce toxicity due to over expression of Cas9.

For ubiquitous expression, can use promoters: CMV, CAG, CBh, PGK, SV40, Ferritin heavy or light chains, etc.

For brain expression, can use promoters: SynapsinI for all neurons, CaMKIIalpha for excitatory neurons, GAD67 or GAD65 or VGAT for GABAergic neurons, etc.

For liver expression, can use Albumin promoter

For lung expression, can use SP-B

For endothelial cells, can use ICAM

For hematopoietic cells can use IFNbeta or CD45

For Osteoblasts can use OG-2

Promoter used to drive guide RNA can include:

Pol III promoters such as U6 or H1

Use of Pol II promoter and intronic cassettes to express gRNA

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

Additional methods for the delivery of nucleic acids to cells are known to those skilled in the art. See, for example. US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4A, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KGI, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassus, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic plants and animals are known in the art, and generally begin with a method of cell transfection, such as described herein.

With recent advances in crop genomics, the ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to U.S. patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety. In an advantageous embodiment of the invention, the CRSIPR/Cas9 system is used to engineer microalgae (Example 7). Accordingly, reference herein to animal cells may also apply, mutatis mutandis, to plant cells unless otherwise apparent.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae). For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations apply as above for methods of modifying a target polynucleotide. In fact, these sampling, culturing and re-introduction options apply across the aspects of the present invention.

In one aspect, the invention provides kits containing any one or more of the elements disclosed in the above methods and compositions. Elements may provide individually or in combinations, and may provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

The break created by the CRISPR complex can be repaired by a repair processes such as the error prone non-homologous end joining (NHEJ) pathway or the high fidelity homology-directed repair (HDR). During these repair processes, an exogenous polynucleotide template can be introduced into the genome sequence. In some methods, the HDR process is used to modify a genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence has about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein. "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knock-out" of the target sequence.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency, for instance as described herein. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive in Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445, 934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent: polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPRTM (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 filed on Dec. 12, 2012 and 61/748,427 filed on Jan. 2, 2013. Such genes, proteins and pathways may be the target polynucleotide of a CRISPR complex.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB |

TABLE A-continued

| DISEASE/DISORDERS | GENE(S) |
|---|---|
| | (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Cc12; Cc2; cp (ceruloplasmin); Timp3; cathepsinD; Vldlr; Ccr2 |
| Schizophrenia | Neuregutin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; OSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn.); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for TBD; IL-6; IL-12 (IL-12a.; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10), Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FILT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |

TABLE B-continued

| | |
|---|---|
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular / Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, .DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr; Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, |

TABLE B-continued

| | |
|---|---|
| | PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NEKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2.; PLK1; AKT2; PIK3CA; CDK8; CREB1; PRKC1; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; RIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; ELF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A ; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; |

TABLE C-continued

| CELLULAR FUNCTION | GENES |
|---|---|
| | PPP1CC; PXN; VIL2; RAF1; GSN; DYRK1A; ITGR1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGE1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1 IKBKG; RELB; MAP3K7; MAP2K2; AKT1; AK2; PIK3R1; CHUK; STAT3; MAP2K1; NEKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NEKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NEKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; |

TABLE C-continued

| CELLULAR FUNCTION | GENES |
|---|---|
| | CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKC1; NFKB2; CAMK2A; PIK3CB; PPP2R1A; PIK3C3; MAPK8; PRKD1; ALDH1A1; MAPK3; NRIP1; KRAS; MAPKI3; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK. |
| PPAr/RXR Signaling | PRKAA2; EP300; INS; SMAD2; TRAF6; PPARA; FASN; RXRA; MAPK1.; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKC1; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKC1; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |

TABLE C-continued

| CELLULAR FUNCTION | GENES |
|---|---|
| NRF2-mediated Oxidative Stress Response | PRKCE; EP300; SOD2; PRKCZ; MAPK1; SQSTM1; NQO1; PIK3CA; PRKC1; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGER; FAS; CSF1; NFKB2; BCL2; MYH9; IGFIR; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIR5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FIT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |

TABLE C-continued

| CELLULAR FUNCTION | GENES |
|---|---|
| Amyotrophie Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; SUN; AKT3 |
| Synaptic, Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NEKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDX/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1.; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKC1; GNAQ; CAMK2A; PRRD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR | IRAK1; MYD88; TRAF6; PPARA; RXRA; ABCA1; MAPK8; ALDH1A1; GSTP1; MAPK9; ABCB1; TRAF2; |

TABLE C-continued

| CELLULAR FUNCTION | GENES |
|---|---|
| Function | TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G-2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/ Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPR1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |

TABLE C-continued

| CELLULAR FUNCTION | GENES |
|---|---|
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press. Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN asn so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion—related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C—C chemokine receptor type 5 (CCR5) encoded by the Ccr5 gene, the IgG receptor IIB (FCGR2b, also termed CD32) encoded by the Fcgr2b gene, or the Fc epsilon R1g (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin I2 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein). VAGFA (vascular endothelial growth factor A), VAGFB (vascular endothelial growth factor B), and VAGFC (vascular endothelial growth factor C), and any combination thereof.

Examples of proteins associated with prion diseases may include SOD I (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS I (nitric oxide synthase 1 (neuronal)), ADRA2A (adrenergic, alpha-2A-, receptor), ADRA2C (adrenergic, alpha-2C—, receptor), TACR1 (tachykinin receptor 1), or HTR2c (5-hydroxytryptamine (serotonin) receptor 2C), for example.

Examples of neurodevelopmental-associated sequences include A2BPI [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LISI-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Improvement of the Cas9 System for In Vivo Application

Applicants conducted a Metagenomic search for a Cas9 with small molecular weight. Most Cas9 orthologs are fairly large. Many known Cas9 orthologs are large and contain more than 1300 amino acids. For example the SpCas9 is around 1368aa long, which is too large to be easily packaged into viral vectors for delivery. A graph representing the length distribution of Cas9 homologs is shown in FIG. 6: The graph is generated from sequences deposited in GenBank. Some of the sequences may have been mis-annotated and therefore the exact frequency for each length may not necessarily be accurate. Nevertheless it provides a glimpse at distribution of Cas9 proteins and suggest that there are shorter Cas9 homologs.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo animal models. In a preferred embodiment of the invention, the Cas9 protein from *S. aureus* is used.

*Campylobacter jejuni* Cas9 (CjCas9)

```
                                                  (SEQ. ID NO: 81)
MARILAFDIGISSIGWAFSENDELKDCGVRIFTKVENPKTGESLALPRRL
ARSARKRLARRKARLNHLKHLIANEFKLNYEDYQSFDESLAKAYKGSLIS
PYELRFRALNELLSKQDFARVILHIAKRRGYDDIKNSDDKEKGAILKAIK
QNEEKLANYQSVGEYLYKEYFQKFKENSKEFTNVRNKKESYERCIAQSFL
KDELKLIFKKQREFGFSFSKKFEEEVLSVAFYKRALKDFSHLVGNCSFFT
DEKRAPKNSPLAFMFVALTRIINLLNNLKNTEGILYTKDDLNALLNEVLK
NGTLTYKQTKKLLGLSDDYEFKGEKGTYFIEFKKYKEFIKALGEHNLSQD
DLNEIAKDITLIKDEIKLKKALAKYDLNQNQIDSLSKLEFKDHLNISFKA
LKLVTPLMLEGKKYDEACNELNLKVAINEDKKDFLPAFNETYYKDEVTNP
VVLRAIKEYRKVLNALLKKYGKVHKINIELAREVGKNHSQRAKIEKEQNE
NYKAKKDAELECEKLGLKINSKNILKLRLFKEQKEFCAYSEGEKIKISDL
QDEKMLEIDHIYPYSRSFDDSYMNKVLVFTKQNQEKLNQTPFEAFGNDSA
KWQKIEVLAKNLPTKKQKRILDKNYKDKEQKNFKDRNLNDTRYIARLVLN
YTKDYLDFLPLSDDENTKLNDTQKGSKVHVEAKSGMLTSALRHTWGFSAK
DRNNHLHHAIDAVIIAYANNSIVKAFSDFKKEQESNSAELYAKKISELDY
KNKRKFFEPFSGFRQKVLDKIDEIFVSKPERKKPSGALHEETFRKEEEFY
QSYGGKEGVLKALELGKIRKVNGKIVKNGDMFRVDIFKHKKTNKFYAVPI
YTMDFALKVLPNKAVARSKKGEIKDWILMDENYEFCFSLYKDSLILIQTK
DMQEPEFVYYNAFTSSTVSLIVSKHDNKFETLSKNQKILFKNANEKEVIA
KSIGIQNLKVFEKYIVSALGEVTKAEFRQREDFKK.
```

The putative tracrRNA element for this CjCas9 is:

(SEQ ID NO: 82)
TATAATCTCATAAGAAATTTAAAAAGGGACTAAAATAAAGAGTTTGCGGG

ACTCTGCGGGGTTACAATCCCCTAAAACCGCTTTTAAAATT

The Direct Repeat sequence is:

(SEQ ID NO: 83)
GTTTTAGTCCCTTTTTAAATTTCTTTATGGTAAAAT

An example of a chimeric guideRNA for CjCas9 is:

(SEQ ID NO: 84)
NNNNNNNNNNNNNNNNNNNNGUUUUAGUCCCGAAAGGGACUAAAAUAAAG

AGUUUGCGGGACUCUGCGGGGUUACAAUCCCCUAAAACCGCUUUU

Example 2

Cas9 Diversity and Chimeric RNAs

The wild-type CRISPR-Cas system is an adaptive immune mechanism against invading exogenous DNA employed by diverse species across bacteria and archaea. The type II CRISPR-Cas system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (FIGS. 4 and 5A-F).

In some embodiments, the tracr mate sequences or the direct repeats are either downloaded from the CRISPRs database or identified in silico by searching for repetitive motifs that are 1. found in a 2 kb window of genomic sequence flanking the type II CRISPR locus, 2. span from 20 to 50 bp, and 3. interspaced by 20 to 50 bp. In some embodiments, 2 of these criteria may be used, for instance 1 and 2, 2 and 3, or 1 and 3. In some embodiments, all 3 criteria may be used. In some embodiments candidate tracrRNA are subsequently predicted by 1. sequence homology to direct repeats (motif search in Geneious with up to 18-bp mismatches), 2. presence of a predicted Rho-independent transcriptional terminator in direction of transcription, and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used. In some embodiments, chimeric synthetic guide RNAs (sgRNAs) designs incorporate at least 12 bp of duplex structure between the direct repeat and tracrRNA.

Figure 8F:
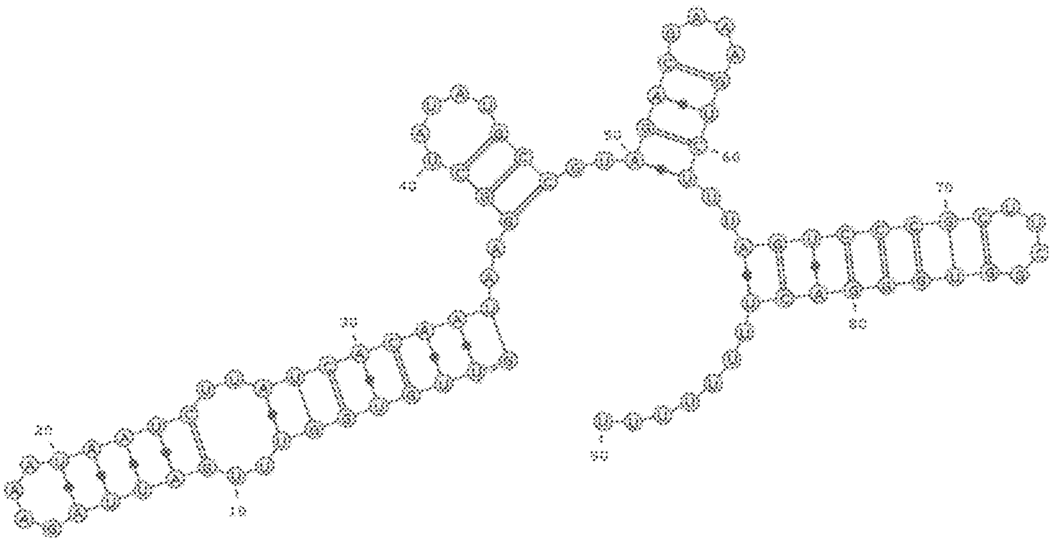
Figure 8H:
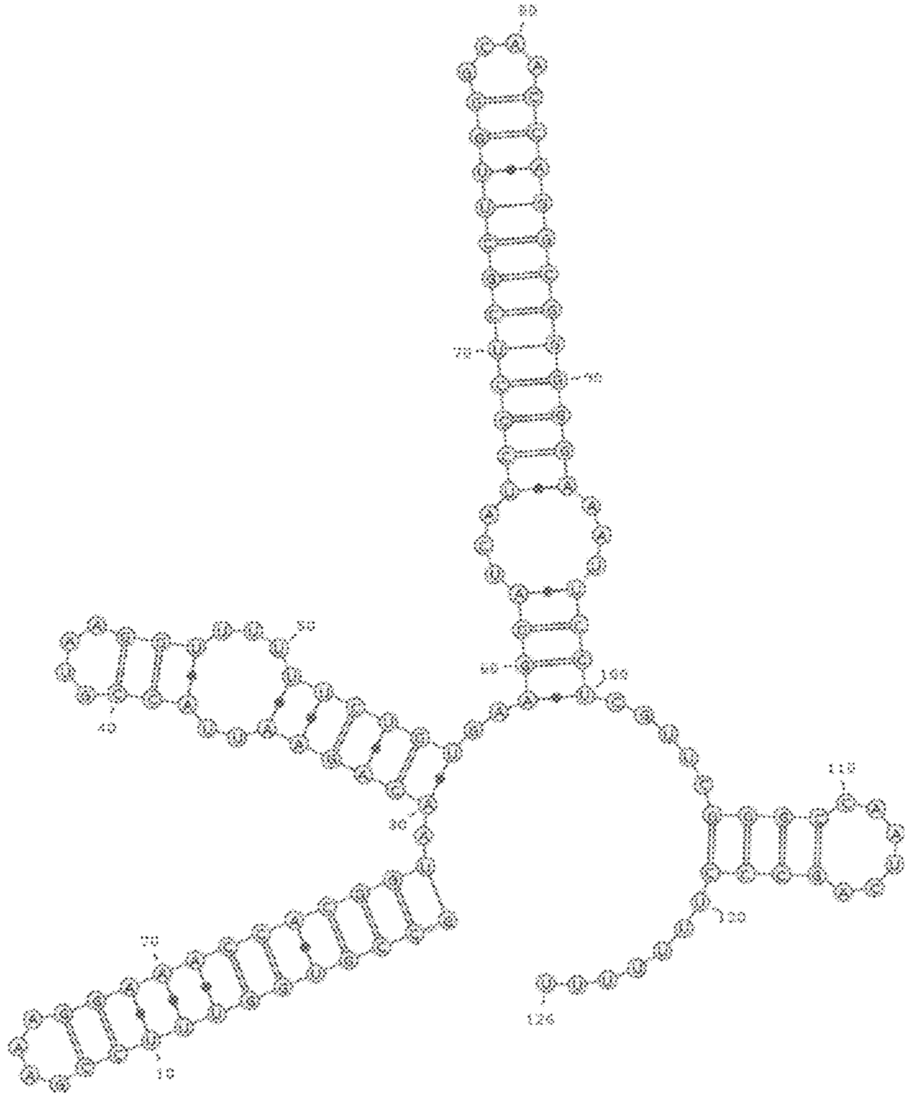
Figure 8I:
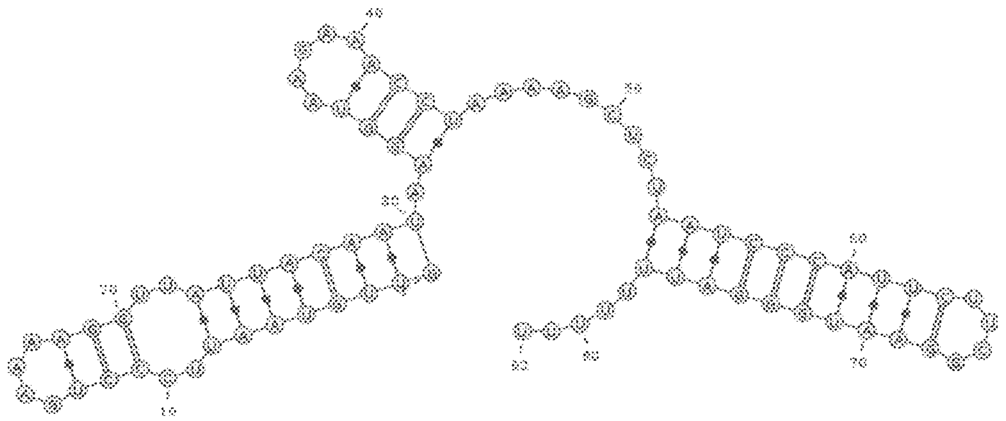
Figure 10A:
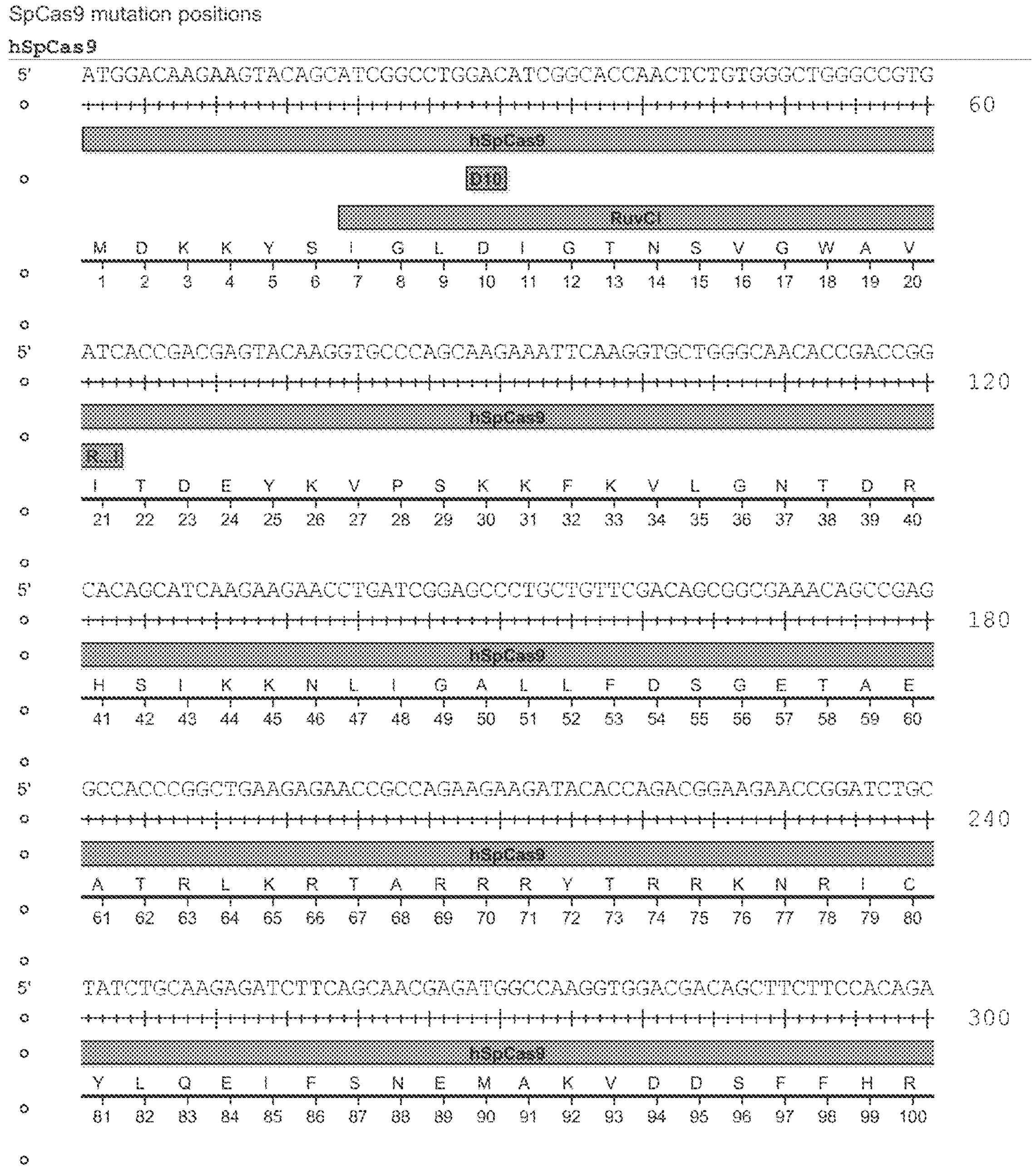
Figure 10M:
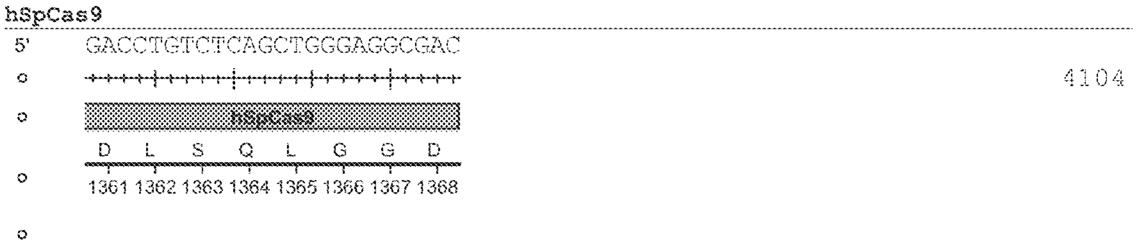

The list of the human codon optimized Cas9 ortholog sequences to pair with the chimeric RNAs provided in FIGS. 8 A-J is provided in FIGS. 9 A-O. Applicants have also shown that the Cas9 orthologs can cleave their targets in in vitro cleavage assays (FIG. 16). The CRISPR loci in some of these families is depicted in FIG. 11. The corresponding guide RNA sequences are shown in FIG. 12. Applicants systematically analyzed the genomic DNA sequence within ~2 kb of the Cas9 proteins using custom computational analysis code and identified direct repeats ranging from 35 bp to 50 bp, with intervening spacers ranging from 29 bp to 35 bp. Based on the direct repeat sequence, Applicants computationally searched for tracrRNA candidate sequences with the following criteria: outside the crRNA array but containing high degree of homology to direct repeats (as required for direct repeat:tracrRNA base-pairing; custom computational analysis), outside the coding regions of the protein components, containing Rho-independent transcriptional termination signals ~60 bp-120 bp downstream from region of homology from with direct repeats, and co-folding with direct repeat to form a duplex, followed by two or more hairpin structures in the distal end of tracrRNA sequence. Based on these prediction criteria, Applicants selected an initial set of 18 Cas9 proteins and their uniquely associated direct repeats and tracrRNAs distributed across all five Cas9 families. Applicants further generated a set of 18 chimeric RNA structures that preserved the sequence and secondary structures of the native direct repeat: tracrRNA duplex while shortening the region of base-pairing and fusing the two RNA elements through an artificial loop (FIGS. 8A-J).

Example 3

Cas9 Orthologs

Applicants have generated codon optimized Cas9 orthologs to advance expression in eukaryotic cells.

Example of a human codon optimized sequence (i.e. being optimized for expression in humans) sequence:SaCas9: is provided below (SEQ ID NO: 85)
ACCGGTGCCACCATGTACCCATACGATGTTCCAGATTACGCTTCGCCGAAGAAAAAGCGCAA

GGTCGAAGCGTCCATGAAAAGGAACTACATTCTGGGGCTGGACATCGGGATTACAAGCGTG

GGGTATGGGATTATTGACTATGAAACAAGGGACGTGATCGACGCAGGCGTCAGACTGTTCA

AGGAGGCCAACGTGGAAAACAATGAGGGACGGAGAAGCAAGAGGGGAGCCAGGCGCCTGA

-continued

AACGACGGAGAAGGCACAGAATCCAGAGGGTGAAGAAACTGCTGTTCGATTACAACCTGCT

GACCGACCATTCTGAGCTGAGTGGAATTAATCCTTATGAAGCCAGGGTGAAAGGCCTGAGTC

AGAAGCTGTCAGAGGAAGAGTTTTCCGCAGCTCTGCTGCACCTGGCTAAGCGCCGAGGAGT

GCATAACGTCAATGAGGTGGAAGAGGACACCGGCAACGAGCTGTCTACAAAGGAACAGATC

TCACGCAATAGCAAAGCTCTGGAAGAGAAGTATGTCGCAGAGCTGCAGCTGGAACGGCTGA

AGAAAGATGGCGAGGTGAGAGGGTCAATTAATAGGTTCAAGACAAGCGACTACGTCAAAGA

AGCCAAGCAGCTGCTGAAAGTGCAGAAGGCTTACCACCAGCTGGATCAGAGCTTCATCGAT

ACTTATATCGACCTGCTGGAGACTCGGAGAACCTACTATGAGGGACCAGGAGAAGGGAGCC

CCTTCGGATGGAAAGACATCAAGGAATGGTACGAGATGCTGATGGGACATTGCACCTATTTT

CCAGAAGAGCTGAGAAGCGTCAAGTACGCTTATAACGCAGATCTGTACAACGCCCTGAATG

ACCTGAACAACCTGGTCATCACCAGGGATGAAAACGAGAAACTGGAATACTATGAGAAGTT

CCAGATCATCGAAAACGTGTTTAAGCAGAAGAAAAAGCCTACACTGAAACAGATTGCTAAG

GAGATCCTGGTCAACGAAGAGGACATCAAGGGCTACCGGGTGACAAGCACTGGAAAACCAG

AGTTCACCAATCTGAAAGTGTATCACGATATTAAGGACATCACAGCACGGAAAGAAATCAT

TGAGAACGCCGAACTGCTGGATCAGATTGCTAAGATCCTGACTATCTACCAGAGCTCCGAGG

ACATCCAGGAAGAGCTGACTAACCTGAACAGCGAGCTGACCCAGGAAGAGATCGAACAGAT

TAGTAATCTGAAGGGGTACACCGGAACACACAACCTGTCCCTGAAAGCTATCAATCTGATTC

TGGATGAGCTGTGGCATACAAACGACAATCAGATTGCAATCTTTAACCGGCTGAAGCTGGTC

CCAAAAAAGGTGGACCTGAGTCAGCAGAAAGAGATCCCAACCACACTGGTGGACGATTTCA

TTCTGTCACCCGTGGTCAAGCGGAGCTTCATCCAGAGCATCAAAGTGATCAACGCCATCATC

AAGAAGTACGGCCTGCCCAATGATATCATTATCGAGCTGGCTAGGGAGAAGAACAGCAAGG

ACGCACAGAAGATGATCAATGAGATGCAGAAACGAAACCGGCAGACCAATGAACGCATTG

AAGAGATTATCCGAACTACCGGGAAAGAGAACGCAAAGTACCTGATTGAAAAAATCAAGCT

GCACGATATGCAGGAGGGAAAGTGTCTGTATTCTCTGGAGGCCATCCCCCTGGAGGACCTGC

TGAACAATCCATTCAACTACGAGGTCGATCATATTATCCCCAGAAGCGTGTCCTTCGACAAT

TCCTTTAACAACAAGGTGCTGGTCAAGCAGGAAGAGAACTCTAAAAAGGGCAATAGGACTC

CTTTCCAGTACCTGTCTAGTTCAGATTCCAAGATCTCTTACGAAACCTTTAAAAAGCACATTC

TGAATCTGGCCAAAGGAAAGGGCCGCATCAGCAAGACCAAAAAGGAGTACCTGCTGGAAG

AGCGGGACATCAACAGATTCTCCGTCCAGAAGGATTTTATTAACCGGAATCTGGTGGACACA

AGATACGCTACTCGCGGCCTGATGAATCTGCTGCGATCCTATTTCCGGGTGAACAATCTGGA

TGTGAAAGTCAAGTCCATCAACGGCGGGTTCACATCTTTTCTGAGGCGCAAATGGAAGTTTA

AAAAGGAGCGCAACAAAGGGTACAAGCACCATGCCGAAGATGCTCTGATTATCGCAAATGC

CGACTTCATCTTTAAGGAGTGGAAAAAGCTGGACAAAGCCAAGAAAGTGATGGAGAACCAG

ATGTTCGAAGAGAAGCAGGCCGAATCTATGCCCGAAATCGAGACAGAACAGGAGTACAAGG

AGATTTTCATCACTCCTCACCAGATCAAGCATATCAAGGATTTCAAGGACTACAAGTACTCT

CACCGGGTGGATAAAAAGCCCAACAGAGAGCTGATCAATGACACCCTGTATAGTACAAGAA

AAGACGATAAGGGGAATACCCTGATTGTGAACAATCTGAACGGACTGTACGACAAAGATAA

TGACAAGCTGAAAAAGCTGATCAACAAAAGTCCCGAGAAGCTGCTGATGTACCACCATGAT

CCTCAGACATATCAGAAACTGAAGCTGATTATGGAGCAGTACGGCGACGAGAAGAACCCAC

TGTATAAGTACTATGAAGAGACTGGGAACTACCTGACCAAGTATAGCAAAAAGGATAATGG

CCCCGTGATCAAGAAGATCAAGTACTATGGGAACAAGCTGAATGCCCATCTGGACATCACA

-continued

```
GACGATTACCCTAACAGTCGCAACAAGGTGGTCAAGCTGTCACTGAAGCCATACAGATTCG

ATGTCTATCTGGACAACGGCGTGTATAAATTTGTGACTGTCAAGAATCTGGATGTCATCAAA

AAGGAGAACTACTATGAAGTGAATAGCAAGTGCTACGAAGAGGCTAAAAAGCTGAAAAAG

ATTAGCAACCAGGCAGAGTTCATCGCCTCCTTTTACAACAACGACCTGATTAAGATCAATGG

CGAACTGTATAGGGTCATCGGGGTGAACAATGATCTGCTGAACCGCATTGAAGTGAATATG

ATTGACATCACTTACCGAGAGTATCTGGAAAACATGAATGATAAGCGCCCCCCTCGAATTAT

CAAAACAATGCCTCTAAGACTCAGAGTATCAAAAAGTACTCAACCGACATTCTGGGAAAC

CTGTATGAGGTGAAGAGCAAAAAGCACCCTCAGATTATCAAAAAGGGCTAAGAATTC
```

Figure 15:
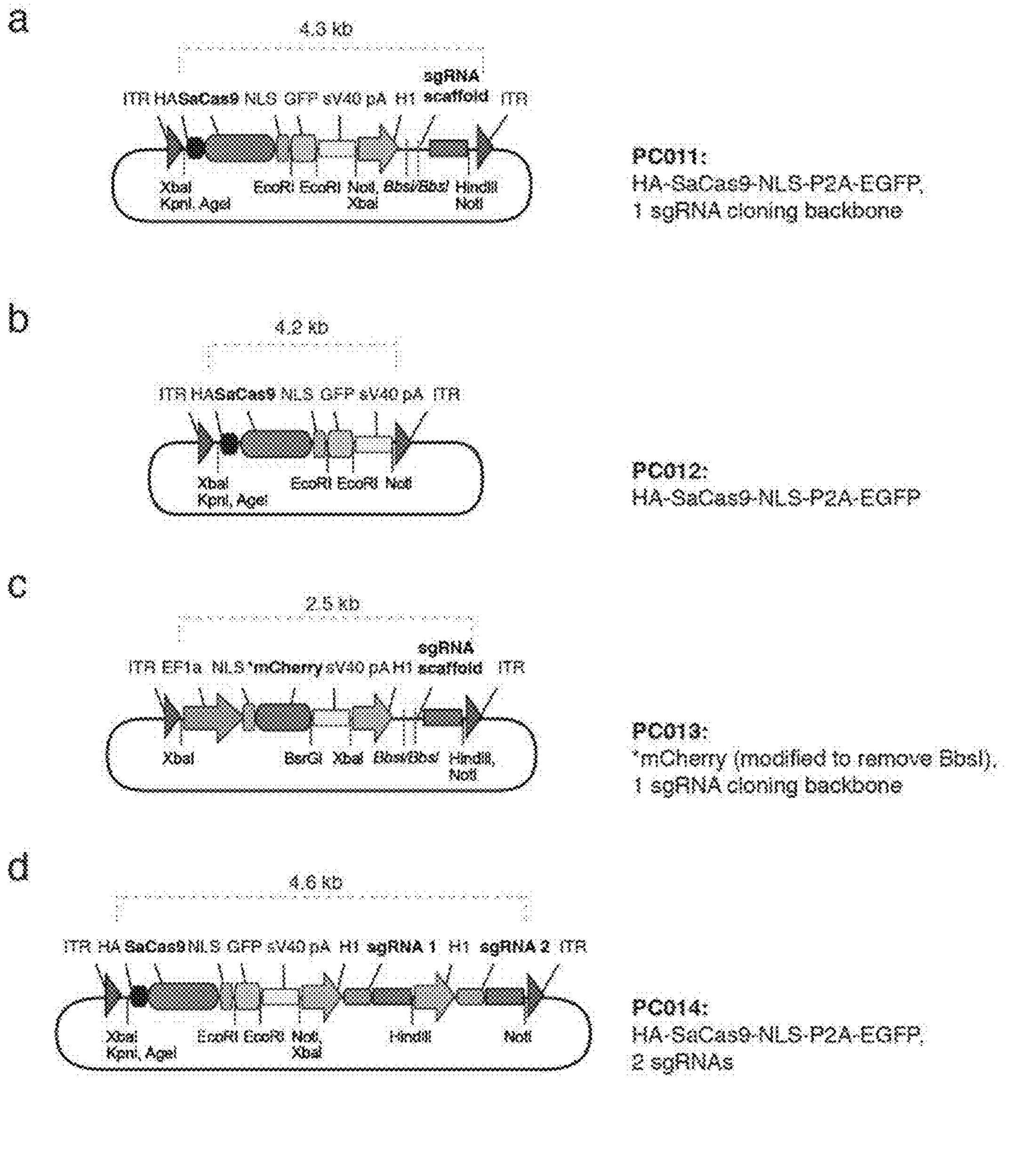
FIG. 15A-D shows single and multiple vector designs for SaCas9.

Applicants analyzed Cas9 orthologs to identify the relevant PAM sequences and the corresponding chimeric guide RNA as indicated in FIG. 13A-II. This expanded set of PAMs provides broader targeting across the genome and also significantly increases the number of unique target sites and provides potential for identifying novel Cas9s with increased levels of specificity in the genome. Applicants determined the PAM for *Staphylococcus aureus* subspecies *Aureus* Cas9 to be NNGRR (FIG. 14). *Staphylococcus aureus* subspecies *Aureus* Cas9 is also known as SaCas9. FIG. 15 *a-d* provides SaCas9 single or multiple vector designs.

Figure 7:
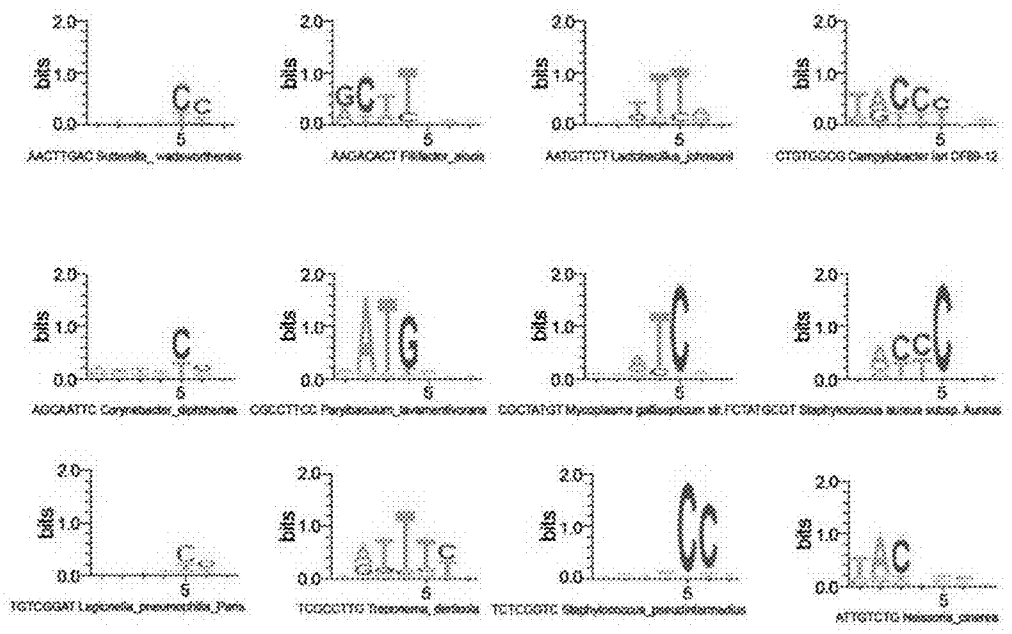
FIG. 7 shows a representation of the sequence logos of the PAMs of the Cas9 orthologs as reverse complements.

FIG. 7 show sequence logos for putative PAMs as indicated by reverse complements. Cas9 orthologs and their respective sgRNAs were used to cleave a library of targets bearing a randomized PAM (7-bp sequence immediately 3' of the target sequence). Cleaved products were isolated and deep-sequenced to yield 7-bp candidate sequences that were permissive to cleavage for each Cas9 ortholog. For each Cas9 ortholog, consensus PAMs were determined by aligning all 7-bp candidate sequences. (FIGS. 7 and 21).

Further work examining the thermodynamics and in vivo stability of sgRNA-DNA duplexes will likely yield additional predictive power for off-target activity, while exploration of SpCas9 mutants and orthologs may yield novel variants with improved specificity. The specificity of Cas9 orthologs can be further evaluated by testing the ability of each Cas9 to tolerate mismatches between the guide RNA and its DNA target.

Example 4

Cas9 Mutations

In this example, Applicants show that the following mutations can convert SpCas9 into a nicking enzyme: D10A, E762A, H840A, N854A, N863A, D986A.

Applicants provide sequences showing where the mutation points are located within the SpCas9 gene (FIG. 10A-M). Applicants also show that the nickases are still able to mediate homologous recombination. Furthermore. SpCas9 with these mutations (individually) reduce the level of double strand break. Cas9 orthologs all share the general organization of 3-4 RuvC domains and a HNH domain (FIG. 19). The 5' most RuvC domain cleaves the non complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

Example 5

Cas9 Functional Optimization

For enhanced function or to develop new functions, Applicants generate chimeric Cas9 proteins by combining fragments from different Cas9 orthologs.

For instance, Applicants fused the N-term of St1Cas9 (fragment from this protein is in bold) with C-term of SpCas9 (fragment from this protein is underlined).

>St1(N)Sp(C)Cas9

(SEQ ID NO: 86)

MSDLVLGLDIGIGSVGVGILNKVTGEIIHKNSRIFPAAQAENNLVRRTNR

QGRRLARRKKHRRVRLNRLFEESGLITDFTKISINLNPYQLRVKGLTDEL

SNEELFIALKNMVKHRGISYLDDASDDGNSSVGDYAQIVKENSKQLETKT

PGQIQLERYQTYGQLRGDFTVEKDGKKHRLINVFPTSAYRSEALRILQTQ

QEFNPQITDEFINRYLEILTGKRKYYHGPGNEKSRTDYGRYRTSGETLDN

IFGILIGKCTFYPDEFRAAKASYTAQEFNLLNDLNNLTVPTETKKLSKEQ

KNQIINYVKNEKAMGPAKLFKYIAKLLSCDVADIKGYRIDKSGKAEIHTF

EAYRKMKTLETLDIEQMDRETLDKLAYVLTLNTEREGIQEALEHEFADGS

FSQKQVDELVQFRKANSSIFGKGWHNFSVKLMMELIPELYETSEEQMTIL

TRLGKQKTTSSSNKTKYIDEKLLTEEIYNPVVAKSVRQAIKIVNAAIKEY

GDFDNIVIEMARENQTTQKGQKNSRERMKRIEEGIKELGSQILKEHPVEN

TQLQNEKLYLYYLQNGRDMYVDQELDINRLSDYDVDHIVPQSFLKDDSID

NKVLTRSDKNRGKSDNVPSEEVVKKMKNYWRQLLNAKLITQRKFDNLTKA

ERGGLSELDKAGFIKRQLVETRQITKHVAQILDSRMNTKYDENDKLIREV

KVITLKSKLVSDFRKDFQFYKVREINNYHHAHDAYLNAVVGTALIKKYPK

LESEFVYGDYKVYDVRKMIAKSEQEIGKATAKYFFYSNIMNFFKTEITLA

NGEIRKRPLIETNGETGEIVWDKGRDFATVRKVLSMPQVNIVKKTEVQTG

GFSKESILPKRNSDKLIARKKDWDPKKYGGFDSPTVAYSVLVVAKVEKGK

SKKLKSVKELLGITIMERSSFEKNPIDFLEAKGYKEVKKDLIIKLPKYSL

FELENGRKRMLASAGELQKGNELALPSKYVNFLYLASHYEKLKGSPEDNE

-continued

QKQLFVEQHKHYLDEIIEQISEFSKRVILADANLDKVLSAYNKHRDKPIR

EQAENIIHLFTLTNLGAPAAFKYFDTTIDRKRYTSTKEVLDATLIHQSIT

GLYETRIDLSQLGGD

>Sp(N)St1(C)Cas9

(SEQ ID NO: 87)

MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKEPENIVIEMARETNEDDEKKAIQKIQKANKDEKDAAMLKAANQYN

GKAELPHSVFHGHKQLATKIRLWHQQGERCLYTGKTISIHDLINNSNQFE

VDHILPLSITFDDSLANKVLVYATANQEKGQRTPYQALDSMDDAWSFREL

KAFVRESKTLSNKKKEYLLTEEDISKFDVRKKFIERNLVDTRYASRVVLN

ALQEHFRAHKIDTKVSVVRGQFTSQLRRHWGIEKTRDTYHHHAVDALIIA

ASSQLNLWKKQKNTLVSYSEDQLLDIETGELISDDEYKESVFKAPYQHFV

DTLKSKEFEDSILFSYQVDSKFNRKISDATIYATRQAKVGKDKADETYVL

GKIKDIYTQDGYDAFMKIYKKDKSKFLMYRHDPQTFEKVIEPILENYPNK

QINEKGKEVPCNPFLKYKEEHGYIRKYSKKGNGPEIKSLKYYDSKLGNHI

DITPKDSNNKVVLQSVSPWRADVYFNKTTGKYEILGLKYADLQFEKGTGT

YKISQEKYNDIKKKEGVDSDSEFKFTLYKNDLLLVKDTETKEQQLFRFLS

RTMPKQKHYVELKPYDKQKFEGGEALIKVLGNVANSGQCKKGLGKSNISI

YKVRTDVLGNQHIIKNEGDKPKLDF

Figure 17:
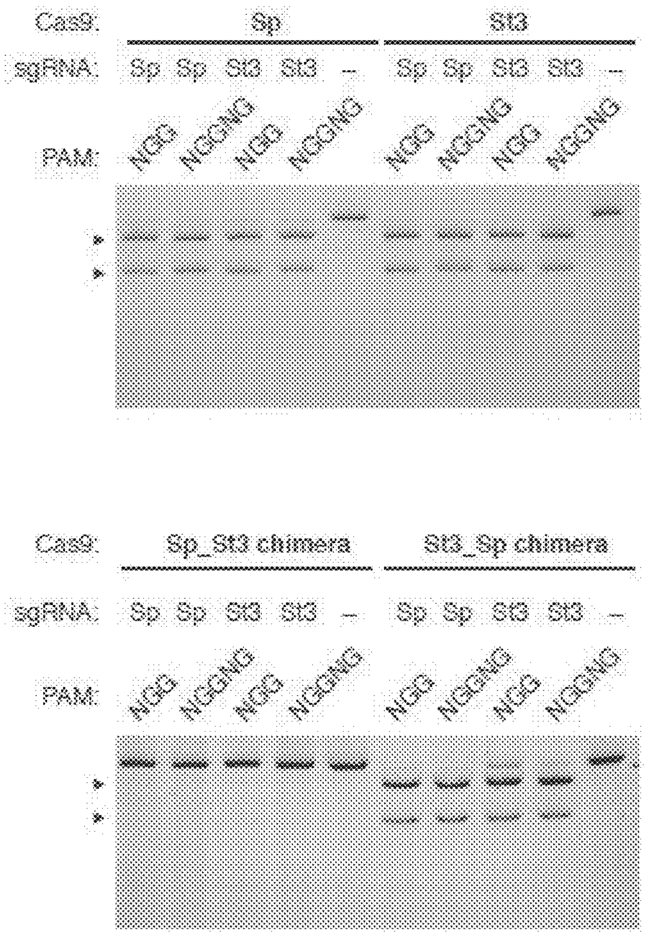
FIG. 17 shows in vitro cleavage by SpCas9, St3Cas9, Sp_St3 chimera and St3_Sp chimera. The PAMs for St3Cas9 and St3_Sp chimeric Cas9 are NGG.
Figure 18:
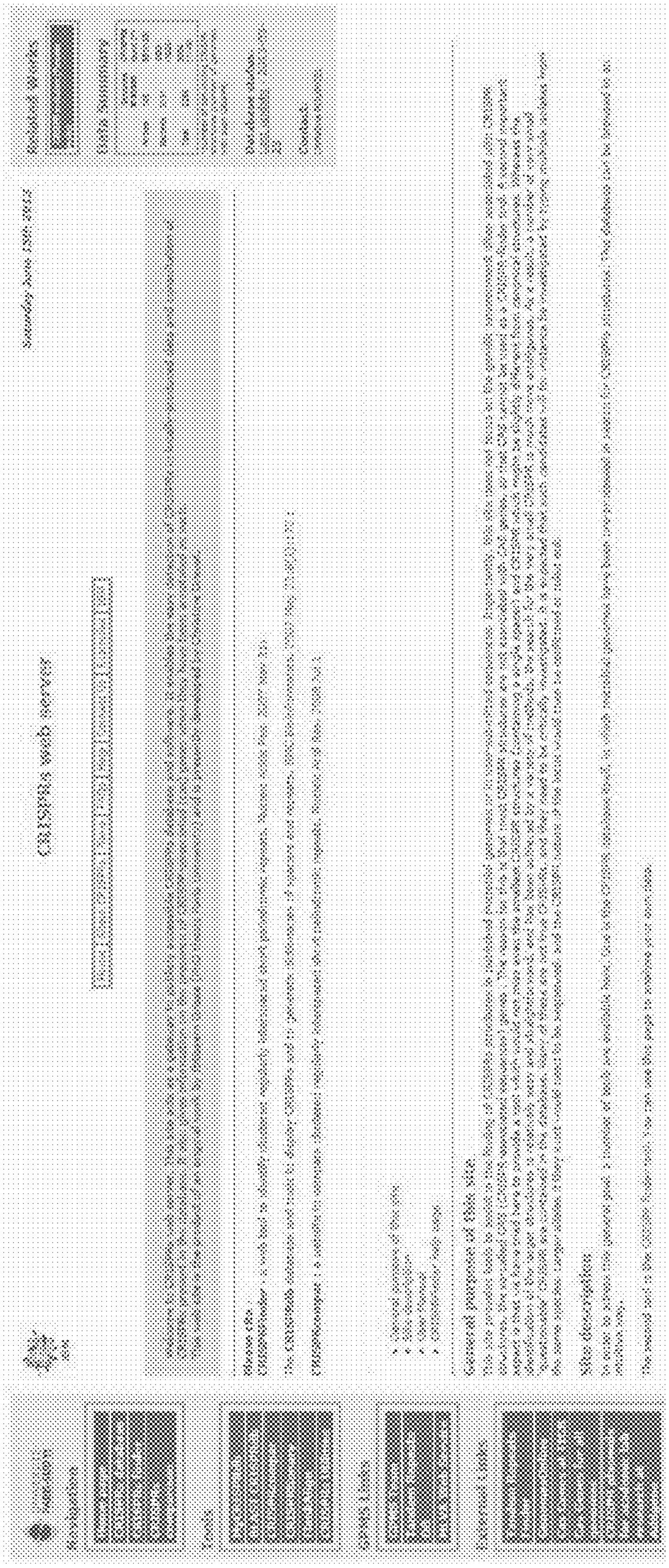
FIG. 18 shows an image of the CRISPRs web server.
Figure 20:
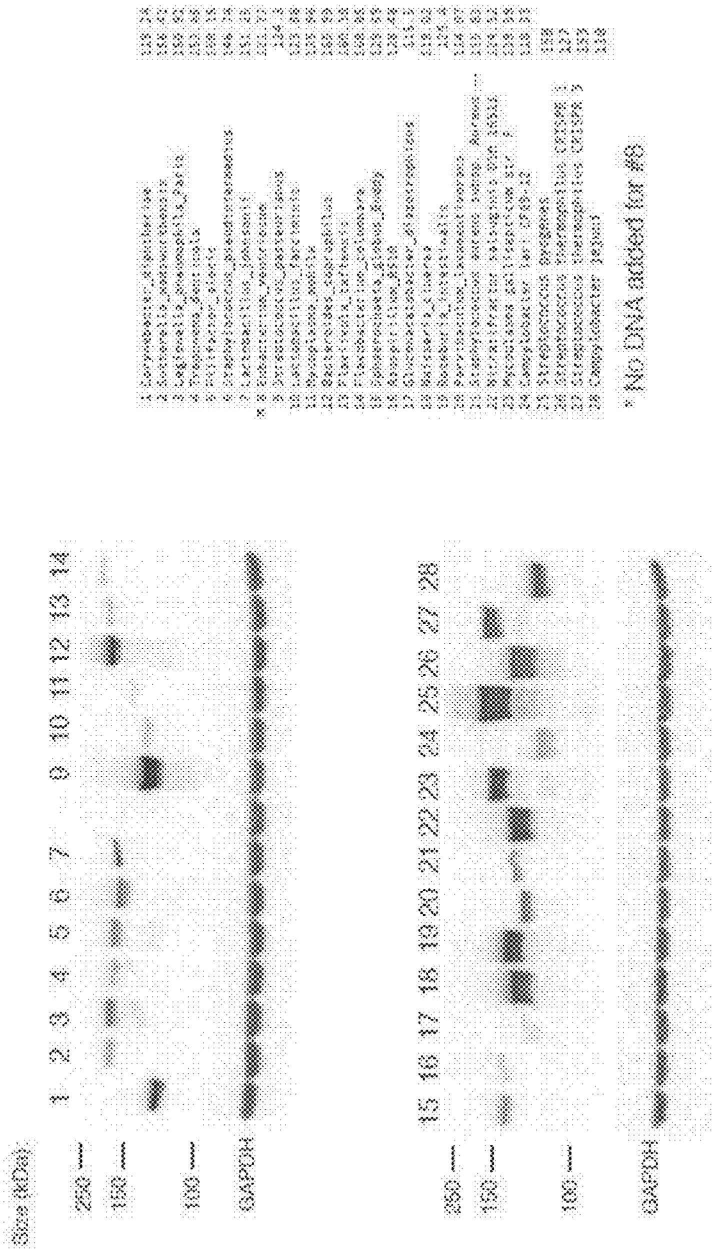
FIG. 20 shows a western blot showing that Cas9 orthologs are expressed in HEK 293FT cells; DNA plasmids encoding Cas9 orthologs are transfected into HEK 293FT cells and cell lysates are harvested for Western blot. No DNA is transfected for Cas9 ortholog #8.
Figure 22:
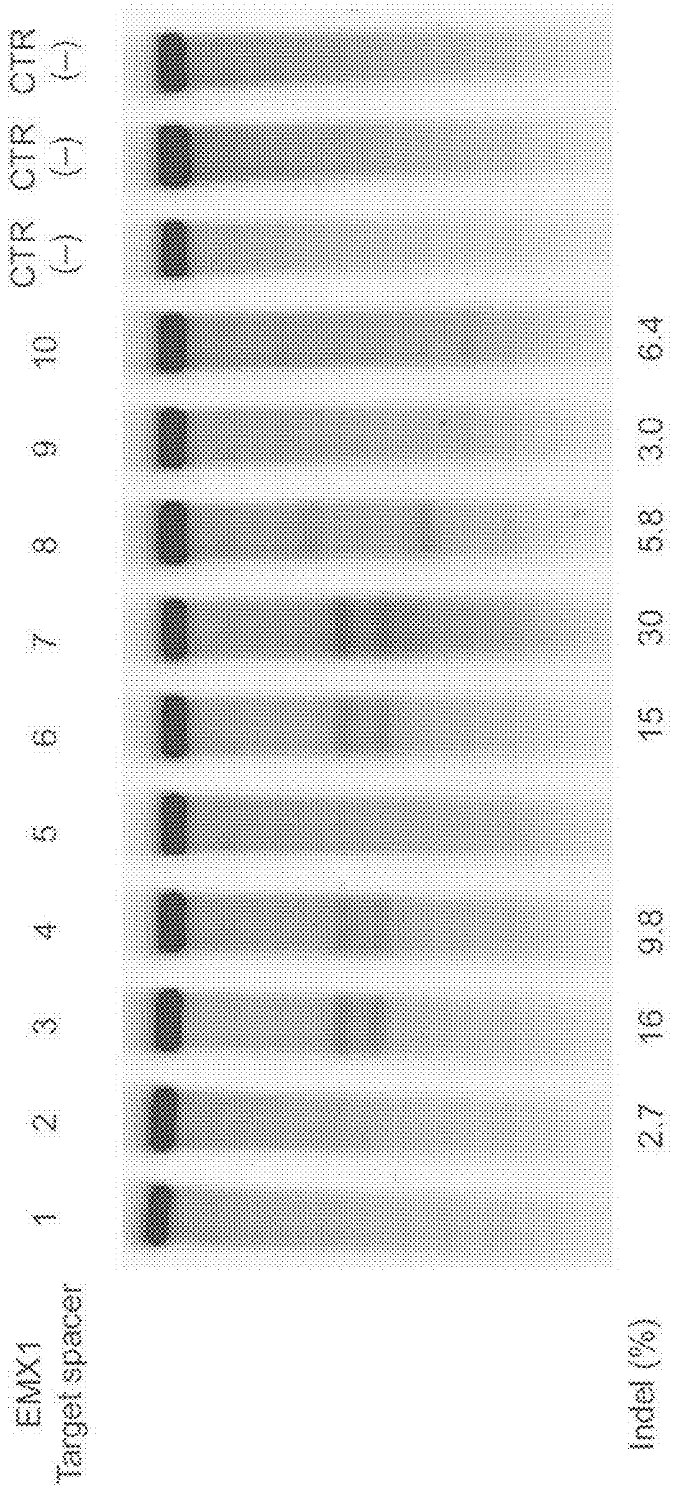
FIG. 22 shows a Representative Surveyor Gel showing genomic cleavage by SaCas9.
Figure 23:
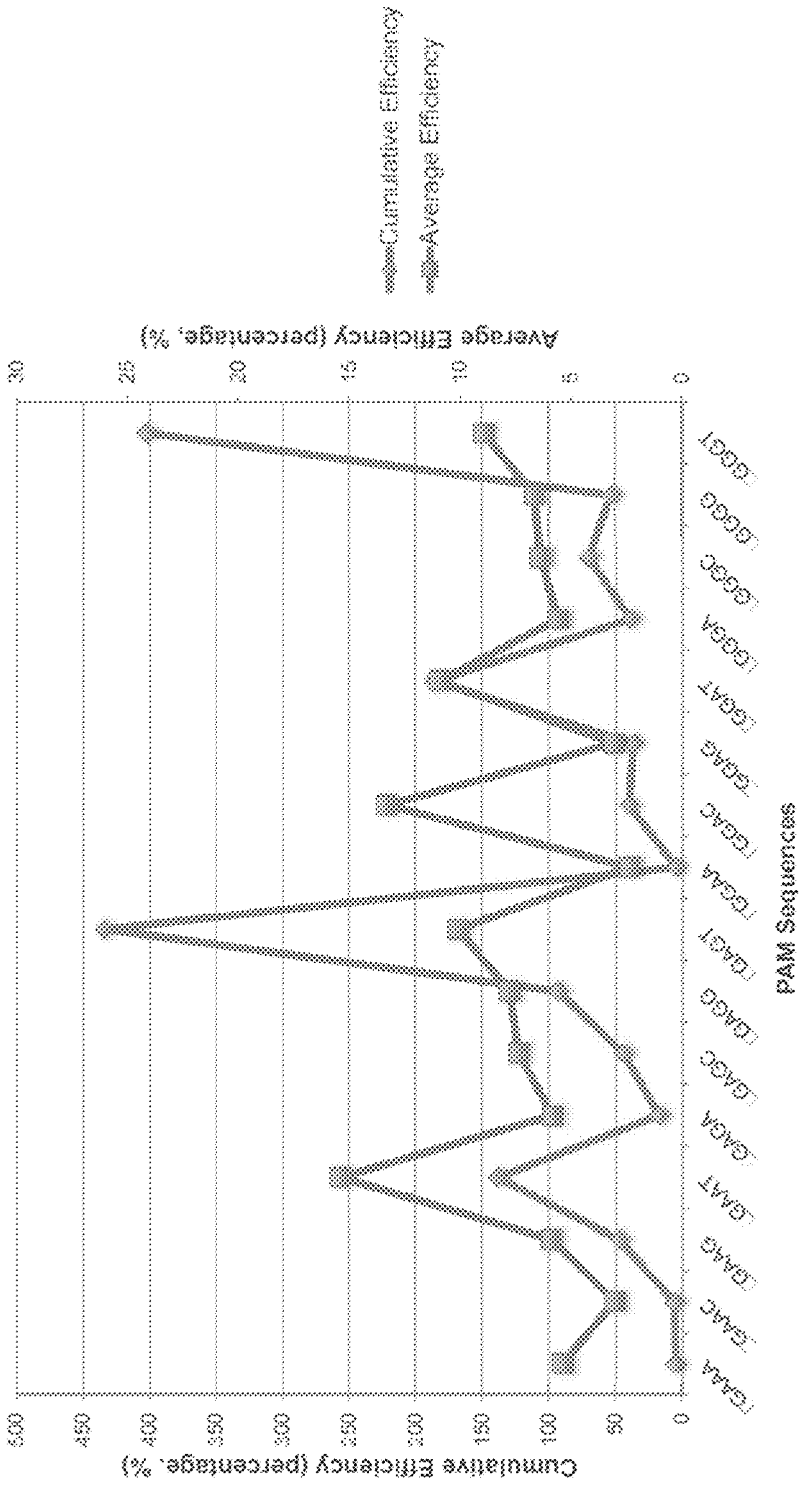
FIG. 23 shows Genome Cleavage Efficiency of PAM Sequences (All targets).
Figure 24:
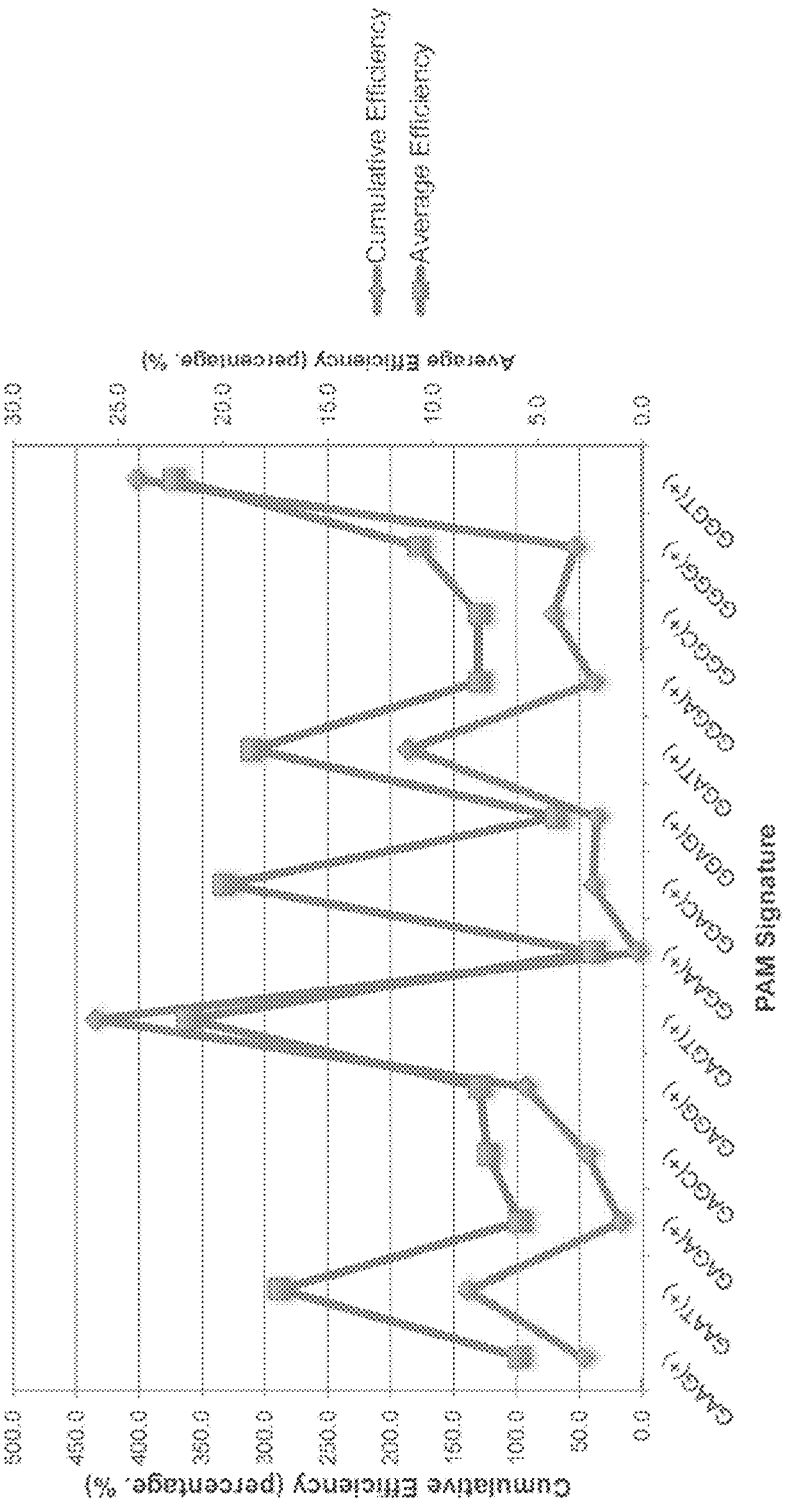
FIG. 24 shows Genome Cleavage Efficiency of PAM Sequences (Cleaved targets)
Figure 25:
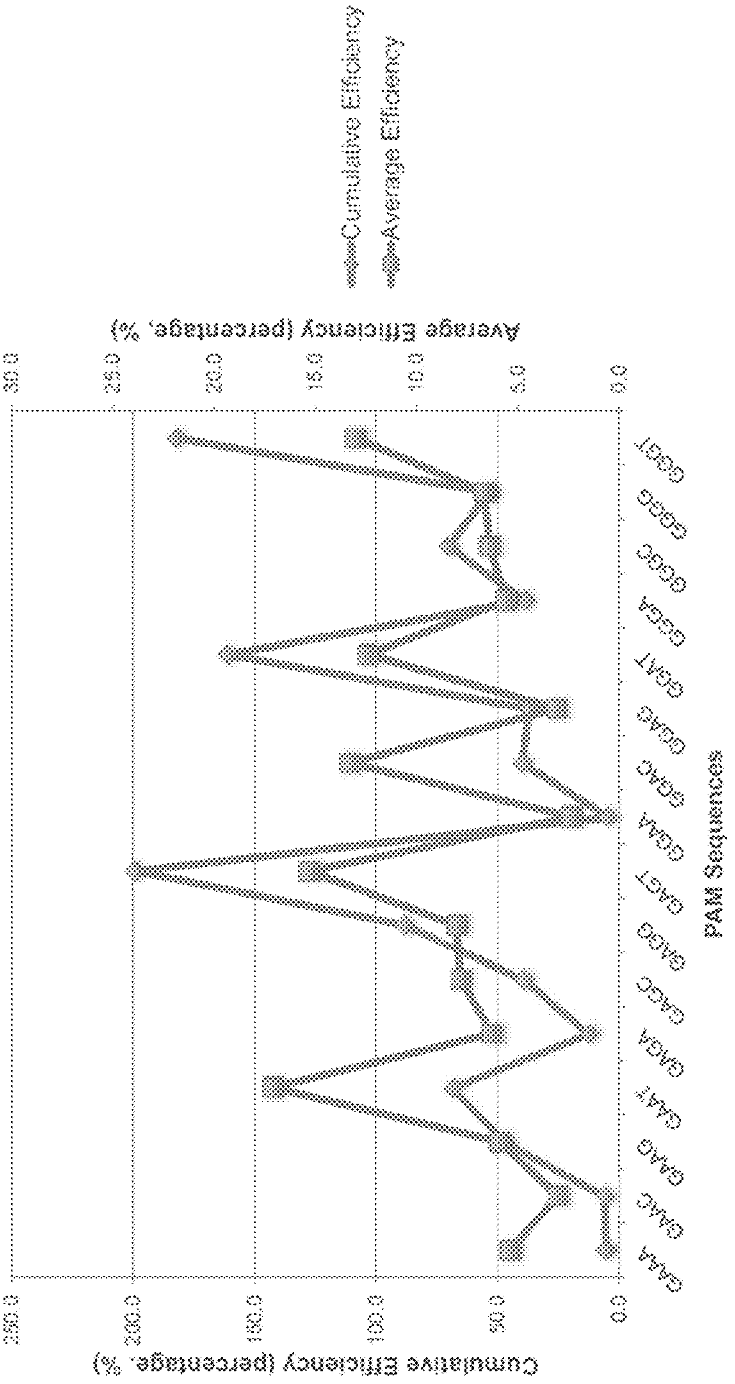
FIG. 25 shows Genome Cleavage Efficiency of PAM Sequences (All targets, discard low-efficiency and orphan targets).
Figure 26:
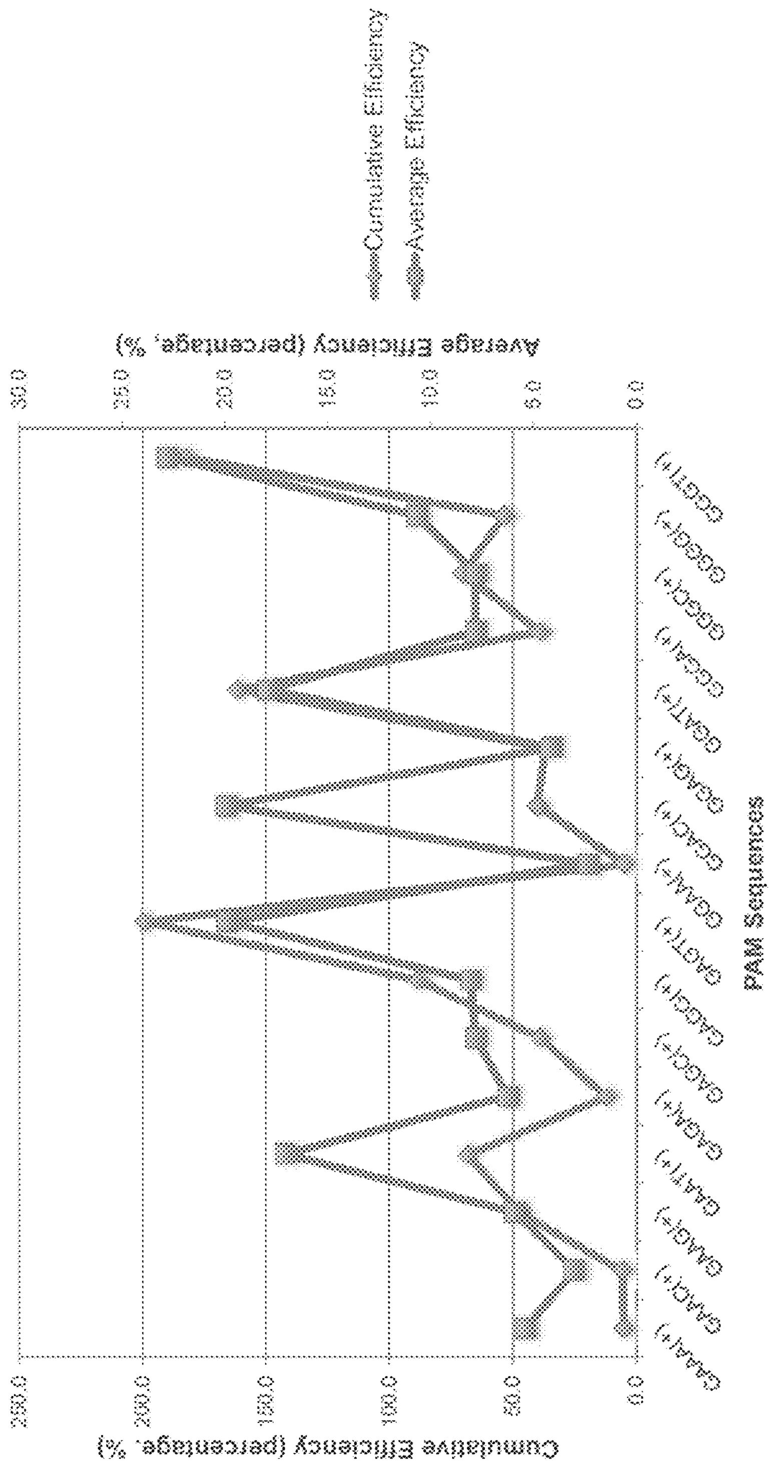
FIG. 26 shows Genome Cleavage Efficiency of PAM Sequences (Cleaved targets, discard low-efficiency and orphan targets).
Figure 27:
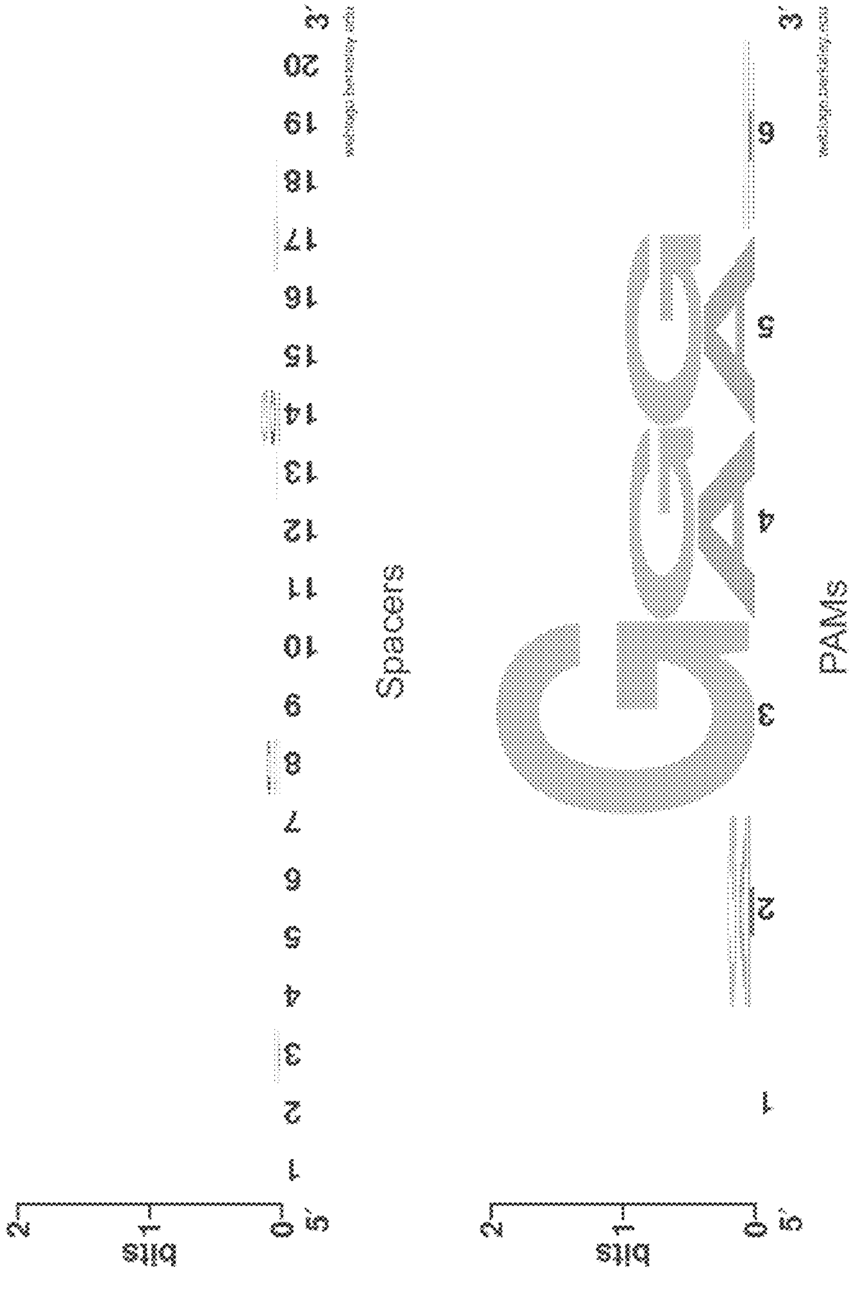
FIG. 27 shows a Sequence Logo for Working Cleaved Spacers & PAMs (New endogenous genome test showing that T is not required).

Applicants have also generated Sp_St3 chimeric proteins and have shown in vitro cleavage by SpCas9, St3Cas9, Sp_St3 chimera and St3_Sp chimera (FIG. 17).

The benefit of making chimeric Cas9 include:

a. reduce toxicity b. improve expression in eukaryotic cells c. enhance specificity d. reduce molecular weight of protein, make protein smaller by combining the smallest domains from different Cas9 homologs.

e. Altering the PAM sequence requirement

Example 6

Cas9 Delivery In Vivo Using AAV Particles or Vectors In Vivo Delivery—AAV Method AAV is advantageous over other viral vectors for a couple of reasons:

Low toxicity (this may be due to the purification method not requiring ultra centrifugation of cell particles that can activate the immune response)

Low probability of causing insertional mutagenesis because it does not integrate into the host genome.

While certain current AAV vectors may accommodate up to 4300 bases of inserted DNA, as an upper limit or a packaging limit, AAV can have of 4.5 or 4.75 KB inserted DNA. This means that DNA encoding a Cas9 enzyme as well as a promoter and transcription terminator have to be all fit into the same viral vector. Constructs larger than 4.5 or 4.75 KB will lead to significantly reduced virus production. SpCas9 is quite large, the gene itself is over 4.1 kb, which makes it difficult for packing into AAV. Therefore embodiments of the invention include utilizing orthologs of Cas9 that are shorter. For example:

| Species | Cas9 Size |
|---|---|
| *Corynebacter diphtheria* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Streptococcus thermophilus* LMD-9 | 3396 |

Figure 3:
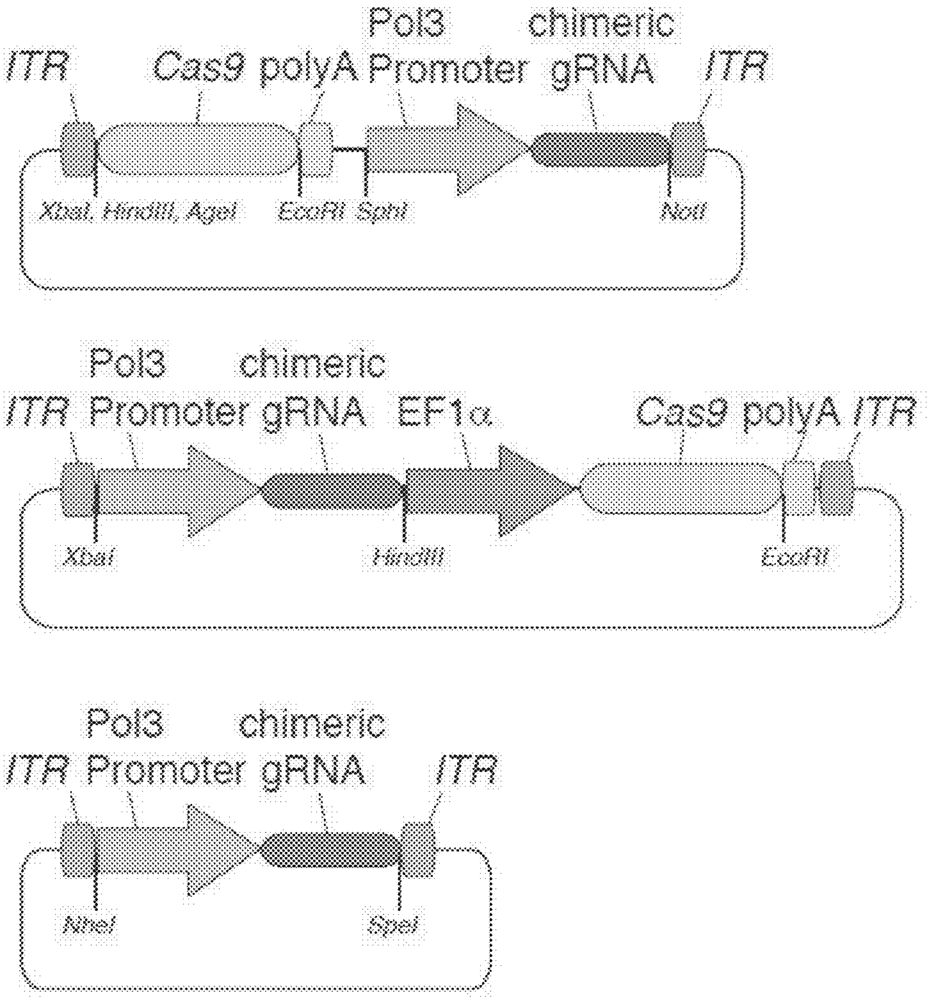
FIG. 3 shows a schematic representation of AAV in vivo delivery plasmids utilizing inverted terminal repeats (ITRs) sequences and guide chimeric RNAs to preferably aid delivery by AAV or AAV-associated systems.
Figure 4A:
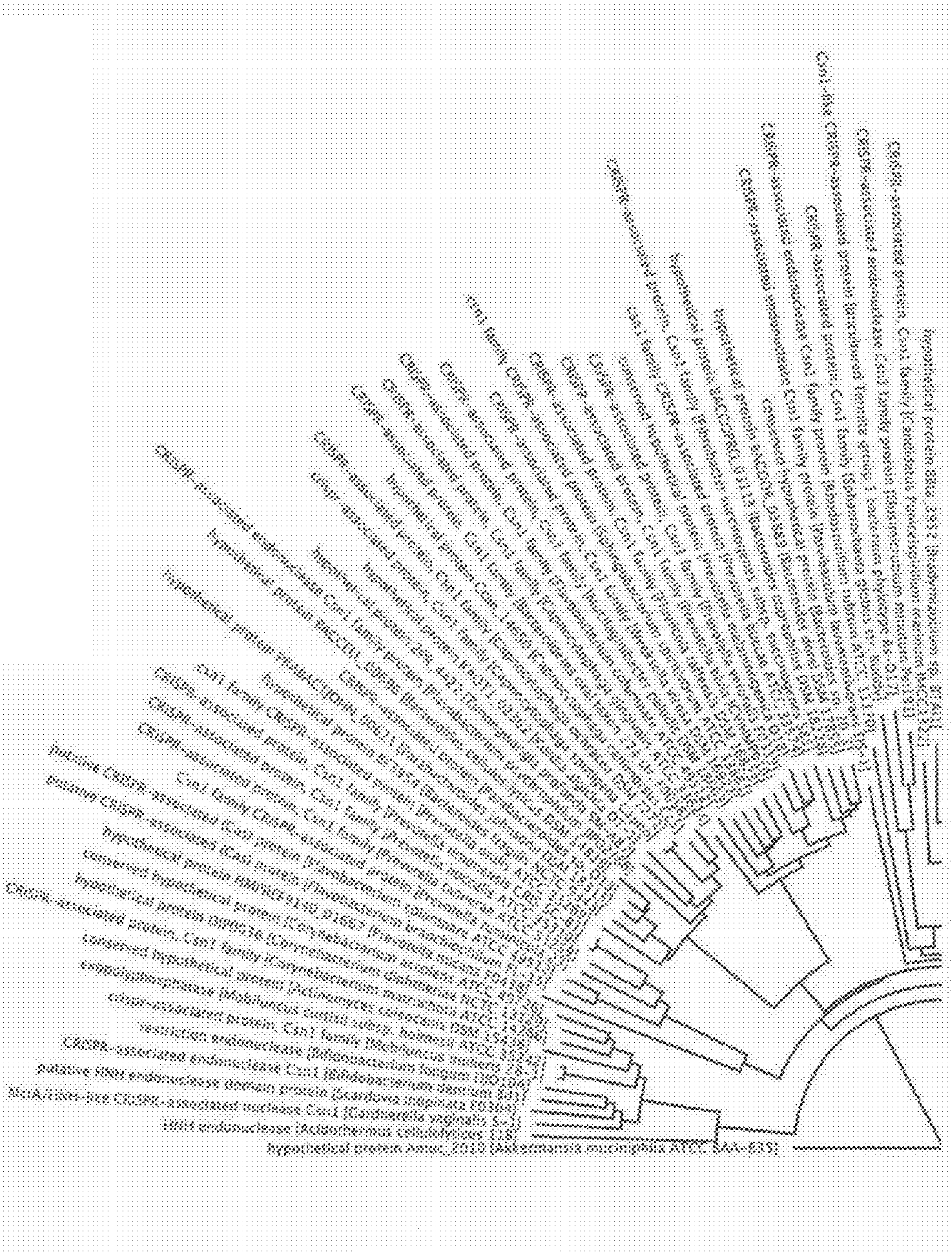
FIG. 4A-D shows a circular depiction of the phylogenetic analysis revealing five families of Cas9s, including three groups of large Cas9s (~1400 amino acids) and two of small Cas9s (~1100 amino acids).
Figure 4B:
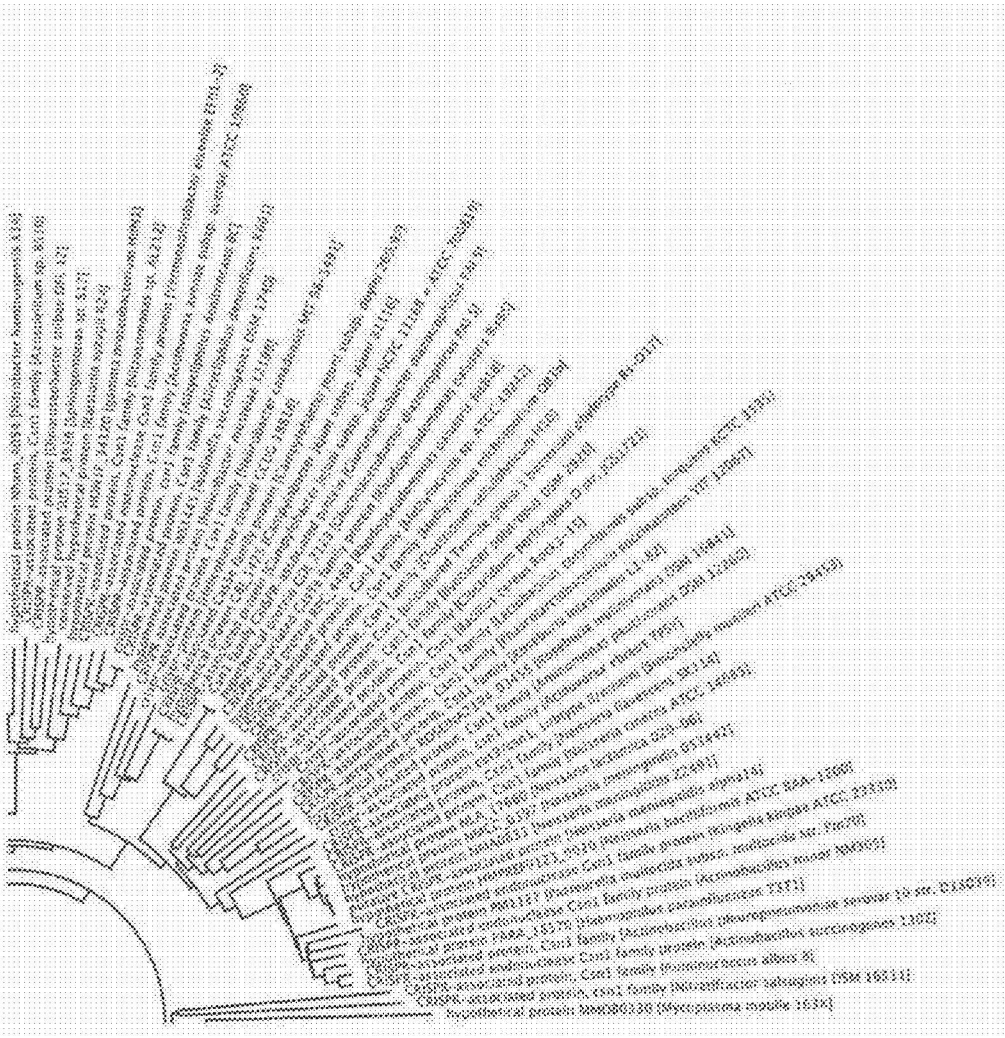
Figure 4C:
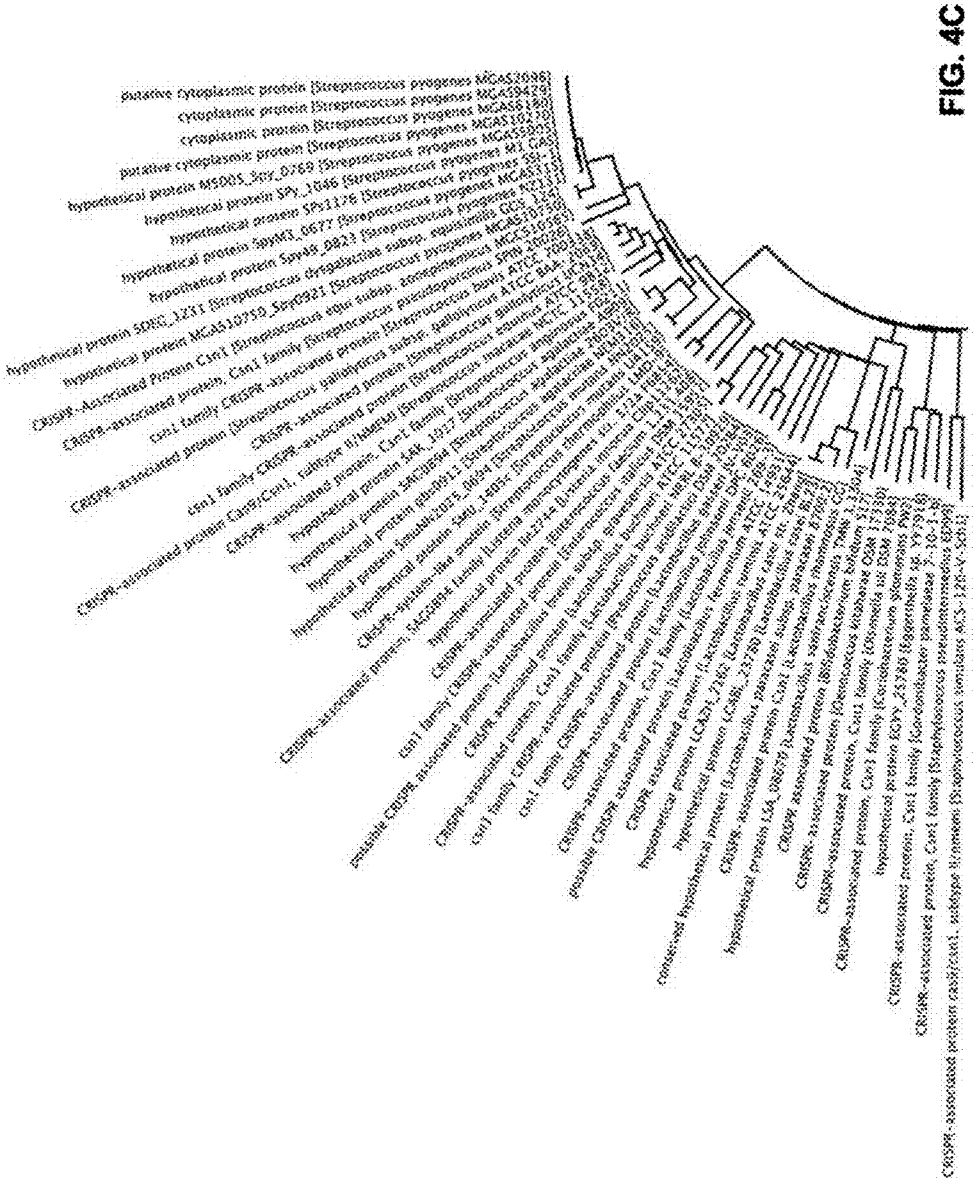
Figure 4D:
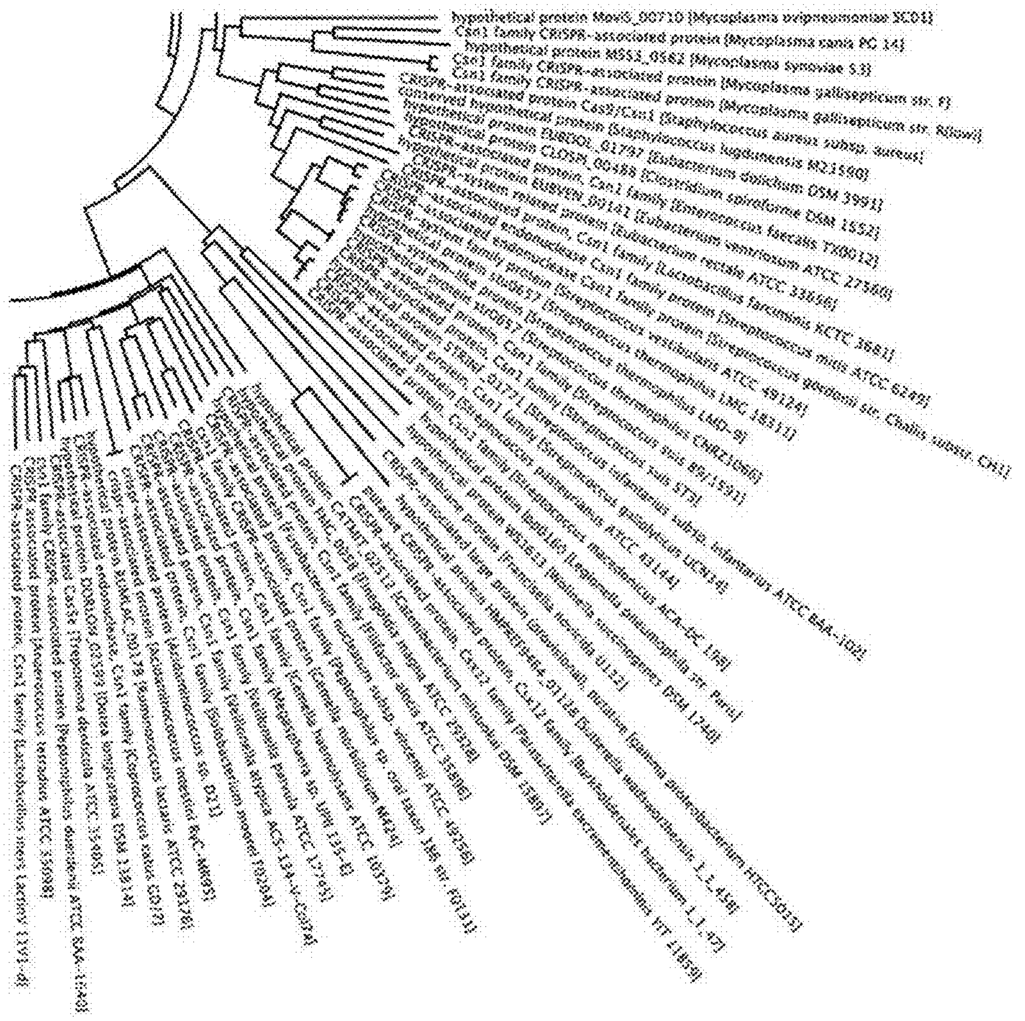
Figure 5A:
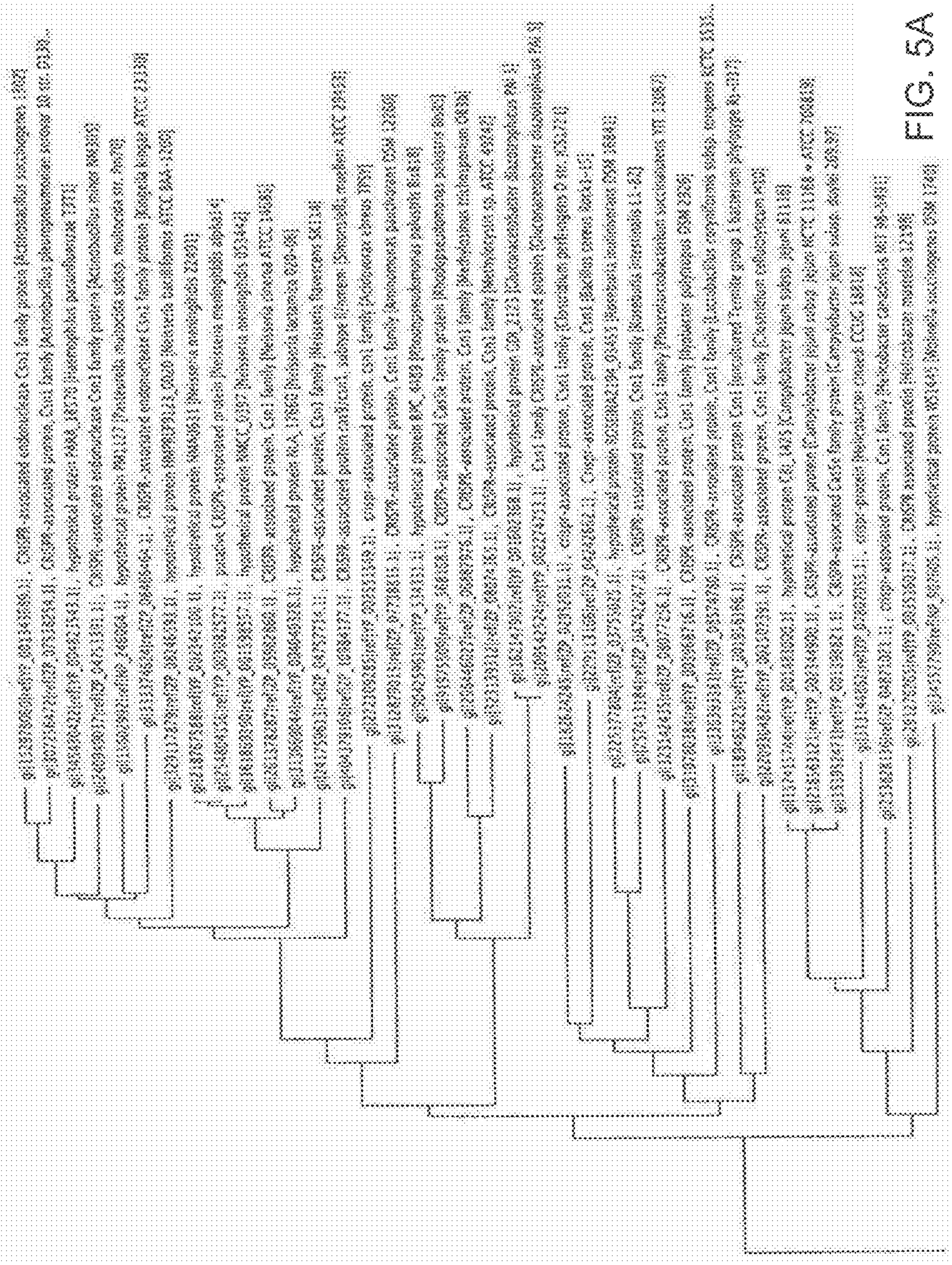
FIG. 5 A-F shows a liner depiction of the phylogenetic analysis revealing five families of Cas9s, including three groups of large Cas9s (~1400 amino acids) and two of small Cas9s (~1100 amino acids).
Figure 5B:
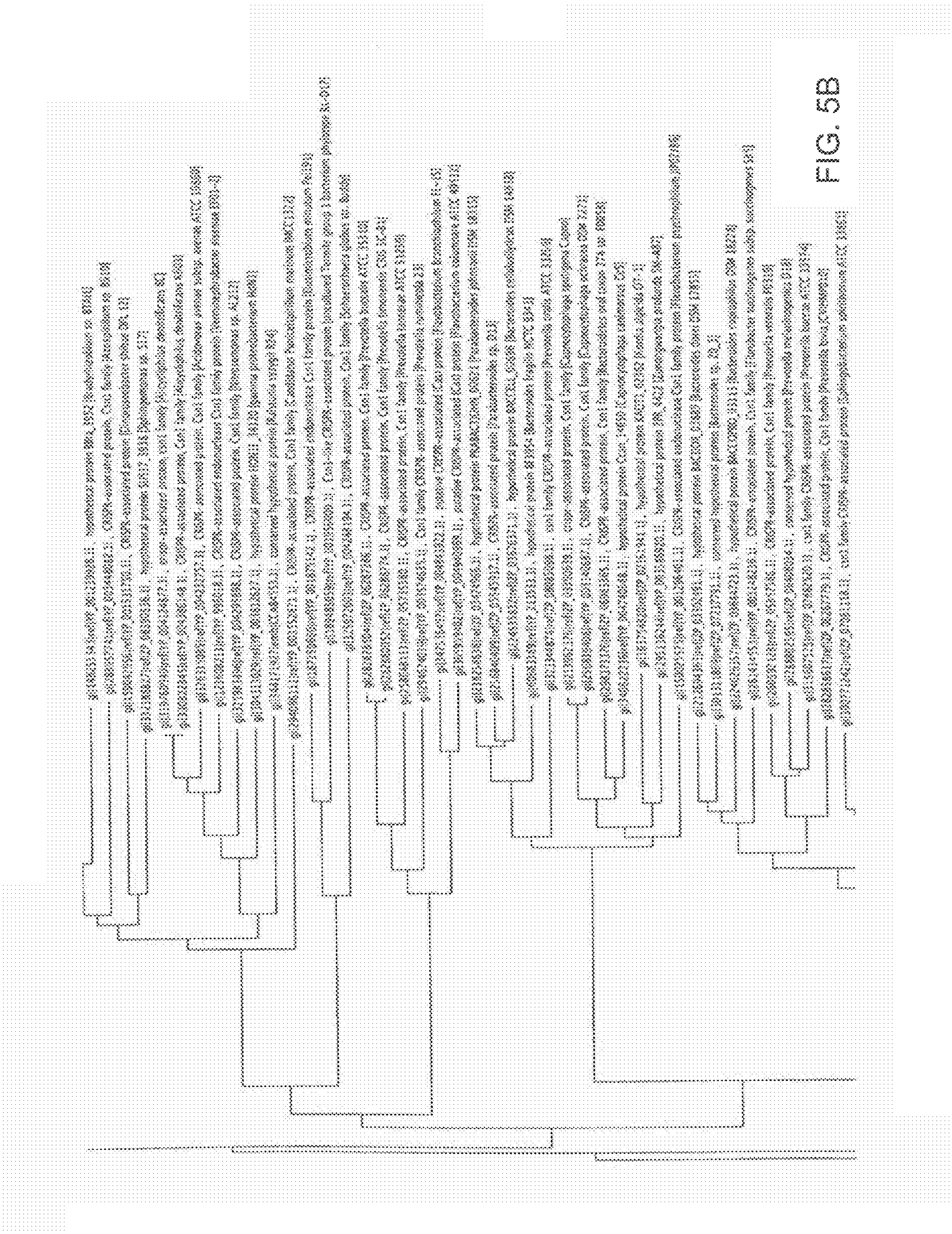
Figure 5C:
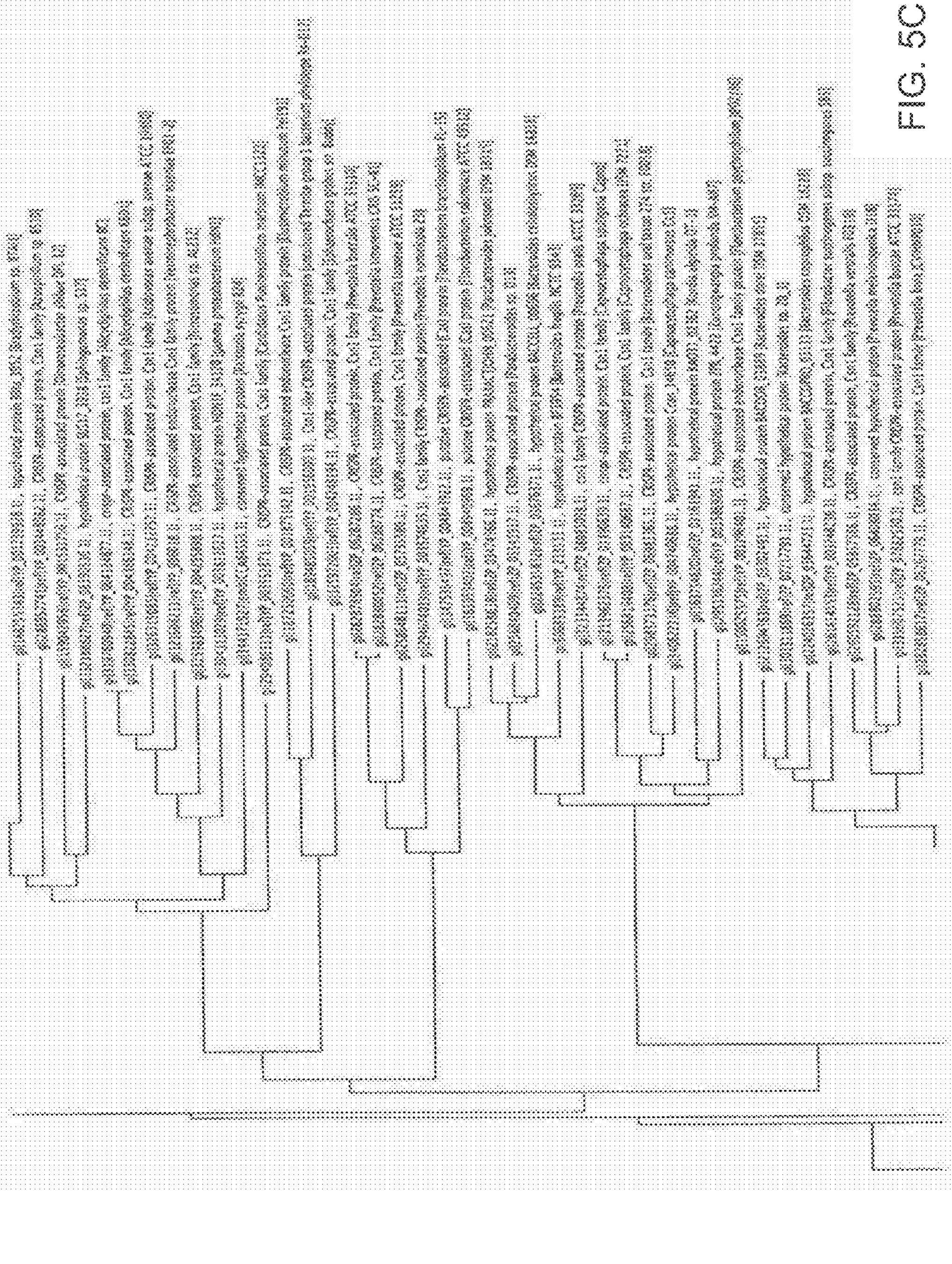
Figure 5D:
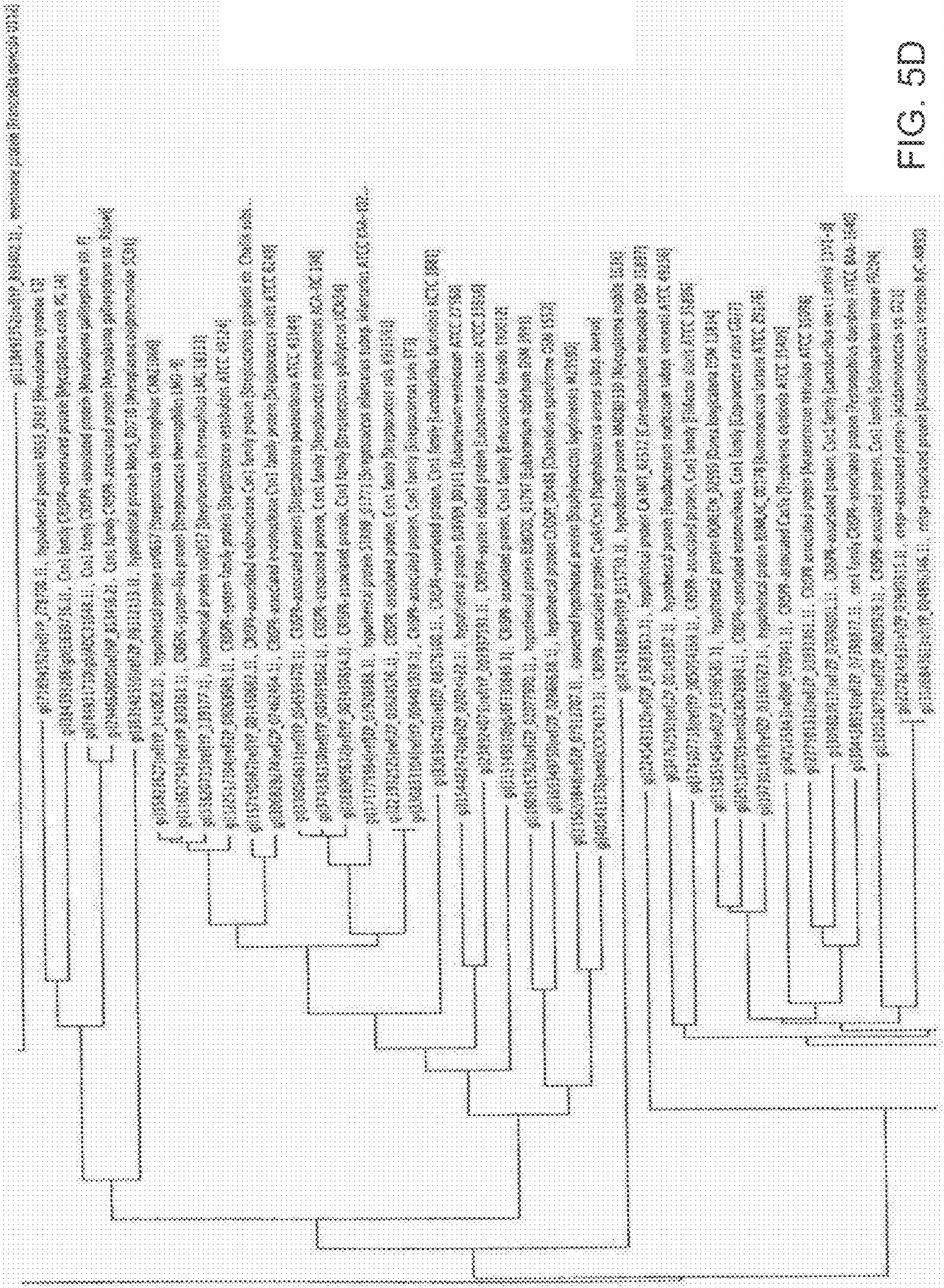
Figure 5E:
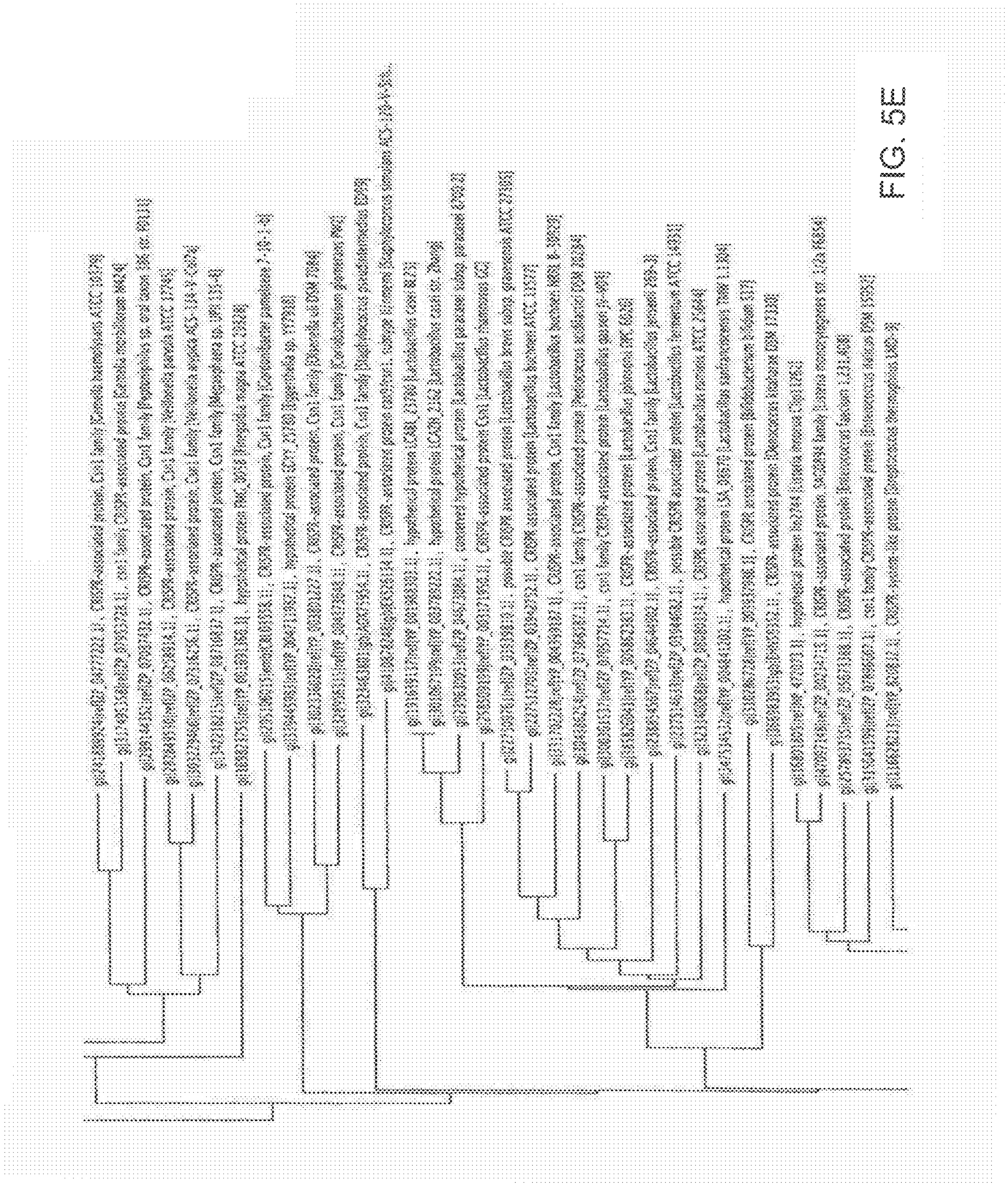
Figure 5F:
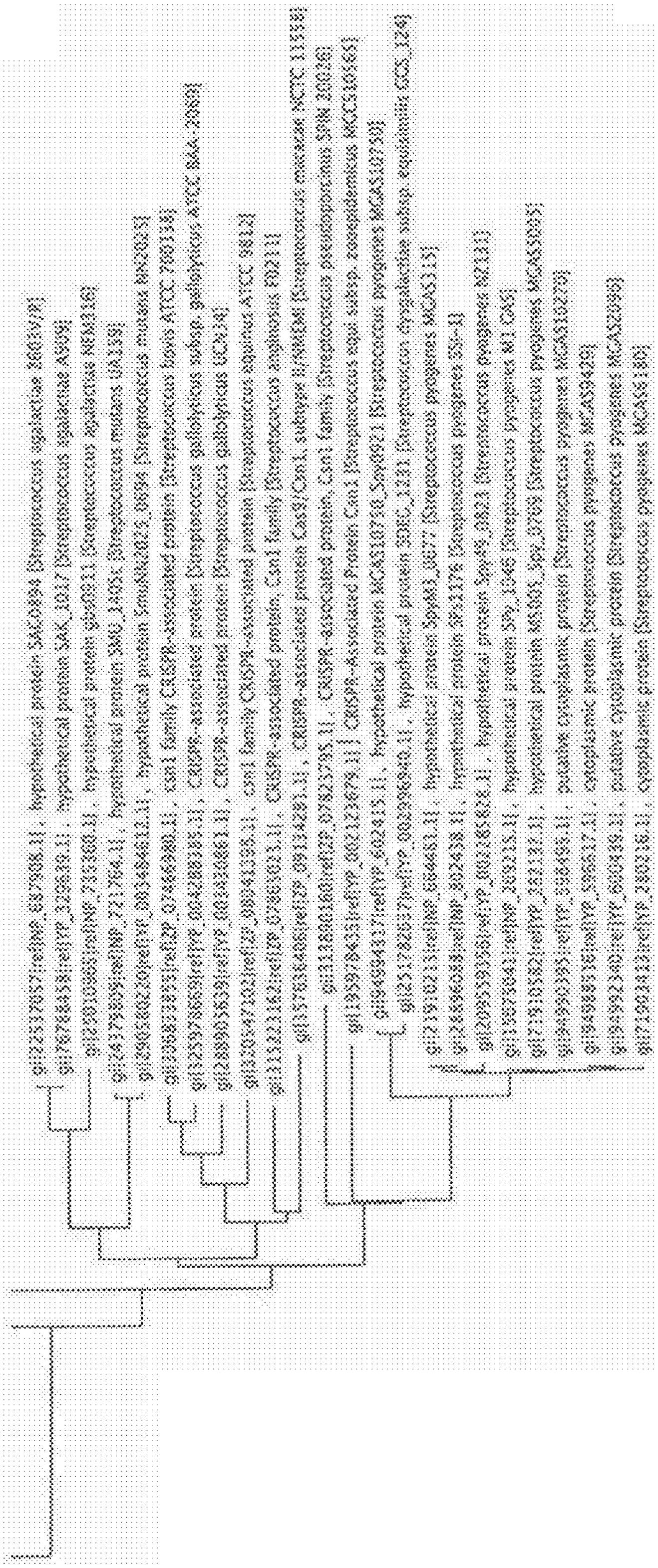

FIG. 3 provides schematic representations of AAV vectors which may be used in methods and compositions of the invention. Packaging is discussed above.

Example 7

Engineering of Microalgae using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

(SEQ ID NO: 88)

TCTTTCTTGCGCTATGACACTTCCAGCAAAAGGTAGGGCGGGCTGCGAGA
CGGCTTCCCGGCGCTGCATGCAACACCGATGATGCTTCGACCCCCCGAAG
CTCCTTCGGGGCTGCATGGGCGCTCCGATGCCGCTCCAGGGCGAGCGCTG
TTTAAATAGCCAGGCCCCCGATTGCAAAGACATTATAGCGAGCTACCAAA
GCCATATTCAAACACCTAGATCACTACCACTTCTACACAGGCCACTCGAG
CTTGTGATCGCACTCCGCTAAGGGGGCGCCTCTTCCTCTTCGTTTCAGTC
ACAACCCGCAAACATGTACCCATACGATGTTCCAGATTACGCTTCGCCGA
AGAAAAAGCGCAAGGTCGAAGCGTCCGACAAGAAGTACAGCATCGGCCTG
GACATCGGCACCAACTCTGTGGGCTGGGCCGTGATCACCGACGAGTACAA
GGTGCCCAGCAAGAAATTCAAGGTGCTGGGCAACACCGACCGGCACAGCA
TCAAGAAGAACCTGATCGGAGCCCTGCTGTTCGACAGCGGCGAAACAGCC
GAGGCCACCCGGCTGAAGAGAACCGCCAGAAGAAGATACACCAGACGGAA
GAACCGGATCTGCTATCTGCAAGAGATCTTCAGCAACGAGATGGCCAAGG
TGGACGACAGCTTCTTCCACAGACTGGAAGAGTCCTTCCTGGTGGAAGAG
GATAAGAAGCACGAGCGGCACCCCATCTTCGGCAACATCGTGGACGAGGT
GGCCTACCACGAGAAGTACCCCACCATCTACCACCTGAGAAAGAAACTGG
TGGACAGCACCGACAAGGCCGACCTGCGGCTGATCTATCTGGCCCTGGCC
CACATGATCAAGTTCCGGGGCCACTTCCTGATCGAGGGCGACCTGAACCC
CGACAACAGCGACGTGGACAAGCTGTTCATCCAGCTGGTGCAGACCTACA
ACCAGCTGTTCGAGGAAAACCCCATCAACGCCAGCGGCGTGGACGCCAAG
GCCATCCTGTCTGCCAGACTGAGCAAGAGCAGACGGCTGGAAAATCTGAT
CGCCCAGCTGCCCGGCGAGAAGAAGAATGGCCTGTTCGGCAACCTGATTG
CCCTGAGCCTGGGCCTGACCCCCAACTTCAAGAGCAACTTCGACCTGGCC
GAGGATGCCAAACTGCAGCTGAGCAAGGACACCTACGACGACGACCTGGA
CAACCTGCTGGCCCAGATCGGCGACCAGTACGCCGACCTGTTTCTGGCCG
CCAAGAACCTGTCCGACGCCATCCTGCTGAGCGACATCCTGAGAGTGAAC
ACCGAGATCACCAAGGCCCCCCTGAGCGCCTCTATGATCAAGAGATACGA
CGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTAC
GCCGGCTACATTGACGGCGGAGCCAGCCAGGAAGAGTTCTACAAGTTCAT
CAAGCCCATCCTGGAAAAGATGGACGGCACCGAGGAACTGCTCGTGAAGC
TGAACAGAGAGGACCTGCTGCGGAAGCAGCGGACCTTCGACAACGGCAGC
ATCCCCCACCAGATCCACCTGGGAGAGCTGCACGCCATTCTGCGGCGGCA
GGAAGATTTTTACCCATTCCTGAAGGACAACCGGGAAAAGATCGAGAAGA
TCCTGACCTTCCGCATCCCCTACTACGTGGGCCCTCTGGCCAGGGGAAAC
AGCAGATTCGCCTGGATGACCAGAAAGAGCGAGGAAACCATCACCCCCTG
GAACTTCGAGGAAGTGGTGGACAAGGGCGCTTCCGCCCAGAGCTTCATCG
AGCGGATGACCAACTTCGATAAGAACCTGCCCAACGAGAAGGTGCTGCCC

-continued

AAGCACAGCCTGCTGTACGAGTACTTCACCGTGTATAACGAGCTGACCAA
AGTGAAATACGTGACCGAGGGAATGAGAAAGCCCGCCTTCCTGAGCGGCG
AGCAGAAAAAGGCCATCGTGGACCTGCTGTTCAAGACCAACCGGAAAGTG
ACCGTGAAGCAGCTGAAAGAGGACTACTTCAAGAAAATCGAGTGCTTCGA
CTCCGTGGAAATCTCCGGCGTGGAAGATCGGTTCAACGCCTCCCTGGGCA
CATACCACGATCTGCTGAAAATTATCAAGGACAAGGACTTCCTGGACAAT
GAGGAAAACGAGGACATTCTGGAAGATATCGTGCTGACCCTGACACTGTT
TGAGGACAGAGAGATGATCGAGGAACGGCTGAAAACCTATGCCCACCTGT
TCGACGACAAAGTGATGAAGCAGCTGAAGCGGCGGAGATACACCGGCTGG
GGCAGGCTGAGCCGGAAGCTGATCAACGGCATCCGGGACAAGCAGTCCGG
CAAGACAATCCTGGATTTCCTGAAGTCCGACGGCTTCGCCAACAGAAACT
TCATGCAGCTGATCCACGACGACAGCCTGACCTTTAAAGAGGACATCCAG
AAAGCCCAGGTGTCCGGCCAGGGCGATAGCCTGCACGAGCACATTGCCAA
TCTGGCCGGCAGCCCCGCCATTAAGAAGGGCATCCTGCAGACAGTGAAGG
TGGTGGACGAGCTCGTGAAAGTGATGGGCCGGCACAAGCCCGAGAACATC
GTGATCGAAATGGCCAGAGAGAACCAGACCACCCAGAAGGGACAGAAGAA
CAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAG
AAGCTGTACCTGTACTACCTGCAGAATGGGCGGGATATGTACGTGGACCA
GGAACTGGACATCAACCGGCTGTCCGACTACGATGTGGACCATATCGTGC
CTCAGAGCTTTCTGAAGGACGACTCCATCGACAACAAGGTGCTGACCAGA
AGCGACAAGAACCGGGGCAAGAGCGACAACGTGCCCTCCGAAGAGGTCGT
GAAGAAGATGAAGAACTACTGGCGGCAGCTGCTGAACGCCAAGCTGATTA
CCCAGAGAAAGTTCGACAATCTGACCAAGGCCGAGAGAGGCGGCCTGAGC
GAACTGGATAAGGCCGGCTTCATCAAGAGACAGCTGGTGGAAACCCGGCA
GATCACAAAGCACGTGGCACAGATCCTGGACTCCCGGATGAACACTAAGT
ACGACGAGAATGACAAGCTGATCCGGGAAGTGAAAGTGATCACCCTGAAG
TCCAAGCTGGTGTCCGATTTCCGGAAGGATTTCCAGTTTTACAAAGTGCG
CGAGATCAACAACTACCACCACGCCCACGACGCCTACCTGAACGCCGTCG
TGGGAACCGCCCTGATCAAAAAGTACCCTAAGCTGGAAAGCGAGTTCGTG
TACGGCGACTACAAGGTGTACGACGTGCGGAAGATGATCGCCAAGAGCGA
GCAGGAAATCGGCAAGGCTACCGCCAAGTACTTCTTCTACAGCAACATCA
TGAACTTTTTCAAGACCGAGATTACCCTGGCCAACGGCGAGATCCGGAAG
CGGCCTCTGATCGAGACAAACGGCGAAACCGGGGAGATCGTGTGGGATAA
GGGCCGGGATTTTGCCACCGTGCGGAAAGTGCTGAGCATGCCCCAAGTGA
ATATCGTGAAAAAGACCGAGGTGCAGACAGGCGGCTTCAGCAAAGAGTCT
ATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTG
TGCTGGTGGTGGCCAAAGTGGAAAAGGGCAAGTCCAAGAAACTGAAGAGT
GTGAAAGAGCTGCTGGGGATCACCATCATGGAAAGAAGCAGCTTCGAGAA

-continued

GAATCCCATCGACTTTCTGGAAGCCAAGGGCTACAAAGAAGTGAAAAAGG

ACCTGATCATCAAGCTGCCTAAGTACTCCCTGTTCGAGCTGGAAAACGGC

CGGAAGAGAATGCTGGCCTCTGCCGGCGAACTGCAGAAGGGAAACGAACT

GGCCCTGCCCTCCAAATATGTGAACTTCCTGTACCTGGCCAGCCACTATG

AGAAGCTGAAGGGCTCCCCCGAGGATAATGAGCAGAAACAGCTGTTTGTG

GAACAGCACAAGCACTACCTGGACGAGATCATCGAGCAGATCAGCGAGTT

CTCCAAGAGAGTGATCCTGGCCGACGCTAATCTGGACAAAGTGCTGTCCG

CCTACAACAAGCACCGGGATAAGCCCATCAGAGAGCAGGCCGAGAATATC

ATCCACCTGTTTACCCTGACCAATCTGGGAGCCCCTGCCGCCTTCAAGTA

-continued

CTTTGACACCACCATCGACCGGAAGAGGTACACCAGCACCAAAGAGGTGC

TGGACGCCACCCTGATCCACCAGAGCATCACCGGCCTGTACGAGACACGG

ATCGACCTGTCTCAGCTGGGAGGCGACAGCCCCAAGAAGAAGAGAAAGGT

GGAGGCCAGCTAAGGATCCGGCAAGACTGGCCCCGCTTGGCAACGCAACA

GTGAGCCCCTCCCTAGTGTGTTTGGGGATGTGACTATGTATTCGTGTGTT

GGCCAACGGGTCAACCCGAACAGATTGATACCCGCCTTGGCATTTCCTGT

CAGAATGTAACGTCAGTTGATGGTACT

Sequence for a cassette driving the expression of T7 polymerase under the control of beta-2 tubulin promoter, followed by the 3' UTR of Cop1:

(SEQ ID NO: 89)

TCTTTCTTGCGCTATGACACTTCCAGCAAAAGGTAGGGCGGGCTGCGAGACGGCTTC

CCGGCGCTGCATGCAACACCGATGATGCTTCGACCCCCCGAAGCTCCTTCGGGGCTG

CATGGGCGCTCCGATGCCGCTCCAGGGCGAGCGCTGTTTAAATAGCCAGGCCCCCG

ATTGCAAAGACATTATAGCGAGCTACCAAAGCCATATTCAAACACCTAGATCACTAC

CACTTCTACACAGGCCACTCGAGCTTGTGATCGCACTCCGCTAAGGGGGCGCCTCTT

CCTCTTCGTTTCAGTCACAACCCGCAAACatgcctaagaagaagaggaaggttaacacgattaacatcgctaag aacgacttctctgacatcgaactggctgctatcccgttcaacactaggctgaccattacggtgagcgtttagctcgcgaacagttggcccttg agcatgagtcttacgagatgggtgaagcacgcttccgcaagatgtttgagcgtcaacttaaagctggtgaggttgcggataacgctgccgcc aagcctctcatcactaccctactccctaagatgattgcacgcatcaacgactggtttgaggaagtgaaagctaagcgcggcaagcgcccga cagccttccagttcctgcaagaaatcaagccggaagccgtagcgtacatcaccattaagaccactctggcttgcctaaccagtgctgacaat acaaccgttcaggctgtagcaagcgcaatcggtcgggccattgaggacgaggctcgcttcggtcgtatccgtgaccttgaagctaagcact tcaagaaaaacgttgaggaacaactcaacaagcgcgtagggcacgtctacaagaaagcatttatgcaagttgtcgaggctgacatgctctct aagggtctactcggtggcgaggcgtggtcttcgtggcataaggaagactctattcatgtaggagtacgctgcatcgagatgctcattgagtca accggaatggttagcttacaccgccaaaatgctggcgtagtaggtcaagactctgagactatcgaactcgcacctgaatacgctgaggctat cgcaacccgtgcaggtgcgctggctggcatctctccgatgttccaaccttgcgtagttcctcctaagccgtggactggcattactggtggtgg ctattgggctaacggtcgtcgtcctctggcgctggtgcgtactcacagtaagaaagcactgatgcgctacgaagacgtttacatgcctgaggt gtacaaagcgattaacattgcgcaaaacaccgcatggaaaatcaacaagaaagtcctagcggtcgccaacgtaatcaccaagtggaagca ttgtccggtcgaggacatccctgcgattgagcgtgaagaactcccgatgaaaccggaagacatcgacatgaatcctgaggctctcaccgcg tggaaacgtgctgccgctgctgtgtaccgcaaggacaaggctcgcaagtctcgccgtatcagccttgagttcatgcttgagcaagccaataa gtttgctaaccataaggccatctggttcccttacaacatggactggcgcggtcgtgtttacgctgtgtcaatgttcaacccgcaaggtaacgat atgaccaaaggactgcttacgctggcgaaaggtaaaccaatcggtaaggaaggttactactggctgaaaatccacggtgcaaactgtgcg ggtgtcgacaaggttccgttccctgagcgcatcaagttcattgaggaaaaccacgagaacatcatggcttgcgctaagtctccactggagaa cacttggtgggctgagcaagattctccgttctgcttccttgcgttctgctttgagtacgctggggtacagcaccacggcctgagctataactgct cccttccgctggcgtttgacgggtcttgctctggcatccagcacttctccgcgatgctccgagatgaggtaggtggtcgcgcggttaacttgc ttcctagtgaaaccgttcaggacatctacgggattgttgctaagaaagtcaacgagattctacaagcagacgcaatcaatgggaccgataac gaagtagttaccgtgaccgatgagaacactggtgaaatctctgagaaagtcaagctgggcactaaggcactggctggtcaatggctggctt acggtgttactcgcagtgtgactaagcgttcagtcatgacgctggcttacgggtccaaagagttcggcttccgtcaacaagtgctggaagata ccattcagccagctattgattccggcaagggtctgatgttcactcagccgaatcaggctgctggatacatggctaagctgatttgggaatctgt gagcgtgacggtggtagctgcggttgaagcaatgaactggcttaagtctgctgctaagctgctggctgctgaggtcaaagataagaagact ggagagattcttcgcaagcgttgcgctgtgcattgggtaactcctgatggtttccctgtgtggcaggaatacaagaagcctattcagacgcgc -continued ttgaacctgatgttcctcggtcagttccgcttacagcctaccattaacaccaacaaagatagcgagattgatgcacacaaacaggagtctggt atcgctcctaactttgtacacagccaagacggtagccaccttcgtaagactgtagtgtgggcacacgagaagtacggaatcgaatcttttgca ctgattcacgactccttcggtacgattccggctgacgctgcgaacctgttcaaagcagtgcgcgaaactatggttgacacatatgagtatgtg atgtactggctgatttctacgaccagttcgctgaccagttgcacgagtctcaattggacaaaatgccagcacttccggctaaaggtaacttgaa cctccgtgacatcttagagtcggacttcgcgttcgcgtaaGGATCCGGCAAGACTGGCCCCGCTTGGCAACG

CAACAGTGAGCCCCTCCCTAGTGTGTTTGGGGATGTGACTATGTATTCGTGTGTTGG

CCAACGGGTCAACCCGAACAGATTGATACCCGCCTTGGCATTTCCTGTCAGAATGTA

ACGTCAGTTGATGGTACT

Sequence of guide RNA driven by the T7 promoter (T7 promoter, Ns represent targeting sequence): gaaatTAATACGACTCACTATA NNNNNNNNNNNNNNNNNNNNgttttagagctaGAAAtagcaagttaaaataaggctagtccgttatcaacttgaaaaagtggcaccgagtcggtgcttttttt (SEQ ID NO: 90)

Gene Delivery:

*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit (website information at tools.invitrogen.com/content/sfs/manuals/geneart_chlamy_kits_man.pdf).

Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 91)

TGCGGTATTTCACACCGCATCAGGTGGCACTTTTCGGGGAAATGTGCGCG

GAACCCCTATTTGTTTATTTTTCTAAATACATTCAAATATGTATCCGCTC

ATGAGATTATCAAAAAGGATCTTCACCTAGATCCTTTTAAATTAAAAATG

AAGTTTTAAATCAATCTAAAGTATATATGAGTAAACTTGGTCTGACAGTT

ACCAATGCTTAATCAGTGAGGCACCTATCTCAGCGATCTGTCTATTTCGT

TCATCCATAGTTGCCTGACTCCCCGTCGTGTAGATAACTACGATACGGGA

GGGCTTACCATCTGGCCCCAGTGCTGCAATGATACCGCGAGACCCACGCT

CACCGGCTCCAGATTTATCAGCAATAAACCAGCCAGCCGGAAGGGCCGAG

CGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATG

GCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCA

GAAGTAAGTTGGCCGCAGTGTTATCACTCATGGTTATGGCAGCACTGCAT

AATTCTCTTACTGTCATGCCATCCGTAAGATGCTTTTCTGTGACTGGTGA

GTACTCAACCAAGTCATTCTGAGAATAGTGTATGCGGCGACCGAGTTGCT

-continued

CTTGCCCGGCGTCAATACGGGATAATACCGCGCCACATAGCAGAACTTTA

AAAGTGCTCATCATTGGAAAACGTTCTTCGGGGCGAAAACTCTCAAGGAT

CTTACCGCTGTTGAGATCCAGTTCGATGTAACCCACTCGTGCACCCAACT

GATCTTCAGCATCTTTTACTTTCACCAGCGTTTCTGGGTGAGCAAAAACA

GGAAGGCAAAATGCCGCAAAAAAGGGAATAAGGGCGACACGGAAATGTTG

AATACTCATACTCTTCCTTTTTCAATATTATTGAAGCATTTATCAGGGTT

ATTGTCTCATGACCAAAATCCCTTAACGTGAGTTTTCGTTCCACTGAGCG

TCAGACCCCGTAGAAAAGATCAAAGGATCTTCTTGAGATCCTTTTTTTCT

GCGCGTAATCTGCTGCTTGCAAACAAAAAAACCACCGCTACCAGCGGTGG

TTTGTTTGCCGGATCAAGAGCTACCAACTCTTTTTCCGAAGGTAACTGGC

TTCAGCAGAGCGCAGATACCAAATACTGTTCTTCTAGTGTAGCCGTAGTT

AGGCCACCACTTCAAGAACTCTGTAGCACCGCCTACATACCTCGCTCTGC

TAATCCTGTTACCAGTGGCTGTTGCCAGTGGCGATAAGTCGTGTCTTACC

GGGTTGGACTCAAGACGATAGTTACCGGATAAGGCGCAGCGGTCGGGCTG

AACGGGGGGTTCGTGCACACAGCCCAGCTTGGAGCGAACGACCTACACCG

AACTGAGATACCTACAGCGTGAGCTATGAGAAAGCGCCACGCTTCCCGAA

GGGAGAAAGGCGGACAGGTATCCGGTAAGCGGCAGGGTCGGAACAGGAGA

GCGCACGAGGGAGCTTCCAGGGGGAAACGCCTGGTATCTTTATAGTCCTG

TCGGGTTTCGCCACCTCTGACTTGAGCGTCGATTTTTGTGATGCTCGTCA

GGGGGGCGGAGCCTATGGAAAAACGCCAGCAACGCGGCCTTTTTACGGTT

CCTGGCCTTTTGCTGGCCTTTTGCTCACATGTTCTTTCCTGCGTTATCCC

CTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGT

CGCTGAGGCTTGACATGATTGGTGCGTATGTTTGTATGAAGCTACAGGAC

TGATTTGGCGGGCTATGAGGGCGGGGGAAGCTCTGGAAGGGCCGCGATGG

GGCGCGCGGCGTCCAGAAGGCGCCATACGGCCCGCTGGCGGCACCCATCC

GGTATAAAAGCCCGCGACCCCGAACGGTGACCTCCACTTTCAGCGACAAA

CGAGCACTTATACATACGCGACTATTCTGCCGCTATACATAACCACTCAG

CTAGCTTAAGATCCCATCAAGCTTGCATGCCGGGCGCGCCAGAAGGAGCG

CAGCCAAACCAGGATGATGTTTGATGGGGTATTTGAGCACTTGCAACCCT

TATCCGGAAGCCCCCTGGCCCACAAAGGCTAGGCGCCAATGCAAGCAGTT

-continued

CGCATGCAGCCCCTGGAGCGGTGCCCTCCTGATAAACCGGCCAGGGGGCC

TATGTTCTTTACTTTTTTACAAGAGAAGTCACTCAACATCTTAAAATGGC

CAGGTGAGTCGACGAGCAAGCCCGGCGGATCAGGCAGCGTGCTTGCAGAT

TTGACTTGCAACGCCCGCATTGTGTCGACGAAGGCTTTTGGCTCCTCTGT

CGCTGTCTCAAGCAGCATCTAACCCTGCGTCGCCGTTTCCATTTGCAGGA

GATTCGAGGTACCATGTACCCATACGATGTTCCAGATTACGCTTCGCCGA

AGAAAAAGCGCAAGGTCGAAGCGTCCGACAAGAAGTACAGCATCGGCCTG

GACATCGGCACCAACTCTGTGGGCTGGGCCGTGATCACCGACGAGTACAA

GGTGCCCAGCAAGAAATTCAAGGTGCTGGGCAACACCGACCGGCACAGCA

TCAAGAAGAACCTGATCGGAGCCCTGCTGTTCGACAGCGGCGAAACAGCC

GAGGCCACCCGGCTGAAGAGAACCGCCAGAAGAAGATACACCAGACGGAA

GAACCGGATCTGCTATCTGCAAGAGATCTTCAGCAACGAGATGGCCAAGG

TGGACGACAGCTTCTTCCACAGACTGGAAGAGTCCTTCCTGGTGGAAGAG

GATAAGAAGCACGAGCGGCACCCCATCTTCGGCAACATCGTGGACGAGGT

GGCCTACCACGAGAAGTACCCCACCATCTACCACCTGAGAAAGAAACTGG

TGGACAGCACCGACAAGGCCGACCTGCGGCTGATCTATCTGGCCCTGGCC

CACATGATCAAGTTCCGGGGCCACTTCCTGATCGAGGGCGACCTGAACCC

CGACAACAGCGACGTGGACAAGCTGTTCATCCAGCTGGTGCAGACCTACA

ACCAGCTGTTCGAGGAAAACCCCATCAACGCCAGCGGCGTGGACGCCAAG

GCCATCCTGTCTGCCAGACTGAGCAAGAGCAGACGGCTGGAAAATCTGAT

CGCCCAGCTGCCCGGCGAGAAGAAGAATGGCCTGTTCGGCAACCTGATTG

CCCTGAGCCTGGGCCTGACCCCCAACTTCAAGAGCAACTTCGACCTGGCC

GAGGATGCCAAACTGCAGCTGAGCAAGGACACCTACGACGACGACCTGGA

CAACCTGCTGGCCCAGATCGGCGACCAGTACGCCGACCTGTTTCTGGCCG

CCAAGAACCTGTCCGACGCCATCCTGCTGAGCGACATCCTGAGAGTGAAC

ACCGAGATCACCAAGGCCCCCCTGAGCGCCTCTATGATCAAGAGATACGA

CGAGCACCACCAGGACCTGACCCTGCTGAAAGCTCTCGTGCGGCAGCAGC

TGCCTGAGAAGTACAAAGAGATTTTCTTCGACCAGAGCAAGAACGGCTAC

GCCGGCTACATTGACGGCGGAGCCAGCCAGGAAGAGTTCTACAAGTTCAT

CAAGCCCATCCTGGAAAAGATGGACGGCACCGAGGAACTGCTCGTGAAGC

TGAACAGAGAGGACCTGCTGCGGAAGCAGCGGACCTTCGACAACGGCAGC

ATCCCCCACCAGATCCACCTGGGAGAGCTGCACGCCATTCTGCGGCGGCA

GGAAGATTTTTACCCATTCCTGAAGGACAACCGGGAAAAGATCGAGAAGA

TCCTGACCTTCCGCATCCCCTACTACGTGGGCCCTCTGGCCAGGGGAAAC

AGCAGATTCGCCTGGATGACCAGAAAGAGCGAGGAAACCATCACCCCCTG

GAACTTCGAGGAAGTGGTGGACAAGGGCGCTTCCGCCCAGAGCTTCATCG

AGCGGATGACCAACTTCGATAAGAACCTGCCCAACGAGAAGGTGCTGCCC

AAGCACAGCCTGCTGTACGAGTACTTCACCGTGTATAACGAGCTGACCAA

AGTGAAATACGTGACCGAGGGAATGAGAAAGCCCGCCTTCCTGAGCGGCG

AGCAGAAAAAGGCCATCGTGGACCTGCTGTTCAAGACCAACCGGAAAGTG

-continued

ACCGTGAAGCAGCTGAAAGAGGACTACTTCAAGAAAATCGAGTGCTTCGA

CTCCGTGGAAATCTCCGGCGTGGAAGATCGGTTCAACGCCTCCCTGGGCA

CATACCACGATCTGCTGAAAATTATCAAGGACAAGGACTTCCTGGACAAT

GAGGAAAACGAGGACATTCTGGAAGATATCGTGCTGACCCTGACACTGTT

TGAGGACAGAGAGATGATCGAGGAACGGCTGAAAACCTATGCCCACCTGT

TCGACGACAAAGTGATGAAGCAGCTGAAGCGGCGGAGATACACCGGCTGG

GGCAGGCTGAGCCGGAAGCTGATCAACGGCATCCGGGACAAGCAGTCCGG

CAAGACAATCCTGGATTTCCTGAAGTCCGACGGCTTCGCCAACAGAAACT

TCATGCAGCTGATCCACGACGACAGCCTGACCTTTAAAGAGGACATCCAG

AAAGCCCAGGTGTCCGGCCAGGGCGATAGCCTGCACGAGCACATTGCCAA

TCTGGCCGGCAGCCCCGCCATTAAGAAGGGCATCCTGCAGACAGTGAAGG

TGGTGGACGAGCTCGTGAAAGTGATGGGCCGGCACAAGCCCGAGAACATC

GTGATCGAAATGGCCAGAGAGAACCAGACCACCCAGAAGGGACAGAAGAA

CAGCCGCGAGAGAATGAAGCGGATCGAAGAGGGCATCAAAGAGCTGGGCA

GCCAGATCCTGAAAGAACACCCCGTGGAAAACACCCAGCTGCAGAACGAG

AAGCTGTACCTGTACTACCTGCAGAATGGGCGGGATATGTACGTGGACCA

GGAACTGGACATCAACCGGCTGTCCGACTACGATGTGGACCATATCGTGC

CTCAGAGCTTTCTGAAGGACGACTCCATCGACAACAAGGTGCTGACCAGA

AGCGACAAGAACCGGGGCAAGAGCGACAACGTGCCCTCCGAAGAGGTCGT

GAAGAAGATGAAGAACTACTGGCGGCAGCTGCTGAACGCCAAGCTGATTA

CCCAGAGAAAGTTCGACAATCTGACCAAGGCCGAGAGAGGCGGCCTGAGC

GAACTGGATAAGGCCGGCTTCATCAAGAGACAGCTGGTGGAAACCCGGCA

GATCACAAAGCACGTGGCACAGATCCTGGACTCCCGGATGAACACTAAGT

ACGACGAGAATGACAAGCTGATCCGGGAAGTGAAAGTGATCACCCTGAAG

TCCAAGCTGGTGTCCGATTTCCGGAAGGATTTCCAGTTTTACAAAGTGCG

CGAGATCAACAACTACCACCACGCCCACGACGCCTACCTGAACGCCGTCG

TGGGAACCGCCCTGATCAAAAAGTACCCTAAGCTGGAAAGCGAGTTCGTG

TACGGCGACTACAAGGTGTACGACGTGCGGAAGATGATCGCCAAGAGCGA

GCAGGAAATCGGCAAGGCTACCGCCAAGTACTTCTTCTACAGCAACATCA

TGAACTTTTTCAAGACCGAGATTACCCTGGCCAACGGCGAGATCCGGAAG

CGGCCTCTGATCGAGACAAACGGCGAAACCGGGGAGATCGTGTGGGATAA

GGGCCGGGATTTTGCCACCGTGCGGAAAGTGCTGAGCATGCCCCAAGTGA

ATATCGTGAAAAAGACCGAGGTGCAGACAGGCGGCTTCAGCAAAGAGTCT

ATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTG

TGCTGGTGGTGGCCAAAGTGGAAAAGGGCAAGTCCAAGAAACTGAAGAGT

GTGAAAGAGCTGCTGGGGATCACCATCATGGAAAGAAGCAGCTTCGAGAA

GAATCCCATCGACTTTCTGGAAGCCAAGGGCTACAAAGAAGTGAAAAAGG

ACCTGATCATCAAGCTGCCTAAGTACTCCCTGTTCGAGCTGGAAAACGGC

CGGAAGAGAATGCTGGCCTCTGCCGGCGAACTGCAGAAGGGAAACGAACT

GGCCCTGCCCTCCAAATATGTGAACTTCCTGTACCTGGCCAGCCACTATG

-continued

```
AGAAGCTGAAGGGCTCCCCCGAGGATAATGAGCAGAAACAGCTGTTTGTG
GAACAGCACAAGCACTACCTGGACGAGATCATCGAGCAGATCAGCGAGTT
CTCCAAGAGAGTGATCCTGGCCGACGCTAATCTGGACAAAGTGCTGTCCG
CCTACAACAAGCACCGGGATAAGCCCATCAGAGAGCAGGCCGAGAATATC
ATCCACCTGTTTACCCTGACCAATCTGGGAGCCCCTGCCGCCTTCAAGTA
CTTTGACACCACCATCGACCGGAAGAGGTACACCAGCACCAAAGAGGTGC
TGGACGCCACCCTGATCCACCAGAGCATCACCGGCCTGTACGAGACACGG
ATCGACCTGTCTCAGCTGGGAGGCGACAGCCCCAAGAAGAAGAGAAAGGT
GGAGGCCAGCTAACATATGATTCGAATGTCTTTCTTGCGCTATGACACTT
CCAGCAAAAGGTAGGGCGGGCTGCGAGACGGCTTCCCGGCGCTGCATGCA
ACACCGATGATGCTTCGACCCCCCGAAGCTCCTTCGGGGCTGCATGGGCG
CTCCGATGCCGCTCCAGGGCGAGCGCTGTTTAAATAGCCAGGCCCCCGAT
TGCAAAGACATTATAGCGAGCTACCAAAGCCATATTCAAACACCTAGATC
ACTACCACTTCTACACAGGCCACTCGAGCTTGTGATCGCACTCCGCTAAG
GGGGCGCCTCTTCCTCTTCGTTTCAGTCACAACCCGCAAACATGACACAA
GAATCCCTGTTACTTCTCGACCGTATTGATTCGGATGATTCCTACGCGAG
CCTGCGGAACGACCAGGAATTCTGGGAGGTGAGTCGACGAGCAAGCCCGG
CGGATCAGGCAGCGTGCTTGCAGATTTGACTTGCAACGCCCGCATTGTGT
CGACGAAGGCTTTTGGCTCCTCTGTCGCTGTCTCAAGCAGCATCTAACCC
TGCGTCGCCGTTTCCATTTGCAGCCGCTGGCCCGCCGAGCCCTGGAGGAG
CTCGGGCTGCCGGTGCCGCCGGTGCTGCGGGTGCCCGGCGAGAGCACCAA
CCCCGTACTGGTCGGCGAGCCCGGCCCGGTGATCAAGCTGTTCGGCGAGC
ACTGGTGCGGTCCGGAGAGCCTCGCGTCGGAGTCGGAGGCGTACGCGGTC
CTGGCGGACGCCCCGGTGCCGGTGCCCCGCCTCCTCGGCCGCGGCGAGCT
GCGGCCCGGCACCGGAGCCTGGCCGTGGCCCTACCTGGTGATGAGCCGGA
TGACCGGCACCACCTGGCGGTCCGCGATGGACGGCACGACCGACCGGAAC
GCGCTGCTCGCCCTGGCCCGCGAACTCGGCCGGGTGCTCGGCCGGCTGCA
CAGGGTGCCGCTGACCGGGAACACCGTGCTCACCCCCCATTCCGAGGTCT
TCCCGGAACTGCTGCGGGAACGCCGCGCGGCGACCGTCGAGGACCACCGC
GGGTGGGGCTACCTCTCGCCCCGGCTGCTGGACCGCCTGGAGGACTGGCT
GCCGGACGTGGACACGCTGCTGGCCGGCCGCGAACCCCGGTTCGTCCACG
GCGACCTGCACGGGACCAACATCTTCGTGGACCTGGCCGCGACCGAGGTC
ACCGGGATCGTCGACTTCACCGACGTCTATGCGGGAGACTCCCGCTACAG
CCTGGTGCAACTGCATCTCAACGCCTTCCGGGGCGACCGCGAGATCCTGG
CCGCGCTGCTCGACGGGGCGCAGTGGAAGCGGACCGAGGACTTCGCCCGC
GAACTGCTCGCCTTCACCTTCCTGCACGACTTCGAGGTGTTCGAGGAGAC
CCCGCTGGATCTCTCCGGCTTCACCGATCCGGAGGAACTGGCGCAGTTCC
TCTGGGGGCCGCCGGACACCGCCCCCGGCGCCTGATAAGGATCCGGCAAG
ACTGGCCCCGCTTGGCAACGCAACAGTGAGCCCCTCCCTAGTGTGTTTGG
GGATGTGACTATGTATTCGTGTGTTGGCCAACGGGTCAACCCGAACAGAT
```

-continued

```
TGATACCCGCCTTGGCATTTCCTGTCAGAATGTAACGTCAGTTGATGGTA

CT
```

For all modified *Chlamydomonas reinhardtii* cells, Applicants use PCR, SURVEYOR nuclease assay, and DNA sequencing to verify successful modification.

Example 8

SaCas9 and PAM Recognition for In Vivo Applications

The project started as Applicants wanted to further explore the diversity of the type II CRISPR/Cas system following the identification of *Streptococcus pyogenes* (Sp) and *Streptococcus thermophiles* (St) CRISPR/Cas system as a functional genome engineering tool in mammalian cells.

By defining new functional type II CRISPR/Cas systems for application in mammalian cells, Applicants will potentially be able to find:

(1) CRISPR/Cas system with higher efficiency and/or specificity (2) CRISPR/Cas system with different Protospacer Adjacent Motif (PAM) that allows the targeting of broader range of genomic loci (3) CRISPR/Cas system with smaller size so Applicants could deliver them in vivo in a single vector with mammalian viral delivery system such as adeno-associated virus (AAV) vectors that has a packaging size limit (the current Sp or St system exceed this limit of 4.7 kb)

and other desirable traits.

Identification and Design of Sa CRISPR/Cas System for In Vivo Application.

Applicants tested a new type II CRISPR/Cas system in *Staphylococcus aureus* (Sa) that works in vitro in dsDNA cleavage assay and identified a putative PAM of NNGRRT. The components of this system are a Cas9 protein from Sa, a guide CRISPR RNA with direct repeats (DR) from Sa that will form a functional guide RNA complex with tracrRNA from Sa. This three-component system is similar to all other type II CRISPR/Cas systems. Hence, Applicants designed a two-component system, where Applicants fused the Sa tracrRNA to the Sa guide CRISPR RNA via a short stem-loop to form a chimeric guide RNA, exactly as Applicants did with the *Streptococcus pyogenes* (Sp) CRISPR/Cas system. This chimeric guide RNA was able to support cleavage of dsDNA in vitro. Therefore, Applicants decided to clone the full two-component system: cas9 and the chimeric guide RNA, into an AAV vector to test its functionality in living organisms.

Applicants chose the AAV system because it is a non-integrating, ssDNA-based, non-immunogenic mammalian virus that has broad-spectrum of tropism in different tissues/organs depending on the serotype that has been shown to be safe for in vivo application and also support long-term expression of transgene in living organisms.

Design of the initial AAV vector has (1) CMV promoter driving SaCas9 protein with a single NLS and a HA epitope tag. (2) human U6 promoter driving the chimeric RNA. These are placed in between two Inverted Terminal Repeats (ITRs) from the most-well studied AAV serotype 2 that serve as the viral packaging signal.

The PAM sequence test on endogenous mammalian genome is as follows: SaCas9 target spacers were selected across multiple genes to cover different potential PAM sequences. Different spacers were cloned into U6-sgRNA (single-guide RNA) expression dsDNA cassette U6-sgRNA expression dsDNA cassette were co-transfected into mammalian cells lines (293FT for human targets, N2a and Hepa for mouse targets). 72 hours following transfection, all genomic DNA were extracted and subjected to surveyor nuclease assay. Run through TBE Page Gel to detect genomic cleavage. Quantify genomic DNA cleavage efficiency and plot. Summary of Genome Cleavage Efficiency and other Statistics on All Tested Targets

| SaCas9 PAM Sequences | Targets Count | Cleavaged Targets Count | Percentage of Cleaved Targets (%) | Cumulative Cleavage Efficiency (%) | Average Spacer GC Content (%) |
|---|---|---|---|---|---|
| GAAA | 1 | 1 | 100.0 | 5.4 | 65.0 |
| GAAC | 2 | 2 | 100.0 | 6.1 | 55.0 |
| GAAG | 8 | 8 | 100.0 | 47.1 | 65.0 |
| GAAT | 9 | 8 | 88.9 | 138.4 | 66.1 |
| GAGA | 3 | 3 | 100.0 | 17.5 | 63.3 |
| GAGC | 6 | 6 | 100.0 | 44.2 | 60.0 |
| GAGG | 12 | 12 | 100.0 | 93.3 | 58.8 |
| GAGT | 44 | 20 | 45.5 | 434.0 | 56.9 |
| GGAA | 2 | 2 | 100.0 | 4.7 | 50.0 |
| GGAC | 3 | 2 | 66.7 | 39.9 | 60.0 |
| GGAG | 12 | 9 | 75.0 | 36.9 | 59.6 |
| GGAT | 20 | 10 | 50.0 | 186.2 | 59.0 |
| GGGA | 7 | 5 | 71.4 | 39.1 | 63.6 |
| GGGC | 11 | 9 | 81.8 | 70.3 | 65.5 |
| GGGG | 8 | 5 | 62.5 | 53.3 | 70.0 |
| GGGT | 45 | 18 | 40.0 | 402.3 | 56.2 |
| Grand Total | 196 | 120 | 61.2 | 1618.6 | 59.4 |

Summary of Genome Cleavage Efficiency and other Statistics on All Tested Targets (cleaned up)

| SaCas9 PAM Sequences | Targets Count | Cleavaged Targets Count | Percentage of Cleaved Targets (%) | Cumulative Cleavage Efficiency (%) | Average Cleavage Efficiency (%) | Average Spacer GC Content (%) |
|---|---|---|---|---|---|---|
| GAAA | 1 | 1 | 100.0 | 5.4 | 5.4 | 65.0 |
| GAAC | 2 | 2 | 100.0 | 6.1 | 3.0 | 55.0 |
| GAAG | 8 | 8 | 100.0 | 47.1 | 5.9 | 65.0 |
| GAAT | 4 | 4 | 100.0 | 68.4 | 17.1 | 65.0 |
| GAGA | 2 | 2 | 100.0 | 12.5 | 6.3 | 67.5 |
| GAGC | 5 | 5 | 100.0 | 39.2 | 7.8 | 61.0 |
| GAGG | 11 | 11 | 100.0 | 88.3 | 8.0 | 58.2 |
| GAGT | 13 | 10 | 76.9 | 199.0 | 15.3 | 56.2 |
| GGAA | 2 | 2 | 100.0 | 4.7 | 2.3 | 50.0 |
| GGAC | 3 | 2 | 66.7 | 39.9 | 13.3 | 60.0 |
| GGAG | 12 | 9 | 75.0 | 36.9 | 3.1 | 59.6 |
| GGAT | 13 | 9 | 69.2 | 161.2 | 12.4 | 58.8 |
| GGGA | 7 | 5 | 71.4 | 39.1 | 5.6 | 63.6 |
| GGGC | 11 | 9 | 81.8 | 70.3 | 6.4 | 65.5 |
| GGGG | 8 | 5 | 62.5 | 53.3 | 6.7 | 70.0 |
| GGGT | 14 | 8 | 57.1 | 182.3 | 13.0 | 54.6 |
| Grand Total | 116 | 92 | 79.3 | 1053.6 | 9.1 | 60.5 |

Results from the PAM test are shown in FIGS. 22-27. A comprehensive test of over 100 targets identified that the PAM for SaCas9 could be described as NNGRR (but not the NNGRRT as indicated earlier).

PAM Test Summary: (1) NNGRR for general SaCas9 PAM—helpful for design new targets, (2) Testing double-nickase with new targets, (3) NNGRG may be a more potent PAM.

REFERENCES

1. Cong, L. et al. Multiplex genome engineering using CRISPR/Cas systems. Science 339, 819-823 (2013)
2. Mali, P. et al. RNA-Guided Human Genome Engineering via Cas9. Science 339, 823-826 (2013).
3. Jinek, M. et al. RNA-programmed genome editing in human cells. eLife 2, e00471 (2013).
4. Cho, S. W., Kim, S., Kim, J. M. & Kim, J. S. Targeted genome engineering in human cells with the Cas9 RNA-guided endonuclease. Nat Biotechnol 31, 230-232 (2013).
5. Deltcheva, E. et al. CRISPR RNA maturation by trans-encoded small RNA and host factor RNase III. Nature 471, 602-607 (2011).
6. Jinek, M. et al. A programmable dual-RNA-guided DNA endonuclease in adaptive bacterial immunity. Science 337, 816-821 (2012).
7. Wang, H. et al. One-Step Generation of Mice Carrying Mutations in Multiple Genes by CRISPR/Cas-Mediated Genome Engineering. Cell 153, 910-918 (2013).
8. Guschin, D. Y. et al. A rapid and general assay for monitoring endogenous gene modification. Methods Mol Biol 649, 247-256 (2010).
9. Bogenhagen, D. F. & Brown. D. D. Nucleotide sequences in *Xenopus* 5S DNA required for transcription termination. Cell 24, 261-270 (1981).
10. Hwang, W. Y. et al. Efficient genome editing in zebrafish using a CRISPR-Cas system. Nat Biotechnol 31, 227-229 (2013).

11. Bultmann, S. et al. Targeted transcriptional activation of silent oct4 pluripotency gene by combining designer TALEs and inhibition of epigenetic modifiers. Nucleic Acids Res 40, 5368-5377 (2012).
12. Valton, J. et al. Overcoming transcription activator-like effector (TALE) DNA binding domain sensitivity to cytosine methylation. J Biol Chem 287, 38427-38432 (2012).
13. Christian, M. et al. Targeting DNA double-strand breaks with TAL effector nucleases. Genetics 186, 757-761 (2010).
14. Miller, J. C. et al. A TALE nuclease architecture for efficient genome editing. Nat Biotechnol 29, 143-148 (2011).
15. Mussolino, C. et al. A novel TALE nuclease scaffold enables high genome editing activity in combination with low toxicity. Nucleic acids research 39, 9283-9293 (2011).
16. Hsu. P. D. & Zhang, F. Dissecting neural function using targeted genome engineering technologies. ACS chemical neuroscience 3, 603-610 (2012).
17. Sanjana, N. E. et al. A transcription activator-like effector toolbox for genome engineering. Nature protocols 7, 171-192 (2012).
18. Porteus, M. H. & Baltimore, D. Chimeric nucleases stimulate gene targeting in human cells. Science 300, 763 (2003).
19. Miller, J. C. et al. An improved zinc-finger nuclease architecture for highly specific genome editing. Nat Biotechnol 25, 778-785 (2007).
20. Sander, J. D. et al. Selection-free zinc-finger-nuclease engineering by context-dependent assembly (CODA). Nat Methods 8, 67-69 (2011).
21. Wood, A. J. et al. Targeted genome editing across species using ZFNs and TALENs. Science 333, 307 (2011).
22. Bobis-Wozowicz, S., Osiak, A., Rahman, S. H. & Cathomen, T. Targeted genome editing in pluripotent stem cells using zinc-finger nucleases. Methods 53, 339-346 (2011).
23. Jiang, W., Bikard, D., Cox, D., Zhang, F. & Marraffini, L. A. RNA-guided editing of bacterial genomes using CRISPR-Cas systems. Nat Biotechnol 31, 233-239 (2013).
24. Qi. L. S. et al. Repurposing CRISPR as an RNA-Guided Platform for Sequence-Specific Control of Gene Expression. Cell 152, 1173-1183 (2013).
25. Michaelis, L. M., Maud "Die kinetik der invertinwirkung.". Biochem. z (1913).
26. Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).
27. Wilson, E. B. Probable inference, the law of succession, and statistical inference. J Am Stat Assoc 22, 209-212 (1927).
28. Ding, Q. et al. A TALEN genome-editing system for generating human stem cell-based disease models. Cell Stem Cell 12, 238-251 (2013).
29. Soldner, F. et al. Generation of isogenic pluripotent stem cells differing exclusively at two early onset Parkinson point mutations. Cell 146, 318-331 (2011).
30. Carlson, D. F. et al. Efficient TALEN-mediated gene knockout in livestock. Proc Natl Acad Sci USA 109, 17382-17387 (2012).
31. Geurts, A. M. et al. Knockout Rats via Embryo Microinjection of Zinc-Finger Nucleases. Science 325, 433-433 (2009).
32. Takasu. Y. et al. Targeted mutagenesis in the silkworm *Bombyx mori* using zinc finger nuclease mRNA injection. Insect Biochem Molec 40, 759-765 (2010).
33. Watanabe, T. et al. Non-transgenic genome modifications in a hemimetabolous insect using zinc-finger and TAL effector nucleases. Nat Commun 3 (2012).
34. Reyon, D. et al. FLASH assembly of TALENs for high-throughput genome editing. Nat Biotechnol 30, 460-465 (2012).
35. Boch, J. et al. Breaking the code of DNA binding specificity of TAL-type III effectors. Science 326, 1509-1512 (2009).
36. Moscou, M. J. & Bogdanove, A. J. A simple cipher governs DNA recognition by TAL effectors. Science 326, 1501 (2009).
37. Deveau, H., Garneau, J. E. & Moineau, S. CRISPR-Cas system and its role in phage-bacteria interactions. Annu Rev Microbiol 64, 475-493 (2010).
38. Horvath, P. & Barrangou, R. CRISPR/Cas, the immune system of bacteria and archaea. Science 327, 167-170 (2010).
39. Makarova, K. S. et al. Evolution and classification of the CRISPR-Cas systems. Nat Rev Microbiol 9, 467-477 (2011).
40. Bhaya, D., Davison, M. & Barrangou, R. CRISPR-Cas systems in bacteria and archaea: versatile small RNAs for adaptive defense and regulation. Annu Rev Genet. 45, 273-297 (2011).
41. Gameau, J. E. et al. The CRISPR/Cas bacterial immune system cleaves bacteriophage and plasmid DNA. Nature 468, 67-71 (2010).
42. Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).
43. Urnov, F. D., Rebar, E. J., Holmes, M. C., Zhang, H. S. & Gregory, P. D. Genome editing with engineered zinc finger nucleases. Nat Rev Genet. 11, 636-646 (2010).
44. Perez, E. E. et al. Establishment of HIV-1 resistance in CD4(+) T cells by genome editing using zinc-finger nucleases. Nat Biotechnol 26, 808-816 (2008).
45. Chen, F. Q. et al. High-frequency genome editing using ssDNA oligonucleotides with zinc-finger nucleases. Nat Methods 8, 753-U796 (2011).
46. Bedell, V. M. et al. In vivo genome editing using a high-efficiency TALEN system. Nature 491, 114-U133 (2012).
47. Saleh-Gohari, N. & Helleday, T. Conservative homologous recombination preferentially repairs DNA double-strand breaks in the S phase of the cell cycle in human cells. Nucleic Acids Res 32, 3683-3688 (2004).
48. Sapranauskas, R. et al. The *Streptococcus thermophilus* CRISPR/Cas system provides immunity in *Escherichia coli*. Nucleic Acids Res 39, 9275-9282 (2011).
49. Shen, B. et al. Generation of gene-modified mice via Cas9/RNA-mediated gene targeting. Cell Res 23, 720-723 (2013).
50. Tuschl, T. Expanding small RNA interference. Nat Biotechnol 20, 446-448 (2002).
51. Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).
52. Thomas, K. R., Folger, K. R. & Capecchi, M. R. High frequency targeting of genes to specific sites in the mammalian genome. Cell 44, 419-428 (1986).
53. Hasty, P., Rivera-Perez, J. & Bradley, A. The length of homology required for gene targeting in embryonic stem cells. Mol Cell Biol 11, 5586-5591 (1991).

54. Wu. S., Ying. G. X., Wu, Q. & Capecchi, M. R. A protocol for constructing gene targeting vectors: generating knock-out mice for the cadherin family and beyond. Nat Protoc 3, 1056-1076 (2008).

55. Oliveira, T. Y. et al. Translocation capture sequencing: a method for high throughput mapping of chromosomal rearrangements. J Immunol Methods 375, 176-181 (2012).

56. Tremblay et al., Transcription Activator-Like Effector Proteins Induce the Expression of the Frataxin Gene; Human Gene Therapy. August 2012, 23(8): 883-890.

57. Shalek et al. Nanowire-mediated delivery enables functional interrogation of primary immune cells: application to the analysis of chronic lymphocytic leukemia. Nano Letters, 2012, Dec. 12; 12(12):6498-504.

58. Pardridge et al. Preparation of Trojan horse liposomes (THLs) for gene transfer across the blood-brain barrier; Cold Spring Harb Protoc; 2010; April; 2010 (4)

59. Plosker G L et al. Fluvastatin: a review of its pharmacology and use in the management of hypercholesterolaemia; Drugs 1996, 51 (3):433-459).

60. Trapani et al. Potential role of nonstatin cholesterol lowering agents; IUBMB Life, Volume 63, Issue 11, pages 964-971, November 2011

61. Birch A M et al. DGAT1 inhibitors as anti-obesity and anti-diabetic agents; Current Opinion in Drug Discovery & Development, 2010, 13(4):489-496

62. Fuchs et al. Killing of leukemic cells with a BCR/ABL fusion gene by RNA interference (RNAi), Oncogene 2002, 21(37):5716-5724.

63. McManaman J L et al. Perilipin-2 Null Mice are Protected Against Diet-Induced Obesity, Adipose Inflammation and Fatty Liver Disease; The Journal of Lipid Research, jlr.M035063. First Published on Feb. 12, 2013.

64. Tang J et al. Inhibition of SREBP by a Small Molecule, Betulin, Improves Hyperlipidemia and Insulin Resistance and Reduces Atherosclerotic Plaques; Cell Metabolism, Volume 13, Issue 1, 44-56, 5 Jan. 2011.

65. Dumitrache et al. Trex2 enables spontaneous sister chromatid exchanges without facilitating DNA double-strand break repair; Genetics. 2011 August; 188(4): 787-797

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of altering expression of at least one gene product in a eukaryotic cell containing and expressing a DNA molecule having a target sequence and encoding said gene product comprising introducing into said eukaryotic cell an engineered, non-naturally occurring Clustered Regularly Interspaced Short Palindromic Repeats (CRISPR)-CRISPR associated (Cas) system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a *Staphylococcus aureus* Cas9 protein, wherein the CRISPR-Cas system further comprises one or more nuclear localization signal(s) (NLS(s)), and components (a) and (b) are located on same or different vectors of the system, whereby the guide RNA targets the target sequence and the Cas9 protein cleaves the DNA molecule;

the method further comprising inserting DNA into a cleaved strand of the DNA molecule;

whereby expression of the at least one gene product is altered; and, wherein the Cas9 protein and the guide RNA do not naturally occur together.

2. The method of claim 1 wherein the inserting of DNA into a cleaved strand of the DNA molecule comprises homologous recombination.

3. The method of claim 1 wherein the *Staphylococcus aureus* Cas9 protein comprises one or more mutations, wherein the mutation comprises a mutation at position 10, 762, 840, 854, 863 or 986 with reference to the position numbering of a *Streptococcus pyogenes* Cas9 protein.

4. The method of claim 1, wherein the insertion generates an altered transcription or translation gene product that is expressed.

5. The method of claim 1, wherein the CRISPR-Cas system comprises a trans-activating cr (tracr) sequence.

6. The method of claim 1, wherein the guide RNA comprises a guide sequence and a tracr sequence.

7. The method of claim 1, wherein the nucleotide sequence encoding the *Staphylococcus aureus* Cas9 protein is codon optimized for expression in the eukaryotic cell.

8. The method of claim 1, wherein the eukaryotic cell is a mammalian cell.

9. The method of claim 1, wherein the eukaryotic cell is a human cell.

10. The method of claim 6, wherein the guide sequence and tracr sequence are chimeric.

11. The method of claim 1, wherein the expression of one or more gene products is decreased.

12. The method of claim 1, wherein the one or more vectors are viral vectors.

13. The method of claim 12, wherein the viral vectors are selected from the group consisting of retroviral, lentiviral, adenoviral, adeno-associated and herpes simplex viral vectors.

14. A CRISPR-Cas system-mediated genome targeting method in a eukaryotic cell containing a DNA molecule having a target sequence comprising introducing into said eukaryotic cell an engineered, non-naturally occurring CRISPR-Cas system comprising one or more vectors comprising:

a) a first regulatory element operable in a eukaryotic cell operably linked to at least one nucleotide sequence encoding a CRISPR-Cas system guide RNA that hybridizes with the target sequence, and b) a second regulatory element operable in a eukaryotic cell operably linked to a nucleotide sequence encoding a *Staphylococcus aureus* Cas9 protein, wherein the CRISPR-Cas system further comprises one or more nuclear localization signal(s) (NLS(s)) and components (a) and (b) are located on same or different vectors of the system;

the method further comprising inserting DNA into a cleaved strand of the DNA molecule;

whereby there is CRISPR-Cas system-mediated genome targeting through the CRISPR-Cas system acting as to the DNA molecule comprising the guide RNA directing sequence-specific binding of the CRISPR-Cas system, whereby there is genome editing; and, wherein the Cas9 protein and the guide RNA do not naturally occur together.

15. The method of claim 14 wherein the inserting of DNA into a cleaved strand of the DNA molecule comprises insertion of a homologous recombination (HR) template into cleaved strand of the DNA molecule.

16. The method of claim 14, wherein expression of two or more gene products is altered by the CRISPR-Cas system-mediated genome targeting.

17. The method of claim 14, wherein the CRISPR-Cas system comprises a tracr sequence.

18. The method of claim 14, wherein the nucleotide sequence encoding the *Staphylococcus aureus* Cas9 protein is codon optimized for expression in the eukaryotic cell.

19. The method of claim 14, wherein the eukaryotic cell is a mammalian or human cell.

20. The method of claim 14, wherein expression of one or more gene products is increased by the CRISPR-Cas system-mediated genome targeting.

21. The method of claim 14, wherein expression of one or more gene products is decreased by the CRISPR-Cas system-mediated genome targeting.

22. The method of claim 14, wherein the *Staphylococcus aureus* Cas9 protein comprises one or more mutations, wherein the mutation comprises a mutation at position 10, 762, 840, 854, 863 or 986 with reference to the position numbering of a *Streptococcus pyogenes* Cas9 protein.

23. The method of claim 14, wherein the one or more vectors are viral vectors.

24. The method of claim 23, wherein the one or more viral vectors are selected from the group consisting of retroviral, lentiviral, adenoviral, adeno-associated and herpes simplex viral vectors.

25. An engineered, programmable, non-naturally occurring Type II CRISPR-Cas system comprising a *Staphylococcus aureus* Cas9 protein, at least one guide RNA that targets and hybridizes to a target sequence of a DNA molecule in a eukaryotic cell, one or more NLS(s), and DNA for insertion into a cleaved strand of the DNA molecule; wherein the Cas9 protein cleaves the DNA molecule, and the DNA for insertion inserts into a cleaved strand of the DNA molecule, whereby the CRISPR-Cas system when introduced into a eukaryotic cell having the DNA molecule provides mediated genome targeting; and, wherein the Cas9 protein and the guide RNA do not naturally occur together.

26. The CRISPR-Cas system of claim 25 wherein the DNA for insertion comprises a homologous recombination (HR) template.

27. The CRISPR-Cas system of claim 25, wherein the *Staphylococcus aureus* Cas9 protein comprises one or more mutations, wherein the mutation comprises a mutation at position 10, 762, 840, 854, 863 or 986 with reference to the position numbering of a *Streptococcus pyogenes* Cas9 protein.

28. The CRISPR-Cas system of claim 25, wherein a nucleotide sequence encoding the *Staphylococcus aureus* Cas9 protein is codon optimized for expression in the eukaryotic cell.

29. The method of claim 14, wherein the guide RNA comprises a guide sequence and a tracr sequence and wherein the guide sequence and tracr sequence are chimeric.

30. The CRISPR-Cas system of claim 25, wherein the guide RNA comprises a guide sequence and a tracr sequence and wherein the guide sequence and tracr sequence are chimeric.

* * * * *

SEQUENCE LISTING

```
<160> NUMBER OF SEQ ID NOS: 228

<210> SEQ ID NO 1
<211> LENGTH: 20
<212> TYPE: DNA
<213> ORGANISM: Homo sapiens

<400> SEQUENCE: 1

gagtccgagc agaagaagaa                                                  20


<210> SEQ ID NO 2
<211> LENGTH: 20
<212> TYPE: DNA
<213> ORGANISM: Homo sapiens

<400> SEQUENCE: 2

gagtcctagc aggagaagaa                                                  20


<210> SEQ ID NO 3
<211> LENGTH: 20
<212> TYPE: DNA
<213> ORGANISM: Homo sapiens

<400> SEQUENCE: 3

gagtctaagc agaagaagaa                                                  20


<210> SEQ ID NO 4
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(44)
```

<223> OTHER INFORMATION: a, c, u, g, unknown or other
<220> FEATURE:
<221> NAME/KEY: modified_base
<222> LOCATION: (47)..(60)
<223> OTHER INFORMATION: a, c, u, g, unknown or other

<400> SEQUENCE: 4
nnnnnnnnnn nnnnnnnnnn ccnnnnnnnn nnnnnnnnnn nnnnggnnnn nnnnnnnnnn 60

<210> SEQ ID NO 5
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(14)
<223> OTHER INFORMATION: a, c, u, g, unknown or other
<220> FEATURE:
<221> NAME/KEY: modified_base
<222> LOCATION: (17)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 5
nnnnnnnnnn nnnnccnnnn nnnnnnnnnn nnnnnnnngg nnnnnnnnnn nnnnnnnnnn 60

<210> SEQ ID NO 6
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(43)
<223> OTHER INFORMATION: a, c, u, g, unknown or other
<220> FEATURE:
<221> NAME/KEY: modified_base
<222> LOCATION: (46)..(60)
<223> OTHER INFORMATION: a, c, u, g, unknown or other

<400> SEQUENCE: 6
nnnnnnnnnn nnnnnnnnnn ccnnnnnnnn nnnnnnnnnn nnnggnnnnn nnnnnnnnnn 60

<210> SEQ ID NO 7
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)

<223> OTHER INFORMATION: a, c, u, g, unknown or other

<400> SEQUENCE: 7
nnnnnnnnnn nnnnnccnnn nnnnnnnnnn nnnnnnnngg nnnnnnnnnn nnnnnnnnnn 60

<210> SEQ ID NO 8
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(42)
<223> OTHER INFORMATION: a, c, u, g, unknown or other
<220> FEATURE:
<221> NAME/KEY: modified_base
<222> LOCATION: (45)..(60)
<223> OTHER INFORMATION: a, c, u, g, unknown or other

<400> SEQUENCE: 8
nnnnnnnnnn nnnnnnnnnn ccnnnnnnnn nnnnnnnnnn nnggnnnnnn nnnnnnnnnn 60

<210> SEQ ID NO 9
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 9
nnnnnnnnnn nnnnnccnnn nnnnnnnnnn nnnnnnnngg nnnnnnnnnn nnnnnnnnnn 60

<210> SEQ ID NO 10
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(41)
<223> OTHER INFORMATION: a, c, u, g, unknown or other
<220> FEATURE:
<221> NAME/KEY: modified_base
<222> LOCATION: (44)..(60)
<223> OTHER INFORMATION: a, c, u, g, unknown or other

<400> SEQUENCE: 10
nnnnnnnnnn nnnnnnnnnn ccnnnnnnnn nnnnnnnnnn nggnnnnnnn nnnnnnnnnn 60

<210> SEQ ID NO 11
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(17)
<223> OTHER INFORMATION: a, c, u, g, unknown or other
<220> FEATURE:
<221> NAME/KEY: modified_base
<222> LOCATION: (20)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 11
nnnnnnnnnn nnnnnnnccn nnnnnnnnnn nnnnnnnngg nnnnnnnnnn nnnnnnnnnn 60

<210> SEQ ID NO 12
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(40)
<223> OTHER INFORMATION: a, c, u, g, unknown or other
<220> FEATURE:
<221> NAME/KEY: modified_base
<222> LOCATION: (43)..(60)
<223> OTHER INFORMATION: a, c, u, g, unknown or other

<400> SEQUENCE: 12
nnnnnnnnnn nnnnnnnnnn ccnnnnnnnn nnnnnnnnnn ggnnnnnnnn nnnnnnnnnn 60

<210> SEQ ID NO 13
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(18)
<223> OTHER INFORMATION: a, c, u, g, unknown or other
<220> FEATURE:
<221> NAME/KEY: modified_base
<222> LOCATION: (21)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 13
nnnnnnnnnn nnnnnnnncc nnnnnnnnnn nnnnnnnngg nnnnnnnnnn nnnnnnnnnn 60

<210> SEQ ID NO 14

<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(39)
<223> OTHER INFORMATION: a, c, u, g, unknown or other
<220> FEATURE:
<221> NAME/KEY: modified_base
<222> LOCATION: (42)..(60)
<223> OTHER INFORMATION: a, c, u, g, unknown or other

<400> SEQUENCE: 14
nnnnnnnnnn nnnnnnnnnn ccnnnnnnnn nnnnnnnnng gnnnnnnnnn nnnnnnnnnn     60

<210> SEQ ID NO 15
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (22)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 15
nnnnnnnnnn nnnnnnnnnc cnnnnnnnnn nnnnnnnngg nnnnnnnnnn nnnnnnnnnn     60

<210> SEQ ID NO 16
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 16
nnnnnnnnnn nnnnnnnnnn ccnnnnnnnn nnnnnnnngg nnnnnnnnnn nnnnnnnnnn     60

<210> SEQ ID NO 17
<211> LENGTH: 60
<212> TYPE: RNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 17
nnnnnnnnnn nnnnnnnnnn ccnnnnnnnn nnnnnnnngg nnnnnnnnnn nnnnnnnnnn 60

<210> SEQ ID NO 18
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(37)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 18
nnnnnnnnnn nnnnnnnnnn ccnnnnnnnn nnnnnnnggn nnnnnnnnnn nnnnnnnnnn 60

<210> SEQ ID NO 19
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (24)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 19
nnnnnnnnnn nnnnnnnnnn nccnnnnnnn nnnnnnnngg nnnnnnnnnn nnnnnnnnnn 60

<210> SEQ ID NO 20
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base -continued
<222> LOCATION: (1)..(20)
<223> OTHER INFORMATION: a, c, u, g, unknown or other
<220> FEATURE:
<221> NAME/KEY: modified_base
<222> LOCATION: (23)..(36)
<223> OTHER INFORMATION: a, c, u, g, unknown or other
<220> FEATURE:
<221> NAME/KEY: modified_base
<222> LOCATION: (39)..(60)
<223> OTHER INFORMATION: a, c, u, g, unknown or other

<400> SEQUENCE: 20
nnnnnnnnnn nnnnnnnnnn ccnnnnnnnn nnnnnnggnn nnnnnnnnnn nnnnnnnnnn 60

<210> SEQ ID NO 21
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 21
nnnnnnnnnn nnnnnnnnnn nnccnnnnnn nnnnnnnngg nnnnnnnnnn nnnnnnnnnn 60

<210> SEQ ID NO 22
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 22
nnnnnnnnnn nnnnnnnnnn ccnnnnnnnn nnnnnggnnn nnnnnnnnnn nnnnnnnnnn 60

<210> SEQ ID NO 23
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 23
nnnnnnnnnn nnnnnnnnnn nnnccnnnnn nnnnnnnngg nnnnnnnnnn nnnnnnnnnn 60

<210> SEQ ID NO 24
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(34)
<223> OTHER INFORMATION: a, c, u, g, unknown or other
<220> FEATURE:
<221> NAME/KEY: modified_base
<222> LOCATION: (37)..(60)
<223> OTHER INFORMATION: a, c, u, g, unknown or other

<400> SEQUENCE: 24
nnnnnnnnnn nnnnnnnnnn ccnnnnnnnn nnnnggnnnn nnnnnnnnnn nnnnnnnnnn 60

<210> SEQ ID NO 25
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: modified_base
<222> LOCATION: (27)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 25
nnnnnnnnnn nnnnnnnnnn nnnnccnnnn nnnnnnnngg nnnnnnnnnn nnnnnnnnnn 60

<210> SEQ ID NO 26
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(33)
<223> OTHER INFORMATION: a, c, u, g, unknown or other
<220> FEATURE:
<221> NAME/KEY: modified_base

```
<222> LOCATION: (36)..(60)
<223> OTHER INFORMATION: a, c, u, g, unknown or other

<400> SEQUENCE: 26

nnnnnnnnnn nnnnnnnnnn ccnnnnnnnn nnnggnnnnn nnnnnnnnnn nnnnnnnnnn     60


<210> SEQ ID NO 27
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: a, c, u, g, unknown or other
<220> FEATURE:
<221> NAME/KEY: modified_base
<222> LOCATION: (28)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 27

nnnnnnnnnn nnnnnnnnnn nnnnnccnnn nnnnnnnngg nnnnnnnnnn nnnnnnnnnn     60


<210> SEQ ID NO 28
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
<220> FEATURE:
<221> NAME/KEY: modified_base
<222> LOCATION: (35)..(60)
<223> OTHER INFORMATION: a, c, u, g, unknown or other

<400> SEQUENCE: 28

nnnnnnnnnn nnnnnnnnnn ccnnnnnnnn nnggnnnnnn nnnnnnnnnn nnnnnnnnnn     60


<210> SEQ ID NO 29
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: a, c, u, g, unknown or other
<220> FEATURE:
<221> NAME/KEY: modified_base
<222> LOCATION: (29)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 29
```

nnnnnnnnnn nnnnnnnnnn nnnnnnccnn nnnnnnnngg nnnnnnnnnn nnnnnnnnnn 60

<210> SEQ ID NO 30
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(31)
<223> OTHER INFORMATION: a, c, u, g, unknown or other
<220> FEATURE:
<221> NAME/KEY: modified_base
<222> LOCATION: (34)..(60)
<223> OTHER INFORMATION: a, c, u, g, unknown or other

<400> SEQUENCE: 30
nnnnnnnnnn nnnnnnnnnn ccnnnnnnnn nggnnnnnnn nnnnnnnnnn nnnnnnnnnn 60

<210> SEQ ID NO 31
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(27)
<223> OTHER INFORMATION: a, c, u, g, unknown or other
<220> FEATURE:
<221> NAME/KEY: modified_base
<222> LOCATION: (30)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 31
nnnnnnnnnn nnnnnnnnnn nnnnnnnccn nnnnnnnngg nnnnnnnnnn nnnnnnnnnn 60

<210> SEQ ID NO 32
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(30)
<223> OTHER INFORMATION: a, c, u, g, unknown or other
<220> FEATURE:
<221> NAME/KEY: modified_base
<222> LOCATION: (33)..(60)
<223> OTHER INFORMATION: a, c, u, g, unknown or other

<400> SEQUENCE: 32
nnnnnnnnnn nnnnnnnnnn ccnnnnnnnn ggnnnnnnnn nnnnnnnnnn nnnnnnnnnn 60

<210> SEQ ID NO 33
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 33
nnnnnnnnnn nnnnnnnnnn nnnnnnnncc nnnnnnnngg nnnnnnnnnn nnnnnnnnnn     60

<210> SEQ ID NO 34
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(29)
<223> OTHER INFORMATION: a, c, u, g, unknown or other
<220> FEATURE:
<221> NAME/KEY: modified_base
<222> LOCATION: (32)..(60)
<223> OTHER INFORMATION: a, c, u, g, unknown or other

<400> SEQUENCE: 34
nnnnnnnnnn nnnnnnnnnn ccnnnnnnng gnnnnnnnnn nnnnnnnnnn nnnnnnnnnn     60

<210> SEQ ID NO 35
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 35
nnnnnnnnnn nnnnnnnnnn nnnnnnnnnc cnnnnnnngg nnnnnnnnnn nnnnnnnnnn     60

<210> SEQ ID NO 36
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(28)
<223> OTHER INFORMATION: a, c, u, g, unknown or other
<220> FEATURE:
<221> NAME/KEY: modified_base
<222> LOCATION: (31)..(60)
<223> OTHER INFORMATION: a, c, u, g, unknown or other

<400> SEQUENCE: 36
nnnnnnnnnn nnnnnnnnnn ccnnnnnngg nnnnnnnnnn nnnnnnnnnn nnnnnnnnnn     60

<210> SEQ ID NO 37
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 37
nnnnnnnnnn nnnnnnnnnn nnnnnnnnnn ccnnnnnngg nnnnnnnnnn nnnnnnnnnn     60

<210> SEQ ID NO 38
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(27)
<223> OTHER INFORMATION: a, c, u, g, unknown or other
<220> FEATURE:
<221> NAME/KEY: modified_base
<222> LOCATION: (30)..(60)
<223> OTHER INFORMATION: a, c, u, g, unknown or other

<400> SEQUENCE: 38
nnnnnnnnnn nnnnnnnnnn ccnnnnnggn nnnnnnnnnn nnnnnnnnnn nnnnnnnnnn     60

<210> SEQ ID NO 39
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 39
nnnnnnnnnn nnnnnnnnnn nnnnnnnnnn nccnnnnngg nnnnnnnnnn nnnnnnnnnn 60

<210> SEQ ID NO 40
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(26)
<223> OTHER INFORMATION: a, c, u, g, unknown or other
<220> FEATURE:
<221> NAME/KEY: modified_base
<222> LOCATION: (29)..(60)
<223> OTHER INFORMATION: a, c, u, g, unknown or other

<400> SEQUENCE: 40
nnnnnnnnnn nnnnnnnnnn ccnnnnggnn nnnnnnnnnn nnnnnnnnnn nnnnnnnnnn 60

<210> SEQ ID NO 41
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 41
nnnnnnnnnn nnnnnnnnnn nnnnnnnnnn nnccnnnngg nnnnnnnnnn nnnnnnnnnn 60

<210> SEQ ID NO 42
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:

<221> NAME/KEY: modified_base
<222> LOCATION: (23)..(25)
<223> OTHER INFORMATION: a, c, u, g, unknown or other
<220> FEATURE:
<221> NAME/KEY: modified_base
<222> LOCATION: (28)..(60)
<223> OTHER INFORMATION: a, c, u, g, unknown or other

<400> SEQUENCE: 42
nnnnnnnnnn nnnnnnnnnn ccnnnggnnn nnnnnnnnnn nnnnnnnnnn nnnnnnnnnn 60

<210> SEQ ID NO 43
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (36)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 43
nnnnnnnnnn nnnnnnnnnn nnnnnnnnnn nnnccnnngg nnnnnnnnnn nnnnnnnnnn 60

<210> SEQ ID NO 44
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(24)
<223> OTHER INFORMATION: a, c, u, g, unknown or other
<220> FEATURE:
<221> NAME/KEY: modified_base
<222> LOCATION: (27)..(60)
<223> OTHER INFORMATION: a, c, u, g, unknown or other

<400> SEQUENCE: 44
nnnnnnnnnn nnnnnnnnnn ccnnggnnnn nnnnnnnnnn nnnnnnnnnn nnnnnnnnnn 60

<210> SEQ ID NO 45
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(34)
<223> OTHER INFORMATION: a, c, u, g, unknown or other
<220> FEATURE:
<221> NAME/KEY: modified_base
<222> LOCATION: (37)..(38)
<223> OTHER INFORMATION: a, c, u, g, unknown or other
<220> FEATURE:

<221> NAME/KEY: modified_base
<222> LOCATION: (41)..(60)
<223> OTHER INFORMATION: a, c, u, g, unknown or other

<400> SEQUENCE: 45
nnnnnnnnnn nnnnnnnnnn nnnnnnnnnn nnnnnccnngg nnnnnnnnnn nnnnnnnnnn 60

<210> SEQ ID NO 46
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 46
nnnnnnnnnn nnnnnnnnnn ccnggnnnnn nnnnnnnnnn nnnnnnnnnn nnnnnnnnnn 60

<210> SEQ ID NO 47
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (38)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 47
nnnnnnnnnn nnnnnnnnnn nnnnnnnnnn nnnnnccngg nnnnnnnnnn nnnnnnnnnn 60

<210> SEQ ID NO 48
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 48
nnnnnnnnnn nnnnnnnnnn nccggnnnnn nnnnnnnnnn nnnnnnnnnn nnnnnnnnnn 60

<210> SEQ ID NO 49
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 49
nnnnnnnnnn nnnnnnnnnn nnnnnnnnnn nnnnnccggn nnnnnnnnnn nnnnnnnnnn 60

<210> SEQ ID NO 50
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 50
nnnnnnnnnn nnnnnnnnnn nnnggnnnnn nnnnnnnnnn nnnnnnnnnn nnnnnnnnnn 60

<210> SEQ ID NO 51
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 51
nnnnnnnnnn nnnnnnnnnn nnnnnnnnnn nnnggccnnn nnnnnnnnnn nnnnnnnnnn 60

<210> SEQ ID NO 52
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other -continued

<400> SEQUENCE: 52
nnnnnnnnnn nnnnnnnnnn nncggnnnnn nnnnnnnnnn nnnnnnnnnn nnnnnnnnnn 60

<210> SEQ ID NO 53
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 53
nnnnnnnnnn nnnnnnnnnn nnnnnnnnnn nnggnccnnn nnnnnnnnnn nnnnnnnnnn 60

<210> SEQ ID NO 54
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 54
nnnnnnnnnn nnnnnnnnnn nnnnnnnnnn nggnnccnnn nnnnnnnnnn nnnnnnnnnn 60

<210> SEQ ID NO 55
<211> LENGTH: 60
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 55
nnnnnnnnnn nnnnnnnnnn nnnnnnnnnn ggnnnccnnn nnnnnnnnnn nnnnnnnnnn 60

<210> SEQ ID NO 56
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 56
nnnnnnnnnn nnnnnnnnnn nnnnnnnnng gnnnnccnnn nnnnnnnnnn nnnnnnnnnn 60

<210> SEQ ID NO 57
<211> LENGTH: 60
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 57
nnnnnnnnnn nnnnnnnnnn nnnnnnnngg nnnnnccnnn nnnnnnnnnn nnnnnnnnnn 60

<210> SEQ ID NO 58
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 58
guuuuagagc ua 12

<210> SEQ ID NO 59
<211> LENGTH: 7
<212> TYPE: PRT
<213> ORGANISM: Simian virus 40

<400> SEQUENCE: 59

Pro Lys Lys Lys Arg Lys Val
1 5

<210> SEQ ID NO 60
<211> LENGTH: 16
<212> TYPE: PRT

<213> ORGANISM: Unknown
<220> FEATURE:
<223> OTHER INFORMATION: Description of Unknown:
Nucleoplasmin bipartite NLS sequence

<400> SEQUENCE: 60

Lys Arg Pro Ala Ala Thr Lys Lys Ala Gly Gln Ala Lys Lys Lys Lys
1 5 10 15

<210> SEQ ID NO 61
<211> LENGTH: 9
<212> TYPE: PRT
<213> ORGANISM: Unknown
<220> FEATURE:
<223> OTHER INFORMATION: Description of Unknown:
C-myc NLS sequence

<400> SEQUENCE: 61

Pro Ala Ala Lys Arg Val Lys Leu Asp
1 5

<210> SEQ ID NO 62
<211> LENGTH: 11
<212> TYPE: PRT
<213> ORGANISM: Unknown
<220> FEATURE:
<223> OTHER INFORMATION: Description of Unknown:
C-myc NLS sequence

<400> SEQUENCE: 62

Arg Gln Arg Arg Asn Glu Leu Lys Arg Ser Pro
1 5 10

<210> SEQ ID NO 63
<211> LENGTH: 38
<212> TYPE: PRT
<213> ORGANISM: Homo sapiens

<400> SEQUENCE: 63

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 64
<211> LENGTH: 42
<212> TYPE: PRT
<213> ORGANISM: Unknown
<220> FEATURE:
<223> OTHER INFORMATION: Description of Unknown:
IBB domain from importin-alpha sequence

<400> SEQUENCE: 64

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 65
<211> LENGTH: 8
<212> TYPE: PRT

<213> ORGANISM: Unknown
<220> FEATURE:
<223> OTHER INFORMATION: Description of Unknown:
Myoma T protein sequence

<400> SEQUENCE: 65

Val Ser Arg Lys Arg Pro Arg Pro
1 5

<210> SEQ ID NO 66
<211> LENGTH: 8
<212> TYPE: PRT
<213> ORGANISM: Unknown
<220> FEATURE:
<223> OTHER INFORMATION: Description of Unknown:
Myoma T protein sequence

<400> SEQUENCE: 66

Pro Pro Lys Lys Ala Arg Glu Asp
1 5

<210> SEQ ID NO 67
<211> LENGTH: 8
<212> TYPE: PRT
<213> ORGANISM: Homo sapiens

<400> SEQUENCE: 67

Pro Gln Pro Lys Lys Lys Pro Leu
1 5

<210> SEQ ID NO 68
<211> LENGTH: 12
<212> TYPE: PRT
<213> ORGANISM: Mus musculus

<400> SEQUENCE: 68

Ser Ala Leu Ile Lys Lys Lys Lys Lys Met Ala Pro
1 5 10

<210> SEQ ID NO 69
<211> LENGTH: 5
<212> TYPE: PRT
<213> ORGANISM: Influenza virus

<400> SEQUENCE: 69

Asp Arg Leu Arg Arg
1 5

<210> SEQ ID NO 70
<211> LENGTH: 7
<212> TYPE: PRT
<213> ORGANISM: Influenza virus

<400> SEQUENCE: 70

Pro Lys Gln Lys Lys Arg Lys
1 5

<210> SEQ ID NO 71
<211> LENGTH: 10
<212> TYPE: PRT
<213> ORGANISM: Hepatitus delta virus

<400> SEQUENCE: 71

Arg Lys Leu Lys Lys Lys Ile Lys Lys Leu
1 5 10

<210> SEQ ID NO 72
<211> LENGTH: 10
<212> TYPE: PRT
<213> ORGANISM: Mus musculus

<400> SEQUENCE: 72

Arg Glu Lys Lys Lys Phe Leu Lys Arg Arg
1 5 10

<210> SEQ ID NO 73
<211> LENGTH: 20
<212> TYPE: PRT
<213> ORGANISM: Homo sapiens

<400> SEQUENCE: 73

Lys Arg Lys Gly Asp Glu Val Asp Gly Val Asp Glu Val Ala Lys Lys
1 5 10 15

Lys Ser Lys Lys
20

<210> SEQ ID NO 74
<211> LENGTH: 17
<212> TYPE: PRT
<213> ORGANISM: Homo sapiens

<400> SEQUENCE: 74

Arg Lys Cys Leu Gln Ala Gly Met Asn Leu Glu Ala Arg Lys Thr Lys
1 5 10 15

Lys

<210> SEQ ID NO 75
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 75
nnnnnnnnnn nnnnnnnnnn gtttttgtac tctcaagatt tagaaataaa tcttgcagaa 60
gctacaaaga taaggcttca tgccgaaatc aacaccctgt cattttatgg cagggtgttt 120
tcgttattta atttttt 137

<210> SEQ ID NO 76
<211> LENGTH: 123
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 76
nnnnnnnnnn nnnnnnnnnn gtttttgtac tctcagaaat gcagaagcta caaagataag 60
gcttcatgcc gaaatcaaca ccctgtcatt ttatggcagg gtgttttcgt tatttaattt 120
ttt 123

<210> SEQ ID NO 77
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 77
nnnnnnnnnn nnnnnnnnnn gtttttgtac tctcagaaat gcagaagcta caaagataag     60
gcttcatgcc gaaatcaaca ccctgtcatt ttatggcagg gtgttttttt               110

<210> SEQ ID NO 78
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 78
nnnnnnnnnn nnnnnnnnnn gttttagagc tagaaatagc aagttaaaat aaggctagtc     60
cgttatcaac ttgaaaaagt ggcaccgagt cggtgctttt tt                       102

<210> SEQ ID NO 79
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 79
nnnnnnnnnn nnnnnnnnnn gttttagagc tagaaatagc aagttaaaat aaggctagtc     60
cgttatcaac ttgaaaaagt gttttttt                                        88

<210> SEQ ID NO 80
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t, g, unknown or other

<400> SEQUENCE: 80
nnnnnnnnnn nnnnnnnnnn gttttagagc tagaaatagc aagttaaaat aaggctagtc     60
cgttatcatt tttttt                                                     76

<210> SEQ ID NO 81

<211> LENGTH: 984
<212> TYPE: PRT
<213> ORGANISM: Campylobacter jejuni

<400> SEQUENCE: 81

```
Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
        355                 360                 365

Lys Lys Ala Leu Ala Lys Tyr Asp Leu Asn Gln Asn Gln Ile Asp Ser
    370                 375                 380

Leu Ser Lys Leu Glu Phe Lys Asp His Leu Asn Ile Ser Phe Lys Ala
```

```
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
    610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Glu Thr Phe Arg Lys Glu Glu Glu Phe Tyr Gln
785                 790                 795                 800

Ser Tyr Gly Gly Lys Glu Gly Val Leu Lys Ala Leu Glu Leu Gly Lys
                805                 810                 815
```

```
Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980
```

<210> SEQ ID NO 82
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82

```
tataatctca taagaaattt aaaaagggac taaaataaag agtttgcggg actctgcggg     60

gttacaatcc cctaaaaccg cttttaaaat t                                    91
```

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83

```
gttttagtcc ctttttaaat ttctttatgg taaaat                               36
```

<210> SEQ ID NO 84
<211> LENGTH: 95
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(20)
<223> OTHER INFORMATION: a, c, u, g, unknown or other

<400> SEQUENCE: 84

```
nnnnnnnnnn nnnnnnnnnn guuuuagucc cgaaagggac uaaaauaaag aguuugcggg     60
```

acucugcggg guuacaaucc ccuaaaaccg cuuuu 95

<210> SEQ ID NO 85
<211> LENGTH: 3243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85
accggtgcca ccatgtaccc atacgatgtt ccagattacg cttcgccgaa gaaaaagcgc 60
aaggtcgaag cgtccatgaa aaggaactac attctggggc tggacatcgg gattacaagc 120
gtggggtatg ggattattga ctatgaaaca agggacgtga tcgacgcagg cgtcagactg 180
ttcaaggagg ccaacgtgga aaacaatgag ggacggagaa gcaagagggg agccaggcgc 240
ctgaaacgac ggagaaggca cagaatccag agggtgaaga aactgctgtt cgattacaac 300
ctgctgaccg accattctga gctgagtgga attaatcctt atgaagccag ggtgaaaggc 360
ctgagtcaga agctgtcaga ggaagagttt tccgcagctc tgctgcacct ggctaagcgc 420
cgaggagtgc ataacgtcaa tgaggtggaa gaggacaccg gcaacgagct gtctacaaag 480
gaacagatct cacgcaatag caaagctctg gaagagaagt atgtcgcaga gctgcagctg 540
gaacggctga agaaagatgg cgaggtgaga gggtcaatta ataggttcaa gacaagcgac 600
tacgtcaaag aagccaagca gctgctgaaa gtgcagaagg cttaccacca gctggatcag 660
agcttcatcg atacttatat cgacctgctg gagactcgga gaacctacta tgagggacca 720
ggagaaggga gccccttcgg atggaaagac atcaaggaat ggtacgagat gctgatggga 780
cattgcacct attttccaga agagctgaga agcgtcaagt acgcttataa cgcagatctg 840
tacaacgccc tgaatgacct gaacaacctg gtcatcacca gggatgaaaa cgagaaactg 900
gaatactatg agaagttcca gatcatcgaa aacgtgttta agcagaagaa aaagcctaca 960
ctgaaacaga ttgctaagga gatcctggtc aacgaagagg acatcaaggg ctaccgggtg 1020
acaagcactg gaaaaccaga gttcaccaat ctgaaagtgt atcacgatat taaggacatc 1080
acagcacgga aagaaatcat tgagaacgcc gaactgctgg atcagattgc taagatcctg 1140
actatctacc agagctccga ggacatccag gaagagctga ctaacctgaa cagcgagctg 1200
acccaggaag agatcgaaca gattagtaat ctgaaggggt acaccggaac acacaacctg 1260
tccctgaaag ctatcaatct gattctggat gagctgtggc atacaaacga caatcagatt 1320
gcaatcttta accggctgaa gctggtccca aaaaaggtgg acctgagtca gcagaaagag 1380
atcccaacca cactggtgga cgatttcatt ctgtcacccg tggtcaagcg gagcttcatc 1440
cagagcatca aagtgatcaa cgccatcatc aagaagtacg gcctgcccaa tgatatcatt 1500
atcgagctgg ctagggagaa gaacagcaag gacgcacaga agatgatcaa tgagatgcag 1560
aaacgaaacc ggcagaccaa tgaacgcatt gaagagatta tccgaactac cgggaaagag 1620
aacgcaaagt acctgattga aaaaatcaag ctgcacgata tgcaggaggg aaagtgtctg 1680
tattctctgg aggccatccc cctggaggac ctgctgaaca atccattcaa ctacgaggtc 1740
gatcatatta tccccagaag cgtgtccttc gacaattcct ttaacaacaa ggtgctggtc 1800
aagcaggaag agaactctaa aaagggcaat aggactcctt tccagtacct gtctagttca 1860
gattccaaga tctcttacga aacctttaaa aagcacattc tgaatctggc caaaggaaag 1920
ggccgcatca gcaagaccaa aaaggagtac ctgctggaag agcgggacat caacagattc 1980

```
tccgtccaga aggattttat taaccggaat ctggtggaca caagatacgc tactcgcggc   2040
ctgatgaatc tgctgcgatc ctatttccgg gtgaacaatc tggatgtgaa agtcaagtcc   2100
atcaacggcg ggttcacatc ttttctgagg cgcaaatgga agtttaaaaa ggagcgcaac   2160
aaagggtaca agcaccatgc cgaagatgct ctgattatcg caaatgccga cttcatcttt   2220
aaggagtgga aaaagctgga caaagccaag aaagtgatgg agaaccagat gttcgaagag   2280
aagcaggccg aatctatgcc cgaaatcgag acagaacagg agtacaagga gattttcatc   2340
actcctcacc agatcaagca tatcaaggat ttcaaggact acaagtactc tcaccgggtg   2400
gataaaaagc ccaacagaga gctgatcaat gacaccctgt atagtacaag aaaagacgat   2460
aaggggaata ccctgattgt gaacaatctg aacggactgt acgacaaaga taatgacaag   2520
ctgaaaaagc tgatcaacaa aagtcccgag aagctgctga tgtaccacca tgatcctcag   2580
acatatcaga aactgaagct gattatggag cagtacggcg acgagaagaa cccactgtat   2640
aagtactatg aagagactgg gaactacctg accaagtata gcaaaaagga taatggcccc   2700
gtgatcaaga agatcaagta ctatgggaac aagctgaatg cccatctgga catcacagac   2760
gattacccta acagtcgcaa caaggtggtc aagctgtcac tgaagccata cagattcgat   2820
gtctatctgg acaacggcgt gtataaattt gtgactgtca agaatctgga tgtcatcaaa   2880
aaggagaact actatgaagt gaatagcaag tgctacgaag aggctaaaaa gctgaaaaag   2940
attagcaacc aggcagagtt catcgcctcc ttttacaaca acgacctgat taagatcaat   3000
ggcgaactgt atagggtcat cggggtgaac aatgatctgc tgaaccgcat tgaagtgaat   3060
atgattgaca tcacttaccg agagtatctg gaaaacatga atgataagcg ccccccctcga   3120
attatcaaaa caattgcctc taagactcag agtatcaaaa agtactcaac cgacattctg   3180
ggaaacctgt atgaggtgaa gagcaaaaag caccctcaga ttatcaaaaa gggctaagaa   3240
ttc                                                                3243
```

```
<210> SEQ ID NO 86
<211> LENGTH: 1115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125
```

-continued

```
Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Asn Gln Thr Thr Gln Lys Gly Gln Lys Asn Ser Arg Glu Arg Met
        515                 520                 525

Lys Arg Ile Glu Glu Gly Ile Lys Glu Leu Gly Ser Gln Ile Leu Lys
    530                 535                 540

Glu His Pro Val Glu Asn Thr Gln Leu Gln Asn Glu Lys Leu Tyr Leu
```

-continued

```
545                 550                 555                 560

Tyr Tyr Leu Gln Asn Gly Arg Asp Met Tyr Val Asp Gln Glu Leu Asp
                565                 570                 575

Ile Asn Arg Leu Ser Asp Tyr Asp Val Asp His Ile Val Pro Gln Ser
            580                 585                 590

Phe Leu Lys Asp Asp Ser Ile Asp Asn Lys Val Leu Thr Arg Ser Asp
        595                 600                 605

Lys Asn Arg Gly Lys Ser Asp Asn Val Pro Ser Glu Glu Val Val Lys
    610                 615                 620

Lys Met Lys Asn Tyr Trp Arg Gln Leu Leu Asn Ala Lys Leu Ile Thr
625                 630                 635                 640

Gln Arg Lys Phe Asp Asn Leu Thr Lys Ala Glu Arg Gly Gly Leu Ser
                645                 650                 655

Glu Leu Asp Lys Ala Gly Phe Ile Lys Arg Gln Leu Val Glu Thr Arg
            660                 665                 670

Gln Ile Thr Lys His Val Ala Gln Ile Leu Asp Ser Arg Met Asn Thr
        675                 680                 685

Lys Tyr Asp Glu Asn Asp Lys Leu Ile Arg Glu Val Lys Val Ile Thr
    690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
                725                 730                 735

Asn Ala Val Val Gly Thr Ala Leu Ile Lys Lys Tyr Pro Lys Leu Glu
            740                 745                 750

Ser Glu Phe Val Tyr Gly Asp Tyr Lys Val Tyr Asp Val Arg Lys Met
        755                 760                 765

Ile Ala Lys Ser Glu Gln Glu Ile Gly Lys Ala Thr Ala Lys Tyr Phe
    770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                805                 810                 815

Gly Glu Ile Val Trp Asp Lys Gly Arg Asp Phe Ala Thr Val Arg Lys
            820                 825                 830

Val Leu Ser Met Pro Gln Val Asn Ile Val Lys Lys Thr Glu Val Gln
        835                 840                 845

Thr Gly Gly Phe Ser Lys Glu Ser Ile Leu Pro Lys Arg Asn Ser Asp
    850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                885                 890                 895

Glu Lys Gly Lys Ser Lys Lys Leu Lys Ser Val Lys Glu Leu Leu Gly
            900                 905                 910

Ile Thr Ile Met Glu Arg Ser Ser Phe Glu Lys Asn Pro Ile Asp Phe
        915                 920                 925

Leu Glu Ala Lys Gly Tyr Lys Glu Val Lys Lys Asp Leu Ile Ile Lys
    930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                965                 970                 975
```

```
Ser Lys Tyr Val Asn Phe Leu Tyr Leu Ala Ser His Tyr Glu Lys Leu
            980                 985                 990

Lys Gly Ser Pro Glu Asp Asn Glu  Gln Lys Gln Leu Phe  Val Glu Gln
        995                 1000                 1005

His Lys  His Tyr Leu Asp Glu  Ile Ile Glu Gln Ile  Ser Glu Phe
    1010                 1015                 1020

Ser Lys  Arg Val Ile Leu Ala  Asp Ala Asn Leu Asp  Lys Val Leu
    1025                 1030                 1035

Ser Ala  Tyr Asn Lys His Arg  Asp Lys Pro Ile Arg  Glu Gln Ala
    1040                 1045                 1050

Glu Asn  Ile Ile His Leu Phe  Thr Leu Thr Asn Leu  Gly Ala Pro
    1055                 1060                 1065

Ala Ala  Phe Lys Tyr Phe Asp  Thr Thr Ile Asp Arg  Lys Arg Tyr
    1070                 1075                 1080

Thr Ser  Thr Lys Glu Val Leu  Asp Ala Thr Leu Ile  His Gln Ser
    1085                 1090                 1095

Ile Thr  Gly Leu Tyr Glu Thr  Arg Ile Asp Leu Ser  Gln Leu Gly
    1100                 1105                 1110

Gly Asp
    1115
```

<210> SEQ ID NO 87
<211> LENGTH: 1374
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
```

```
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

```
Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Thr Asn
        755                 760                 765

Glu Asp Asp Glu Lys Lys Ala Ile Gln Lys Ile Gln Lys Ala Asn Lys
    770                 775                 780

Asp Glu Lys Asp Ala Ala Met Leu Lys Ala Ala Asn Gln Tyr Asn Gly
785                 790                 795                 800

Lys Ala Glu Leu Pro His Ser Val Phe His Gly His Lys Gln Leu Ala
                805                 810                 815

Thr Lys Ile Arg Leu Trp His Gln Gln Gly Glu Arg Cys Leu Tyr Thr
            820                 825                 830

Gly Lys Thr Ile Ser Ile His Asp Leu Ile Asn Asn Ser Asn Gln Phe
        835                 840                 845

Glu Val Asp His Ile Leu Pro Leu Ser Ile Thr Phe Asp Asp Ser Leu
    850                 855                 860

Ala Asn Lys Val Leu Val Tyr Ala Thr Ala Asn Gln Glu Lys Gly Gln
865                 870                 875                 880

Arg Thr Pro Tyr Gln Ala Leu Asp Ser Met Asp Asp Ala Trp Ser Phe
                885                 890                 895

Arg Glu Leu Lys Ala Phe Val Arg Glu Ser Lys Thr Leu Ser Asn Lys
            900                 905                 910

Lys Lys Glu Tyr Leu Leu Thr Glu Glu Asp Ile Ser Lys Phe Asp Val
        915                 920                 925

Arg Lys Lys Phe Ile Glu Arg Asn Leu Val Asp Thr Arg Tyr Ala Ser
    930                 935                 940

Arg Val Val Leu Asn Ala Leu Gln Glu His Phe Arg Ala His Lys Ile
945                 950                 955                 960

Asp Thr Lys Val Ser Val Val Arg Gly Gln Phe Thr Ser Gln Leu Arg
                965                 970                 975

Arg His Trp Gly Ile Glu Lys Thr Arg Asp Thr Tyr His His His Ala
            980                 985                 990

Val Asp Ala Leu Ile Ile Ala Ala  Ser Ser Gln Leu Asn  Leu Trp Lys
        995                 1000                 1005

Lys Gln  Lys Asn Thr Leu Val  Ser Tyr Ser Glu Asp  Gln Leu Leu
    1010                 1015                 1020

Asp Ile  Glu Thr Gly Glu Leu  Ile Ser Asp Asp Glu  Tyr Lys Glu
    1025                 1030                 1035
```

-continued

```
Ser Val  Phe Lys Ala Pro Tyr  Gln His Phe Val Asp  Thr Leu Lys
    1040                 1045                 1050

Ser Lys  Glu Phe Glu Asp Ser  Ile Leu Phe Ser Tyr  Gln Val Asp
    1055                 1060                 1065

Ser Lys  Phe Asn Arg Lys Ile  Ser Asp Ala Thr Ile  Tyr Ala Thr
    1070                 1075                 1080

Arg Gln  Ala Lys Val Gly Lys  Asp Lys Ala Asp Glu  Thr Tyr Val
    1085                 1090                 1095

Leu Gly  Lys Ile Lys Asp Ile  Tyr Thr Gln Asp Gly  Tyr Asp Ala
    1100                 1105                 1110

Phe Met  Lys Ile Tyr Lys Lys  Asp Lys Ser Lys Phe  Leu Met Tyr
    1115                 1120                 1125

Arg His  Asp Pro Gln Thr Phe  Glu Lys Val Ile Glu  Pro Ile Leu
    1130                 1135                 1140

Glu Asn  Tyr Pro Asn Lys Gln  Ile Asn Glu Lys Gly  Lys Glu Val
    1145                 1150                 1155

Pro Cys  Asn Pro Phe Leu Lys  Tyr Lys Glu Glu His  Gly Tyr Ile
    1160                 1165                 1170

Arg Lys  Tyr Ser Lys Lys Gly  Asn Gly Pro Glu Ile  Lys Ser Leu
    1175                 1180                 1185

Lys Tyr  Tyr Asp Ser Lys Leu  Gly Asn His Ile Asp  Ile Thr Pro
    1190                 1195                 1200

Lys Asp  Ser Asn Asn Lys Val  Val Leu Gln Ser Val  Ser Pro Trp
    1205                 1210                 1215

Arg Ala  Asp Val Tyr Phe Asn  Lys Thr Thr Gly Lys  Tyr Glu Ile
    1220                 1225                 1230

Leu Gly  Leu Lys Tyr Ala Asp  Leu Gln Phe Glu Lys  Gly Thr Gly
    1235                 1240                 1245

Thr Tyr  Lys Ile Ser Gln Glu  Lys Tyr Asn Asp Ile  Lys Lys Lys
    1250                 1255                 1260

Glu Gly  Val Asp Ser Asp Ser  Glu Phe Lys Phe Thr  Leu Tyr Lys
    1265                 1270                 1275

Asn Asp  Leu Leu Leu Val Lys  Asp Thr Glu Thr Lys  Glu Gln Gln
    1280                 1285                 1290

Leu Phe  Arg Phe Leu Ser Arg  Thr Met Pro Lys Gln  Lys His Tyr
    1295                 1300                 1305

Val Glu  Leu Lys Pro Tyr Asp  Lys Gln Lys Phe Glu  Gly Gly Glu
    1310                 1315                 1320

Ala Leu  Ile Lys Val Leu Gly  Asn Val Ala Asn Ser  Gly Gln Cys
    1325                 1330                 1335

Lys Lys  Gly Leu Gly Lys Ser  Asn Ile Ser Ile Tyr  Lys Val Arg
    1340                 1345                 1350

Thr Asp  Val Leu Gly Asn Gln  His Ile Ile Lys Asn  Glu Gly Asp
    1355                 1360                 1365

Lys Pro  Lys Leu Asp Phe
    1370
```

<210> SEQ ID NO 88
<211> LENGTH: 4677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

-continued

```
tctttcttgc gctatgacac ttccagcaaa aggtagggcg ggctgcgaga cggcttcccg     60
gcgctgcatg caacaccgat gatgcttcga ccccccgaag ctccttcggg gctgcatggg    120
cgctccgatg ccgctccagg gcgagcgctg tttaaatagc caggcccccg attgcaaaga    180
cattatagcg agctaccaaa gccatattca aacacctaga tcactaccac ttctacacag    240
gccactcgag cttgtgatcg cactccgcta agggggcgcc tcttcctctt cgtttcagtc    300
acaacccgca aacatgtacc catacgatgt tccagattac gcttcgccga agaaaaagcg    360
caaggtcgaa gcgtccgaca agaagtacag catcggcctg gacatcggca ccaactctgt    420
gggctgggcc gtgatcaccg acgagtacaa ggtgcccagc aagaaattca aggtgctggg    480
caacaccgac cggcacagca tcaagaagaa cctgatcgga gccctgctgt tcgacagcgg    540
cgaaacagcc gaggccaccc ggctgaagag aaccgccaga agaagataca ccagacggaa    600
gaaccggatc tgctatctgc aagagatctt cagcaacgag atggccaagg tggacgacag    660
cttcttccac agactggaag agtccttcct ggtggaagag gataagaagc acgagcggca    720
ccccatcttc ggcaacatcg tggacgaggt ggcctaccac gagaagtacc ccaccatcta    780
ccacctgaga aagaaactgg tggacagcac cgacaaggcc gacctgcggc tgatctatct    840
ggccctggcc cacatgatca agttccgggg ccacttcctg atcgagggcg acctgaaccc    900
cgacaacagc gacgtggaca agctgttcat ccagctggtg cagacctaca accagctgtt    960
cgaggaaaac cccatcaacg ccagcggcgt ggacgccaag gccatcctgt ctgccagact   1020
gagcaagagc agacggctgg aaaatctgat cgcccagctg cccggcgaga agaagaatgg   1080
cctgttcggc aacctgattg ccctgagcct gggcctgacc cccaacttca agagcaactt   1140
cgacctggcc gaggatgcca aactgcagct gagcaaggac acctacgacg acgacctgga   1200
caacctgctg gcccagatcg gcgaccagta cgccgacctg tttctggccg ccaagaacct   1260
gtccgacgcc atcctgctga gcgacatcct gagagtgaac accgagatca ccaaggcccc   1320
cctgagcgcc tctatgatca agagatacga cgagcaccac caggacctga ccctgctgaa   1380
agctctcgtg cggcagcagc tgcctgagaa gtacaaagag attttcttcg accagagcaa   1440
gaacggctac gccggctaca ttgacggcgg agccagccag gaagagttct acaagttcat   1500
caagcccatc ctggaaaaga tggacggcac cgaggaactg ctcgtgaagc tgaacagaga   1560
ggacctgctg cggaagcagc ggaccttcga caacggcagc atcccccacc agatccacct   1620
gggagagctg cacgccattc tgcggcggca ggaagatttt tacccattcc tgaaggacaa   1680
ccgggaaaag atcgagaaga tcctgacctt ccgcatcccc tactacgtgg gccctctggc   1740
caggggaaac agcagattcg cctggatgac cagaaagagc gaggaaacca tcaccccctg   1800
gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg gaatgagaaa   1980
gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca cataccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
```

-continued

```
caccggctgg ggcaggctga gccggaagct gatcaacggc atccgggaca agcagtccgg   2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga gaaccagacc acccagaagg gacagaagaa   2700
cagccgcgag agaatgaagc ggatcgaaga gggcatcaaa gagctgggca gccagatcct   2760
gaaagaacac cccgtggaaa acacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccggatg aacactaagt acgacgagaa tgacaagctg atccgggaag tgaaagtgat   3240
caccctgaag tccaagctgg tgtccgattt ccggaaggat ttccagtttt acaaagtgcg   3300
cgagatcaac aactaccacc acgcccacga cgcctacctg aacgccgtcg tgggaaccgc   3360
cctgatcaaa aagtacccta agctggaaag cgagttcgtg tacggcgact acaaggtgta   3420
cgacgtgcgg aagatgatcg ccaagagcga gcaggaaatc ggcaaggcta ccgccaagta   3480
cttcttctac agcaacatca tgaacttttt caagaccgag attaccctgg ccaacggcga   3540
gatccggaag cggcctctga tcgagacaaa cggcgaaacc ggggagatcg tgtgggataa   3600
gggccgggat tttgccaccg tgcggaaagt gctgagcatg ccccaagtga atatcgtgaa   3660
aaagaccgag gtgcagacag gcggcttcag caaagagtct atcctgccca agaggaacag   3720
cgataagctg atcgccagaa agaaggactg ggaccctaag aagtacggcg gcttcgacag   3780
ccccaccgtg gcctattctg tgctggtggt ggccaaagtg gaaaagggca agtccaagaa   3840
actgaagagt gtgaaagagc tgctggggat caccatcatg gaaagaagca gcttcgagaa   3900
gaatcccatc gactttctgg aagccaaggg ctacaaagaa gtgaaaaagg acctgatcat   3960
caagctgcct aagtactccc tgttcgagct ggaaaacggc cggaagagaa tgctggcctc   4020
tgccggcgaa ctgcagaagg gaaacgaact ggccctgccc tccaaatatg tgaacttcct   4080
gtacctggcc agccactatg agaagctgaa gggctccccc gaggataatg agcagaaaca   4140
gctgtttgtg gaacagcaca agcactacct ggacgagatc atcgagcaga tcagcgagtt   4200
ctccaagaga gtgatcctgg ccgacgctaa tctggacaaa gtgctgtccg cctacaacaa   4260
gcaccgggat aagcccatca gagagcaggc cgagaatatc atccacctgt ttaccctgac   4320
caatctggga gccccctgccg ccttcaagta ctttgacacc accatcgacc ggaagaggta   4380
caccagcacc aaagaggtgc tggacgccac cctgatccac cagagcatca ccggcctgta   4440
cgagacacgg atcgacctgt ctcagctggg aggcgacagc cccaagaaga agagaaaggt   4500
ggaggccagc taaggatccg gcaagactgg ccccgcttgg caacgcaaca gtgagcccct   4560
ccctagtgtg tttggggatg tgactatgta ttcgtgtgtt ggccaacggg tcaacccgaa   4620
cagattgata cccgccttgg catttcctgt cagaatgtaa cgtcagttga tggtact      4677
```

<210> SEQ ID NO 89
<211> LENGTH: 3150
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
tctttcttgc gctatgacac ttccagcaaa aggtagggcg ggctgcgaga cggcttcccg     60
gcgctgcatg caacaccgat gatgcttcga ccccccgaag ctccttcggg gctgcatggg    120
cgctccgatg ccgctccagg gcgagcgctg tttaaatagc caggcccccg attgcaaaga    180
cattatagcg agctaccaaa gccatattca aacacctaga tcactaccac ttctacacag    240
gccactcgag cttgtgatcg cactccgcta agggggcgcc tcttcctctt cgtttcagtc    300
acaacccgca aacatgccta agaagaagag gaaggttaac acgattaaca tcgctaagaa    360
cgacttctct gacatcgaac tggctgctat cccgttcaac actctggctg accattacgg    420
tgagcgttta gctcgcgaac agttggccct tgagcatgag tcttacgaga tgggtgaagc    480
acgcttccgc aagatgtttg agcgtcaact taaagctggt gaggttgcgg ataacgctgc    540
cgccaagcct ctcatcacta ccctactccc taagatgatt gcacgcatca acgactggtt    600
tgaggaagtg aaagctaagc gcggcaagcg cccgacagcc ttccagttcc tgcaagaaat    660
caagccggaa gccgtagcgt acatcaccat taagaccact ctggcttgcc taaccagtgc    720
tgacaataca accgttcagg ctgtagcaag cgcaatcggt cgggccattg aggacgaggc    780
tcgcttcggt cgtatccgtg accttgaagc taagcacttc aagaaaaacg ttgaggaaca    840
actcaacaag cgcgtagggc acgtctacaa gaaagcattt atgcaagttg tcgaggctga    900
catgctctct aagggtctac tcggtggcga ggcgtggtct tcgtggcata aggaagactc    960
tattcatgta ggagtacgct gcatcgagat gctcattgag tcaaccggaa tggttagctt   1020
acaccgccaa aatgctggcg tagtaggtca agactctgag actatcgaac tcgcacctga   1080
atacgctgag gctatcgcaa cccgtgcagg tgcgctggct ggcatctctc cgatgttcca   1140
accttgcgta gttcctccta agccgtggac tggcattact ggtggtggct attgggctaa   1200
cggtcgtcgt cctctggcgc tggtgcgtac tcacagtaag aaagcactga tgcgctacga   1260
agacgtttac atgcctgagg tgtacaaagc gattaacatt gcgcaaaaca ccgcatggaa   1320
aatcaacaag aaagtcctag cggtcgccaa cgtaatcacc aagtggaagc attgtccggt   1380
cgaggacatc cctgcgattg agcgtgaaga actcccgatg aaaccggaag acatcgacat   1440
gaatcctgag gctctcaccg cgtggaaacg tgctgccgct gctgtgtacc gcaaggacaa   1500
ggctcgcaag tctcgccgta tcagccttga gttcatgctt gagcaagcca ataagtttgc   1560
taaccataag gccatctggt tcccttacaa catggactgg cgcggtcgtg tttacgctgt   1620
gtcaatgttc aacccgcaag gtaacgatat gaccaaagga ctgcttacgc tggcgaaagg   1680
taaaccaatc ggtaaggaag gttactactg gctgaaaatc cacggtgcaa actgtgcggg   1740
tgtcgacaag gttccgttcc ctgagcgcat caagttcatt gaggaaaacc acgagaacat   1800
catggcttgc gctaagtctc cactggagaa cacttggtgg gctgagcaag attctccgtt   1860
ctgcttcctt gcgttctgct ttgagtacgc tggggtacag caccacggcc tgagctataa   1920
ctgctccctt ccgctggcgt ttgacgggtc ttgctctggc atccagcact tctccgcgat   1980
gctccgagat gaggtaggtg gtcgcgcggt taacttgctt cctagtgaaa ccgttcagga   2040
catctacggg attgttgcta agaaagtcaa cgagattcta caagcagacg caatcaatgg   2100
```

gaccgataac gaagtagtta ccgtgaccga tgagaacact ggtgaaatct ctgagaaagt 2160
caagctgggc actaaggcac tggctggtca atggctggct tacggtgtta ctcgcagtgt 2220
gactaagcgt tcagtcatga cgctggctta cgggtccaaa gagttcggct tccgtcaaca 2280
agtgctggaa gataccattc agccagctat tgattccggc aagggtctga tgttcactca 2340
gccgaatcag gctgctggat acatggctaa gctgatttgg gaatctgtga gcgtgacggt 2400
ggtagctgcg gttgaagcaa tgaactggct taagtctgct gctaagctgc tggctgctga 2460
ggtcaaagat aagaagactg gagagattct tcgcaagcgt tgcgctgtgc attgggtaac 2520
tcctgatggt ttccctgtgt ggcaggaata caagaagcct attcagacgc gcttgaacct 2580
gatgttcctc ggtcagttcc gcttacagcc taccattaac accaacaaag atagcgagat 2640
tgatgcacac aaacaggagt ctggtatcgc tcctaacttt gtacacagcc aagacggtag 2700
ccaccttcgt aagactgtag tgtgggcaca cgagaagtac ggaatcgaat cttttgcact 2760
gattcacgac tccttcggta cgattccggc tgacgctgcg aacctgttca aagcagtgcg 2820
cgaaactatg gttgacacat atgagtcttg tgatgtactg gctgatttct acgaccagtt 2880
cgctgaccag ttgcacgagt ctcaattgga caaaatgcca gcacttccgg ctaaaggtaa 2940
cttgaacctc cgtgacatct tagagtcgga cttcgcgttc gcgtaaggat ccggcaagac 3000
tggccccgct tggcaacgca acagtgagcc cctccctagt gtgtttgggg atgtgactat 3060
gtattcgtgt gttggccaac gggtcaaccc gaacagattg atacccgcct tggcatttcc 3120
tgtcagaatg taacgtcagt tgatggtact 3150

<210> SEQ ID NO 90
<211> LENGTH: 125
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (23)..(42)
<223> OTHER INFORMATION: a, c, t, g, unknown or other

<400> SEQUENCE: 90
gaaattaata cgactcacta tannnnnnnn nnnnnnnnnn nngttttaga gctagaaata 60
gcaagttaaa ataaggctag tccgttatca acttgaaaaa gtggcaccga gtcggtgctt 120
ttttt 125

<210> SEQ ID NO 91
<211> LENGTH: 8452
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 91
tgcggtattt cacaccgcat caggtggcac ttttcgggga aatgtgcgcg gaacccctat 60
ttgtttattt ttctaaatac attcaaatat gtatccgctc atgagattat caaaaaggat 120
cttcacctag atccttttaa attaaaaatg aagttttaaa tcaatctaaa gtatatatga 180
gtaaacttgg tctgacagtt accaatgctt aatcagtgag gcacctatct cagcgatctg 240
tctatttcgt tcatccatag ttgcctgact ccccgtcgtg tagataacta cgatacggga 300

```
gggcttacca tctggcccca gtgctgcaat gataccgcga gacccacgct caccggctcc    360
agatttatca gcaataaacc agccagccgg aagggccgag cgcagaagtg gtcctgcaac    420
tttatccgcc tccatccagt ctattaattg ttgccgggaa gctagagtaa gtagttcgcc    480
agttaatagt ttgcgcaacg ttgttgccat tgctacaggc atcgtggtgt cacgctcgtc    540
gtttggtatg gcttcattca gctccggttc ccaacgatca aggcgagtta catgatcccc    600
catgttgtgc aaaaaagcgg ttagctcctt cggtcctccg atcgttgtca gaagtaagtt    660
ggccgcagtg ttatcactca tggttatggc agcactgcat aattctctta ctgtcatgcc    720
atccgtaaga tgcttttctg tgactggtga gtactcaacc aagtcattct gagaatagtg    780
tatgcggcga ccgagttgct cttgcccggc gtcaatacgg gataataccg cgccacatag    840
cagaacttta aaagtgctca tcattggaaa acgttcttcg gggcgaaaac tctcaaggat    900
cttaccgctg ttgagatcca gttcgatgta acccactcgt gcacccaact gatcttcagc    960
atcttttact ttcaccagcg tttctgggtg agcaaaaaca ggaaggcaaa atgccgcaaa   1020
aaagggaata agggcgacac ggaaatgttg aatactcata ctcttccttt ttcaatatta   1080
ttgaagcatt tatcagggtt attgtctcat gaccaaaatc ccttaacgtg agttttcgtt   1140
ccactgagcg tcagaccccg tagaaaagat caaaggatct tcttgagatc cttttttttct  1200
gcgcgtaatc tgctgcttgc aaacaaaaaa accaccgcta ccagcggtgg tttgtttgcc   1260
ggatcaagag ctaccaactc tttttccgaa ggtaactggc ttcagcagag cgcagatacc   1320
aaatactgtt cttctagtgt agccgtagtt aggccaccac ttcaagaact ctgtagcacc   1380
gcctacatac ctcgctctgc taatcctgtt accagtggct gttgccagtg gcgataagtc   1440
gtgtcttacc gggttggact caagacgata gttaccggat aaggcgcagc ggtcgggctg   1500
aacggggggt tcgtgcacac agcccagctt ggagcgaacg acctacaccg aactgagata   1560
cctacagcgt gagctatgag aaagcgccac gcttcccgaa gggagaaagg cggacaggta   1620
tccggtaagc ggcagggtcg gaacaggaga gcgcacgagg gagcttccag ggggaaacgc   1680
ctggtatctt tatagtcctg tcgggtttcg ccacctctga cttgagcgtc gatttttgtg   1740
atgctcgtca ggggggcgga gcctatggaa aaacgccagc aacgcggcct ttttacggtt   1800
cctggccttt tgctggcctt ttgctcacat gttctttcct gcgttatccc ctgattctgt   1860
ggataaccgt attaccgcct ttgagtgagc tgataccgct cgccgcagcc gaacgaccga   1920
gcgcagcgag tcagtgagcg aggaagcggt cgctgaggct tgacatgatt ggtgcgtatg   1980
tttgtatgaa gctacaggac tgatttggcg ggctatgagg gcgggggaag ctctggaagg   2040
gccgcgatgg ggcgcgcggc gtccagaagg cgccatacgg cccgctggcg gcacccatcc   2100
ggtataaaag cccgcgaccc cgaacggtga cctccacttt cagcgacaaa cgagcactta   2160
tacatacgcg actattctgc cgctatacat aaccactcag ctagcttaag atcccatcaa   2220
gcttgcatgc cgggcgcgcc agaaggagcg cagccaaacc aggatgatgt ttgatggggt   2280
atttgagcac ttgcaaccct tatccggaag ccccctggcc cacaaaggct aggcgccaat   2340
gcaagcagtt cgcatgcagc ccctggagcg gtgccctcct gataaaccgg ccagggggcc   2400
tatgttcttt actttttttac aagagaagtc actcaacatc ttaaaatggc caggtgagtc  2460
gacgagcaag cccggcggat caggcagcgt gcttgcagat ttgacttgca acgcccgcat   2520
tgtgtcgacg aaggcttttg gctcctctgt cgctgtctca agcagcatct aaccctgcgt   2580
cgccgtttcc atttgcagga gattcgaggt accatgtacc catacgatgt tccagattac   2640
gcttcgccga agaaaaagcg caaggtcgaa gcgtccgaca agaagtacag catcggcctg   2700
```

```
gacatcggca ccaactctgt gggctgggcc gtgatcaccg acgagtacaa ggtgcccagc   2760
aagaaattca aggtgctggg caacaccgac cggcacagca tcaagaagaa cctgatcgga   2820
gccctgctgt tcgacagcgg cgaaacagcc gaggccaccc ggctgaagag aaccgccaga   2880
agaagataca ccagacggaa gaaccggatc tgctatctgc aagagatctt cagcaacgag   2940
atggccaagg tggacgacag cttcttccac agactggaag agtccttcct ggtggaagag   3000
gataagaagc acgagcggca ccccatcttc ggcaacatcg tggacgaggt ggcctaccac   3060
gagaagtacc ccaccatcta ccacctgaga aagaaactgg tggacagcac cgacaaggcc   3120
gacctgcggc tgatctatct ggccctggcc cacatgatca agttccgggg ccacttcctg   3180
atcgagggcg acctgaaccc cgacaacagc gacgtggaca agctgttcat ccagctggtg   3240
cagacctaca accagctgtt cgaggaaaac cccatcaacg ccagcggcgt ggacgccaag   3300
gccatcctgt ctgccagact gagcaagagc agacggctgg aaaatctgat cgcccagctg   3360
cccggcgaga agaagaatgg cctgttcggc aacctgattg ccctgagcct gggcctgacc   3420
cccaacttca agagcaactt cgacctggcc gaggatgcca aactgcagct gagcaaggac   3480
acctacgacg acgacctgga caacctgctg gcccagatcg gcgaccagta cgccgacctg   3540
tttctggccg ccaagaacct gtccgacgcc atcctgctga gcgacatcct gagagtgaac   3600
accgagatca ccaaggcccc cctgagcgcc tctatgatca agagatacga cgagcaccac   3660
caggacctga ccctgctgaa agctctcgtg cggcagcagc tgcctgagaa gtacaaagag   3720
attttcttcg accagagcaa gaacggctac gccggctaca ttgacggcgg agccagccag   3780
gaagagttct acaagttcat caagcccatc ctggaaaaga tggacggcac cgaggaactg   3840
ctcgtgaagc tgaacagaga ggacctgctg cggaagcagc ggaccttcga caacggcagc   3900
atcccccacc agatccacct gggagagctg cacgccattc tgcggcggca ggaagatttt   3960
tacccattcc tgaaggacaa ccgggaaaag atcgagaaga tcctgacctt ccgcatcccc   4020
tactacgtgg gccctctggc caggggaaac agcagattcg cctggatgac cagaaagagc   4080
gaggaaacca tcaccccctg gaacttcgag gaagtggtgg acaagggcgc ttccgcccag   4140
agcttcatcg agcggatgac caacttcgat aagaacctgc ccaacgagaa ggtgctgccc   4200
aagcacagcc tgctgtacga gtacttcacc gtgtataacg agctgaccaa agtgaaatac   4260
gtgaccgagg gaatgagaaa gcccgccttc ctgagcggcg agcagaaaaa ggccatcgtg   4320
gacctgctgt tcaagaccaa ccggaaagtg accgtgaagc agctgaaaga ggactacttc   4380
aagaaaatcg agtgcttcga ctccgtggaa atctccggcg tggaagatcg gttcaacgcc   4440
tccctgggca cataccacga tctgctgaaa attatcaagg acaaggactt cctggacaat   4500
gaggaaaacg aggacattct ggaagatatc gtgctgaccc tgacactgtt tgaggacaga   4560
gagatgatcg aggaacggct gaaaacctat gcccacctgt tcgacgacaa agtgatgaag   4620
cagctgaagc ggcggagata caccggctgg ggcaggctga gccggaagct gatcaacggc   4680
atccgggaca agcagtccgg caagacaatc ctggatttcc tgaagtccga cggcttcgcc   4740
aacagaaact tcatgcagct gatccacgac gacagcctga cctttaaaga ggacatccag   4800
aaagcccagg tgtccggcca gggcgatagc ctgcacgagc acattgccaa tctggccggc   4860
agccccgcca ttaagaaggg catcctgcag acagtgaagg tggtggacga gctcgtgaaa   4920
gtgatgggcc ggcacaagcc cgagaacatc gtgatcgaaa tggccagaga gaaccagacc   4980
acccagaagg gacagaagaa cagccgcgag agaatgaagc ggatcgaaga gggcatcaaa   5040
```

-continued

```
gagctgggca gccagatcct gaaagaacac cccgtggaaa acacccagct gcagaacgag   5100
aagctgtacc tgtactacct gcagaatggg cgggatatgt acgtggacca ggaactggac   5160
atcaaccggc tgtccgacta cgatgtggac catatcgtgc ctcagagctt tctgaaggac   5220
gactccatcg acaacaaggt gctgaccaga agcgacaaga accggggcaa gagcgacaac   5280
gtgccctccg aagaggtcgt gaagaagatg aagaactact ggcggcagct gctgaacgcc   5340
aagctgatta cccagagaaa gttcgacaat ctgaccaagg ccgagagagg cggcctgagc   5400
gaactggata aggccggctt catcaagaga cagctggtgg aaacccggca gatcacaaag   5460
cacgtggcac agatcctgga ctcccggatg aacactaagt acgacgagaa tgacaagctg   5520
atccgggaag tgaaagtgat caccctgaag tccaagctgg tgtccgattt ccggaaggat   5580
ttccagtttt acaaagtgcg cgagatcaac aactaccacc acgcccacga cgcctacctg   5640
aacgccgtcg tgggaaccgc cctgatcaaa aagtacccta agctggaaag cgagttcgtg   5700
tacggcgact acaaggtgta cgacgtgcgg aagatgatcg ccaagagcga gcaggaaatc   5760
ggcaaggcta ccgccaagta cttcttctac agcaacatca tgaacttttt caagaccgag   5820
attaccctgg ccaacggcga gatccggaag cggcctctga tcgagacaaa cggcgaaacc   5880
ggggagatcg tgtgggataa gggccgggat tttgccaccg tgcggaaagt gctgagcatg   5940
ccccaagtga atatcgtgaa aaagaccgag gtgcagacag gcggcttcag caaagagtct   6000
atcctgccca agaggaacag cgataagctg atcgccagaa agaaggactg ggaccctaag   6060
aagtacggcg gcttcgacag ccccaccgtg gcctattctg tgctggtggt ggccaaagtg   6120
gaaaagggca agtccaagaa actgaagagt gtgaaagagc tgctggggat caccatcatg   6180
gaaagaagca gcttcgagaa gaatcccatc gactttctgg aagccaaggg ctacaaagaa   6240
gtgaaaaagg acctgatcat caagctgcct aagtactccc tgttcgagct ggaaaacggc   6300
cggaagagaa tgctggcctc tgccggcgaa ctgcagaagg gaaacgaact ggccctgccc   6360
tccaaatatg tgaacttcct gtacctggcc agccactatg agaagctgaa gggctccccc   6420
gaggataatg agcagaaaca gctgtttgtg gaacagcaca agcactacct ggacgagatc   6480
atcgagcaga tcagcgagtt ctccaagaga gtgatcctgg ccgacgctaa tctggacaaa   6540
gtgctgtccg cctacaacaa gcaccgggat aagcccatca gagagcaggc cgagaatatc   6600
atccacctgt ttaccctgac caatctggga gcccctgccg ccttcaagta ctttgacacc   6660
accatcgacc ggaagaggta caccagcacc aaagaggtgc tggacgccac cctgatccac   6720
cagagcatca ccggcctgta cgagacacgg atcgacctgt ctcagctggg aggcgacagc   6780
cccaagaaga agagaaaggt ggaggccagc taacatatga ttcgaatgtc tttcttgcgc   6840
tatgacactt ccagcaaaag gtagggcggg ctgcgagacg gcttcccggc gctgcatgca   6900
acaccgatga tgcttcgacc ccccgaagct ccttcggggc tgcatgggcg ctccgatgcc   6960
gctccagggc gagcgctgtt taaatagcca ggcccccgat tgcaaagaca ttatagcgag   7020
ctaccaaagc catattcaaa cacctagatc actaccactt ctacacaggc cactcgagct   7080
tgtgatcgca ctccgctaag gggcgcctc ttcctcttcg tttcagtcac aacccgcaaa   7140
catgacacaa gaatccctgt tacttctcga ccgtattgat tcggatgatt cctacgcgag   7200
cctgcggaac gaccaggaat tctgggaggt gagtcgacga gcaagcccgg cggatcaggc   7260
agcgtgcttg cagatttgac ttgcaacgcc cgcattgtgt cgacgaaggc ttttggctcc   7320
tctgtcgctg tctcaagcag catctaaccc tgcgtcgccg tttccatttg cagccgctgg   7380
cccgccgagc cctggaggag ctcgggctgc cggtgccgcc ggtgctgcgg gtgcccggcg   7440
```

agagcaccaa ccccgtactg gtcggcgagc ccggcccggt gatcaagctg ttcggcgagc 7500
actggtgcgg tccggagagc ctcgcgtcgg agtcggaggc gtacgcggtc ctggcggacg 7560
ccccggtgcc ggtgccccgc ctcctcggcc gcggcgagct gcggcccggc accggagcct 7620
ggccgtggcc ctacctggtg atgagccgga tgaccggcac cacctggcgg tccgcgatgg 7680
acggcacgac cgaccggaac gcgctgctcg ccctggcccg cgaactcggc cgggtgctcg 7740
gccggctgca cagggtgccg ctgaccggga acaccgtgct cacccccccat tccgaggtct 7800 tcccggaact gctgcgggaa cgccgcgcgg cgaccgtcga ggaccaccgc gggtggggct 7860
acctctcgcc ccggctgctg gaccgcctgg aggactggct gccggacgtg gacacgctgc 7920
tggccggccg cgaaccccgg ttcgtccacg gcgacctgca cgggaccaac atcttcgtgg 7980
acctggccgc gaccgaggtc accgggatcg tcgacttcac cgacgtctat gcgggagact 8040
cccgctacag cctggtgcaa ctgcatctca acgccttccg ggcgaccgc gagatcctgg 8100 ccgcgctgct cgacggggcg cagtggaagc ggaccgagga cttcgcccgc gaactgctcg 8160
ccttcacctt cctgcacgac ttcgaggtgt tcgaggagac cccgctggat ctctccggct 8220
tcaccgatcc ggaggaactg gcgcagttcc tctgggggcc gccggacacc gcccccggcg 8280
cctgataagg atccggcaag actggccccg cttggcaacg caacagtgag cccctcccta 8340
gtgtgtttgg ggatgtgact atgtattcgt gtgttggcca acgggtcaac ccgaacagat 8400
tgatacccgc cttggcattt cctgtcagaa tgtaacgtca gttgatggta ct 8452

<210> SEQ ID NO 92
<211> LENGTH: 102
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 92
gttttagagc tatgctgttt tgaatggtcc caaaacggaa gggcctgagt ccgagcagaa 60
gaagaagttt tagagctatg ctgttttgaa tggtcccaaa ac 102

<210> SEQ ID NO 93
<211> LENGTH: 100
<212> TYPE: DNA
<213> ORGANISM: Homo sapiens

<400> SEQUENCE: 93
cggaggacaa agtacaaacg gcagaagctg gaggaggaag ggcctgagtc cgagcagaag 60
aagaagggct cccatcacat caaccggtgg cgcattgcca 100

<210> SEQ ID NO 94
<211> LENGTH: 50
<212> TYPE: DNA
<213> ORGANISM: Homo sapiens

<400> SEQUENCE: 94
agctggagga ggaagggcct gagtccgagc agaagaagaa gggctcccac 50

<210> SEQ ID NO 95
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 95
gaguccgagc agaagaagaa guuuuagagc 30

<210> SEQ ID NO 96
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 96
agctggagga ggaagggcct gagtccgagc agaagagaag ggctcccat 49

<210> SEQ ID NO 97
<211> LENGTH: 53
<212> TYPE: DNA
<213> ORGANISM: Homo sapiens

<400> SEQUENCE: 97
ctggaggagg aagggcctga gtccgagcag aagaagaagg gctcccatca cat 53

<210> SEQ ID NO 98
<211> LENGTH: 52
<212> TYPE: DNA
<213> ORGANISM: Homo sapiens

<400> SEQUENCE: 98
ctggaggagg aagggcctga gtccgagcag aagagaaggg ctcccatcac at 52

<210> SEQ ID NO 99
<211> LENGTH: 54
<212> TYPE: DNA
<213> ORGANISM: Homo sapiens

<400> SEQUENCE: 99
ctggaggagg aagggcctga gtccgagcag aagaaagaag ggctcccatc acat 54

<210> SEQ ID NO 100
<211> LENGTH: 50
<212> TYPE: DNA
<213> ORGANISM: Homo sapiens

<400> SEQUENCE: 100
ctggaggagg aagggcctga gtccgagcag aagaagggct cccatcacat 50

<210> SEQ ID NO 101
<211> LENGTH: 47
<212> TYPE: DNA
<213> ORGANISM: Homo sapiens

<400> SEQUENCE: 101
ctggaggagg aagggcctga gcccgagcag aagggctccc atcacat 47

<210> SEQ ID NO 102
<211> LENGTH: 155
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 102
guuucagugc uauaggaaac uauaggaaau caccuucggg ugagcugaaa uccccuaaag 60
cuaagauuga auccggccac uaucuauuag uagauauccg gauauucuga uauaaaaccu 120
cauucuuuga uuagaccaaa ggaugagguu uuuuu 155

<210> SEQ ID NO 103
<211> LENGTH: 107
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 103
guuugagagu uggaaacaac gaguucaaau aagaauucau caaaaucguc ccuuuuggga 60
ccgcucauug uggagcauca aggcuuaaca ugguuaagcc uuuuuuu 107

<210> SEQ ID NO 104
<211> LENGTH: 99
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 104
guuugagagu aggaaacuac acgguucaaa uaaagaauuu uucuaaucgc ccaaugggcc 60
cauauugaua uggaugaaac ucgcuuagcg aguuuuuuu 99

<210> SEQ ID NO 105
<211> LENGTH: 91
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 105
guuuuagcac uagaaauagu uaaguuaaaa caagcuuaaa gcgucaaugu aauauuuuau 60
uaacacccua cugugucagu gggguuuuuu u 91

<210> SEQ ID NO 106
<211> LENGTH: 94
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 106
guuuuagaug gugaaaacca gauuuaaaau caagcaaugc aucuuuugau gcaaaguuuc 60
aauauuuguc ccacguuauc gagggacuuu uuuu 94

<210> SEQ ID NO 107
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 107
auuuuaguac cuggaaacag aucuacuaaa acaaggcuuu augccgaaau caagagcacc 60
gacgggugcu cuuuuuuu         78

<210> SEQ ID NO 108
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
guuuuuguac ucgaaagagc cuacaaagau aaggcuuuau gccgaauuca agcaccccau         60
guuuugacau gaggugcuuu uuuu         84

<210> SEQ ID NO 109
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
guuuuuguac cuuagaaaua agaucuacaa aaauaaggau uuauuccgaa uuuaccaccu         60
auuuuaauua auaggugguu uuuuu         85

<210> SEQ ID NO 110
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 110
guugugauuu gcuuucauuu gaaaaauuga agcaaaucac aauaaggauu auuccguugu         60
gaaaacaauu aaagcggucu ugcaaaaggu cgcuuuuuuu         100

<210> SEQ ID NO 111
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 111
guugugauuc gcuuucaaug aaaauugaag cgaaucacaa uaaggauuau uccguuguga         60
aaacauuuac uacggggcau cgaaagacug ccucguuuuu uu         102

<210> SEQ ID NO 112
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
guugugguuu gauuagaaau aaucuuauca caauaaggcu auaugccgua gacgaaaguc         60
uuuagucccg cuucgguggg acuuuuuuuu         90

-continued

<210> SEQ ID NO 113
<211> LENGTH: 78
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 113
guuggggaug accgcgaaag cgauuaucuc uaauaagacu uaagucgcaa aaugcucccu 60
auuuugggag cuuuuuuu 78

<210> SEQ ID NO 114
<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
guugcggcug gagaaaucca gccguuaaca uguucccuuc ggggagcacg aaaugcgggg 60
cgggccacgg uccgccccuu uuuuu 85

<210> SEQ ID NO 115
<211> LENGTH: 126
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 115
gccgugguuu ccgaaaggaa accacgguaa cagaauuacc guaagguuuu uucugugaag 60
gaucaucccu cgcuugggca accaggcggg ggaaauuccu cguucgggcc aaucagcccu 120
uuuuuu 126

<210> SEQ ID NO 116
<211> LENGTH: 82
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 116
guuguaauuc ccugaaaagg uuauuacaau aagguaagaa accuaaaagc ucuaauccca 60
uucuucggaa ugggauuuuu uu 82

<210> SEQ ID NO 117
<211> LENGTH: 83
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 117
guuuuaguac ucuggaaaca gaaucuacua aaacaaggca aaaugccgug uuuaucucgu 60
caacuuguug gcgagauuuu uuu 83

<210> SEQ ID NO 118
<211> LENGTH: 94

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
guuuuagcac uguacaagaa auugucgugc uaaaauaagg cgcuguuaau gcagcugccg 60
cauccgccag agcauuuaug cucuggcuuu uuuu 94

<210> SEQ ID NO 119
<211> LENGTH: 4350
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119
accggtgcca ccatgtaccc atacgatgtt ccagattacg cttcgccgaa gaaaaagcgc 60
aaggtcgaag cgtccatgac tcagagcgag cgacgatttt cttgcagcat tggcattgac 120
atgggggcta agtacactgg ggtgttctac gcactgttcg accgggagga actgccccaca 180 aacctgaaca gcaaggccat gaccctggtc atgcctgaga cagggccaag atacgtgcag 240
gcacagagaa ctgccgtcag acacaggctg cgcggacaga agagatatac cctggctagg 300
aaactggcat ttctggtggt cgacgatatg atcaagaaac aggaaaagag gctgactgat 360
gaggaatgga aacgaggacg ggaggccctg tccggcctgc tgaagcggag agggtactct 420
cggcccaacg ctgacggcga agatctgacc cctctggaga atgtgagagc agacgtgttc 480
gccgctcatc ctgccttcag cacatatttt tccgaagtgc gctctctggc tgagcagtgg 540
gaggagttca ccgcaaacat cagcaatgtc gagaagtttc tgggcgaccc aaacatcccc 600
gccgataaag agttcattga atttgccgtg gctgaagggc tgattgacaa gaccgagaag 660
aaagcctacc agtcagctct gagcaccctg agggcaaacg ccaatgtgct gacaggactg 720
cggcagatgg gccacaagcc tagatcagaa tattttaaag caatcgaggc cgacctgaag 780
aaagatagcc gcctggccaa gattaacgaa gcattcggag gagcagagcg cctggctcga 840
ctgctgggaa acctgtccaa tctgcagctg cgggcagaaa gatggtactt caatgccccc 900
gacatcatga aggatagggg ctgggagcct gatcgcttca agaaaacact ggtgcgggct 960
tttaagttct ttcacccagc aaaggaccag aacaaacagc atctggaact gatcaaacag 1020
attgagaaca gcgaagatat cattgagact ctgtgcaccc tggacccaaa cagaaccatc 1080 ccccctttacg aggatcagaa caataggcgc ccacccctgg accagactct gctgctgagt 1140
cccgaaaagc tgacccggca gtatggcgag atctggaaaa catggagcgc cagactgacc 1200
tccgctgaac ccacactggc acctgcagcc gagattctgg aaagatctac cgacaggaag 1260
agtcgcgtgg cagtcaacgg acacgagcca ctgcctacac tggcttacca gctgagttat 1320
gcactgcaga gagccttcga caggtcaaaa gccctggatc catatgctct gagggcactg 1380
gctgcaggct caaaaagcaa taagctgaca tccgcccgca ctgctctgga gaactgcatc 1440
ggaggccaga atgtgaaaac cttcctggac tgtgcccgac ggtactatcg ggaagcagac 1500
gatgccaaag tcgggctgtg gttcgacaac gccgatggac tgctggagag atctgacctg 1560
catcctccaa tgaagaaaaa gatcctgccc ctgctggtgg ccaatattct gcagacagat 1620
gaaaccacag gccagaagtt tctggacgag atctggcgaa aacagattaa ggggcgggaa 1680
actgtggcta gccgatgtgc acggatcgag acagtgcgga aatccttcgg gggaggcttt 1740
aacattgcct acaataccgc tcagtatagg gaggtgaaca agctgccccg caatgcccag 1800
gataaagaac tgctgacaat cagagatagg gtggctgaga ctgcagactt cattgccgct 1860
aacctggggc tgtctgacga gcagaaaaga aagttcgcca atccttttag tctggctcag 1920
ttctacaccc tgatcgagac agaagtgtcc ggattttctg caactaccct ggccgtccac 1980
ctggagaacg cctggaggat gacaatcaag gatgctgtga ttaatgggga aactgtcaga 2040
gcagcacagt gcagcaggct gcctgcagag acagctcgcc cattcgatgg actggtgaga 2100
aggctggtcg acagacaggc ttgggagatc gcaaagaggg tgtcaactga cattcagagc 2160
aaagtcgatt tctccaacgg catcgtggac gtcagcattt ttgtggagga aaataagttc 2220
gagttttccg catctgtggc cgatctgaaa aagaacaaac gggtcaaaga caagatgctg 2280
tccgaggccg aaaagctgga aaccagatgg ctgatcaaaa atgagcggat caagaaggcc 2340
agccggggaa cttgtcccta caccggcgat aggctggctg aggggggaga aatcgaccac 2400
attctgcccc gaagcctgat caaggatgcc cggggaattg tgtttaacgc tgagcctaat 2460
ctgatctatg caagctcccg cggcaaccag ctgaaaaaga atcagcgata cagtctgtca 2520
gatctgaagg ccaactatcg gaatgagatc ttcaaaacta gcaacatcgc tgcaattacc 2580
gccgagattg aggacgtggt cactaagctg cagcagaccc atagactgaa attctttgat 2640
ctgctgaatg agcacgaaca ggactgcgtg cggcacgccc tgttcctgga cgatggcagc 2700
gaagctcgcg acgcagtgct ggagctgctg gcaacacagc gccgaactcg cgtcaacggg 2760
acacagatct ggatgattaa gaacctggcc aacaagatcc gagaggaact gcagaattgg 2820
tgtaagacaa ctaacaatag actgcacttt caggccgctg caactaacgt gtccgatgca 2880
aagaatctga ggctgaaact ggcccagaac cagcccgact tcgagaagcc agatatccag 2940
cccattgcca gccattccat cgacgccctg tgctctttcg ctgtggggag tgctgacgca 3000
gaacgcgatc agaatggatt tgactacctg gatggcaaga ccgtgctggg actgtatcca 3060
cagagctgtg aggtcattca cctgcaggcc aagccccagg aggaaaaaag tcatttcgat 3120
tcagtggcta tctttaagga aggcatctac gcagagcagt tcctgcctat ctttaccctg 3180
aacgaaaaga tctggattgg atatgagaca ctgaatgcca aaggcgaaag atgcggggct 3240
attgaggtga gtggcaaaca gccaaaggag ctgctggaaa tgctggcccc cttctttaac 3300
aagcctgtgg gcgacctgtc agcccacgct acttaccgga tcctgaaaaa gcctgcatat 3360
gagtttctgg caaaggcagc tctgcagcca ctgagcgcag aggaaaaaag actggcagcc 3420
ctgctggatg ctctgcgcta ctgtaccagt cgaaagtcac tgatgagcct gttcatggct 3480
gcaaacggga aatccctgaa aaagcgggag gacgtgctga aacccaagct gttccagctg 3540
aaggtcgagc tgaaaggcga aaagagcttc aagctgaacg ggagcctgac cctgcctgtg 3600
aagcaggact ggctgagaat ctgcgatagc ccagaactgg cagacgcctt tggcaaaccc 3660
tgttccgccg atgagctgac atctaagctg gctcgcattt ggaaacgacc tgtgatgcgg 3720
gatctggctc atgcaccagt ccggagagag ttcagcctgc ccgcaatcga caacccaagt 3780
ggagggttca ggattaggcg caccaacctg tttggcaatg agctgtacca ggtgcacgcc 3840
atcaacgcta aaaagtatcg cggcttcgcc tccgctgggt ctaatgtcga ctggtccaag 3900
gggatcctgt ttaacgagct gcagcatgaa aatctgaccg agtgcggagg caggttcatt 3960
acaagcgccg atgtgactcc tatgtccgaa tggcgcaagg tggtcgcaga ggacaacctg 4020
tctatctgga ttgctccagg gacagaagga cgacggtacg tgagggtcga gacaacattc 4080

-continued atccaggcca gtcactggtt tgaacagtca gtggagaatt gggccattac tagtcctctg 4140
tcactgccag cttccttcaa ggtggacaaa ccagctgagt ttcagaaggc agtcggaacc 4200
gagctgtcag aactgctggg ccagcccagg agcgaaatct tcattgagaa cgtgggcaat 4260
gccaagcata tccgcttttg gtacattgtg gtgagcagca acaaaaagat gaacgagtct 4320
tacaacaatg tgtctaagag ttaagaattc 4350

<210> SEQ ID NO 120
<211> LENGTH: 4269
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120
accggtgcca ccatgtaccc atacgatgtt ccagattacg cttcgccgaa gaaaaagcgc 60
aaggtcgaag cgtccatgaa aaaagaaatc aaagactact tcctggggct ggatgtgggg 120
actgggagcg tggggtgggc tgtgaccgat actgactaca aactgctgaa ggctaaccga 180
aaagacctgt ggggcatgag atgcttcgag acagccgaaa ctgctgaggt gcggagactg 240
cacaggggag ccaggcgccg aatcgagcgg agaaagaaac gcattaagct gctgcaggag 300
ctgttctctc aggaaatcgc caaaaccgat gagggcttct ttcagagaat gaaggaaagc 360 ccctttttacg ctgaggacaa aacaatcctg caggaaaaca ctctgttcaa tgacaaggat 420
tttgctgata agacttacca caaagcatat cctaccatta atcatctgat caaggcttgg 480
attgagaaca aggtgaaacc agacccccga ctgctgtacc tggcatgtca caacatcatt 540
aagaaaaggg gacatttcct gtttgaaggc gacttcgatt cagagaatca gtttgatacc 600
agcatccagg cactgttcga gtatctgcgc gaggacatgg aggtggacat cgatgccgac 660
agccagaagg tcaaagagat tctgaaggat agctccctga agaactctga aaaacagagt 720
cggctgaata agatcctggg gctgaagcct tccgacaaac agaagaaagc catcacaaac 780
ctgatttctg gaaacaagat caatttcgcc gatctgtacg acaatccaga tctgaaggac 840
gctgagaaaa actcaatcag cttctccaag gacgattttg atgcactgag tgacgatctg 900
gcctcaattc tgggcgacag ctttgaactg ctgctgaagg ccaaagctgt ctataactgc 960
tctgtgctga gtaaggtcat cggggacgag cagtacctga gcttcgccaa ggtgaaaatc 1020
tacgaaaagc acaaaaccga tctgacaaag ctgaaaaacg tgatcaagaa acatttcccc 1080
aaggactaca agaaggtctt tggatacaac aagaacgaga aaaacaacaa caattactcc 1140
ggctatgtgg gagtctgtaa gaccaagagt aagaaactga tcattaacaa ctcagtcaac 1200
caggaagatt tctacaagtt tctgaaaact atcctgtcag ccaagagcga gatcaaggaa 1260
gtgaatgaca tcctgaccga gattgaaact ggcacctttc tgccaaagca gatctctaaa 1320
agtaacgcag agattcccta tcagctgagg aaaatggagc tggaaaagat cctgtccaat 1380
gccgaaaagc acttctcttt tctgaagcag aaagacgaaa aggactgtc acatagcgag 1440 aagatcatta tgctgctgac cttcaagatc ccttactata ttggcccaat caacgataat 1500
cacaagaaat tctttcccga cagatgctgg gtggtcaaga aagagaaatc cccttctggc 1560
aagaccacac catggaactt ctttgatcat atcgacaagg aaaaaacagc agaggccttc 1620
attacttcta ggaccaattt ttgcacttac ctggtgggag agagcgtcct gcctaagtct 1680
agtctgctgt actccgaata taccgtgctg aacgagatca acaatctgca gatcattatc 1740
gatggcaaga atatttgtga catcaagctg aaacagaaga tctacgagga cctgttcaag 1800
aagtacaaga aaattaccca gaagcagatc agcaccttca tcaagcacga aggcatctgc 1860
aacaaaaccg atgaagtgat catcctgggg attgacaagg aatgtacatc aagcctgaaa 1920
agctacatcg agctgaaaaa cattttcggc aagcaggtgg atgagatctc cactaagaat 1980
atgctggagg aaattatcag atgggctacc atctacgacg agggggaagg aaagaccatc 2040
ctgaaaacaa agatcaaggc agaatacgga aagtattgct ccgacgagca gattaagaaa 2100
atcctgaacc tgaagttctc cggctggggg cgactgtctc ggaaatttct ggagacagtg 2160
actagtgaaa tgcccggctt ctcagaacct gtcaatatta tcaccgccat gagggagaca 2220
cagaacaatc tgatggagct gctgtcctct gagttcacct tcaccgagaa cattaagaaa 2280
atcaattctg gattcgaaga tgccgagaag cagtttagtt acgacggcct ggtgaaacca 2340
ctgtttctga gtccctcagt caagaaaatg ctgtggcaga ccctgaagct ggtgaaagag 2400
attagccata tcacacaggc ccccccctaag aaaattttca tcgaaatggc aaagggggcc 2460
gagctggaac ctgctcggac taagaccaga ctgaaaatcc tgcaggatct gtataacaat 2520
tgtaagaacg atgctgacgc cttcagctca gagatcaaag acctgagcgg aaagattgag 2580
aacgaagata atctgaggct gcgctccgac aagctgtacc tgtactatac tcagctgggg 2640
aaatgcatgt attgtggaaa gccaattgag atcggccacg tgttcgatac ctcaaactac 2700
gatattgacc atatctatcc ccagagcaag atcaaagacg atagcatttc caatcgggtg 2760
ctggtctgca gctcctgtaa caagaacaag gaggacaagt acccactgaa atcagagatc 2820
cagagcaagc agcgcggctt ctggaacttt ctgcagcgaa acaatttcat ttctctggag 2880
aagctgaata gactgacaag ggccactcca atcagtgacg atgagacagc caagtttatt 2940
gctaggcagc tggtggaaac tcgccaggct accaaggtgg ccgctaaagt cctggaaaag 3000
atgttccccg agacaaaaat cgtgtacagc aaggccgaga ctgtctccat gttccggaac 3060
aagtttgata tcgtgaagtg cagagaaatt aacgattttc accatgctca cgacgcatac 3120
ctgaatatcg tggtcggcaa cgtgtataat accaagttca caaacaatcc ttggaacttt 3180
atcaaggaga aaagagataa tccaaagatt gctgacacct acaactacta taaggtgttc 3240
gattatgacg tcaaaaggaa caatatcaca gcatgggaga aggggaaaac tattatcacc 3300
gtgaaagaca tgctgaagag aaacacacca atctacacta ggcaggcagc ctgtaagaaa 3360
ggggagctgt tcaatcagac cattatgaag aaaggactgg gccagcaccc cctgaagaaa 3420
gaaggacctt tttccaatat ctctaaatac ggcgggtata acaaggtgag cgctgcatac 3480
tatacactga ttgagtatga ggaaaagggc aacaaaatcc gctccctgga aactattccc 3540
ctgtacctgg tgaaagatat ccagaaggat caggacgtcc tgaagtctta tctgacagac 3600
ctgctgggga agaaagagtt caagatcctg gtgcccaaga tcaagatcaa cagcctgctg 3660
aagatcaatg ggtttccttg ccatattaca ggaaaaacta acgatagttt cctgctgcgc 3720
cctgccgtgc agttttgctg ttcaaacaat gaggtcctgt acttcaagaa aattatccgg 3780
ttttccgaaa tccgctctca gcgagagaag atcgggaaaa caattagccc atacgaggac 3840
ctgagcttcc ggtcatatat caaggagaac ctgtggaaga aaactaagaa cgatgaaatc 3900
ggagagaagg aattttacga cctgctgcag aagaaaaacc tggagatcta tgatatgctg 3960
ctgactaagc acaaagacac catctacaag aaacgcccta attctgccac cattgatatc 4020
ctggtgaagg ggaaagagaa gttcaaaagc ctgattatcg aaaaccagtt tgaagtgatc 4080
ctggagatcc tgaagctgtt ttctgcaaca cggaatgtca gtgacctgca gcatatcgga 4140
ggcagcaagt actccggcgt ggccaaaatc gggaacaaga tctctagtct ggataactgt 4200
atcctgatct atcagtccat caccggcatc ttcgagaaac ggatcgacct gctgaaggtg 4260
taagaattc 4269

<210> SEQ ID NO 121
<211> LENGTH: 4179
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 121
accggtgcca ccatgtaccc atacgatgtt ccagattacg cttcgccgaa gaaaaagcgc 60
aaggtcgaag cgtccatgac caaggagtat tacctggggc tggatgtggg gaccaattcc 120
gtgggatggg cagtgaccga ttctcagtac aacctgtgca agtttaagaa aaaggatatg 180
tggggcatcc ggctgttcga aagcgccaac acagcaaagg accggagact gcagagaggg 240
aataggcgcc gactggagcg gaaaaagcag agaattgatc tgctgcagga aatcttctcc 300
ccagagatct gcaagattga ccccactttc tttatccgac tgaacgaatc ccggctgcac 360
ctggaggaca agtctaacga tttcaaatac ccactgttta ttgagaagga ctattctgat 420
atcgagtact ataaagagtt ccccaccatt tttcacctga ggaagcatct gatcgagagt 480
gaggaaaaac aggatatccg gctgatctac ctggccctgc acaacatcat taagacccga 540
ggacattttc tgattgacgg cgatctgcag agcgccaagc agctgaggcc catcctggat 600
acattcctgc tgtccctgca ggaggaacag aacctgtcag tgagcctgtc cgaaaatcag 660
aaggacgagt atgaggaaat tctgaaaaac cgcagcatcg ccaagtccga aaaagtgaaa 720
aagctgaaga atctgtttga gatctcagac gagctggaaa aagaggagaa gaaggcccag 780
agcgccgtga tcgagaactt ctgcaagttt atcgtgggaa ataagggcga tgtctgtaaa 840
ttcctgcggg tgtctaagga ggaactggag attgactctt tcagtttttc agagggcaag 900
tacgaggacg acatcgtgaa aaacctggag gaaaaagtgc ctgaaaaggt ctacctgttt 960
gagcagatga aggcaatgta tgattggaat attctggtcg acatcctgga aaccgaggaa 1020
tacatcagct tcgccaaagt gaagcagtat gagaaacaca agactaacct gcggctgctg 1080
agagacatca ttctgaaata ctgcaccaag gatgagtata atcggatgtt taacgacgag 1140
aaggaagctg gcagctacac cgcatatgtg gggaaactga aaaagaacaa caagaagtac 1200
tggatcgaga aaaagagaaa tcccgaggag ttctacaaat ccctgggcaa gctgctggat 1260
aaaattgagc ctctgaagga ggacctggaa gtgctgacta tgatgatcga ggagtgtaag 1320
aaccacaccc tgctgccaat tcagaaaaat aaggacaacg gcgtgatccc ccaccaggtg 1380
catgaggtcg aactgaaaaa gatcctggaa aatgccaaaa agtactattc cttcctgacc 1440
gagacagaca aggatgggta ctcagtggtc cagaaaatcg agagcatttt caggtttcgc 1500
atcccctact atgtggggcc tctgagtacc cggcaccagg aaaagggatc aaacgtgtgg 1560
atggtcagaa aacctggcag ggaggatcgc atctacccat ggaatatgga ggaaatcatt 1620
gactttgaga agagcaacga aaatttcatt acacggatga ctaacaaatg tacatatctg 1680
atcggggaag atgtcctgcc caagcattct ctgctgtaca gtaaatatat ggtgctgaat 1740
gagctgaaca atgtgaaggt cagaggaaaa aagctgccta catctctgaa acagaaggtg 1800

```
ttcgaggacc tgtttgaaaa caaatccaaa gtgactggaa agaatctgct ggagtacctg   1860
cagatccagg acaaagatat ccagattgac gatctgtctg gcttcgacaa ggacttcaag   1920
accagcctga agagctatct ggacttcaaa aagcagattt ttggggagga aatcgagaag   1980
gaaagcattc agaacatgat cgaagatatc attaagtgga tcaccatcta cggcaatgac   2040
aaggagatgc tgaaacgagt gattcgggct aattatagca accagctgac agaggaacag   2100
atgaaaaaga tcactggatt tcagtacagt ggctgggggga acttctcaaa gatgtttctg   2160
aaagggatca gcggatccga cgtgagcacc ggcgaaacat tcgacatcat taccgcaatg   2220
tgggagacag acaacaatct gatgcagatc ctgtcaaaaa agttcacctt tatggacaac   2280
gtcgaggact tcaacagcgg caaggtcggg aaaatcgaca agattactta cgatagcacc   2340
gtgaaggaaa tgttcctgtc ccctgagaac aaaagggccg tctggcagac cattcaggtg   2400
gctgaggaga tcaagaaagt gatgggctgc gagccaaaaa agatctttat tgaaatggca   2460
cggggcgggg agaaggtgaa aaagaggaca aaatctcgca aggcccagct gctggagctg   2520
tacgccgctt gcgaggaaga ttgtagagaa ctgatcaagg agattgagga ccgggacgag   2580
agggacttca atagcatgaa gctgtttctg tactataccc agttcgggaa atgtatgtat   2640
tccggcgacg acatcgatat taacgagctg attcgcggca attctaagtg ggaccgagat   2700
cacatctacc cccagagcaa aattaaggac gattccatcg ataacctggt gctggtcaat   2760
aagacatata atgccaaaaa gtccaatgag ctgctgtctg aggacatcca gaaaaagatg   2820
cattcattct ggctgagcct gctgaacaaa aagctgatca ctaaaagcaa gtacgaccgc   2880
ctgactcgaa agggcgactt taccgatgag gaactgagtg ggttcatcgc tagacagctg   2940
gtggaaacaa ggcagtcaac taaggcaatc gccgatatct tcaagcagat ctacagctcc   3000
gaggtggtct atgtgaagag cagcctggtg agcgacttca ggaaaaagcc actgaactac   3060
ctgaagtctc ggagagtcaa tgattaccac catgcaaaag acgcctatct gaacattgtg   3120
gtcgggaacg tgtacaacaa aaagtttacc agtaatccca tccagtggat gaaaaagaat   3180
cgcgatacaa actatagcct gaacaaggtg ttcgaacacg acgtggtcat taacggagaa   3240
gtgatctggg aaaagtgcac ataccatgag gacactaata cctatgatgg aggcactctg   3300
gaccgaatcc ggaagattgt ggaacgcgat aacattctgt acaccgagta cgcttattgt   3360
gagaagggcg aactgtttaa tgcaaccatc cagaacaaaa atggaaactc cacagtctct   3420
ctgaaaaagg gcctggacgt gaaaaagtac gggggatact tcagcgccaa cacaagttac   3480
ttctcactga tcgagtttga ggacaagaag gggggatagag caaggcacat cattggagtg   3540
cctatctata ttgcaaacat gctggagcat tctccaagtg ccttcctgga gtactgcgaa   3600
cagaaggggt atcagaatgt gcggattctg gtcgagaaaa tcaaaaagaa cagcctgctg   3660
atcattaatg gataccctct gcgcattcga ggcgagaacg aagtggatac ttcctttaag   3720
agggccatcc agctgaagct ggaccagaaa aactatgagc tggtccgcaa tatcgagaag   3780
ttcctggaaa aatacgtgga gaaaaaggga aactatccaa ttgacgagaa tagagatcac   3840
atcacacatg aaaagatgaa ccagctgtac gaggtgctgc tgtccaaaat gaaaaagttc   3900
aacaagaagg gcatggccga cccctctgat aggatcgaaa agagtaagcc taaattcatc   3960
aagctggagg acctgatcga taagattaat gtgatcaaca aaatgctgaa cctgctgcgc   4020
tgtgacaatg atactaaggc cgacctgtct ctgattgagc tgcccaaaaa cgctgggagt   4080
ttcgtggtca aaaagaatac catcggaaag tcaaaaatca tcctggtgaa tcagagcgtg   4140
actggactgt acgagaatag acgggaactg taagaattc                          4179
```

<210> SEQ ID NO 122
<211> LENGTH: 4086
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 122
accggtgcca ccatgtaccc atacgatgtt ccagattacg cttcgccgaa gaaaaagcgc 60
aaggtcgaag cgtccatggg gaggaaacct tacattctgt ctctggatat tggaactggg 120
tccgtcggct acgcttgcat ggataaagga ttcaacgtgc tgaagtacca cgacaaagat 180
gccctgggag tgtatctgtt cgacggcgct ctgactgcac aggagcggag acagtttagg 240
acctccaggc gccgaaagaa ccggagaatc aaacgcctgg gcctgctgca ggaactgctg 300
gcacccctgg tgcagaaccc taatttctac cagtttcagc ggcagttcgc ctggaagaac 360
gacaatatgg attttaagaa caagagcctg tctgaggtgc tgagcttcct gggatatgaa 420
tccaagaaat accctaccat ctaccacctg caggaggctc tgctgctgaa agacgagaag 480
tttgatccag aactgatcta catggcactg tatcatctgg tgaaatacag aggccacttt 540
ctgttcgatc atctgaagat cgagaacctg actaacaatg acaatatgca cgatttcgtg 600
gagctgattg aaacctatga gaacctgaac aatatcaagc tgaatctgga ctacgagaaa 660
accaaagtga tctatgagat tctgaaagac aacgaaatga ctaagaatga tagagccaaa 720
agggtcaaga acatggagaa gaaactggaa cagttctcta tcatgctgct ggggctgaag 780
ttcaatgagg gaaaactgtt taaccacgcc gataatgctg aggaactgaa gggggctaac 840
cagagccata catttgcaga caactacgag gaaaatctga ctcccttcct gaccgtggaa 900
cagtcagagt ttattgaaag ggccaacaaa atctatctga gcctgactct gcaggatatc 960
ctgaagggca agaaatcaat ggctatgagc aaagtggccg cttacgacaa gttcagaaat 1020
gagctgaaac aggtgaagga cattgtctat aaggctgatt ctaccaggac acagttcaag 1080
aaaatctttg tgagctccaa gaaaagtctg aagcagtacg acgcaactcc caacgatcag 1140
accttctcta gtctgtgcct gtttgaccag tacctgattc gcccaaagaa acagtatagc 1200
ctgctgatca aggagctgaa gaaaatcatt ccccaggact ccgaactgta ctttgaggca 1260
gaaaatgata ccctgctgaa ggtgctgaac accacagaca atgctagcat ccctatgcag 1320
attaacctgt acgaggcaga aaccatcctg cgaaatcagc agaaatatca cgccgagatc 1380
acagatgaga tgattgaaaa ggtgctgtct ctgatccagt tccgcattcc atactatgtg 1440
gggcccctgg tcaacgacca tacagccagt aagtttggat ggatggagcg caaaagtaac 1500
gaatcaatca agccttggaa tttcgacgag gtggtcgatc gaagtaaatc agccactcag 1560
tttattaggc gcatgaccaa caagtgttcc tacctgatca atgaggatgt gctgccaaaa 1620
aactctctgc tgtatcagga gatggaagtc ctgaacgaac tgaatgccac acagatcagg 1680
ctgcagactg acccaaaaaa ccgcaagtac cgaatgatgc cccagattaa gctgttcgct 1740
gtggagcaca tctttaagaa atataaaacc gtcagccatt ccaagttcct ggaaattatg 1800
ctgaacagca atcacaggga gaactttatg aatcatggag aaaagctgag tatcttcggc 1860
acacaggacg ataagaaatt tgcatcaaag ctgtcaagct accaggacat gactaaaatc 1920
ttcggggata ttgagggaaa gcgcgcccag attgaggaaa tcattcagtg gatcaccatt 1980
tttgaggaca agaaaatcct ggtgcagaag ctgaaagagt gctatcctga actgacatcc 2040

```
aagcagatca accagctgaa gaaactgaat tactctggct gggggaggct gagtgagaag   2100

ctgctgactc acgcctatca gggccatagc atcattgaac tgctgcgcca ctccgatgag   2160

aatttcatgg aaattctgac caacgacgtg tacgggttcc agaattttat caaagaggaa   2220

aaccaggtcc agagcaataa gatccagcat caggatattg ccaacctgac tacctctccc   2280

gctctgaaga aggcatctg gagtacaatt aagctggtgc gggagctgac ttccattttc   2340

ggggagcctg aaaagatcat tatggagttt gctaccgagg accagcagaa aggcaagaaa   2400

cagaaatcaa gaaagcagct gtgggacgat aacatcaaga aaaataagct gaaaagcgtg   2460

gacgagtaca aatatatcat tgatgtcgcc aataagctga acaatgagca gctgcagcag   2520

gaaaaactgt ggctgtacct gagccagaac ggcaagtgta tgtatagcgg gcagtccatc   2580

gacctggatg ccctgctgtc ccccaatgct accaagcact acgaggtgga tcatattttc   2640

cctcggagct tcatcaagga cgatagcatt gacaacaagg tgctggtcat caagaaaatg   2700

aatcagacaa agggcgatca ggtgcccctg cagttcattc agcagcctta cgagagaatc   2760

gcatattgga agagcctgaa caaagccggg ctgatctctg atagtaaact gcacaagctg   2820

atgaaaccag agttcacagc tatggacaag gaaggcttca tccagcggca gctggtggag   2880

actagacaga tcagcgtgca tgtccgggat tttctgaaag aggaataccc taataccaaa   2940

gtgatcccaa tgaaggccaa aatggtgagc gagttccgga agaaatttga catcccaaag   3000

attagacaga tgaacgacgc acaccatgcc atcgatgctt acctgaatgg cgtggtctat   3060

cacggggcac agctggccta ccccaacgtg gacctgtttg atttcaattt taagtgggag   3120

aaagtccgag aaaagtggaa agccctggga gagttcaaca caaagcagaa atctcgggaa   3180

ctgttctttt tcaagaaact ggagaagatg gaagtgtccc agggcgagcg gctgatctct   3240

aagatcaagc tggacatgaa ccacttcaag atcaactact ccagaaagct ggccaacatc   3300

cctcagcagt tttataatca gaccgcagtg tctccaaaga cagccgagct gaaatacgaa   3360

tctaacaaga gtaatgaggt ggtctataag ggactgacac cataccagac ttatgtggtc   3420

gccatcaaga gcgtgaacaa gaaaggcaag gagaaaatgg aataccagat gatcgaccac   3480

tacgtgttcg atttttataa attccagaac ggcaatgaga aggaactggc tctgtacctg   3540

gcacagaggg agaacaagga cgaagtgctg gatgctcaga ttgtctatag tctgaataag   3600

ggggatctgc tgtacatcaa caatcatccc tgctatttcg tgtcacgcaa agaggtcatc   3660

aacgcaaagc agtttgagct gaccgtggaa cagcagctgt ctctgtacaa cgtgatgaac   3720

aacaaggaga caaatgtcga aaagctgctg atcgagtatg acttcattgc cgagaaagtg   3780

atcaacgaat accaccatta tctgaatagc aagctgaaag aaaagcgagt ccggaccttt   3840

ttctcagaga gcaaccagac acacgaggac ttcatcaagg ccctggacga gctgtttaag   3900

gtggtcaccg catccgccac aaggtctgat aaaatcggga gtcgcaagaa cagcatgact   3960

catcgagcct tcctgggaaa aggcaaggac gtgaagattg cttacacctc catctctgga   4020

ctgaaaacaa ctaaacctaa gagtctgttt aagctggccg agtcaagaaa cgaactgtaa   4080

gaattc                                                              4086
```

<210> SEQ ID NO 123
<211> LENGTH: 4209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
accggtgcca ccatgtaccc atacgatgtt ccagattacg cttcgccgaa gaaaaagcgc 60
aaggtcgaag cgtccatgac aaaaatcaaa gacgactaca tcgtgggact ggacatcggc 120
acagactcct gcgggtgggt ggctatgaac agcaataatg acattctgaa actgcagggc 180
aagaccgcaa tcgggtcacg cctgttcgag ggagggaaga gcgcagctga acggagactg 240
tttcgcacca cacacaggcg catcaaacga cggagatggc gactgaagct gctggaggag 300
ttcttcgacc cctacatggc agaggtggat ccttatttct ttgcccggct gaaggaatct 360
ggcctgagtc cactggacaa aagaaagacc gtgagctcca ttgtgttccc cacatccgcc 420
gaggataaga agttctacga cgattaccct acaatctacc atctgaggta taaactgatg 480
actgaggacg aaaagttcga tctgcgcgaa gtgtacctgg ctatccacca tatcattaag 540
taccgaggaa acttcctgta taataccagt gtgaaagact tcaaggcatc aaagatcgat 600
gtcaaatcta gtatcgagaa gctgaacgag ctgtatgaaa atctgggcct ggacctgaac 660
gtggagttca acattagcaa tactgccgag atcgaaaagg tgctgaaaga caagcagatc 720
ttcaagcggg ataaagtcaa gaaaattgcc gagctgtttg ctatcaaaac cgacaacaag 780
gaacagagca agagaatcaa agatatttcc aaacaggtgg ccaatgctgt cctggggtac 840
aagaccaggt tcgacacaat cgctctgaaa gagatttcca aggacgaact gtctgattgg 900
aacttcaaac tgtcagacat cgatgcagac agcaagtttg aggccctgat gggaaacctg 960
gatgagaatg aacaggccat cctgctgact attaaggagc tgtttaacga agtgaccctg 1020
aatggaattg tcgaggacgg caacaccctg agcgaatcca tgatcaacaa gtacaatgat 1080
caccgggacg atctgaagct gctgaaagaa gtgatcgaaa atcatattga cagaaagaaa 1140
gccaaggagc tggcactggc ctacgatctg tatgtcaaca ataggcacgg acagctgctg 1200
caggctaaga aaaagctggg caaaatcaag ccccgctcta aggaggactt ctacaaagtg 1260
gtcaacaaga atctggacga ttcacgggca agcaaggaga tcaaaaagaa aattgaactg 1320
gacagcttta tgcctaagca gagaaccaac gccaatggcg tgatcccata ccagctgcag 1380
cagctggagc tggataagat catcgaaaac cagtctaagt actatccatt cctgaaggag 1440
attaatcccg tgtcaagcca cctgaaagag gccccctata agctggacga actgatccga 1500
tttcgggtgc cttactatgt cggcccccctg atttctccta acgagagtac caaggatatc 1560
cagacaaaga aaaaccagaa tttcgcctgg atgattcgca aagaggaagg gcgaatcaca 1620
ccttggaact ttgaccagaa ggtggatcga attgagagcg ccaataagtt catcaaacgg 1680
atgactacca aggacactta cctgtttggg gaggatgtgc tgccagctaa cagcctgctg 1740
tatcagaagt tcaccgtcct gaacgaactg aacaacatcc ggattaatgg aaaaagaatc 1800
tccgtggacc tgaagcagga gatctacgaa aacctgttta agaaacacac aactgtgacc 1860
gtcaagaaac tggagaatta tctgaaggaa aaccataatc tggtgaaagt cgagatcaag 1920
gggctggccg atgaaaagaa attcaacagc ggactgacca catacaatag attcaagaac 1980
ctgaacatct ttgacaacca gattgacgat ctgaagtaca ggaacgattt cgagaagatc 2040
atcgaatggt ctacaatttt tgaggacaag agtatctaca aagaaaagct gaggagcatc 2100
gattggctga acgagaagca gattaacgct ctgtctaata tcagactgca ggggtgggga 2160
aggctgagta agaaactgct ggcacagctg cacgaccata atggccagac catcattgag 2220
cagctgtggg attcccagaa caatttcatg cagattgtga cacaggccga ctttaaagat 2280
gctatcgcaa aggccaacca gaatctgctg gtggctacct cagtcgagga cattctgaac 2340
aatgcataca caagccccgc aaacaagaaa gccatcagac aggtcatcaa ggtggtcgac 2400
gatatcgtga aggcagcctc cggaaaggtc ccaaaacaga tcgccattga gttcactagg 2460
gatgctgacg aaaatcccaa gagaagtcag accaggggct caaagctgca gaaagtgtac 2520
aaggacctga gcactgagct ggcctccaag accattgctg aggaactgaa cgaagcaatc 2580
aaagacaaga aactggtgca ggataagtac tatctgtact ttatgcagct ggggcgggac 2640
gcctatacag gagagcctat caatatcgat gaaatccaga agtacgatat cgaccacatt 2700
ctgccacagt ctttcatcaa ggacgatgcc ctggacaaca gggtgctggt gagccgggct 2760
gtgaacaatg gcaaatctga taatgtgcct gtcaagctgt ttggcaacga gatggctgca 2820
aatctgggga tgactatcag gaaaatgtgg gaggaatgga agaacatcgg cctgattagc 2880
aaaacaaagt acaacaatct gctgactgat cccgaccaca ttaacaagta taagagtgcc 2940
gggttcatca ggcgccagct ggtggagaca tcacagatca tcaagctggt gagcactatc 3000
ctgcagagtc gctaccctaa cactgaaatc attaccgtga aggctaagta caatcattat 3060
ctgcgggaga aatttgacct gtataagagc agagaagtca acgactacca ccatgctatt 3120
gatgcatatc tgtccgccat ctgcggaaat ctgctgtacc agaactatcc aaatctgcgg 3180
cccttctttg tgtacggcca gtataagaaa ttctcctctg atcctgacaa agagaaggcc 3240
atttttaaca aaacccgcaa gttctccttt atctctcagc tgctgaaaaa caagagtgag 3300
aacagcaagg aaatcgctaa gaaactgaaa cgggcatacc agttcaagta tatgctggtg 3360
tctcgagaga ctgaaacccg ggaccaggag atgttcaaaa tgaccgtgta cccccggttc 3420
agccacgata cagtcaaggc tcctaggaac ctgattccaa agaaaatggg catgtcccct 3480
gacatctacg gaggctatac aaacaattct gacgcataca tggtcatcgt ccgcattgat 3540
aagaaaaagg gaactgagta taagatcctg ggcattccaa cccgggaact ggtgaatctg 3600
aaaaaggccg agaaggagga ccattacaaa agctatctga aggagatcct gacaccaagg 3660
attctgtaca acaaaaatgg gaagcgcgat aaaaagatca cttccttcga aattgtgaaa 3720
tctaagatcc cctataagca ggtcatccag gatggggaca aaaagtttat gctgggaagt 3780
tcaacatacg tgtataacgc aaagcagctg acactgagca ctgagtccat gaaagccatc 3840
actaacaatt tcgataagga cagcgatgag aacgacgctc tgattaaggc atacgatgaa 3900
atcctggaca aagtggataa gtatctgcca ctgttcgaca tcaacaagtt ccgggagaag 3960
ctgcacagtg ggcgagaaaa gttcatcaag ctgagcctgg aggacaaaaa ggataccatc 4020
ctgaaagtgc tggaaggact gcatgataac gctgtcatga caaagatccc tactattggc 4080
ctgtccacac cactggggtt catgcagttt cccaacggcg tgattctgag cgagaatgcc 4140
aaactgatct accagtcccc caccgggctg ttcaaaaagt cagtgaagat cagcgacctg 4200
taagaattc 4209

<210> SEQ ID NO 124
<211> LENGTH: 3405
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 124
accggtgcca ccatgtaccc atacgatgtt ccagattacg cttcgccgaa gaaaaagcgc 60

```
aaggtcgaag cgtccatggg ctacactgtg ggactggata ttggggtggc ttccgtcggg    120
gtggctgtgc tggatgagaa tgacaacatc gtggaggctg tgtcaaacat ctttgatgaa    180
gccgacacaa gcaacaataa ggtgcggaga actctgaggg agggcaggcg cacaaagcgg    240
cggcagaaaa cccgcattga ggacttcaag cagctgtggg agacttcagg ctacatcatt    300
cctcacaagc tgcatctgaa tatcattgag ctgcgcaaca aagggctgac cgaactgctg    360
agcctggatg agctgtattg cgtgctgctg tccatgctga agcaccgggg gatctcctac    420
ctggaggacg ccgacgatgg cgagaagggg aatgcctata agaaaggact ggcttttaac    480
gaaaaacagc tgaaggagaa aatgccatgt gagatccagc tggaacgcat gaagaaatac    540
gggaagtacc atggagagtt catcatcgaa attaatgatg agaaggaata ccagagcaac    600
gtgttcacca caaaggctta taagaaggag ctggaaaaga tcttcgagac acagcggtgc    660
aacggcaaca agatcaacac aaagttcatt aagaaataca tggagatcta cgaacgaaag    720
cgggaatact atatcggacc aggcaatgag aaaagcagaa cagactacgg catctatact    780
accaggactg atgaggaagg gaatttcatc gacgagaaga acatttttgg caaactgatc    840
gggaagtgta gtgtgtaccc cgaggaatat agagcaagct ccgcctcata caccgcccag    900
gagttcaatc tgctgaacga tctgaacaat ctgaaaatca acaatgagaa gctgacagaa    960
tttcagaaga aagagattgt cgaaatcatt aaggacgctt ctagtgtgaa catgaggaaa   1020
atcattaaga aagtcatcga tgaggacatt gaacagtaca gcggagcacg aatcgataag   1080
aaaggcaagg aaatctacca caccttcgag atctatcgga agctgaagaa agagctgaaa   1140
acaatcaatg tggatatcga ctcttttact agagaggaac tggataagac catggacatc   1200
ctgaccctga acacagagag ggaaagtatt gtgaaggcct tcgacgaaca gaaatttgtc   1260
tacgaggaaa atctgatcaa gaaactgatt gagtttcgga agaacaatca gagactgttc   1320
agcggctggc atagtttttc atacaaggct atgctgcagc tgatcccagt gatgtacaag   1380
gagcccaaag aacagatgca gctgctgacc gaaatgaacg tgttcaaaag taagaaagag   1440
aagtacgtca actacaagta catcccagag aacgaagtgg tcaaggagat ctataacccc   1500
gtggtcgtga agagcattag aacaactgtg aaaattctga atgcactgat caagaaatac   1560
gggtatcctg aatccgtcgt gatcgagatg ccaagggata agaactctga cgatgagaag   1620
gaaaagatcg acatgaacca gaagaaaaac caggaggaat acgagaaaat cctgaacaag   1680
atctacgatg agaagggaat cgaaattacc aacaaggact acaagaaaca gaagaaactg   1740
gtgctgaagc tgaaactgtg gaacgagcag gaaggactgt gcctgtattc cggcaagaaa   1800
atcgctattg aggatctgct gaatcacccc gagttctttg aaattgacca tatcattcct   1860
aagagcatct ccctggacga ttctcgcagt aacaaggtcc tggtgtacaa aacagaaaat   1920
tctatcaagg agaacgatac cccctaccac tatctgacac ggattaacgg aaagtggggc   1980
tttgacgaat ataaagctaa tgtgctggag ctgagaaggc gcggcaagat cgacgataag   2040
aaagtgaaca atctgctgtg catggaggat atcactaaga ttgacgtcgt gaaagggttc   2100
attaaccgca atctgaacga caccagatac gcatccaggg tggtgctgaa cgaaatgcag   2160
tccttctttg agtctcgaaa gtactgtaat actaaggtca aagtgatccg aggctctctg   2220
acctatcaga tgcggcagga tctgcacctg aagaaaaaca gagaggaatc atacagccac   2280
catgctgtgg acgcaatgct gatcgcattc tcccagaagg ggtacgaggc ctataggaag   2340
atccagaaag attgctacga ctttgagaca ggcgaaattc tggacaagga aaaatggaat   2400
aagtacattg acgatgacga gtttgatgac atcctgtata aagagaggat gaacgaaatc   2460
```

cgcaagaaaa tcattgaggc cgaggaaaag gtgaagtaca actacaagat cgataagaag 2520
tgcaatcgcg ggctgtgtaa ccagactatc tacgggaccc gagaaaagga cggaaaaatc 2580
cacaagattt caagctacaa catctatgat gacaaggagt gtaattccct gaagaaaatg 2640
attaacagtg ggaaaggatc agatctgctg atgtacaaca atgatcctaa gacatatcgc 2700
gacatgctga aaatcctgga aacttactcc tctgagaaga atccattcgt ggcatataac 2760
aaagagacag gagactactt tcggaaatat tctaagaatc acaacggacc caaggtcgag 2820
aaggtgaaat actatagcgg ccagatcaac tcctgcatcg atatttctca caagtacggc 2880
catgccaaaa atagtaagaa agtcgtgctg gtgtcactga acccttatag aaccgacgtc 2940
tactatgata atgacacagg caagtactat ctggtcgggg tgaagtacaa tcatatcaaa 3000
tgtgtcggaa acaagtacgt gattgatagc gagacatata acgaactgct gaggaaggag 3060
ggcgtgctga acagcgatga gaacctggag gacctgaaca gcaaaaacat cacttacaag 3120
ttcagtctgt acaagaacga catcatccag tacgagaagg gcggggaata ctatacagag 3180
cgctttctga gccgaatcaa agaacagaag aacctgattg agactaaacc catcaataag 3240
cctaacttcc agcggaagaa taagaaaggc gagtgggaaa ataccagaaa ccagatcgcc 3300
ctggctaaga ctaaatacgt ggggaagctg gtcaccgatg tgctgggaaa ctgttacatc 3360
gtgaacatgg agaagttctc cctggtcgtg gacaaataag aattc 3405

<210> SEQ ID NO 125
<211> LENGTH: 3474
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125
accggtgcca ccatgtaccc atacgatgtt ccagattacg cttcgccgaa gaaaaagcgc 60
aaggtcgaag cgtccatgac taacggcaag attctggggc tggacattgg catcgcaagc 120
gtgggggtgg ggattattga ggcaaaaact ggaaaggtgg tgcatgccaa ttcccggctg 180
ttctctgccg ctaacgctga gaacaatgca gaacggagag ggtttagggg atctaggcgc 240
ctgaatcgac ggaagaaaca ccgcgtgaag cgagtccggg atctgttcga gaaatacgga 300
atcgtcaccg actttcgcaa cctgaatctg aacccttatg agctgcgagt gaagggcctg 360
accgaacagc tgaaaaacga ggaactgttc gcagccctga gaacaatctc taagagaagg 420
gggattagtt acctggacga tgccgaggac gatagtaccg gatcaacaga ctatgctaag 480
agcatcgatg agaatcgccg actgctgaaa aacaagacac caggccagat tcagctggag 540
aggctggaaa agtacggcca gctgcgcggg aatttcaccg tctatgacga gaacggggaa 600
gcccatcgcc tgatcaatgt gtttagtaca tcagattacg agaaagaagc acggaagatc 660
ctggagacac aggccgacta caacaagaaa atcacagctg agttcattga cgattatgtg 720
gaaatcctga cccagaaacg aaagtactat cacggccccg ggaacgaaaa gagccggact 780
gactacggac ggttccggac cgatgggacc acactggaga atattttcgg aatcctgatt 840
ggcaagtgca acttttaccc tgatgaatat cgagcaagca aggccagcta caccgcacag 900
gagtataatt tcctgaacga cctgaacaat ctgaaggtga gcaccgaaac agggaagctg 960
tcaacagagc agaaagaaag cctggtggag tttgccaaga atactgctac cctgggaccc 1020
gctaaactgc tgaaggagat cgcaaaaatt ctggactgta aggtggatga gatcaaagga 1080

```
tacagagagg acgataaagg caagccagat ctgcatacct tcgagcccta taggaaactg   1140
aagtttaatc tggaaagcat caacattgac gatctgtccc gcgaagtgat cgacaagctg   1200
gctgatattc tgactctgaa caccgagaga gaaggaatcg aggacgcaat taagaggaat   1260
ctgccaaacc agttcacaga ggaacagatc agcgagatca tcaaggtgcg gaagagccag   1320
tccactgctt tcaataaggg ctggcactct tttagtgcaa aactgatgaa cgagctgatc   1380
cccgaactgt acgccacctc cgacgagcag atgacaattc tgactcggct ggaaaaattc   1440
aaggtcaata agaaaagctc caaaaacaca aagactatcg acgagaagga agtcactgat   1500
gagatctaca atcctgtggt cgccaagagc gtgagacaga ccatcaaaat cattaacgct   1560
gcagtcaaga aatatggcga cttcgataag atcgtgattg aaatgccacg ggataaaaat   1620
gctgacgatg agaagaagtt catcgacaag agaaataagg agaacaagaa ggaaaaggac   1680
gatgccctga aaagggccgc ttacctgtat aattctagtg acaagctgcc cgatgaggtg   1740
ttccacggca acaagcagct ggaaaccaaa atccgactgt ggtatcagca gggggagcgg   1800
tgcctgtata gtggaaagcc catctcaatt caggagctgg tgcataactc taacaatttc   1860
gaaatcgatc acattctgcc tctgtcactg agctttgacg atagtctggc caataaggtg   1920
ctggtctacg cttggacaaa ccaggagaaa ggccagaaaa ccccttatca ggtcatcgac   1980
tccatggatg cagcctggtc tttcagggag atgaaggact acgtgctgaa acagaaggga   2040
ctgggcaaga aaaagcgcga ctatctgctg actaccgaga acatcgataa gattgaagtg   2100
aagaagaagt tcatcgagag gaatctggtg gatactcgct acgcatctcg agtggtcctg   2160
aactctctgc agagtgccct gagagagctg ggaaagacac ctaaggtgtc tgtggtcagg   2220
ggacagttca ccagtcagct gcggagaaaa tggaagatcg ataagagccg cgagacatac   2280
caccatcacg cagtggacgc cctgatcatt gctgcatcaa gccagctgaa actgtgggag   2340
aagcaggaca atcccatgtt tgtggattat ggcaagaacc aggtggtcga caaacagact   2400
ggggagatcc tgtccgtgtc tgacgatgag tacaaggaac tggtgttcca gccccccttat   2460
cagggctttg tgaataccat ctcctctaaa gggttcgagg acgaaattct gtttagctac   2520
caggtggatt ccaaatataa ccggaaggtc agtgacgcaa ccatctactc aacaagaaaa   2580
gccaagattg gcaaggataa gaaagaggaa acctacgtgc tgggaaaaat caaggacatc   2640
tactcccaga atggcttcga taccttcatc aagaagtaca acaaagataa gactcagttc   2700
ctgatgtatc agaaggactc tctgacatgg gagaacgtga tcgaagtcat tctgagggac   2760
tacccaacaa ctaagaaaag cgaggacggc aaaaatgatg tgaagtgcaa ccccttttgag   2820
gaatacaggc gcgagaatgg gctgatctgt aagtattcca agaaagggaa aggaactccc   2880
atcaagagcc tgaagtacta tgacaagaaa ctggggaact gcatcgatat taccccagag   2940
gaatcacgca ataaggtcat cctgcagagc attaaccctt ggcgagccga cgtgtacttc   3000
aatccagaga cactgaagta cgaactgatg ggcctgaaat attcagatct gagctttgaa   3060
aagggcactg ggaactacca tatcagccag gagaaatatg acgctatcaa agagaaggaa   3120
ggaattggca agaaatccga gttcaagttt acactgtacc gcaacgacct gatcctgatc   3180
aaggatatcg ccagtggcga gcaggaaatc tacagattcc tgtcaagaac tatgcccaat   3240
gtgaaccact acgtcgagct gaagccttac gacaaggaaa agttcgataa cgtgcaggag   3300
ctggtcgaag cactgggaga ggcagataaa gtgggacgat gtatcaaagg actgaataag   3360
ccaaacatca gcatctacaa ggtgagaacc gacgtcctgg gaaacaaata tttcgtgaag   3420
```

-continued aaaaagggcg acaaacccaa gctggatttt aagaacaaca agaagtaaga attc 3474

<210> SEQ ID NO 126
<211> LENGTH: 3462
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 126
accggtgcca ccatgtaccc atacgatgtt ccagattacg cttcgccgaa gaaaaagcgc 60
aaggtcgaag cgtccatggc cgaccgaatc tctctggggc tggacattgg ggtggcaagc 120
gtggggttct cagtgctgga cattgataag ggaaaagtca ttgagctggg cgccaggctg 180
ttctctgcta ctgtggccgc tggcaaccag gatcgaagag acatgcgagg agccaggcgc 240
ctgctgaacc ggaacaagca gcgacggcag gataccggaa agctgttcaa gaaatttggc 300
ctgatcgacg attttgataa gggcagcttc tacgacaact ttaatcagaa cctgaatcct 360
tatgagctga gagtgaaagg cctgacagaa cagctgacta aggaggaact ggccgagtct 420
ctgtaccaga tcgtgaaaca tagggggatt agttatgcac tgaaggacgc cgatgtggac 480
gaaggcggga cagactactc agtcagcctg aaaatcaaca gccaggagct ggcagaaaag 540
actccagccc agattcagct gcagagactg aatgattatg gaaaggtgag gggccaggtg 600
gtcatcggcg acgatccaga caaccagaag gtgctgctga atgtgttccc cacatcagct 660
tacgagaaag aagcaaagca gatcattgcc actcagcagc agttctatcc tgagagcctg 720
accgacaagt tcaccgagga atactgccag atcctgactc gcaagcgaga ttattttgtg 780
gggccaggaa acgagaaaag ccggaccgac tacgggatct acaagactga tggaagaacc 840
ctggacaatc tgttcgagga actgatcggc cacgataaga tctaccccga ggaactgcgg 900
gcatctgcag ccagttatac cgcccagctg tttaacgtgc tgaatgacct gaacaatctg 960
agaatcctga actacgagga tgggaaactg acaaaggagg acaaggaaaa gatcatcgct 1020
gaaattaaga acaacaccac aactatcaac atgctgaatg tgattaagaa agtcgccggg 1080
tgttccaagg acgatatcaa aggattccga gtgaatgaga aggataaacc cgaaatcagc 1140
tccatgcctg tgtaccgcaa aattcataag gacctgctga aggccggcgt ggatatctca 1200
gactggcccg tcgagttcat cgacgaactg agctttattc tgacactgaa cactgagaat 1260
ggggaaattc gcaaacagct gaacaatcga ctggccccta agttcgattt tctgaacgct 1320
gacctgatcc agctgatcat tgataataag gactcctttg agattaagac taacaacaag 1380
tggcacagat tcagcgtgaa aaccatgaac aaactgatcc cagagatgat ggaaagaccc 1440
gtggagcaga tgaccctgct gaatgaaatg ggactggtca agaaagataa gaaacgcttt 1500
gagaacaata agtacctgcc ttacaaggaa atcgcaaagg acattttcaa cccagtggcc 1560
tccaaatctg tccgcgaggc cctgaagatc gtgaatgctg tcctgaagaa atacggccac 1620
attgattatc tggtggtcga aatgcctcgg gataaaaacc tgaaggagga acaggacaat 1680
atcaaggagt tccagaacaa aaataagaaa gctaaggacg ctgcattcga agcatttgtg 1740
aaatcagtcg ggagcgagca gagagtgaag gaagccctgt ctaaaaaccg gaagctgcag 1800
atgaagatga gactgtggta tcagcagcag gagatcgatc catataatgg aaagacaatc 1860
gatgccactg acctgattaa caatcctgat aagttcgaga ttgaccatat cattccacag 1920
agtatctcat tttacgacag tattaacaat aagaccctgt gcttcgcctc aatgaaccag 1980

```
gtgaaaggac agaaaacccc ctacgagttt atgctggaag gccacgggca gtcctatgac   2040
aagttcaaag ctacagtgat ggcaaacaag aattttggca aggctaaaag ggcaaactac   2100
ctgttcgagg aaaatgtgag cgatatcgag actcggaaga gattcctgtc ccgcaacctg   2160
gtggacaccc gatattctag tcgggtggtg ctgaacagcc tgcaggattt ctttcgggag   2220
aaatctgccg acaccaaggt gacagtcatt cgcggcaagt ttacctccaa catgcgaaaa   2280
cattggcaca tcgataagac tagggagaca ttccaccatc acgccattga cgcttctatc   2340
attgccgcta caccatttct gcgcatgtgg aagaaaggag gcactatctt ccccgtgaag   2400
gtcggagaag aaagtatcga tattgagaca ggcgaaattc tggacgataa gaattttgac   2460
aaagcaatgt acgaggaacc ctatagtggc ttcgtgtcag agatcatgaa cgccgacgat   2520
cggatcaagt tcagccacca ggtggataag aaaatgaata ggaaggtgag cgacgccacc   2580
atctacagta ctcgcaccgg gaaactggct aaggataaga aagacgctga gtacatcgtg   2640
gcaaaggtca aagatatcta cagcgtggac ggattcaaga agttcaagaa agtctacgat   2700
aaggacaaaa ccaagtttct gctgtacaaa tatgatccta ggacattctc aaagctggag   2760
cgcatcatta gcgattgccc agacaaagtg gaaaaggtcc agacaaacgg caaagtgaag   2820
gctgtcgata tcagtccatt cgagatgtac agaagggacc atgggatgat caagaaatac   2880
tcaaagaaag gaaacggccc cgccatcaag cagctgaagt acctggataa gaaactgggc   2940
agccacatcg acattacccc cgcaaacgcc aatggaaaac acgtgatcct gcagagtctg   3000
aagccttgga gaaccgacgt ctatctgaac cacgagacag gcgagtacga aatcatgggg   3060
attaagtata gcgatctgaa gttcaacaag aatgaggggt acggaatcaa gaaagacaag   3120
tatctggaaa ttaagaaagt ggaggaagtc tccgagaagt ctgagttcat gtttagcctg   3180
tacaggaagg atcgcgtgaa agtccaggac atgaaaaccg gcgagtccgt ggaactgctg   3240
ttctggagca ggaacttttc caataagaaa tacgctgagc tgaagcccat ctcccaggca   3300
gaaaacgaca agaaactgcc tgtgtatggc aaagggagac tgatcaagag gctgattccc   3360
aaaaactgta agatctggaa agtgaatacc acaattctgg gcgatcccta ctatctggag   3420
aaagaaagcg actcccctaa ggatatcctg gactaagaat tc                      3462
```

<210> SEQ ID NO 127
<211> LENGTH: 4611
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 127

```
accggtgcca ccatgtaccc atacgatgtt ccagattacg cttcgccgaa gaaaaagcgc     60
aaggtcgaag cgtccatgaa gaaaacactg ggactggacc tggggactaa cagcattggg    120
tgggccgtca tcaactcaaa catcgactca gaaggaaaag aaaagctggt ggggatcagc    180
tcctgcggaa gccggatcat tcctatggac gctaccacac tgggagattt cggaaagggc    240
aacactaaaa gtccagtggc agagcgaacc cgactgcggg gcattcggag actgctggaa    300
aggtcactgc tgaggcgcga gcgactgcac cgagtgctgt cagtcatggg gttcctgcca    360
gagcattacg ctagccagct ggaccgctat ggaaagtttc tgccagaaac cgagcccaag    420
ctggcatggt acaaagacga tagcggcagg tatcagttcc tgtttcagaa gtccttccac    480
gagatgctgg aggactttcg acagcatcag ccagaactgg tggcaggaga gaagaaaatc    540
```

-continued

```
ccttacgatt ggacaatcta ctatctgcgg aagaaagcac tgtctcagga gatcactaag    600
gaggaactgg cctggattct gctgaatttc aaccagaaac gcggctacta tcagctgcga    660
ggggaggaag agcaggaaga gaacaataag agcgtggagt atcacgccct gaaagtggtg    720
agcgtcgagg actctggaga aagaaagggc aaagatatct ggtacaatgt gactctggag    780
aacggatggg tctatcgacg ggctagcaac attcccctgg actggaccgg caaggtgaaa    840
gagttcgtgg tcactaccga gctggacgat gccgggaacc caaagaaaga taaggaagga    900
aatgtgaaaa gatcctttag ggcaccaaag gaggacgatt gggggctgct gaaaactagg    960
acccaggctc agatcgacga atccggcaag accgtgggaa cttacatcta cgagtctctg   1020
ctgtgtatgc ccaaccagaa gatccgggga aaactggtga ggaccattga acgcaagtac   1080
tataaagacg agctgagaca gatcctggtg aagcagagcg agttccacgc cgctctgcag   1140
gatcataatc tgctgctgtc ctgtatcgaa gagctgtacc ctaacaatga ggcccacaga   1200
aggctgctga gcgccagcag cttcatctac ttcctgatcg aggacattct gttttatcag   1260
cgcccactga agtcccagaa agggctgatc gataactgcc cctacgagtc tcacatctac   1320
aaggataaga aagatggaag tctgcaccat gtgcctctga agtgtgtcag caaatcccat   1380
ccactgttcc aggaatttcg cctgtggcag ttcctgtcta acctgcgaat ctaccagaga   1440
gagaggatga tggacggcag tctgaaactg gacgtggatg tcacccggga gttcctgccc   1500
tcagaagagg actacgtgaa gctgtttgat tggctgaatg agagaaagga aatctctcag   1560
aaattcctgc tggcttataa accttttggg ctgaagaaaa acgaacaggc aaattacaga   1620
tggaactatg tggaggacaa gagctacccc tgcaacgaga cacgggcaga aatcaagagc   1680
agactgtcca aagccggagt gcctgaagag tttctgactg aagagaagga agaggccctg   1740
tggcacatcc tgtattctat tagtgataag aaagagctga ctaaggctct gggcaccttc   1800
gcagccaaaa actgtctgaa tgagtctttc gtggaagtct ttgccaagat ccccccctttt   1860
gagtcaaact acgctgcata tagcctgaag gctattagga aactgctggc actgatgcgc   1920
atggggaagt actggaatga acaggccatc gacaggcaga ctcgcgatcg aatcgagaaa   1980
attctgaccg gagagtatga cgaaacaatc cggagcagag tgagggagaa ggcaatgctg   2040
ctgaccgata ttagcagctt ccggggcctg cctctgtggc tggcctgtta catcgtgtat   2100
gaccgccact cagagagcaa ggaactggtc aaatgggaga caccagccga catcgatcat   2160
ttcctgtcca agtttaaaca gaacagcctg cggaacccca tcgtggaaca ggtcattaca   2220
gagtccctgc gcactgtgcg agacatttgg aagcaggagg gaaaaatcga tgagattcac   2280
gtggaactgg gccgggagat gaagaaccct gcaaaagagc gcgcccgaat tacagctcag   2340
gtgcaggaaa atgagaacac taatctgaga atcaaggctc tgctggcaga gttcatgaac   2400
cccgaatttg agattgaaaa tgtgcatcca tactcacccg gccagcagga aatcctgcgg   2460
atctacgagg acggcgtgct gagcgggatc gctgagaagg atctgcctga cgatatcaca   2520
gcaattctga agaaattccg agaaaacgac gtgaagaaac ggccaacaac tagcgaagtc   2580
ctgcggtaca aactgtggct ggagcagcgg tacagatccc catataccgg aagagtgatc   2640
cccctgggca agctgttcac acctgcttac gagatcgaac acgtgattcc ccagagccgg   2700
tattttgacg attccatctc taacaaagtg atctgcgaaa gtgccgtcaa taagctgaaa   2760
gataactgtc tgggctatga gttcatcaag aaacattccg gggagatggt ggaactgggg   2820
aatggagaga cagtgcccgt gttcagcgtg gaagagtacg aacggttcgt caaggagtct   2880
tacttcggca acagtaagaa aatgaagaaa ctgctgctgg aggacatccc agatagcttc   2940
```

```
attgagagac agctgaatga cagtcgatac atctcacggg tggtcacatc tctgctgagt   3000
aacctggtgt gcgaagaggg agagcaggat ggcctgtcca agaatgtgat cgtctgtacc   3060
ggcgggatta cagacaggct gaagaaagat tggggagtgc aggaagtctg gaaccgcatc   3120
attctgcctc ggttcctgag actgaatgag atcaccggac ggacagactt tacaagtact   3180
tcagtgaacg gccacctgct gcctgccctg ccactgtacc tgcagaaggg ctttaataag   3240
aaaagaattg accataggca ccatgccatg gatgctatcg tgattgcctg cgctaaccgg   3300
aatatcgtca actacctgaa caattcctct gctagaaaga acagcgaaat tagccgatat   3360
gacctgcagc ggctgctgtg tgagaaggtg aaaaccgatg ccaacggcaa ttacaagtgg   3420
atcctgagga aaccatggga gacattcacc caggatgtgt atgccgctct gacaaacatc   3480
gtggtcagct ttaagcagaa tctgcgcgtg attaatcgaa ccacaaacta ctatcagcac   3540
tacaacgagg caggggaaaa gcgcatgatc cctcagacca aaggcgacag atgggccatt   3600
agaaagccaa tgcataaaga tactgtgtat ggcgaagtca atctgagaaa ggagaaaacc   3660
ctgccactga gggacgtggt caagaacccc agtatcgtgg tcgataaatc actgaagaac   3720
aagctgtacg agctgctgaa gagccagtat gacctgaagg caatcgccaa atacttcgag   3780
acacaccagg acgtgtgggc agatgtcaac ctgaagaaaa ttaaggtgta ctacttcact   3840
aaggagacaa acgaaagatt ctttgccact aggaagagcc tggacccatc ctttgatcag   3900
aagaaaatcg aagaggaagt gactgatacc ggcgtccaga agattctgct gcaccatctg   3960
cagcagaaca ataacgaccc tgatatggcc ttttccccag acggcatcga taggatgaac   4020
cagaatatga ccattctgaa tgacgggaag tggcaccagc ccatctacaa agtgcgcaca   4080
tatgaaaagg cagataaatt cgccgtcggc gagtctggga acaaggccaa gaaatttgtg   4140
gaagcagcca aggcaccaa tctgttcttt gccgtgtacg agagtgtcca ggaggacgaa   4200
gctatcggga agcaggtctg caaacggaca ttcgccacta tccccctgaa cgaagtgatc   4260
aagagaaaga aacagggcct gcccgctgca cctgaggacc tgaacgggaa tctgcccaag   4320
tttgtgctga gccctaacga tctggtctac ctgcccaccg aggaagagag gaatagttca   4380
cgcatcattc agcctctgga cagggagcgc atctataaga tggtgagctc ctctgggagt   4440
cagtgcttct ttatcaaagt gttcgtcgcc aattcaattt gggataagaa cgaatacagc   4500
agcctgaaca agatggagag ggctattaca aacgaaatga tcaaggagat ttgtgtgcct   4560
atcaaaattg accgcctggg caatgtcagc ctgatccaga tttaagaatt c            4611
```

<210> SEQ ID NO 128
<211> LENGTH: 4458
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

```
accggtgcca ccatgtaccc atacgatgtt ccagattacg cttcgccgaa gaaaaagcgc     60
aaggtcgaag cgtccatgac aaagactatt ctgggactgg atctggggac taacagcatt    120
ggatgggcac tgattaacca ggacttcgat aacaaaaagg gggagatcct gggcatgggc    180
agccggatca ttcctatgac acaggatatt aaggacgagt tcggaaaagg caactctatc    240
agtcagacag ctgagcgaac tcgactgcgg ggagtccgga gactgatcca cagaactctg    300
ctgaggcgcg agcggctgca tagagtgctg aatatcattg gcttcctgcc agaacactat    360
```

-continued

```
gccaaccaga ttgactttga gaagaggttc ggcaagttca agcctgaatc tgagccaaaa    420
atcagtttcg atggaaatga cgtgttcctg tttgagaaga gctaccagga aatgctggtc    480
gactttaaaa tccaccagcc acagctggtg agcaacggca agaaaattcc ccatgactgg    540
acaatctact atctgagaaa gaaagctctg tctaagaaaa ttgagaagga ggaactggca    600
tggatcctgc tgaacttcaa tcagaaacgg ggatactatc agctgagagg cgaggaagag    660
gaagagacac caaataagct ggtggagttt catagcctga aaattgtgga ggtcaacgcc    720
gatgaacccc agaaaggaaa gcctgagatc tggtactcac tggtgctgga aaacggctgg    780
gtctatcgac gggctagcaa gactcccctg ttcgattgga aagacaagat tagggagttt    840
atcgtgacca cagaaatcaa caatgatgga actgtcaaaa ccgacaagga gggcaccgaa    900
aagaggagct tccgcgcacc aaaacccgag gactggactc tgcagaagaa aaagaccgag    960
ttcgagctgt caaagagcgg gaatgaagtg ggagccttca tctacgaaag tatcctgcag   1020
aaacccaacc agaagattag aggcaaactg atttcaacca tcgagaggaa attttataag   1080
gaagagctga aaccatcct gaaaacacag ctgttctttc acaaagaact gaaggatgag   1140
aaactgtaca atgcctgcat cgaagagctg tataagaaca atgaagctca ccggagcctg   1200
ctgtccaaca aggggttcga gcatctgttt attaacgaca tcctgttcta ccagcgacct   1260
ctgcggtcta aaaagagtca gatctcaaac tgcccactgg agaagcgcac atataaaaag   1320
gaggggattg aaatcactga gggcatcaaa gtgatctcca aatctaatcc aatctaccag   1380
gagttccggc tgtggcagtg gattagcaac ctgtccctgt attgtatcga acccaccgag   1440
acaaatgtga cttcaacctt tctgaacagc attgaagatt acgagaatct gttcgaattt   1500
ctgaacaatc gcaaggaaat cgagcagaag cacctgctga aatatctgct ggagaaccag   1560
gggtttaaag gaaagctgct gacaaacgaa ctggagaagt tccgctggaa ttttgtcgct   1620
gacaaaaagt acccctgtaa tgagacaggc agcctgctgc atactcggct gagcaaagtg   1680
aagaacattt cccctgattt cctgaccaag gaaatcgagc accagctgtg gcatatcatc   1740
tacagcgtga ccgacaagat tgaatatgag caggccctga aacctttgc tcggaaaaac   1800
aatctggatg tggactcctt ctttgagcac ttcaaaaaga tccccccttt tgagtctacc   1860
tacggagcat atagtgaaaa ggccatcaag aagctgctgc cactgatcag actgggcaaa   1920
tactggaact gggaggccat tgatagtatc tcaaaggaca ggattagtaa aatcctgtca   1980
ggggaatacg atgagaacat taagaacaga gtgagggaga aagcagtcca cctgacctcc   2040
gaaaacaatt tccagggact gcaggagtgg ctggccaagt acatcgtcta tgatcgccat   2100
tctgagggca atgacctggg gaagtggact agcgtgtccg acctggagac atacctgaag   2160
gagttcaagc agcatagcct gcggaaccct attgtggagc aggtcatcac agaaactctg   2220
agagtggtca aggatatttg gatcaagcac gggaaaggaa ccgaaaattt ctttgacgaa   2280
atccatgtgg agctgggccg ggaaatgaag aacaattccg aggatcgcaa acgactgacc   2340
aacacaatta ctgaaaacga gaatacaaac ctgagaatca aggccctgct gatggaaatg   2400
atgaatgata acgacgtgga gaacgtcagg ccttactctc caagtcagca ggagattctg   2460
aagatctatg aggacggagc tctgaatagc aacatcgagc tggacgatga aattgtgaag   2520
atctccaaaa aggcagagcc caccaaatct gaactgcagc gctacaagct gtggctggag   2580
cagaaatacc gatcccctta tactggccag gtcatcccac tgaacaagct gttcacctct   2640
gaatatgaga tcgaacacgt ggtccctcag agtcgcttct ttgacgatag cttcagcaac   2700
```

aaagtgatct gcgagtcagc cgtcaacaag cggaaggata accagctggg gctgcagttc 2760
atcaagaacc atagcggaga aaaagtggag ctgggcttcg ggaaggtggt ccaggtcttt 2820
acagaagagc agtacctgga ttttgtgaag gagcactata gcaaaaatcg ctccaagcat 2880
aacaaactgc tgctggaaga gattcccgag aagatgatcg aaaggcagct gaatgacact 2940
cgctacatca gtaagttcgt gagctccatt ctgtccaaca tcgtcagatc tgagaaggac 3000
gatgacggcc tgaatagcaa aaacattctg cctggaaatg gcaagatcac taccgaactg 3060
aaaagggact gggggctgaa tgatgtgtgg aacgacctga ttctgccaag attcgagagg 3120
atgaatacca tcacaaacag cgatctgttt acaacttaca acgacaagta tcagaaacac 3180
ctgcccaccg tgcctttcga gtactccaag ggctttcaga aaaagcgcat tgatcaccga 3240
caccatgcta tggacgcact ggtcatcgca tgtgccacac gggatcatct gaatctgatg 3300
aacaatcagt ctgccaagag tgaactgaaa cgatacgacc tgcagaacaa gctgcggaaa 3360
aaggagcctt acttcaacca gaaggagaac aaacagaagg aagccttcaa ggattttatc 3420
aaaccatggg gcactttcac cgaggacagc aagaatgctc tggaaaaaat cattatctcc 3480
tttaagcaga acctgagagt gatcaacaag gcaacaaact catacgagag ctataaggat 3540
gaggacggga atctgaggat cggcaaggat gggaaaccag agaagggcct gatcaagcag 3600
aaggggctga actgggcaat cagaaagccc ctgcacaaag acaccgtgtc aggccagatt 3660
aacctgagca ggatcaagct gcccaatggg aaaatcctga cagccactcg caagaatctg 3720
gataccagtt tcgacctgaa aacaattgag aactcaatca ccgacacagg cattcagaaa 3780
atcctgaaga attacctgct gtccaaggaa tctccagagc tggccttctc tcccgagggc 3840
ctggaagaga tgaacaatga gatcgaaaag tacaacaatg ggaaatttca ccatcctatt 3900
aacaaggcta ggatctatga actggggagc aaattcaatg tcggacagac aggcaacaga 3960
agggataagt ttgtggaggc cgctaaagga actaatctgt tctttgctat ctaccaggac 4020
gagaataaga accgctctta tgaaactatt cccctgaacg aagtgatcga gcaccagaag 4080
tggcgagcaa gtctgcctaa ggaagagcag gagaaaattc cactggtgcc cgtcaacaag 4140
ctgaagggga ccttcatctt ttccctgtct cccaacgatc tggtgtacgt cccttccaat 4200
gacgagctgg aacgaagtgc ttcaattgac ttctctaagc tgaaaaagga acagatcaac 4260
cggctgtata aaatggtgtc tagttcagga tcccagtgct tctttgtgaa gagtgaggtc 4320
gcaacctcag tggtcaacaa aatggaatac agcagcctga acaagatgga gaagtctatc 4380
gataacctga tggtgaagga gatttgtatc aaactgaaga ttgacaggct gggcaacatc 4440
agcaaggcct aagaattc 4458

<210> SEQ ID NO 129
<211> LENGTH: 4689
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129
accggtgcca ccatgtaccc atacgatgtt ccagattacg cttcgccgaa gaaaaagcgc 60
aaggtcgaag cgtccatgac caaaatcctg gggctggacc tggggactaa tagcatcggg 120
tgggcaatcc gcgacacaga aaatgagggc atcaatcaga tcctggacaa gggcgcccgc 180
attttcagcg agggagtgaa gtccgagaat ggcaaagaaa tcagtagggc agctgaacga 240

-continued

```
accgcttacc ggagcgcaag aaagatcaaa tatcggagaa aactgcggaa gtacgagaca    300
ctgaaggtgc tgtcaattaa cggaatgtgc cccctgagcg tggaggaagt cgaacagtgg    360
aagaaatctg gcttcaagga atatcccctg aatcctgagt ttctggattg gctgcggacc    420
aacgaggaca agaacatcaa tccttacctg ttcagagata aagctagcaa gcagaaagtg    480
acactgtttg aactgggaag agctctgtat cacatcgcac agaggcgcgg cttcctgagt    540
aacaggctgg accagtcagc cgagggcgtc tttgaggaac ataatcctca gatccagaac    600
ctgattgagg acctggacag ctccaacaca attctgaatg agctgaagga atactatatc    660
aatctgggga tcattgacga gactgaaaag tccggcttca agaaagacct ggatgagggg    720
gaaaagaaac tgaagtcact gtacaacagc ctggtggcca tcacaaagaa aaacgctaac    780
gatatcgaaa cttgcaagca ggagctgatc gctagactga ataagaaaga ggacctgggc    840
aaggtcaaag ggaagatcaa agatatttct caggcaatgc tggacaggaa ctttaagact    900
ctgggacagt atttcttttc actgtacaac aaggagcgaa tccggaacca gtataccagc    960
cgcgaggaac actacctgga ggagttcatc attatctgtc agacccaggg gatcgaggga   1020
attaacacaa atgagaagct gcctgagaag aagttcaccg gcctggcaaa agatctgtat   1080
cgagccattt tctttcagcg gccactgaaa tcccagaagg gcctgatcgg gaagtgctct   1140
ttcgagaaga acaagtctcg ctgtgccgtg agtcacccag actatgagga atttcgaatg   1200
tggagctacc tgaacacaat caaaattggc actcagtccg agaaaaccct gcgcttcctg   1260
acactggagg aaaagctgaa actggtgccc aagttctacc gaaagagtga tttcaacttc   1320
gaggtgctgg ctaaggagct ggtcgaaaaa ggagcatcat tcggctacta caagtctagt   1380
aagaaaaatg agttctttta ctggttcaac tataagccca ccgattcagt gagcgcctgc   1440
gtggtgagcg cttctctgga gaacgcaatc ggcaaggact ggaagatcaa gactttcgaa   1500
tatcagacta gaaacaccga gaagaatgaa gtgaccaaat ccgtcgatta caaggacctg   1560
tggcacctgc tgtccgtggc aacatctgat acttacctgt atgactttgc catcgaaaag   1620
ctgaaactgg agcctaaaaa cgcaaaggcc ttcagcaaga caaaactgaa gaaagacttt   1680
gccagtctgt cactggcagc catcgctaaa attctgccat atctgaagca gggcctgctg   1740
tactcccacg ccgtgttcat ggctaacatc gagaatattg tcgacgccga tatctggaag   1800
gatgaggaac agcagaagtt catccagtcc aagattgtgg agctggtcga caattatatc   1860
gtggaaaagt ctaaactgga gctgatcaat gggctgctga agatctacaa caccgaggat   1920
aaggaaggac ggaaagtgta ctattcaaag gaggctgaaa gcctgttcga ggcagacctg   1980
agaaagaaac tggtcccctt ctacaaggct aacatcatca tcgaggaaca cgagcaggaa   2040
atcattttcc aggatctgtt tcctatcctg atggaccagc tgaagaaaca ggagttcatc   2100
aaaattggca gactggataa gcagattgaa gccttcctgg aggggggaaaa tgaggaagga   2160
cagatctttt gtaaccacac agataagctg aagaaactgt accatccaag cgacatcgag   2220
gtgtttaaga aaaagactat caaagatgag tgggggaatg aaaaggtggt cctgggatcc   2280
ccactgacca catctatcaa gaaccccatg gcaatgagag ccctgcacca gctgaggaag   2340
gtgctgaata cactgattgc caacgaccag atcgacgagg atactcggat ccatattgag   2400
atggccagag aactgaacga tgctaataag cgaaaaggca tccaggactt ccagaacgag   2460
aacaagaagt ttcgggagga agccatcaag gagatcaaga agctgtacct ggaggaatgc   2520
cacaaagacg tgaaccccac cgaggacgat atcctgaggt atcagctgtg gctggaacag   2580
ggaaagtgcg agatctacga ggaaggcaac aatatcagca tttgtgatat cattggcagc   2640
```

```
aatccctcct atgacatcga gcataccatt cctcggagca tctcccagga taacagccag   2700

atgaacaaga cactgtgtag cctgaagttc aacagatcca tcaaaaagca gaagatgcca   2760

gtggagctgt ccaactacaa tgacattctg cccaggatcg cacactggaa aaaggaggcc   2820

gaggaactga ctaggcagat cgaaaccatt tctcgcagca tcaagagcgc tgcaaccaag   2880

gtggccaagg ataagaacat cagaaagagg cattacctga cactgaagcg agactatatt   2940

ctggggaaat acgagcggtt cacttgggag gaacctaaag tgggctttaa aaactcccag   3000

atcccagaca ctgggatcat taccaagtac gctcaggcat atctgaaatc ttacttcaaa   3060

agggtggaga gtgtcaaggg aggagcagtg gctgagttcc ggaaactgtg ggcatccag    3120

gaatctttta tcgatgagaa ctggtggaag cactataagg acaaagatag agacaaacat   3180

acccaccata caatcgacgc aatcactatt gcctgtatgc ccaaggataa atacgacctg   3240

ctggcacacg cctggaggct ggaggatgaa caggacaaaa aggccgctaa ggtgctgatc   3300

gagcaggcca aaccatggaa aaccttcaag gaggatatcg aaaagattga gactgaaatc   3360

ctggtgagcc attttacccc cgacaacgtc aaaaagcagt caaagagcat catcaagaat   3420

cgcggcaaaa aggtgtacgt cctgaagaac gagctgcctg tgaacttcaa gaacaagatc   3480

gaagggaagg attatttcaa gctgaaattt gacagcaaga ttctgtacaa aatccccaaa   3540

aagaaagaga agcagaccga tacattctat gaggaactgc ctaaaaacta cctgaatgga   3600

gtggaaggca aggactactt caaaatcaat actaccggca agaccttcta caaaatccca   3660

atttttaacc agggcgacac aatccggggg agcctgcacc aggagacaac ttacggagcc   3720

attaagctgc cagatatcga cattgaaaca aagaaacccc tgcatactga taagggaggc   3780

ttcattctga agaaagacat caaaggcaat gagattgtgt tctttgtggt ccgcaaggaa   3840

atctctaaaa ttagtgagaa cgatgtgcag aatatcgtcg acaacgtggt ccggaagaaa   3900

attgagaatg ctatcgcaaa ctccctgatc acttttaaga tcgtgaagaa aaagaaagtg   3960

gccgtcatca aagagggggt caccatttgg atgagggagc ccaacattga aaaggggatc   4020

gagggaatcc ctattaagaa agtgcgcatc attaccaatt ctgtcaaaaa ccctatcgag   4080

attaaggtgc acagtccact gtccaagtct cgccacaagc ataaacagaa ggtctacggc   4140

cagaacgatg agaattatgc catggctctg tacgaactgg acgggaagcg ggagttcgaa   4200

ctgatcaaca attttaatct ggccaagctg ctgaaacaga gtcagtcata ctatccactg   4260

cataaagaga aggaaatcaa gggaaagaaa attctggtgc ccatcgagaa gagaaacaac   4320

aaggatgtca tcctgaagag gggccagcag gtggtgttct acgacaaaac cgtggagaac   4380

cccaaggata tctctgaaat cattgacttt cgcgagcgaa tctacatcat tgaagggctg   4440

accatccaga gacagaaaga taagaaaaca tccaaagtga atgagtacgg aatcattcag   4500

ctgcgccact tcaaggaagc tcgaaaaagt gaggaaatct caaaggataa cttcaaacct   4560

gacggcgagt tcaagatcaa cgagaataag ccaactagga aaatgaacca taatcagttc   4620

accgcctttg tggaggggat cgacttcaag gtcctgccta gcggaaagtt tcagaaaatt   4680

taagaattc                                                           4689
```

<210> SEQ ID NO 130
<211> LENGTH: 3621
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
accggtgcca ccatgtaccc atacgatgtt ccagattacg cttcgccgaa gaaaaagcgc 60
aaggtcgaag cgtccatgag caagaaagtc agtagacgct atgaagaaca ggcacaggag 120
atttgtcaga ggctggggag tagaccttat tccatcgggc tggacctggg agtgggatct 180
atcggagtgg cagtcgccgc ttacgaccca attaagaaac agccctccga tctggtgttc 240
gtcagctcca ggatttttat cccttctacc ggcgcagccg agcggagaca gaagagagga 300
cagaggaaca gcctgcgcca ccgagcaaat cgcctgaaat tcctgtggaa gctgctggct 360
gaacgaaacc tgatgctgtc atatagcgag caggacgtgc cagatcctgc acggctgaga 420
tttgaggacg ctgtggtccg agcaaaccca tacgagctgc ggctgaaggg cctgaatgaa 480
cagctgaccc tgagcgagct ggggtatgca ctgtaccaca tcgccaatca taggggatct 540
agttcagtgc gcacattcct ggatgaggaa aagagctccg acgataagaa actggaggaa 600
cagcaggcta tgacagaaca gctggcaaaa gagaagggaa tttccacttt catcgaagtg 660
ctgacagcct ttaacactaa tggcctgatc gggtacagga actccgagtc tgtgaagagt 720
aagggcgtgc cagtccccac tcgcgacatc atttcaaatg agattgatgt gctgctgcag 780
acccagaagc agttctatca ggaaatcctg tcagacgagt actgcgatcg gattgtcagc 840
gcaatcctgt ttgaaaacga gaagatcgtg ccagaagccg gctgctgtcc ctatttccct 900
gacgagaaga aactgcccag atgtcacttt ctgaatgagg aaaggcgcct gtgggaagcc 960
attaacaatg ctaggatcaa gatgcccatg caggagggcg ctgcaaaacg ctaccagagt 1020
gcttcattca gcgacgagca gagacacatt ctgtttcata tcgcaaggag cgggactgat 1080
atcaccccta aactggtgca gaaggagttc ccagccctga aacctccat cattgtgctg 1140
cagggaaaag agaaggctat tcagaagatc gcaggcttcc gatttcgacg gctggaggaa 1200
aaatcttttt ggaagagact gagtgaggaa cagaaggacg atttctttag cgcctggaca 1260
aacactcctg acgataaaag actgtccaag tacctgatga aacacctgct gctgacagaa 1320
aatgaggtgg tcgacgccct gaaaaccgtg agcctgattg gagattatgg cccaatcggc 1380
aagaccgcaa cacagctgct gatgaaacat ctggaggatg gcctgactta caccgaagcc 1440
ctggagcggg gaatggaaac cggcgagttc caggaactgt cagtgtggga gcagcagagc 1500
ctgctgccct actatgggca gatcctgaca ggatctactc aggccctgat ggggaagtat 1560
tggcactctg cttttaaaga aaagagagac agtgagggat tctttaagcc taacacaaat 1620
agcgatgagg aaaaatacgg caggattgcc aacccagtgg tccatcagac tctgaacgaa 1680
ctgcgcaagc tgatgaatga gctgattacc atcctgggag ctaaacctca ggagatcaca 1740
gtggaactgg cacgagagct gaaggtcgga gctgagaaaa gagaggacat cattaagcag 1800
cagaccaaac aggaaaagga ggctgtgctg gcatatagca agtactgcga gcccaacaat 1860
ctggacaaaa ggtatattga aaggttccgc ctgctggagg atcaggcctt tgtgtgccct 1920
tactgtctgg agcacattag cgtcgcagat atcgcagctg gaagggcaga cgtggatcat 1980
atcttcccac gcgacgatac agctgacaac tcctacggga ataaggtggt cgcacaccga 2040
cagtgtaacg atatcaaggg aaagcggacc ccctatgcag ccttcagtaa tacatcagcc 2100
tggggcccca tcatgcatta cctggacgaa acccctggga tgtggcgcaa aagaaggaag 2160
tttgagacaa acgaggaaga gtatgctaag tacctgcagt caaaaggctt cgtgagcagg 2220
tttgaaagcg ataactccta tatcgcaaaa gctgcaaagg agtacctgcg ctgcctgttc 2280

```
aatccaaaca atgtgactgc cgtcgggtcc ctgaagggaa tggagacatc tatcctgcgg   2340

aaggcctgga atctgcaggg aattgacgat ctgctgggca gccggcactg gagtaaggac   2400

gccgatacca gccccacaat gcgcaaaaac cgggacgaca atcggcacca tggcctggac   2460

gccatcgtgg ctctgtattg ttccagatct ctggtccaga tgattaacac catgtccgag   2520

cagggcaagc gagcagtgga aatcgaggct atgattccta tcccagggta cgcatccgaa   2580

ccaaatctgt ctttcgaagc ccagcgggag ctgtttagaa agaaaatcct ggagttcatg   2640

gacctgcacg cctttgtgag tatgaaaacc gacaacgatg caaatggcgc cctgctgaaa   2700

gatactgtgt attcaattct gggagcagac acccagggag aggatctggt gttcgtggtc   2760

aagaaaaaga ttaaggacat cggcgtgaaa atcggggatt atgaagaggt cgcatctgcc   2820

attcgaggcc ggatcaccga caaacagcca aagtggtatc ccatggaaat gaaagataag   2880

atcgagcagc tgcagtctaa gaacgaagcc gctctgcaga aatacaagga gagtctggtg   2940

caggcagccg ctgtcctgga agagagtaat aggaagctga ttgagtcagg caaaaagccc   3000

atccagctga gtgaaaaaac aatttcaaaa aaggccctgg agctggtggg cgggtactat   3060

tacctgatta gcaacaacaa gcgcacaaag actttcgtgg tcaaggaacc ttcaaacgag   3120

gtgaaagggt tcgcatttga cactggaagc aatctgtgcc tggactttta tcacgatgcc   3180

cagggaaagc tgtgtggcga gatcattaga aaaatccagg ctatgaaccc ttcctataag   3240

ccagcataca tgaaacaggg gtattctctg tacgtgagac tgtaccaggg cgacgtgtgc   3300

gagctgaggg caagcgatct gactgaagca gagtccaacc tggccaagac cacacatgtc   3360

cgcctgccca atgctaaacc tgggcgaacc ttcgtgatca ttatcacctt tacagagatg   3420

gggtctggat atcagatcta cttcagcaac ctggccaagt ccaaaaaggg acaggacact   3480

agttttaccc tgactaccat caagaattat gatgtgcgga aagtccagct gtctagtgcc   3540

gggctggtga gatacgtcag ccctctgctg gtggacaaaa tcgagaagga tgaagtcgct   3600

ctgtgtggag agtaagaatt c                                               3621
```

<210> SEQ ID NO 131
<211> LENGTH: 3588
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
accggtgcca ccatgtaccc atacgatgtt ccagattacg cttcgccgaa gaaaaagcgc     60

aaggtcgaag cgtccatggc aagacctgca tttcgggcac ctcggagaga acacgtcaac    120

ggctggaccc ctgacccaca tcggattagc aaaccctttt tcatcctggt gagctggcac    180

ctgctgtccc gggtggtcat tgacagctcc tctggatgct tcccaggcac cagccgggac    240

cacaccgaca agtttgccga gtgggaatgt gctgtgcagc cctacaggct gagtttcgac    300

ctggggacca actcaatcgg atggggcctg ctgaatctgg atcgccaggg aaaaccaagg    360

gagatccgag cactggggtc ccgcatcttc agcgacggac gggatcccca ggacaaggct    420

tctctggctg tggcacggag actggccaga cagatgaggc gccgacggga cagatatctg    480

actagaagga ccaggctgat gggagctctg gtgcgcttcg gcctgatgcc agcagaccct    540

gcagctagga agcgcctgga agtggccgtc gatccatacc tggcacgaga gcgggccaca    600

agagaaaggc tggagccctt cgaaatcggg agggccctgt ttcacctgaa ccagcgccga    660
```

```
ggatataaac ccgtgcgcac cgccacaaag cctgatgagg aagccggcaa ggtgaaagag     720
gctgtcgaaa ggctggaggc agcaatcgct gcagccggag cacctactct gggagcttgg     780
ttcgcatggc gaaaaacacg aggagaaact ctgcgagcac gactggctgg gaagggaaaa     840
gaggctgcat acccattcta tcccgcacgg agaatgctgg aggccgaatt tgacactctg     900
tgggcagagc aggccaggca ccatccagat ctgctgaccg ccgaagctcg cgagatcctg     960
cggcacagaa tttttcatca gcggcccctg aagccacctc cagtgggaag atgcactctg    1020
taccctgacg atgggagagc tcctagggca ctgccaagcg ctcagaggct gcgcctgttc    1080
caggagctgg ccagcctgag agtgatccac ctggacctgt ccgaacgccc tctgacccca    1140
gctgagcgag atcggattgt ggcatttgtc cagggcagac cccctaaagc cggaaggaag    1200
cctggcaaag tgcagaagag cgtcccattc gaaaagctga gggggctgct ggagctgcca    1260
ccaggcactg ggttttctct ggagagtgac aaacggcctg aactgctggg cgacgagaca    1320
ggcgccagaa tcgcaccagc attcggacct ggatggacag ctctgcctct ggaggaacag    1380
gacgccctgg tggaactgct gctgacagag gcagaaccag agagggcaat tgcagctctg    1440
actgcacgat gggctctgga cgaggcaact gcagcaaagc tggctggagc aaccctgcca    1500
gattttcacg gacgatatgg caggcgcgca gtggctgaac tgctgcctgt cctggaacgc    1560
gagacacgag gcgacccaga tgggagagtg aggcccatcc ggctggacga ggcagtgaaa    1620
ctgctgagag gcgggaagga tcactcagac ttcagccggg aaggagctct gctggacgca    1680
ctgccctact atggagccgt gctggagaga catgtcgctt ttgggacagg aaaccccgca    1740
gatcctgagg aaaagcgggt gggaagagtc gccaatccca ctgtgcacat cgctctgaac    1800
cagctgcggc atctggtgaa tgcaattctg gccaggcacg gccgccctga ggaaatcgtg    1860
attgagctgg cacgggacct gaaaaggtct gccgaagatc gacggagaga ggacaagcgg    1920
caggccgata accagaaaag aaatgaggaa cgcaagcgac tgatcctgag tctgggagag    1980
cgcccaaccc cacgaaacct gctgaagctg cggctgtggg aggaacaggg cccagtggaa    2040
aataggcgct gcccctactc tggggagaca attagtatga gaatgctgct gagcgagcag    2100
gtggacatcg atcacattct gccattcagc gtgtccctgg acgattccgc tgcaaacaag    2160
gtggtctgtc tgcgggaggc caacagaatc aagcggaata gatctccctg ggaggccttc    2220
ggccatgaca gtgagagatg ggcagggatt ctggcacgag cagaagctct gcccaagaac    2280
aaaaggtggc gctttgctcc tgacgcactg gagaaactgg aaggagaggg aggcctgcga    2340
gcacgacacc tgaatgatac aaggcatctg agtcgcctgg ccgtggagta tctgcggtgc    2400
gtctgtccta aggtgcgggt gagcccaggc cgactgactg cactgctgcg acggagatgg    2460
ggcatcgacg ccattctggc agaagcagat ggacctccac cagaagtgcc cgcagagaca    2520
ctggaccctt ccccagctga gaagaaccga gcagaccacc ggcaccatgc cctggatgct    2580
gtggtcatcg gctgtattga tcgctcaatg gtgcagcgag tccagctggc cgctgcaagc    2640
gcagaaagag aggccgctgc aagggaggac aatatcaggc gcgtgctgga gggattcaaa    2700
gaggaacctt gggatggctt tagagctgaa ctggagcgac gggcacggac catcgtggtg    2760
agccacagac cagaacatgg gattggggga gccctgcata aggagacagc ttacgggcct    2820
gtggaccctc cagaggaagg attcaacctg gtggtcagga aaccaatcga cggcctgtca    2880
aaggatgaga ttaatagcgt gcgggacccc cggctgagaa gggcactgat cgatcgcctg    2940
gccattcgcc gacgggatgc taacgaccct gctaccgcac tggccaaagc agctgaggat    3000
ctggcagcac agccagcctc ccgcggcatc agaagggtgc gggtcctgaa gaaagaatct    3060
```

aaccccatta gggtggagca cggcgggaat ccaagtggac cccgctcagg aggccctttt 3120
cataagctgc tgctggcagg agaggtgcac catgtggacg tcgcactgcg agcagatggc 3180
cgccgatggg tgggacactg ggtcacactg ttcgaggcac atgggggacg gggagcagac 3240
ggagctgcag ccccacctag actgggcgat ggggaaagat ttctgatgag gctgcacaag 3300
ggagactgcc tgaaactgga gcataagggc agagtgaggg tcatgcaggt ggtcaaactg 3360
gaacctagtt caaatagcgt ggtcgtggtc gagccacacc aggtgaaaac cgacagatcc 3420
aaacatgtca agatctcttg tgatcagctg cgcgctcgag gagcacggag agtgaccgtc 3480
gatccactgg gacgggtgag agtccacgcc ccaggagcta gggtgggaat cggaggggac 3540
gccggacgaa ccgctatgga acccgcagag gatattagct aagaattc 3588

<210> SEQ ID NO 132
<211> LENGTH: 3234
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 132
accggtgcca ccatgtaccc atacgatgtt ccagattacg cttcgccgaa gaaaaagcgc 60
aaggtcgaag cgtccatggg agagaatatg attgacgaga gtctgacctt cggcattgac 120
ctggggattg ggagttgtgg gtgggcagtg ctgaggcggc caagcgcctt cggacggaag 180
ggcgtgatcg agggaatggg ctcctggtgc tttgacgtcc ccgagacatc taaagaacgg 240
actcctacca accagatccg gagatccaat agactgctga ggcgcgtgat ccgacggaga 300
aggaaccgga tggccgctat tcgccgactg ctgcacgcag caggcctgct gccatcaacc 360
gacagcgatg ccctgaagcg gcccggacat gatccttggg aactgagggc acgaggcctg 420
gacaagccac tgaaacccgt ggagttcgct gtggtcctgg gccacatcgc aaagcggaga 480
gggtttaaat ccgctgcaaa gagaaaagcc acaaacatta gctccgacga taagaaaatg 540
ctgacagccc tggaggctac tcgagaacgg ctggggagat acaggaccgt gggagaaatg 600
ttcgccaggg accctgattt tgcttctagg cgccgaaatc gcgagggcaa gtatgatagg 660
accacagctc gcgacgatct ggagcacgaa gtgcacgccc tgttcgcagc tcagcggaga 720
ctgggacagg gatttgccag tccagaactg gaggaggcct tcaccgcttc agcatttcat 780
cagaggccca tgcaggacag cgagcgcctg gtgggattct gcccttttga gcgaaccgaa 840
aagcgggcag ccaaactgac accctctttc gagcgctttc gactgctggc ccggctgctg 900
aacctgagaa tcactacccc agacggagag cggcccctga cagtggatga aattgctctg 960
gtcacccggg acctgggcaa gaccgcaaaa ctgagtatca agcgggtgag aactctgatt 1020
ggactggagg acaatcagag gttcacaact atccgccccg aggacgaaga tcgagacatt 1080
gtggctcgga caggcggggc aatgacaggg actgccaccc tgaggaaggc actgggagag 1140
gccctgtgga ctgatatgca ggagcgccct gaacagctgg acgctatcgt gcaggtcctg 1200
agcttctttg aggccaacga aacaatcact gagaagctga gggaaattgg cctgactctg 1260
gccgtgctgg acgtcctgct gaccgcactg gatgccggag tgttcgccaa gtttaaaggc 1320
gctgcacaca tcagcaccaa agccgctagg aatctgctgc cacatctgga gcagggcagg 1380
cgctacgatg aggcctgcac aatggcaggg tatgaccacg cagcctcccg cctgtctcac 1440
catggccaga tcgtggcaaa gacacagttc aacgccctgg tcactgagat cggcgaatcc 1500
attgccaatc caatcgctcg gaaggcactg atcgaggggc tgaaacagat ttgggccatg 1560
agaaaccact gggggctgcc cggaagtatc catgtggagc tggcccggga tgtcggcaac 1620
tcaattgaaa agcgacggga gattgaaaag cacatcgaga aaaatactgc cctgagggct 1680
cgcgagagaa gggaggtgca tgatctgctg gacctggaag atgtcaatgg cgacaccctg 1740
ctgcgatacc ggctgtggaa ggagcaggga ggcaaatgcc tgtatacagg gaaggccatc 1800
cacattcggc agatcgctgc aactgacaac tccgtgcagg tcgatcatat tctgccttgg 1860
agccggttcg gcgacgatag ttttaacaac aagaccctgt gtctggcctc tgctaatcag 1920
cagaagaaaa ggtcaacacc atacgagtgg ctgagcggcc agactgggga tgcatggaac 1980
gccttcgtgc agcgcatcga gacaaataag gaactgagag ggtttaagaa aaggaactat 2040
ctgctgaaga atgctaaaga ggcagaggaa aaattcagaa gcaggaacct gaatgacacc 2100
agatacgccg ctaggctgtt cgcagaggcc gtgaagctgc tgtatgcctt tggggagaga 2160
caggaaaaag gggggaaaccg ccgagtgttt actcggcctg gagcactgac cgcagcactg 2220
agacaggctt ggggagtgga gagcctgaag aaacaggatg ggaagcgcat caatgacgat 2280
cgacaccatg ccctggatgc tctgaccgtg gctgcagtcg acgaggccga aattcagagg 2340
ctgacaaaat cattccacga gtgggaacag cagggcctgg ggcggcctct gcggagagtg 2400
gagccacctt gggagagctt ccgggcagac gtcgaggcta cctaccctga agtgtttgtc 2460
gcacggccag agaggcgccg agcaagagga gaaggccatg ccgctaccat ccggcaggtg 2520
aaggagagag aatgcacacc aattgtgttt gagagaaagg ctgtctctag tctgaaagag 2580
gcagacctgg aacgaatcaa agatggcgag cgcaacgaag caattgtgga ggccatcagg 2640
agctggattg ccactggacg cccagctgat gcaccaccac gctcccccg aggcgacatc 2700 attaccaaga tcaggctggc caccaccatc aaggcagccg tgcctgtccg cggagggacc 2760
gcaggaaggg gagaaatggt gcgcgcagat gtgttcagca agccaaaccg gagagggaaa 2820
gacgagtggt atctggtgcc cgtgtatcca caccagatca tgaacaggaa ggcttggccc 2880
aaacctccaa tgcgctcaat tgtggccaat aaggatgagg acgaatggac cgaagtggga 2940
cctgaacacc agttccggtt tagcctgtac cctagatcca atatcgagat cattaggcca 3000
tctggagaag tgatcgaagg atatttcgtc ggcctgcatc gcaacactgg cgctctgacc 3060
atcagtgcac acaatgatcc caagagtatc cattcaggca ttgggaccaa gacactgctg 3120
gccatttcca aataccaggt ggacagattc ggcagaaagt ctccagtgcg caaagaggtc 3180
cgaacttggc acggggaagc ctgtatctct cccacccccc ctggataaga attc 3234

<210> SEQ ID NO 133
<211> LENGTH: 3504
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
accggtgcca ccatgtaccc atacgatgtt ccagattacg cttcgccgaa gaaaaagcgc 60
aaggtcgaag cgtccatgag agagaacggg agtgacgaaa ggcggaggaa tatggacgaa 120
aaaatggatt acaggattgg gctggacatc ggcatcgcat cagtggggtg ggccgtcctg 180
cagaacaatt cagacgatga gcctgtgagg attgtcgacc tgggagtgcg cattttcgat 240
accgcagaga tcccaaagac aggcgaaagc ctggcaggac cccggagagc agctcgaacc 300

```
acaaggcgcc gactgcggag aaggaaacac cgcctggacc gaatcaagtg gctgttcgag    360
aaccaggggc tgatcaatat tgacgatttt ctgaagagat acaacatggc cggactgcca    420
gatgtgtacc agctgcggta tgaggctctg gacagaaaac tgaccgatga ggaactggcc    480
caggtgctgc tgcacatcgc taagcatcgg ggcttcagaa gcaccaggaa agccgagaca    540
gcagccaagg aaaacggggc agtgctgaag gccacagacg agaatcagaa acgaatgcag    600
gaaaagggat acaggacagt gggcgagatg atctacctgg acgaggcctt ccggactggc    660
tgctcttgga gtgagaaagg gtacatcctg accccccgca acaaggctga aaattatcag    720
cacacaatgc tgcgggcaat gctggtggag gaagtcaagg agattttcag ctcccagcgc    780
cgactgggca acgaaaaagc cactgaggaa ctggaggaaa agtacctgga gatcatgacc    840
tcccagcgct cttttgacct ggggcctgga atgcagccag atgggaagcc ctccccttat    900
gcaatggagg gcttctctga cagagtgggg aaatgtactt ttctggggga tcagggagag    960
ctgaggggcg ctaaggggac ctacacagcc gaatatttcg tggctctgca gaaaatcaac   1020
cacacaaagc tggtcaatca ggacggcgag acaaggaatt tcactgagga agagcggaga   1080
gccctgactc tgctgctgtt tacccagaaa gaggtgaagt acgctgcagt ccgcaagaaa   1140
ctgggcctgc ctgaggacat cctgttctac aacctgaact acaagaaggc cgctactaaa   1200
gaagagcagc agaaggagaa ccagaatacc gaaaaagcca agtttatcgg gatgccatac   1260
tatcacgatt acaagaaatg cctggaagag agagtgaagt atctgaccga gaacgaagtc   1320
agggacctgt ttgatgagat cggaatgatt ctgacttgtt acaaaaatga cgattcccgc   1380
accgaacgac tggccaagct gggactggtg cccatcgaga tggaaggcct gctggcttat   1440
actcctacca aattccagca tctgtctatg aaggcaatgc ggaacatcat tccctttctg   1500
gagaaaggga tgacctacga caaggcttgc gaagaggcag gatatgactt caaagccgat   1560
agcaagggga ctaaacagaa gctgctgacc ggagagaacg tgaatcagac aatcaacgaa   1620
attactaatc ctgtggtcaa acgctcagtg agccagacag tgaaggtcat taacgccatc   1680
attcggactt acggcagtcc acaggctatc aatattgagc tggcaagaga aatgtcaaag   1740
acctttgaag agaggcgcaa aatcaagggg gacatggaga aacggcagaa gaacaatgaa   1800
gatgtgaaga aacagattca ggagctggga aaactgtctc ctacaggcca ggacatcctg   1860
aagtacagac tgtggcagga gcagcagggg atttgtatgt atagtggaaa aaccatccca   1920
ctggaagagc tgttcaagcc cggctacgac atcgatcaca ttctgcccta ttcaattaca   1980
ttcgacgata gctttaggaa caaagtgctg gtcacatccc aggagaacag acagaagggc   2040
aataggactc cttacgagta tatggggaac gacgaacagc gctggaatga gtttgaaacc   2100
agggtgaaaa ctaccatccg cgattacaag aaacagcaga agctgctgaa gaaacatttc   2160
tctgaagagg aaaggagtga gtttaaagaa cggaacctga cagacactaa gtacatcaca   2220
accgtgatct acaacatgat cagacagaat ctggagatgg ccccccctgaa ccgccctgaa   2280
aagaaaaagc aggtgcgggc tgtcaatggc gcaattaccg cctacctgcg aaaacggtgg   2340
gggctgccac agaagaatcg ggagacagac acacaccatg ctatggatgc agtggtcatc   2400
gcctgctgta ccgacggcat gatccagaaa attagtagat acacaaaggt gagagagagg   2460
tgctattcaa agggaacaga gttcgtcgat gcagagactg gcgaaatctt tagacccgag   2520
gactacagca gggccgagtg ggatgaaatt ttcggcgtgc acatcccaaa gccctgggag   2580
acatttcgcg ccgaactgga cgtccgaatg gggacgatc caaagggatt cctggacact    2640
```

```
catagcgatg tggctctgga gctggattat cccgagtaca tctacgaaaa cctgcggcct   2700

atcttcgtga gcagaatgcc aaatcacaag gtcaccggag cagcccatgc tgacacaatt   2760

cggtccccaa gacactttaa agatgagggc atcgtgctga ctaagaccgc actgaccgac   2820

ctgaaactgg acaaggatgg ggagatcgac ggatactata acccccagtc cgatctgctg   2880

ctgtacgaag cactgaaaaa gcagctgctg ctgtatggca atgatgccaa aaaggccttc   2940

gctcaggact ttcataaacc caaggccgat ggaactgagg gccctgtggt caggaaggtg   3000

aagatccaga aaaagcagac catgggagtg ttcgtcgact ctggcaacgg gattgccgag   3060

aatggcggga tggtgcgcat cgatgtgttc cgagtcaacg gcaagtacta ttttgtgccc   3120

gtctacaccg ctgacgtggt caaaaaggtg ctgcctaata gggccagtac agctcacaag   3180

ccatacggcg agtggaaagt gatggaggac aaggatttcc tgtttagtct gtattcacgc   3240

gacctgatcc atatcaagtc taaaaaggat atccctatta agatggtgaa cggaggcatg   3300

gaggggatca aggaaaccta cgcatactat attggagccg acatcagcgc tgcaaatatc   3360

cagggcattg cccacgattc caggtataaa ttccgcggac tggcattca gtctctggac   3420

gtgctggaga agtgtcagat cgatgtgctg ggacatgtca gcgtggtccg atccgaaaag   3480

cggatgggct ttagctaaga attc                                          3504
```

<210> SEQ ID NO 134
<211> LENGTH: 3243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
accggtgcca ccatgtaccc atacgatgtt ccagattacg cttcgccgaa gaaaaagcgc     60

aaggtcgaag cgtccatgaa aaggaactac attctggggc tggacatcgg gattacaagc    120

gtggggtatg ggattattga ctatgaaaca agggacgtga tcgacgcagg cgtcagactg    180

ttcaaggagg ccaacgtgga aaacaatgag ggacggagaa gcaagagggg agccaggcgc    240

ctgaaacgac ggagaaggca cagaatccag agggtgaaga aactgctgtt cgattacaac    300

ctgctgaccg accattctga gctgagtgga attaatcctt atgaagccag ggtgaaaggc    360

ctgagtcaga agctgtcaga ggaagagttt tccgcagctc tgctgcacct ggctaagcgc    420

cgaggagtgc ataacgtcaa tgaggtggaa gaggacaccg gcaacgagct gtctacaaag    480

gaacagatct cacgcaatag caaagctctg gaagagaagt atgtcgcaga gctgcagctg    540

gaacggctga agaaagatgg cgaggtgaga gggtcaatta ataggttcaa gacaagcgac    600

tacgtcaaag aagccaagca gctgctgaaa gtgcagaagg cttaccacca gctggatcag    660

agcttcatcg atacttatat cgacctgctg gagactcgga gaacctacta tgagggacca    720

ggagaaggga gccccttcgg atggaaagac atcaaggaat ggtacgagat gctgatggga    780

cattgcacct attttccaga agagctgaga agcgtcaagt acgcttataa cgcagatctg    840

tacaacgccc tgaatgacct gaacaacctg gtcatcacca gggatgaaaa cgagaaactg    900

gaatactatg agaagttcca gatcatcgaa aacgtgttta agcagaagaa aaagcctaca    960

ctgaaacaga ttgctaagga gatcctggtc aacgaagagg acatcaaggg ctaccgggtg   1020

acaagcactg gaaaaccaga gttcaccaat ctgaaagtgt atcacgatat taaggacatc   1080

acagcacgga aagaaatcat tgagaacgcc gaactgctgg atcagattgc taagatcctg   1140
```

-continued

```
actatctacc agagctccga ggacatccag gaagagctga ctaacctgaa cagcgagctg   1200
acccaggaag agatcgaaca gattagtaat ctgaaggggt acaccggaac acacaacctg   1260
tccctgaaag ctatcaatct gattctggat gagctgtggc atacaaacga caatcagatt   1320
gcaatcttta accggctgaa gctggtccca aaaaaggtgg acctgagtca gcagaaagag   1380
atcccaacca cactggtgga cgatttcatt ctgtcacccg tggtcaagcg gagcttcatc   1440
cagagcatca aagtgatcaa cgccatcatc aagaagtacg gcctgcccaa tgatatcatt   1500
atcgagctgg ctagggagaa gaacagcaag gacgcacaga agatgatcaa tgagatgcag   1560
aaacgaaacc ggcagaccaa tgaacgcatt gaagagatta tccgaactac cgggaaagag   1620
aacgcaaagt acctgattga aaaaatcaag ctgcacgata tgcaggaggg aaagtgtctg   1680
tattctctgg aggccatccc cctggaggac ctgctgaaca atccattcaa ctacgaggtc   1740
gatcatatta tccccagaag cgtgtccttc gacaattcct ttaacaacaa ggtgctggtc   1800
aagcaggaag agaactctaa aaagggcaat aggactcctt tccagtacct gtctagttca   1860
gattccaaga tctcttacga aacctttaaa aagcacattc tgaatctggc caaaggaaag   1920
ggccgcatca gcaagaccaa aaaggagtac ctgctggaag agcgggacat caacagattc   1980
tccgtccaga aggattttat taaccggaat ctggtggaca caagatacgc tactcgcggc   2040
ctgatgaatc tgctgcgatc ctatttccgg gtgaacaatc tggatgtgaa agtcaagtcc   2100
atcaacggcg ggttcacatc ttttctgagg cgcaaatgga agtttaaaaa ggagcgcaac   2160
aaagggtaca agcaccatgc cgaagatgct ctgattatcg caaatgccga cttcatcttt   2220
aaggagtgga aaaagctgga caaagccaag aaagtgatgg agaaccagat gttcgaagag   2280
aagcaggccg aatctatgcc cgaaatcgag acagaacagg agtacaagga gattttcatc   2340
actcctcacc agatcaagca tatcaaggat ttcaaggact acaagtactc tcaccgggtg   2400
gataaaaagc ccaacagaga gctgatcaat gacaccctgt atagtacaag aaaagacgat   2460
aaggggaata ccctgattgt gaacaatctg aacggactgt acgacaaaga taatgacaag   2520
ctgaaaaagc tgatcaacaa aagtcccgag aagctgctga tgtaccacca tgatcctcag   2580
acatatcaga aactgaagct gattatggag cagtacggcg acgagaagaa cccactgtat   2640
aagtactatg aagagactgg gaactacctg accaagtata gcaaaaagga taatggcccc   2700
gtgatcaaga agatcaagta ctatgggaac aagctgaatg cccatctgga catcacagac   2760
gattacccta acagtcgcaa caaggtggtc aagctgtcac tgaagccata cagattcgat   2820
gtctatctgg acaacggcgt gtataaattt gtgactgtca agaatctgga tgtcatcaaa   2880
aaggagaact actatgaagt gaatagcaag tgctacgaag aggctaaaaa gctgaaaaag   2940
attagcaacc aggcagagtt catcgcctcc ttttacaaca acgacctgat taagatcaat   3000
ggcgaactgt atagggtcat cggggtgaac aatgatctgc tgaaccgcat tgaagtgaat   3060
atgattgaca tcacttaccg agagtatctg gaaaacatga atgataagcg ccccccctcga   3120
attatcaaaa caattgcctc taagactcag agtatcaaaa agtactcaac cgacattctg   3180
ggaaacctgt atgaggtgaa gagcaaaaag caccctcaga ttatcaaaaa gggctaagaa   3240
ttc                                                                 3243
```

<210> SEQ ID NO 135
<211> LENGTH: 3243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
accggtgcca ccatgtaccc atacgatgtt ccagattacg cttcgccgaa gaaaaagcgc     60
aaggtcgaag cgtccatgaa aaggaactac attctggggc tggacatcgg gattacaagc    120
gtggggtatg ggattattga ctatgaaaca agggacgtga tcgacgcagg cgtcagactg    180
ttcaaggagg ccaacgtgga aaacaatgag ggacggagaa gcaagagggg agccaggcgc    240
ctgaaacgac ggagaaggca cagaatccag agggtgaaga aactgctgtt cgattacaac    300
ctgctgaccg accattctga gctgagtgga attaatcctt atgaagccag ggtgaaaggc    360
ctgagtcaga agctgtcaga ggaagagttt tccgcagctc tgctgcacct ggctaagcgc    420
cgaggagtgc ataacgtcaa tgaggtggaa gaggacaccg gcaacgagct gtctacaaag    480
gaacagatct cacgcaatag caaagctctg gaagagaagt atgtcgcaga gctgcagctg    540
gaacggctga agaaagatgg cgaggtgaga gggtcaatta ataggttcaa gacaagcgac    600
tacgtcaaag aagccaagca gctgctgaaa gtgcagaagg cttaccacca gctggatcag    660
agcttcatcg atacttatat cgacctgctg gagactcgga gaacctacta tgagggacca    720
ggagaaggga gccccttcgg atggaaagac atcaaggaat ggtacgagat gctgatggga    780
cattgcacct attttccaga agagctgaga agcgtcaagt acgcttataa cgcagatctg    840
tacaacgccc tgaatgacct gaacaacctg gtcatcacca gggatgaaaa cgagaaactg    900
gaatactatg agaagttcca gatcatcgaa aacgtgttta agcagaagaa aaagcctaca    960
ctgaaacaga ttgctaagga gatcctggtc aacgaagagg acatcaaggg ctaccgggtg   1020
acaagcactg gaaaaccaga gttcaccaat ctgaaagtgt atcacgatat taaggacatc   1080
acagcacgga aagaaatcat tgagaacgcc gaactgctgg atcagattgc taagatcctg   1140
actatctacc agagctccga ggacatccag gaagagctga ctaacctgaa cagcgagctg   1200
acccaggaag agatcgaaca gattagtaat ctgaaggggt acaccggaac acacaacctg   1260
tccctgaaag ctatcaatct gattctggat gagctgtggc atacaaacga caatcagatt   1320
gcaatcttta accggctgaa gctggtccca aaaaaggtgg acctgagtca gcagaaagag   1380
atcccaacca cactggtgga cgatttcatt ctgtcacccg tggtcaagcg gagcttcatc   1440
cagagcatca aagtgatcaa cgccatcatc aagaagtacg gcctgcccaa tgatatcatt   1500
atcgagctgg ctagggagaa gaacagcaag gacgcacaga agatgatcaa tgagatgcag   1560
aaacgaaacc ggcagaccaa tgaacgcatt gaagagatta tccgaactac cgggaaagag   1620
aacgcaaagt acctgattga aaaaatcaag ctgcacgata tgcaggaggg aaagtgtctg   1680
tattctctgg aggccatccc cctggaggac ctgctgaaca atccattcaa ctacgaggtc   1740
gatcatatta tccccagaag cgtgtccttc gacaattcct ttaacaacaa ggtgctggtc   1800
aagcaggaag agaactctaa aaagggcaat aggactcctt tccagtacct gtctagttca   1860
gattccaaga tctcttacga aacctttaaa aagcacattc tgaatctggc caaaggaaag   1920
ggccgcatca gcaagaccaa aaaggagtac ctgctggaag agcgggacat caacagattc   1980
tccgtccaga aggattttat taaccggaat ctggtggaca caagatacgc tactcgcggc   2040
ctgatgaatc tgctgcgatc ctatttccgg gtgaacaatc tggatgtgaa agtcaagtcc   2100
atcaacggcg ggttcacatc ttttctgagg cgcaaatgga agtttaaaaa ggagcgcaac   2160
aaagggtaca agcaccatgc cgaagatgct ctgattatcg caaatgccga cttcatcttt   2220
aaggagtgga aaaagctgga caaagccaag aaagtgatgg agaaccagat gttcgaagag   2280
```

aagcaggccg aatctatgcc cgaaatcgag acagaacagg agtacaagga gattttcatc 2340
actcctcacc agatcaagca tatcaaggat ttcaaggact acaagtactc tcaccgggtg 2400
gataaaaagc ccaacagaga gctgatcaat gacaccctgt atagtacaag aaaagacgat 2460
aaggggaata ccctgattgt gaacaatctg aacggactgt acgacaaaga taatgacaag 2520
ctgaaaaagc tgatcaacaa aagtcccgag aagctgctga tgtaccacca tgatcctcag 2580
acatatcaga aactgaagct gattatggag cagtacggcg acgagaagaa cccactgtat 2640
aagtactatg aagagactgg gaactacctg accaagtata gcaaaaagga taatggcccc 2700
gtgatcaaga agatcaagta ctatgggaac aagctgaatg cccatctgga catcacagac 2760
gattacccta acagtcgcaa caaggtggtc aagctgtcac tgaagccata cagattcgat 2820
gtctatctgg acaacggcgt gtataaattt gtgactgtca agaatctgga tgtcatcaaa 2880
aaggagaact actatgaagt gaatagcaag tgctacgaag aggctaaaaa gctgaaaaag 2940
attagcaacc aggcagagtt catcgcctcc ttttacaaca acgacctgat taagatcaat 3000
ggcgaactgt atagggtcat cggggtgaac aatgatctgc tgaaccgcat tgaagtgaat 3060
atgattgaca tcacttaccg agagtatctg gaaaacatga atgataagcg ccccccctcga 3120 attatcaaaa caattgcctc taagactcag agtatcaaaa agtactcaac cgacattctg 3180
ggaaacctgt atgaggtgaa gagcaaaaag caccctcaga ttatcaaaaa gggctaagaa 3240
ttc 3243

<210> SEQ ID NO 136
<211> LENGTH: 3891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
accggtgcca ccatgtaccc atacgatgtt ccagattacg cttcgccgaa gaaaaagcgc 60
aaggtcgaag cgtccatgaa caatagcatc aaatctaaac ctgaagtgac catcgggctg 120
gacctgggag tgggaagcgt ggggtgggca atcgtggata acgaaacaaa catcattcac 180
catctgggct ccaggctgtt ttctcaggcc aagactgctg aggatcggag atctttccgc 240
ggggtgaggc gcctgatccg acggagaaaa tacaagctga aacgattcgt caatctgatt 300
tggaagtaca acagctattt cggcttcaag aacaaagagg acatcctgaa caattatcag 360
gagcagcaga agctgcacaa taccgtgctg aacctgaaat cagaggcact gaatgccaag 420
atcgatccta aagcactgag ctggattctg cacgactacc tgaagaacag aggccatttt 480
tatgaggaca atagggattt caacgtgtac ccaacaaagg agctggccaa gtacttcgat 540
aagtacgggt actacaaggg aatcattgac agcaaggagg acaatgataa caaactggag 600
gaagagctga caaagtacaa attctccaat aagcactggc tggaagaggt gaagaaagtc 660
ctgtctaacc agactggcct gccagaaaag tttaaagaag agtatgagtc actgttcagc 720
tacgtgagaa attattcaga gggcccaggg agcatcaact ctgtcagtcc ctacgggatc 780
taccatctgg acgaaaaaga gggaaaggtg gtccagaagt acaacaacat ctgggataag 840
acaatcggaa agtgcaacat cttccctgac gagtatagag ctcccaagaa cagtcctatc 900
gcaatgattt tcaatgaaat caacgagctg tccacaatca ggtcatacag catctacctg 960
actggctggt tcattaatca ggagttcaag aaagcctacc tgaacaagct gctggatctg 1020
ctgatcaaaa ccaacggaga gaagccaatt gacgcaaggc agttcaagaa actgcgcgaa 1080
gagacaatcg ccgaaagcat tggcaaagag acactgaagg atgtggagaa tgaagagaaa 1140
ctggaaaagg aggaccacaa gtggaaactg aagggactga agctgaatac caacggcaaa 1200
atccagtaca acgatctgag ctccctggct aagtttgtgc acaaactgaa gcagcatctg 1260
aaactggatt tcctgctgga ggaccagtat gcaacactgg acaagatcaa tttcctgcag 1320
tccctgtttg tgtacctggg caagcacctg agatattcca atagggtcga ttctgccaac 1380
ctgaaggaat tttccgactc taacaaactg ttcgagcgca tcctgcagaa acagaaggat 1440
gggctgttca agctgtttga acagactgac aaagacgatg agaagatcct ggcccagaca 1500
catagtctgt caactaaggc catgctgctg gctattaccc ggatgacaaa tctggacaac 1560
gatgaggaca accagaaaaa caatgacaag ggctggaatt ttgaggccat caaaaacttc 1620
gatcagaagt ttatcgacat caccaagaaa aacaacaacc tgagcctgaa acagaataag 1680
cgctacctgg acgatcgatt catcaacgat gctattctgt cccctggggt gaagcgaatc 1740
ctgcgggagg caaccaaggt ctttaatgcc attctgaaac agttctctga agagtacgac 1800
gtgacaaagg tggtcatcga actggctcgc gagctgagcg aagagaagga actggagaac 1860
acaaagaact acaagaaact gatcaagaaa aacggcgaca agattagtga gggcctgaaa 1920
gcactgggga tctcagaaga tgagatcaaa gacattctga agagtcccac taaatcatac 1980
aagtttctgc tgtggctgca gcaggaccac atcgatcctt atagcctgaa ggagatcgcc 2040
ttcgacgata tttttaccaa aacagaaaag ttcgagatcg accatatcat tccctacagc 2100
atttccttcg acgattctag ttcaaacaag ctgctggtgc tggctgaaag taatcaggca 2160
aagtcaaacc agactcctta tgagttcatc agctccggaa acgcaggcat taagtgggaa 2220
gattacgagg cctattgccg caagttcaag gatggggact ctagtctgct ggacagcacc 2280
cagcggtcca agaaattcgc caaaatgatg aaaaccgata cctcaagcaa gtacgacatc 2340
ggatttctgg ctcgaaatct gaacgatact cggtacgcaa ccattgtgtt ccgggacgcc 2400
ctggaggact atgctaataa ccacctggtc gaggacaaac ccatgtttaa ggtggtctgt 2460
atcaatgggt ccgtgacctc tttcctgcgg aagaactttg acgattcctc ttacgccaag 2520
aaagatagag acaagaatat ccaccatgct gtggatgcaa gtatcatctc aattttcagc 2580
aacgagacaa agactctgtt caaccagctg actcagtttg ctgactataa actgttcaag 2640
aacaccgatg gcagctggaa gaaaatcgac cctaagacag ggtggtcac tgaagtgacc 2700 gacgagaatt ggaagcagat tagggtgcgc aaccaggtga gcgaaatcgc caaagtcatt 2760
gagaagtaca tccaggatag caacatcgaa agaaaggcta ggtattcccg caaaatcgag 2820
aataagacta acatttccct gtttaatgac accgtgtact ctgccaagaa agtcggctat 2880
gaggatcaga tcaaaagaaa gaacctgaaa accctggaca ttcacgaatc tgctaaagag 2940
aataagaaca gtaaagtgaa gcggcagttt gtctacagaa agctggtgaa tgtcagcctg 3000
ctgaataacg ataagctggc agacctgttc gccgaaaaag aggatatcct gatgtatagg 3060
gccaatccat gggtcatcaa cctggctgag cagattttca atgaatacac tgagaacaag 3120
aaaatcaagt cccagaacgt gtttgaaaaa tatatgctgg acctgaccaa agagttcccc 3180
gagaagttca gcgagtttct ggtgaagtcc atgctgagaa acaagaccgc catcatctac 3240
gacgataaga aaaacattgt ccatcgaatc aaacggctga agatgctgag ttcagaactg 3300
aaagagaata agctgtctaa cgtgatcatt aggtctaaga atcagagtgg gaccaaactg 3360
tcataccagg atacaatcaa cagcctggcc ctgatgatta tgcgcagcat cgaccctact 3420
gctaagaaac agtatattcg agtgccactg aataccctga acctgcacct gggagatcat 3480
gactttgatc tgcacaatat ggatgcttac ctgaagaaac caaaattcgt gaagtatctg 3540
aaagcaaacg aaatcggcga cgagtacaag ccctggaggg tcctgacatc tggcactctg 3600
ctgatccata agaaggataa gaaactgatg tacatcagct ccttccagaa tctgaacgac 3660
gtgatcgaaa ttaagaatct gatcgaaacc gagtataaag agaacgacga ttctgatagt 3720
aagaaaaaga aaaaggcaaa ccgctttctg atgaccctga gcacaatcct gaatgactac 3780
attctgctgg acgccaagga taacttcgac atcctggggc tgtctaaaaa tcggatcgat 3840
gagattctga acagtaagct gggactggac aagattgtga aataagaatt c 3891

<210> SEQ ID NO 137
<211> LENGTH: 3093
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137
accggtgcca ccatgtaccc atacgatgtt ccagattacg cttcgccgaa gaaaaagcgc 60
aaggtcgaag cgtccatgag gattctgggg tttgacattg gcattaacag catcgggtgg 120
gcttttgtgg agaacgacga actgaaggac tgcggagtgc ggatcttcac aaaggccgag 180
aacccaaaaa ataaggaaag cctggcactg ccccggagaa atgcacgcag ctccaggcgc 240
cgactgaaac ggagaaaggc ccggctgatc gctattaaga gaatcctggc caaagagctg 300
aagctgaact acaaggacta tgtcgcagct gatggagagc tgccaaaggc ctacgaagga 360
tccctggcat ctgtgtacga gctgcggtat aaggccctga cacagaacct ggaaactaaa 420
gatctggcca gagtgatcct gcacattgct aagcataggg ggtacatgaa caagaacgag 480
aagaaatcaa acgacgctaa gaaaggaaag atcctgagcg ctctgaaaaa caatgcactg 540
aagctggaga actaccagag cgtgggcgaa tacttctaca aggagttctt tcagaaatac 600
aagaaaaaca caaagaactt catcaagatc cgcaacacta aggataatta caacaattgc 660
gtgctgtcta gtgacctgga aaaagagctg aagctgatcc tggaaaaaca gaaggagttc 720
ggctacaact actctgaaga tttcatcaac gagattctga aggtcgcctt ctttcagcgg 780
cccctgaagg acttcagtca cctggtgggg gcctgcactt tctttgagga agagaaaagg 840
gcctgtaaga acagctactc tgcctgggag tttgtggctc tgaccaagat cattaacgag 900
atcaagagcc tggagaagat cagcggcgaa attgtgccaa cccagacaat caacgaggtc 960
ctgaatctga tcctggacaa ggggtctatc acctacaaga aattcagaag ttgtatcaat 1020
ctgcatgaga gtatcagctt caagagcctg aagtatgata aagaaaacgc cgagaatgct 1080
aaactgatcg acttccgcaa gctggtggag tttaagaaag ccctgggagt ccacagcctg 1140
tcccggcagg aactggatca gatctccact catatcaccc tgattaagga caacgtgaag 1200
ctgaaaaccg tcctggagaa atacaacctg agtaatgaac agatcaacaa tctgctggaa 1260
attgagttca acgattatat caacctgagc ttcaaggccc tgggaatgat tctgccactg 1320
atgcgcgagg gcaaacgata cgacgaggcc tgcgagatcg ccaatctgaa acctaagacc 1380
gtggacgaga agaaagattt cctgccagca ttttgtgatt ccattttcgc ccacgagctg 1440
tctaaccccg tggtcaatag ggctatcagc gaataccgca aggtgctgaa cgcactgctg 1500

```
aagaaatatg gaaaggtcca caaaattcat ctggagctgg ctcgcgacgt gggcctgtcc   1560

aagaaagcac gagagaagat cgaaaaagag cagaaggaaa accaggccgt gaatgcatgg   1620

gccctgaagg aatgcgagaa tattggcctg aaggccagcg caaagaacat cctgaaactg   1680

aagctgtgga aagaacagaa ggagatctgt atctactccg gaaataagat ctctattgag   1740

cacctgaaag atgaaaaggc cctggaggtg gaccatatct acccctattc taggagtttc   1800

gacgattctt ttatcaacaa agtgctggtg ttcaccaagg aaaatcagga gaaactgaac   1860

aagacacctt tcgaggcctt tggcaagaat attgaaaaat ggagcaagat ccagaccctg   1920

gctcagaacc tgccatacaa gaaaaagaat aagattctgg acgagaactt caaagataag   1980

cagcaggagg actttatctc tcgaaatctg aacgacaccc ggtatatcgc tacactgatt   2040

gcaaaataca caaaggagta tctgaacttc ctgctgctga gcgaaaatga gaacgccaat   2100

ctgaagagtg gcgaaaaagg gtcaaagatc cacgtgcaga ctattagcgg gatgctgacc   2160

tccgtcctga ggcacacatg gggtttgac aaaaaggatc gcaacaatca tctgcaccat   2220

gcactggatg ccatcattgt ggcctacagt acaaattcaa tcattaaggc tttcagcgat   2280

ttccggaaaa accaggagct gctgaaggcc agattctacg ctaaagaact gacttccgat   2340

aactataaac atcaggtcaa gttctttgag cctttcaaga gttttagaga aaaaatcctg   2400

tcaaagatcg acgagatttt cgtgtccaaa ccacctcgaa agcgagctag gcgcgcactg   2460

cacaaggata cctttcattc tgagaacaag atcattgaca agtgcagcta caactccaag   2520

gaaggcctgc agattgccct gagctgtgga agagtgagga aaatcggcac taagtatgtc   2580

gagaatgata ccatcgtgag ggtcgacatt ttcaaaaagc agaacaagtt ttacgctatc   2640

ccaatctacg caatggattt tgccctgggg atcctgccca ataagatcgt gattactgga   2700

aaagataaga acaataaccc caaacagtgg cagaccattg acgaatcata cgagttctgc   2760

tttagcctgt ataagaatga cctgatcctg ctgcagaaaa agaacatgca ggaacctgag   2820

ttcgcctact ataacgattt ttcaatcagc acatcaagca tttgtgtgga gaaacacgac   2880

aacaagttcg aaaatctgac tagcaaccag aagctgctgt tttccaatgc aaaagagggc   2940

tctgtgaagg tcgaaagtct ggggatccag aacctgaaag tgttcgagaa gtacatcatt   3000

acccccctgg gagataaaat taaggctgac tttcagcctc gagaaaacat cagcctgaaa   3060

accagtaaaa agtatggcct gaggtaagaa ttc                                3093
```

<210> SEQ ID NO 138
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 138

```
atg gac aag aag tac agc atc ggc ctg gac atc ggc acc aac tct gtg       48
Met Asp Lys Lys Tyr Ser Ile Gly Leu Asp Ile Gly Thr Asn Ser Val
1               5                   10                  15

ggc tgg gcc gtg atc acc gac gag tac aag gtg ccc agc aag aaa ttc       96
Gly Trp Ala Val Ile Thr Asp Glu Tyr Lys Val Pro Ser Lys Lys Phe
            20                  25                  30

aag gtg ctg ggc aac acc gac cgg cac agc atc aag aag aac ctg atc      144
Lys Val Leu Gly Asn Thr Asp Arg His Ser Ile Lys Lys Asn Leu Ile
        35                  40                  45

gga gcc ctg ctg ttc gac agc ggc gaa aca gcc gag gcc acc cgg ctg      192
Gly Ala Leu Leu Phe Asp Ser Gly Glu Thr Ala Glu Ala Thr Arg Leu
```

-continued

```
    50                  55                  60

aag aga acc gcc aga aga aga tac acc aga cgg aag aac cgg atc tgc      240
Lys Arg Thr Ala Arg Arg Arg Tyr Thr Arg Arg Lys Asn Arg Ile Cys
65                  70                  75                  80

tat ctg caa gag atc ttc agc aac gag atg gcc aag gtg gac gac agc      288
Tyr Leu Gln Glu Ile Phe Ser Asn Glu Met Ala Lys Val Asp Asp Ser
                85                  90                  95

ttc ttc cac aga ctg gaa gag tcc ttc ctg gtg gaa gag gat aag aag      336
Phe Phe His Arg Leu Glu Glu Ser Phe Leu Val Glu Glu Asp Lys Lys
            100                 105                 110

cac gag cgg cac ccc atc ttc ggc aac atc gtg gac gag gtg gcc tac      384
His Glu Arg His Pro Ile Phe Gly Asn Ile Val Asp Glu Val Ala Tyr
        115                 120                 125

cac gag aag tac ccc acc atc tac cac ctg aga aag aaa ctg gtg gac      432
His Glu Lys Tyr Pro Thr Ile Tyr His Leu Arg Lys Lys Leu Val Asp
    130                 135                 140

agc acc gac aag gcc gac ctg cgg ctg atc tat ctg gcc ctg gcc cac      480
Ser Thr Asp Lys Ala Asp Leu Arg Leu Ile Tyr Leu Ala Leu Ala His
145                 150                 155                 160

atg atc aag ttc cgg ggc cac ttc ctg atc gag ggc gac ctg aac ccc      528
Met Ile Lys Phe Arg Gly His Phe Leu Ile Glu Gly Asp Leu Asn Pro
                165                 170                 175

gac aac agc gac gtg gac aag ctg ttc atc cag ctg gtg cag acc tac      576
Asp Asn Ser Asp Val Asp Lys Leu Phe Ile Gln Leu Val Gln Thr Tyr
            180                 185                 190

aac cag ctg ttc gag gaa aac ccc atc aac gcc agc ggc gtg gac gcc      624
Asn Gln Leu Phe Glu Glu Asn Pro Ile Asn Ala Ser Gly Val Asp Ala
        195                 200                 205

aag gcc atc ctg tct gcc aga ctg agc aag agc aga cgg ctg gaa aat      672
Lys Ala Ile Leu Ser Ala Arg Leu Ser Lys Ser Arg Arg Leu Glu Asn
    210                 215                 220

ctg atc gcc cag ctg ccc ggc gag aag aag aat ggc ctg ttc ggc aac      720
Leu Ile Ala Gln Leu Pro Gly Glu Lys Lys Asn Gly Leu Phe Gly Asn
225                 230                 235                 240

ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
                245                 250                 255

gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
            260                 265                 270

gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
        275                 280                 285

ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
    290                 295                 300

atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305                 310                 315                 320

atg atc aag aga tac gac gag cac cac cag gac ctg acc ctg ctg aaa     1008
Met Ile Lys Arg Tyr Asp Glu His His Gln Asp Leu Thr Leu Leu Lys
                325                 330                 335

gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350

gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
        355                 360                 365

cag gaa gag ttc tac aag ttc atc aag ccc atc ctg gaa aag atg gac     1152
```

```
Gln Glu Glu Phe Tyr Lys Phe Ile Lys Pro Ile Leu Glu Lys Met Asp
    370                 375                 380

ggc acc gag gaa ctg ctc gtg aag ctg aac aga gag gac ctg ctg cgg      1200
Gly Thr Glu Glu Leu Leu Val Lys Leu Asn Arg Glu Asp Leu Leu Arg
385                 390                 395                 400

aag cag cgg acc ttc gac aac ggc agc atc ccc cac cag atc cac ctg      1248
Lys Gln Arg Thr Phe Asp Asn Gly Ser Ile Pro His Gln Ile His Leu
                405                 410                 415

gga gag ctg cac gcc att ctg cgg cgg cag gaa gat ttt tac cca ttc      1296
Gly Glu Leu His Ala Ile Leu Arg Arg Gln Glu Asp Phe Tyr Pro Phe
            420                 425                 430

ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
        435                 440                 445

ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
    450                 455                 460

atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465                 470                 475                 480

gtg gtg gac aag ggc gct tcc gcc cag agc ttc atc gag cgg atg acc      1488
Val Val Asp Lys Gly Ala Ser Ala Gln Ser Phe Ile Glu Arg Met Thr
                485                 490                 495

aac ttc gat aag aac ctg ccc aac gag aag gtg ctg ccc aag cac agc      1536
Asn Phe Asp Lys Asn Leu Pro Asn Glu Lys Val Leu Pro Lys His Ser
            500                 505                 510

ctg ctg tac gag tac ttc acc gtg tat aac gag ctg acc aaa gtg aaa      1584
Leu Leu Tyr Glu Tyr Phe Thr Val Tyr Asn Glu Leu Thr Lys Val Lys
        515                 520                 525

tac gtg acc gag gga atg aga aag ccc gcc ttc ctg agc ggc gag cag      1632
Tyr Val Thr Glu Gly Met Arg Lys Pro Ala Phe Leu Ser Gly Glu Gln
    530                 535                 540

aaa aag gcc atc gtg gac ctg ctg ttc aag acc aac cgg aaa gtg acc      1680
Lys Lys Ala Ile Val Asp Leu Leu Phe Lys Thr Asn Arg Lys Val Thr
545                 550                 555                 560

gtg aag cag ctg aaa gag gac tac ttc aag aaa atc gag tgc ttc gac      1728
Val Lys Gln Leu Lys Glu Asp Tyr Phe Lys Lys Ile Glu Cys Phe Asp
                565                 570                 575

tcc gtg gaa atc tcc ggc gtg gaa gat cgg ttc aac gcc tcc ctg ggc      1776
Ser Val Glu Ile Ser Gly Val Glu Asp Arg Phe Asn Ala Ser Leu Gly
            580                 585                 590

aca tac cac gat ctg ctg aaa att atc aag gac aag gac ttc ctg gac      1824
Thr Tyr His Asp Leu Leu Lys Ile Ile Lys Asp Lys Asp Phe Leu Asp
        595                 600                 605

aat gag gaa aac gag gac att ctg gaa gat atc gtg ctg acc ctg aca      1872
Asn Glu Glu Asn Glu Asp Ile Leu Glu Asp Ile Val Leu Thr Leu Thr
    610                 615                 620

ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625                 630                 635                 640

cac ctg ttc gac gac aaa gtg atg aag cag ctg aag cgg cgg aga tac      1968
His Leu Phe Asp Asp Lys Val Met Lys Gln Leu Lys Arg Arg Arg Tyr
                645                 650                 655

acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
            660                 665                 670

aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
        675                 680                 685
```

```
gcc aac aga aac ttc atg cag ctg atc cac gac gac agc ctg acc ttt      2112
Ala Asn Arg Asn Phe Met Gln Leu Ile His Asp Asp Ser Leu Thr Phe
    690                 695                 700

aaa gag gac atc cag aaa gcc cag gtg tcc ggc cag ggc gat agc ctg      2160
Lys Glu Asp Ile Gln Lys Ala Gln Val Ser Gly Gln Gly Asp Ser Leu
705                 710                 715                 720

cac gag cac att gcc aat ctg gcc ggc agc ccc gcc att aag aag ggc      2208
His Glu His Ile Ala Asn Leu Ala Gly Ser Pro Ala Ile Lys Lys Gly
                725                 730                 735

atc ctg cag aca gtg aag gtg gtg gac gag ctc gtg aaa gtg atg ggc      2256
Ile Leu Gln Thr Val Lys Val Val Asp Glu Leu Val Lys Val Met Gly
            740                 745                 750

cgg cac aag ccc gag aac atc gtg atc gcc atg gcc aga gag aac cag      2304
Arg His Lys Pro Glu Asn Ile Val Ile Ala Met Ala Arg Glu Asn Gln
        755                 760                 765

acc acc cag aag gga cag aag aac agc cgc gag aga atg aag cgg atc      2352
Thr Thr Gln Lys Gly Gln Lys Asn Ser Arg Glu Arg Met Lys Arg Ile
    770                 775                 780

gaa gag ggc atc aaa gag ctg ggc agc cag atc ctg aaa gaa cac ccc      2400
Glu Glu Gly Ile Lys Glu Leu Gly Ser Gln Ile Leu Lys Glu His Pro
785                 790                 795                 800

gtg gaa aac acc cag ctg cag aac gag aag ctg tac ctg tac tac ctg      2448
Val Glu Asn Thr Gln Leu Gln Asn Glu Lys Leu Tyr Leu Tyr Tyr Leu
                805                 810                 815

cag aat ggg cgg gat atg tac gtg gac cag gaa ctg gac atc aac cgg      2496
Gln Asn Gly Arg Asp Met Tyr Val Asp Gln Glu Leu Asp Ile Asn Arg
            820                 825                 830

ctg tcc gac tac gat gtg gac gcc atc gtg cct cag agc ttt ctg aag      2544
Leu Ser Asp Tyr Asp Val Asp Ala Ile Val Pro Gln Ser Phe Leu Lys
        835                 840                 845

gac gac tcc atc gac gcc aag gtg ctg acc aga agc gac aag gcc cgg      2592
Asp Asp Ser Ile Asp Ala Lys Val Leu Thr Arg Ser Asp Lys Ala Arg
    850                 855                 860

ggc aag agc gac aac gtg ccc tcc gaa gag gtc gtg aag aag atg aag      2640
Gly Lys Ser Asp Asn Val Pro Ser Glu Glu Val Val Lys Lys Met Lys
865                 870                 875                 880

aac tac tgg cgg cag ctg ctg aac gcc aag ctg att acc cag aga aag      2688
Asn Tyr Trp Arg Gln Leu Leu Asn Ala Lys Leu Ile Thr Gln Arg Lys
                885                 890                 895

ttc gac aat ctg acc aag gcc gag aga ggc ggc ctg agc gaa ctg gat      2736
Phe Asp Asn Leu Thr Lys Ala Glu Arg Gly Gly Leu Ser Glu Leu Asp
            900                 905                 910

aag gcc ggc ttc atc aag aga cag ctg gtg gaa acc cgg cag atc aca      2784
Lys Ala Gly Phe Ile Lys Arg Gln Leu Val Glu Thr Arg Gln Ile Thr
        915                 920                 925

aag cac gtg gca cag atc ctg gac tcc cgg atg aac act aag tac gac      2832
Lys His Val Ala Gln Ile Leu Asp Ser Arg Met Asn Thr Lys Tyr Asp
    930                 935                 940

gag aat gac aag ctg atc cgg gaa gtg aaa gtg atc acc ctg aag tcc      2880
Glu Asn Asp Lys Leu Ile Arg Glu Val Lys Val Ile Thr Leu Lys Ser
945                 950                 955                 960

aag ctg gtg tcc gat ttc cgg aag gat ttc cag ttt tac aaa gtg cgc      2928
Lys Leu Val Ser Asp Phe Arg Lys Asp Phe Gln Phe Tyr Lys Val Arg
                965                 970                 975

gag atc aac aac tac cac cac gcc cac gcc gcc tac ctg aac gcc gtc      2976
Glu Ile Asn Asn Tyr His His Ala His Ala Ala Tyr Leu Asn Ala Val
            980                 985                 990

gtg gga acc gcc ctg atc aaa aag  tac cct aag ctg gaa  agc gag ttc    3024
Val Gly Thr Ala Leu Ile Lys Lys  Tyr Pro Lys Leu Glu  Ser Glu Phe
        995                 1000                 1005
```

-continued

```
gtg tac  ggc gac tac aag gtg  tac gac gtg cgg aag  atg atc gcc       3069
Val Tyr  Gly Asp Tyr Lys Val  Tyr Asp Val Arg Lys  Met Ile Ala
    1010                 1015                 1020

aag agc  gag cag gaa atc ggc  aag gct acc gcc aag  tac ttc ttc       3114
Lys Ser  Glu Gln Glu Ile Gly  Lys Ala Thr Ala Lys  Tyr Phe Phe
    1025                 1030                 1035

tac agc  aac atc atg aac ttt  ttc aag acc gag att  acc ctg gcc       3159
Tyr Ser  Asn Ile Met Asn Phe  Phe Lys Thr Glu Ile  Thr Leu Ala
    1040                 1045                 1050

aac ggc  gag atc cgg aag cgg  cct ctg atc gag aca  aac ggc gaa       3204
Asn Gly  Glu Ile Arg Lys Arg  Pro Leu Ile Glu Thr  Asn Gly Glu
    1055                 1060                 1065

acc ggg  gag atc gtg tgg gat  aag ggc cgg gat ttt  gcc acc gtg       3249
Thr Gly  Glu Ile Val Trp Asp  Lys Gly Arg Asp Phe  Ala Thr Val
    1070                 1075                 1080

cgg aaa  gtg ctg agc atg ccc  caa gtg aat atc gtg  aaa aag acc       3294
Arg Lys  Val Leu Ser Met Pro  Gln Val Asn Ile Val  Lys Lys Thr
    1085                 1090                 1095

gag gtg  cag aca ggc ggc ttc  agc aaa gag tct atc  ctg ccc aag       3339
Glu Val  Gln Thr Gly Gly Phe  Ser Lys Glu Ser Ile  Leu Pro Lys
    1100                 1105                 1110

agg aac  agc gat aag ctg atc  gcc aga aag aag gac  tgg gac cct       3384
Arg Asn  Ser Asp Lys Leu Ile  Ala Arg Lys Lys Asp  Trp Asp Pro
    1115                 1120                 1125

aag aag  tac ggc ggc ttc gac  agc ccc acc gtg gcc  tat tct gtg       3429
Lys Lys  Tyr Gly Gly Phe Asp  Ser Pro Thr Val Ala  Tyr Ser Val
    1130                 1135                 1140

ctg gtg  gtg gcc aaa gtg gaa  aag ggc aag tcc aag  aaa ctg aag       3474
Leu Val  Val Ala Lys Val Glu  Lys Gly Lys Ser Lys  Lys Leu Lys
    1145                 1150                 1155

agt gtg  aaa gag ctg ctg ggg  atc acc atc atg gaa  aga agc agc       3519
Ser Val  Lys Glu Leu Leu Gly  Ile Thr Ile Met Glu  Arg Ser Ser
    1160                 1165                 1170

ttc gag  aag aat ccc atc gac  ttt ctg gaa gcc aag  ggc tac aaa       3564
Phe Glu  Lys Asn Pro Ile Asp  Phe Leu Glu Ala Lys  Gly Tyr Lys
    1175                 1180                 1185

gaa gtg  aaa aag gac ctg atc  atc aag ctg cct aag  tac tcc ctg       3609
Glu Val  Lys Lys Asp Leu Ile  Ile Lys Leu Pro Lys  Tyr Ser Leu
    1190                 1195                 1200

ttc gag  ctg gaa aac ggc cgg  aag aga atg ctg gcc  tct gcc ggc       3654
Phe Glu  Leu Glu Asn Gly Arg  Lys Arg Met Leu Ala  Ser Ala Gly
    1205                 1210                 1215

gaa ctg  cag aag gga aac gaa  ctg gcc ctg ccc tcc  aaa tat gtg       3699
Glu Leu  Gln Lys Gly Asn Glu  Leu Ala Leu Pro Ser  Lys Tyr Val
    1220                 1225                 1230

aac ttc  ctg tac ctg gcc agc  cac tat gag aag ctg  aag ggc tcc       3744
Asn Phe  Leu Tyr Leu Ala Ser  His Tyr Glu Lys Leu  Lys Gly Ser
    1235                 1240                 1245

ccc gag  gat aat gag cag aaa  cag ctg ttt gtg gaa  cag cac aag       3789
Pro Glu  Asp Asn Glu Gln Lys  Gln Leu Phe Val Glu  Gln His Lys
    1250                 1255                 1260

cac tac  ctg gac gag atc atc  gag cag atc agc gag  ttc tcc aag       3834
His Tyr  Leu Asp Glu Ile Ile  Glu Gln Ile Ser Glu  Phe Ser Lys
    1265                 1270                 1275

aga gtg  atc ctg gcc gac gct  aat ctg gac aaa gtg  ctg tcc gcc       3879
Arg Val  Ile Leu Ala Asp Ala  Asn Leu Asp Lys Val  Leu Ser Ala
    1280                 1285                 1290

tac aac  aag cac cgg gat aag  ccc atc aga gag cag  gcc gag aat       3924
Tyr Asn  Lys His Arg Asp Lys  Pro Ile Arg Glu Gln  Ala Glu Asn
```

```
    1295                1300                1305

atc atc  cac ctg ttt acc ctg  acc aat ctg gga gcc  cct gcc gcc      3969
Ile Ile  His Leu Phe Thr Leu  Thr Asn Leu Gly Ala  Pro Ala Ala
    1310                1315                1320

ttc aag  tac ttt gac acc acc  atc gac cgg aag agg  tac acc agc      4014
Phe Lys  Tyr Phe Asp Thr Thr  Ile Asp Arg Lys Arg  Tyr Thr Ser
    1325                1330                1335

acc aaa  gag gtg ctg gac gcc  acc ctg atc cac cag  agc atc acc      4059
Thr Lys  Glu Val Leu Asp Ala  Thr Leu Ile His Gln  Ser Ile Thr
    1340                1345                1350

ggc ctg  tac gag aca cgg atc  gac ctg tct cag ctg  gga ggc gac      4104
Gly Leu  Tyr Glu Thr Arg Ile  Asp Leu Ser Gln Leu  Gly Gly Asp
    1355                1360                1365


<210> SEQ ID NO 139
<211> LENGTH: 1368
<212> TYPE: PRT
<213> ORGANISM: Homo sapiens

<400> SEQUENCE: 139

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Ala Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Ala Lys Val Leu Thr Arg Ser Asp Lys Ala Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Ala Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
```

```
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

<210> SEQ ID NO 140
<211> LENGTH: 155
<212> TYPE: RNA
<213> ORGANISM: Suterella wadsworthensis

<400> SEQUENCE: 140

guuucagugc uauaggaaac uauaggaaau caccuucggg ugagcugaaa uccccuaaag     60

cuaagauuga auccggccac uaucuauuag uagauauccg gauauucuga uauaaaaccu    120

cauucuuuga uuagaccaaa ggaugagguu uuuuu                               155


<210> SEQ ID NO 141
<211> LENGTH: 107
<212> TYPE: RNA
<213> ORGANISM: Treponema denticola

<400> SEQUENCE: 141

guuugagagu uggaaacaac gaguucaaau aagaauucau caaaaucguc ccuuuuggga     60

ccgcucauug uggagcauca aggcuuaaca ugguuaagcc uuuuuuu                  107


<210> SEQ ID NO 142
<211> LENGTH: 99
```

<212> TYPE: RNA
<213> ORGANISM: Filifactor alocis

<400> SEQUENCE: 142
guuugagagu aggaaacuac acgguucaaa uaaagaauuu uucuaaucgc ccaaugggcc 60
cauauugaua uggaugaaac ucgcuuagcg aguuuuuuu 99

<210> SEQ ID NO 143
<211> LENGTH: 91
<212> TYPE: RNA
<213> ORGANISM: Staphylococcus pseudintermedius

<400> SEQUENCE: 143
guuuuagcac uagaaauagu uaaguuaaaa caagcuuaaa gcgucaaugu aauauuuuau 60
uaacacccua cugugucagu gggguuuuuu u 91

<210> SEQ ID NO 144
<211> LENGTH: 94
<212> TYPE: RNA
<213> ORGANISM: Lactobacillus johnsonii

<400> SEQUENCE: 144
guuuuagaug gugaaaacca gauuuaaaau caagcaaugc aucuuuugau gcaaaguuuc 60
aauauuuguc ccacguuauc gagggacuuu uuuu 94

<210> SEQ ID NO 145
<211> LENGTH: 78
<212> TYPE: RNA
<213> ORGANISM: Eubacterium ventriosum

<400> SEQUENCE: 145
auuuuaguac cuggaaacag aucuacuaaa acaaggcuuu augccgaaau caagagcacc 60
gacgggugcu cuuuuuuu 78

<210> SEQ ID NO 146
<211> LENGTH: 84
<212> TYPE: RNA
<213> ORGANISM: Streptococcus pasteurianus

<400> SEQUENCE: 146
guuuuuguac ucgaaagagc cuacaaagau aaggcuuuau gccgaauuca agcaccccau 60
guuuugacau gaggugcuuu uuuu 84

<210> SEQ ID NO 147
<211> LENGTH: 85
<212> TYPE: RNA
<213> ORGANISM: Lactobacillus farciminis

<400> SEQUENCE: 147
guuuuuguac cuuagaaaua agaucuacaa aaauaaggau uuauuccgaa uuuaccaccu 60
auuuuaauua auagguggu uuuuu 85

<210> SEQ ID NO 148
<211> LENGTH: 100
<212> TYPE: RNA
<213> ORGANISM: Bacteroides coprophilus

<400> SEQUENCE: 148
guugugauuu gcuuucauuu gaaaaauuga agcaaaucac aauaaggauu auuccguugu 60
gaaaacaauu aaagcggucu ugcaaaaggu cgcuuuuuuu 100

<210> SEQ ID NO 149
<211> LENGTH: 102
<212> TYPE: RNA
<213> ORGANISM: Fluviicola taffensis

<400> SEQUENCE: 149
guugugauuc gcuuucaaug aaaauugaag cgaaucacaa uaaggauuau uccguuguga 60
aaacauuuac uacggggcau cgaaagacug ccucguuuuu uu 102

<210> SEQ ID NO 150
<211> LENGTH: 90
<212> TYPE: RNA
<213> ORGANISM: Flavobacterium columnare

<400> SEQUENCE: 150
guugugguuu gauuagaaau aaucuuauca caauaaggcu auaugccgua gacgaaaguc 60
uuuagucccg cuucggguggg acuuuuuuuu 90

<210> SEQ ID NO 151
<211> LENGTH: 78
<212> TYPE: RNA
<213> ORGANISM: Sphaerochaeta globus

<400> SEQUENCE: 151
guuggggaug accgcgaaag cgauuaucuc uaauaagacu uaagucgcaa aaugcucccu 60
auuuugggag cuuuuuuu 78

<210> SEQ ID NO 152
<211> LENGTH: 85
<212> TYPE: RNA
<213> ORGANISM: Azospirillum sp.

<400> SEQUENCE: 152
guugcggcug gagaaaucca gccguuaaca uguucccuuc ggggagcacg aaaugcgggg 60
cgggccacgg uccgccccuu uuuuu 85

<210> SEQ ID NO 153
<211> LENGTH: 126
<212> TYPE: RNA
<213> ORGANISM: Gluconacetobacter diazotrophicus

<400> SEQUENCE: 153
gccgugguuu ccgaaaggaa accacgguaa cagaauuacc guaagguuuu uucugugaag 60
gaucaucccu cgcuugggca accaggcggg ggaaauuccu cguucgggcc aaucagcccu 120
uuuuuu 126

<210> SEQ ID NO 154
<211> LENGTH: 82
<212> TYPE: RNA
<213> ORGANISM: Roseburia intestinalis

<400> SEQUENCE: 154
guuguaauuc ccugaaaagg uuauuacaau aagguaagaa accuaaaagc ucuaauccca 60
uucuucggaa ugggauuuuu uu 82

<210> SEQ ID NO 155
<211> LENGTH: 83

<212> TYPE: RNA
<213> ORGANISM: Staphylococcus aureus

<400> SEQUENCE: 155
guuuuaguac ucuggaaaca gaaucuacua aaacaaggca aaaugccgug uuuaucucgu 60
caacuuguug gcgagauuuu uuu 83

<210> SEQ ID NO 156
<211> LENGTH: 94
<212> TYPE: RNA
<213> ORGANISM: Mycoplasma gallisepticum

<400> SEQUENCE: 156
guuuuagcac uguacaagaa auugucgugc uaaaauaagg cgcuguuaau gcagcugccg 60
cauccgccag agcauuuaug cucuggcuuu uuuu 94

<210> SEQ ID NO 157
<211> LENGTH: 117
<212> TYPE: RNA
<213> ORGANISM: Campylobacter lari

<400> SEQUENCE: 157
guuuuagucu cugaaaagag acuaaaauaa gugguuuuug gucauccacg cagguuaca 60 aucccuuuaa aaccauuaaa auucaaauaa acuagguugu aucaacuuag uuuuuuu 117

<210> SEQ ID NO 158
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 158
nnnnnnnnnn nnnnnnnnnn acugggguuc aggaaacuga accucaguaa gcauuggcuc 60
guuuccaaug uugauugcuc cgccggugcu ccuuauuuuu aagggcgccg gcuuuuuuu 119

<210> SEQ ID NO 159
<211> LENGTH: 1084
<212> TYPE: PRT
<213> ORGANISM: Corynebacterium diphtheriae

<400> SEQUENCE: 159

Met Lys Tyr His Val Gly Ile Asp Val Gly Thr Phe Ser Val Gly Leu
1               5                   10                  15

Ala Ala Ile Glu Val Asp Asp Ala Gly Met Pro Ile Lys Thr Leu Ser
            20                  25                  30

Leu Val Ser His Ile His Asp Ser Gly Leu Asp Pro Asp Glu Ile Lys
        35                  40                  45

Ser Ala Val Thr Arg Leu Ala Ser Ser Gly Ile Ala Arg Arg Thr Arg
    50                  55                  60

Arg Leu Tyr Arg Arg Lys Arg Arg Arg Leu Gln Gln Leu Asp Lys Phe
65                  70                  75                  80

Ile Gln Arg Gln Gly Trp Pro Val Ile Glu Leu Glu Asp Tyr Ser Asp
                85                  90                  95

Pro Leu Tyr Pro Trp Lys Val Arg Ala Glu Leu Ala Ala Ser Tyr Ile

-continued

```
            100                 105                 110

Ala Asp Glu Lys Glu Arg Gly Glu Lys Leu Ser Val Ala Leu Arg His
        115                 120                 125

Ile Ala Arg His Arg Gly Trp Arg Asn Pro Tyr Ala Lys Val Ser Ser
    130                 135                 140

Leu Tyr Leu Pro Asp Gly Pro Ser Asp Ala Phe Lys Ala Ile Arg Glu
145                 150                 155                 160

Glu Ile Lys Arg Ala Ser Gly Gln Pro Val Pro Glu Thr Ala Thr Val
                165                 170                 175

Gly Gln Met Val Thr Leu Cys Glu Leu Gly Thr Leu Lys Leu Arg Gly
            180                 185                 190

Glu Gly Gly Val Leu Ser Ala Arg Leu Gln Gln Ser Asp Tyr Ala Arg
        195                 200                 205

Glu Ile Gln Glu Ile Cys Arg Met Gln Glu Ile Gly Gln Glu Leu Tyr
    210                 215                 220

Arg Lys Ile Ile Asp Val Val Phe Ala Ala Glu Ser Pro Lys Gly Ser
225                 230                 235                 240

Ala Ser Ser Arg Val Gly Lys Asp Pro Leu Gln Pro Gly Lys Asn Arg
                245                 250                 255

Ala Leu Lys Ala Ser Asp Ala Phe Gln Arg Tyr Arg Ile Ala Ala Leu
            260                 265                 270

Ile Gly Asn Leu Arg Val Arg Val Asp Gly Glu Lys Arg Ile Leu Ser
        275                 280                 285

Val Glu Glu Lys Asn Leu Val Phe Asp His Leu Val Asn Leu Thr Pro
    290                 295                 300

Lys Lys Glu Pro Glu Trp Val Thr Ile Ala Glu Ile Leu Gly Ile Asp
305                 310                 315                 320

Arg Gly Gln Leu Ile Gly Thr Ala Thr Met Thr Asp Asp Gly Glu Arg
                325                 330                 335

Ala Gly Ala Arg Pro Pro Thr His Asp Thr Asn Arg Ser Ile Val Asn
            340                 345                 350

Ser Arg Ile Ala Pro Leu Val Asp Trp Trp Lys Thr Ala Ser Ala Leu
        355                 360                 365

Glu Gln His Ala Met Val Lys Ala Leu Ser Asn Ala Glu Val Asp Asp
    370                 375                 380

Phe Asp Ser Pro Glu Gly Ala Lys Val Gln Ala Phe Phe Ala Asp Leu
385                 390                 395                 400

Asp Asp Asp Val His Ala Lys Leu Asp Ser Leu His Leu Pro Val Gly
                405                 410                 415

Arg Ala Ala Tyr Ser Glu Asp Thr Leu Val Arg Leu Thr Arg Arg Met
            420                 425                 430

Leu Ser Asp Gly Val Asp Leu Tyr Thr Ala Arg Leu Gln Glu Phe Gly
        435                 440                 445

Ile Glu Pro Ser Trp Thr Pro Pro Thr Pro Arg Ile Gly Glu Pro Val
    450                 455                 460

Gly Asn Pro Ala Val Asp Arg Val Leu Lys Thr Val Ser Arg Trp Leu
465                 470                 475                 480

Glu Ser Ala Thr Lys Thr Trp Gly Ala Pro Glu Arg Val Ile Ile Glu
                485                 490                 495

His Val Arg Glu Gly Phe Val Thr Glu Lys Arg Ala Arg Glu Met Asp
            500                 505                 510

Gly Asp Met Arg Arg Arg Ala Ala Arg Asn Ala Lys Leu Phe Gln Glu
        515                 520                 525
```

```
Met Gln Glu Lys Leu Asn Val Gln Gly Lys Pro Ser Arg Ala Asp Leu
    530                 535                 540

Trp Arg Tyr Gln Ser Val Gln Arg Gln Asn Cys Gln Cys Ala Tyr Cys
545                 550                 555                 560

Gly Ser Pro Ile Thr Phe Ser Asn Ser Glu Met Asp His Ile Val Pro
                565                 570                 575

Arg Ala Gly Gln Gly Ser Thr Asn Thr Arg Glu Asn Leu Val Ala Val
            580                 585                 590

Cys His Arg Cys Asn Gln Ser Lys Gly Asn Thr Pro Phe Ala Ile Trp
        595                 600                 605

Ala Lys Asn Thr Ser Ile Glu Gly Val Ser Val Lys Glu Ala Val Glu
    610                 615                 620

Arg Thr Arg His Trp Val Thr Asp Thr Gly Met Arg Ser Thr Asp Phe
625                 630                 635                 640

Lys Lys Phe Thr Lys Ala Val Val Glu Arg Phe Gln Arg Ala Thr Met
                645                 650                 655

Asp Glu Glu Ile Asp Ala Arg Ser Met Glu Ser Val Ala Trp Met Ala
            660                 665                 670

Asn Glu Leu Arg Ser Arg Val Ala Gln His Phe Ala Ser His Gly Thr
        675                 680                 685

Thr Val Arg Val Tyr Arg Gly Ser Leu Thr Ala Glu Ala Arg Arg Ala
    690                 695                 700

Ser Gly Ile Ser Gly Lys Leu Lys Phe Phe Asp Gly Val Gly Lys Ser
705                 710                 715                 720

Arg Leu Asp Arg Arg His His Ala Ile Asp Ala Ala Val Ile Ala Phe
                725                 730                 735

Thr Ser Asp Tyr Val Ala Glu Thr Leu Ala Val Arg Ser Asn Leu Lys
            740                 745                 750

Gln Ser Gln Ala His Arg Gln Glu Ala Pro Gln Trp Arg Glu Phe Thr
        755                 760                 765

Gly Lys Asp Ala Glu His Arg Ala Ala Trp Arg Val Trp Cys Gln Lys
    770                 775                 780

Met Glu Lys Leu Ser Ala Leu Leu Thr Glu Asp Leu Arg Asp Asp Arg
785                 790                 795                 800

Val Val Val Met Ser Asn Val Arg Leu Arg Leu Gly Asn Gly Ser Ala
                805                 810                 815

His Lys Glu Thr Ile Gly Lys Leu Ser Lys Val Lys Leu Ser Ser Gln
            820                 825                 830

Leu Ser Val Ser Asp Ile Asp Lys Ala Ser Ser Glu Ala Leu Trp Cys
        835                 840                 845

Ala Leu Thr Arg Glu Pro Gly Phe Asp Pro Lys Glu Gly Leu Pro Ala
    850                 855                 860

Asn Pro Glu Arg His Ile Arg Val Asn Gly Thr His Val Tyr Ala Gly
865                 870                 875                 880

Asp Asn Ile Gly Leu Phe Pro Val Ser Ala Gly Ser Ile Ala Leu Arg
                885                 890                 895

Gly Gly Tyr Ala Glu Leu Gly Ser Ser Phe His His Ala Arg Val Tyr
            900                 905                 910

Lys Ile Thr Ser Gly Lys Lys Pro Ala Phe Ala Met Leu Arg Val Tyr
        915                 920                 925

Thr Ile Asp Leu Leu Pro Tyr Arg Asn Gln Asp Leu Phe Ser Val Glu
    930                 935                 940
```

```
Leu Lys Pro Gln Thr Met Ser Met Arg Gln Ala Glu Lys Lys Leu Arg
945                 950                 955                 960

Asp Ala Leu Ala Thr Gly Asn Ala Glu Tyr Leu Gly Trp Leu Val Val
                965                 970                 975

Asp Asp Glu Leu Val Val Asp Thr Ser Lys Ile Ala Thr Asp Gln Val
            980                 985                 990

Lys Ala Val Glu Ala Glu Leu Gly  Thr Ile Arg Arg Trp  Arg Val Asp
        995                 1000                 1005

Gly Phe  Phe Ser Pro Ser Lys  Leu Arg Leu Arg Pro  Leu Gln Met
    1010                 1015                 1020

Ser Lys  Glu Gly Ile Lys Lys  Glu Ser Ala Pro Glu  Leu Ser Lys
    1025                 1030                 1035

Ile Ile  Asp Arg Pro Gly Trp  Leu Pro Ala Val Asn  Lys Leu Phe
    1040                 1045                 1050

Ser Asp  Gly Asn Val Thr Val  Val Arg Arg Asp Ser  Leu Gly Arg
    1055                 1060                 1065

Val Arg  Leu Glu Ser Thr Ala  His Leu Pro Val Thr  Trp Lys Val
    1070                 1075                 1080

Gln


<210> SEQ ID NO 160
<211> LENGTH: 3336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

accggtgcca ccatgtaccc atacgatgtt ccagattacg cttcgccgaa gaaaaagcgc     60

aaggtcgaag cgtccatgaa gtaccatgtc ggaatcgatg tcggaacctt ttctgtgggg    120

ctggctgcta ttgaagtgga tgacgctgga atgcctatta agaccctgag tctggtgtca    180

cacattcatg actcaggact ggatcctgac gagatcaaga gcgctgtgac caggctggca    240

agctccggaa tcgcccggag aacaaggcgc ctgtaccgac ggaagagaag gcgcctgcag    300

cagctggata agttcatcca gaggcagggc tggccagtga tcgagctgga agattacagc    360

gacccccctgt atccttggaa ggtgcgcgcc gaactggccg cttcttatat tgctgacgag    420

aaggaacggg gggagaaact gagtgtggct ctgagacaca tcgcaaggca tcgcggatgg    480

aggaaccctt acgccaaggt gtctagtctg tatctgccag atggccccctc agacgccttc    540

aaggctatta gggaggaaat caaacgcgct agcggccagc ctgtgccaga gactgcaacc    600

gtcgggcaga tggtgaccct gtgcgaactg ggcacactga agctgcgagg agagggagga    660

gtgctgagtg cacggctgca gcagtcagat tacgcccgcg agatccagga aatttgtcga    720

atgcaggaga tcggccagga actgtatcgc aagatcattg acgtggtgtt cgcagccgag    780

tccccaaagg gctctgcctc aagccgggtg gggaaagatc ctctgcagcc aggaaagaac    840

agagcactga aagccagcga cgcttttcag cgataccgga ttgctgcact gatcggcaat    900

ctgagagtca gggtggatgg ggagaagagg attctgagcg tggaggagaa gaacctggtg    960

ttcgaccacc tggtgaatct gactccaaag aaagagcccg aatgggtgac catcgccgaa   1020

attctgggca tcgatcgcgg gcagctgatc ggaacagcta ctatgaccga cgatggagag   1080

cgagcaggag cccgaccccc tacacacgat actaacagaa gtattgtgaa cagccggatc   1140

gcaccactgg tcgactggtg gaaaacagct agcgcactgg agcagcacgc catggtgaag   1200
```

```
gcactgtcca acgccgaagt cgacgatttt gattctcccg agggagcaaa agtgcaggca   1260
ttctttgccg atctggacga tgacgtccac gccaagctgg acagcctgca tctgcctgtg   1320
ggacgagcag cttactccga ggacactctg gtcagactga cccgacggat gctgagtgat   1380
ggggtggacc tgtataccgc ccggctgcag gagttcggaa ttgaacctag ctggacccca   1440
cccacaccaa gaatcggaga gcctgtcggc aatccagccg tcgaccgggt gctgaaaaca   1500
gtgagcagat ggctggaatc cgcaacaaag acttggggcg ccccagagag ggtcatcatt   1560
gagcacgtgc gcgaaggctt cgtcactgag aaacgcgctc gagaaatgga tggggacatg   1620
agaaggcgcg cagcccggaa cgccaagctg tttcaggaga tgcaggaaaa gctgaatgtg   1680
cagggcaaac ccagtcgagc cgatctgtgg agataccagt cagtgcagag acagaactgc   1740
cagtgtgcct attgcgggtc ccaattacc ttttctaata gtgaaatgga ccacatcgtg   1800
cccagagcag ggcagggatc caccaacaca agggagaatc tggtcgccgt gtgccatcgc   1860
tgtaaccagt ctaagggcaa tacacccttc gctatttggg caaaaaacac ttctatcgaa   1920
ggggtcagtg tgaaggaggc cgtggaacgg accagacatt gggtcactga taccggcatg   1980
agaagcactg acttcaagaa gttcaccaag gctgtggtcg agcggtttca gagagcaaca   2040
atggatgagg aaatcgacgc cagaagcatg gaatccgtcg cctggatggc taatgagctg   2100
aggagccgcg tggctcagca cttcgcatcc catggaacca cagtcagggt gtaccgaggc   2160
agcctgacag cagaggctcg acgggcatct gggatcagtg gaaagctgaa attctttgat   2220
ggcgtgggga agtccaggct ggatagaagg caccatgcta ttgacgctgc agtgatcgca   2280
ttcacctctg actatgtggc cgaaacactg gctgtccgct caaacctgaa acagagccag   2340
gcccaccgac aggaggctcc tcagtggaga gagttcaccg gcaaggatgc agagcatcga   2400
gcagcttgga gagtgtggtg ccagaagatg gaaaaactga gcgccctgct gaccgaggac   2460
ctgcgagatg accgggtggt cgtgatgtct aacgtgcgac tgcggctggg aaatggcagt   2520
gcccacaagg aaaccattgg caaactgtca aaggtgaaac tgtcctctca gctgtcagtc   2580
agcgatatcg acaaagcaag ttcagaggcc ctgtggtgtg ctctgaccag agagcccgga   2640
ttcgatccta aggaaggcct gcccgctaac cctgagagac acatcagggt gaatgggaca   2700
catgtctacg ccggggacaa tattggactg tttccagtgt cagcaggaag catcgcactg   2760
aggggaggat acgcagagct gggcagctcc ttccaccatg ctcgcgtgta taaaattact   2820
tccggcaaga aacccgcatt tgccatgctg agggtgtaca ccatcgatct gctgccttat   2880
cgcaaccagg acctgtttag cgtggaactg aagccacaga caatgtccat gaggcaggct   2940
gagaagaaac tgcgcgacgc tctggcaact gggaatgcag aatatctggg atggctggtc   3000
gtggatgacg agctggtcgt ggatacatct aagattgcca ctgaccaggt caaagcagtg   3060
gaggccgaac tggggactat ccgccgatgg cgggtggatg gattcttttc cccctctaaa   3120
ctgagactga ggcctctgca gatgtccaag gaggggatca agaaagagtc cgctcccgaa   3180
ctgtctaaaa tcattgacag accaggatgg ctgcccgccg tgaacaagct gttctctgat   3240
ggaaatgtca ccgtcgtgcg gagagactct ctgggacgcg tgcgactgga gagtacagcc   3300
cacctgcctg tcacttggaa ggtgcagtaa gaattc                             3336
```

<210> SEQ ID NO 161
<211> LENGTH: 175
<212> TYPE: RNA
<213> ORGANISM: Artificial Sequence
<220> FEATURE:

<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 161
nnnnnnnnnn nnnnnnnnnn guuucagugc uauaggaaac uauaggaaau caccuucggg 60
ugagcugaaa uccccuaaag cuaagauuga auccggccac uaucuauuag uagauauccg 120
gauauucuga uauaaaaccu cauucuuuga uuagaccaaa ggaugagguu uuuuu 175

<210> SEQ ID NO 162
<211> LENGTH: 1422
<212> TYPE: PRT
<213> ORGANISM: Sutterella wadsworthensis

<400> SEQUENCE: 162

Met Thr Gln Ser Glu Arg Arg Phe Ser Cys Ser Ile Gly Ile Asp Met
1 5 10 15

Gly Ala Lys Tyr Thr Gly Val Phe Tyr Ala Leu Phe Asp Arg Glu Glu
20 25 30

Leu Pro Thr Asn Leu Asn Ser Lys Ala Met Thr Leu Val Met Pro Glu
35 40 45

Thr Gly Pro Arg Tyr Val Gln Ala Gln Arg Thr Ala Val Arg His Arg
50 55 60

Leu Arg Gly Gln Lys Arg Tyr Thr Leu Ala Arg Lys Leu Ala Phe Leu
65 70 75 80

Val Val Asp Asp Met Ile Lys Lys Gln Glu Lys Arg Leu Thr Asp Glu
85 90 95

Glu Trp Lys Arg Gly Arg Glu Ala Leu Ser Gly Leu Leu Lys Arg Arg
100 105 110

Gly Tyr Ser Arg Pro Asn Ala Asp Gly Glu Asp Leu Thr Pro Leu Glu
115 120 125

Asn Val Arg Ala Asp Val Phe Ala Ala His Pro Ala Phe Ser Thr Tyr
130 135 140

Phe Ser Glu Val Arg Ser Leu Ala Glu Gln Trp Glu Glu Phe Thr Ala
145 150 155 160

Asn Ile Ser Asn Val Glu Lys Phe Leu Gly Asp Pro Asn Ile Pro Ala
165 170 175

Asp Lys Glu Phe Ile Glu Phe Ala Val Ala Glu Gly Leu Ile Asp Lys
180 185 190

Thr Glu Lys Lys Ala Tyr Gln Ser Ala Leu Ser Thr Leu Arg Ala Asn
195 200 205

Ala Asn Val Leu Thr Gly Leu Arg Gln Met Gly His Lys Pro Arg Ser
210 215 220

Glu Tyr Phe Lys Ala Ile Glu Ala Asp Leu Lys Lys Asp Ser Arg Leu
225 230 235 240

Ala Lys Ile Asn Glu Ala Phe Gly Gly Ala Glu Arg Leu Ala Arg Leu
245 250 255

Leu Gly Asn Leu Ser Asn Leu Gln Leu Arg Ala Glu Arg Trp Tyr Phe
260 265 270

Asn Ala Pro Asp Ile Met Lys Asp Arg Gly Trp Glu Pro Asp Arg Phe
275 280 285

Lys Lys Thr Leu Val Arg Ala Phe Lys Phe Phe His Pro Ala Lys Asp
290 295 300

Gln Asn Lys Gln His Leu Glu Leu Ile Lys Gln Ile Glu Asn Ser Glu
305 310 315 320

Asp Ile Ile Glu Thr Leu Cys Thr Leu Asp Pro Asn Arg Thr Ile Pro
325 330 335

Pro Tyr Glu Asp Gln Asn Asn Arg Arg Pro Pro Leu Asp Gln Thr Leu
340 345 350

Leu Leu Ser Pro Glu Lys Leu Thr Arg Gln Tyr Gly Glu Ile Trp Lys
355 360 365

Thr Trp Ser Ala Arg Leu Thr Ser Ala Glu Pro Thr Leu Ala Pro Ala
370 375 380

Ala Glu Ile Leu Glu Arg Ser Thr Asp Arg Lys Ser Arg Val Ala Val
385 390 395 400

Asn Gly His Glu Pro Leu Pro Thr Leu Ala Tyr Gln Leu Ser Tyr Ala
405 410 415

Leu Gln Arg Ala Phe Asp Arg Ser Lys Ala Leu Asp Pro Tyr Ala Leu
420 425 430

Arg Ala Leu Ala Ala Gly Ser Lys Ser Asn Lys Leu Thr Ser Ala Arg
435 440 445

Thr Ala Leu Glu Asn Cys Ile Gly Gly Gln Asn Val Lys Thr Phe Leu
450 455 460

Asp Cys Ala Arg Arg Tyr Tyr Arg Glu Ala Asp Asp Ala Lys Val Gly
465 470 475 480

Leu Trp Phe Asp Asn Ala Asp Gly Leu Leu Glu Arg Ser Asp Leu His
485 490 495

Pro Pro Met Lys Lys Lys Ile Leu Pro Leu Leu Val Ala Asn Ile Leu
500 505 510

Gln Thr Asp Glu Thr Thr Gly Gln Lys Phe Leu Asp Glu Ile Trp Arg
515 520 525

Lys Gln Ile Lys Gly Arg Glu Thr Val Ala Ser Arg Cys Ala Arg Ile
530 535 540

Glu Thr Val Arg Lys Ser Phe Gly Gly Gly Phe Asn Ile Ala Tyr Asn
545 550 555 560

Thr Ala Gln Tyr Arg Glu Val Asn Lys Leu Pro Arg Asn Ala Gln Asp
565 570 575

Lys Glu Leu Leu Thr Ile Arg Asp Arg Val Ala Glu Thr Ala Asp Phe
580 585 590

Ile Ala Ala Asn Leu Gly Leu Ser Asp Glu Gln Lys Arg Lys Phe Ala
595 600 605

Asn Pro Phe Ser Leu Ala Gln Phe Tyr Thr Leu Ile Glu Thr Glu Val
610 615 620

Ser Gly Phe Ser Ala Thr Thr Leu Ala Val His Leu Glu Asn Ala Trp
625 630 635 640

Arg Met Thr Ile Lys Asp Ala Val Ile Asn Gly Glu Thr Val Arg Ala
645 650 655

Ala Gln Cys Ser Arg Leu Pro Ala Glu Thr Ala Arg Pro Phe Asp Gly
660 665 670

Leu Val Arg Arg Leu Val Asp Arg Gln Ala Trp Glu Ile Ala Lys Arg
675 680 685

Val Ser Thr Asp Ile Gln Ser Lys Val Asp Phe Ser Asn Gly Ile Val
690 695 700

Asp Val Ser Ile Phe Val Glu Glu Asn Lys Phe Glu Phe Ser Ala Ser
705 710 715 720

```
Val Ala Asp Leu Lys Lys Asn Lys Arg Val Lys Asp Lys Met Leu Ser
                725                 730                 735

Glu Ala Glu Lys Leu Glu Thr Arg Trp Leu Ile Lys Asn Glu Arg Ile
            740                 745                 750

Lys Lys Ala Ser Arg Gly Thr Cys Pro Tyr Thr Gly Asp Arg Leu Ala
        755                 760                 765

Glu Gly Gly Glu Ile Asp His Ile Leu Pro Arg Ser Leu Ile Lys Asp
    770                 775                 780

Ala Arg Gly Ile Val Phe Asn Ala Glu Pro Asn Leu Ile Tyr Ala Ser
785                 790                 795                 800

Ser Arg Gly Asn Gln Leu Lys Lys Asn Gln Arg Tyr Ser Leu Ser Asp
                805                 810                 815

Leu Lys Ala Asn Tyr Arg Asn Glu Ile Phe Lys Thr Ser Asn Ile Ala
            820                 825                 830

Ala Ile Thr Ala Glu Ile Glu Asp Val Val Thr Lys Leu Gln Gln Thr
        835                 840                 845

His Arg Leu Lys Phe Phe Asp Leu Leu Asn Glu His Glu Gln Asp Cys
    850                 855                 860

Val Arg His Ala Leu Phe Leu Asp Asp Gly Ser Glu Ala Arg Asp Ala
865                 870                 875                 880

Val Leu Glu Leu Leu Ala Thr Gln Arg Arg Thr Arg Val Asn Gly Thr
                885                 890                 895

Gln Ile Trp Met Ile Lys Asn Leu Ala Asn Lys Ile Arg Glu Glu Leu
            900                 905                 910

Gln Asn Trp Cys Lys Thr Thr Asn Asn Arg Leu His Phe Gln Ala Ala
        915                 920                 925

Ala Thr Asn Val Ser Asp Ala Lys Asn Leu Arg Leu Lys Leu Ala Gln
    930                 935                 940

Asn Gln Pro Asp Phe Glu Lys Pro Asp Ile Gln Pro Ile Ala Ser His
945                 950                 955                 960

Ser Ile Asp Ala Leu Cys Ser Phe Ala Val Gly Ser Ala Asp Ala Glu
                965                 970                 975

Arg Asp Gln Asn Gly Phe Asp Tyr Leu Asp Gly Lys Thr Val Leu Gly
            980                 985                 990

Leu Tyr Pro Gln Ser Cys Glu Val  Ile His Leu Gln Ala  Lys Pro Gln
        995                 1000                 1005

Glu Glu  Lys Ser His Phe Asp  Ser Val Ala Ile Phe  Lys Glu Gly
    1010                 1015                 1020

Ile Tyr  Ala Glu Gln Phe Leu  Pro Ile Phe Thr Leu  Asn Glu Lys
    1025                 1030                 1035

Ile Trp  Ile Gly Tyr Glu Thr  Leu Asn Ala Lys Gly  Glu Arg Cys
    1040                 1045                 1050

Gly Ala  Ile Glu Val Ser Gly  Lys Gln Pro Lys Glu  Leu Leu Glu
    1055                 1060                 1065

Met Leu  Ala Pro Phe Phe Asn  Lys Pro Val Gly Asp  Leu Ser Ala
    1070                 1075                 1080

His Ala  Thr Tyr Arg Ile Leu  Lys Lys Pro Ala Tyr  Glu Phe Leu
    1085                 1090                 1095

Ala Lys  Ala Ala Leu Gln Pro  Leu Ser Ala Glu Glu  Lys Arg Leu
    1100                 1105                 1110

Ala Ala  Leu Leu Asp Ala Leu  Arg Tyr Cys Thr Ser  Arg Lys Ser
    1115                 1120                 1125

Leu Met  Ser Leu Phe Met Ala  Ala Asn Gly Lys Ser  Leu Lys Lys
```

1130 1135 1140

Arg Glu Asp Val Leu Lys Pro Lys Leu Phe Gln Leu Lys Val Glu
1145 1150 1155

Leu Lys Gly Glu Lys Ser Phe Lys Leu Asn Gly Ser Leu Thr Leu
1160 1165 1170

Pro Val Lys Gln Asp Trp Leu Arg Ile Cys Asp Ser Pro Glu Leu
1175 1180 1185

Ala Asp Ala Phe Gly Lys Pro Cys Ser Ala Asp Glu Leu Thr Ser
1190 1195 1200

Lys Leu Ala Arg Ile Trp Lys Arg Pro Val Met Arg Asp Leu Ala
1205 1210 1215

His Ala Pro Val Arg Arg Glu Phe Ser Leu Pro Ala Ile Asp Asn
1220 1225 1230

Pro Ser Gly Gly Phe Arg Ile Arg Arg Thr Asn Leu Phe Gly Asn
1235 1240 1245

Glu Leu Tyr Gln Val His Ala Ile Asn Ala Lys Lys Tyr Arg Gly
1250 1255 1260

Phe Ala Ser Ala Gly Ser Asn Val Asp Trp Ser Lys Gly Ile Leu
1265 1270 1275

Phe Asn Glu Leu Gln His Glu Asn Leu Thr Glu Cys Gly Gly Arg
1280 1285 1290

Phe Ile Thr Ser Ala Asp Val Thr Pro Met Ser Glu Trp Arg Lys
1295 1300 1305

Val Val Ala Glu Asp Asn Leu Ser Ile Trp Ile Ala Pro Gly Thr
1310 1315 1320

Glu Gly Arg Arg Tyr Val Arg Val Glu Thr Thr Phe Ile Gln Ala
1325 1330 1335

Ser His Trp Phe Glu Gln Ser Val Glu Asn Trp Ala Ile Thr Ser
1340 1345 1350

Pro Leu Ser Leu Pro Ala Ser Phe Lys Val Asp Lys Pro Ala Glu
1355 1360 1365

Phe Gln Lys Ala Val Gly Thr Glu Leu Ser Glu Leu Leu Gly Gln
1370 1375 1380

Pro Arg Ser Glu Ile Phe Ile Glu Asn Val Gly Asn Ala Lys His
1385 1390 1395

Ile Arg Phe Trp Tyr Ile Val Val Ser Ser Asn Lys Lys Met Asn
1400 1405 1410

Glu Ser Tyr Asn Asn Val Ser Lys Ser
1415 1420

<210> SEQ ID NO 163
<211> LENGTH: 4350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163
accggtgcca ccatgtaccc atacgatgtt ccagattacg cttcgccgaa gaaaaagcgc 60
aaggtcgaag cgtccatgac tcagagcgag cgacgatttt cttgcagcat tggcattgac 120
atgggggcta agtacactgg ggtgttctac gcactgttcg accgggagga actgcccaca 180
aacctgaaca gcaaggccat gaccctggtc atgcctgaga cagggccaag atacgtgcag 240
gcacagagaa ctgccgtcag acacaggctg cgcggacaga agagatatac cctggctagg 300

```
aaactggcat ttctggtggt cgacgatatg atcaagaaac aggaaaagag gctgactgat    360
gaggaatgga aacgaggacg ggaggccctg tccggcctgc tgaagcggag agggtactct    420
cggcccaacg ctgacggcga agatctgacc cctctggaga atgtgagagc agacgtgttc    480
gccgctcatc ctgccttcag cacatatttt tccgaagtgc gctctctggc tgagcagtgg    540
gaggagttca ccgcaaacat cagcaatgtc gagaagtttc tgggcgaccc aaacatcccc    600
gccgataaag agttcattga atttgccgtg gctgaagggc tgattgacaa gaccgagaag    660
aaagcctacc agtcagctct gagcaccctg agggcaaacg ccaatgtgct gacaggactg    720
cggcagatgg gccacaagcc tagatcagaa tattttaaag caatcgaggc cgacctgaag    780
aaagatagcc gcctggccaa gattaacgaa gcattcggag gagcagagcg cctggctcga    840
ctgctgggaa acctgtccaa tctgcagctg cgggcagaaa gatggtactt caatgccccc    900
gacatcatga aggatagggg ctgggagcct gatcgcttca agaaaacact ggtgcgggct    960
tttaagttct ttcacccagc aaaggaccag aacaaacagc atctggaact gatcaaacag   1020
attgagaaca gcgaagatat cattgagact ctgtgcaccc tggacccaaa cagaaccatc   1080
ccccttacg aggatcagaa caataggcgc ccacccctgg accagactct gctgctgagt    1140
cccgaaaagc tgacccggca gtatggcgag atctggaaaa catggagcgc cagactgacc   1200
tccgctgaac ccacactggc acctgcagcc gagattctgg aaagatctac cgacaggaag   1260
agtcgcgtgg cagtcaacgg acacgagcca ctgcctacac tggcttacca gctgagttat   1320
gcactgcaga gagccttcga caggtcaaaa gccctggatc catatgctct gagggcactg   1380
gctgcaggct caaaaagcaa taagctgaca tccgcccgca ctgctctgga gaactgcatc   1440
ggaggccaga atgtgaaaac cttcctggac tgtgcccgac ggtactatcg ggaagcagac   1500
gatgccaaag tcgggctgtg gttcgacaac gccgatggac tgctggagag atctgacctg   1560
catcctccaa tgaagaaaaa gatcctgccc ctgctggtgg ccaatattct gcagacagat   1620
gaaaccacag gccagaagtt tctggacgag atctggcgaa aacagattaa ggggcgggaa   1680
actgtggcta gccgatgtgc acggatcgag acagtgcgga aatccttcgg gggaggcttt   1740
aacattgcct acaataccgc tcagtatagg gaggtgaaca agctgccccg caatgcccag   1800
gataaagaac tgctgacaat cagagatagg gtggctgaga ctgcagactt cattgccgct   1860
aacctggggc tgtctgacga gcagaaaaga aagttcgcca atcctttttag tctggctcag  1920
ttctacaccc tgatcgagac agaagtgtcc ggattttctg caactaccct ggccgtccac   1980
ctggagaacg cctggaggat gacaatcaag gatgctgtga ttaatgggga aactgtcaga   2040
gcagcacagt gcagcaggct gcctgcagag acagctcgcc cattcgatgg actggtgaga   2100
aggctggtcg acagacaggc ttgggagatc gcaaagaggg tgtcaactga cattcagagc   2160
aaagtcgatt tctccaacgg catcgtggac gtcagcattt ttgtggagga aaataagttc   2220
gagttttccg catctgtggc cgatctgaaa aagaacaaac gggtcaaaga caagatgctg   2280
tccgaggccg aaaagctgga aaccagatgg ctgatcaaaa atgagcggat caagaaggcc   2340
agccggggaa cttgtcccta caccggcgat aggctggctg aggggggaga aatcgaccac   2400
attctgcccc gaagcctgat caaggatgcc cggggaattg tgtttaacgc tgagcctaat   2460
ctgatctatg caagctcccg cggcaaccag ctgaaaaaga atcagcgata cagtctgtca   2520
gatctgaagg ccaactatcg gaatgagatc ttcaaaacta gcaacatcgc tgcaattacc   2580
gccgagattg aggacgtggt cactaagctg cagcagaccc atagactgaa attctttgat   2640
```

```
ctgctgaatg agcacgaaca ggactgcgtg cggcacgccc tgttcctgga cgatggcagc   2700

gaagctcgcg acgcagtgct ggagctgctg gcaacacagc gccgaactcg cgtcaacggg   2760

acacagatct ggatgattaa gaacctggcc aacaagatcc gagaggaact gcagaattgg   2820

tgtaagacaa ctaacaatag actgcacttt caggccgctg caactaacgt gtccgatgca   2880

aagaatctga ggctgaaact ggcccagaac cagcccgact tcgagaagcc agatatccag   2940

cccattgcca gccattccat cgacgccctg tgctctttcg ctgtggggag tgctgacgca   3000

gaacgcgatc agaatggatt tgactacctg gatggcaaga ccgtgctggg actgtatcca   3060

cagagctgtg aggtcattca cctgcaggcc aagccccagg aggaaaaaag tcatttcgat   3120

tcagtggcta tctttaagga aggcatctac gcagagcagt tcctgcctat ctttaccctg   3180

aacgaaaaga tctggattgg atatgagaca ctgaatgcca aaggcgaaag atgcggggct   3240

attgaggtga gtggcaaaca gccaaaggag ctgctggaaa tgctggcccc cttctttaac   3300

aagcctgtgg gcgacctgtc agcccacgct acttaccgga tcctgaaaaa gcctgcatat   3360

gagtttctgg caaaggcagc tctgcagcca ctgagcgcag aggaaaaaag actggcagcc   3420

ctgctggatg ctctgcgcta ctgtaccagt cgaaagtcac tgatgagcct gttcatggct   3480

gcaaacggga aatccctgaa aaagcgggag gacgtgctga aacccaagct gttccagctg   3540

aaggtcgagc tgaaaggcga aaagagcttc aagctgaacg ggagcctgac cctgcctgtg   3600

aagcaggact ggctgagaat ctgcgatagc ccagaactgg cagacgcctt tggcaaaccc   3660

tgttccgccg atgagctgac atctaagctg gctcgcattt ggaaacgacc tgtgatgcgg   3720

gatctggctc atgcaccagt ccggagagag ttcagcctgc ccgcaatcga caacccaagt   3780

ggagggttca ggattaggcg caccaacctg tttggcaatg agctgtacca ggtgcacgcc   3840

atcaacgcta aaaagtatcg cggcttcgcc tccgctgggt ctaatgtcga ctggtccaag   3900

gggatcctgt ttaacgagct gcagcatgaa aatctgaccg agtgcggagg caggttcatt   3960

acaagcgccg atgtgactcc tatgtccgaa tggcgcaagg tggtcgcaga ggacaacctg   4020

tctatctgga ttgctccagg gacagaagga cgacggtacg tgagggtcga gacaacattc   4080

atccaggcca gtcactggtt tgaacagtca gtggagaatt gggccattac tagtcctctg   4140

tcactgccag cttccttcaa ggtggacaaa ccagctgagt ttcagaaggc agtcggaacc   4200

gagctgtcag aactgctggg ccagcccagg agcgaaatct tcattgagaa cgtgggcaat   4260

gccaagcata tccgcttttg gtacattgtg gtgagcagca acaaaaagat gaacgagtct   4320

tacaacaatg tgtctaagag ttaagaattc                                    4350
```

<210> SEQ ID NO 164
<211> LENGTH: 112
<212> TYPE: RNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 164

```
nnnnnnnnnn nnnnnnnnnn guuucagugg ugaaaacccu gaaaucaaca aaauuaaaga     60

uugaaucguu uuucuaugcu cgucuuaaua gcgagcauau aacgauuuuu uu            112
```

<210> SEQ ID NO 165

<211> LENGTH: 1372
<212> TYPE: PRT
<213> ORGANISM: Legionella pneumophila

<400> SEQUENCE: 165

Met Glu Ser Ser Gln Ile Leu Ser Pro Ile Gly Ile Asp Leu Gly Gly
1 5 10 15

Lys Phe Thr Gly Val Cys Leu Ser His Leu Glu Ala Phe Ala Glu Leu
20 25 30

Pro Asn His Ala Asn Thr Lys Tyr Ser Val Ile Leu Ile Asp His Asn
35 40 45

Asn Phe Gln Leu Ser Gln Ala Gln Arg Arg Ala Thr Arg His Arg Val
50 55 60

Arg Asn Lys Lys Arg Asn Gln Phe Val Lys Arg Val Ala Leu Gln Leu
65 70 75 80

Phe Gln His Ile Leu Ser Arg Asp Leu Asn Ala Lys Glu Glu Thr Ala
85 90 95

Leu Cys His Tyr Leu Asn Asn Arg Gly Tyr Thr Tyr Val Asp Thr Asp
100 105 110

Leu Asp Glu Tyr Ile Lys Asp Glu Thr Thr Ile Asn Leu Leu Lys Glu
115 120 125

Leu Leu Pro Ser Glu Ser Glu His Asn Phe Ile Asp Trp Phe Leu Gln
130 135 140

Lys Met Gln Ser Ser Glu Phe Arg Lys Ile Leu Val Ser Lys Val Glu
145 150 155 160

Glu Lys Lys Asp Asp Lys Glu Leu Lys Asn Ala Val Lys Asn Ile Lys
165 170 175

Asn Phe Ile Thr Gly Phe Glu Lys Asn Ser Val Glu Gly His Arg His
180 185 190

Arg Lys Val Tyr Phe Glu Asn Ile Lys Ser Asp Ile Thr Lys Asp Asn
195 200 205

Gln Leu Asp Ser Ile Lys Lys Lys Ile Pro Ser Val Cys Leu Ser Asn
210 215 220

Leu Leu Gly His Leu Ser Asn Leu Gln Trp Lys Asn Leu His Arg Tyr
225 230 235 240

Leu Ala Lys Asn Pro Lys Gln Phe Asp Glu Gln Thr Phe Gly Asn Glu
245 250 255

Phe Leu Arg Met Leu Lys Asn Phe Arg His Leu Lys Gly Ser Gln Glu
260 265 270

Ser Leu Ala Val Arg Asn Leu Ile Gln Gln Leu Glu Gln Ser Gln Asp
275 280 285

Tyr Ile Ser Ile Leu Glu Lys Thr Pro Pro Glu Ile Thr Ile Pro Pro
290 295 300

Tyr Glu Ala Arg Thr Asn Thr Gly Met Glu Lys Asp Gln Ser Leu Leu
305 310 315 320

Leu Asn Pro Glu Lys Leu Asn Asn Leu Tyr Pro Asn Trp Arg Asn Leu
325 330 335

Ile Pro Gly Ile Ile Asp Ala His Pro Phe Leu Glu Lys Asp Leu Glu
340 345 350

His Thr Lys Leu Arg Asp Arg Lys Arg Ile Ile Ser Pro Ser Lys Gln
355 360 365

Asp Glu Lys Arg Asp Ser Tyr Ile Leu Gln Arg Tyr Leu Asp Leu Asn
370 375 380

Lys Lys Ile Asp Lys Phe Lys Ile Lys Lys Gln Leu Ser Phe Leu Gly

```
385                 390                 395                 400

Gln Gly Lys Gln Leu Pro Ala Asn Leu Ile Glu Thr Gln Lys Glu Met
                405                 410                 415

Glu Thr His Phe Asn Ser Ser Leu Val Ser Val Leu Ile Gln Ile Ala
            420                 425                 430

Ser Ala Tyr Asn Lys Glu Arg Glu Asp Ala Ala Gln Gly Ile Trp Phe
        435                 440                 445

Asp Asn Ala Phe Ser Leu Cys Glu Leu Ser Asn Ile Asn Pro Pro Arg
    450                 455                 460

Lys Gln Lys Ile Leu Pro Leu Leu Val Gly Ala Ile Leu Ser Glu Asp
465                 470                 475                 480

Phe Ile Asn Asn Lys Asp Lys Trp Ala Lys Phe Lys Ile Phe Trp Asn
                485                 490                 495

Thr His Lys Ile Gly Arg Thr Ser Leu Lys Ser Lys Cys Lys Glu Ile
            500                 505                 510

Glu Glu Ala Arg Lys Asn Ser Gly Asn Ala Phe Lys Ile Asp Tyr Glu
        515                 520                 525

Glu Ala Leu Asn His Pro Glu His Ser Asn Asn Lys Ala Leu Ile Lys
    530                 535                 540

Ile Ile Gln Thr Ile Pro Asp Ile Ile Gln Ala Ile Gln Ser His Leu
545                 550                 555                 560

Gly His Asn Asp Ser Gln Ala Leu Ile Tyr His Asn Pro Phe Ser Leu
                565                 570                 575

Ser Gln Leu Tyr Thr Ile Leu Glu Thr Lys Arg Asp Gly Phe His Lys
            580                 585                 590

Asn Cys Val Ala Val Thr Cys Glu Asn Tyr Trp Arg Ser Gln Lys Thr
        595                 600                 605

Glu Ile Asp Pro Glu Ile Ser Tyr Ala Ser Arg Leu Pro Ala Asp Ser
    610                 615                 620

Val Arg Pro Phe Asp Gly Val Leu Ala Arg Met Met Gln Arg Leu Ala
625                 630                 635                 640

Tyr Glu Ile Ala Met Ala Lys Trp Glu Gln Ile Lys His Ile Pro Asp
                645                 650                 655

Asn Ser Ser Leu Leu Ile Pro Ile Tyr Leu Glu Gln Asn Arg Phe Glu
            660                 665                 670

Phe Glu Glu Ser Phe Lys Lys Ile Lys Gly Ser Ser Ser Asp Lys Thr
        675                 680                 685

Leu Glu Gln Ala Ile Glu Lys Gln Asn Ile Gln Trp Glu Glu Lys Phe
    690                 695                 700

Gln Arg Ile Ile Asn Ala Ser Met Asn Ile Cys Pro Tyr Lys Gly Ala
705                 710                 715                 720

Ser Ile Gly Gly Gln Gly Glu Ile Asp His Ile Tyr Pro Arg Ser Leu
                725                 730                 735

Ser Lys Lys His Phe Gly Val Ile Phe Asn Ser Glu Val Asn Leu Ile
            740                 745                 750

Tyr Cys Ser Ser Gln Gly Asn Arg Glu Lys Lys Glu Glu His Tyr Leu
        755                 760                 765

Leu Glu His Leu Ser Pro Leu Tyr Leu Lys His Gln Phe Gly Thr Asp
    770                 775                 780

Asn Val Ser Asp Ile Lys Asn Phe Ile Ser Gln Asn Val Ala Asn Ile
785                 790                 795                 800

Lys Lys Tyr Ile Ser Phe His Leu Leu Thr Pro Glu Gln Gln Lys Ala
                805                 810                 815
```

```
Ala Arg His Ala Leu Phe Leu Asp Tyr Asp Asp Glu Ala Phe Lys Thr
            820                 825                 830

Ile Thr Lys Phe Leu Met Ser Gln Gln Lys Ala Arg Val Asn Gly Thr
        835                 840                 845

Gln Lys Phe Leu Gly Lys Gln Ile Met Glu Phe Leu Ser Thr Leu Ala
    850                 855                 860

Asp Ser Lys Gln Leu Gln Leu Glu Phe Ser Ile Lys Gln Ile Thr Ala
865                 870                 875                 880

Glu Glu Val His Asp His Arg Glu Leu Leu Ser Lys Gln Glu Pro Lys
                885                 890                 895

Leu Val Lys Ser Arg Gln Gln Ser Phe Pro Ser His Ala Ile Asp Ala
            900                 905                 910

Thr Leu Thr Met Ser Ile Gly Leu Lys Glu Phe Pro Gln Phe Ser Gln
        915                 920                 925

Glu Leu Asp Asn Ser Trp Phe Ile Asn His Leu Met Pro Asp Glu Val
    930                 935                 940

His Leu Asn Pro Val Arg Ser Lys Glu Lys Tyr Asn Lys Pro Asn Ile
945                 950                 955                 960

Ser Ser Thr Pro Leu Phe Lys Asp Ser Leu Tyr Ala Glu Arg Phe Ile
                965                 970                 975

Pro Val Trp Val Lys Gly Glu Thr Phe Ala Ile Gly Phe Ser Glu Lys
            980                 985                 990

Asp Leu Phe Glu Ile Lys Pro Ser  Asn Lys Glu Lys Leu  Phe Thr Leu
        995                 1000                1005

Leu Lys  Thr Tyr Ser Thr Lys  Asn Pro Gly Glu Ser  Leu Gln Glu
    1010                1015                1020

Leu Gln  Ala Lys Ser Lys Ala  Lys Trp Leu Tyr Phe  Pro Ile Asn
    1025                1030                1035

Lys Thr  Leu Ala Leu Glu Phe  Leu His His Tyr Phe  His Lys Glu
    1040                1045                1050

Ile Val  Thr Pro Asp Asp Thr  Thr Val Cys His Phe  Ile Asn Ser
    1055                1060                1065

Leu Arg  Tyr Tyr Thr Lys Lys  Glu Ser Ile Thr Val  Lys Ile Leu
    1070                1075                1080

Lys Glu  Pro Met Pro Val Leu  Ser Val Lys Phe Glu  Ser Ser Lys
    1085                1090                1095

Lys Asn  Val Leu Gly Ser Phe  Lys His Thr Ile Ala  Leu Pro Ala
    1100                1105                1110

Thr Lys  Asp Trp Glu Arg Leu  Phe Asn His Pro Asn  Phe Leu Ala
    1115                1120                1125

Leu Lys  Ala Asn Pro Ala Pro  Asn Pro Lys Glu Phe  Asn Glu Phe
    1130                1135                1140

Ile Arg  Lys Tyr Phe Leu Ser  Asp Asn Asn Pro Asn  Ser Asp Ile
    1145                1150                1155

Pro Asn  Asn Gly His Asn Ile  Lys Pro Gln Lys His  Lys Ala Val
    1160                1165                1170

Arg Lys  Val Phe Ser Leu Pro  Val Ile Pro Gly Asn  Ala Gly Thr
    1175                1180                1185

Met Met  Arg Ile Arg Arg Lys  Asp Asn Lys Gly Gln  Pro Leu Tyr
    1190                1195                1200

Gln Leu  Gln Thr Ile Asp Asp  Thr Pro Ser Met Gly  Ile Gln Ile
    1205                1210                1215
```

```
Asn Glu  Asp Arg Leu Val Lys  Gln Glu Val Leu Met  Asp Ala Tyr
    1220                 1225                 1230

Lys Thr  Arg Asn Leu Ser Thr  Ile Asp Gly Ile Asn  Asn Ser Glu
    1235                 1240                 1245

Gly Gln  Ala Tyr Ala Thr Phe  Asp Asn Trp Leu Thr  Leu Pro Val
    1250                 1255                 1260

Ser Thr  Phe Lys Pro Glu Ile  Ile Lys Leu Glu Met  Lys Pro His
    1265                 1270                 1275

Ser Lys  Thr Arg Arg Tyr Ile  Arg Ile Thr Gln Ser  Leu Ala Asp
    1280                 1285                 1290

Phe Ile  Lys Thr Ile Asp Glu  Ala Leu Met Ile Lys  Pro Ser Asp
    1295                 1300                 1305

Ser Ile  Asp Asp Pro Leu Asn  Met Pro Asn Glu Ile  Val Cys Lys
    1310                 1315                 1320

Asn Lys  Leu Phe Gly Asn Glu  Leu Lys Pro Arg Asp  Gly Lys Met
    1325                 1330                 1335

Lys Ile  Val Ser Thr Gly Lys  Ile Val Thr Tyr Glu  Phe Glu Ser
    1340                 1345                 1350

Asp Ser  Thr Pro Gln Trp Ile  Gln Thr Leu Tyr Val  Thr Gln Leu
    1355                 1360                 1365

Lys Lys  Gln Pro
    1370
```

<210> SEQ ID NO 166
<211> LENGTH: 4200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 166

```
accggtgcca ccatgtaccc atacgatgtt ccagattacg cttcgccgaa gaaaaagcgc     60

aaggtcgaag cgtccatgga gtcctctcag atcctgtcac ctatcggcat cgacctgggc    120

ggaaagttta ctggagtctg cctgtcacac ctggaagcat ttgctgagct gcctaaccac    180

gcaaatacaa agtactcagt gatcctgatt gatcataaca atttccagct gagccaggca    240

cagcggagag ccactagaca cagggtgcgc aacaagaaaa gaaatcagtt cgtgaagagg    300

gtcgccctgc agctgtttca gcacatcctg tcccgggacc tgaacgccaa ggaggaaacc    360

gctctgtgcc attacctgaa caatagaggc tacacctatg tggacacaga tctggacgag    420

tatatcaaag atgaaaccac aattaacctg ctgaaggagc tgctgccaag cgagtccgaa    480

cataatttca ttgactggtt tctgcagaag atgcagagct ccgagttccg gaagatcctg    540

gtgagcaaag tcgaggaaaa gaaagacgat aaagaactga agaacgccgt gaagaacatc    600

aagaacttca tcaccggatt cgagaaaaat agcgtggaag gccaccgaca tcggaaggtc    660

tactttgaga acatcaagtc cgatattaca aaagacaatc agctggattc tatcaagaaa    720

aagattccta gcgtgtgtct gtccaacctg ctgggccacc tgtccaacct gcagtggaag    780

aatctgcata ggtatctggc caaaaatcca aagcagttcg acgagcagac cttcgggaac    840

gaatttctgc ggatgctgaa gaattttcga cacctgaaag gatctcagga gagtctggct    900

gtgcgcaacc tgatccagca gctggaacag tctcaggatt acatcagtat cctggagaaa    960

acccccccctg aaatcaccat tccaccctat gaggcccgga caaacactgg catggaaaaa   1020

gaccagagcc tgctgctgaa ccccgagaag ctgaacaatc tgtacccaaa ctggagaaat   1080
```

```
ctgatccccg ggatcattga cgcccaccct ttcctggaga aggatctgga acatacaaag   1140
ctgagagaca ggaaacgcat catttctccc agtaaacagg acgagaagcg ggatagctac   1200
atcctgcaga gatatctgga cctgaacaaa aagatcgata agttcaagat caagaagcag   1260
ctgagctttc tgggacaggg caaacagctg cctgctaacc tgatcgagac acagaaggag   1320
atggaaactc acttcaattc tagtctggtg tctgtcctga tccagattgc tagtgcatac   1380
aacaaggaga gggaagatgc cgctcagggg atctggttcg acaatgcctt ttcactgtgc   1440
gagctgagca acatcaatcc tccacgcaaa cagaagattc tgcccctgct ggtgggagca   1500
atcctgagcg aggacttcat taacaacaag gataagtggg ccaaattcaa gatcttttgg   1560
aacacccaca agattgggcg aacatcactg aaaagcaagt gtaaagagat cgaggaagcc   1620
cggaagaaca gtggaaacgc ttttaaaatc gactacgagg aagctctgaa tcacccagag   1680
cattcaaaca acaaggccct gatcaagatc attcagacca ttcccgatat cattcaggcc   1740
atccagtcac acctgggaca taacgacagc caggctctga tctaccacaa tcctttctca   1800
ctgagccagc tgtatactat cctggagaca aagagggatg gctttcataa aaactgcgtg   1860
gccgtcactt gtgaaaatta ctggcggagc cagaaaaccg agatcgaccc agaaatttcc   1920
tatgcatcta ggctgccagc agacagtgtg cgccccttcg atggcgtcct ggcacgaatg   1980
atgcagcggc tggcctacga gatcgccatg gctaagtggg aacagatcaa acacattcct   2040
gataactcaa gcctgctgat cccaatctac ctggagcaga atcggttcga atttgaggag   2100
agcttcaaga agatcaaggg gtcctctagt gacaaaaccc tggagcaggc catcgaaaag   2160
cagaacattc agtgggagga aaagttccag agaatcatta acgcaagtat gaatatctgc   2220
ccttacaagg gcgcctcaat tggcgggcag gggggagatcg accacatcta cccaaggtcc   2280
ctgtctaaaa agcatttcgg cgtgatcttt aactccgaag tcaatctgat ctactgttca   2340
agccagggga atcgcgagaa aaaggaggaa cactacctgc tggaacatct gtctccactg   2400
tatctgaaac accagttcgg cactgacaac gtgtccgata tcaagaattt tatttctcag   2460
aacgtcgcta atatcaaaaa gtacatttcc ttccacctgc tgaccccaga gcagcagaag   2520
gcagcacggc acgccctgtt tctggattat gacgatgaag cattcaaaac cattacaaag   2580
tttctgatgt ctcagcagaa ggccagagtg aacggcacac agaaattcct ggggaagcag   2640
atcatggagt ttctgtccac tctggcagat tctaaacagc tgcagctgga gttcagcatc   2700
aagcagatta ccgccgagga agtgcacgac catagagagc tgctgtctaa gcaggaaccc   2760
aaactggtca agagtaggca gcagagtttc ccttcacacg ctatcgacgc aactctgacc   2820
atgtctattg ggctgaagga gttcccacag tttagtcagg aactggataa ctcatggttt   2880
atcaatcacc tgatgccaga cgaggtgcat ctgaaccccg tccggagcaa ggaaaagtac   2940
aacaaaccta acatctcctc tactccactg ttcaaggatt ccctgtatgc tgagcggttc   3000
atccccgtgt gggtcaaggg agaaaccttc gcaatcggct ttagcgagaa ggacctgttc   3060
gagatcaagc cctccaacaa ggagaaactg tttacactgc tgaaaaccta cagtactaaa   3120
aatcctggcg agtcactgca ggaactgcag gctaagagca aagcaaagtg gctgtacttc   3180
ccaatcaaca aaaccctggc cctggagttc ctgcaccatt attttcacaa ggaaatcgtg   3240
acacccgacg atactaccgt ctgccatttc atcaactcac tgagatacta cactaaaaag   3300
gagagcatca ccgtgaaaat tctgaaggaa cccatgcctg tgctgtccgt caagttcgag   3360
agttcaaaaa agaacgtgct gggatctttt aaacacacaa tcgccctgcc tgctactaag   3420
```

gattgggaga ggctgttcaa ccatccaaat tttctggcac tgaaggccaa cccagctccc 3480
aatcctaaag agttcaatga gttcatccgc aagtacttcc tgagcgacaa caatcccaac 3540
tccgatatcc ctaacaatgg ccacaatatc aagccccaga aacataaggc cgtgcgaaag 3600
gtctttagcc tgccagtgat ccccgggaac gctggaacca tgatgcgcat taggcgcaaa 3660
gacaataagg gacagccact gtatcagctg cagacaatcg acgatactcc cagcatgggc 3720
atccagatta acgaggatcg cctggtgaaa caggaagtcc tgatggacgc ctacaagaca 3780
cgaaatctga gcactatcga tgggattaac aattccgagg gacaggcata tgccacattc 3840
gacaactggc tgaccctgcc cgtgagcacc ttcaagcctg agatcatcaa gctggaaatg 3900
aagcctcact ctaaaacccg acggtacatc agaattacac agagtctggc cgacttcatc 3960
aaaactattg atgaggctct gatgatcaag cccagtgact caattgacga tcctctgaac 4020
atgccaaatg agatcgtgtg taaaaacaag ctgttcggga atgaactgaa gcctagggat 4080
ggaaaaatga agatcgtgag cactggcaag attgtcacct acgagtttga aagcgactcc 4140
accccccagt ggatccagac cctgtatgtg acacagctga aaaagcagcc ttaagaattc 4200

<210> SEQ ID NO 167
<211> LENGTH: 127
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 167
nnnnnnnnnn nnnnnnnnnn guuugagagu uggaaacaac gaguucaaau aagaauucau 60
caaaaucguc ccuuuuggga ccgcucauug uggagcauca aggcuuaaca ugguuaagcc 120
uuuuuuu 127

<210> SEQ ID NO 168
<211> LENGTH: 1395
<212> TYPE: PRT
<213> ORGANISM: Treponema denticola

<400> SEQUENCE: 168

Met Lys Lys Glu Ile Lys Asp Tyr Phe Leu Gly Leu Asp Val Gly Thr
1 5 10 15

Gly Ser Val Gly Trp Ala Val Thr Asp Thr Asp Tyr Lys Leu Leu Lys
20 25 30

Ala Asn Arg Lys Asp Leu Trp Gly Met Arg Cys Phe Glu Thr Ala Glu
35 40 45

Thr Ala Glu Val Arg Arg Leu His Arg Gly Ala Arg Arg Arg Ile Glu
50 55 60

Arg Arg Lys Lys Arg Ile Lys Leu Leu Gln Glu Leu Phe Ser Gln Glu
65 70 75 80

Ile Ala Lys Thr Asp Glu Gly Phe Phe Gln Arg Met Lys Glu Ser Pro
85 90 95

Phe Tyr Ala Glu Asp Lys Thr Ile Leu Gln Glu Asn Thr Leu Phe Asn
100 105 110

Asp Lys Asp Phe Ala Asp Lys Thr Tyr His Lys Ala Tyr Pro Thr Ile
115 120 125

```
Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
            500                 505                 510

Glu Ala Phe Ile Thr Ser Arg Thr Asn Phe Cys Thr Tyr Leu Val Gly
        515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Ile Asp Gly Lys Asn Ile
```

-continued

```
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
        595                 600                 605

Glu Cys Thr Ser Ser Leu Lys Ser Tyr Ile Glu Leu Lys Asn Ile Phe
    610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
            660                 665                 670

Ile Lys Lys Ile Leu Asn Leu Lys Phe Ser Gly Trp Gly Arg Leu Ser
        675                 680                 685

Arg Lys Phe Leu Glu Thr Val Thr Ser Glu Met Pro Gly Phe Ser Glu
    690                 695                 700

Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
                725                 730                 735

Asn Ser Gly Phe Glu Asp Ala Glu Lys Gln Phe Ser Tyr Asp Gly Leu
            740                 745                 750

Val Lys Pro Leu Phe Leu Ser Pro Ser Val Lys Lys Met Leu Trp Gln
        755                 760                 765

Thr Leu Lys Leu Val Lys Glu Ile Ser His Ile Thr Gln Ala Pro Pro
    770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
                805                 810                 815

Lys Asn Asp Ala Asp Ala Phe Ser Ser Glu Ile Lys Asp Leu Ser Gly
            820                 825                 830

Lys Ile Glu Asn Glu Asp Asn Leu Arg Leu Arg Ser Asp Lys Leu Tyr
        835                 840                 845

Leu Tyr Tyr Thr Gln Leu Gly Lys Cys Met Tyr Cys Gly Lys Pro Ile
    850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
                885                 890                 895

Val Cys Ser Ser Cys Asn Lys Asn Lys Glu Asp Lys Tyr Pro Leu Lys
            900                 905                 910

Ser Glu Ile Gln Ser Lys Gln Arg Gly Phe Trp Asn Phe Leu Gln Arg
        915                 920                 925

Asn Asn Phe Ile Ser Leu Glu Lys Leu Asn Arg Leu Thr Arg Ala Thr
    930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
                965                 970                 975
```

Phe Pro Glu Thr Lys Ile Val Tyr Ser Lys Ala Glu Thr Val Ser Met
980 985 990

Phe Arg Asn Lys Phe Asp Ile Val Lys Cys Arg Glu Ile Asn Asp Phe
995 1000 1005

His His Ala His Asp Ala Tyr Leu Asn Ile Val Val Gly Asn Val
1010 1015 1020

Tyr Asn Thr Lys Phe Thr Asn Asn Pro Trp Asn Phe Ile Lys Glu
1025 1030 1035

Lys Arg Asp Asn Pro Lys Ile Ala Asp Thr Tyr Asn Tyr Tyr Lys
1040 1045 1050

Val Phe Asp Tyr Asp Val Lys Arg Asn Asn Ile Thr Ala Trp Glu
1055 1060 1065

Lys Gly Lys Thr Ile Ile Thr Val Lys Asp Met Leu Lys Arg Asn
1070 1075 1080

Thr Pro Ile Tyr Thr Arg Gln Ala Ala Cys Lys Lys Gly Glu Leu
1085 1090 1095

Phe Asn Gln Thr Ile Met Lys Lys Gly Leu Gly Gln His Pro Leu
1100 1105 1110

Lys Lys Glu Gly Pro Phe Ser Asn Ile Ser Lys Tyr Gly Gly Tyr
1115 1120 1125

Asn Lys Val Ser Ala Ala Tyr Tyr Thr Leu Ile Glu Tyr Glu Glu
1130 1135 1140

Lys Gly Asn Lys Ile Arg Ser Leu Glu Thr Ile Pro Leu Tyr Leu
1145 1150 1155

Val Lys Asp Ile Gln Lys Asp Gln Asp Val Leu Lys Ser Tyr Leu
1160 1165 1170

Thr Asp Leu Leu Gly Lys Lys Glu Phe Lys Ile Leu Val Pro Lys
1175 1180 1185

Ile Lys Ile Asn Ser Leu Leu Lys Ile Asn Gly Phe Pro Cys His
1190 1195 1200

Ile Thr Gly Lys Thr Asn Asp Ser Phe Leu Leu Arg Pro Ala Val
1205 1210 1215

Gln Phe Cys Cys Ser Asn Asn Glu Val Leu Tyr Phe Lys Lys Ile
1220 1225 1230

Ile Arg Phe Ser Glu Ile Arg Ser Gln Arg Glu Lys Ile Gly Lys
1235 1240 1245

Thr Ile Ser Pro Tyr Glu Asp Leu Ser Phe Arg Ser Tyr Ile Lys
1250 1255 1260

Glu Asn Leu Trp Lys Lys Thr Lys Asn Asp Glu Ile Gly Glu Lys
1265 1270 1275

Glu Phe Tyr Asp Leu Leu Gln Lys Lys Asn Leu Glu Ile Tyr Asp
1280 1285 1290

Met Leu Leu Thr Lys His Lys Asp Thr Ile Tyr Lys Lys Arg Pro
1295 1300 1305

Asn Ser Ala Thr Ile Asp Ile Leu Val Lys Gly Lys Glu Lys Phe
1310 1315 1320

Lys Ser Leu Ile Ile Glu Asn Gln Phe Glu Val Ile Leu Glu Ile
1325 1330 1335

Leu Lys Leu Phe Ser Ala Thr Arg Asn Val Ser Asp Leu Gln His
1340 1345 1350

Ile Gly Gly Ser Lys Tyr Ser Gly Val Ala Lys Ile Gly Asn Lys
1355 1360 1365

```
Ile Ser  Ser Leu Asp Asn Cys  Ile Leu Ile Tyr Gln  Ser Ile Thr
    1370                 1375                 1380

Gly Ile  Phe Glu Lys Arg Ile  Asp Leu Leu Lys Val
    1385                 1390                 1395
```

<210> SEQ ID NO 169
<211> LENGTH: 4269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
accggtgcca ccatgtaccc atacgatgtt ccagattacg cttcgccgaa gaaaaagcgc     60

aaggtcgaag cgtccatgaa aaaagaaatc aaagactact tcctggggct ggatgtgggg    120

actgggagcg tggggtgggc tgtgaccgat actgactaca aactgctgaa ggctaaccga    180

aaagacctgt ggggcatgag atgcttcgag acagccgaaa ctgctgaggt gcggagactg    240

cacaggggag ccaggcgccg aatcgagcgg agaaagaaac gcattaagct gctgcaggag    300

ctgttctctc aggaaatcgc caaaaccgat gagggcttct ttcagagaat gaaggaaagc    360

ccctttacg ctgaggacaa aacaatcctg caggaaaaca ctctgttcaa tgacaaggat     420

tttgctgata agacttacca caaagcatat cctaccatta atcatctgat caaggcttgg    480

attgagaaca aggtgaaacc agacccccga ctgctgtacc tggcatgtca caacatcatt    540

aagaaaaggg gacatttcct gtttgaaggc gacttcgatt cagagaatca gtttgatacc    600

agcatccagg cactgttcga gtatctgcgc gaggacatgg aggtggacat cgatgccgac    660

agccagaagg tcaaagagat tctgaaggat agctccctga agaactctga aaaacagagt    720

cggctgaata agatcctggg gctgaagcct tccgacaaac agaagaaagc catcacaaac    780

ctgatttctg gaaacaagat caatttcgcc gatctgtacg acaatccaga tctgaaggac    840

gctgagaaaa actcaatcag cttctccaag gacgattttg atgcactgag tgacgatctg    900

gcctcaattc tgggcgacag ctttgaactg ctgctgaagg ccaaagctgt ctataactgc    960

tctgtgctga gtaaggtcat cggggacgag cagtacctga gcttcgccaa ggtgaaaatc   1020

tacgaaaagc acaaaaccga tctgacaaag ctgaaaaacg tgatcaagaa acatttcccc   1080

aaggactaca agaaggtctt tggatacaac aagaacgaga aaaacaacaa caattactcc   1140

ggctatgtgg gagtctgtaa gaccaagagt aagaaactga tcattaacaa ctcagtcaac   1200

caggaagatt tctacaagtt tctgaaaact atcctgtcag ccaagagcga gatcaaggaa   1260

gtgaatgaca tcctgaccga gattgaaact ggcacctttc tgccaaagca gatctctaaa   1320

agtaacgcag agattcccta tcagctgagg aaaatggagc tggaaaagat cctgtccaat   1380

gccgaaaagc acttctcttt tctgaagcag aaagacgaaa aggactgtc acatagcgag    1440

aagatcatta tgctgctgac cttcaagatc ccttactata ttggcccaat caacgataat   1500

cacaagaaat tctttcccga cagatgctgg gtggtcaaga aagagaaatc cccttctggc   1560

aagaccacac catggaactt ctttgatcat atcgacaagg aaaaaacagc agaggccttc   1620

attacttcta ggaccaattt ttgcacttac ctggtgggag agagcgtcct gcctaagtct   1680

agtctgctgt actccgaata taccgtgctg aacgagatca acaatctgca gatcattatc   1740

gatggcaaga atatttgtga catcaagctg aaacagaaga tctacgagga cctgttcaag   1800

aagtacaaga aaattaccca gaagcagatc agcaccttca tcaagcacga aggcatctgc   1860
```

-continued aacaaaaccg atgaagtgat catcctgggg attgacaagg aatgtacatc aagcctgaaa 1920
agctacatcg agctgaaaaa cattttcggc aagcaggtgg atgagatctc cactaagaat 1980
atgctggagg aaattatcag atgggctacc atctacgacg agggggaagg aaagaccatc 2040
ctgaaaacaa agatcaaggc agaatacgga aagtattgct ccgacgagca gattaagaaa 2100
atcctgaacc tgaagttctc cggctggggg cgactgtctc ggaaatttct ggagacagtg 2160
actagtgaaa tgcccggctt ctcagaacct gtcaatatta tcaccgccat gagggagaca 2220
cagaacaatc tgatggagct gctgtcctct gagttcacct tcaccgagaa cattaagaaa 2280
atcaattctg gattcgaaga tgccgagaag cagtttagtt acgacggcct ggtgaaacca 2340
ctgtttctga gtccctcagt caagaaaatg ctgtggcaga ccctgaagct ggtgaaagag 2400
attagccata tcacacaggc ccccccctaag aaaattttca tcgaaatggc aaagggggcc 2460
gagctggaac ctgctcggac taagaccaga ctgaaaatcc tgcaggatct gtataacaat 2520
tgtaagaacg atgctgacgc cttcagctca gagatcaaag acctgagcgg aaagattgag 2580
aacgaagata atctgaggct gcgctccgac aagctgtacc tgtactatac tcagctgggg 2640
aaatgcatgt attgtggaaa gccaattgag atcggccacg tgttcgatac ctcaaactac 2700
gatattgacc atatctatcc ccagagcaag atcaaagacg atagcatttc caatcgggtg 2760
ctggtctgca gctcctgtaa caagaacaag gaggacaagt acccactgaa atcagagatc 2820
cagagcaagc agcgcggctt ctggaacttt ctgcagcgaa acaatttcat ttctctggag 2880
aagctgaata gactgacaag ggccactcca atcagtgacg atgagacagc caagtttatt 2940
gctaggcagc tggtggaaac tcgccaggct accaaggtgg ccgctaaagt cctggaaaag 3000
atgttccccg agacaaaaat cgtgtacagc aaggccgaga ctgtctccat gttccggaac 3060
aagtttgata tcgtgaagtg cagagaaatt aacgattttc accatgctca cgacgcatac 3120
ctgaatatcg tggtcggcaa cgtgtataat accaagttca caaacaatcc ttggaacttt 3180
atcaaggaga aaagagataa tccaaagatt gctgacacct acaactacta taaggtgttc 3240
gattatgacg tcaaaaggaa caatatcaca gcatgggaga aggggaaaac tattatcacc 3300
gtgaaagaca tgctgaagag aaacacacca atctacacta ggcaggcagc ctgtaagaaa 3360
ggggagctgt tcaatcagac cattatgaag aaaggactgg gccagcaccc cctgaagaaa 3420
gaaggacctt tttccaatat ctctaaatac ggcgggtata acaaggtgag cgctgcatac 3480
tatacactga ttgagtatga ggaaaagggc aacaaaatcc gctccctgga aactattccc 3540
ctgtacctgg tgaaagatat ccagaaggat caggacgtcc tgaagtctta tctgacagac 3600
ctgctgggga agaaagagtt caagatcctg gtgcccaaga tcaagatcaa cagcctgctg 3660
aagatcaatg ggtttccttg ccatattaca ggaaaaacta acgatagttt cctgctgcgc 3720
cctgccgtgc agttttgctg ttcaaacaat gaggtcctgt acttcaagaa aattatccgg 3780
ttttccgaaa tccgctctca gcgagagaag atcgggaaaa caattagccc atacgaggac 3840
ctgagcttcc ggtcatatat caaggagaac ctgtggaaga aaactaagaa cgatgaaatc 3900
ggagagaagg aattttacga cctgctgcag aagaaaaacc tggagatcta tgatatgctg 3960
ctgactaagc acaaagacac catctacaag aaacgcccta attctgccac cattgatatc 4020
ctggtgaagg ggaaagagaa gttcaaaagc ctgattatcg aaaaccagtt tgaagtgatc 4080
ctggagatcc tgaagctgtt ttctgcaaca cggaatgtca gtgacctgca gcatatcgga 4140
ggcagcaagt actccggcgt ggccaaaatc gggaacaaga tctctagtct ggataactgt 4200
atcctgatct atcagtccat caccggcatc ttcgagaaac ggatcgacct gctgaaggtg 4260
taagaattc 4269

<210> SEQ ID NO 170
<211> LENGTH: 119
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 170
nnnnnnnnnn nnnnnnnnnn guuugagagu aggaaacuac acgguucaaa uaaagaauuu 60
uucuaaucgc ccaaugggcc cauauugaua uggaugaaac ucgcuuagcg aguuuuuuu 119

<210> SEQ ID NO 171
<211> LENGTH: 1365
<212> TYPE: PRT
<213> ORGANISM: Filifactor alocis

<400> SEQUENCE: 171

Met Thr Lys Glu Tyr Tyr Leu Gly Leu Asp Val Gly Thr Asn Ser Val
1 5 10 15

Gly Trp Ala Val Thr Asp Ser Gln Tyr Asn Leu Cys Lys Phe Lys Lys
20 25 30

Lys Asp Met Trp Gly Ile Arg Leu Phe Glu Ser Ala Asn Thr Ala Lys
35 40 45

Asp Arg Arg Leu Gln Arg Gly Asn Arg Arg Arg Leu Glu Arg Lys Lys
50 55 60

Gln Arg Ile Asp Leu Leu Gln Glu Ile Phe Ser Pro Glu Ile Cys Lys
65 70 75 80

Ile Asp Pro Thr Phe Phe Ile Arg Leu Asn Glu Ser Arg Leu His Leu
85 90 95

Glu Asp Lys Ser Asn Asp Phe Lys Tyr Pro Leu Phe Ile Glu Lys Asp
100 105 110

Tyr Ser Asp Ile Glu Tyr Tyr Lys Glu Phe Pro Thr Ile Phe His Leu
115 120 125

Arg Lys His Leu Ile Glu Ser Glu Glu Lys Gln Asp Ile Arg Leu Ile
130 135 140

Tyr Leu Ala Leu His Asn Ile Ile Lys Thr Arg Gly His Phe Leu Ile
145 150 155 160

Asp Gly Asp Leu Gln Ser Ala Lys Gln Leu Arg Pro Ile Leu Asp Thr
165 170 175

Phe Leu Leu Ser Leu Gln Glu Glu Gln Asn Leu Ser Val Ser Leu Ser
180 185 190

Glu Asn Gln Lys Asp Glu Tyr Glu Glu Ile Leu Lys Asn Arg Ser Ile
195 200 205

Ala Lys Ser Glu Lys Val Lys Lys Leu Lys Asn Leu Phe Glu Ile Ser
210 215 220

Asp Glu Leu Glu Lys Glu Glu Lys Lys Ala Gln Ser Ala Val Ile Glu
225 230 235 240

Asn Phe Cys Lys Phe Ile Val Gly Asn Lys Gly Asp Val Cys Lys Phe
245 250 255

Leu Arg Val Ser Lys Glu Glu Leu Glu Ile Asp Ser Phe Ser Phe Ser

```
            260                 265                 270

Glu Gly Lys Tyr Glu Asp Asp Ile Val Lys Asn Leu Glu Glu Lys Val
        275                 280                 285

Pro Glu Lys Val Tyr Leu Phe Glu Gln Met Lys Ala Met Tyr Asp Trp
    290                 295                 300

Asn Ile Leu Val Asp Ile Leu Glu Thr Glu Glu Tyr Ile Ser Phe Ala
305                 310                 315                 320

Lys Val Lys Gln Tyr Glu Lys His Lys Thr Asn Leu Arg Leu Leu Arg
                325                 330                 335

Asp Ile Ile Leu Lys Tyr Cys Thr Lys Asp Glu Tyr Asn Arg Met Phe
            340                 345                 350

Asn Asp Glu Lys Glu Ala Gly Ser Tyr Thr Ala Tyr Val Gly Lys Leu
        355                 360                 365

Lys Lys Asn Asn Lys Lys Tyr Trp Ile Glu Lys Lys Arg Asn Pro Glu
    370                 375                 380

Glu Phe Tyr Lys Ser Leu Gly Lys Leu Leu Asp Lys Ile Glu Pro Leu
385                 390                 395                 400

Lys Glu Asp Leu Glu Val Leu Thr Met Met Ile Glu Glu Cys Lys Asn
                405                 410                 415

His Thr Leu Leu Pro Ile Gln Lys Asn Lys Asp Asn Gly Val Ile Pro
            420                 425                 430

His Gln Val His Glu Val Glu Leu Lys Lys Ile Leu Glu Asn Ala Lys
        435                 440                 445

Lys Tyr Tyr Ser Phe Leu Thr Glu Thr Asp Lys Asp Gly Tyr Ser Val
    450                 455                 460

Val Gln Lys Ile Glu Ser Ile Phe Arg Phe Arg Ile Pro Tyr Tyr Val
465                 470                 475                 480

Gly Pro Leu Ser Thr Arg His Gln Glu Lys Gly Ser Asn Val Trp Met
                485                 490                 495

Val Arg Lys Pro Gly Arg Glu Asp Arg Ile Tyr Pro Trp Asn Met Glu
            500                 505                 510

Glu Ile Ile Asp Phe Glu Lys Ser Asn Glu Asn Phe Ile Thr Arg Met
        515                 520                 525

Thr Asn Lys Cys Thr Tyr Leu Ile Gly Glu Asp Val Leu Pro Lys His
    530                 535                 540

Ser Leu Leu Tyr Ser Lys Tyr Met Val Leu Asn Glu Leu Asn Asn Val
545                 550                 555                 560

Lys Val Arg Gly Lys Lys Leu Pro Thr Ser Leu Lys Gln Lys Val Phe
                565                 570                 575

Glu Asp Leu Phe Glu Asn Lys Ser Lys Val Thr Gly Lys Asn Leu Leu
            580                 585                 590

Glu Tyr Leu Gln Ile Gln Asp Lys Asp Ile Gln Ile Asp Asp Leu Ser
        595                 600                 605

Gly Phe Asp Lys Asp Phe Lys Thr Ser Leu Lys Ser Tyr Leu Asp Phe
    610                 615                 620

Lys Lys Gln Ile Phe Gly Glu Glu Ile Glu Lys Glu Ser Ile Gln Asn
625                 630                 635                 640

Met Ile Glu Asp Ile Ile Lys Trp Ile Thr Ile Tyr Gly Asn Asp Lys
                645                 650                 655

Glu Met Leu Lys Arg Val Ile Arg Ala Asn Tyr Ser Asn Gln Leu Thr
            660                 665                 670

Glu Glu Gln Met Lys Lys Ile Thr Gly Phe Gln Tyr Ser Gly Trp Gly
        675                 680                 685
```

```
Asn Phe Ser Lys Met Phe Leu Lys Gly Ile Ser Gly Ser Asp Val Ser
    690                 695                 700

Thr Gly Glu Thr Phe Asp Ile Ile Thr Ala Met Trp Glu Thr Asp Asn
705                 710                 715                 720

Asn Leu Met Gln Ile Leu Ser Lys Lys Phe Thr Phe Met Asp Asn Val
                725                 730                 735

Glu Asp Phe Asn Ser Gly Lys Val Gly Lys Ile Asp Lys Ile Thr Tyr
            740                 745                 750

Asp Ser Thr Val Lys Glu Met Phe Leu Ser Pro Glu Asn Lys Arg Ala
        755                 760                 765

Val Trp Gln Thr Ile Gln Val Ala Glu Glu Ile Lys Lys Val Met Gly
    770                 775                 780

Cys Glu Pro Lys Lys Ile Phe Ile Glu Met Ala Arg Gly Gly Glu Lys
785                 790                 795                 800

Val Lys Lys Arg Thr Lys Ser Arg Lys Ala Gln Leu Leu Glu Leu Tyr
                805                 810                 815

Ala Ala Cys Glu Glu Asp Cys Arg Glu Leu Ile Lys Glu Ile Glu Asp
            820                 825                 830

Arg Asp Glu Arg Asp Phe Asn Ser Met Lys Leu Phe Leu Tyr Tyr Thr
        835                 840                 845

Gln Phe Gly Lys Cys Met Tyr Ser Gly Asp Asp Ile Asp Ile Asn Glu
    850                 855                 860

Leu Ile Arg Gly Asn Ser Lys Trp Asp Arg Asp His Ile Tyr Pro Gln
865                 870                 875                 880

Ser Lys Ile Lys Asp Asp Ser Ile Asp Asn Leu Val Leu Val Asn Lys
                885                 890                 895

Thr Tyr Asn Ala Lys Lys Ser Asn Glu Leu Leu Ser Glu Asp Ile Gln
            900                 905                 910

Lys Lys Met His Ser Phe Trp Leu Ser Leu Leu Asn Lys Lys Leu Ile
        915                 920                 925

Thr Lys Ser Lys Tyr Asp Arg Leu Thr Arg Lys Gly Asp Phe Thr Asp
    930                 935                 940

Glu Glu Leu Ser Gly Phe Ile Ala Arg Gln Leu Val Glu Thr Arg Gln
945                 950                 955                 960

Ser Thr Lys Ala Ile Ala Asp Ile Phe Lys Gln Ile Tyr Ser Ser Glu
                965                 970                 975

Val Val Tyr Val Lys Ser Ser Leu Val Ser Asp Phe Arg Lys Lys Pro
            980                 985                 990

Leu Asn Tyr Leu Lys Ser Arg Arg  Val Asn Asp Tyr His  His Ala Lys
        995                 1000                1005

Asp Ala  Tyr Leu Asn Ile Val  Val Gly Asn Val Tyr  Asn Lys Lys
    1010                1015                1020

Phe Thr  Ser Asn Pro Ile Gln  Trp Met Lys Lys Asn  Arg Asp Thr
    1025                1030                1035

Asn Tyr  Ser Leu Asn Lys Val  Phe Glu His Asp Val  Val Ile Asn
    1040                1045                1050

Gly Glu  Val Ile Trp Glu Lys  Cys Thr Tyr His Glu  Asp Thr Asn
    1055                1060                1065

Thr Tyr  Asp Gly Gly Thr Leu  Asp Arg Ile Arg Lys  Ile Val Glu
    1070                1075                1080

Arg Asp  Asn Ile Leu Tyr Thr  Glu Tyr Ala Tyr Cys  Glu Lys Gly
    1085                1090                1095
```

-continued

```
Glu Leu  Phe Asn Ala Thr Ile  Gln Asn Lys Asn Gly  Asn Ser Thr
    1100                 1105                 1110

Val Ser  Leu Lys Lys Gly Leu  Asp Val Lys Lys Tyr  Gly Gly Tyr
    1115                 1120                 1125

Phe Ser  Ala Asn Thr Ser Tyr  Phe Ser Leu Ile Glu  Phe Glu Asp
    1130                 1135                 1140

Lys Lys  Gly Asp Arg Ala Arg  His Ile Ile Gly Val  Pro Ile Tyr
    1145                 1150                 1155

Ile Ala  Asn Met Leu Glu His  Ser Pro Ser Ala Phe  Leu Glu Tyr
    1160                 1165                 1170

Cys Glu  Gln Lys Gly Tyr Gln  Asn Val Arg Ile Leu  Val Glu Lys
    1175                 1180                 1185

Ile Lys  Lys Asn Ser Leu Leu  Ile Ile Asn Gly Tyr  Pro Leu Arg
    1190                 1195                 1200

Ile Arg  Gly Glu Asn Glu Val  Asp Thr Ser Phe Lys  Arg Ala Ile
    1205                 1210                 1215

Gln Leu  Lys Leu Asp Gln Lys  Asn Tyr Glu Leu Val  Arg Asn Ile
    1220                 1225                 1230

Glu Lys  Phe Leu Glu Lys Tyr  Val Glu Lys Lys Gly  Asn Tyr Pro
    1235                 1240                 1245

Ile Asp  Glu Asn Arg Asp His  Ile Thr His Glu Lys  Met Asn Gln
    1250                 1255                 1260

Leu Tyr  Glu Val Leu Leu Ser  Lys Met Lys Lys Phe  Asn Lys Lys
    1265                 1270                 1275

Gly Met  Ala Asp Pro Ser Asp  Arg Ile Glu Lys Ser  Lys Pro Lys
    1280                 1285                 1290

Phe Ile  Lys Leu Glu Asp Leu  Ile Asp Lys Ile Asn  Val Ile Asn
    1295                 1300                 1305

Lys Met  Leu Asn Leu Leu Arg  Cys Asp Asn Asp Thr  Lys Ala Asp
    1310                 1315                 1320

Leu Ser  Leu Ile Glu Leu Pro  Lys Asn Ala Gly Ser  Phe Val Val
    1325                 1330                 1335

Lys Lys  Asn Thr Ile Gly Lys  Ser Lys Ile Ile Leu  Val Asn Gln
    1340                 1345                 1350

Ser Val  Thr Gly Leu Tyr Glu  Asn Arg Arg Glu Leu
    1355                 1360                 1365
```

<210> SEQ ID NO 172
<211> LENGTH: 4179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172

```
accggtgcca ccatgtaccc atacgatgtt ccagattacg cttcgccgaa gaaaaagcgc      60

aaggtcgaag cgtccatgac caaggagtat tacctggggc tggatgtggg gaccaattcc     120

gtgggatggg cagtgaccga ttctcagtac aacctgtgca agtttaagaa aaaggatatg     180

tggggcatcc ggctgttcga aagcgccaac acagcaaagg accggagact gcagagaggg     240

aataggcgcc gactggagcg gaaaaagcag agaattgatc tgctgcagga aatcttctcc     300

ccagagatct gcaagattga ccccactttc tttatccgac tgaacgaatc ccggctgcac     360

ctggaggaca agtctaacga tttcaaatac ccactgttta ttgagaagga ctattctgat     420
```

```
atcgagtact ataaagagtt ccccaccatt tttcacctga ggaagcatct gatcgagagt    480
gaggaaaaac aggatatccg gctgatctac ctggccctgc acaacatcat taagacccga    540
ggacattttc tgattgacgg cgatctgcag agcgccaagc agctgaggcc catcctggat    600
acattcctgc tgtccctgca ggaggaacag aacctgtcag tgagcctgtc cgaaaatcag    660
aaggacgagt atgaggaaat tctgaaaaac cgcagcatcg ccaagtccga aaaagtgaaa    720
aagctgaaga atctgtttga gatctcagac gagctggaaa aagaggagaa gaaggcccag    780
agcgccgtga tcgagaactt ctgcaagttt atcgtgggaa ataagggcga tgtctgtaaa    840
ttcctgcggg tgtctaagga ggaactggag attgactctt tcagtttttc agagggcaag    900
tacgaggacg acatcgtgaa aaacctggag gaaaaagtgc ctgaaaaggt ctacctgttt    960
gagcagatga aggcaatgta tgattggaat attctggtcg acatcctgga aaccgaggaa   1020
tacatcagct tcgccaaagt gaagcagtat gagaaacaca agactaacct gcggctgctg   1080
agagacatca ttctgaaata ctgcaccaag gatgagtata atcggatgtt taacgacgag   1140
aaggaagctg gcagctacac cgcatatgtg gggaaactga aaaagaacaa caagaagtac   1200
tggatcgaga aaaagagaaa tcccgaggag ttctacaaat ccctgggcaa gctgctggat   1260
aaaattgagc ctctgaagga ggacctggaa gtgctgacta tgatgatcga ggagtgtaag   1320
aaccacaccc tgctgccaat tcagaaaaat aaggacaacg gcgtgatccc ccaccaggtg   1380
catgaggtcg aactgaaaaa gatcctggaa aatgccaaaa agtactattc cttcctgacc   1440
gagacagaca aggatgggta ctcagtggtc cagaaaatcg agagcatttt caggtttcgc   1500
atcccctact atgtggggcc tctgagtacc cggcaccagg aaaagggatc aaacgtgtgg   1560
atggtcagaa aacctggcag ggaggatcgc atctacccat ggaatatgga ggaaatcatt   1620
gactttgaga agagcaacga aaatttcatt acacggatga ctaacaaatg tacatatctg   1680
atcggggaag atgtcctgcc caagcattct ctgctgtaca gtaaatatat ggtgctgaat   1740
gagctgaaca atgtgaaggt cagaggaaaa aagctgccta catctctgaa acagaaggtg   1800
ttcgaggacc tgtttgaaaa caaatccaaa gtgactggaa agaatctgct ggagtacctg   1860
cagatccagg acaaagatat ccagattgac gatctgtctg gcttcgacaa ggacttcaag   1920
accagcctga agagctatct ggacttcaaa aagcagattt tggggagga aatcgagaag   1980
gaaagcattc agaacatgat cgaagatatc attaagtgga tcaccatcta cggcaatgac   2040
aaggagatgc tgaaacgagt gattcgggct aattatagca accagctgac agaggaacag   2100
atgaaaaaga tcactggatt tcagtacagt ggctgggga acttctcaaa gatgtttctg   2160
aaagggatca gcggatccga cgtgagcacc ggcgaaacat tcgacatcat taccgcaatg   2220
tgggagacag acaacaatct gatgcagatc ctgtcaaaaa agttcacctt tatggacaac   2280
gtcgaggact tcaacagcgg caaggtcggg aaaatcgaca agattactta cgatagcacc   2340
gtgaaggaaa tgttcctgtc ccctgagaac aaaagggccg tctggcagac cattcaggtg   2400
gctgaggaga tcaagaaagt gatgggctgc gagccaaaaa agatctttat tgaaatggca   2460
cggggcgggg agaaggtgaa aaagaggaca aaatctcgca aggcccagct gctggagctg   2520
tacgccgctt gcgaggaaga ttgtagagaa ctgatcaagg agattgagga ccgggacgag   2580
agggacttca atagcatgaa gctgtttctg tactataccc agttcgggaa atgtatgtat   2640
tccggcgacg acatcgatat taacgagctg attcgcggca attctaagtg ggaccgagat   2700
cacatctacc cccagagcaa aattaaggac gattccatcg ataacctggt gctggtcaat   2760
aagacatata atgccaaaaa gtccaatgag ctgctgtctg aggacatcca gaaaaagatg   2820
```

cattcattct ggctgagcct gctgaacaaa aagctgatca ctaaaagcaa gtacgaccgc 2880
ctgactcgaa agggcgactt taccgatgag gaactgagtg ggttcatcgc tagacagctg 2940
gtggaaacaa ggcagtcaac taaggcaatc gccgatatct tcaagcagat ctacagctcc 3000
gaggtggtct atgtgaagag cagcctggtg agcgacttca ggaaaaagcc actgaactac 3060
ctgaagtctc ggagagtcaa tgattaccac catgcaaaag acgcctatct gaacattgtg 3120
gtcgggaacg tgtacaacaa aaagtttacc agtaatccca tccagtggat gaaaaagaat 3180
cgcgatacaa actatagcct gaacaaggtg ttcgaacacg acgtggtcat taacggagaa 3240
gtgatctggg aaaagtgcac ataccatgag gacactaata cctatgatgg aggcactctg 3300
gaccgaatcc ggaagattgt ggaacgcgat aacattctgt acaccgagta cgcttattgt 3360
gagaagggcg aactgtttaa tgcaaccatc cagaacaaaa atggaaactc cacagtctct 3420
ctgaaaaagg gcctggacgt gaaaaagtac gggggatact tcagcgccaa cacaagttac 3480
ttctcactga tcgagtttga ggacaagaag gggggatagag caaggcacat cattggagtg 3540
cctatctata ttgcaaacat gctggagcat tctccaagtg ccttcctgga gtactgcgaa 3600
cagaaggggt atcagaatgt gcggattctg gtcgagaaaa tcaaaaagaa cagcctgctg 3660
atcattaatg gataccctct gcgcattcga ggcgagaacg aagtggatac ttcctttaag 3720
agggccatcc agctgaagct ggaccagaaa aactatgagc tggtccgcaa tatcgagaag 3780
ttcctggaaa aatacgtgga gaaaaaggga aactatccaa ttgacgagaa tagagatcac 3840
atcacacatg aaaagatgaa ccagctgtac gaggtgctgc tgtccaaaat gaaaaagttc 3900
aacaagaagg gcatggccga cccctctgat aggatcgaaa agagtaagcc taaattcatc 3960
aagctggagg acctgatcga taagattaat gtgatcaaca aaatgctgaa cctgctgcgc 4020
tgtgacaatg atactaaggc cgacctgtct ctgattgagc tgcccaaaaa cgctgggagt 4080
ttcgtggtca aaaagaatac catcggaaag tcaaaaatca tcctggtgaa tcagagcgtg 4140
actggactgt acgagaatag acgggaactg taagaattc 4179

<210> SEQ ID NO 173
<211> LENGTH: 111
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 173
nnnnnnnnnn nnnnnnnnnn guuuuagcac uagaaauagu uaaguuaaaa caagcuuaaa 60
gcgucaaugu aauauuuuau uaacacccua cugugucagu gggguuuuuu u 111

<210> SEQ ID NO 174
<211> LENGTH: 1334
<212> TYPE: PRT
<213> ORGANISM: Staphylococcus pseudintermedius

<400> SEQUENCE: 174

Met Gly Arg Lys Pro Tyr Ile Leu Ser Leu Asp Ile Gly Thr Gly Ser
1 5 10 15

Val Gly Tyr Ala Cys Met Asp Lys Gly Phe Asn Val Leu Lys Tyr His
20 25 30

```
Asp Lys Asp Ala Leu Gly Val Tyr Leu Phe Asp Gly Ala Leu Thr Ala
        35                  40                  45

Gln Glu Arg Arg Gln Phe Arg Thr Ser Arg Arg Arg Lys Asn Arg Arg
    50                  55                  60

Ile Lys Arg Leu Gly Leu Leu Gln Glu Leu Leu Ala Pro Leu Val Gln
65                  70                  75                  80

Asn Pro Asn Phe Tyr Gln Phe Gln Arg Gln Phe Ala Trp Lys Asn Asp
                85                  90                  95

Asn Met Asp Phe Lys Asn Lys Ser Leu Ser Glu Val Leu Ser Phe Leu
            100                 105                 110

Gly Tyr Glu Ser Lys Lys Tyr Pro Thr Ile Tyr His Leu Gln Glu Ala
        115                 120                 125

Leu Leu Leu Lys Asp Glu Lys Phe Asp Pro Glu Leu Ile Tyr Met Ala
    130                 135                 140

Leu Tyr His Leu Val Lys Tyr Arg Gly His Phe Leu Phe Asp His Leu
145                 150                 155                 160

Lys Ile Glu Asn Leu Thr Asn Asn Asp Asn Met His Asp Phe Val Glu
                165                 170                 175

Leu Ile Glu Thr Tyr Glu Asn Leu Asn Asn Ile Lys Leu Asn Leu Asp
            180                 185                 190

Tyr Glu Lys Thr Lys Val Ile Tyr Glu Ile Leu Lys Asp Asn Glu Met
        195                 200                 205

Thr Lys Asn Asp Arg Ala Lys Arg Val Lys Asn Met Glu Lys Lys Leu
    210                 215                 220

Glu Gln Phe Ser Ile Met Leu Leu Gly Leu Lys Phe Asn Glu Gly Lys
225                 230                 235                 240

Leu Phe Asn His Ala Asp Asn Ala Glu Glu Leu Lys Gly Ala Asn Gln
                245                 250                 255

Ser His Thr Phe Ala Asp Asn Tyr Glu Glu Asn Leu Thr Pro Phe Leu
            260                 265                 270

Thr Val Glu Gln Ser Glu Phe Ile Glu Arg Ala Asn Lys Ile Tyr Leu
        275                 280                 285

Ser Leu Thr Leu Gln Asp Ile Leu Lys Gly Lys Lys Ser Met Ala Met
    290                 295                 300

Ser Lys Val Ala Ala Tyr Asp Lys Phe Arg Asn Glu Leu Lys Gln Val
305                 310                 315                 320

Lys Asp Ile Val Tyr Lys Ala Asp Ser Thr Arg Thr Gln Phe Lys Lys
                325                 330                 335

Ile Phe Val Ser Ser Lys Lys Ser Leu Lys Gln Tyr Asp Ala Thr Pro
            340                 345                 350

Asn Asp Gln Thr Phe Ser Ser Leu Cys Leu Phe Asp Gln Tyr Leu Ile
        355                 360                 365

Arg Pro Lys Lys Gln Tyr Ser Leu Leu Ile Lys Glu Leu Lys Lys Ile
    370                 375                 380

Ile Pro Gln Asp Ser Glu Leu Tyr Phe Glu Ala Glu Asn Asp Thr Leu
385                 390                 395                 400

Leu Lys Val Leu Asn Thr Thr Asp Asn Ala Ser Ile Pro Met Gln Ile
                405                 410                 415

Asn Leu Tyr Glu Ala Glu Thr Ile Leu Arg Asn Gln Gln Lys Tyr His
            420                 425                 430

Ala Glu Ile Thr Asp Glu Met Ile Glu Lys Val Leu Ser Leu Ile Gln
        435                 440                 445
```

```
Phe Arg Ile Pro Tyr Tyr Val Gly Pro Leu Val Asn Asp His Thr Ala
    450                 455                 460

Ser Lys Phe Gly Trp Met Glu Arg Lys Ser Asn Glu Ser Ile Lys Pro
465                 470                 475                 480

Trp Asn Phe Asp Glu Val Val Asp Arg Ser Lys Ser Ala Thr Gln Phe
                485                 490                 495

Ile Arg Arg Met Thr Asn Lys Cys Ser Tyr Leu Ile Asn Glu Asp Val
            500                 505                 510

Leu Pro Lys Asn Ser Leu Leu Tyr Gln Glu Met Glu Val Leu Asn Glu
        515                 520                 525

Leu Asn Ala Thr Gln Ile Arg Leu Gln Thr Asp Pro Lys Asn Arg Lys
    530                 535                 540

Tyr Arg Met Met Pro Gln Ile Lys Leu Phe Ala Val Glu His Ile Phe
545                 550                 555                 560

Lys Lys Tyr Lys Thr Val Ser His Ser Lys Phe Leu Glu Ile Met Leu
                565                 570                 575

Asn Ser Asn His Arg Glu Asn Phe Met Asn His Gly Glu Lys Leu Ser
            580                 585                 590

Ile Phe Gly Thr Gln Asp Asp Lys Lys Phe Ala Ser Lys Leu Ser Ser
        595                 600                 605

Tyr Gln Asp Met Thr Lys Ile Phe Gly Asp Ile Glu Gly Lys Arg Ala
    610                 615                 620

Gln Ile Glu Glu Ile Ile Gln Trp Ile Thr Ile Phe Glu Asp Lys Lys
625                 630                 635                 640

Ile Leu Val Gln Lys Leu Lys Glu Cys Tyr Pro Glu Leu Thr Ser Lys
                645                 650                 655

Gln Ile Asn Gln Leu Lys Lys Leu Asn Tyr Ser Gly Trp Gly Arg Leu
            660                 665                 670

Ser Glu Lys Leu Leu Thr His Ala Tyr Gln Gly His Ser Ile Ile Glu
        675                 680                 685

Leu Leu Arg His Ser Asp Glu Asn Phe Met Glu Ile Leu Thr Asn Asp
    690                 695                 700

Val Tyr Gly Phe Gln Asn Phe Ile Lys Glu Glu Asn Gln Val Gln Ser
705                 710                 715                 720

Asn Lys Ile Gln His Gln Asp Ile Ala Asn Leu Thr Thr Ser Pro Ala
                725                 730                 735

Leu Lys Lys Gly Ile Trp Ser Thr Ile Lys Leu Val Arg Glu Leu Thr
            740                 745                 750

Ser Ile Phe Gly Glu Pro Glu Lys Ile Ile Met Glu Phe Ala Thr Glu
        755                 760                 765

Asp Gln Gln Lys Gly Lys Lys Gln Lys Ser Arg Lys Gln Leu Trp Asp
    770                 775                 780

Asp Asn Ile Lys Lys Asn Lys Leu Lys Ser Val Asp Glu Tyr Lys Tyr
785                 790                 795                 800

Ile Ile Asp Val Ala Asn Lys Leu Asn Asn Glu Gln Leu Gln Gln Glu
                805                 810                 815

Lys Leu Trp Leu Tyr Leu Ser Gln Asn Gly Lys Cys Met Tyr Ser Gly
            820                 825                 830

Gln Ser Ile Asp Leu Asp Ala Leu Leu Ser Pro Asn Ala Thr Lys His
        835                 840                 845

Tyr Glu Val Asp His Ile Phe Pro Arg Ser Phe Ile Lys Asp Asp Ser
    850                 855                 860

Ile Asp Asn Lys Val Leu Val Ile Lys Lys Met Asn Gln Thr Lys Gly
```

```
865                 870                 875                 880

Asp Gln Val Pro Leu Gln Phe Ile Gln Gln Pro Tyr Glu Arg Ile Ala
                885                 890                 895

Tyr Trp Lys Ser Leu Asn Lys Ala Gly Leu Ile Ser Asp Ser Lys Leu
            900                 905                 910

His Lys Leu Met Lys Pro Glu Phe Thr Ala Met Asp Lys Glu Gly Phe
        915                 920                 925

Ile Gln Arg Gln Leu Val Glu Thr Arg Gln Ile Ser Val His Val Arg
    930                 935                 940

Asp Phe Leu Lys Glu Glu Tyr Pro Asn Thr Lys Val Ile Pro Met Lys
945                 950                 955                 960

Ala Lys Met Val Ser Glu Phe Arg Lys Lys Phe Asp Ile Pro Lys Ile
                965                 970                 975

Arg Gln Met Asn Asp Ala His His Ala Ile Asp Ala Tyr Leu Asn Gly
            980                 985                 990

Val Val Tyr His Gly Ala Gln Leu  Ala Tyr Pro Asn Val  Asp Leu Phe
        995                 1000                1005

Asp Phe  Asn Phe Lys Trp Glu  Lys Val Arg Glu Lys  Trp Lys Ala
    1010                 1015                 1020

Leu Gly  Glu Phe Asn Thr Lys  Gln Lys Ser Arg Glu  Leu Phe Phe
    1025                 1030                 1035

Phe Lys  Lys Leu Glu Lys Met  Glu Val Ser Gln Gly  Glu Arg Leu
    1040                 1045                 1050

Ile Ser  Lys Ile Lys Leu Asp  Met Asn His Phe Lys  Ile Asn Tyr
    1055                 1060                 1065

Ser Arg  Lys Leu Ala Asn Ile  Pro Gln Gln Phe Tyr  Asn Gln Thr
    1070                 1075                 1080

Ala Val  Ser Pro Lys Thr Ala  Glu Leu Lys Tyr Glu  Ser Asn Lys
    1085                 1090                 1095

Ser Asn  Glu Val Val Tyr Lys  Gly Leu Thr Pro Tyr  Gln Thr Tyr
    1100                 1105                 1110

Val Val  Ala Ile Lys Ser Val  Asn Lys Lys Gly Lys  Glu Lys Met
    1115                 1120                 1125

Glu Tyr  Gln Met Ile Asp His  Tyr Val Phe Asp Phe  Tyr Lys Phe
    1130                 1135                 1140

Gln Asn  Gly Asn Glu Lys Glu  Leu Ala Leu Tyr Leu  Ala Gln Arg
    1145                 1150                 1155

Glu Asn  Lys Asp Glu Val Leu  Asp Ala Gln Ile Val  Tyr Ser Leu
    1160                 1165                 1170

Asn Lys  Gly Asp Leu Leu Tyr  Ile Asn Asn His Pro  Cys Tyr Phe
    1175                 1180                 1185

Val Ser  Arg Lys Glu Val Ile  Asn Ala Lys Gln Phe  Glu Leu Thr
    1190                 1195                 1200

Val Glu  Gln Gln Leu Ser Leu  Tyr Asn Val Met Asn  Asn Lys Glu
    1205                 1210                 1215

Thr Asn  Val Glu Lys Leu Leu  Ile Glu Tyr Asp Phe  Ile Ala Glu
    1220                 1225                 1230

Lys Val  Ile Asn Glu Tyr His  His Tyr Leu Asn Ser  Lys Leu Lys
    1235                 1240                 1245

Glu Lys  Arg Val Arg Thr Phe  Phe Ser Glu Ser Asn  Gln Thr His
    1250                 1255                 1260

Glu Asp  Phe Ile Lys Ala Leu  Asp Glu Leu Phe Lys  Val Val Thr
    1265                 1270                 1275
```

```
Ala Ser  Ala Thr Arg Ser Asp  Lys Ile Gly Ser Arg  Lys Asn Ser
    1280                 1285                 1290

Met Thr  His Arg Ala Phe Leu  Gly Lys Gly Lys Asp  Val Lys Ile
    1295                 1300                 1305

Ala Tyr  Thr Ser Ile Ser Gly  Leu Lys Thr Thr Lys  Pro Lys Ser
    1310                 1315                 1320

Leu Phe  Lys Leu Ala Glu Ser  Arg Asn Glu Leu
    1325                 1330


<210> SEQ ID NO 175
<211> LENGTH: 4086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175

accggtgcca ccatgtaccc atacgatgtt ccagattacg cttcgccgaa gaaaaagcgc     60

aaggtcgaag cgtccatggg gaggaaacct tacattctgt ctctggatat tggaactggg    120

tccgtcggct acgcttgcat ggataaagga ttcaacgtgc tgaagtacca cgacaaagat    180

gccctgggag tgtatctgtt cgacggcgct ctgactgcac aggagcggag acagtttagg    240

acctccaggc gccgaaagaa ccggagaatc aaacgcctgg gcctgctgca ggaactgctg    300

gcacccctgg tgcagaaccc taatttctac cagtttcagc ggcagttcgc ctggaagaac    360

gacaatatgg attttaagaa caagagcctg tctgaggtgc tgagcttcct gggatatgaa    420

tccaagaaat accctaccat ctaccacctg caggaggctc tgctgctgaa agacgagaag    480

tttgatccag aactgatcta catggcactg tatcatctgg tgaaatacag aggccacttt    540

ctgttcgatc atctgaagat cgagaacctg actaacaatg acaatatgca cgatttcgtg    600

gagctgattg aaacctatga gaacctgaac aatatcaagc tgaatctgga ctacgagaaa    660

accaaagtga tctatgagat tctgaaagac aacgaaatga ctaagaatga tagagccaaa    720

agggtcaaga acatggagaa gaaactggaa cagttctcta tcatgctgct ggggctgaag    780

ttcaatgagg gaaaactgtt taaccacgcc gataatgctg aggaactgaa gggggctaac    840

cagagccata catttgcaga caactacgag gaaaatctga ctcccttcct gaccgtggaa    900

cagtcagagt ttattgaaag ggccaacaaa atctatctga gcctgactct gcaggatatc    960

ctgaagggca agaaatcaat ggctatgagc aaagtggccg cttacgacaa gttcagaaat   1020

gagctgaaac aggtgaagga cattgtctat aaggctgatt ctaccaggac acagttcaag   1080

aaaatctttg tgagctccaa gaaaagtctg aagcagtacg acgcaactcc caacgatcag   1140

accttctcta gtctgtgcct gtttgaccag tacctgattc gcccaaagaa acagtatagc   1200

ctgctgatca aggagctgaa gaaaatcatt ccccaggact ccgaactgta ctttgaggca   1260

gaaaatgata ccctgctgaa ggtgctgaac accacagaca atgctagcat ccctatgcag   1320

attaacctgt acgaggcaga aaccatcctg cgaaatcagc agaaatatca cgccgagatc   1380

acagatgaga tgattgaaaa ggtgctgtct ctgatccagt tccgcattcc atactatgtg   1440

gggcccctgg tcaacgacca tacagccagt aagtttggat ggatggagcg caaaagtaac   1500

gaatcaatca agccttggaa tttcgacgag gtggtcgatc gaagtaaatc agccactcag   1560

tttattaggc gcatgaccaa caagtgttcc tacctgatca atgaggatgt gctgccaaaa   1620

aactctctgc tgtatcagga gatggaagtc ctgaacgaac tgaatgccac acagatcagg   1680
```

```
ctgcagactg acccaaaaaa ccgcaagtac cgaatgatgc cccagattaa gctgttcgct   1740
gtggagcaca tctttaagaa atataaaacc gtcagccatt ccaagttcct ggaaattatg   1800
ctgaacagca atcacaggga gaactttatg aatcatggag aaaagctgag tatcttcggc   1860
acacaggacg ataagaaatt tgcatcaaag ctgtcaagct accaggacat gactaaaatc   1920
ttcggggata ttgagggaaa gcgcgcccag attgaggaaa tcattcagtg gatcaccatt   1980
tttgaggaca agaaaatcct ggtgcagaag ctgaaagagt gctatcctga actgacatcc   2040
aagcagatca accagctgaa gaaactgaat tactctggct gggggaggct gagtgagaag   2100
ctgctgactc acgcctatca gggccatagc atcattgaac tgctgcgcca ctccgatgag   2160
aatttcatgg aaattctgac caacgacgtg tacgggttcc agaattttat caaagaggaa   2220
aaccaggtcc agagcaataa gatccagcat caggatattg ccaacctgac tacctctccc   2280
gctctgaaga aggcatctgg gagtacaatt aagctggtgc gggagctgac ttccattttc   2340
ggggagcctg aaaagatcat tatggagttt gctaccgagg accagcagaa aggcaagaaa   2400
cagaaatcaa gaaagcagct gtgggacgat aacatcaaga aaaataagct gaaaagcgtg   2460
gacgagtaca aatatatcat tgatgtcgcc aataagctga acaatgagca gctgcagcag   2520
gaaaaactgt ggctgtacct gagccagaac ggcaagtgta tgtatagcgg gcagtccatc   2580
gacctggatg ccctgctgtc ccccaatgct accaagcact acgaggtgga tcatattttc   2640
cctcggagct tcatcaagga cgatagcatt gacaacaagg tgctggtcat caagaaaatg   2700
aatcagacaa agggcgatca ggtgcccctg cagttcattc agcagcctta cgagagaatc   2760
gcatattgga agagcctgaa caaagccggg ctgatctctg atagtaaact gcacaagctg   2820
atgaaaccag agttcacagc tatggacaag gaaggcttca tccagcggca gctggtggag   2880
actagacaga tcagcgtgca tgtccgggat tttctgaaag aggaataccc taataccaaa   2940
gtgatcccaa tgaaggccaa aatggtgagc gagttccgga agaaatttga catcccaaag   3000
attagacaga tgaacgacgc acaccatgcc atcgatgctt acctgaatgg cgtggtctat   3060
cacggggcac agctggccta ccccaacgtg gacctgtttg atttcaattt taagtgggag   3120
aaagtccgag aaaagtggaa agccctggga gagttcaaca caaagcagaa atctcgggaa   3180
ctgttctttt tcaagaaact ggagaagatg gaagtgtccc agggcgagcg gctgatctct   3240
aagatcaagc tggacatgaa ccacttcaag atcaactact ccagaaagct ggccaacatc   3300
cctcagcagt tttataatca gaccgcagtg tctccaaaga cagccgagct gaaatacgaa   3360
tctaacaaga gtaatgaggt ggtctataag ggactgacac cataccagac ttatgtggtc   3420
gccatcaaga gcgtgaacaa gaaaggcaag gagaaaatgg aataccagat gatcgaccac   3480
tacgtgttcg atttttataa attccagaac ggcaatgaga aggaactggc tctgtacctg   3540
gcacagaggg agaacaagga cgaagtgctg gatgctcaga ttgtctatag tctgaataag   3600
ggggatctgc tgtacatcaa caatcatccc tgctatttcg tgtcacgcaa agaggtcatc   3660
aacgcaaagc agtttgagct gaccgtggaa cagcagctgt ctctgtacaa cgtgatgaac   3720
aacaaggaga caaatgtcga aaagctgctg atcgagtatg acttcattgc cgagaaagtg   3780
atcaacgaat accaccatta tctgaatagc aagctgaaag aaaagcgagt ccggaccttt   3840
ttctcagaga gcaaccagac acacgaggac ttcatcaagg ccctggacga gctgtttaag   3900
gtggtcaccg catccgccac aaggtctgat aaaatcggga gtcgcaagaa cagcatgact   3960
catcgagcct tcctgggaaa aggcaaggac gtgaagattg cttacacctc catctctgga   4020
```

-continued

```
ctgaaaacaa ctaaacctaa gagtctgttt aagctggccg agtcaagaaa cgaactgtaa    4080

gaattc                                                               4086
```

<210> SEQ ID NO 176
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 176

```
nnnnnnnnnn nnnnnnnnnn guuuuagaug gugaaaacca gauuuaaaau caagcaaugc     60

aucuuuugau gcaaaguuuc aauauuuguc ccacguuauc gagggacuuu uuuu          114
```

<210> SEQ ID NO 177
<211> LENGTH: 1375
<212> TYPE: PRT
<213> ORGANISM: Lactobacillus johnsonii

<400> SEQUENCE: 177

```
Met Thr Lys Ile Lys Asp Asp Tyr Ile Val Gly Leu Asp Ile Gly Thr
1               5                   10                  15

Asp Ser Cys Gly Trp Val Ala Met Asn Ser Asn Asn Asp Ile Leu Lys
            20                  25                  30

Leu Gln Gly Lys Thr Ala Ile Gly Ser Arg Leu Phe Glu Gly Gly Lys
        35                  40                  45

Ser Ala Ala Glu Arg Arg Leu Phe Arg Thr Thr His Arg Arg Ile Lys
    50                  55                  60

Arg Arg Arg Trp Arg Leu Lys Leu Leu Glu Glu Phe Phe Asp Pro Tyr
65                  70                  75                  80

Met Ala Glu Val Asp Pro Tyr Phe Phe Ala Arg Leu Lys Glu Ser Gly
                85                  90                  95

Leu Ser Pro Leu Asp Lys Arg Lys Thr Val Ser Ser Ile Val Phe Pro
            100                 105                 110

Thr Ser Ala Glu Asp Lys Lys Phe Tyr Asp Asp Tyr Pro Thr Ile Tyr
        115                 120                 125

His Leu Arg Tyr Lys Leu Met Thr Glu Asp Glu Lys Phe Asp Leu Arg
    130                 135                 140

Glu Val Tyr Leu Ala Ile His His Ile Ile Lys Tyr Arg Gly Asn Phe
145                 150                 155                 160

Leu Tyr Asn Thr Ser Val Lys Asp Phe Lys Ala Ser Lys Ile Asp Val
                165                 170                 175

Lys Ser Ser Ile Glu Lys Leu Asn Glu Leu Tyr Glu Asn Leu Gly Leu
            180                 185                 190

Asp Leu Asn Val Glu Phe Asn Ile Ser Asn Thr Ala Glu Ile Glu Lys
        195                 200                 205

Val Leu Lys Asp Lys Gln Ile Phe Lys Arg Asp Lys Val Lys Lys Ile
    210                 215                 220

Ala Glu Leu Phe Ala Ile Lys Thr Asp Asn Lys Glu Gln Ser Lys Arg
225                 230                 235                 240

Ile Lys Asp Ile Ser Lys Gln Val Ala Asn Ala Val Leu Gly Tyr Lys
                245                 250                 255
```

```
Thr Arg Phe Asp Thr Ile Ala Leu Lys Glu Ile Ser Lys Asp Glu Leu
            260                 265                 270

Ser Asp Trp Asn Phe Lys Leu Ser Asp Ile Asp Ala Asp Ser Lys Phe
        275                 280                 285

Glu Ala Leu Met Gly Asn Leu Asp Glu Asn Glu Gln Ala Ile Leu Leu
    290                 295                 300

Thr Ile Lys Glu Leu Phe Asn Glu Val Thr Leu Asn Gly Ile Val Glu
305                 310                 315                 320

Asp Gly Asn Thr Leu Ser Glu Ser Met Ile Asn Lys Tyr Asn Asp His
                325                 330                 335

Arg Asp Asp Leu Lys Leu Leu Lys Glu Val Ile Glu Asn His Ile Asp
            340                 345                 350

Arg Lys Lys Ala Lys Glu Leu Ala Leu Ala Tyr Asp Leu Tyr Val Asn
        355                 360                 365

Asn Arg His Gly Gln Leu Leu Gln Ala Lys Lys Lys Leu Gly Lys Ile
    370                 375                 380

Lys Pro Arg Ser Lys Glu Asp Phe Tyr Lys Val Val Asn Lys Asn Leu
385                 390                 395                 400

Asp Asp Ser Arg Ala Ser Lys Glu Ile Lys Lys Lys Ile Glu Leu Asp
                405                 410                 415

Ser Phe Met Pro Lys Gln Arg Thr Asn Ala Asn Gly Val Ile Pro Tyr
            420                 425                 430

Gln Leu Gln Gln Leu Glu Leu Asp Lys Ile Ile Glu Asn Gln Ser Lys
        435                 440                 445

Tyr Tyr Pro Phe Leu Lys Glu Ile Asn Pro Val Ser Ser His Leu Lys
    450                 455                 460

Glu Ala Pro Tyr Lys Leu Asp Glu Leu Ile Arg Phe Arg Val Pro Tyr
465                 470                 475                 480

Tyr Val Gly Pro Leu Ile Ser Pro Asn Glu Ser Thr Lys Asp Ile Gln
                485                 490                 495

Thr Lys Lys Asn Gln Asn Phe Ala Trp Met Ile Arg Lys Glu Glu Gly
            500                 505                 510

Arg Ile Thr Pro Trp Asn Phe Asp Gln Lys Val Asp Arg Ile Glu Ser
        515                 520                 525

Ala Asn Lys Phe Ile Lys Arg Met Thr Thr Lys Asp Thr Tyr Leu Phe
    530                 535                 540

Gly Glu Asp Val Leu Pro Ala Asn Ser Leu Leu Tyr Gln Lys Phe Thr
545                 550                 555                 560

Val Leu Asn Glu Leu Asn Asn Ile Arg Ile Asn Gly Lys Arg Ile Ser
                565                 570                 575

Val Asp Leu Lys Gln Glu Ile Tyr Glu Asn Leu Phe Lys Lys His Thr
            580                 585                 590

Thr Val Thr Val Lys Lys Leu Glu Asn Tyr Leu Lys Glu Asn His Asn
        595                 600                 605

Leu Val Lys Val Glu Ile Lys Gly Leu Ala Asp Glu Lys Lys Phe Asn
    610                 615                 620

Ser Gly Leu Thr Thr Tyr Asn Arg Phe Lys Asn Leu Asn Ile Phe Asp
625                 630                 635                 640

Asn Gln Ile Asp Asp Leu Lys Tyr Arg Asn Asp Phe Glu Lys Ile Ile
                645                 650                 655

Glu Trp Ser Thr Ile Phe Glu Asp Lys Ser Ile Tyr Lys Glu Lys Leu
            660                 665                 670

Arg Ser Ile Asp Trp Leu Asn Glu Lys Gln Ile Asn Ala Leu Ser Asn
```

```
        675                 680                 685

Ile Arg Leu Gln Gly Trp Gly Arg Leu Ser Lys Lys Leu Leu Ala Gln
    690                 695                 700

Leu His Asp His Asn Gly Gln Thr Ile Ile Glu Gln Leu Trp Asp Ser
705                 710                 715                 720

Gln Asn Asn Phe Met Gln Ile Val Thr Gln Ala Asp Phe Lys Asp Ala
                725                 730                 735

Ile Ala Lys Ala Asn Gln Asn Leu Leu Val Ala Thr Ser Val Glu Asp
            740                 745                 750

Ile Leu Asn Asn Ala Tyr Thr Ser Pro Ala Asn Lys Lys Ala Ile Arg
        755                 760                 765

Gln Val Ile Lys Val Val Asp Asp Ile Val Lys Ala Ala Ser Gly Lys
    770                 775                 780

Val Pro Lys Gln Ile Ala Ile Glu Phe Thr Arg Asp Ala Asp Glu Asn
785                 790                 795                 800

Pro Lys Arg Ser Gln Thr Arg Gly Ser Lys Leu Gln Lys Val Tyr Lys
                805                 810                 815

Asp Leu Ser Thr Glu Leu Ala Ser Lys Thr Ile Ala Glu Glu Leu Asn
            820                 825                 830

Glu Ala Ile Lys Asp Lys Lys Leu Val Gln Asp Lys Tyr Tyr Leu Tyr
        835                 840                 845

Phe Met Gln Leu Gly Arg Asp Ala Tyr Thr Gly Glu Pro Ile Asn Ile
    850                 855                 860

Asp Glu Ile Gln Lys Tyr Asp Ile Asp His Ile Leu Pro Gln Ser Phe
865                 870                 875                 880

Ile Lys Asp Asp Ala Leu Asp Asn Arg Val Leu Val Ser Arg Ala Val
                885                 890                 895

Asn Asn Gly Lys Ser Asp Asn Val Pro Val Lys Leu Phe Gly Asn Glu
            900                 905                 910

Met Ala Ala Asn Leu Gly Met Thr Ile Arg Lys Met Trp Glu Glu Trp
        915                 920                 925

Lys Asn Ile Gly Leu Ile Ser Lys Thr Lys Tyr Asn Asn Leu Leu Thr
    930                 935                 940

Asp Pro Asp His Ile Asn Lys Tyr Lys Ser Ala Gly Phe Ile Arg Arg
945                 950                 955                 960

Gln Leu Val Glu Thr Ser Gln Ile Ile Lys Leu Val Ser Thr Ile Leu
                965                 970                 975

Gln Ser Arg Tyr Pro Asn Thr Glu Ile Ile Thr Val Lys Ala Lys Tyr
            980                 985                 990

Asn His Tyr Leu Arg Glu Lys Phe  Asp Leu Tyr Lys Ser  Arg Glu Val
        995                 1000                1005

Asn Asp  Tyr His His Ala Ile  Asp Ala Tyr Leu Ser  Ala Ile Cys
    1010                1015                1020

Gly Asn  Leu Leu Tyr Gln Asn  Tyr Pro Asn Leu Arg  Pro Phe Phe
    1025                1030                1035

Val Tyr  Gly Gln Tyr Lys Lys  Phe Ser Ser Asp Pro  Asp Lys Glu
    1040                1045                1050

Lys Ala  Ile Phe Asn Lys Thr  Arg Lys Phe Ser Phe  Ile Ser Gln
    1055                1060                1065

Leu Leu  Lys Asn Lys Ser Glu  Asn Ser Lys Glu Ile  Ala Lys Lys
    1070                1075                1080

Leu Lys  Arg Ala Tyr Gln Phe  Lys Tyr Met Leu Val  Ser Arg Glu
    1085                1090                1095
```

```
Thr Glu  Thr Arg Asp Gln Glu  Met Phe Lys Met Thr  Val Tyr Pro
    1100                 1105                 1110

Arg Phe  Ser His Asp Thr Val  Lys Ala Pro Arg Asn  Leu Ile Pro
    1115                 1120                 1125

Lys Lys  Met Gly Met Ser Pro  Asp Ile Tyr Gly Gly  Tyr Thr Asn
    1130                 1135                 1140

Asn Ser  Asp Ala Tyr Met Val  Ile Val Arg Ile Asp  Lys Lys Lys
    1145                 1150                 1155

Gly Thr  Glu Tyr Lys Ile Leu  Gly Ile Pro Thr Arg  Glu Leu Val
    1160                 1165                 1170

Asn Leu  Lys Lys Ala Glu Lys  Glu Asp His Tyr Lys  Ser Tyr Leu
    1175                 1180                 1185

Lys Glu  Ile Leu Thr Pro Arg  Ile Leu Tyr Asn Lys  Asn Gly Lys
    1190                 1195                 1200

Arg Asp  Lys Lys Ile Thr Ser  Phe Glu Ile Val Lys  Ser Lys Ile
    1205                 1210                 1215

Pro Tyr  Lys Gln Val Ile Gln  Asp Gly Asp Lys Lys  Phe Met Leu
    1220                 1225                 1230

Gly Ser  Ser Thr Tyr Val Tyr  Asn Ala Lys Gln Leu  Thr Leu Ser
    1235                 1240                 1245

Thr Glu  Ser Met Lys Ala Ile  Thr Asn Asn Phe Asp  Lys Asp Ser
    1250                 1255                 1260

Asp Glu  Asn Asp Ala Leu Ile  Lys Ala Tyr Asp Glu  Ile Leu Asp
    1265                 1270                 1275

Lys Val  Asp Lys Tyr Leu Pro  Leu Phe Asp Ile Asn  Lys Phe Arg
    1280                 1285                 1290

Glu Lys  Leu His Ser Gly Arg  Glu Lys Phe Ile Lys  Leu Ser Leu
    1295                 1300                 1305

Glu Asp  Lys Lys Asp Thr Ile  Leu Lys Val Leu Glu  Gly Leu His
    1310                 1315                 1320

Asp Asn  Ala Val Met Thr Lys  Ile Pro Thr Ile Gly  Leu Ser Thr
    1325                 1330                 1335

Pro Leu  Gly Phe Met Gln Phe  Pro Asn Gly Val Ile  Leu Ser Glu
    1340                 1345                 1350

Asn Ala  Lys Leu Ile Tyr Gln  Ser Pro Thr Gly Leu  Phe Lys Lys
    1355                 1360                 1365

Ser Val  Lys Ile Ser Asp Leu
    1370                 1375
```

<210> SEQ ID NO 178
<211> LENGTH: 4209
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 178

```
accggtgcca ccatgtaccc atacgatgtt ccagattacg cttcgccgaa gaaaaagcgc     60

aaggtcgaag cgtccatgac aaaaatcaaa gacgactaca tcgtgggact ggacatcggc    120

acagactcct gcgggtgggt ggctatgaac agcaataatg acattctgaa actgcagggc    180

aagaccgcaa tcgggtcacg cctgttcgag ggagggaaga gcgcagctga acggagactg    240

tttcgcacca cacacaggcg catcaaacga cggagatggc gactgaagct gctggaggag    300
```

-continued

```
ttcttcgacc cctacatggc agaggtggat ccttatttct ttgcccggct gaaggaatct    360
ggcctgagtc cactggacaa aagaaagacc gtgagctcca ttgtgttccc cacatccgcc    420
gaggataaga agttctacga cgattaccct acaatctacc atctgaggta taaactgatg    480
actgaggacg aaaagttcga tctgcgcgaa gtgtacctgg ctatccacca tatcattaag    540
taccgaggaa acttcctgta taataccagt gtgaaagact tcaaggcatc aaagatcgat    600
gtcaaatcta gtatcgagaa gctgaacgag ctgtatgaaa atctgggcct ggacctgaac    660
gtggagttca acattagcaa tactgccgag atcgaaaagg tgctgaaaga caagcagatc    720
ttcaagcggg ataaagtcaa gaaaattgcc gagctgtttg ctatcaaaac cgacaacaag    780
gaacagagca agagaatcaa agatatttcc aaacaggtgg ccaatgctgt cctggggtac    840
aagaccaggt tcgacacaat cgctctgaaa gagatttcca aggacgaact gtctgattgg    900
aacttcaaac tgtcagacat cgatgcagac agcaagtttg aggccctgat gggaaacctg    960
gatgagaatg aacaggccat cctgctgact attaaggagc tgtttaacga agtgaccctg   1020
aatggaattg tcgaggacgg caacaccctg agcgaatcca tgatcaacaa gtacaatgat   1080
caccgggacg atctgaagct gctgaaagaa gtgatcgaaa atcatattga cagaaagaaa   1140
gccaaggagc tggcactggc ctacgatctg tatgtcaaca ataggcacgg acagctgctg   1200
caggctaaga aaaagctggg caaaatcaag ccccgctcta aggaggactt ctacaaagtg   1260
gtcaacaaga atctggacga ttcacgggca agcaaggaga tcaaaaagaa aattgaactg   1320
gacagcttta tgcctaagca gagaaccaac gccaatggcg tgatcccata ccagctgcag   1380
cagctggagc tggataagat catcgaaaac cagtctaagt actatccatt cctgaaggag   1440
attaatcccg tgtcaagcca cctgaaagag gccccctata agctggacga actgatccga   1500
tttcgggtgc cttactatgt cggcccccctg atttctccta acgagagtac caaggatatc   1560
cagacaaaga aaaaccagaa tttcgcctgg atgattcgca aagaggaagg gcgaatcaca   1620
ccttggaact ttgaccagaa ggtggatcga attgagagcg ccaataagtt catcaaacgg   1680
atgactacca aggacactta cctgtttggg gaggatgtgc tgccagctaa cagcctgctg   1740
tatcagaagt tcaccgtcct gaacgaactg aacaacatcc ggattaatgg aaaaagaatc   1800
tccgtggacc tgaagcagga gatctacgaa aacctgttta agaaacacac aactgtgacc   1860
gtcaagaaac tggagaatta tctgaaggaa aaccataatc tggtgaaagt cgagatcaag   1920
gggctggccg atgaaaagaa attcaacagc ggactgacca catacaatag attcaagaac   1980
ctgaacatct ttgacaacca gattgacgat ctgaagtaca ggaacgattt cgagaagatc   2040
atcgaatggt ctacaatttt tgaggacaag agtatctaca aagaaaagct gaggagcatc   2100
gattggctga acgagaagca gattaacgct ctgtctaata tcagactgca ggggtgggga   2160
aggctgagta agaaactgct ggcacagctg cacgaccata atggccagac catcattgag   2220
cagctgtggg attcccagaa caatttcatg cagattgtga cacaggccga ctttaaagat   2280
gctatcgcaa aggccaacca gaatctgctg gtggctacct cagtcgagga cattctgaac   2340
aatgcataca caagccccgc aaacaagaaa gccatcagac aggtcatcaa ggtggtcgac   2400
gatatcgtga aggcagcctc cggaaaggtc ccaaaacaga tcgccattga gttcactagg   2460
gatgctgacg aaaatcccaa gagaagtcag accaggggct caaagctgca gaaagtgtac   2520
aaggacctga gcactgagct ggcctccaag accattgctg aggaactgaa cgaagcaatc   2580
aaagacaaga aactggtgca ggataagtac tatctgtact ttatgcagct ggggcgggac   2640
gcctatacag gagagcctat caatatcgat gaaatccaga agtacgatat cgaccacatt   2700
```

ctgccacagt ctttcatcaa ggacgatgcc ctggacaaca gggtgctggt gagccgggct 2760
gtgaacaatg gcaaatctga taatgtgcct gtcaagctgt ttggcaacga gatggctgca 2820
aatctgggga tgactatcag gaaaatgtgg gaggaatgga agaacatcgg cctgattagc 2880
aaaacaaagt acaacaatct gctgactgat cccgaccaca ttaacaagta taagagtgcc 2940
gggttcatca ggcgccagct ggtggagaca tcacagatca tcaagctggt gagcactatc 3000
ctgcagagtc gctaccctaa cactgaaatc attaccgtga aggctaagta caatcattat 3060
ctgcgggaga aatttgacct gtataagagc agagaagtca acgactacca ccatgctatt 3120
gatgcatatc tgtccgccat ctgcggaaat ctgctgtacc agaactatcc aaatctgcgg 3180
cccttctttg tgtacggcca gtataagaaa ttctcctctg atcctgacaa agagaaggcc 3240
atttttaaca aaacccgcaa gttctccttt atctctcagc tgctgaaaaa caagagtgag 3300
aacagcaagg aaatcgctaa gaaactgaaa cgggcatacc agttcaagta tatgctggtg 3360
tctcgagaga ctgaaacccg ggaccaggag atgttcaaaa tgaccgtgta cccccggttc 3420
agccacgata cagtcaaggc tcctaggaac ctgattccaa agaaaatggg catgtcccct 3480
gacatctacg gaggctatac aaacaattct gacgcataca tggtcatcgt ccgcattgat 3540
aagaaaaagg gaactgagta taagatcctg ggcattccaa cccgggaact ggtgaatctg 3600
aaaaaggccg agaaggagga ccattacaaa agctatctga aggagatcct gacaccaagg 3660
attctgtaca acaaaaatgg gaagcgcgat aaaaagatca cttccttcga aattgtgaaa 3720
tctaagatcc cctataagca ggtcatccag gatggggaca aaaagtttat gctgggaagt 3780
tcaacatacg tgtataacgc aaagcagctg acactgagca ctgagtccat gaaagccatc 3840
actaacaatt tcgataagga cagcgatgag aacgacgctc tgattaaggc atacgatgaa 3900
atcctggaca aagtggataa gtatctgcca ctgttcgaca tcaacaagtt ccgggagaag 3960
ctgcacagtg ggcgagaaaa gttcatcaag ctgagcctgg aggacaaaaa ggataccatc 4020
ctgaaagtgc tggaaggact gcatgataac gctgtcatga caaagatccc tactattggc 4080
ctgtccacac cactggggtt catgcagttt cccaacggcg tgattctgag cgagaatgcc 4140
aaactgatct accagtcccc caccgggctg ttcaaaaagt cagtgaagat cagcgacctg 4200
taagaattc 4209

<210> SEQ ID NO 179
<211> LENGTH: 178
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 179
nnnnnnnnnn nnnnnnnnnn guuguagcuc ccauucucga aagagaaccg uugcuacaau 60
aaggccgucu gaaaagaugu gccgcaacgc ucugccccuu aaagcuucug cuuuaagggg 120
caucguuuau uucgguuaaa aaugccgucu gaaaccgguu uuuagguuuc agacggca 178

<210> SEQ ID NO 180
<211> LENGTH: 1082
<212> TYPE: PRT
<213> ORGANISM: Neisseria cinerea

<400> SEQUENCE: 180

Met Ala Ala Phe Lys Pro Asn Pro Met Asn Tyr Ile Leu Gly Leu Asp
1               5                   10                  15

Ile Gly Ile Ala Ser Val Gly Trp Ala Ile Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Ala Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Thr His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Asn Arg Lys Asp Leu
        195                 200                 205

Gln Ala Glu Leu Asn Leu Leu Phe Glu Lys Gln Lys Glu Phe Gly Asn
    210                 215                 220

Pro His Val Ser Asp Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Thr Glu Pro Lys Ala Ala Lys Asn Thr Tyr
            260                 265                 270

Thr Ala Glu Arg Phe Val Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

Arg Lys Leu Leu Asp Leu Asp Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
        355                 360                 365

Lys Ser Pro Leu Asn Leu Ser Pro Glu Leu Gln Asp Glu Ile Gly Thr
    370                 375                 380

Ala Phe Ser Leu Phe Lys Thr Asp Glu Asp Ile Thr Gly Arg Leu Lys
385                 390                 395                 400

Asp Arg Val Gln Pro Glu Ile Leu Glu Ala Leu Leu Lys His Ile Ser

```
                405                 410                 415

Phe Asp Lys Phe Val Gln Ile Ser Leu Lys Ala Leu Arg Arg Ile Val
            420                 425                 430

Pro Leu Met Glu Gln Gly Asn Arg Tyr Asp Glu Ala Cys Thr Glu Ile
        435                 440                 445

Tyr Gly Asp His Tyr Gly Lys Lys Asn Thr Glu Glu Lys Ile Tyr Leu
    450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ser Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Ala Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Ile Asn Arg Phe Leu Cys Gln Phe Val Ala Asp His Met Leu Leu Thr
        675                 680                 685

Gly Lys Gly Lys Arg Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Ile Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Ala His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Lys Tyr Val Thr Pro Leu Phe Ile Ser Arg
            820                 825                 830
```

```
Ala Pro Asn Arg Lys Met Ser Gly Gln Gly His Met Glu Thr Val Lys
        835                 840                 845

Ser Ala Lys Arg Leu Asp Glu Gly Ile Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val His Asn His Asn Gly Ile Ala Asp Asn
    930                 935                 940

Ala Thr Ile Val Arg Val Asp Val Phe Glu Lys Gly Gly Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Thr Val Met Asp
            980                 985                 990

Asp Ser Phe Glu Phe Lys Phe Val  Leu Tyr Ala Asn Asp  Leu Ile Lys
        995                 1000                1005

Leu Thr  Ala Lys Lys Asn Glu  Phe Leu Gly Tyr Phe  Val Ser Leu
    1010                1015                1020

Asn Arg  Ala Thr Gly Ala Ile  Asp Ile Arg Thr His  Asp Thr Asp
    1025                1030                1035

Ser Thr  Lys Gly Lys Asn Gly  Ile Phe Gln Ser Val  Gly Val Lys
    1040                1045                1050

Thr Ala  Leu Ser Phe Gln Lys  Tyr Gln Ile Asp Glu  Leu Gly Lys
    1055                1060                1065

Glu Ile  Arg Pro Cys Arg Leu  Lys Lys Arg Pro Pro  Val Arg
    1070                1075                1080
```

<210> SEQ ID NO 181
<211> LENGTH: 3330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181

```
accggtgcca ccatgtaccc atacgatgtt ccagattacg cttcgccgaa gaaaaagcgc      60

aaggtcgaag cgtccatggc tgccttcaaa cctaatccta tgaactacat cctgggcctg     120

gacattggaa tcgcttctgt cgggtgggct atcgtggaaa tcgacgagga agagaaccct     180

atcagactga ttgatctggg agtcagagtg tttgaaaggg cagaggtgcc aaagaccggc     240

gactccctgg ccgctgcacg gagactggct cggtctgtca ggcgcctgac acgacggaga     300

gcacacaggc tgctgcgagc taggcgcctg ctgaagagag agggcgtgct gcaggccgct     360

gacttcgatg aaaacggcct gatcaagagc ctgcccaata ctccttggca gctgagagca     420

gccgctctgg acaggaagct gaccccactg gagtggtctg ccgtgctgct gcacctgatc     480

aagcatcgcg gctacctgag tcagcgaaaa aatgaagggg agacagcaga taaggagctg     540

ggagcactgc tgaaaggagt ggccgacaac actcatgctc tgcagaccgg cgattttagg     600
```

-continued

```
acacccgctg agctggcact gaataagttc gaaaaagaga gtggacacat tcgaaaccag     660
cggggcgact attcacatac cttcaaccgc aaggatctgc aggccgagct gaatctgctg     720
tttgaaaagc agaaagagtt cgggaatccc cacgtgtccg acgggctgaa agaaggaatc     780
gagacactgc tgatgactca gaggcctgca ctgtctggcg atgccgtgca gaagatgctg     840
gggcattgca cctttgaacc aacagagccc aaggcagcca aaaacaccta cacagccgag     900
aggttcgtgt ggctgacaaa gctgaacaat ctgcgcatcc tggaacaggg cagtgagcgg     960
cccctgactg acaccgaaag agccacactg atggatgagc cttacaggaa gtctaaactg    1020
acttatgccc aggctcgcaa gctgctggac ctggacgata ctgccttctt taagggcctg    1080
aggtacggga aagataatgc agaagccagc accctgatgg agatgaaggc ctatcacgct    1140
atctcccgcg ccctggaaaa agagggcctg aaggacaaga aatctcccct gaacctgagt    1200
cctgaactgc aggatgagat tgggaccgct tttagcctgt tcaagactga cgaggatatc    1260
accggacgcc tgaaagaccg agtgcagccc gaaattctgg aggcactgct gaagcacatc    1320
agttttgata aattcgtgca gatttcactg aaggccctgc gacggatcgt ccctctgatg    1380
gagcagggca atcggtacga cgaggcctgc accgagatct acggagatca ttatggcaag    1440
aaaaacacag aagagaaaat ctatctgccc cctattcctg ccgacgagat ccggaatcca    1500
gtggtcctga gagctctgtc acaggcaaga aaagtgatca acggagtggt cagaaggtac    1560
ggcagccctg ctaggatcca cattgaaacc gcacgcgaag tgggaaagtc ctttaaagac    1620
cgcaaggaaa tcgagaagcg acaggaagag aatagaaaag atagggaaaa gtctgctgca    1680
aaattcaggg agtactttcc aaacttcgtg ggcgaaccca agagtaaaga catcctgaag    1740
ctgcgcctgt acgagcagca gcacgggaag tgtctgtata gcggaaaaga aattaacctg    1800
ggccggctga atgaaaaggg ctatgtggag atcgatcatg cactgccctt ttccagaaca    1860
tgggacgatt ctttcaacaa taaggtcctg gctctgggga gcgagaacca gaacaaggga    1920
aatcagactc cttacgaata tttcaacggg aaggacaata gccgagaatg gcaggagttt    1980
aaagcccgcg tggagacaag ccggttccca cgaagcaaga aacagcggat tctgctgcag    2040
aagtttgacg aagatggatt caaagagaga aacctgaatg acacccggta catcaacaga    2100
tttctgtgcc agttcgtggc tgatcacatg ctgctgaccg gaaagggcaa acgccgagtc    2160
tttgcaagca acggccagat cacaaatctg ctgaggggct tctgggggct gcggaaggtg    2220
agagccgaga atgaccgcca ccatgcactg gatgccgtgg tcgtggcttg ttccactatt    2280
gcaatgcagc agaagatcac caggtttgtg cgctataaag agatgaacgc cttcgacgga    2340
aagacaattg ataaagaaac tggcgaggtg ctgcaccaga aggcacattt tcctcagcca    2400
tgggagttct tcgcccagga agtgatgatc cgggtctttg ggaagcctga cggaaaacca    2460
gagttcgaag aggccgatac ccccagaaaag ctgcggacac tgctggctga aaaactgagc    2520
tccagacccg aggcagtgca caagtacgtc acccccctgt tcattagcag ggcccctaat    2580
cgcaaaatgt ccgggcaggg acatatggag actgtgaaat cagctaagcg gctggacgaa    2640
ggcatcagcg tgctgagagt cccactgacc cagctgaagc tgaaagatct ggagaagatg    2700
gtgaaccggg aaagagagcc caagctgtat gaagctctga aagcaagact ggaggcccac    2760
aaggacgatc cagctaaagc atttgccgag cccttctaca aatatgacaa ggccggcaat    2820
cggacacagc aggtgaaggc tgtcagagtg gagcaggtcc agaaaactgg ggtctgggtg    2880
cacaaccata atggaattgc cgacaacgct acaatcgtcc gggtggatgt gttcgagaaa    2940
```

```
ggcgggaagt actatctggt gcctatctac tcctggcagg tcgccaaggg aatcctgcca   3000

gatagagctg tcgtgcaggg caaagacgaa gaggattgga ctgtgatgga cgattctttc   3060

gagtttaagt tcgtcctgta cgcaaacgac ctgatcaagc tgacagccaa gaaaaatgaa   3120

tttctggggt atttcgtgtc actgaacagg gcaactggag ccatcgatat tcgcacacat   3180

gacactgata gcaccaaggg aaaaaacggc atctttcagt ctgtgggcgt caagaccgcc   3240

ctgagtttcc agaaatatca gattgacgaa ctggggaagg agatccgacc ctgtcggctg   3300

aagaaacgac cacccgtgcg gtaagaattc                                    3330
```

```
<210> SEQ ID NO 182
<211> LENGTH: 145
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 182

nnnnnnnnnn nnnnnnnnnn gcugcggauu gcgggaaauc gcuuuucgca agcaaauuga     60

ccccuugugc gggcucggca ucccaagguc agcugccggu uauuaucgaa aaggcccacc    120

gcaagcagcg cgugggccuu uuuuu                                          145
```

```
<210> SEQ ID NO 183
<211> LENGTH: 1037
<212> TYPE: PRT
<213> ORGANISM: Parvibaculum lavamentivorans

<400> SEQUENCE: 183

Met Glu Arg Ile Phe Gly Phe Asp Ile Gly Thr Thr Ser Ile Gly Phe
1               5                   10                  15

Ser Val Ile Asp Tyr Ser Ser Thr Gln Ser Ala Gly Asn Ile Gln Arg
            20                  25                  30

Leu Gly Val Arg Ile Phe Pro Glu Ala Arg Asp Pro Asp Gly Thr Pro
        35                  40                  45

Leu Asn Gln Gln Arg Arg Gln Lys Arg Met Met Arg Arg Gln Leu Arg
    50                  55                  60

Arg Arg Arg Ile Arg Arg Lys Ala Leu Asn Glu Thr Leu His Glu Ala
65                  70                  75                  80

Gly Phe Leu Pro Ala Tyr Gly Ser Ala Asp Trp Pro Val Val Met Ala
                85                  90                  95

Asp Glu Pro Tyr Glu Leu Arg Arg Arg Gly Leu Glu Glu Gly Leu Ser
            100                 105                 110

Ala Tyr Glu Phe Gly Arg Ala Ile Tyr His Leu Ala Gln His Arg His
        115                 120                 125

Phe Lys Gly Arg Glu Leu Glu Glu Ser Asp Thr Pro Asp Pro Asp Val
    130                 135                 140

Asp Asp Glu Lys Glu Ala Ala Asn Glu Arg Ala Ala Thr Leu Lys Ala
145                 150                 155                 160

Leu Lys Asn Glu Gln Thr Thr Leu Gly Ala Trp Leu Ala Arg Arg Pro
                165                 170                 175

Pro Ser Asp Arg Lys Arg Gly Ile His Ala His Arg Asn Val Val Ala
            180                 185                 190
```

```
Glu Glu Phe Glu Arg Leu Trp Glu Val Gln Ser Lys Phe His Pro Ala
        195                 200                 205

Leu Lys Ser Glu Glu Met Arg Ala Arg Ile Ser Asp Thr Ile Phe Ala
    210                 215                 220

Gln Arg Pro Val Phe Trp Arg Lys Asn Thr Leu Gly Glu Cys Arg Phe
225                 230                 235                 240

Met Pro Gly Glu Pro Leu Cys Pro Lys Gly Ser Trp Leu Ser Gln Gln
                245                 250                 255

Arg Arg Met Leu Glu Lys Leu Asn Asn Leu Ala Ile Ala Gly Gly Asn
            260                 265                 270

Ala Arg Pro Leu Asp Ala Glu Glu Arg Asp Ala Ile Leu Ser Lys Leu
        275                 280                 285

Gln Gln Gln Ala Ser Met Ser Trp Pro Gly Val Arg Ser Ala Leu Lys
    290                 295                 300

Ala Leu Tyr Lys Gln Arg Gly Glu Pro Gly Ala Glu Lys Ser Leu Lys
305                 310                 315                 320

Phe Asn Leu Glu Leu Gly Gly Glu Ser Lys Leu Leu Gly Asn Ala Leu
                325                 330                 335

Glu Ala Lys Leu Ala Asp Met Phe Gly Pro Asp Trp Pro Ala His Pro
            340                 345                 350

Arg Lys Gln Glu Ile Arg His Ala Val His Glu Arg Leu Trp Ala Ala
        355                 360                 365

Asp Tyr Gly Glu Thr Pro Asp Lys Lys Arg Val Ile Ile Leu Ser Glu
    370                 375                 380

Lys Asp Arg Lys Ala His Arg Glu Ala Ala Ala Asn Ser Phe Val Ala
385                 390                 395                 400

Asp Phe Gly Ile Thr Gly Glu Gln Ala Ala Gln Leu Gln Ala Leu Lys
                405                 410                 415

Leu Pro Thr Gly Trp Glu Pro Tyr Ser Ile Pro Ala Leu Asn Leu Phe
            420                 425                 430

Leu Ala Glu Leu Glu Lys Gly Glu Arg Phe Gly Ala Leu Val Asn Gly
        435                 440                 445

Pro Asp Trp Glu Gly Trp Arg Arg Thr Asn Phe Pro His Arg Asn Gln
    450                 455                 460

Pro Thr Gly Glu Ile Leu Asp Lys Leu Pro Ser Pro Ala Ser Lys Glu
465                 470                 475                 480

Glu Arg Glu Arg Ile Ser Gln Leu Arg Asn Pro Thr Val Val Arg Thr
                485                 490                 495

Gln Asn Glu Leu Arg Lys Val Val Asn Asn Leu Ile Gly Leu Tyr Gly
            500                 505                 510

Lys Pro Asp Arg Ile Arg Ile Glu Val Gly Arg Asp Val Gly Lys Ser
        515                 520                 525

Lys Arg Glu Arg Glu Glu Ile Gln Ser Gly Ile Arg Arg Asn Glu Lys
    530                 535                 540

Gln Arg Lys Lys Ala Thr Glu Asp Leu Ile Lys Asn Gly Ile Ala Asn
545                 550                 555                 560

Pro Ser Arg Asp Asp Val Glu Lys Trp Ile Leu Trp Lys Glu Gly Gln
                565                 570                 575

Glu Arg Cys Pro Tyr Thr Gly Asp Gln Ile Gly Phe Asn Ala Leu Phe
            580                 585                 590

Arg Glu Gly Arg Tyr Glu Val Glu His Ile Trp Pro Arg Ser Arg Ser
        595                 600                 605

Phe Asp Asn Ser Pro Arg Asn Lys Thr Leu Cys Arg Lys Asp Val Asn
```

```
    610                 615                 620

Ile Glu Lys Gly Asn Arg Met Pro Phe Glu Ala Phe Gly His Asp Glu
625                 630                 635                 640

Asp Arg Trp Ser Ala Ile Gln Ile Arg Leu Gln Gly Met Val Ser Ala
                645                 650                 655

Lys Gly Gly Thr Gly Met Ser Pro Gly Lys Val Lys Arg Phe Leu Ala
            660                 665                 670

Lys Thr Met Pro Glu Asp Phe Ala Ala Arg Gln Leu Asn Asp Thr Arg
        675                 680                 685

Tyr Ala Ala Lys Gln Ile Leu Ala Gln Leu Lys Arg Leu Trp Pro Asp
    690                 695                 700

Met Gly Pro Glu Ala Pro Val Lys Val Glu Ala Val Thr Gly Gln Val
705                 710                 715                 720

Thr Ala Gln Leu Arg Lys Leu Trp Thr Leu Asn Asn Ile Leu Ala Asp
                725                 730                 735

Asp Gly Glu Lys Thr Arg Ala Asp His Arg His His Ala Ile Asp Ala
            740                 745                 750

Leu Thr Val Ala Cys Thr His Pro Gly Met Thr Asn Lys Leu Ser Arg
        755                 760                 765

Tyr Trp Gln Leu Arg Asp Asp Pro Arg Ala Glu Lys Pro Ala Leu Thr
    770                 775                 780

Pro Pro Trp Asp Thr Ile Arg Ala Asp Ala Glu Lys Ala Val Ser Glu
785                 790                 795                 800

Ile Val Val Ser His Arg Val Arg Lys Lys Val Ser Gly Pro Leu His
                805                 810                 815

Lys Glu Thr Thr Tyr Gly Asp Thr Gly Thr Asp Ile Lys Thr Lys Ser
            820                 825                 830

Gly Thr Tyr Arg Gln Phe Val Thr Arg Lys Lys Ile Glu Ser Leu Ser
        835                 840                 845

Lys Gly Glu Leu Asp Glu Ile Arg Asp Pro Arg Ile Lys Glu Ile Val
    850                 855                 860

Ala Ala His Val Ala Gly Arg Gly Gly Asp Pro Lys Lys Ala Phe Pro
865                 870                 875                 880

Pro Tyr Pro Cys Val Ser Pro Gly Gly Pro Glu Ile Arg Lys Val Arg
                885                 890                 895

Leu Thr Ser Lys Gln Gln Leu Asn Leu Met Ala Gln Thr Gly Asn Gly
            900                 905                 910

Tyr Ala Asp Leu Gly Ser Asn His His Ile Ala Ile Tyr Arg Leu Pro
        915                 920                 925

Asp Gly Lys Ala Asp Phe Glu Ile Val Ser Leu Phe Asp Ala Ser Arg
    930                 935                 940

Arg Leu Ala Gln Arg Asn Pro Ile Val Gln Arg Thr Arg Ala Asp Gly
945                 950                 955                 960

Ala Ser Phe Val Met Ser Leu Ala Ala Gly Glu Ala Ile Met Ile Pro
                965                 970                 975

Glu Gly Ser Lys Lys Gly Ile Trp Ile Val Gln Gly Val Trp Ala Ser
            980                 985                 990

Gly Gln Val Val Leu Glu Arg Asp  Thr Asp Ala Asp His  Ser Thr Thr
        995                 1000                1005

Thr Arg  Pro Met Pro Asn Pro  Ile Leu Lys Asp Asp  Ala Lys Lys
    1010                1015                1020

Val Ser  Ile Asp Pro Ile Gly  Arg Val Arg Pro Ser  Asn Asp
    1025                1030                1035
```

<210> SEQ ID NO 184
<211> LENGTH: 3195
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184
accggtgcca ccatgtaccc atacgatgtt ccagattacg cttcgccgaa gaaaaagcgc 60
aaggtcgaag cgtccatgga gaggattttc ggctttgaca tcggcacaac aagtatcgga 120
ttcagcgtga ttgattacag tagcacccag tccgcaggca acatccagag gctgggcgtg 180
cgcattttcc ctgaggcaag ggacccagat gggaccccc tgaaccagca gcggagacag 240
aaacgcatga tgaggcgcca gctgcgacgg agaaggattc gccgaaaggc actgaatgag 300
acactgcacg aagccggctt tctgccagct tacgggtctg cagattggcc cgtggtcatg 360
gccgacgagc cttatgaact gcggagaagg ggactggagg aaggcctgag tgcttacgag 420
ttcggacggg caatctatca tctggcccag caccggcatt ttaaaggcag agaactggag 480
gaatccgata cacccgaccc tgatgtggac gatgagaagg aagccgctaa cgagagagca 540
gccactctga aggccctgaa aaatgaacag accacactgg gagcatggct ggcccgccga 600 ccccccttctg accgcaagcg aggaatccac gcccatagga acgtggtcgc tgaggagttc 660
gagcgcctgt gggaagtgca gtccaagttt caccccgctc tgaaatctga ggaaatgcgg 720
gcaagaatca gtgatacaat ttcgcccag aggcctgtgt tttggcgcaa gaacactctg 780
ggagagtgca gattcatgcc tggcgaacca ctgtgtccca aggggtcctg gctgtctcag 840
cagcggagaa tgctggagaa actgaacaat ctggctatcg caggcgggaa tgctaggcca 900
ctggatgcag aggaacgcga cgccattctg agtaagctgc agcagcaggc cagcatgtcc 960
tggccaggcg tgcggtcagc tctgaaggca ctgtacaaac agagaggcga gcccggggct 1020
gaaaagagcc tgaaattcaa cctggagctg ggaggcgaat ccaagctgct gggaaatgcc 1080
ctggaggcta aactggcaga tatgtttggc cctgactggc cagctcaccc ccgaaagcag 1140
gagatccggc acgcagtgca tgaacggctg tgggctgcag attacggcga gacacccgac 1200
aagaaaagag tcatcattct gtccgagaag gatcgaaaag ctcatcggga agccgctgca 1260
aactctttcg tggcagactt tggaattact ggcgagcagg cagctcagct gcaggccctg 1320
aagctgccaa ccggctggga accttatagc atcccagcac tgaacctgtt cctggccgag 1380
ctggaaaagg gggagaggtt tggagccctg gtgaatggac ctgattggga aggctggagg 1440
cgcacaaact tcccccaccg caatcagcct actggggaga tcctggacaa gctgccaagt 1500
cccgcctcaa aagaggaaag ggaacgcatt agccagctgc gcaacccaac cgtggtccga 1560
acacagaatg agctgagaaa ggtggtcaac aatctgatcg ggctgtatgg aaaacccgat 1620
cgaatccgga ttgaagtggg ccgggacgtc gggaagtcca aaagagaaag ggaggaaatc 1680
cagtctggca ttcgacggaa cgagaagcag agaaagaaag ccactgaaga tctgatcaaa 1740
aacggaattg ctaatcctag ccgggacgat gtggagaagt ggatcctgtg gaaagagggc 1800
caggaaagat gcccatacac cggcgaccag attggcttca atgccctgtt tagagaaggc 1860
agatatgagg tggaacacat ctggcctcgc tctcgaagtt ttgataacag cccaaggaat 1920
aagacactgt gtcgcaaaga cgtgaacatc gagaagggaa ataggatgcc tttcgaggca 1980
tttggccatg acgaagatcg gtggagcgcc atccagatta gactgcaggg catggtgtca 2040
gccaaagggg gaactgggat gagccccgga aaggtcaaac gcttcctggc taagaccatg 2100
cctgaggatt ttgcagcccg gcagctgaac gacacaagat acgctgcaaa gcagatcctg 2160
gcccagctga aaaggctgtg gccagacatg ggacctgagg ctccagtgaa ggtcgaagca 2220
gtgactggac aggtcaccgc ccagctgcgc aaactgtgga ctctgaacaa tattctggct 2280
gacgatgggg agaaaaccag agcagatcac aggcaccatg ccatcgacgc tctgacagtg 2340
gcctgcactc atcctggaat gaccaacaag ctgagcaggt attggcagct gcgcgacgat 2400
ccacgagcag agaagccagc tctgactcca ccctgggata ccatccgcgc cgacgctgag 2460
aaagccgtgt ctgaaattgt ggtcagtcac cgggtgagaa agaaagtcag cggcccactg 2520
cataaggaga ctacctacgg cgatacaggg actgacatta agaccaaatc cggcacatat 2580
agacagttcg tgaccaggaa gaaaatcgag tcactgagca agggggagct ggatgaaatt 2640
cgcgaccccc gaatcaaaga aattgtggca gctcacgtcg caggacgagg aggcgacccc 2700
aagaaggcct tccctccata cccctgtgtg tctcccggag gccctgagat ccggaaggtc 2760
agactgacca gtaaacagca gctgaacctg atggcccaga cagggaatgg atacgctgac 2820
ctgggctcca accaccatat cgcaatctac cggctgcccg atgggaaggc cgacttcgag 2880
attgtgtcac tgtttgatgc tagcagaagg ctggcacaga gaaatccaat cgtgcagagg 2940
acacgagcag acggagccag cttcgtcatg tccctggcag ccggagaggc catcatgatt 3000
cccgaaggct caaagaaagg gatctggatt gtgcagggag tctgggcaag cggacaggtg 3060
gtcctggaga gggacaccga tgctgaccac tctacaacta cccgccctat gccaaacccc 3120
atcctgaagg acgatgccaa gaaagtgagt atcgatccta ttggccgagt ccggccatca 3180
aatgactaag aattc 3195

<210> SEQ ID NO 185
<211> LENGTH: 103
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 185
nnnnnnnnnn nnnnnnnnnn guuuuaguac ucuggaaaca gaaucuacua aaacaaggca 60
aaaugccgug uuuaucucgu caacuuguug gcgagauuuu uuu 103

<210> SEQ ID NO 186
<211> LENGTH: 1053
<212> TYPE: PRT
<213> ORGANISM: Staphylococcus aureus

<400> SEQUENCE: 186

Met Lys Arg Asn Tyr Ile Leu Gly Leu Asp Ile Gly Ile Thr Ser Val
1 5 10 15

Gly Tyr Gly Ile Ile Asp Tyr Glu Thr Arg Asp Val Ile Asp Ala Gly
20 25 30

Val Arg Leu Phe Lys Glu Ala Asn Val Glu Asn Asn Glu Gly Arg Arg
35 40 45

Ser Lys Arg Gly Ala Arg Arg Leu Lys Arg Arg Arg Arg His Arg Ile
50 55 60

```
Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480
```

```
Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
```

```
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050


<210> SEQ ID NO 187
<211> LENGTH: 3243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187

accggtgcca ccatgtaccc atacgatgtt ccagattacg cttcgccgaa gaaaaagcgc     60

aaggtcgaag cgtccatgaa aaggaactac attctggggc tggacatcgg gattacaagc    120

gtggggtatg ggattattga ctatgaaaca agggacgtga tcgacgcagg cgtcagactg    180

ttcaaggagg ccaacgtgga aaacaatgag ggacggagaa gcaagagggg agccaggcgc    240

ctgaaacgac ggagaaggca cagaatccag agggtgaaga aactgctgtt cgattacaac    300

ctgctgaccg accattctga gctgagtgga attaatcctt atgaagccag ggtgaaaggc    360

ctgagtcaga agctgtcaga ggaagagttt tccgcagctc tgctgcacct ggctaagcgc    420

cgaggagtgc ataacgtcaa tgaggtggaa gaggacaccg gcaacgagct gtctacaaag    480

gaacagatct cacgcaatag caaagctctg gaagagaagt atgtcgcaga gctgcagctg    540

gaacggctga agaaagatgg cgaggtgaga gggtcaatta ataggttcaa gacaagcgac    600

tacgtcaaag aagccaagca gctgctgaaa gtgcagaagg cttaccacca gctggatcag    660

agcttcatcg atacttatat cgacctgctg gagactcgga gaacctacta tgagggacca    720

ggagaaggga gccccttcgg atggaaagac atcaaggaat ggtacgagat gctgatggga    780

cattgcacct attttccaga agagctgaga agcgtcaagt acgcttataa cgcagatctg    840

tacaacgccc tgaatgacct gaacaacctg gtcatcacca gggatgaaaa cgagaaactg    900

gaatactatg agaagttcca gatcatcgaa aacgtgttta agcagaagaa aaagcctaca    960

ctgaaacaga ttgctaagga gatcctggtc aacgaagagg acatcaaggg ctaccgggtg   1020

acaagcactg gaaaaccaga gttcaccaat ctgaaagtgt atcacgatat taaggacatc   1080

acagcacgga aagaaatcat tgagaacgcc gaactgctgg atcagattgc taagatcctg   1140

actatctacc agagctccga ggacatccag gaagagctga ctaacctgaa cagcgagctg   1200
```

```
acccaggaag agatcgaaca gattagtaat ctgaaggggt acaccggaac acacaacctg   1260

tccctgaaag ctatcaatct gattctggat gagctgtggc atacaaacga caatcagatt   1320

gcaatcttta accggctgaa gctggtccca aaaaaggtgg acctgagtca gcagaaagag   1380

atcccaacca cactggtgga cgatttcatt ctgtcacccg tggtcaagcg gagcttcatc   1440

cagagcatca aagtgatcaa cgccatcatc aagaagtacg gcctgcccaa tgatatcatt   1500

atcgagctgg ctagggagaa gaacagcaag gacgcacaga agatgatcaa tgagatgcag   1560

aaacgaaacc ggcagaccaa tgaacgcatt gaagagatta tccgaactac cgggaaagag   1620

aacgcaaagt acctgattga aaaaatcaag ctgcacgata tgcaggaggg aaagtgtctg   1680

tattctctgg aggccatccc cctggaggac ctgctgaaca atccattcaa ctacgaggtc   1740

gatcatatta tccccagaag cgtgtccttc gacaattcct ttaacaacaa ggtgctggtc   1800

aagcaggaag agaactctaa aaagggcaat aggactcctt tccagtacct gtctagttca   1860

gattccaaga tctcttacga aacctttaaa aagcacattc tgaatctggc caaaggaaag   1920

ggccgcatca gcaagaccaa aaaggagtac ctgctggaag agcgggacat caacagattc   1980

tccgtccaga aggattttat taaccggaat ctggtggaca caagatacgc tactcgcggc   2040

ctgatgaatc tgctgcgatc ctatttccgg gtgaacaatc tggatgtgaa agtcaagtcc   2100

atcaacggcg ggttcacatc ttttctgagg cgcaaatgga agtttaaaaa ggagcgcaac   2160

aaagggtaca agcaccatgc cgaagatgct ctgattatcg caaatgccga cttcatcttt   2220

aaggagtgga aaaagctgga caaagccaag aaagtgatgg agaaccagat gttcgaagag   2280

aagcaggccg aatctatgcc cgaaatcgag acagaacagg agtacaagga gattttcatc   2340

actcctcacc agatcaagca tatcaaggat ttcaaggact acaagtactc tcaccgggtg   2400

gataaaaagc ccaacagaga gctgatcaat gacaccctgt atagtacaag aaaagacgat   2460

aaggggaata ccctgattgt gaacaatctg aacggactgt acgacaaaga taatgacaag   2520

ctgaaaaagc tgatcaacaa aagtcccgag aagctgctga tgtaccacca tgatcctcag   2580

acatatcaga aactgaagct gattatggag cagtacggcg acgagaagaa cccactgtat   2640

aagtactatg aagagactgg gaactacctg accaagtata gcaaaaagga taatggcccc   2700

gtgatcaaga agatcaagta ctatgggaac aagctgaatg cccatctgga catcacagac   2760

gattacccta acagtcgcaa caaggtggtc aagctgtcac tgaagccata cagattcgat   2820

gtctatctgg acaacggcgt gtataaattt gtgactgtca agaatctgga tgtcatcaaa   2880

aaggagaact actatgaagt gaatagcaag tgctacgaag aggctaaaaa gctgaaaaag   2940

attagcaacc aggcagagtt catcgcctcc ttttacaaca acgacctgat taagatcaat   3000

ggcgaactgt atagggtcat cggggtgaac aatgatctgc tgaaccgcat tgaagtgaat   3060

atgattgaca tcacttaccg agagtatctg gaaaacatga atgataagcg ccccccctcga   3120

attatcaaaa caattgcctc taagactcag agtatcaaaa agtactcaac cgacattctg   3180

ggaaacctgt atgaggtgaa gagcaaaaag caccctcaga ttatcaaaaa gggctaagaa   3240

ttc                                                                 3243
```

<210> SEQ ID NO 188
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide <220> FEATURE:
<221> NAME/KEY: modified_base
<222> LOCATION: (1)..(20)
<223> OTHER INFORMATION: a, c, u, g, unknown or other

<400> SEQUENCE: 188
nnnnnnnnnn nnnnnnnnnn guuuuagcac uguacaagaa auugucgugc uaaaauaagg 60
cgcuguuaau gcagcugccg cauccgccag agcauuuaug cucuggcuuu uuuu 114

<210> SEQ ID NO 189
<211> LENGTH: 1269
<212> TYPE: PRT
<213> ORGANISM: Mycoplasma gallisepticum

<400> SEQUENCE: 189

Met Asn Asn Ser Ile Lys Ser Lys Pro Glu Val Thr Ile Gly Leu Asp
1 5 10 15

Leu Gly Val Gly Ser Val Gly Trp Ala Ile Val Asp Asn Glu Thr Asn
20 25 30

Ile Ile His His Leu Gly Ser Arg Leu Phe Ser Gln Ala Lys Thr Ala
35 40 45

Glu Asp Arg Arg Ser Phe Arg Gly Val Arg Arg Leu Ile Arg Arg Arg
50 55 60

Lys Tyr Lys Leu Lys Arg Phe Val Asn Leu Ile Trp Lys Tyr Asn Ser
65 70 75 80

Tyr Phe Gly Phe Lys Asn Lys Glu Asp Ile Leu Asn Asn Tyr Gln Glu
85 90 95

Gln Gln Lys Leu His Asn Thr Val Leu Asn Leu Lys Ser Glu Ala Leu
100 105 110

Asn Ala Lys Ile Asp Pro Lys Ala Leu Ser Trp Ile Leu His Asp Tyr
115 120 125

Leu Lys Asn Arg Gly His Phe Tyr Glu Asp Asn Arg Asp Phe Asn Val
130 135 140

Tyr Pro Thr Lys Glu Leu Ala Lys Tyr Phe Asp Lys Tyr Gly Tyr Tyr
145 150 155 160

Lys Gly Ile Ile Asp Ser Lys Glu Asp Asn Asp Asn Lys Leu Glu Glu
165 170 175

Glu Leu Thr Lys Tyr Lys Phe Ser Asn Lys His Trp Leu Glu Glu Val
180 185 190

Lys Lys Val Leu Ser Asn Gln Thr Gly Leu Pro Glu Lys Phe Lys Glu
195 200 205

Glu Tyr Glu Ser Leu Phe Ser Tyr Val Arg Asn Tyr Ser Glu Gly Pro
210 215 220

Gly Ser Ile Asn Ser Val Ser Pro Tyr Gly Ile Tyr His Leu Asp Glu
225 230 235 240

Lys Glu Gly Lys Val Val Gln Lys Tyr Asn Asn Ile Trp Asp Lys Thr
245 250 255

Ile Gly Lys Cys Asn Ile Phe Pro Asp Glu Tyr Arg Ala Pro Lys Asn
260 265 270

Ser Pro Ile Ala Met Ile Phe Asn Glu Ile Asn Glu Leu Ser Thr Ile
275 280 285

Arg Ser Tyr Ser Ile Tyr Leu Thr Gly Trp Phe Ile Asn Gln Glu Phe
290 295 300

Lys Lys Ala Tyr Leu Asn Lys Leu Leu Asp Leu Leu Ile Lys Thr Asn
305 310 315 320

```
Gly Glu Lys Pro Ile Asp Ala Arg Gln Phe Lys Lys Leu Arg Glu Glu
                325                 330                 335

Thr Ile Ala Glu Ser Ile Gly Lys Glu Thr Leu Lys Asp Val Glu Asn
            340                 345                 350

Glu Glu Lys Leu Glu Lys Glu Asp His Lys Trp Lys Leu Lys Gly Leu
        355                 360                 365

Lys Leu Asn Thr Asn Gly Lys Ile Gln Tyr Asn Asp Leu Ser Ser Leu
    370                 375                 380

Ala Lys Phe Val His Lys Leu Lys Gln His Leu Lys Leu Asp Phe Leu
385                 390                 395                 400

Leu Glu Asp Gln Tyr Ala Thr Leu Asp Lys Ile Asn Phe Leu Gln Ser
                405                 410                 415

Leu Phe Val Tyr Leu Gly Lys His Leu Arg Tyr Ser Asn Arg Val Asp
            420                 425                 430

Ser Ala Asn Leu Lys Glu Phe Ser Asp Ser Asn Lys Leu Phe Glu Arg
        435                 440                 445

Ile Leu Gln Lys Gln Lys Asp Gly Leu Phe Lys Leu Phe Glu Gln Thr
    450                 455                 460

Asp Lys Asp Asp Glu Lys Ile Leu Ala Gln Thr His Ser Leu Ser Thr
465                 470                 475                 480

Lys Ala Met Leu Leu Ala Ile Thr Arg Met Thr Asn Leu Asp Asn Asp
                485                 490                 495

Glu Asp Asn Gln Lys Asn Asn Asp Lys Gly Trp Asn Phe Glu Ala Ile
            500                 505                 510

Lys Asn Phe Asp Gln Lys Phe Ile Asp Ile Thr Lys Lys Asn Asn Asn
        515                 520                 525

Leu Ser Leu Lys Gln Asn Lys Arg Tyr Leu Asp Asp Arg Phe Ile Asn
    530                 535                 540

Asp Ala Ile Leu Ser Pro Gly Val Lys Arg Ile Leu Arg Glu Ala Thr
545                 550                 555                 560

Lys Val Phe Asn Ala Ile Leu Lys Gln Phe Ser Glu Glu Tyr Asp Val
                565                 570                 575

Thr Lys Val Val Ile Glu Leu Ala Arg Glu Leu Ser Glu Glu Lys Glu
            580                 585                 590

Leu Glu Asn Thr Lys Asn Tyr Lys Lys Leu Ile Lys Lys Asn Gly Asp
        595                 600                 605

Lys Ile Ser Glu Gly Leu Lys Ala Leu Gly Ile Ser Glu Asp Glu Ile
    610                 615                 620

Lys Asp Ile Leu Lys Ser Pro Thr Lys Ser Tyr Lys Phe Leu Leu Trp
625                 630                 635                 640

Leu Gln Gln Asp His Ile Asp Pro Tyr Ser Leu Lys Glu Ile Ala Phe
                645                 650                 655

Asp Asp Ile Phe Thr Lys Thr Glu Lys Phe Glu Ile Asp His Ile Ile
            660                 665                 670

Pro Tyr Ser Ile Ser Phe Asp Asp Ser Ser Ser Asn Lys Leu Leu Val
        675                 680                 685

Leu Ala Glu Ser Asn Gln Ala Lys Ser Asn Gln Thr Pro Tyr Glu Phe
    690                 695                 700

Ile Ser Ser Gly Asn Ala Gly Ile Lys Trp Glu Asp Tyr Glu Ala Tyr
705                 710                 715                 720

Cys Arg Lys Phe Lys Asp Gly Asp Ser Ser Leu Leu Asp Ser Thr Gln
                725                 730                 735

Arg Ser Lys Lys Phe Ala Lys Met Met Lys Thr Asp Thr Ser Ser Lys
```

```
            740                 745                 750

Tyr Asp Ile Gly Phe Leu Ala Arg Asn Leu Asn Asp Thr Arg Tyr Ala
        755                 760                 765

Thr Ile Val Phe Arg Asp Ala Leu Glu Asp Tyr Ala Asn Asn His Leu
    770                 775                 780

Val Glu Asp Lys Pro Met Phe Lys Val Val Cys Ile Asn Gly Ser Val
785                 790                 795                 800

Thr Ser Phe Leu Arg Lys Asn Phe Asp Asp Ser Ser Tyr Ala Lys Lys
                805                 810                 815

Asp Arg Asp Lys Asn Ile His His Ala Val Asp Ala Ser Ile Ile Ser
            820                 825                 830

Ile Phe Ser Asn Glu Thr Lys Thr Leu Phe Asn Gln Leu Thr Gln Phe
        835                 840                 845

Ala Asp Tyr Lys Leu Phe Lys Asn Thr Asp Gly Ser Trp Lys Lys Ile
    850                 855                 860

Asp Pro Lys Thr Gly Val Val Thr Glu Val Thr Asp Glu Asn Trp Lys
865                 870                 875                 880

Gln Ile Arg Val Arg Asn Gln Val Ser Glu Ile Ala Lys Val Ile Glu
                885                 890                 895

Lys Tyr Ile Gln Asp Ser Asn Ile Glu Arg Lys Ala Arg Tyr Ser Arg
            900                 905                 910

Lys Ile Glu Asn Lys Thr Asn Ile Ser Leu Phe Asn Asp Thr Val Tyr
        915                 920                 925

Ser Ala Lys Lys Val Gly Tyr Glu Asp Gln Ile Lys Arg Lys Asn Leu
    930                 935                 940

Lys Thr Leu Asp Ile His Glu Ser Ala Lys Glu Asn Lys Asn Ser Lys
945                 950                 955                 960

Val Lys Arg Gln Phe Val Tyr Arg Lys Leu Val Asn Val Ser Leu Leu
                965                 970                 975

Asn Asn Asp Lys Leu Ala Asp Leu Phe Ala Glu Lys Glu Asp Ile Leu
            980                 985                 990

Met Tyr Arg Ala Asn Pro Trp Val  Ile Asn Leu Ala Glu  Gln Ile Phe
        995                 1000                1005

Asn Glu  Tyr Thr Glu Asn Lys  Lys Ile Lys Ser Gln  Asn Val Phe
    1010                1015                1020

Glu Lys  Tyr Met Leu Asp Leu  Thr Lys Glu Phe Pro  Glu Lys Phe
    1025                1030                1035

Ser Glu  Phe Leu Val Lys Ser  Met Leu Arg Asn Lys  Thr Ala Ile
    1040                1045                1050

Ile Tyr  Asp Asp Lys Lys Asn  Ile Val His Arg Ile  Lys Arg Leu
    1055                1060                1065

Lys Met  Leu Ser Ser Glu Leu  Lys Glu Asn Lys Leu  Ser Asn Val
    1070                1075                1080

Ile Ile  Arg Ser Lys Asn Gln  Ser Gly Thr Lys Leu  Ser Tyr Gln
    1085                1090                1095

Asp Thr  Ile Asn Ser Leu Ala  Leu Met Ile Met Arg  Ser Ile Asp
    1100                1105                1110

Pro Thr  Ala Lys Lys Gln Tyr  Ile Arg Val Pro Leu  Asn Thr Leu
    1115                1120                1125

Asn Leu  His Leu Gly Asp His  Asp Phe Asp Leu His  Asn Met Asp
    1130                1135                1140

Ala Tyr  Leu Lys Lys Pro Lys  Phe Val Lys Tyr Leu  Lys Ala Asn
    1145                1150                1155
```

```
Glu Ile  Gly Asp Glu Tyr Lys  Pro Trp Arg Val Leu  Thr Ser Gly
    1160                 1165                 1170

Thr Leu  Leu Ile His Lys Lys  Asp Lys Lys Leu Met  Tyr Ile Ser
    1175                 1180                 1185

Ser Phe  Gln Asn Leu Asn Asp  Val Ile Glu Ile Lys  Asn Leu Ile
    1190                 1195                 1200

Glu Thr  Glu Tyr Lys Glu Asn  Asp Asp Ser Asp Ser  Lys Lys Lys
    1205                 1210                 1215

Lys Lys  Ala Asn Arg Phe Leu  Met Thr Leu Ser Thr  Ile Leu Asn
    1220                 1225                 1230

Asp Tyr  Ile Leu Leu Asp Ala  Lys Asp Asn Phe Asp  Ile Leu Gly
    1235                 1240                 1245

Leu Ser  Lys Asn Arg Ile Asp  Glu Ile Leu Asn Ser  Lys Leu Gly
    1250                 1255                 1260

Leu Asp  Lys Ile Val Lys
    1265
```

<210> SEQ ID NO 190
<211> LENGTH: 3891
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190

```
accggtgcca ccatgtaccc atacgatgtt ccagattacg cttcgccgaa gaaaaagcgc     60

aaggtcgaag cgtccatgaa caatagcatc aaatctaaac ctgaagtgac catcgggctg    120

gacctgggag tgggaagcgt ggggtgggca atcgtggata acgaaacaaa catcattcac    180

catctgggct ccaggctgtt ttctcaggcc aagactgctg aggatcggag atctttccgc    240

ggggtgaggc gcctgatccg acggagaaaa tacaagctga aacgattcgt caatctgatt    300

tggaagtaca acagctattt cggcttcaag aacaaagagg acatcctgaa caattatcag    360

gagcagcaga agctgcacaa taccgtgctg aacctgaaat cagaggcact gaatgccaag    420

atcgatccta aagcactgag ctggattctg cacgactacc tgaagaacag aggccatttt    480

tatgaggaca atagggattt caacgtgtac ccaacaaagg agctggccaa gtacttcgat    540

aagtacgggt actacaaggg aatcattgac agcaaggagg acaatgataa caaactggag    600

gaagagctga caaagtacaa attctccaat aagcactggc tggaagaggt gaagaaagtc    660

ctgtctaacc agactggcct gccagaaaag tttaaagaag agtatgagtc actgttcagc    720

tacgtgagaa attattcaga gggcccaggg agcatcaact ctgtcagtcc ctacgggatc    780

taccatctgg acgaaaaaga gggaaaggtg gtccagaagt acaacaacat ctgggataag    840

acaatcggaa agtgcaacat cttccctgac gagtatagag ctcccaagaa cagtcctatc    900

gcaatgattt tcaatgaaat caacgagctg tccacaatca ggtcatacag catctacctg    960

actggctggt tcattaatca ggagttcaag aaagcctacc tgaacaagct gctggatctg   1020

ctgatcaaaa ccaacggaga gaagccaatt gacgcaaggc agttcaagaa actgcgcgaa   1080

gagacaatcg ccgaaagcat tggcaaagag acactgaagg atgtggagaa tgaagagaaa   1140

ctggaaaagg aggaccacaa gtggaaactg aagggactga agctgaatac caacggcaaa   1200

atccagtaca acgatctgag ctccctggct aagtttgtgc acaaactgaa gcagcatctg   1260

aaactggatt tcctgctgga ggaccagtat gcaacactgg acaagatcaa tttcctgcag   1320
```

```
tccctgtttg tgtacctggg caagcacctg agatattcca atagggtcga ttctgccaac   1380
ctgaaggaat tttccgactc taacaaactg ttcgagcgca tcctgcagaa acagaaggat   1440
gggctgttca agctgtttga acagactgac aaagacgatg agaagatcct ggcccagaca   1500
catagtctgt caactaaggc catgctgctg gctattaccc ggatgacaaa tctggacaac   1560
gatgaggaca accagaaaaa caatgacaag ggctggaatt ttgaggccat caaaaacttc   1620
gatcagaagt ttatcgacat caccaagaaa aacaacaacc tgagcctgaa acagaataag   1680
cgctacctgg acgatcgatt catcaacgat gctattctgt cccctggggt gaagcgaatc   1740
ctgcgggagg caaccaaggt ctttaatgcc attctgaaac agttctctga agagtacgac   1800
gtgacaaagg tggtcatcga actggctcgc gagctgagcg aagagaagga actggagaac   1860
acaaagaact acaagaaact gatcaagaaa aacggcgaca agattagtga gggcctgaaa   1920
gcactgggga tctcagaaga tgagatcaaa gacattctga agagtcccac taaatcatac   1980
aagtttctgc tgtggctgca gcaggaccac atcgatcctt atagcctgaa ggagatcgcc   2040
ttcgacgata tttttaccaa aacagaaaag ttcgagatcg accatatcat tccctacagc   2100
atttccttcg acgattctag ttcaaacaag ctgctggtgc tggctgaaag taatcaggca   2160
aagtcaaacc agactcctta tgagttcatc agctccggaa acgcaggcat taagtgggaa   2220
gattacgagg cctattgccg caagttcaag gatggggact ctagtctgct ggacagcacc   2280
cagcggtcca agaaattcgc caaaatgatg aaaaccgata cctcaagcaa gtacgacatc   2340
ggatttctgg ctcgaaatct gaacgatact cggtacgcaa ccattgtgtt ccgggacgcc   2400
ctggaggact atgctaataa ccacctggtc gaggacaaac ccatgtttaa ggtggtctgt   2460
atcaatgggt ccgtgacctc tttcctgcgg aagaactttg acgattcctc ttacgccaag   2520
aaagatagag acaagaatat ccaccatgct gtggatgcaa gtatcatctc aattttcagc   2580
aacgagacaa agactctgtt caaccagctg actcagtttg ctgactataa actgttcaag   2640
aacaccgatg gcagctggaa gaaaatcgac cctaagacag ggtggtcac tgaagtgacc   2700
gacgagaatt ggaagcagat tagggtgcgc aaccaggtga gcgaaatcgc caaagtcatt   2760
gagaagtaca tccaggatag caacatcgaa agaaaggcta ggtattcccg caaaatcgag   2820
aataagacta acatttccct gtttaatgac accgtgtact ctgccaagaa agtcggctat   2880
gaggatcaga tcaaaagaaa gaacctgaaa accctggaca ttcacgaatc tgctaaagag   2940
aataagaaca gtaaagtgaa gcggcagttt gtctacagaa agctggtgaa tgtcagcctg   3000
ctgaataacg ataagctggc agacctgttc gccgaaaaag aggatatcct gatgtatagg   3060
gccaatccat gggtcatcaa cctggctgag cagattttca atgaatacac tgagaacaag   3120
aaaatcaagt cccagaacgt gtttgaaaaa tatatgctgg acctgaccaa agagttcccc   3180
gagaagttca gcgagtttct ggtgaagtcc atgctgagaa acaagaccgc catcatctac   3240
gacgataaga aaaacattgt ccatcgaatc aaacggctga agatgctgag ttcagaactg   3300
aaagagaata agctgtctaa cgtgatcatt aggtctaaga atcagagtgg gaccaaactg   3360
tcataccagg atacaatcaa cagcctggcc ctgatgatta tgcgcagcat cgaccctact   3420
gctaagaaac agtatattcg agtgccactg aataccctga acctgcacct gggagatcat   3480
gactttgatc tgcacaatat ggatgcttac ctgaagaaac caaaattcgt gaagtatctg   3540
aaagcaaacg aaatcggcga cgagtacaag ccctggaggg tcctgacatc tggcactctg   3600
ctgatccata agaaggataa gaaactgatg tacatcagct ccttccagaa tctgaacgac   3660
```

gtgatcgaaa ttaagaatct gatcgaaacc gagtataaag agaacgacga ttctgatagt 3720
aagaaaaaga aaaaggcaaa ccgctttctg atgaccctga gcacaatcct gaatgactac 3780
attctgctgg acgccaagga taacttcgac atcctggggc tgtctaaaaa tcggatcgat 3840
gagattctga acagtaagct gggactggac aagattgtga aataagaatt c 3891

<210> SEQ ID NO 191
<211> LENGTH: 137
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 191
nnnnnnnnnn nnnnnnnnnn guuuuagucu cugaaaagag acuaaaauaa gugguuuuug 60
gucauccacg cagguuuaca aucccuuuaa aaccauuaaa auucaaauaa acuagguugu 120
aucaacuuag uuuuuuu 137

<210> SEQ ID NO 192
<211> LENGTH: 1003
<212> TYPE: PRT
<213> ORGANISM: Campylobacter lari

<400> SEQUENCE: 192

Met Arg Ile Leu Gly Phe Asp Ile Gly Ile Asn Ser Ile Gly Trp Ala
1 5 10 15

Phe Val Glu Asn Asp Glu Leu Lys Asp Cys Gly Val Arg Ile Phe Thr
20 25 30

Lys Ala Glu Asn Pro Lys Asn Lys Glu Ser Leu Ala Leu Pro Arg Arg
35 40 45

Asn Ala Arg Ser Ser Arg Arg Arg Leu Lys Arg Arg Lys Ala Arg Leu
50 55 60

Ile Ala Ile Lys Arg Ile Leu Ala Lys Glu Leu Lys Leu Asn Tyr Lys
65 70 75 80

Asp Tyr Val Ala Ala Asp Gly Glu Leu Pro Lys Ala Tyr Glu Gly Ser
85 90 95

Leu Ala Ser Val Tyr Glu Leu Arg Tyr Lys Ala Leu Thr Gln Asn Leu
100 105 110

Glu Thr Lys Asp Leu Ala Arg Val Ile Leu His Ile Ala Lys His Arg
115 120 125

Gly Tyr Met Asn Lys Asn Glu Lys Lys Ser Asn Asp Ala Lys Lys Gly
130 135 140

Lys Ile Leu Ser Ala Leu Lys Asn Asn Ala Leu Lys Leu Glu Asn Tyr
145 150 155 160

Gln Ser Val Gly Glu Tyr Phe Tyr Lys Glu Phe Phe Gln Lys Tyr Lys
165 170 175

Lys Asn Thr Lys Asn Phe Ile Lys Ile Arg Asn Thr Lys Asp Asn Tyr
180 185 190

Asn Asn Cys Val Leu Ser Ser Asp Leu Glu Lys Glu Leu Lys Leu Ile
195 200 205

Leu Glu Lys Gln Lys Glu Phe Gly Tyr Asn Tyr Ser Glu Asp Phe Ile
210 215 220

```
Asn Glu Ile Leu Lys Val Ala Phe Phe Gln Arg Pro Leu Lys Asp Phe
225                 230                 235                 240

Ser His Leu Val Gly Ala Cys Thr Phe Phe Glu Glu Glu Lys Arg Ala
                245                 250                 255

Cys Lys Asn Ser Tyr Ser Ala Trp Glu Phe Val Ala Leu Thr Lys Ile
            260                 265                 270

Ile Asn Glu Ile Lys Ser Leu Glu Lys Ile Ser Gly Glu Ile Val Pro
        275                 280                 285

Thr Gln Thr Ile Asn Glu Val Leu Asn Leu Ile Leu Asp Lys Gly Ser
    290                 295                 300

Ile Thr Tyr Lys Lys Phe Arg Ser Cys Ile Asn Leu His Glu Ser Ile
305                 310                 315                 320

Ser Phe Lys Ser Leu Lys Tyr Asp Lys Glu Asn Ala Glu Asn Ala Lys
                325                 330                 335

Leu Ile Asp Phe Arg Lys Leu Val Glu Phe Lys Lys Ala Leu Gly Val
            340                 345                 350

His Ser Leu Ser Arg Gln Glu Leu Asp Gln Ile Ser Thr His Ile Thr
        355                 360                 365

Leu Ile Lys Asp Asn Val Lys Leu Lys Thr Val Leu Glu Lys Tyr Asn
    370                 375                 380

Leu Ser Asn Glu Gln Ile Asn Asn Leu Leu Glu Ile Glu Phe Asn Asp
385                 390                 395                 400

Tyr Ile Asn Leu Ser Phe Lys Ala Leu Gly Met Ile Leu Pro Leu Met
                405                 410                 415

Arg Glu Gly Lys Arg Tyr Asp Glu Ala Cys Glu Ile Ala Asn Leu Lys
            420                 425                 430

Pro Lys Thr Val Asp Glu Lys Lys Asp Phe Leu Pro Ala Phe Cys Asp
        435                 440                 445

Ser Ile Phe Ala His Glu Leu Ser Asn Pro Val Val Asn Arg Ala Ile
    450                 455                 460

Ser Glu Tyr Arg Lys Val Leu Asn Ala Leu Leu Lys Lys Tyr Gly Lys
465                 470                 475                 480

Val His Lys Ile His Leu Glu Leu Ala Arg Asp Val Gly Leu Ser Lys
                485                 490                 495

Lys Ala Arg Glu Lys Ile Glu Lys Glu Gln Lys Glu Asn Gln Ala Val
            500                 505                 510

Asn Ala Trp Ala Leu Lys Glu Cys Glu Asn Ile Gly Leu Lys Ala Ser
        515                 520                 525

Ala Lys Asn Ile Leu Lys Leu Lys Leu Trp Lys Glu Gln Lys Glu Ile
    530                 535                 540

Cys Ile Tyr Ser Gly Asn Lys Ile Ser Ile Glu His Leu Lys Asp Glu
545                 550                 555                 560

Lys Ala Leu Glu Val Asp His Ile Tyr Pro Tyr Ser Arg Ser Phe Asp
                565                 570                 575

Asp Ser Phe Ile Asn Lys Val Leu Val Phe Thr Lys Glu Asn Gln Glu
            580                 585                 590

Lys Leu Asn Lys Thr Pro Phe Glu Ala Phe Gly Lys Asn Ile Glu Lys
        595                 600                 605

Trp Ser Lys Ile Gln Thr Leu Ala Gln Asn Leu Pro Tyr Lys Lys Lys
    610                 615                 620

Asn Lys Ile Leu Asp Glu Asn Phe Lys Asp Lys Gln Gln Glu Asp Phe
625                 630                 635                 640

Ile Ser Arg Asn Leu Asn Asp Thr Arg Tyr Ile Ala Thr Leu Ile Ala
```

-continued

```
                645                 650                 655

Lys Tyr Thr Lys Glu Tyr Leu Asn Phe Leu Leu Leu Ser Glu Asn Glu
            660                 665                 670

Asn Ala Asn Leu Lys Ser Gly Glu Lys Gly Ser Lys Ile His Val Gln
        675                 680                 685

Thr Ile Ser Gly Met Leu Thr Ser Val Leu Arg His Thr Trp Gly Phe
    690                 695                 700

Asp Lys Lys Asp Arg Asn Asn His Leu His His Ala Leu Asp Ala Ile
705                 710                 715                 720

Ile Val Ala Tyr Ser Thr Asn Ser Ile Ile Lys Ala Phe Ser Asp Phe
                725                 730                 735

Arg Lys Asn Gln Glu Leu Leu Lys Ala Arg Phe Tyr Ala Lys Glu Leu
            740                 745                 750

Thr Ser Asp Asn Tyr Lys His Gln Val Lys Phe Phe Glu Pro Phe Lys
        755                 760                 765

Ser Phe Arg Glu Lys Ile Leu Ser Lys Ile Asp Glu Ile Phe Val Ser
    770                 775                 780

Lys Pro Pro Arg Lys Arg Ala Arg Arg Ala Leu His Lys Asp Thr Phe
785                 790                 795                 800

His Ser Glu Asn Lys Ile Ile Asp Lys Cys Ser Tyr Asn Ser Lys Glu
                805                 810                 815

Gly Leu Gln Ile Ala Leu Ser Cys Gly Arg Val Arg Lys Ile Gly Thr
            820                 825                 830

Lys Tyr Val Glu Asn Asp Thr Ile Val Arg Val Asp Ile Phe Lys Lys
        835                 840                 845

Gln Asn Lys Phe Tyr Ala Ile Pro Ile Tyr Ala Met Asp Phe Ala Leu
    850                 855                 860

Gly Ile Leu Pro Asn Lys Ile Val Ile Thr Gly Lys Asp Lys Asn Asn
865                 870                 875                 880

Asn Pro Lys Gln Trp Gln Thr Ile Asp Glu Ser Tyr Glu Phe Cys Phe
                885                 890                 895

Ser Leu Tyr Lys Asn Asp Leu Ile Leu Leu Gln Lys Lys Asn Met Gln
            900                 905                 910

Glu Pro Glu Phe Ala Tyr Tyr Asn Asp Phe Ser Ile Ser Thr Ser Ser
        915                 920                 925

Ile Cys Val Glu Lys His Asp Asn Lys Phe Glu Asn Leu Thr Ser Asn
    930                 935                 940

Gln Lys Leu Leu Phe Ser Asn Ala Lys Glu Gly Ser Val Lys Val Glu
945                 950                 955                 960

Ser Leu Gly Ile Gln Asn Leu Lys Val Phe Glu Lys Tyr Ile Ile Thr
                965                 970                 975

Pro Leu Gly Asp Lys Ile Lys Ala Asp Phe Gln Pro Arg Glu Asn Ile
            980                 985                 990

Ser Leu Lys Thr Ser Lys Lys Tyr  Gly Leu Arg
        995                 1000
```

<210> SEQ ID NO 193
<211> LENGTH: 3093
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

-continued accggtgcca ccatgtaccc atacgatgtt ccagattacg cttcgccgaa gaaaaagcgc 60
aaggtcgaag cgtccatgag gattctgggg tttgacattg gcattaacag catcgggtgg 120
gcttttgtgg agaacgacga actgaaggac tgcggagtgc ggatcttcac aaaggccgag 180
aacccaaaaa ataaggaaag cctggcactg ccccggagaa atgcacgcag ctccaggcgc 240
cgactgaaac ggagaaaggc ccggctgatc gctattaaga gaatcctggc caaagagctg 300
aagctgaact acaaggacta tgtcgcagct gatggagagc tgccaaaggc ctacgaagga 360
tccctggcat ctgtgtacga gctgcggtat aaggccctga cacagaacct ggaaactaaa 420
gatctggcca gagtgatcct gcacattgct aagcataggg ggtacatgaa caagaacgag 480
aagaaatcaa acgacgctaa gaaaggaaag atcctgagcg ctctgaaaaa caatgcactg 540
aagctggaga actaccagag cgtgggcgaa tacttctaca aggagttctt tcagaaatac 600
aagaaaaaca caaagaactt catcaagatc cgcaacacta aggataatta caacaattgc 660
gtgctgtcta gtgacctgga aaaagagctg aagctgatcc tggaaaaaca gaaggagttc 720
ggctacaact actctgaaga tttcatcaac gagattctga aggtcgcctt ctttcagcgg 780
cccctgaagg acttcagtca cctggtgggg gcctgcactt tctttgagga agagaaaagg 840
gcctgtaaga acagctactc tgcctgggag tttgtggctc tgaccaagat cattaacgag 900
atcaagagcc tggagaagat cagcggcgaa attgtgccaa cccagacaat caacgaggtc 960
ctgaatctga tcctggacaa ggggtctatc acctacaaga aattcagaag ttgtatcaat 1020
ctgcatgaga gtatcagctt caagagcctg aagtatgata aagaaaacgc cgagaatgct 1080
aaactgatcg acttccgcaa gctggtggag tttaagaaag ccctgggagt ccacagcctg 1140
tcccggcagg aactggatca gatctccact catatcaccc tgattaagga caacgtgaag 1200
ctgaaaaccg tcctggagaa atacaacctg agtaatgaac agatcaacaa tctgctggaa 1260
attgagttca acgattatat caacctgagc ttcaaggccc tgggaatgat tctgccactg 1320
atgcgcgagg gcaaacgata cgacgaggcc tgcgagatcg ccaatctgaa acctaagacc 1380
gtggacgaga agaaagattt cctgccagca ttttgtgatt ccattttcgc ccacgagctg 1440
tctaaccccg tggtcaatag ggctatcagc gaataccgca aggtgctgaa cgcactgctg 1500
aagaaatatg gaaaggtcca caaaattcat ctggagctgg ctcgcgacgt gggcctgtcc 1560
aagaaagcac gagagaagat cgaaaaagag cagaaggaaa accaggccgt gaatgcatgg 1620
gccctgaagg aatgcgagaa tattggcctg aaggccagcg caaagaacat cctgaaactg 1680
aagctgtgga aagaacagaa ggagatctgt atctactccg gaaataagat ctctattgag 1740
cacctgaaag atgaaaaggc cctggaggtg gaccatatct acccctattc taggagtttc 1800
gacgattctt ttatcaacaa agtgctggtg ttcaccaagg aaaatcagga gaaactgaac 1860
aagacacctt tcgaggcctt tggcaagaat attgaaaaat ggagcaagat ccagaccctg 1920
gctcagaacc tgccatacaa gaaaaagaat aagattctgg acgagaactt caaagataag 1980
cagcaggagg actttatctc tcgaaatctg aacgacaccc ggtatatcgc tacactgatt 2040
gcaaaataca caaaggagta tctgaacttc ctgctgctga gcgaaaatga gaacgccaat 2100
ctgaagagtg gcgaaaaagg gtcaaagatc cacgtgcaga ctattagcgg gatgctgacc 2160
tccgtcctga ggcacacatg gggtttgac aaaaaggatc gcaacaatca tctgcaccat 2220
gcactggatg ccatcattgt ggcctacagt acaaattcaa tcattaaggc tttcagcgat 2280
ttccggaaaa accaggagct gctgaaggcc agattctacg ctaaagaact gacttccgat 2340
aactataaac atcaggtcaa gttctttgag cctttcaaga gttttagaga aaaaatcctg 2400
tcaaagatcg acgagatttt cgtgtccaaa ccacctcgaa agcgagctag gcgcgcactg 2460
cacaaggata cctttcattc tgagaacaag atcattgaca agtgcagcta caactccaag 2520
gaaggcctgc agattgccct gagctgtgga agagtgagga aaatcggcac taagtatgtc 2580
gagaatgata ccatcgtgag ggtcgacatt ttcaaaaagc agaacaagtt ttacgctatc 2640
ccaatctacg caatggattt tgccctgggg atcctgccca ataagatcgt gattactgga 2700
aaagataaga acaataaccc caaacagtgg cagaccattg acgaatcata cgagttctgc 2760
tttagcctgt ataagaatga cctgatcctg ctgcagaaaa agaacatgca ggaacctgag 2820
ttcgcctact ataacgattt ttcaatcagc acatcaagca tttgtgtgga gaaacacgac 2880
aacaagttcg aaaatctgac tagcaaccag aagctgctgt tttccaatgc aaaagagggc 2940
tctgtgaagg tcgaaagtct ggggatccag aacctgaaag tgttcgagaa gtacatcatt 3000
acccccctgg gagataaaat taaggctgac tttcagcctc gagaaaacat cagcctgaaa 3060
accagtaaaa agtatggcct gaggtaagaa ttc 3093

<210> SEQ ID NO 194
<211> LENGTH: 103
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1)..(20)
<223> OTHER INFORMATION: a, c, u, g, unknown or other

<400> SEQUENCE: 194
nnnnnnnnnn nnnnnnnnnn guuuuagagc uagaaauagc aaguuaaaau aaggcuaguc 60
cguuaucaac uugaaaaagu ggcaccgagu cggugcuuuu uuu 103

<210> SEQ ID NO 195
<211> LENGTH: 1368
<212> TYPE: PRT
<213> ORGANISM: Streptococcus pyogenes

<400> SEQUENCE: 195

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
```

```
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990
```

```
Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 196
<211> LENGTH: 4218

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
accggtgcca ccatgtaccc atacgatgtt ccagattacg cttcgccgaa gaaaaagcgc 60
aaggtcgaag cgtccgacaa gaagtacagc atcggcctgg acatcggcac caactctgtg 120
ggctgggccg tgatcaccga cgagtacaag gtgcccagca agaaattcaa ggtgctgggc 180
aacaccgacc ggcacagcat caagaagaac ctgatcggag ccctgctgtt cgacagcggc 240
gaaacagccg aggccacccg gctgaagaga accgccagaa gaagatacac cagacggaag 300
aaccggatct gctatctgca agagatcttc agcaacgaga tggccaaggt ggacgacagc 360
ttcttccaca gactggaaga gtccttcctg gtggaagagg ataagaagca cgagcggcac 420
cccatcttcg gcaacatcgt ggacgaggtg gcctaccacg agaagtaccc caccatctac 480
cacctgagaa agaaactggt ggacagcacc gacaaggccg acctgcggct gatctatctg 540
gccctggccc acatgatcaa gttccggggc cacttcctga tcgagggcga cctgaacccc 600
gacaacagcg acgtggacaa gctgttcatc cagctggtgc agacctacaa ccagctgttc 660
gaggaaaacc ccatcaacgc cagcggcgtg gacgccaagg ccatcctgtc tgccagactg 720
agcaagagca gacggctgga aaatctgatc gcccagctgc ccggcgagaa gaagaatggc 780
ctgttcggca acctgattgc cctgagcctg ggcctgaccc ccaacttcaa gagcaacttc 840
gacctggccg aggatgccaa actgcagctg agcaaggaca cctacgacga cgacctggac 900
aacctgctgg cccagatcgg cgaccagtac gccgacctgt ttctggccgc caagaacctg 960
tccgacgcca tcctgctgag cgacatcctg agagtgaaca ccgagatcac caaggccccc 1020
ctgagcgcct ctatgatcaa gagatacgac gagcaccacc aggacctgac cctgctgaaa 1080
gctctcgtgc ggcagcagct gcctgagaag tacaaagaga ttttcttcga ccagagcaag 1140
aacggctacg ccggctacat tgacggcgga gccagccagg aagagttcta caagttcatc 1200
aagcccatcc tggaaaagat ggacggcacc gaggaactgc tcgtgaagct gaacagagag 1260
gacctgctgc ggaagcagcg gaccttcgac aacggcagca tcccccacca gatccacctg 1320
ggagagctgc acgccattct gcggcggcag gaagattttt acccattcct gaaggacaac 1380
cgggaaaaga tcgagaagat cctgaccttc cgcatcccct actacgtggg ccctctggcc 1440
aggggaaaca gcagattcgc ctggatgacc agaaagagcg aggaaaccat caccccctgg 1500
aacttcgagg aagtggtgga caagggcgct tccgcccaga gcttcatcga gcggatgacc 1560
aacttcgata agaacctgcc caacgagaag gtgctgccca agcacagcct gctgtacgag 1620
tacttcaccg tgtataacga gctgaccaaa gtgaaatacg tgaccgaggg aatgagaaag 1680
cccgccttcc tgagcggcga gcagaaaaag gccatcgtgg acctgctgtt caagaccaac 1740
cggaaagtga ccgtgaagca gctgaaagag gactacttca agaaaatcga gtgcttcgac 1800
tccgtggaaa tctccggcgt ggaagatcgg ttcaacgcct ccctgggcac ataccacgat 1860
ctgctgaaaa ttatcaagga caaggacttc ctggacaatg aggaaaacga ggacattctg 1920
gaagatatcg tgctgaccct gacactgttt gaggacagag agatgatcga ggaacggctg 1980
aaaacctatg cccacctgtt cgacgacaaa gtgatgaagc agctgaagcg gcggagatac 2040
accggctggg gcaggctgag ccggaagctg atcaacggca tccgggacaa gcagtccggc 2100
aagacaatcc tggatttcct gaagtccgac ggcttcgcca acagaaactt catgcagctg 2160

```
atccacgacg acagcctgac ctttaaagag gacatccaga aagcccaggt gtccggccag   2220
ggcgatagcc tgcacgagca cattgccaat ctggccggca gccccgccat taagaagggc   2280
atcctgcaga cagtgaaggt ggtggacgag ctcgtgaaag tgatgggccg gcacaagccc   2340
gagaacatcg tgatcgaaat ggccagagag aaccagacca cccagaaggg acagaagaac   2400
agccgcgaga gaatgaagcg gatcgaagag ggcatcaaag agctgggcag ccagatcctg   2460
aaagaacacc ccgtggaaaa cacccagctg cagaacgaga agctgtacct gtactacctg   2520
cagaatgggc gggatatgta cgtggaccag gaactggaca tcaaccggct gtccgactac   2580
gatgtggacc atatcgtgcc tcagagcttt ctgaaggacg actccatcga caacaaggtg   2640
ctgaccagaa gcgacaagaa ccggggcaag agcgacaacg tgccctccga agaggtcgtg   2700
aagaagatga agaactactg gcggcagctg ctgaacgcca agctgattac ccagagaaag   2760
ttcgacaatc tgaccaaggc cgagagaggc ggcctgagcg aactggataa ggccggcttc   2820
atcaagagac agctggtgga aacccggcag atcacaaagc acgtggcaca gatcctggac   2880
tcccggatga acactaagta cgacgagaat gacaagctga tccgggaagt gaaagtgatc   2940
accctgaagt ccaagctggt gtccgatttc cggaaggatt tccagtttta caaagtgcgc   3000
gagatcaaca actaccacca cgcccacgac gcctacctga acgccgtcgt gggaaccgcc   3060
ctgatcaaaa agtaccctaa gctggaaagc gagttcgtgt acggcgacta caaggtgtac   3120
gacgtgcgga agatgatcgc caagagcgag caggaaatcg gcaaggctac cgccaagtac   3180
ttcttctaca gcaacatcat gaactttttc aagaccgaga ttaccctggc caacggcgag   3240
atccggaagc ggcctctgat cgagacaaac ggcgaaaccg gggagatcgt gtgggataag   3300
ggccgggatt ttgccaccgt gcggaaagtg ctgagcatgc cccaagtgaa tatcgtgaaa   3360
aagaccgagg tgcagacagg cggcttcagc aaagagtcta tcctgcccaa gaggaacagc   3420
gataagctga tcgccagaaa gaaggactgg gaccctaaga agtacggcgg cttcgacagc   3480
cccaccgtgg cctattctgt gctggtggtg gccaaagtgg aaaagggcaa gtccaagaaa   3540
ctgaagagtg tgaaagagct gctggggatc accatcatgg aaagaagcag cttcgagaag   3600
aatcccatcg actttctgga agccaagggc tacaaagaag tgaaaaagga cctgatcatc   3660
aagctgccta agtactccct gttcgagctg gaaaacggcc ggaagagaat gctggcctct   3720
gccggcgaac tgcagaaggg aaacgaactg gccctgccct ccaaatatgt gaacttcctg   3780
tacctggcca gccactatga gaagctgaag ggctcccccg aggataatga gcagaaacag   3840
ctgtttgtgg aacagcacaa gcactacctg gacgagatca tcgagcagat cagcgagttc   3900
tccaagagag tgatcctggc cgacgctaat ctggacaaag tgctgtccgc ctacaacaag   3960
caccgggata agcccatcag agagcaggcc gagaatatca tccacctgtt taccctgacc   4020
aatctgggag cccctgccgc cttcaagtac tttgacacca ccatcgaccg gaagaggtac   4080
accagcacca aagaggtgct ggacgccacc ctgatccacc agagcatcac cggcctgtac   4140
gagacacgga tcgacctgtc tcagctggga ggcgacagcc ccaagaagaa gagaaaggtg   4200
gaggccagct aagaattc                                                 4218
```

<210> SEQ ID NO 197
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide <220> FEATURE:
<221> NAME/KEY: modified_base
<222> LOCATION: (1)..(20)
<223> OTHER INFORMATION: a, c, u, g, unknown or other

<400> SEQUENCE: 197
nnnnnnnnnn nnnnnnnnnn guuuuuguac ucucaagauu uagaaacuug cagaagcuac 60
aaagauaagg cuucaugccg aaaucaacac ccugucauuu uauggcaggg uguuuu 116

<210> SEQ ID NO 198
<211> LENGTH: 1120
<212> TYPE: PRT
<213> ORGANISM: Streptococcus thermophilus

<400> SEQUENCE: 198

Met Ser Asp Leu Val Leu Gly Leu Asp Ile Gly Ile Gly Ser Val Gly
1 5 10 15

Val Gly Ile Leu Asn Lys Val Thr Gly Glu Ile Ile His Lys Asn Ser
20 25 30

Arg Ile Phe Pro Ala Ala Gln Ala Glu Asn Asn Leu Val Arg Arg Thr
35 40 45

Asn Arg Gln Gly Arg Arg Leu Ala Arg Arg Lys Lys His Arg Arg Val
50 55 60

Arg Leu Asn Arg Leu Phe Glu Glu Ser Gly Leu Ile Thr Asp Phe Thr
65 70 75 80

Lys Ile Ser Ile Asn Leu Asn Pro Tyr Gln Leu Arg Val Lys Gly Leu
85 90 95

Thr Asp Glu Leu Ser Asn Glu Glu Leu Phe Ile Ala Leu Lys Asn Met
100 105 110

Val Lys His Arg Gly Ile Ser Tyr Leu Asp Asp Ala Ser Asp Asp Gly
115 120 125

Asn Ser Ser Val Gly Asp Tyr Ala Gln Ile Val Lys Glu Asn Ser Lys
130 135 140

Gln Leu Glu Thr Lys Thr Pro Gly Gln Ile Gln Leu Glu Arg Tyr Gln
145 150 155 160

Thr Tyr Gly Gln Leu Arg Gly Asp Phe Thr Val Glu Lys Asp Gly Lys
165 170 175

Lys His Arg Leu Ile Asn Val Phe Pro Thr Ser Ala Tyr Arg Ser Glu
180 185 190

Ala Leu Arg Ile Leu Gln Thr Gln Gln Glu Phe Asn Pro Gln Ile Thr
195 200 205

Asp Glu Phe Ile Asn Arg Tyr Leu Glu Ile Leu Thr Gly Lys Arg Lys
210 215 220

Tyr Tyr His Gly Pro Gly Asn Glu Lys Ser Arg Thr Asp Tyr Gly Arg
225 230 235 240

Tyr Arg Thr Ser Gly Glu Thr Leu Asp Asn Ile Phe Gly Ile Leu Ile
245 250 255

Gly Lys Cys Thr Phe Tyr Pro Asp Glu Phe Arg Ala Ala Lys Ala Ser
260 265 270

Tyr Thr Ala Gln Glu Phe Asn Leu Leu Asn Asp Leu Asn Asn Leu Thr
275 280 285

Val Pro Thr Glu Thr Lys Lys Leu Ser Lys Glu Gln Lys Asn Gln Ile
290 295 300

Ile Asn Tyr Val Lys Asn Glu Lys Ala Met Gly Pro Ala Lys Leu Phe
305 310 315 320

```
Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
    530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
    610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
```

```
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser  Gln Glu Lys Tyr Asn  Asp Ile Lys
        995                 1000                1005

Lys Lys  Glu Gly Val Asp Ser  Asp Ser Glu Phe Lys  Phe Thr Leu
    1010                1015                1020

Tyr Lys  Asn Asp Leu Leu Leu  Val Lys Asp Thr Glu  Thr Lys Glu
    1025                1030                1035

Gln Gln  Leu Phe Arg Phe Leu  Ser Arg Thr Met Pro  Lys Gln Lys
    1040                1045                1050

His Tyr  Val Glu Leu Lys Pro  Tyr Asp Lys Gln Lys  Phe Glu Gly
    1055                1060                1065

Gly Glu  Ala Leu Ile Lys Val  Leu Gly Asn Val Ala  Asn Ser Gly
    1070                1075                1080

Gln Cys  Lys Lys Gly Leu Gly  Lys Ser Asn Ile Ser  Ile Tyr Lys
    1085                1090                1095

Val Arg  Thr Asp Val Leu Gly  Asn Gln His Ile Ile  Lys Asn Glu
    1100                1105                1110

Gly Asp  Lys Pro Lys Leu Met
    1115                1120
```

<210> SEQ ID NO 199
<211> LENGTH: 3477
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 199
accggtgcca ccatgtaccc atacgatgtt ccagattacg cttcgccgaa gaaaaagcgc 60
aaggtcgaag cgtcctccga cctggtactt ggactggata ttggtatcgg ttcggtggga 120
gtcggaatcc tcaacaaggt cacgggggag atcattcaca agaactcgcg gatcttcccc 180
gcagctcagg ctgagaacaa cttggtgcgg agaacgaata ggcagggcag gcgactggcg 240
aggaggaaga aacacaggag agtccgattg aaccggctgt tcgaggagtc cggtttgatc 300
accgacttta cgaaaatctc gattaacctt aatccctatc agcttcgggt gaaaggcctg 360
acagacgaac tttcgaatga ggaacttttc atcgcgctga aaaacatggt caagcacaga 420
gggatttcct acctcgatga cgcctcggat gacggaaatt cctcagtagg agattatgca 480
cagatcgtga aagagaactc aaagcaactg gaaacaaaga caccggggca gatccaactt 540
gaaagatacc agacatacgg acagctcaga ggagatttta cggtggagaa ggacggtaaa 600
aagcacagac tcattaacgt atttcccacg tcggcgtaca gatccgaagc gctccgcatc 660
cttcagactc aacaggagtt caacccgcaa attactgatg agttcatcaa ccgctatttg 720
gaaatcttga ccggaaagcg caagtattat catgggccgg gtaatgagaa atccagaaca 780
gattacggcc gatacagaac ttcgggggaa accttggata acatctttgg tattttgatt 840
ggaaagtgca ccttttaccc ggacgagttt cgagcggcca aggcgtcata cacagcacaa 900
gagtttaatc tcttgaatga tttgaacaac ttgacggtcc ccacggagac aaagaagctc 960
tccaaagagc aaaagaacca aatcatcaac tacgtcaaga acgagaaggc tatggggcca 1020
gcgaagctgt tcaagtatat cgctaaactt ctcagctgtg atgtggcgga catcaaaggg 1080
taccgaatcg acaagtcggg aaaagcggaa attcacacgt ttgaagcata tcgaaagatg 1140
aaaacgttgg aaacactgga cattgagcag atggaccggg aaacgctcga caaactggca 1200
tacgtgctca cgttgaatac tgaacgagag ggaatccaag aggcccttga acatgagttc 1260
gccgatggat cgttcagcca gaagcaggtc gacgaacttg tgcaattccg caaggcgaat 1320
agctccatct tcgggaaggg atggcacaac ttttcggtca aactcatgat ggagttgatc 1380
ccagaacttt atgagacttc ggaggagcaa atgacgatct tgacgcgctt ggggaaacag 1440
aaaacgacaa gctcatcgaa caaaactaag tacattgatg agaaattgct gacggaagaa 1500
atctataatc cggtagtagc gaaatcggta agacaagcga tcaaaatcgt gaacgcggcg 1560
atcaaggaat atggtgactt tgataacatc gtaattgaaa tggctagaga gacgaacgaa 1620
gatgacgaga aaaaggcaat ccagaagatc cagaaggcca acaaggatga aaaagatgca 1680
gcgatgctta aagcggccaa ccaatacaat ggaaaggcgg agctgcccca ttcagtgttt 1740
cacggtcata aacagttggc gaccaagatc cgactctggc atcagcaggg tgagcggtgt 1800
ctctacaccg gaaagactat ctccatccat gacttgatta acaattcgaa ccagtttgaa 1860
gtggatcata ttctgcccct gtcaatcacc tttgacgact cgcttgcgaa caaggtgctc 1920
gtgtacgcaa cggcaaatca ggagaaaggc cagcggactc cgtatcaggc gctcgactca 1980
atggacgatg cgtggtcatt ccgggagctg aaggcgttcg tacgcgagag caagacactg 2040
agcaacaaaa agaaagagta tctgctgaca gaggaggaca tctcgaaatt cgatgtcagg 2100
aagaagttca tcgagcggaa tcttgtcgac actcgctacg cttccagagt agtactgaac 2160
gcgctccagg aacactttag agcgcacaaa attgacacga aggtgtcagt ggtgagaggg 2220
cagttcacat cccaactccg ccgacattgg ggcatcgaaa agacgcggga cacatatcac 2280
catcatgcgg tggacgcgct gattattgcc gcttcgtccc agttgaatct ctggaaaaag 2340
cagaagaaca cgctggtgtc gtattcggag gatcagcttt tggacatcga aaccggggag 2400
ctgatttccg acgatgaata caaagaatcg gtgtttaagg caccatatca gcatttcgtg 2460
gacacgctga agagcaaaga gtttgaggac agcatcctct tttcgtacca agtggactcg 2520
aagtttaatc gcaagatttc agacgccaca atctacgcga cgaggcaggc gaaggtgggc 2580
aaagataaag cagatgaaac ctacgtcctt ggtaaaatca aggacatcta cactcaggac 2640
gggtacgatg cgttcatgaa aatctacaag aaggataagt cgaagtttct catgtaccgc 2700
cacgatccac agactttcga aaaagtcatt gagcctattt tggagaacta ccctaacaag 2760
caaatcaacg agaaagggaa agaagtcccg tgcaacccct ttctgaagta caaggaagag 2820
cacggttata tccgcaaata ctcgaagaaa ggaaatgggc ctgagattaa gtcgcttaag 2880
tattacgact caaagttggg taaccacatc gacattaccc cgaaagactc caacaacaaa 2940
gtcgtgttgc agtccgtctc gccctggcga gcagatgtgt attttaataa gacgaccggc 3000
aaatatgaga tccttggact caaatacgca gaccttcaat tcgaaaaggg gacgggcact 3060
tataagattt cacaagagaa gtacaacgac atcaagaaaa aggaaggggt cgattcagat 3120
tcggagttca aattcaccct ctacaaaaac gacctcctgc ttgtgaagga cacagaaacg 3180
aaggagcagc agctctttcg gttcctctca cgcacgatgc ccaaacaaaa acattacgtc 3240
gaacttaaac cttacgataa gcaaaagttt gaagggggag aggcactgat caaagtattg 3300
ggtaacgtag ccaatagcgg acagtgtaag aaagggctgg gaaagtccaa tatctcgatc 3360
tataaagtac gaacagatgt attgggaaac cagcatatca tcaaaaatga gggggataaa 3420
cccaaactcg atttcagccc caagaagaag agaaaggtgg aggccagcta agaattc 3477

<210> SEQ ID NO 200
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
gcccgggtgg aactggtagc catgaat 27

<210> SEQ ID NO 201
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
gttgaagatg aagcccagag cggagt 26

<210> SEQ ID NO 202
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
gcttccgacg aggtggccat caaggat 27

<210> SEQ ID NO 203
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
gcaccatctc tccgtggtac cccgggt 27

<210> SEQ ID NO 204
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
ggtggaactg gtagccatga atgaga 26

<210> SEQ ID NO 205
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205
gccatgaatg agaccgaccc aaagagc 27

<210> SEQ ID NO 206
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 206
gcatcctcgt gggcacttcc gacgagg 27

<210> SEQ ID NO 207
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 207
gcagagcgga gtgctgttct cccaagt 27

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 208
ggtcggtctc attcatggct accagt 26

<210> SEQ ID NO 209
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 209
gcaataaaag gtgctattgc tatagt 26

<210> SEQ ID NO 210
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 210
gtactcaacc aagtcattct gagaat 26

<210> SEQ ID NO 211
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(7)
<223> OTHER INFORMATION: a, c, t, g, unknown or other

<400> SEQUENCE: 211
nnnnnnngta ctcaaccaag tcattc 26

<210> SEQ ID NO 212
<211> LENGTH: 1121
<212> TYPE: PRT
<213> ORGANISM: Streptococcus thermophilus

<400> SEQUENCE: 212

Met Ser Asp Leu Val Leu Gly Leu Asp Ile Gly Ile Gly Ser Val Gly
1 5 10 15

Val Gly Ile Leu Asn Lys Val Thr Gly Glu Ile Ile His Lys Asn Ser
20 25 30

Arg Ile Phe Pro Ala Ala Gln Ala Glu Asn Asn Leu Val Arg Arg Thr
35 40 45

Asn Arg Gln Gly Arg Arg Leu Ala Arg Arg Lys Lys His Arg Arg Val
50 55 60

Arg Leu Asn Arg Leu Phe Glu Glu Ser Gly Leu Ile Thr Asp Phe Thr
65 70 75 80

Lys Ile Ser Ile Asn Leu Asn Pro Tyr Gln Leu Arg Val Lys Gly Leu
85 90 95

Thr Asp Glu Leu Ser Asn Glu Glu Leu Phe Ile Ala Leu Lys Asn Met
100 105 110

Val Lys His Arg Gly Ile Ser Tyr Leu Asp Asp Ala Ser Asp Asp Gly
115 120 125

Asn Ser Ser Val Gly Asp Tyr Ala Gln Ile Val Lys Glu Asn Ser Lys
130 135 140

-continued

```
Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
    530                 535                 540

Tyr Asn Gly Lys Ala Glu Leu Pro His Ser Val Phe His Gly His Lys
545                 550                 555                 560
```

```
Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
    610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
    770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Glu Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
        915                 920                 925

Gly Pro Glu Ile Lys Ser Leu Lys Tyr Tyr Asp Ser Lys Leu Gly Asn
    930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Glu Lys
```

```
            980                 985                 990

Gly Thr Gly Thr Tyr Lys Ile Ser  Gln Glu Lys Tyr Asn  Asp Ile Lys
        995                 1000                1005

Lys Lys  Glu Gly Val Asp Ser  Asp Ser Glu Phe Lys  Phe Thr Leu
    1010                 1015                 1020

Tyr Lys  Asn Asp Leu Leu Leu  Val Lys Asp Thr Glu  Thr Lys Glu
    1025                 1030                 1035

Gln Gln  Leu Phe Arg Phe Leu  Ser Arg Thr Met Pro  Lys Gln Lys
    1040                 1045                 1050

His Tyr  Val Glu Leu Lys Pro  Tyr Asp Lys Gln Lys  Phe Glu Gly
    1055                 1060                 1065

Gly Glu  Ala Leu Ile Lys Val  Leu Gly Asn Val Ala  Asn Ser Gly
    1070                 1075                 1080

Gln Cys  Lys Lys Gly Leu Gly  Lys Ser Asn Ile Ser  Ile Tyr Lys
    1085                 1090                 1095

Val Arg  Thr Asp Val Leu Gly  Asn Gln His Ile Ile  Lys Asn Glu
    1100                 1105                 1110

Gly Asp  Lys Pro Lys Leu Asp  Phe
    1115                 1120
```

<210> SEQ ID NO 213
<211> LENGTH: 20
<212> TYPE: DNA
<213> ORGANISM: Corynebacter diphtheriae

<400> SEQUENCE: 213
aaaagggaat aagggcgaca 20

<210> SEQ ID NO 214
<211> LENGTH: 27
<212> TYPE: DNA
<213> ORGANISM: Sutterella wadsworthensis
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(7)
<223> OTHER INFORMATION: a, c, t, g, unknown or other

<400> SEQUENCE: 214
nggnnnncat tctgagaata gtgtatg 27

<210> SEQ ID NO 215
<211> LENGTH: 20
<212> TYPE: DNA
<213> ORGANISM: Sutterella wadsworthensis

<400> SEQUENCE: 215
gcgaccgagt tgctcttgcc 20

<210> SEQ ID NO 216
<211> LENGTH: 27
<212> TYPE: DNA
<213> ORGANISM: Legionella pneumophila
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(7)

<223> OTHER INFORMATION: a, c, t, g, unknown or other

<400> SEQUENCE: 216
nggnnnncat tctgagaata gtgtatg 27

<210> SEQ ID NO 217
<211> LENGTH: 20
<212> TYPE: DNA
<213> ORGANISM: Legionella pneumophila

<400> SEQUENCE: 217
gcgaccgagt tgctcttgcc 20

<210> SEQ ID NO 218
<211> LENGTH: 27
<212> TYPE: DNA
<213> ORGANISM: Filifactor alocis
<220> FEATURE:
<221> NAME/KEY: modified_base
<222> LOCATION: (1)..(3)
<223> OTHER INFORMATION: a, c, t, g, unknown or other

<400> SEQUENCE: 218
nnnaagcttg agtactcacc agtcaca 27

<210> SEQ ID NO 219
<211> LENGTH: 20
<212> TYPE: DNA
<213> ORGANISM: Filifactor alocis

<400> SEQUENCE: 219
ctcttccttt ttcaatatta 20

<210> SEQ ID NO 220
<211> LENGTH: 27
<212> TYPE: DNA
<213> ORGANISM: Lactobacillus johnsonii
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(7)
<223> OTHER INFORMATION: a, c, t, g, unknown or other

<400> SEQUENCE: 220
nnaaanntaa atgcttcaat aatattg 27

<210> SEQ ID NO 221
<211> LENGTH: 20
<212> TYPE: DNA
<213> ORGANISM: Lactobacillus johnsonii

<400> SEQUENCE: 221
aaagggaata agggcgacac 20

<210> SEQ ID NO 222
<211> LENGTH: 27
<212> TYPE: DNA
<213> ORGANISM: Parvibaculum lavamentivorans
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 222
nnncatnaaa ggaagagtat gagtatt 27

<210> SEQ ID NO 223
<211> LENGTH: 20
<212> TYPE: DNA
<213> ORGANISM: Staphylococcus aureus

<400> SEQUENCE: 223
ctattctcag aatgacttgg 20

<210> SEQ ID NO 224
<211> LENGTH: 27
<212> TYPE: DNA
<213> ORGANISM: Mycoplasma gallisepticum
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other

<400> SEQUENCE: 224
nnganggagt cacagaaaag catctta 27

<210> SEQ ID NO 225
<211> LENGTH: 20
<212> TYPE: DNA
<213> ORGANISM: Mycoplasma gallisepticum

<400> SEQUENCE: 225
gtttctgggt gagcaaaaac 20

<210> SEQ ID NO 226
<211> LENGTH: 27
<212> TYPE: DNA
<213> ORGANISM: Campylobacter lari
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other

<400> SEQUENCE: 226
nngggnagaa ggcaaaatgc cgcaaaa 27

<210> SEQ ID NO 227
<211> LENGTH: 20
<212> TYPE: DNA
<213> ORGANISM: Campylobacter lari

<400> SEQUENCE: 227
ggtattatcc cgtattgacg 20

<210> SEQ ID NO 228
<211> LENGTH: 20
<212> TYPE: DNA
<213> ORGANISM: Unknown
<220> FEATURE:

-continued

```
<223> OTHER INFORMATION: Description of Unknown:
      SpCas9 oligonucleotide

<400> SEQUENCE: 228

gggactcaac caagtcattc                                         20
```